US009694063B2

(12) United States Patent
Scarselli et al.

(10) Patent No.: US 9,694,063 B2
(45) Date of Patent: Jul. 4, 2017

(54) CLOSTRIDIUM DIFFICILE TOXIN-BASED VACCINE

(71) Applicant: GlaxoSmithKline Biologicals SA, Rixensart (BE)

(72) Inventors: Maria Scarselli, Siena (IT); Mariagrazia Pizza, Siena (IT); Rosanna Leuzzi, Siena (IT); Maria Arico, Poggibonsi (IT); Manuele Martinelli, Arezzo (IT); Gillian Douce, Glasgow (GB)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 14/363,387

(22) PCT Filed: Dec. 7, 2012

(86) PCT No.: PCT/IB2012/002955
§ 371 (c)(1),
(2) Date: Jun. 6, 2014

(87) PCT Pub. No.: WO2013/084071
PCT Pub. Date: Jun. 13, 2013

(65) Prior Publication Data

US 2015/0132333 A1 May 14, 2015

(30) Foreign Application Priority Data

Dec. 8, 2011 (GB) .................................. 1121149.7
Sep. 27, 2012 (GB) .................................. 1217321.7

(51) Int. Cl.
*A61K 39/08* (2006.01)
*C07K 14/33* (2006.01)
*A61K 39/00* (2006.01)

(52) U.S. Cl.
CPC .............. *A61K 39/08* (2013.01); *C07K 14/33* (2013.01); *A61K 2039/55505* (2013.01); *A61K 2039/55566* (2013.01); *A61K 2039/70* (2013.01); *C07K 2319/20* (2013.01)

(58) Field of Classification Search
CPC ............................ A61K 39/08; A61K 2300/00
USPC ............................ 424/184.1, 247.1; 530/350
See application file for complete search history.

(56) References Cited

U.S. PATENT DOCUMENTS 6,290,960 B1 9/2001 Kink et al.
6,733,760 B1 * 5/2004 Wilkins ................. C07K 14/33 424/184.1
9,290,565 B2 * 3/2016 Castado ................. A61K 39/08
2002/0009429 A1 * 1/2002 Bostwick .............. A23L 1/3056 424/93.1
2003/0129198 A1 * 7/2003 Wilkins ................. C07K 14/33 424/190.1
2004/0235139 A1 * 11/2004 Demain ................... C12N 1/20 435/252.7
2010/0290987 A1 * 11/2010 Gross ....................... C07K 7/06 424/1.69
2010/0291152 A1 * 11/2010 Shone .................... A61K 39/07 424/246.1
2011/0053244 A1 * 3/2011 Oyler ..................... C07K 14/33 435/188
2012/0269841 A1 * 10/2012 Sidhu ..................... C07K 14/33 424/190.1
2013/0053244 A1 * 2/2013 Devisetty ............... A01N 37/42 504/136
2013/0266583 A1 * 10/2013 Shone .................... C07K 14/33 424/167.1
2013/0288374 A1 * 10/2013 Oyler ..................... C07K 14/33 435/377
2014/0093529 A1 * 4/2014 Castado ................. A61K 39/08 424/190.1
2015/0044250 A1 * 2/2015 Heinrichs .............. C07K 14/33 424/190.1
2015/0125927 A1 * 5/2015 Ruppen .................. C07K 14/33 435/193
2015/0313985 A1 * 11/2015 Castado ................. A61K 39/08 424/190.1

FOREIGN PATENT DOCUMENTS

WO 96/12802 A1 5/1996
WO 97/02836 A1 1/1997
WO 98/08540 A1 3/1998
WO 9859053 A1 12/1998
WO 00/61761 10/2000
WO 00/61762 10/2000
WO 01/85748 * 11/2001 ............ C07H 19/00
(Continued)

OTHER PUBLICATIONS

Barbut, F et al, Journal of Clinical Microbiology, Mar. 1993, vol. 31(3), pp. 740-742, Comparison of enterotoxin production, cytotoxin production, serogrouping and antimnicrobial susceptibilities of Clostridium difficile strains isolated from AIDS and Human Immunodeficiency Virus Negative Patients.*
DiBella, S et al, Review, Toxins, 2016, vol. 8(134) pp. 1-25.*
Ho, "Crystal structure of receptor-binding C-terminal repeats from Clostridium difficile toxin A," Proceedings of The National Academy of Sciences, vol. 102, No. 51, Dec. 13, 2005, pp. 18373-18378.
Kotloff et al, "Safety and immunogenicity of increasing doses of a clostridium difficile toxoid administered to healthy adults," Infection and Immunity, vol. 69, No. 2, Feb. 1, 2001, pp. 988-995.
International Search Report for PCT/IB12/002955, mailed Aug. 1, 2013, 8 pages.
(Continued)

*Primary Examiner* — Albert Navarro
(74) *Attorney, Agent, or Firm* — Birch, Stewart, Kolasch & Birch, LLP

(57) ABSTRACT

The present invention relates to recombinant fragments of *C. difficile* TcdA and TcdB that may be used in the development of vaccines against *C. difficile* associated disease. More particularly it relates to combinations comprising a ToxB-GT antigen and a TcdA antigen or a ToxA-GT antigen and a TcdB antigen.

21 Claims, 65 Drawing Sheets

(56) References Cited

FOREIGN PATENT DOCUMENTS

| | | | | |
|---|---|---|---|---|
| WO | 02/079410 | * | 10/2002 | |
| WO | 2004/041857 | A2 | 5/2004 | |
| WO | 2006/071877 | A2 | 7/2006 | |
| WO | 2006/121422 | A2 | 11/2006 | |
| WO | 2007/146139 | A2 | 12/2007 | |
| WO | 2008/014733 | A1 | 2/2008 | |
| WO | 2008152429 | A1 | 12/2008 | |
| WO | 2010017383 | A1 | 2/2010 | |
| WO | 2010/094970 | A1 | 8/2010 | |
| WO | 2011/031568 | A2 | 3/2011 | |
| WO | 2011/060431 | A2 | 5/2011 | |
| WO | 2011/063346 | A1 | 5/2011 | |
| WO | 2011/067616 | A1 | 6/2011 | |
| WO | 2011/068953 | * | 6/2011 | ............. A61K 39/08 |
| WO | 2011068953 | A2 | 6/2011 | |
| WO | 2011/126811 | A2 | 10/2011 | |
| WO | 2012/028741 | A1 | 3/2012 | |
| WO | 2012/036706 | A1 | 3/2012 | |
| WO | 2012/046061 | A2 | 4/2012 | |
| WO | 2012/118693 | A1 | 9/2012 | |
| WO | 2012/143902 | A1 | 10/2012 | |
| WO | 2012/163810 | A1 | 12/2012 | |
| WO | 2012/163811 | A1 | 12/2012 | |
| WO | 2012/163817 | A2 | 12/2012 | |

OTHER PUBLICATIONS

D'Urzo et al., "The structure of Clostridium difficile toxin A glucosyltransferase domain bound to Mn2+ and UDP provides insights into glucosyltransferase activity and product release," The FEBS Journal, 279 (2012) pp. 3085-3097.

Foglia et al., "Clostridium difficile: Development of a novel candidate vaccine," Vaccine 30 (2012) pp. 4307-4309.

Gardiner et al., "A DNA vaccine targeting the receptor-binding domain of Clostridium difficile toxin A," Vaccine 27 (2009) pp. 3598-3604.

GB Application No. 1121149.7, Search Report Under Section 17, dated Mar. 20, 2012.

Greenberg et al., "Phase I dose finding studies of an adjuvanted Clostridium difficile toxoid vaccine," Vaccine 30, 2012, pp. 2245-2249.

Kim et al., "Immunization of Adult Hamsters against Clostridium difficile-Associated Ileocecitis and Transfer of Protection to Infant Hamsters," Infection and Immunity, Dec. 1987, vol. 55, No. 12, pp. 2984-2992.

Leuzzi et al., "Protective Efficacy Induced by Recombinant Clostridium difficile Toxin Fragments," Infection and Immunity, Aug. 2013, vol. 81, No. 8, pp. 2851-2860.

Lyerly et al., "Vaccination against Lethal Clostridium difficile Enterocolitis with a Nontoxic Recombinant Peptide of Toxin A," Current Microbiology, vol. 21 (1990), pp. 29-32.

Lyras et al., "Toxin B is essential for virulence of Clostridium difficile," Nature, Apr. 2009, 458(7242); pp. 1176-1179.

Permpoonpattana et al., "Immunization with Bacillus Spores Expressing Toxin A Peptide Repeats Protects against Infection with Clostridium difficile Strains Producing Toxins A and B," Infection and Immunity, Jun. 2011, vol. 79, No. 6, pp. 2295-2302.

Ryan et al., "Protective Immunity against Clostridium difficile Toxin A Induced by Oral Immunization with a Live, Attenuated Vibrio cholerae Vector Strain," Infection and Immunity, Jul. 1997, vol. 65, No. 7, pp. 2941-2949.

Seregin et al., "Adenovirus-based vaccination against Clostridium difficile toxin A allows for rapid humoral immunity and complete protection from toxin A lethal challenge in mice," Vaccine 30 (2012) pp. 1492-1501.

Sougioultzis et al., "Clostridium difficile Toxoid Vaccine in Recurrent C. difficile-Associated Diarrhea," Gastroenterology, 2005, vol. 128, pp. 764-770.

Spencer et al., "Evaluation of the protective immunity induced by recombinant fragments of Clostridium difficile toxin A and B in the hamster model," University of Glasgow, 1 page, shown at the 4th International Clostridium Difficile Symposium in Bled, Slovenia, Sep. 19-22, 2012.

Spencer et al., "Protective Efficacy Induced by Recombinant Clostridium difficile Toxin Fragments," University of Glasgow, 1 page, shown at the 4th International Clostridium Difficile Symposium in Bled, Slovenia, Sep. 19-22, 2012.

Steele et al., "Antibody Against TcdB, but Not TcdA, Prevents Development of Gastrointestinal and Systemic Clostridium difficile Disease," The Journal of Infectious Diseases, 2013, vol. 207, pp. 323-330.

Tian et al., "A novel fusion protein containing the receptor binding domains of C. difficile toxin A and toxin B elicits protective immunity against lethal toxin and spore challenge in preclinical efficacy models," Vaccine 30 (2012) pp. 4249-4258.

Wang et al., "A Chimeric Toxin Vaccine Protects against Primary and Recurrent Clostridium difficile Infection," Infection and Immunity, Aug. 2012, vol. 80, No. 8, pp. 2678-2688.

Ward et al., "Local and Systemic Neutralizing Antibody Responses Induced by Intranasal Immunization with the Nontoxic Binding Domain of Toxin A from Clostridium difficile," Infection and Immunity, Oct. 1999, vol. 67, No. 10, pp. 5124-5132.

* cited by examiner

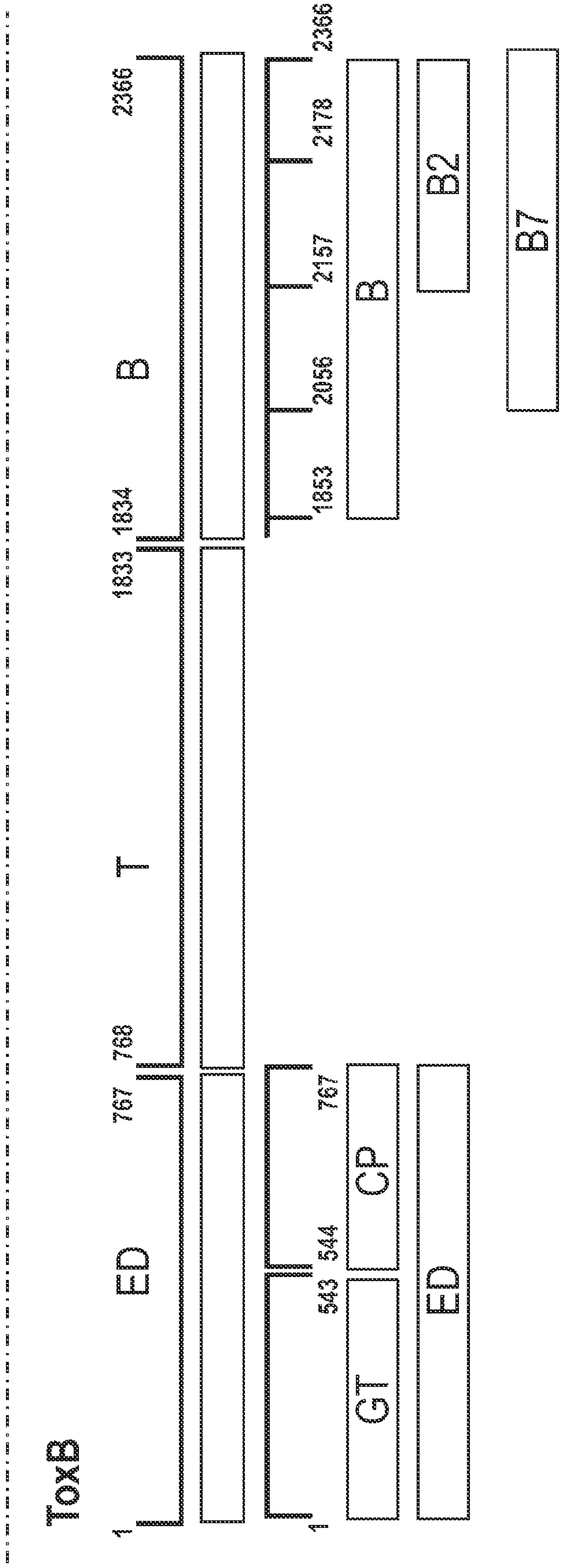
FIG. 1(contd)

Toxin A fragments

Bar chart with y-axis "GMT UE/ml" ranging from 0 to 3000, and x-axis "Antigen" with categories: p5/6 Alum, p5/6 MF59, TOXA_B2 Alum, TOXA_B2 MF59, TOXA_CP Alum.

*FIG. 9(contd)*

Toxin B fragments

Bar chart: GMT UE/ml vs Antigen
- TOXB_B Alum: ~1300
- TOXB_B MF59: ~800
- TOXB_B2 Alum: ~1500
- TOXB_ED Alum: ~600
- TOXB_ED MF59: ~100
- TOXB_GT Alum: ~500
- TOXB_CP Alum: ~150

FIG. 13(contd)
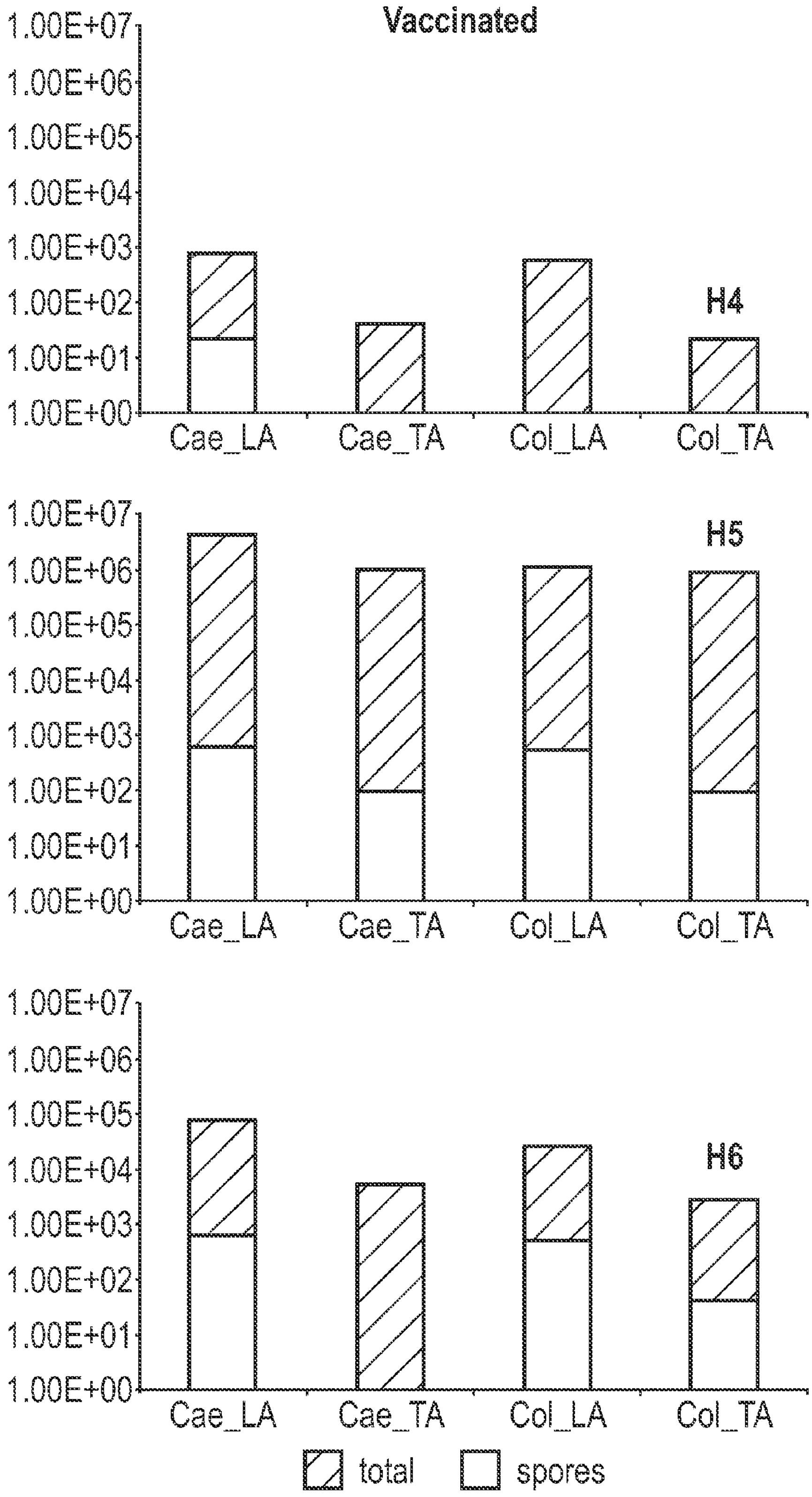

FIG. 13(contd)
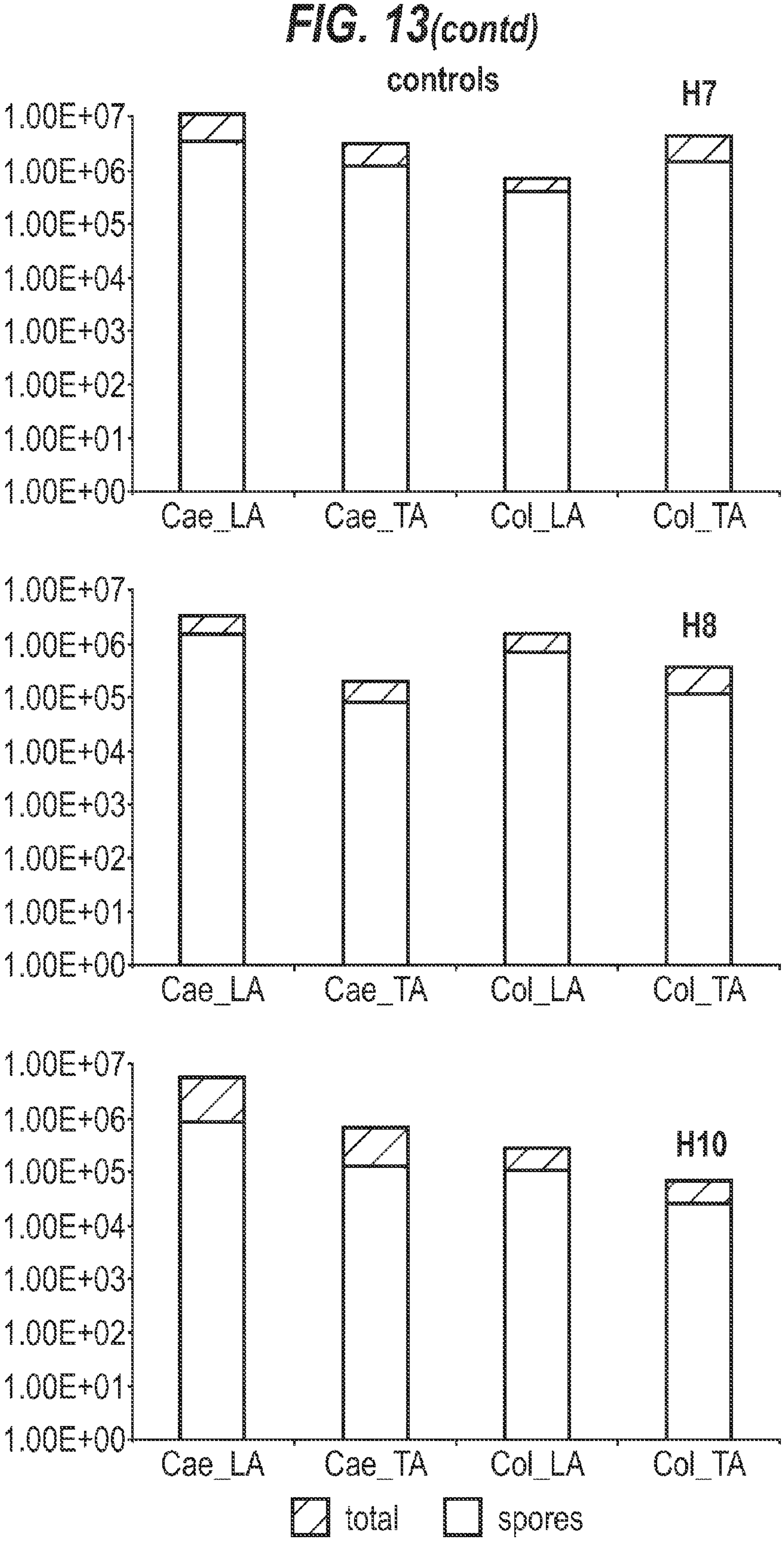

FIG. 17(contd)
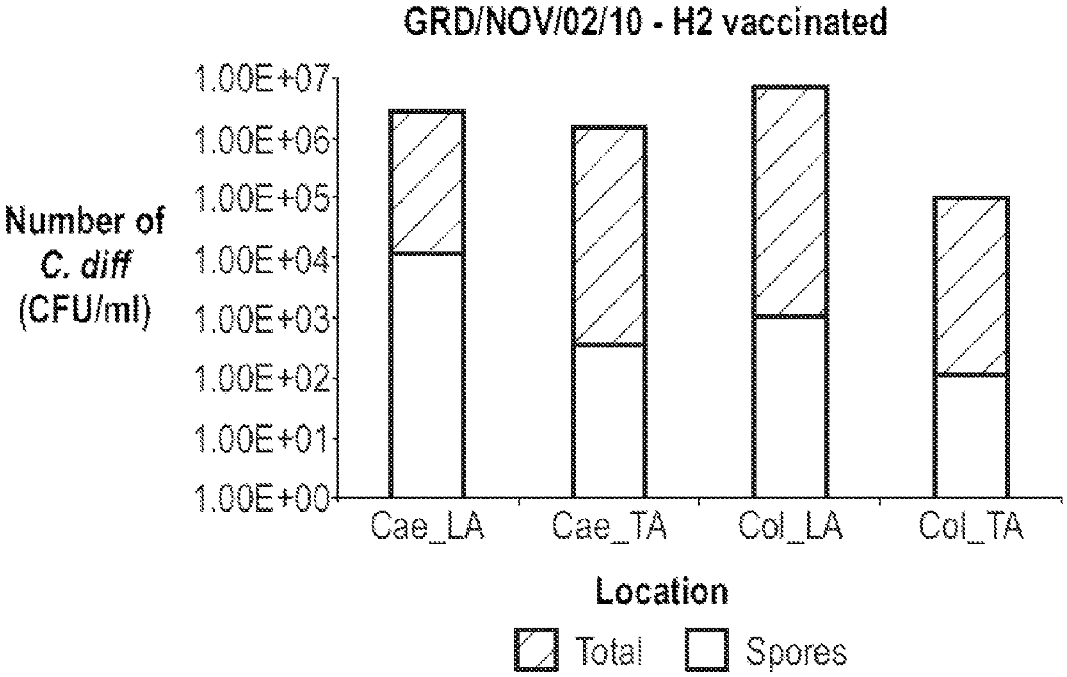
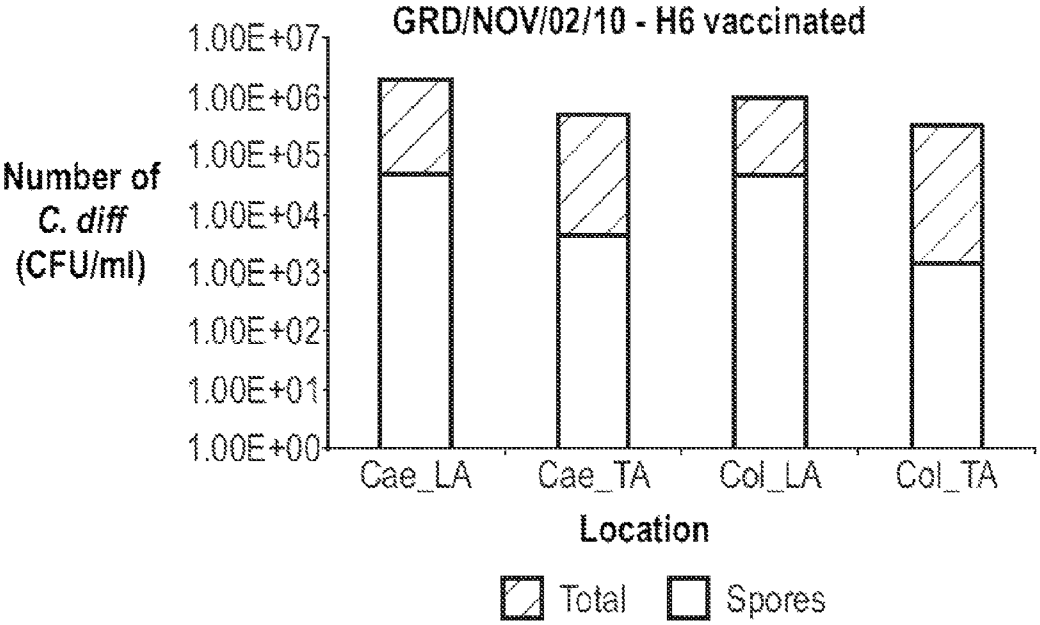

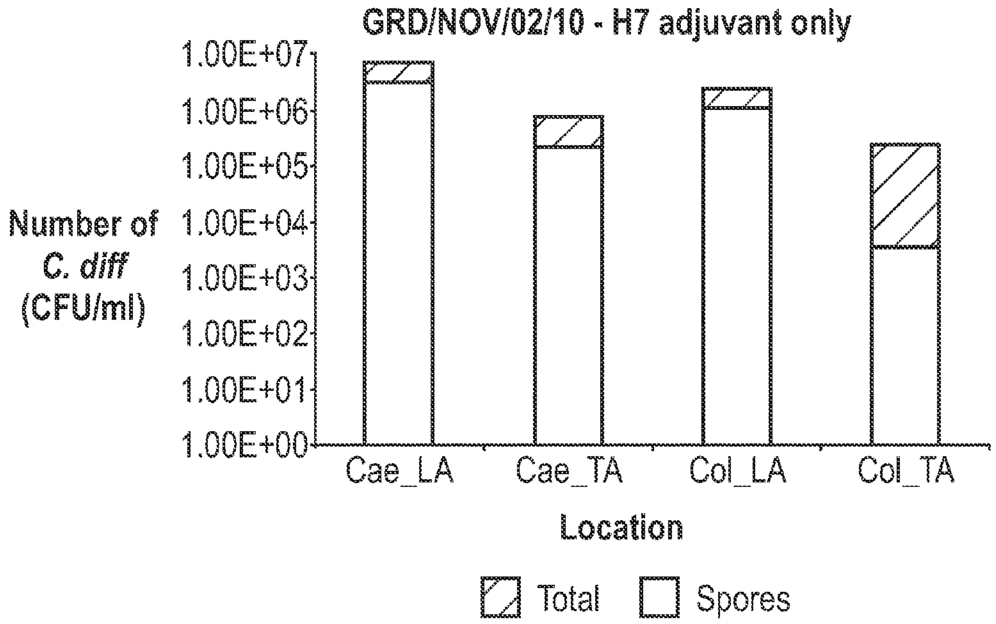
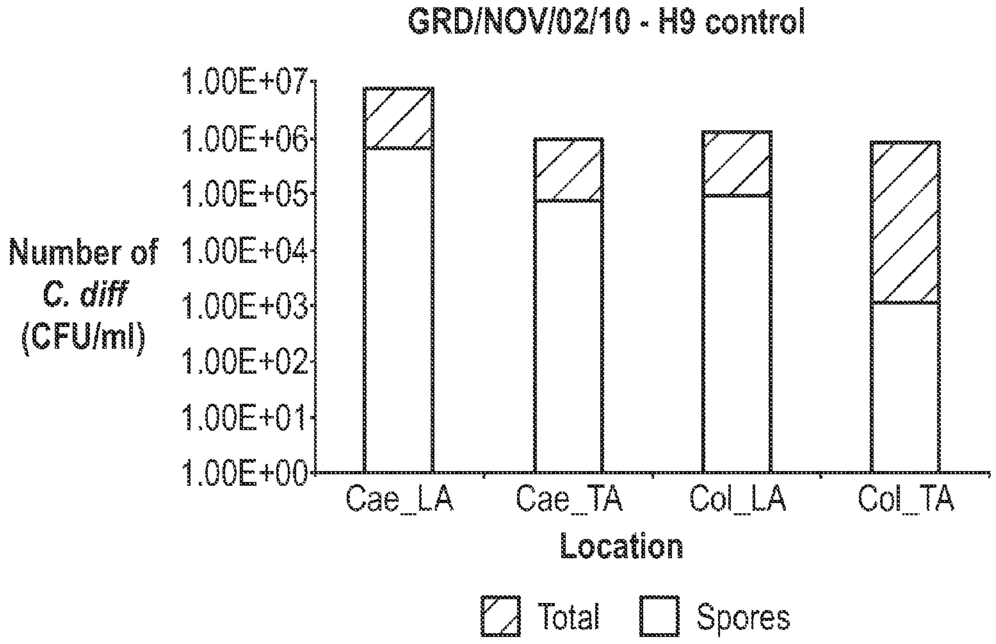
*FIG. 17(contd)*

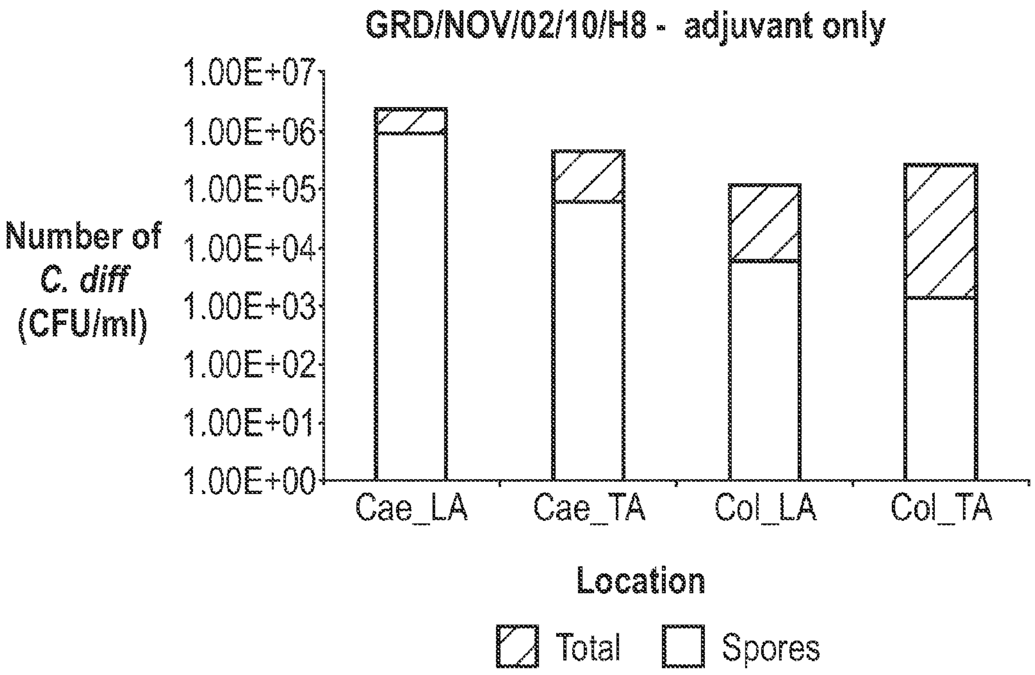
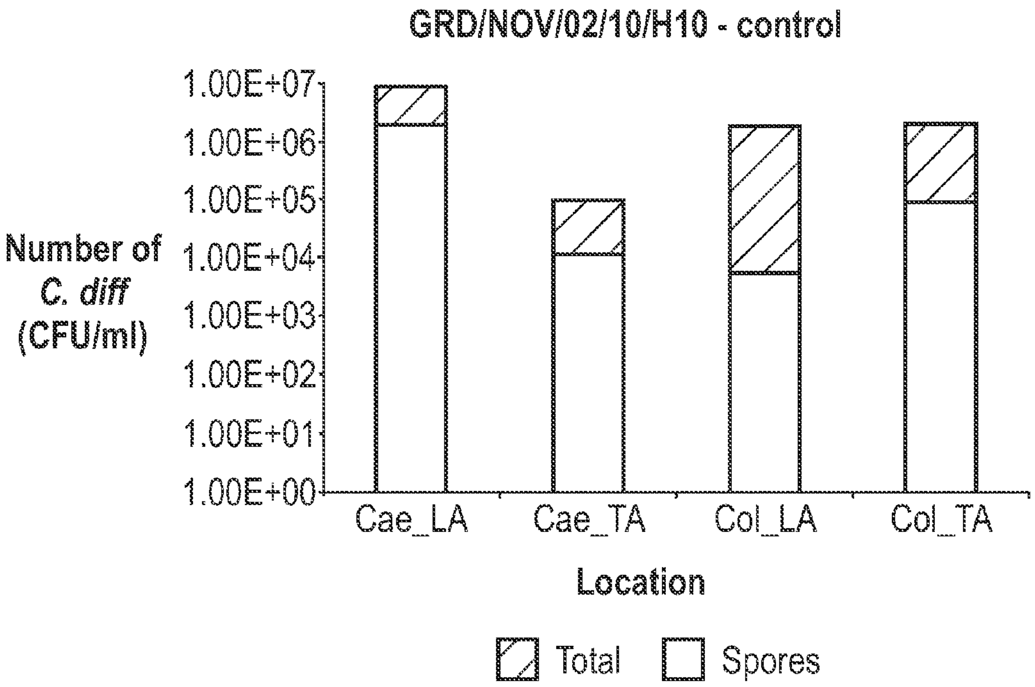
*FIG. 17(contd)*

*FIG. 18(contd)*
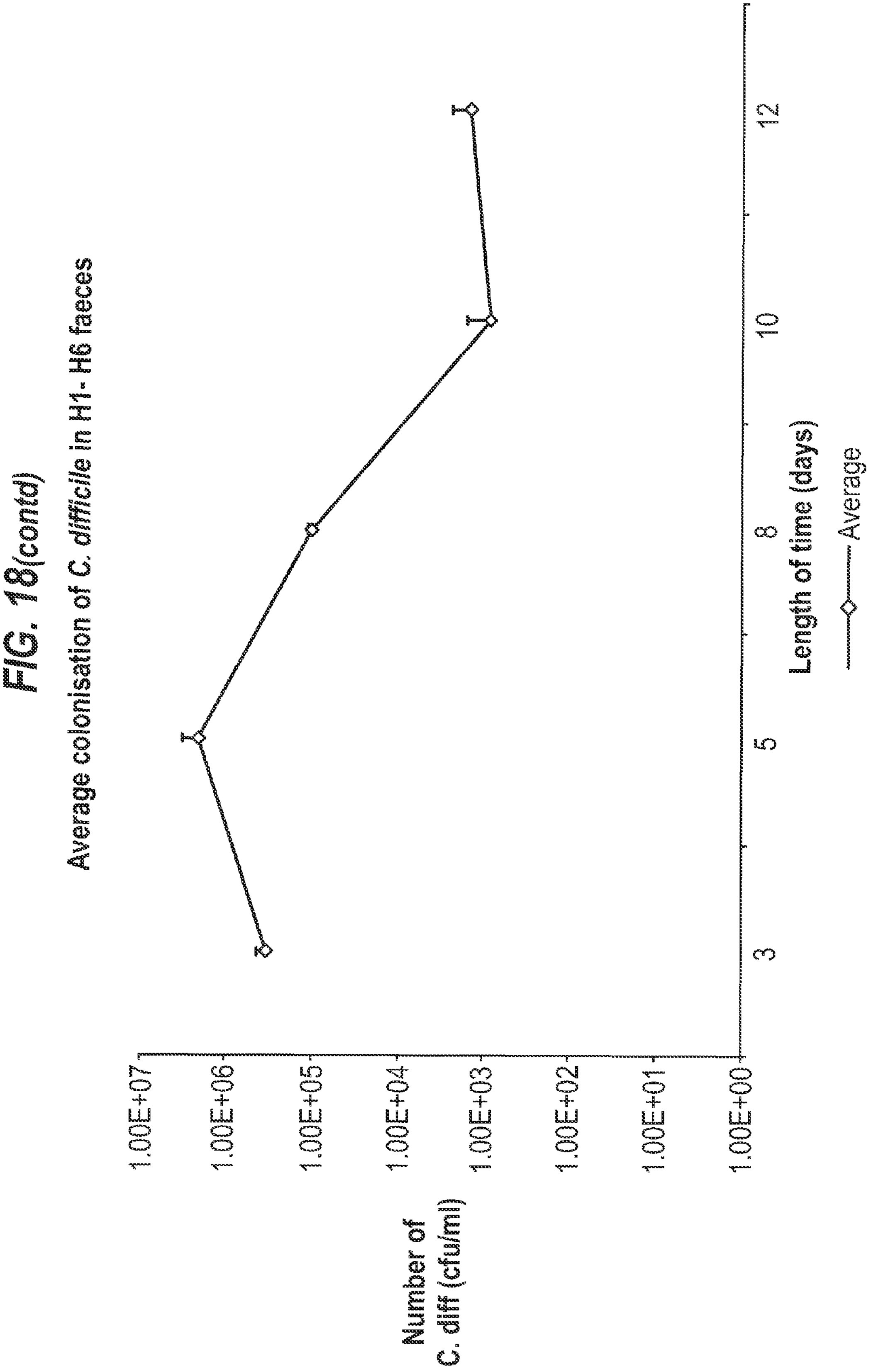

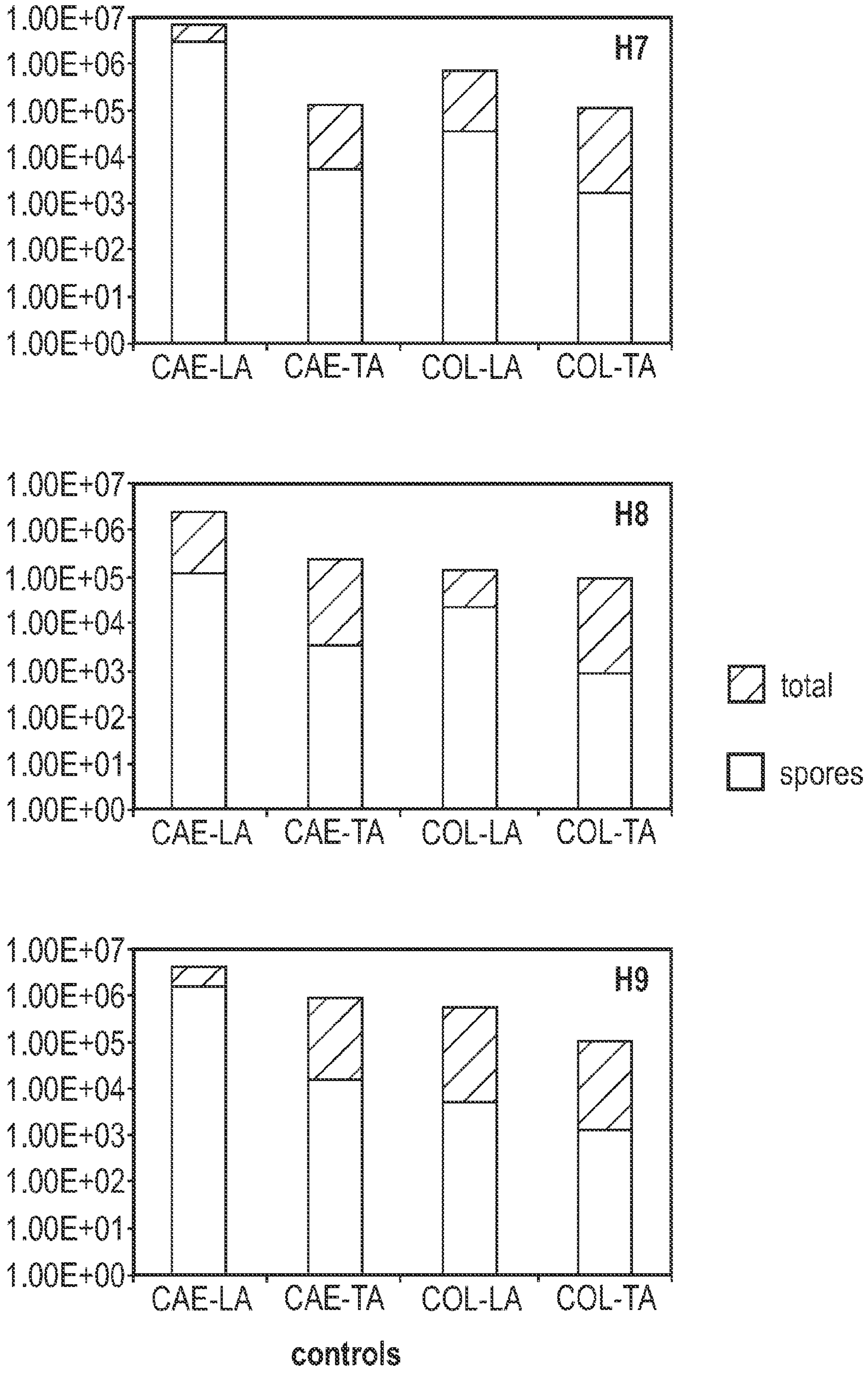
FIG. 19(contd)

Shedding of *C. difficile* spores from vaccinated animals

FIG. 21(contd)
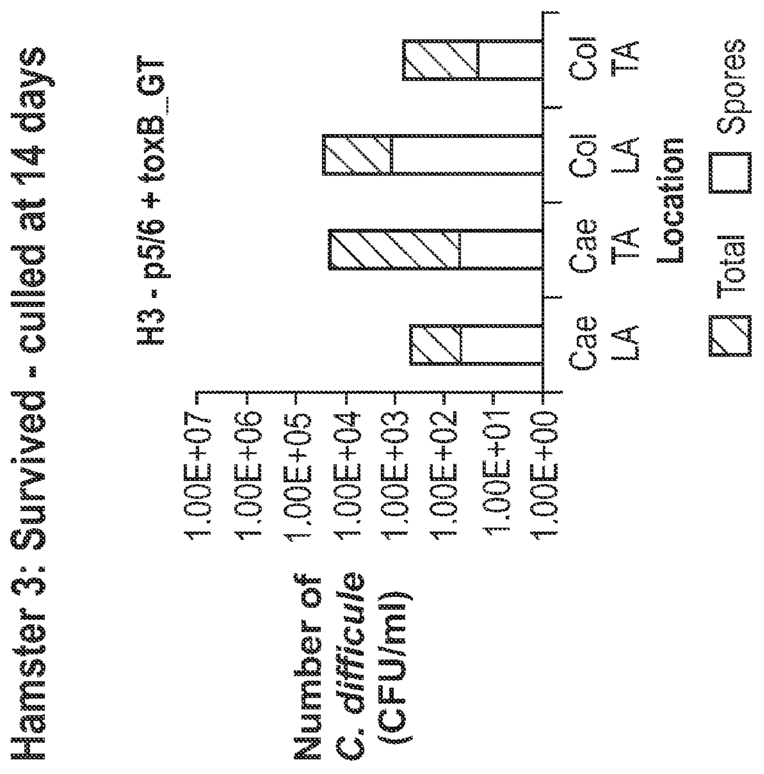
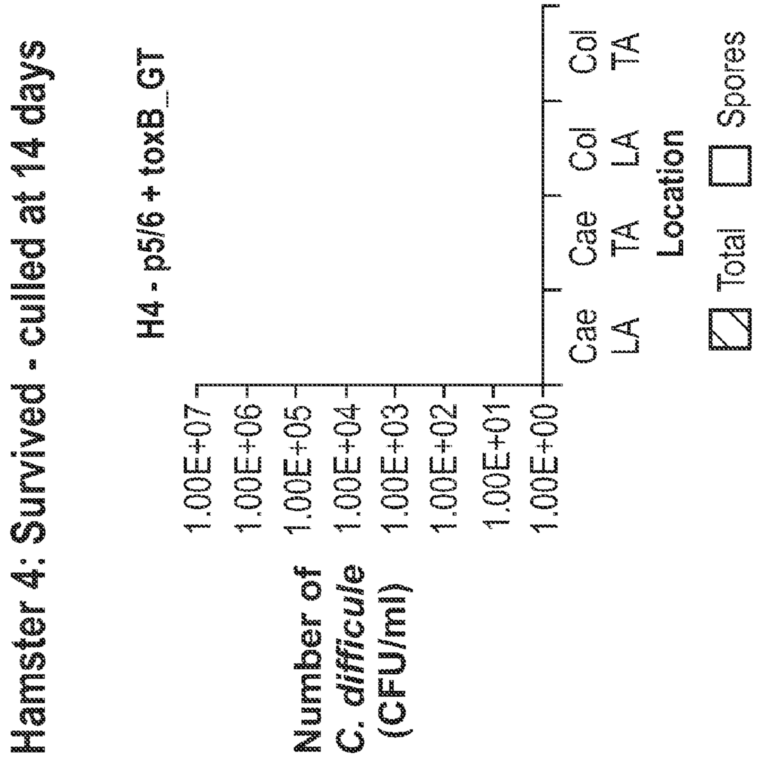

FIG. 21(contd)
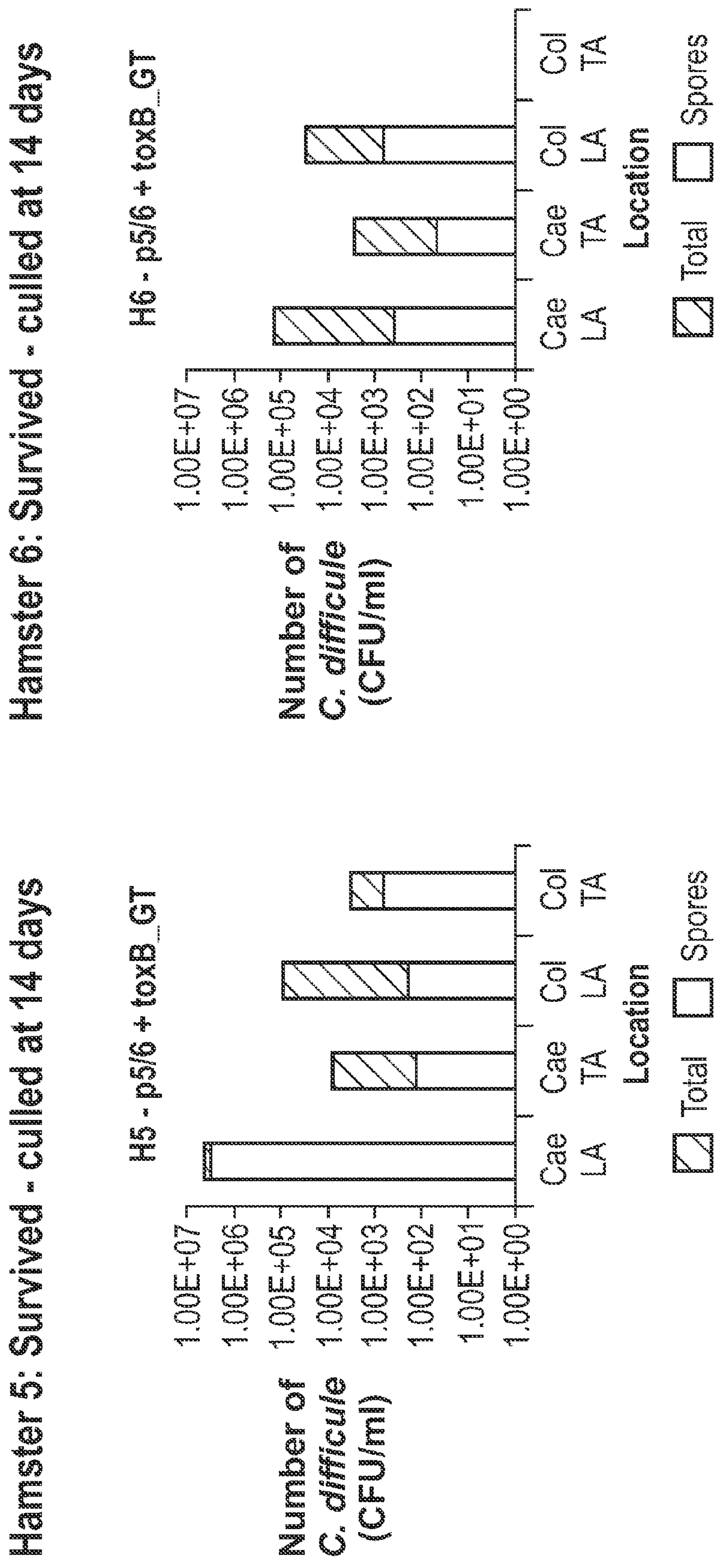

FIG. 21(contd)
Hamster 7. Time to >35°C - 37h 21m:
Time to cull - 37h 36m. Temp at cull 34.47°C
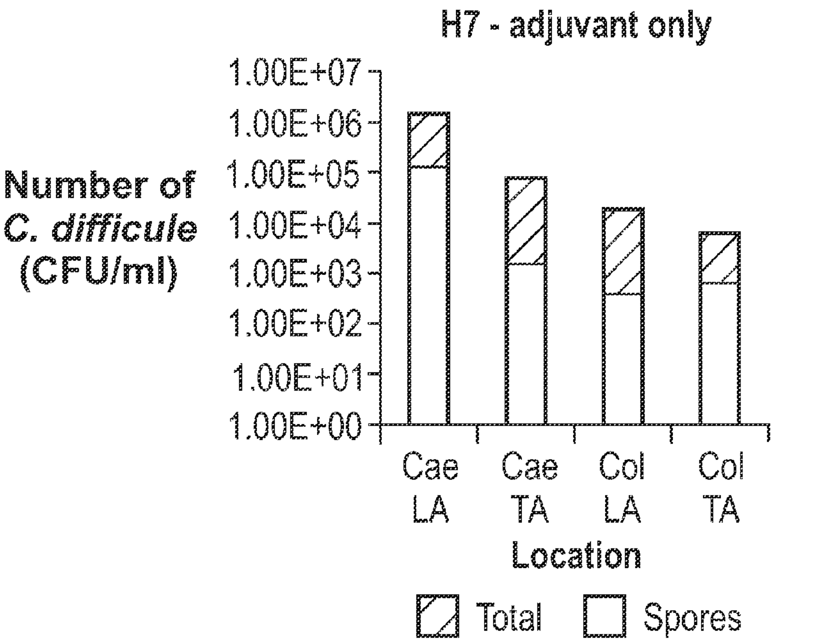
Hamster 8. Time to >35°C - 30h 01m:
Time to cull - 30h 56m. Temp at cull 30.55°C
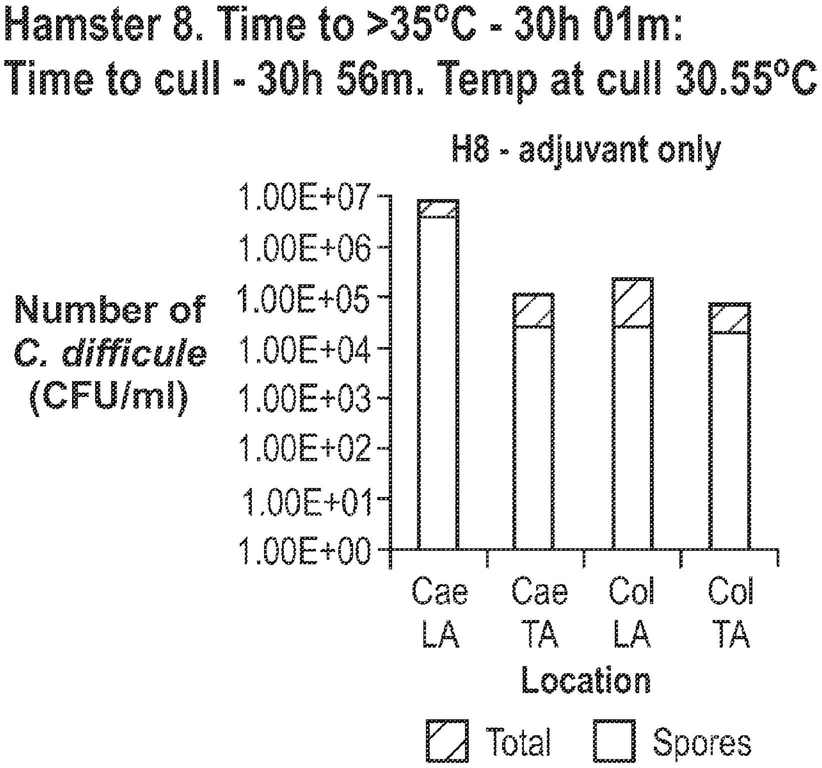

FIG. 22(contd)
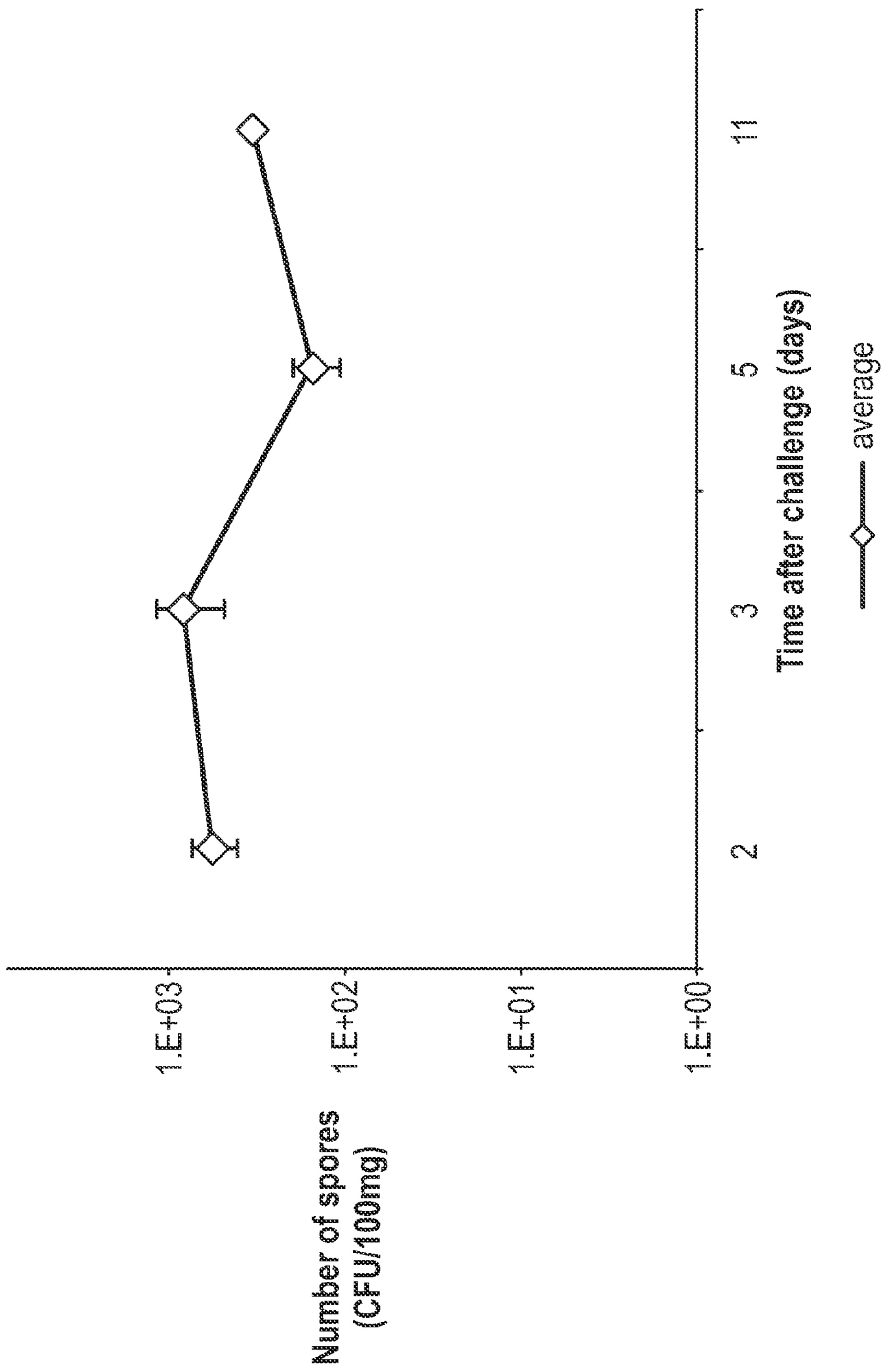

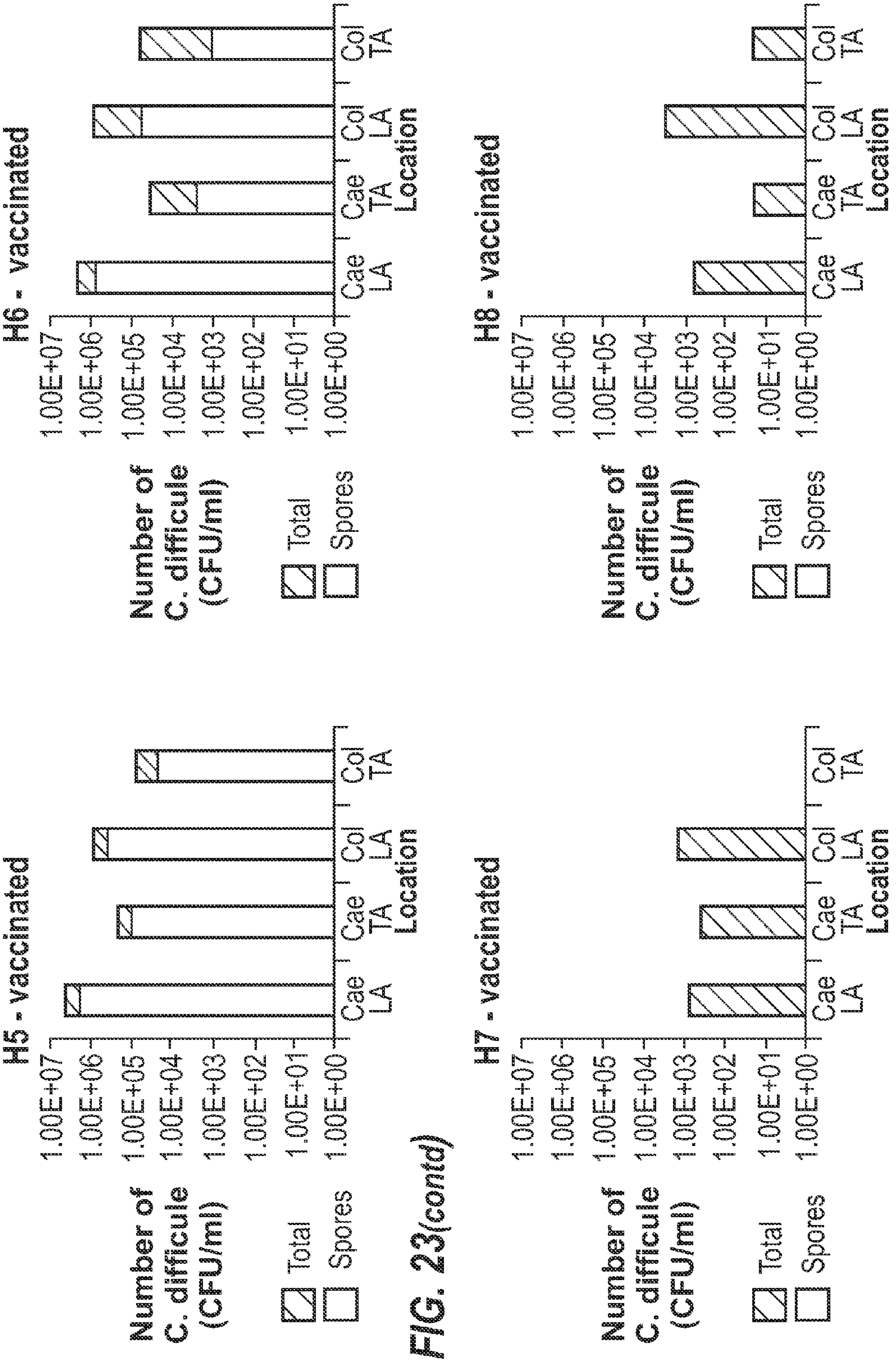
FIG. 23(contd)

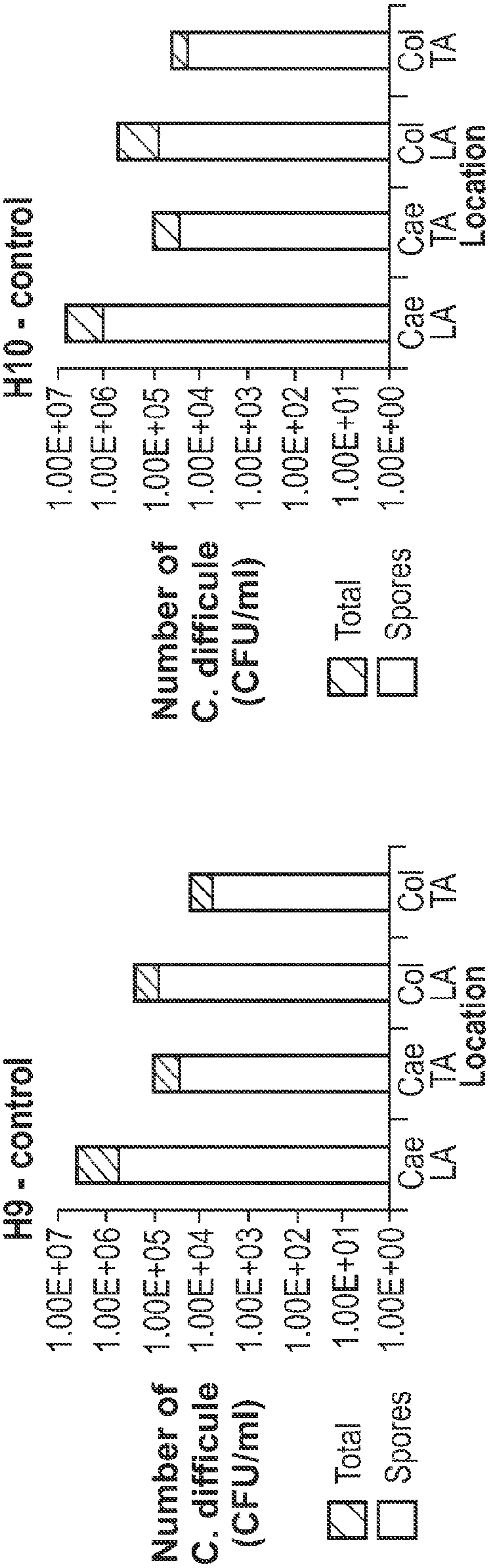
*FIG. 23(contd)*

FIG. 26(a)(contd)
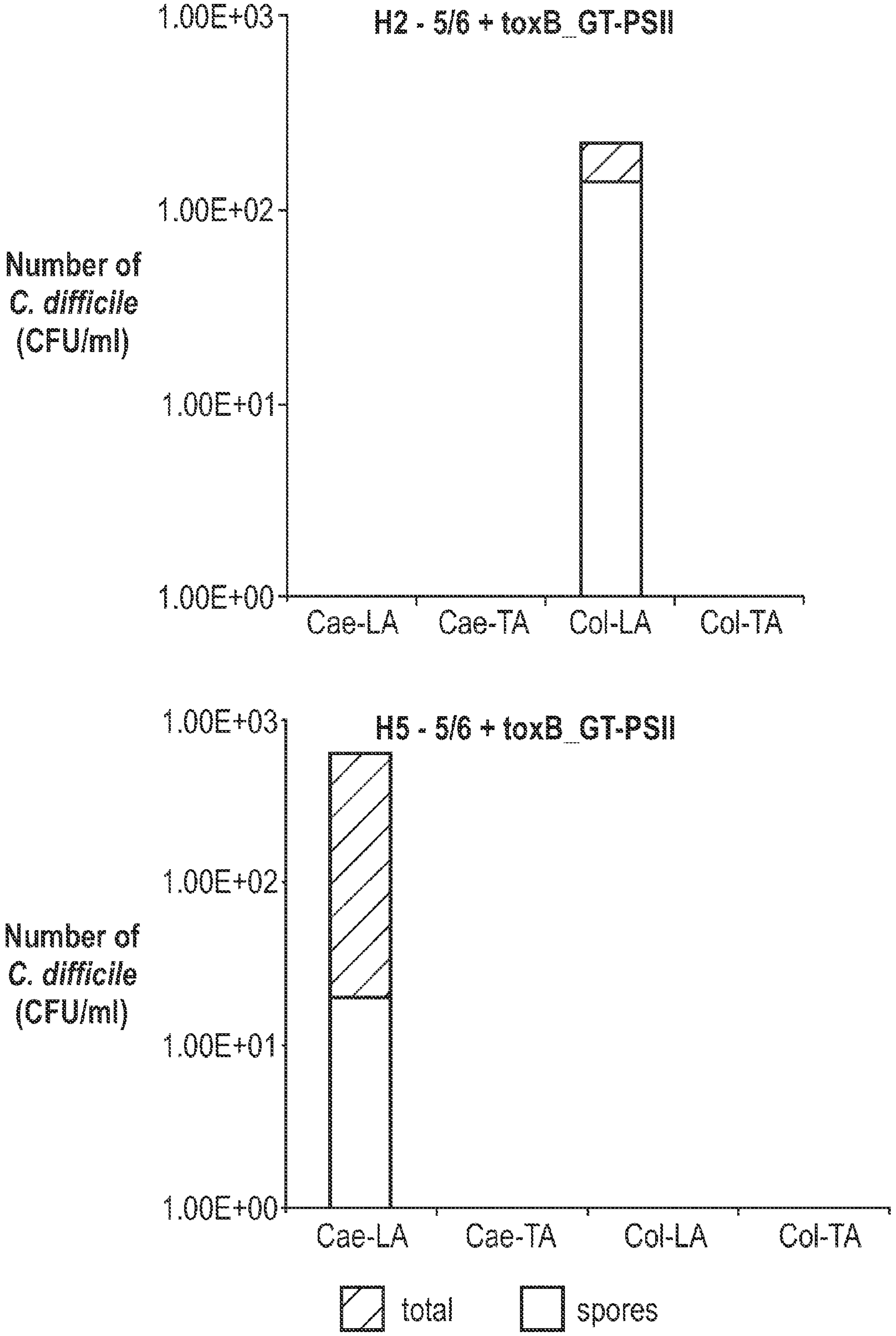

FIG. 26(a)(contd)
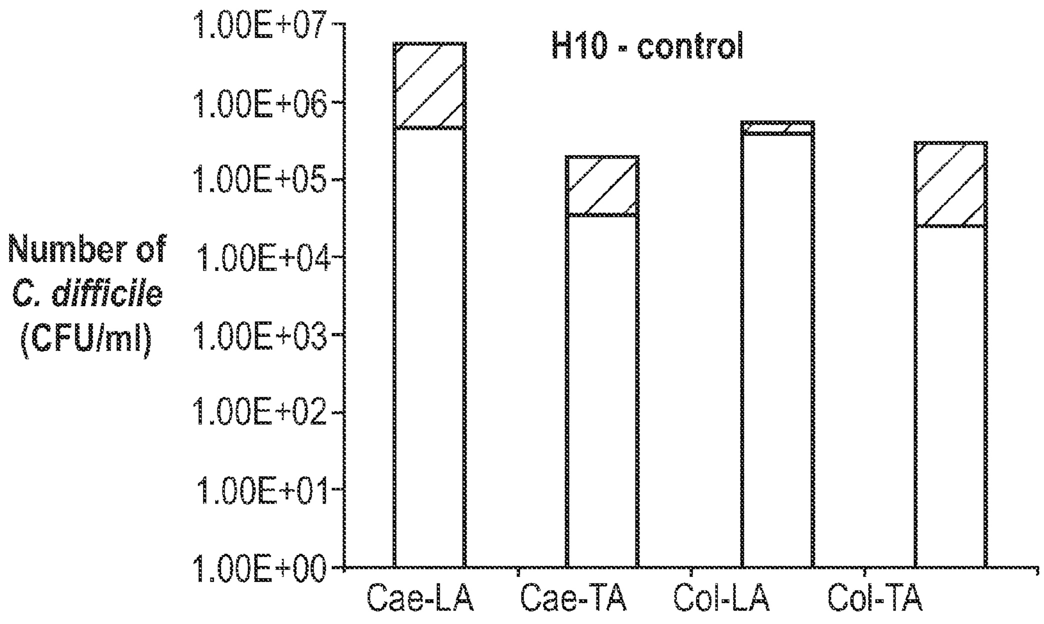
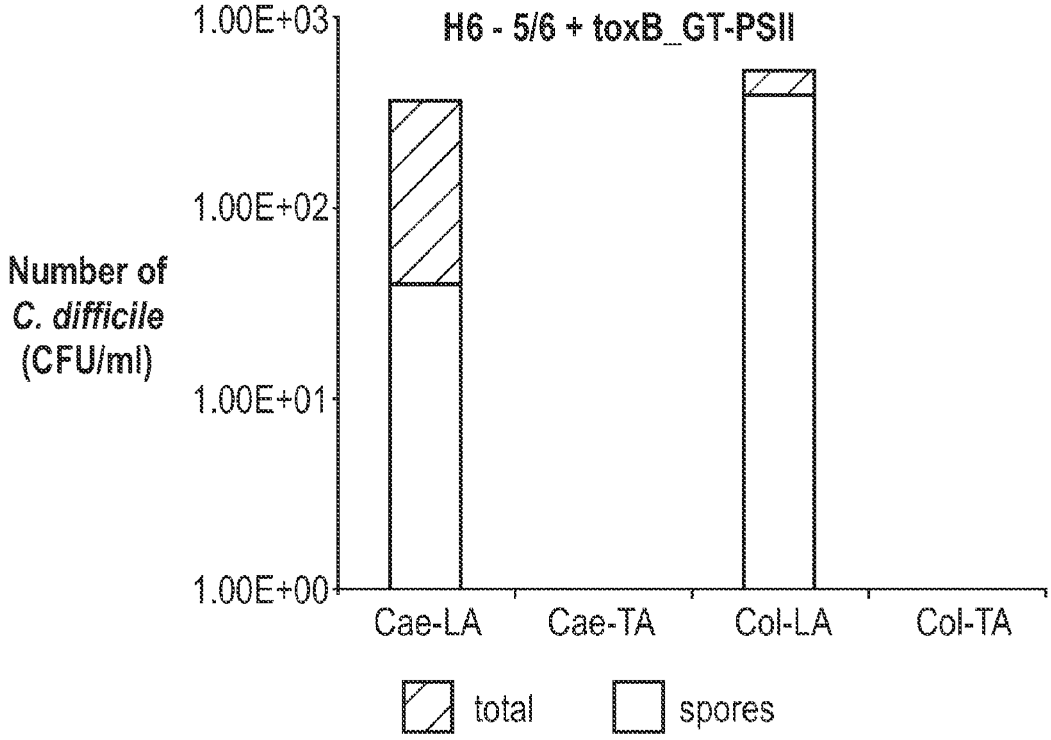

Hamster 7, Survived -
Culled at 14 days

Hamster 9 Control. Time to <35°C: 33h 37m:
temp at cull: 20.0°C

FIG. 26(b)(contd)
Hamster 8, Survived - Culled at 14 days
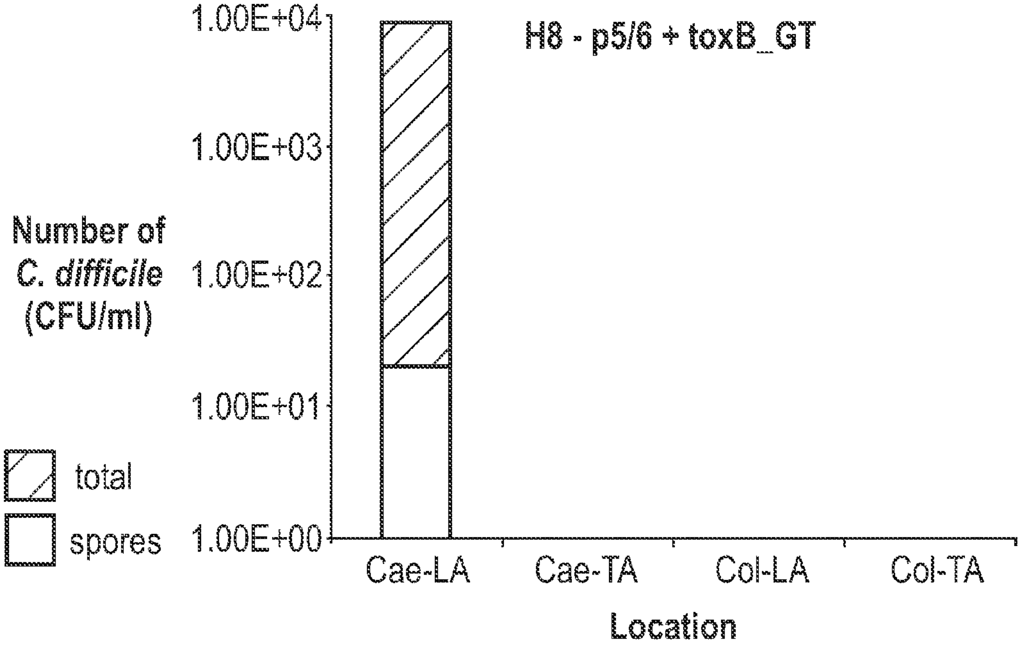
Hamster 10 Control. Time to <35°C: 54h 26m: temp at cull: 29.88°C
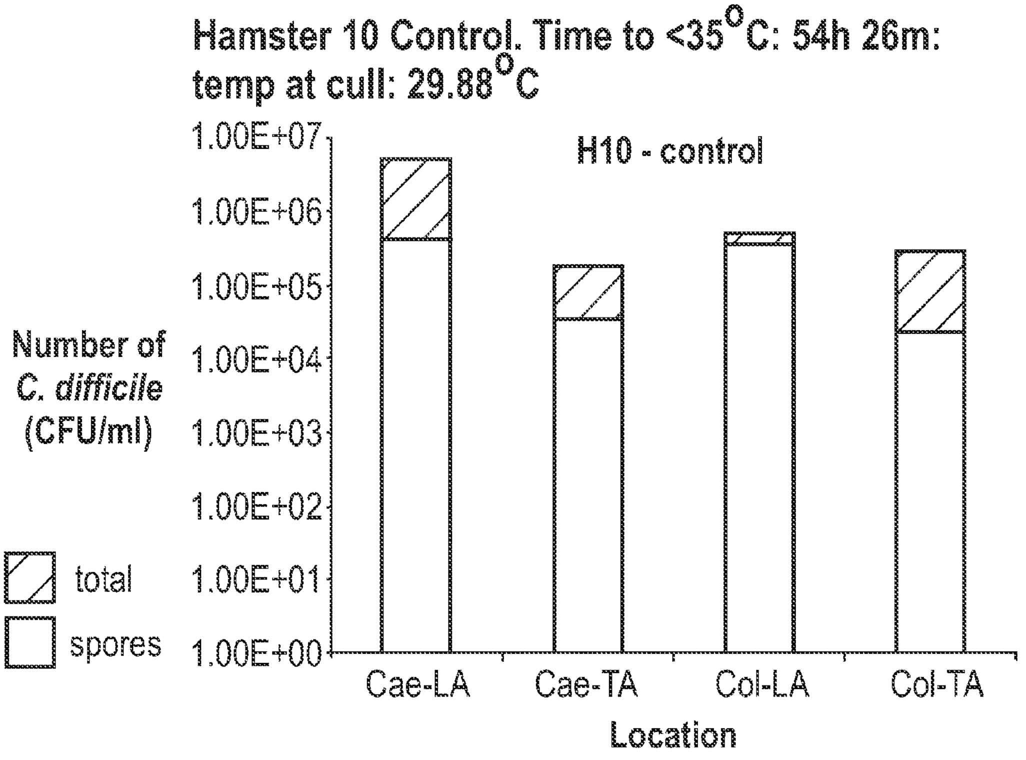

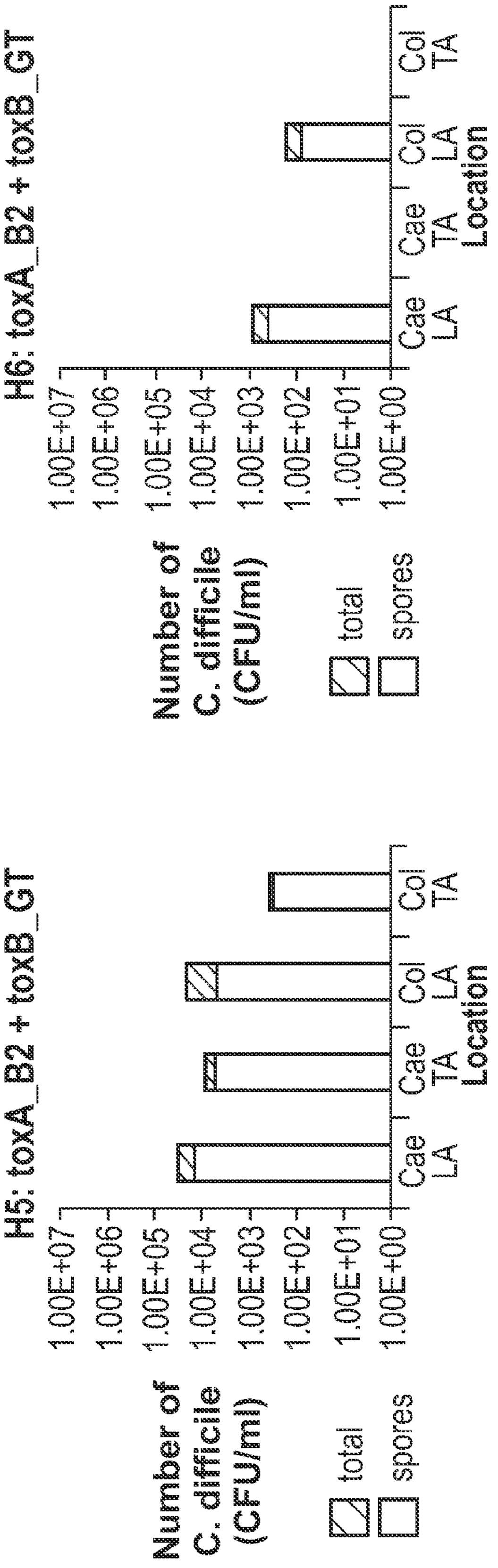
*FIG. 28(a)(contd)*

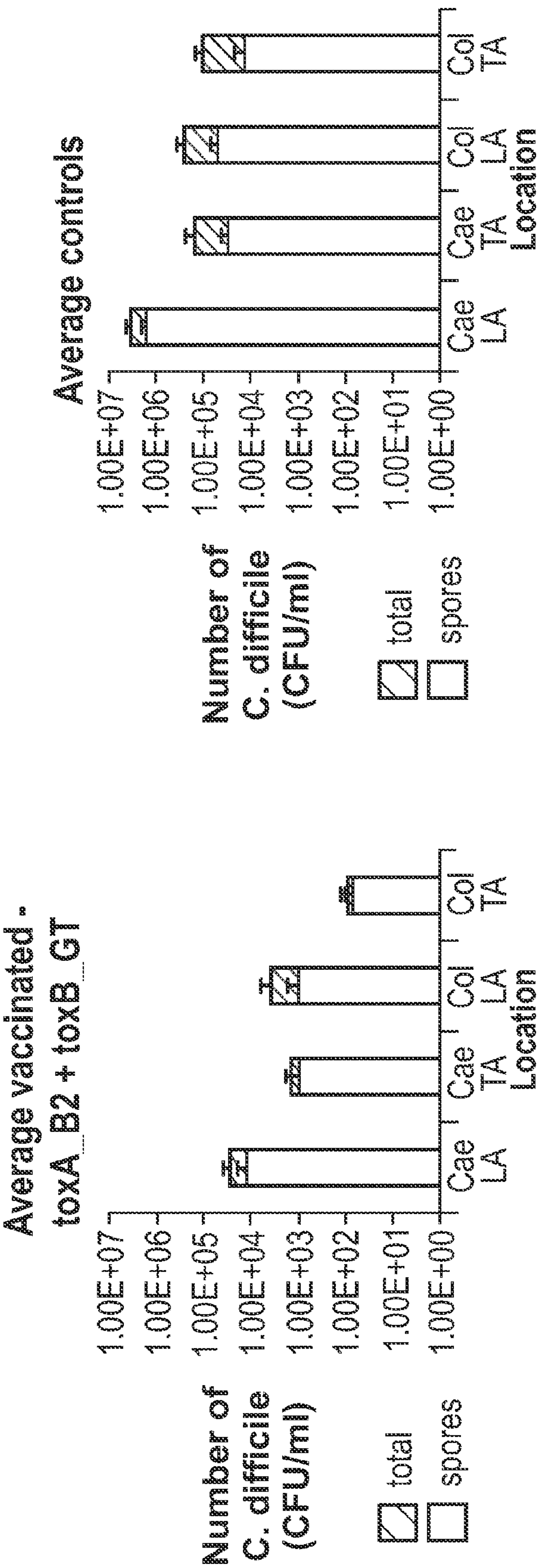
FIG. 28(b)(contd)

FIG. 30(contd)
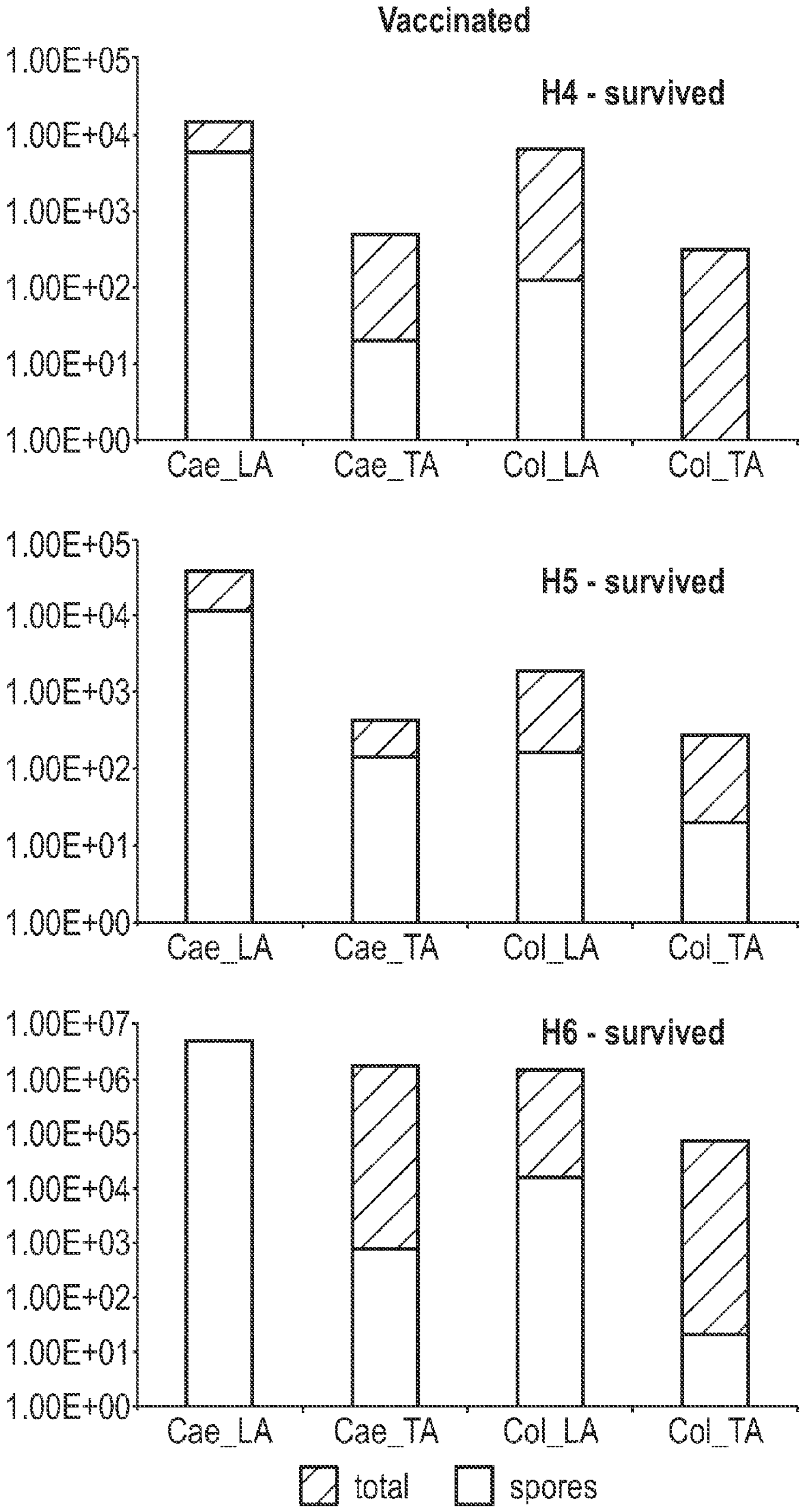

FIG. 30(contd)
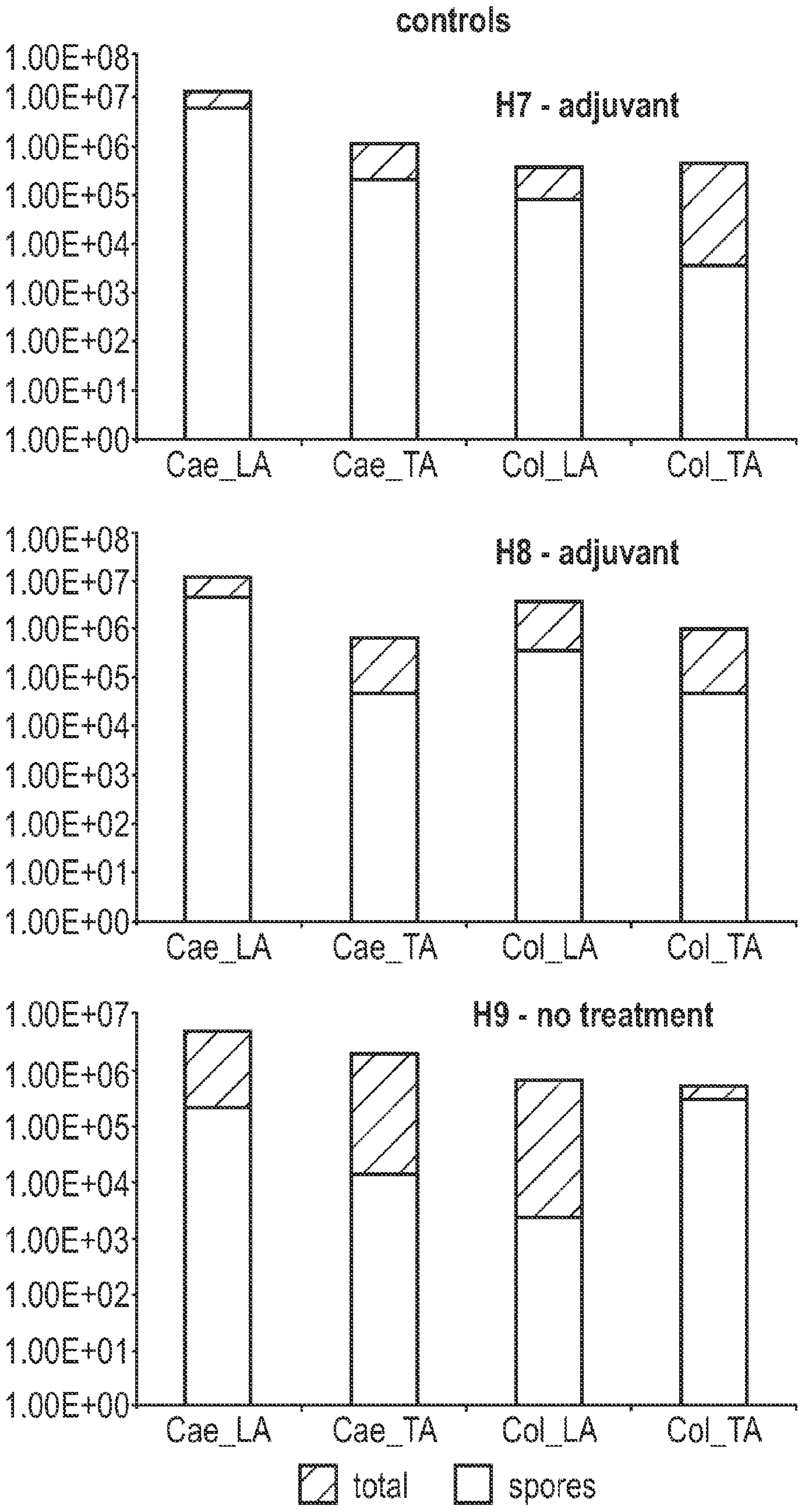

*FIG. 32(contd)*
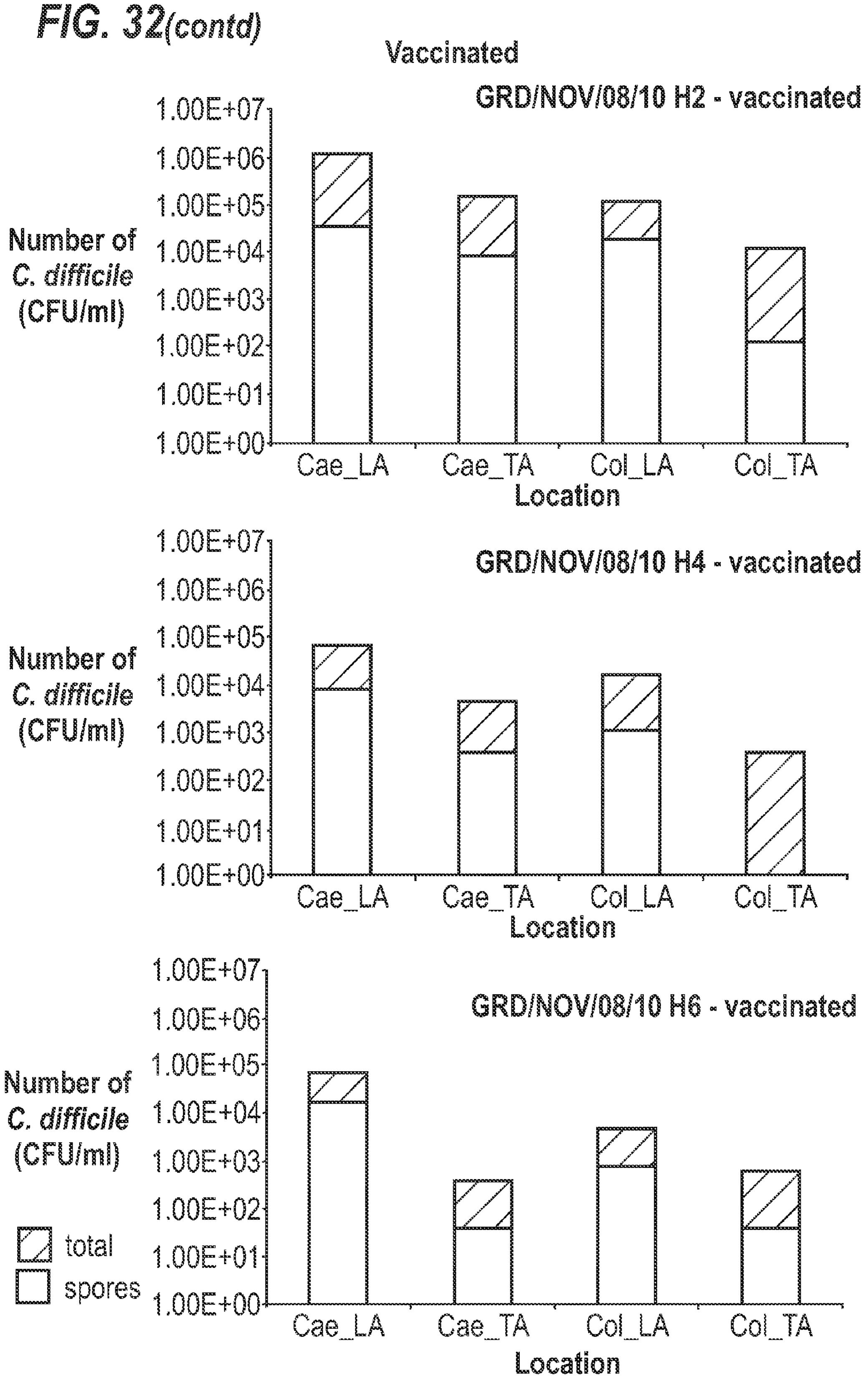

FIG. 32(contd)
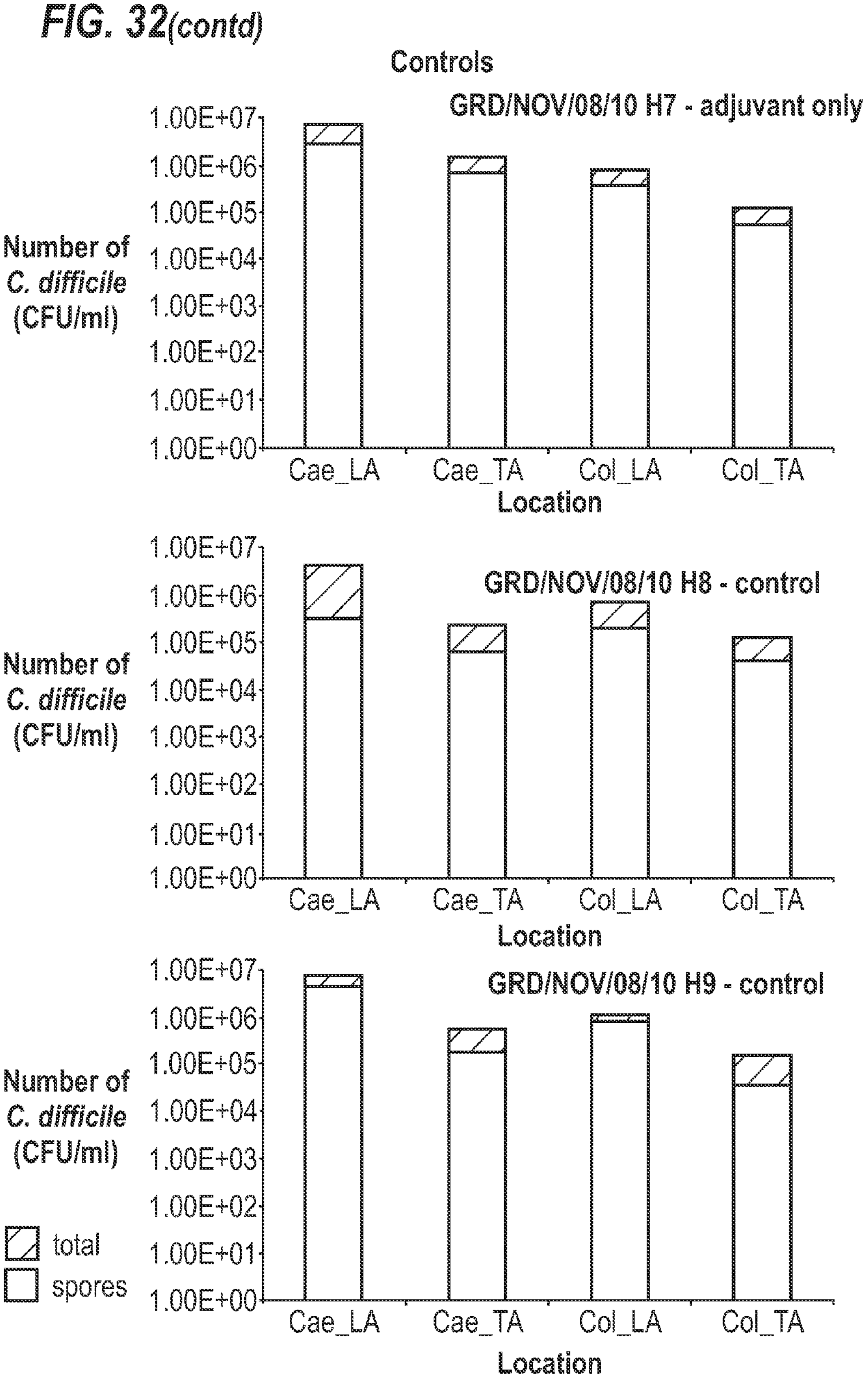

*FIG. 34(contd)*
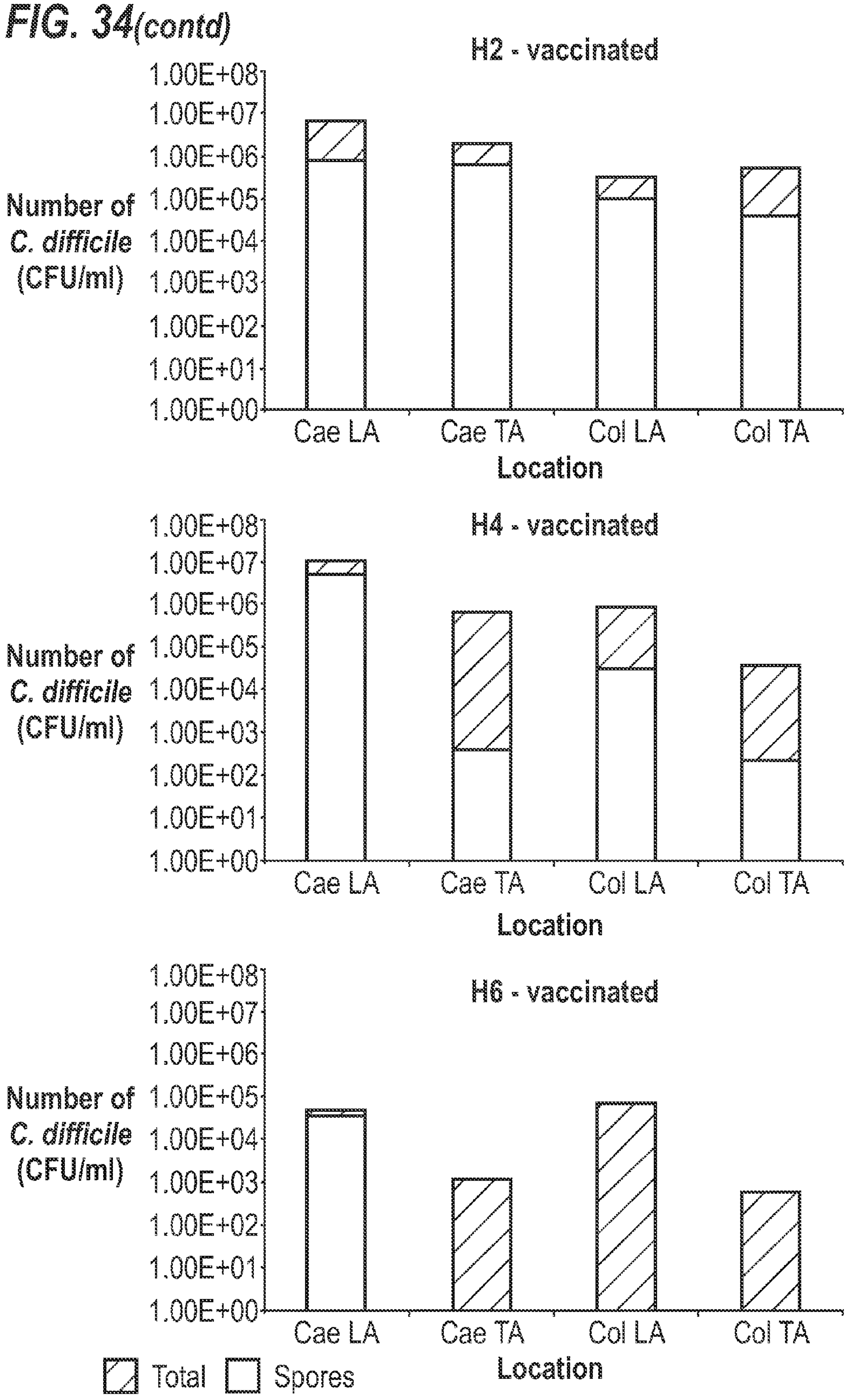

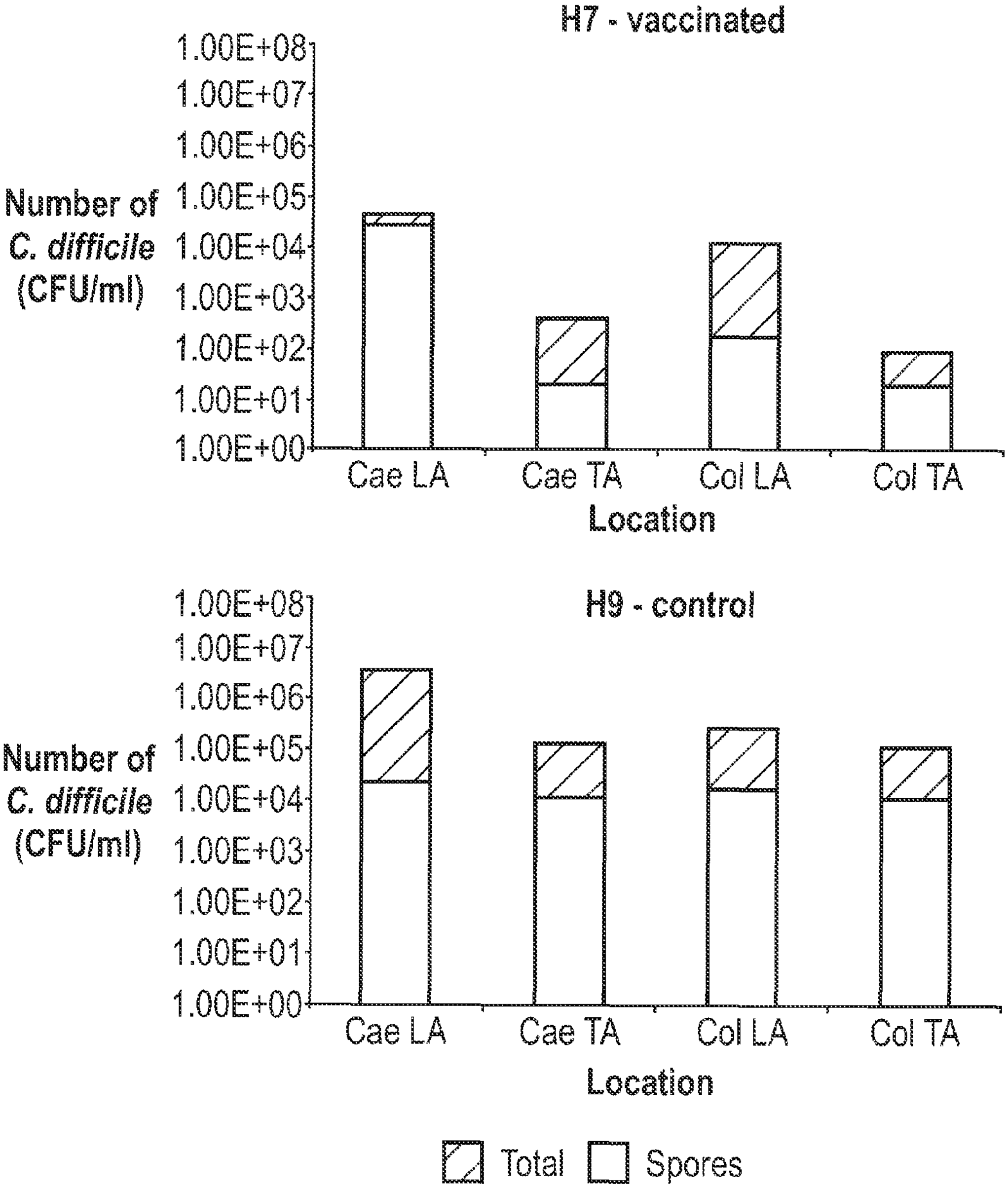
*FIG. 34(contd)*

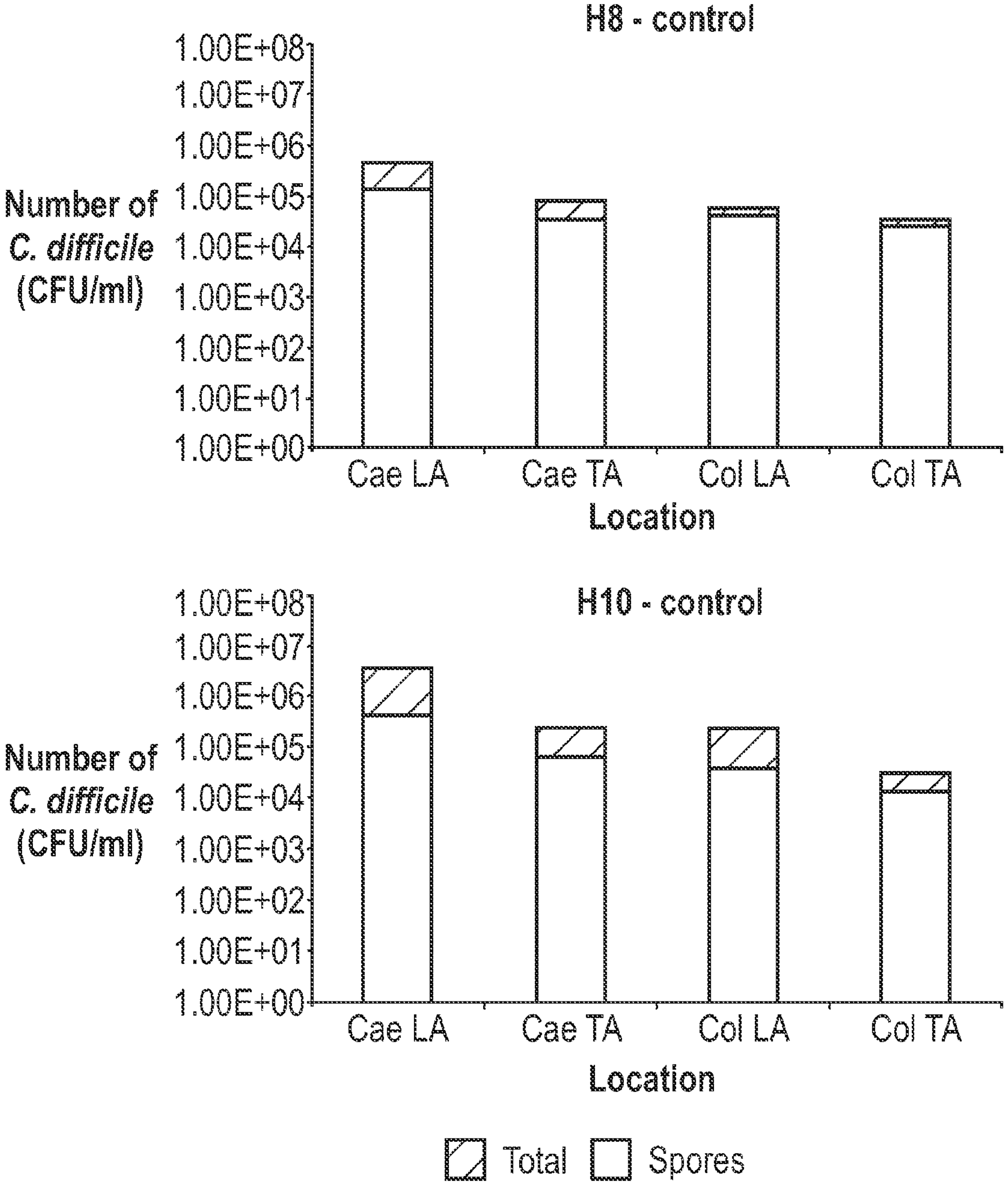
*FIG. 34(contd)*

SEQUENCE LISTING

<160> NUMBER OF SEQ ID NOS: 112

<210> SEQ ID NO 1
<211> LENGTH: 2710
<212> TYPE: PRT
<213> ORGANISM: Clostridium difficile

<400> SEQUENCE: 1

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

```
Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala Ile Met Ser Asp Leu Ser Ser Lys Glu Tyr Ile Phe Phe Asp Ser
    770                 775                 780

Ile Asp Asn Lys Leu Lys Ala Lys Ser Lys Asn Ile Pro Gly Leu Ala
```

-continued

```
785                 790                 795                 800

Ser Ile Ser Glu Asp Ile Lys Thr Leu Leu Leu Asp Ala Ser Val Ser
                805                 810                 815

Pro Asp Thr Lys Phe Ile Leu Asn Asn Leu Lys Leu Asn Ile Glu Ser
            820                 825                 830

Ser Ile Gly Asp Tyr Ile Tyr Tyr Glu Lys Leu Glu Pro Val Lys Asn
        835                 840                 845

Ile Ile His Asn Ser Ile Asp Asp Leu Ile Asp Glu Phe Asn Leu Leu
    850                 855                 860

Glu Asn Val Ser Asp Glu Leu Tyr Glu Leu Lys Lys Leu Asn Asn Leu
865                 870                 875                 880

Asp Glu Lys Tyr Leu Ile Ser Phe Glu Asp Ile Ser Lys Asn Asn Ser
                885                 890                 895

Thr Tyr Ser Val Arg Phe Ile Asn Lys Ser Asn Gly Glu Ser Val Tyr
            900                 905                 910

Val Glu Thr Glu Lys Glu Ile Phe Ser Lys Tyr Ser Glu His Ile Thr
        915                 920                 925

Lys Glu Ile Ser Thr Ile Lys Asn Ser Ile Ile Thr Asp Val Asn Gly
    930                 935                 940

Asn Leu Leu Asp Asn Ile Gln Leu Asp His Thr Ser Gln Val Asn Thr
945                 950                 955                 960

Leu Asn Ala Ala Phe Phe Ile Gln Ser Leu Ile Asp Tyr Ser Ser Asn
                965                 970                 975

Lys Asp Val Leu Asn Asp Leu Ser Thr Ser Val Lys Val Gln Leu Tyr
            980                 985                 990

Ala Gln Leu Phe Ser Thr Gly Leu  Asn Thr Ile Tyr Asp  Ser Ile Gln
        995                 1000                1005

Leu Val  Asn Leu Ile Ser Asn  Ala Val Asn Asp Thr  Ile Asn Val
    1010                 1015                1020

Leu Pro  Thr Ile Thr Glu Gly  Ile Pro Ile Val Ser  Thr Ile Leu
    1025                 1030                1035

Asp Gly  Ile Asn Leu Gly Ala  Ala Ile Lys Glu Leu  Leu Asp Glu
    1040                 1045                1050

His Asp  Pro Leu Leu Lys Lys  Glu Leu Glu Ala Lys  Val Gly Val
    1055                 1060                1065

Leu Ala  Ile Asn Met Ser Leu  Ser Ile Ala Ala Thr  Val Ala Ser
    1070                 1075                1080

Ile Val  Gly Ile Gly Ala Glu  Val Thr Ile Phe Leu  Leu Pro Ile
    1085                 1090                1095

Ala Gly  Ile Ser Ala Gly Ile  Pro Ser Leu Val Asn  Asn Glu Leu
    1100                 1105                1110

Ile Leu  His Asp Lys Ala Thr  Ser Val Val Asn Tyr  Phe Asn His
    1115                 1120                1125

Leu Ser  Glu Ser Lys Lys Tyr  Gly Pro Leu Lys Thr  Glu Asp Asp
    1130                 1135                1140

Lys Ile  Leu Val Pro Ile Asp  Asp Leu Val Ile Ser  Glu Ile Asp
    1145                 1150                1155

Phe Asn  Asn Asn Ser Ile Lys  Leu Gly Thr Cys Asn  Ile Leu Ala
    1160                 1165                1170

Met Glu  Gly Gly Ser Gly His  Thr Val Thr Gly Asn  Ile Asp His
    1175                 1180                1185

Phe Phe  Ser Ser Pro Ser Ile  Ser Ser His Ile Pro  Ser Leu Ser
    1190                 1195                1200
```

```
Ile Tyr  Ser Ala Ile Gly Ile  Glu Thr Glu Asn Leu  Asp Phe Ser
    1205                 1210                 1215

Lys Lys  Ile Met Met Leu Pro  Asn Ala Pro Ser Arg  Val Phe Trp
    1220                 1225                 1230

Trp Glu  Thr Gly Ala Val Pro  Gly Leu Arg Ser Leu  Glu Asn Asp
    1235                 1240                 1245

Gly Thr  Arg Leu Leu Asp Ser  Ile Arg Asp Leu Tyr  Pro Gly Lys
    1250                 1255                 1260

Phe Tyr  Trp Arg Phe Tyr Ala  Phe Phe Asp Tyr Ala  Ile Thr Thr
    1265                 1270                 1275

Leu Lys  Pro Val Tyr Glu Asp  Thr Asn Ile Lys Ile  Lys Leu Asp
    1280                 1285                 1290

Lys Asp  Thr Arg Asn Phe Ile  Met Pro Thr Ile Thr  Thr Asn Glu
    1295                 1300                 1305

Ile Arg  Asn Lys Leu Ser Tyr  Ser Phe Asp Gly Ala  Gly Gly Thr
    1310                 1315                 1320

Tyr Ser  Leu Leu Leu Ser Ser  Tyr Pro Ile Ser Thr  Asn Ile Asn
    1325                 1330                 1335

Leu Ser  Lys Asp Asp Leu Trp  Ile Phe Asn Ile Asp  Asn Glu Val
    1340                 1345                 1350

Arg Glu  Ile Ser Ile Glu Asn  Gly Thr Ile Lys Lys  Gly Lys Leu
    1355                 1360                 1365

Ile Lys  Asp Val Leu Ser Lys  Ile Asp Ile Asn Lys  Asn Lys Leu
    1370                 1375                 1380

Ile Ile  Gly Asn Gln Thr Ile  Asp Phe Ser Gly Asp  Ile Asp Asn
    1385                 1390                 1395

Lys Asp  Arg Tyr Ile Phe Leu  Thr Cys Glu Leu Asp  Asp Lys Ile
    1400                 1405                 1410

Ser Leu  Ile Ile Glu Ile Asn  Leu Val Ala Lys Ser  Tyr Ser Leu
    1415                 1420                 1425

Leu Leu  Ser Gly Asp Lys Asn  Tyr Leu Ile Ser Asn  Leu Ser Asn
    1430                 1435                 1440

Ile Ile  Glu Lys Ile Asn Thr  Leu Gly Leu Asp Ser  Lys Asn Ile
    1445                 1450                 1455

Ala Tyr  Asn Tyr Thr Asp Glu  Ser Asn Asn Lys Tyr  Phe Gly Ala
    1460                 1465                 1470

Ile Ser  Lys Thr Ser Gln Lys  Ser Ile Ile His Tyr  Lys Lys Asp
    1475                 1480                 1485

Ser Lys  Asn Ile Leu Glu Phe  Tyr Asn Asp Ser Thr  Leu Glu Phe
    1490                 1495                 1500

Asn Ser  Lys Asp Phe Ile Ala  Glu Asp Ile Asn Val  Phe Met Lys
    1505                 1510                 1515

Asp Asp  Ile Asn Thr Ile Thr  Gly Lys Tyr Tyr Val  Asp Asn Asn
    1520                 1525                 1530

Thr Asp  Lys Ser Ile Asp Phe  Ser Ile Ser Leu Val  Ser Lys Asn
    1535                 1540                 1545

Gln Val  Lys Val Asn Gly Leu  Tyr Leu Asn Glu Ser  Val Tyr Ser
    1550                 1555                 1560

Ser Tyr  Leu Asp Phe Val Lys  Asn Ser Asp Gly His  His Asn Thr
    1565                 1570                 1575

Ser Asn  Phe Met Asn Leu Phe  Leu Asp Asn Ile Ser  Phe Trp Lys
    1580                 1585                 1590
```

```
Leu Phe  Gly Phe Glu Asn Ile  Asn Phe Val Ile Asp  Lys Tyr Phe
    1595                 1600                 1605

Thr Leu  Val Gly Lys Thr Asn  Leu Gly Tyr Val Glu  Phe Ile Cys
    1610                 1615                 1620

Asp Asn  Asn Lys Asn Ile Asp  Ile Tyr Phe Gly Glu  Trp Lys Thr
    1625                 1630                 1635

Ser Ser  Ser Lys Ser Thr Ile  Phe Ser Gly Asn Gly  Arg Asn Val
    1640                 1645                 1650

Val Val  Glu Pro Ile Tyr Asn  Pro Asp Thr Gly Glu  Asp Ile Ser
    1655                 1660                 1665

Thr Ser  Leu Asp Phe Ser Tyr  Glu Pro Leu Tyr Gly  Ile Asp Arg
    1670                 1675                 1680

Tyr Ile  Asn Lys Val Leu Ile  Ala Pro Asp Leu Tyr  Thr Ser Leu
    1685                 1690                 1695

Ile Asn  Ile Asn Thr Asn Tyr  Tyr Ser Asn Glu Tyr  Tyr Pro Glu
    1700                 1705                 1710

Ile Ile  Val Leu Asn Pro Asn  Thr Phe His Lys Lys  Val Asn Ile
    1715                 1720                 1725

Asn Leu  Asp Ser Ser Ser Phe  Glu Tyr Lys Trp Ser  Thr Glu Gly
    1730                 1735                 1740

Ser Asp  Phe Ile Leu Val Arg  Tyr Leu Glu Glu Ser  Asn Lys Lys
    1745                 1750                 1755

Ile Leu  Gln Lys Ile Arg Ile  Lys Gly Ile Leu Ser  Asn Thr Gln
    1760                 1765                 1770

Ser Phe  Asn Lys Met Ser Ile  Asp Phe Lys Asp Ile  Lys Lys Leu
    1775                 1780                 1785

Ser Leu  Gly Tyr Ile Met Ser  Asn Phe Lys Ser Phe  Asn Ser Glu
    1790                 1795                 1800

Asn Glu  Leu Asp Arg Asp His  Leu Gly Phe Lys Ile  Ile Asp Asn
    1805                 1810                 1815

Lys Thr  Tyr Tyr Tyr Asp Glu  Asp Ser Lys Leu Val  Lys Gly Leu
    1820                 1825                 1830

Ile Asn  Ile Asn Asn Ser Leu  Phe Tyr Phe Asp Pro  Ile Glu Phe
    1835                 1840                 1845

Asn Leu  Val Thr Gly Trp Gln  Thr Ile Asn Gly Lys  Lys Tyr Tyr
    1850                 1855                 1860

Phe Asp  Ile Asn Thr Gly Ala  Ala Leu Ile Ser Tyr  Lys Ile Ile
    1865                 1870                 1875

Asn Gly  Lys His Phe Tyr Phe  Asn Asn Asp Gly Val  Met Gln Leu
    1880                 1885                 1890

Gly Val  Phe Lys Gly Pro Asp  Gly Phe Glu Tyr Phe  Ala Pro Ala
    1895                 1900                 1905

Asn Thr  Gln Asn Asn Asn Ile  Glu Gly Gln Ala Ile  Val Tyr Gln
    1910                 1915                 1920

Ser Lys  Phe Leu Thr Leu Asn  Gly Lys Lys Tyr Tyr  Phe Asp Asn
    1925                 1930                 1935

Asp Ser  Lys Ala Val Thr Gly  Trp Arg Ile Ile Asn  Asn Glu Lys
    1940                 1945                 1950

Tyr Tyr  Phe Asn Pro Asn Asn  Ala Ile Ala Ala Val  Gly Leu Gln
    1955                 1960                 1965

Val Ile  Asp Asn Asn Lys Tyr  Tyr Phe Asn Pro Asp  Thr Ala Ile
    1970                 1975                 1980

Ile Ser  Lys Gly Trp Gln Thr  Val Asn Gly Ser Arg  Tyr Tyr Phe
```

```
    1985                1990                1995

Asp Thr  Asp Thr Ala Ile Ala  Phe Asn Gly Tyr Lys  Thr Ile Asp
    2000                2005                2010

Gly Lys  His Phe Tyr Phe Asp  Ser Asp Cys Val Val  Lys Ile Gly
    2015                2020                2025

Val Phe  Ser Thr Ser Asn Gly  Phe Glu Tyr Phe Ala  Pro Ala Asn
    2030                2035                2040

Thr Tyr  Asn Asn Asn Ile Glu  Gly Gln Ala Ile Val  Tyr Gln Ser
    2045                2050                2055

Lys Phe  Leu Thr Leu Asn Gly  Lys Lys Tyr Tyr Phe  Asp Asn Asn
    2060                2065                2070

Ser Lys  Ala Val Thr Gly Trp  Gln Thr Ile Asp Ser  Lys Lys Tyr
    2075                2080                2085

Tyr Phe  Asn Thr Asn Thr Ala  Glu Ala Ala Thr Gly  Trp Gln Thr
    2090                2095                2100

Ile Asp  Gly Lys Lys Tyr Tyr  Phe Asn Thr Asn Thr  Ala Glu Ala
    2105                2110                2115

Ala Thr  Gly Trp Gln Thr Ile  Asp Gly Lys Lys Tyr  Tyr Phe Asn
    2120                2125                2130

Thr Asn  Thr Ala Ile Ala Ser  Thr Gly Tyr Thr Ile  Ile Asn Gly
    2135                2140                2145

Lys His  Phe Tyr Phe Asn Thr  Asp Gly Ile Met Gln  Ile Gly Val
    2150                2155                2160

Phe Lys  Gly Pro Asn Gly Phe  Glu Tyr Phe Ala Pro  Ala Asn Thr
    2165                2170                2175

Asp Ala  Asn Asn Ile Glu Gly  Gln Ala Ile Leu Tyr  Gln Asn Glu
    2180                2185                2190

Phe Leu  Thr Leu Asn Gly Lys  Lys Tyr Tyr Phe Gly  Ser Asp Ser
    2195                2200                2205

Lys Ala  Val Thr Gly Trp Arg  Ile Ile Asn Asn Lys  Lys Tyr Tyr
    2210                2215                2220

Phe Asn  Pro Asn Asn Ala Ile  Ala Ala Ile His Leu  Cys Thr Ile
    2225                2230                2235

Asn Asn  Asp Lys Tyr Tyr Phe  Ser Tyr Asp Gly Ile  Leu Gln Asn
    2240                2245                2250

Gly Tyr  Ile Thr Ile Glu Arg  Asn Asn Phe Tyr Phe  Asp Ala Asn
    2255                2260                2265

Asn Glu  Ser Lys Met Val Thr  Gly Val Phe Lys Gly  Pro Asn Gly
    2270                2275                2280

Phe Glu  Tyr Phe Ala Pro Ala  Asn Thr His Asn Asn  Asn Ile Glu
    2285                2290                2295

Gly Gln  Ala Ile Val Tyr Gln  Asn Lys Phe Leu Thr  Leu Asn Gly
    2300                2305                2310

Lys Lys  Tyr Tyr Phe Asp Asn  Asp Ser Lys Ala Val  Thr Gly Trp
    2315                2320                2325

Gln Thr  Ile Asp Gly Lys Lys  Tyr Tyr Phe Asn Leu  Asn Thr Ala
    2330                2335                2340

Glu Ala  Ala Thr Gly Trp Gln  Thr Ile Asp Gly Lys  Lys Tyr Tyr
    2345                2350                2355

Phe Asn  Leu Asn Thr Ala Glu  Ala Ala Thr Gly Trp  Gln Thr Ile
    2360                2365                2370

Asp Gly  Lys Lys Tyr Tyr Phe  Asn Thr Asn Thr Phe  Ile Ala Ser
    2375                2380                2385
```

Thr Gly Tyr Thr Ser Ile Asn Gly Lys His Phe Tyr Phe Asn Thr
2390 2395 2400

Asp Gly Ile Met Gln Ile Gly Val Phe Lys Gly Pro Asn Gly Phe
2405 2410 2415

Glu Tyr Phe Ala Pro Ala Asn Thr His Asn Asn Asn Ile Glu Gly
2420 2425 2430

Gln Ala Ile Leu Tyr Gln Asn Lys Phe Leu Thr Leu Asn Gly Lys
2435 2440 2445

Lys Tyr Tyr Phe Gly Ser Asp Ser Lys Ala Val Thr Gly Leu Arg
2450 2455 2460

Thr Ile Asp Gly Lys Lys Tyr Tyr Phe Asn Thr Asn Thr Ala Val
2465 2470 2475

Ala Val Thr Gly Trp Gln Thr Ile Asn Gly Lys Lys Tyr Tyr Phe
2480 2485 2490

Asn Thr Asn Thr Ser Ile Ala Ser Thr Gly Tyr Thr Ile Ile Ser
2495 2500 2505

Gly Lys His Phe Tyr Phe Asn Thr Asp Gly Ile Met Gln Ile Gly
2510 2515 2520

Val Phe Lys Gly Pro Asp Gly Phe Glu Tyr Phe Ala Pro Ala Asn
2525 2530 2535

Thr Asp Ala Asn Asn Ile Glu Gly Gln Ala Ile Arg Tyr Gln Asn
2540 2545 2550

Arg Phe Leu Tyr Leu His Asp Asn Ile Tyr Tyr Phe Gly Asn Asn
2555 2560 2565

Ser Lys Ala Ala Thr Gly Trp Val Thr Ile Asp Gly Asn Arg Tyr
2570 2575 2580

Tyr Phe Glu Pro Asn Thr Ala Met Gly Ala Asn Gly Tyr Lys Thr
2585 2590 2595

Ile Asp Asn Lys Asn Phe Tyr Phe Arg Asn Gly Leu Pro Gln Ile
2600 2605 2610

Gly Val Phe Lys Gly Ser Asn Gly Phe Glu Tyr Phe Ala Pro Ala
2615 2620 2625

Asn Thr Asp Ala Asn Asn Ile Glu Gly Gln Ala Ile Arg Tyr Gln
2630 2635 2640

Asn Arg Phe Leu His Leu Leu Gly Lys Ile Tyr Tyr Phe Gly Asn
2645 2650 2655

Asn Ser Lys Ala Val Thr Gly Trp Gln Thr Ile Asn Gly Lys Val
2660 2665 2670

Tyr Tyr Phe Met Pro Asp Thr Ala Met Ala Ala Ala Gly Gly Leu
2675 2680 2685

Phe Glu Ile Asp Gly Val Ile Tyr Phe Phe Gly Val Asp Gly Val
2690 2695 2700

Lys Ala Pro Gly Ile Tyr Gly
2705 2710

<210> SEQ ID NO 2
<211> LENGTH: 2366
<212> TYPE: PRT
<213> ORGANISM: Clostridium difficile

<400> SEQUENCE: 2

Met Ser Leu Val Asn Arg Lys Gln Leu Glu Lys Met Ala Asn Val Arg
1 5 10 15

Phe Arg Thr Gln Glu Asp Glu Tyr Val Ala Ile Leu Asp Ala Leu Glu

-continued

```
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445
```

```
Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser Ile
        755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
785                 790                 795                 800

Leu Gln Glu Ile Arg Asn Asn Ser Asn Ser Ser Asp Ile Glu Leu Glu
                805                 810                 815

Glu Lys Val Met Leu Thr Glu Cys Glu Ile Asn Val Ile Ser Asn Ile
            820                 825                 830

Asp Thr Gln Ile Val Glu Glu Arg Ile Glu Glu Ala Lys Asn Leu Thr
        835                 840                 845

Ser Asp Ser Ile Asn Tyr Ile Lys Asp Glu Phe Lys Leu Ile Glu Ser
    850                 855                 860
```

-continued

```
Ile Ser Asp Ala Leu Cys Asp Leu Lys Gln Gln Asn Glu Leu Glu Asp
865                 870                 875                 880

Ser His Phe Ile Ser Phe Glu Asp Ile Ser Glu Thr Asp Glu Gly Phe
                885                 890                 895

Ser Ile Arg Phe Ile Asn Lys Glu Thr Gly Glu Ser Ile Phe Val Glu
            900                 905                 910

Thr Glu Lys Thr Ile Phe Ser Glu Tyr Ala Asn His Ile Thr Glu Glu
        915                 920                 925

Ile Ser Lys Ile Lys Gly Thr Ile Phe Asp Thr Val Asn Gly Lys Leu
    930                 935                 940

Val Lys Lys Val Asn Leu Asp Thr Thr His Glu Val Asn Thr Leu Asn
945                 950                 955                 960

Ala Ala Phe Phe Ile Gln Ser Leu Ile Glu Tyr Asn Ser Ser Lys Glu
                965                 970                 975

Ser Leu Ser Asn Leu Ser Val Ala Met Lys Val Gln Val Tyr Ala Gln
            980                 985                 990

Leu Phe Ser Thr Gly Leu Asn Thr  Ile Thr Asp Ala Ala  Lys Val Val
        995                 1000                1005

Glu Leu  Val Ser Thr Ala Leu  Asp Glu Thr Ile Asp  Leu Leu Pro
    1010                 1015                1020

Thr Leu  Ser Glu Gly Leu Pro  Ile Ile Ala Thr Ile  Ile Asp Gly
    1025                 1030                1035

Val Ser  Leu Gly Ala Ala Ile  Lys Glu Leu Ser Glu  Thr Ser Asp
    1040                 1045                1050

Pro Leu  Leu Arg Gln Glu Ile  Glu Ala Lys Ile Gly  Ile Met Ala
    1055                 1060                1065

Val Asn  Leu Thr Thr Ala Thr  Thr Ala Ile Ile Thr  Ser Ser Leu
    1070                 1075                1080

Gly Ile  Ala Ser Gly Phe Ser  Ile Leu Leu Val Pro  Leu Ala Gly
    1085                 1090                1095

Ile Ser  Ala Gly Ile Pro Ser  Leu Val Asn Asn Glu  Leu Val Leu
    1100                 1105                1110

Arg Asp  Lys Ala Thr Lys Val  Val Asp Tyr Phe Lys  His Val Ser
    1115                 1120                1125

Leu Val  Glu Thr Glu Gly Val  Phe Thr Leu Leu Asp  Asp Lys Ile
    1130                 1135                1140

Met Met  Pro Gln Asp Asp Leu  Val Ile Ser Glu Ile  Asp Phe Asn
    1145                 1150                1155

Asn Asn  Ser Ile Val Leu Gly  Lys Cys Glu Ile Trp  Arg Met Glu
    1160                 1165                1170

Gly Gly  Ser Gly His Thr Val  Thr Asp Asp Ile Asp  His Phe Phe
    1175                 1180                1185

Ser Ala  Pro Ser Ile Thr Tyr  Arg Glu Pro His Leu  Ser Ile Tyr
    1190                 1195                1200

Asp Val  Leu Glu Val Gln Lys  Glu Glu Leu Asp Leu  Ser Lys Asp
    1205                 1210                1215

Leu Met  Val Leu Pro Asn Ala  Pro Asn Arg Val Phe  Ala Trp Glu
    1220                 1225                1230

Thr Gly  Trp Thr Pro Gly Leu  Arg Ser Leu Glu Asn  Asp Gly Thr
    1235                 1240                1245

Lys Leu  Leu Asp Arg Ile Arg  Asp Asn Tyr Glu Gly  Glu Phe Tyr
    1250                 1255                1260

Trp Arg  Tyr Phe Ala Phe Ile  Ala Asp Ala Leu Ile  Thr Thr Leu
```

```
    1265                1270                1275

Lys Pro  Arg Tyr Glu Asp Thr  Asn Ile Arg Ile Asn  Leu Asp Ser
    1280                1285                1290

Asn Thr  Arg Ser Phe Ile Val  Pro Ile Ile Thr Thr  Glu Tyr Ile
    1295                1300                1305

Arg Glu  Lys Leu Ser Tyr Ser  Phe Tyr Gly Ser Gly  Gly Thr Tyr
    1310                1315                1320

Ala Leu  Ser Leu Ser Gln Tyr  Asn Met Gly Ile Asn  Ile Glu Leu
    1325                1330                1335

Ser Glu  Ser Asp Val Trp Ile  Ile Asp Val Asp Asn  Val Val Arg
    1340                1345                1350

Asp Val  Thr Ile Glu Ser Asp  Lys Ile Lys Lys Gly  Asp Leu Ile
    1355                1360                1365

Glu Gly  Ile Leu Ser Thr Leu  Ser Ile Glu Glu Asn  Lys Ile Ile
    1370                1375                1380

Leu Asn  Ser His Glu Ile Asn  Phe Ser Gly Glu Val  Asn Gly Ser
    1385                1390                1395

Asn Gly  Phe Val Ser Leu Thr  Phe Ser Ile Leu Glu  Gly Ile Asn
    1400                1405                1410

Ala Ile  Ile Glu Val Asp Leu  Leu Ser Lys Ser Tyr  Lys Leu Leu
    1415                1420                1425

Ile Ser  Gly Glu Leu Lys Ile  Leu Met Leu Asn Ser  Asn His Ile
    1430                1435                1440

Gln Gln  Lys Ile Asp Tyr Ile  Gly Phe Asn Ser Glu  Leu Gln Lys
    1445                1450                1455

Asn Ile  Pro Tyr Ser Phe Val  Asp Ser Glu Gly Lys  Glu Asn Gly
    1460                1465                1470

Phe Ile  Asn Gly Ser Thr Lys  Glu Gly Leu Phe Val  Ser Glu Leu
    1475                1480                1485

Pro Asp  Val Val Leu Ile Ser  Lys Val Tyr Met Asp  Asp Ser Lys
    1490                1495                1500

Pro Ser  Phe Gly Tyr Tyr Ser  Asn Asn Leu Lys Asp  Val Lys Val
    1505                1510                1515

Ile Thr  Lys Asp Asn Val Asn  Ile Leu Thr Gly Tyr  Tyr Leu Lys
    1520                1525                1530

Asp Asp  Ile Lys Ile Ser Leu  Ser Leu Thr Leu Gln  Asp Glu Lys
    1535                1540                1545

Thr Ile  Lys Leu Asn Ser Val  His Leu Asp Glu Ser  Gly Val Ala
    1550                1555                1560

Glu Ile  Leu Lys Phe Met Asn  Arg Lys Gly Asn Thr  Asn Thr Ser
    1565                1570                1575

Asp Ser  Leu Met Ser Phe Leu  Glu Ser Met Asn Ile  Lys Ser Ile
    1580                1585                1590

Phe Val  Asn Phe Leu Gln Ser  Asn Ile Lys Phe Ile  Leu Asp Ala
    1595                1600                1605

Asn Phe  Ile Ile Ser Gly Thr  Thr Ser Ile Gly Gln  Phe Glu Phe
    1610                1615                1620

Ile Cys  Asp Glu Asn Asp Asn  Ile Gln Pro Tyr Phe  Ile Lys Phe
    1625                1630                1635

Asn Thr  Leu Glu Thr Asn Tyr  Thr Leu Tyr Val Gly  Asn Arg Gln
    1640                1645                1650

Asn Met  Ile Val Glu Pro Asn  Tyr Asp Leu Asp Asp  Ser Gly Asp
    1655                1660                1665
```

```
Ile Ser Ser Thr Val Ile Asn Phe Ser Gln Lys Tyr Leu Tyr Gly
    1670                1675                1680

Ile Asp Ser Cys Val Asn Lys Val Val Ile Ser Pro Asn Ile Tyr
    1685                1690                1695

Thr Asp Glu Ile Asn Ile Thr Pro Val Tyr Glu Thr Asn Asn Thr
    1700                1705                1710

Tyr Pro Glu Val Ile Val Leu Asp Ala Asn Tyr Ile Asn Glu Lys
    1715                1720                1725

Ile Asn Val Asn Ile Asn Asp Leu Ser Ile Arg Tyr Val Trp Ser
    1730                1735                1740

Asn Asp Gly Asn Asp Phe Ile Leu Met Ser Thr Ser Glu Glu Asn
    1745                1750                1755

Lys Val Ser Gln Val Lys Ile Arg Phe Val Asn Val Phe Lys Asp
    1760                1765                1770

Lys Thr Leu Ala Asn Lys Leu Ser Phe Asn Phe Ser Asp Lys Gln
    1775                1780                1785

Asp Val Pro Val Ser Glu Ile Ile Leu Ser Phe Thr Pro Ser Tyr
    1790                1795                1800

Tyr Glu Asp Gly Leu Ile Gly Tyr Asp Leu Gly Leu Val Ser Leu
    1805                1810                1815

Tyr Asn Glu Lys Phe Tyr Ile Asn Asn Phe Gly Met Met Val Ser
    1820                1825                1830

Gly Leu Ile Tyr Ile Asn Asp Ser Leu Tyr Tyr Phe Lys Pro Pro
    1835                1840                1845

Val Asn Asn Leu Ile Thr Gly Phe Val Thr Val Gly Asp Asp Lys
    1850                1855                1860

Tyr Tyr Phe Asn Pro Ile Asn Gly Gly Ala Ala Ser Ile Gly Glu
    1865                1870                1875

Thr Ile Ile Asp Asp Lys Asn Tyr Tyr Phe Asn Gln Ser Gly Val
    1880                1885                1890

Leu Gln Thr Gly Val Phe Ser Thr Glu Asp Gly Phe Lys Tyr Phe
    1895                1900                1905

Ala Pro Ala Asn Thr Leu Asp Glu Asn Leu Glu Gly Glu Ala Ile
    1910                1915                1920

Asp Phe Thr Gly Lys Leu Ile Ile Asp Glu Asn Ile Tyr Tyr Phe
    1925                1930                1935

Asp Asp Asn Tyr Arg Gly Ala Val Glu Trp Lys Glu Leu Asp Gly
    1940                1945                1950

Glu Met His Tyr Phe Ser Pro Glu Thr Gly Lys Ala Phe Lys Gly
    1955                1960                1965

Leu Asn Gln Ile Gly Asp Tyr Lys Tyr Tyr Phe Asn Ser Asp Gly
    1970                1975                1980

Val Met Gln Lys Gly Phe Val Ser Ile Asn Asp Asn Lys His Tyr
    1985                1990                1995

Phe Asp Asp Ser Gly Val Met Lys Val Gly Tyr Thr Glu Ile Asp
    2000                2005                2010

Gly Lys His Phe Tyr Phe Ala Glu Asn Gly Glu Met Gln Ile Gly
    2015                2020                2025

Val Phe Asn Thr Glu Asp Gly Phe Lys Tyr Phe Ala His His Asn
    2030                2035                2040

Glu Asp Leu Gly Asn Glu Glu Gly Glu Glu Ile Ser Tyr Ser Gly
    2045                2050                2055
```

-continued

```
Ile Leu  Asn Phe Asn Asn Lys  Ile Tyr Tyr Phe Asp  Asp Ser Phe
    2060                 2065                 2070

Thr Ala  Val Val Gly Trp Lys  Asp Leu Glu Asp Gly  Ser Lys Tyr
    2075                 2080                 2085

Tyr Phe  Asp Glu Asp Thr Ala  Glu Ala Tyr Ile Gly  Leu Ser Leu
    2090                 2095                 2100

Ile Asn  Asp Gly Gln Tyr Tyr  Phe Asn Asp Asp Gly  Ile Met Gln
    2105                 2110                 2115

Val Gly  Phe Val Thr Ile Asn  Asp Lys Val Phe Tyr  Phe Ser Asp
    2120                 2125                 2130

Ser Gly  Ile Ile Glu Ser Gly  Val Gln Asn Ile Asp  Asp Asn Tyr
    2135                 2140                 2145

Phe Tyr  Ile Asp Asp Asn Gly  Ile Val Gln Ile Gly  Val Phe Asp
    2150                 2155                 2160

Thr Ser  Asp Gly Tyr Lys Tyr  Phe Ala Pro Ala Asn  Thr Val Asn
    2165                 2170                 2175

Asp Asn  Ile Tyr Gly Gln Ala  Val Glu Tyr Ser Gly  Leu Val Arg
    2180                 2185                 2190

Val Gly  Glu Asp Val Tyr Tyr  Phe Gly Glu Thr Tyr  Thr Ile Glu
    2195                 2200                 2205

Thr Gly  Trp Ile Tyr Asp Met  Glu Asn Glu Ser Asp  Lys Tyr Tyr
    2210                 2215                 2220

Phe Asn  Pro Glu Thr Lys Lys  Ala Cys Lys Gly Ile  Asn Leu Ile
    2225                 2230                 2235

Asp Asp  Ile Lys Tyr Tyr Phe  Asp Glu Lys Gly Ile  Met Arg Thr
    2240                 2245                 2250

Gly Leu  Ile Ser Phe Glu Asn  Asn Asn Tyr Tyr Phe  Asn Glu Asn
    2255                 2260                 2265

Gly Glu  Met Gln Phe Gly Tyr  Ile Asn Ile Glu Asp  Lys Met Phe
    2270                 2275                 2280

Tyr Phe  Gly Glu Asp Gly Val  Met Gln Ile Gly Val  Phe Asn Thr
    2285                 2290                 2295

Pro Asp  Gly Phe Lys Tyr Phe  Ala His Gln Asn Thr  Leu Asp Glu
    2300                 2305                 2310

Asn Phe  Glu Gly Glu Ser Ile  Asn Tyr Thr Gly Trp  Leu Asp Leu
    2315                 2320                 2325

Asp Glu  Lys Arg Tyr Tyr Phe  Thr Asp Glu Tyr Ile  Ala Ala Thr
    2330                 2335                 2340

Gly Ser  Val Ile Ile Asp Gly  Glu Glu Tyr Tyr Phe  Asp Pro Asp
    2345                 2350                 2355

Thr Ala  Gln Leu Val Ile Ser  Glu
    2360                 2365
```

<210> SEQ ID NO 3
<211> LENGTH: 769
<212> TYPE: PRT
<213> ORGANISM: Clostridium difficile

<400> SEQUENCE: 3

```
Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45
```

-continued

```
Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460
```

-continued

Ile Ser Leu Ser Gly Pro Gly Ala Tyr Ala Ser Ala Tyr Tyr Asp Phe
465 470 475 480

Ile Asn Leu Gln Glu Asn Thr Ile Glu Lys Thr Leu Lys Ala Ser Asp
485 490 495

Leu Ile Glu Phe Lys Phe Pro Glu Asn Asn Leu Ser Gln Leu Thr Glu
500 505 510

Gln Glu Ile Asn Ser Leu Trp Ser Phe Asp Gln Ala Ser Ala Lys Tyr
515 520 525

Gln Phe Glu Lys Tyr Val Arg Asp Tyr Thr Gly Gly Ser Leu Ser Glu
530 535 540

Asp Asn Gly Val Asp Phe Asn Lys Asn Thr Ala Leu Asp Lys Asn Tyr
545 550 555 560

Leu Leu Asn Asn Lys Ile Pro Ser Asn Asn Val Glu Glu Ala Gly Ser
565 570 575

Lys Asn Tyr Val His Tyr Ile Ile Gln Leu Gln Gly Asp Asp Ile Ser
580 585 590

Tyr Glu Ala Thr Cys Asn Leu Phe Ser Lys Asn Pro Lys Asn Ser Ile
595 600 605

Ile Ile Gln Arg Asn Met Asn Glu Ser Ala Lys Ser Tyr Phe Leu Ser
610 615 620

Asp Asp Gly Glu Ser Ile Leu Glu Leu Asn Lys Tyr Arg Ile Pro Glu
625 630 635 640

Arg Leu Lys Asn Lys Glu Lys Val Lys Val Thr Phe Ile Gly His Gly
645 650 655

Lys Asp Glu Phe Asn Thr Ser Glu Phe Ala Arg Leu Ser Val Asp Ser
660 665 670

Leu Ser Asn Glu Ile Ser Ser Phe Leu Asp Thr Ile Lys Leu Asp Ile
675 680 685

Ser Pro Lys Asn Val Glu Val Asn Leu Leu Gly Cys Asn Met Phe Ser
690 695 700

Tyr Asp Phe Asn Val Glu Glu Thr Tyr Pro Gly Lys Leu Leu Leu Ser
705 710 715 720

Ile Met Asp Lys Ile Thr Ser Thr Leu Pro Asp Val Asn Lys Asn Ser
725 730 735

Ile Thr Ile Gly Ala Asn Gln Tyr Glu Val Arg Ile Asn Ser Glu Gly
740 745 750

Arg Lys Glu Leu Leu Ala His Ser Gly Lys Trp Ile Asn Lys Glu Glu
755 760 765

Ala

<210> SEQ ID NO 4
<211> LENGTH: 541
<212> TYPE: PRT
<213> ORGANISM: Clostridium difficile

<400> SEQUENCE: 4

Met Ser Leu Ile Ser Lys Glu Glu Leu Ile Lys Leu Ala Tyr Ser Ile
1 5 10 15

Arg Pro Arg Glu Asn Glu Tyr Lys Thr Ile Leu Thr Asn Leu Asp Glu
20 25 30

Tyr Asn Lys Leu Thr Thr Asn Asn Asn Glu Asn Lys Tyr Leu Gln Leu
35 40 45

Lys Lys Leu Asn Glu Ser Ile Asp Val Phe Met Asn Lys Tyr Lys Thr
50 55 60

-continued

```
Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Tyr Leu Asp Val Asp Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
```

```
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser
    530                 535                 540


<210> SEQ ID NO 5
<211> LENGTH: 228
<212> TYPE: PRT
<213> ORGANISM: Clostridium difficile

<400> SEQUENCE: 5

Leu Ser Glu Asp Asn Gly Val Asp Phe Asn Lys Asn Thr Ala Leu Asp
1               5                   10                  15

Lys Asn Tyr Leu Leu Asn Asn Lys Ile Pro Ser Asn Asn Val Glu Glu
            20                  25                  30

Ala Gly Ser Lys Asn Tyr Val His Tyr Ile Ile Gln Leu Gln Gly Asp
        35                  40                  45

Asp Ile Ser Tyr Glu Ala Thr Cys Asn Leu Phe Ser Lys Asn Pro Lys
    50                  55                  60

Asn Ser Ile Ile Ile Gln Arg Asn Met Asn Glu Ser Ala Lys Ser Tyr
65                  70                  75                  80

Phe Leu Ser Asp Asp Gly Glu Ser Ile Leu Glu Leu Asn Lys Tyr Arg
                85                  90                  95

Ile Pro Glu Arg Leu Lys Asn Lys Glu Lys Val Lys Val Thr Phe Ile
            100                 105                 110

Gly His Gly Lys Asp Glu Phe Asn Thr Ser Glu Phe Ala Arg Leu Ser
        115                 120                 125

Val Asp Ser Leu Ser Asn Glu Ile Ser Ser Phe Leu Asp Thr Ile Lys
    130                 135                 140

Leu Asp Ile Ser Pro Lys Asn Val Glu Val Asn Leu Leu Gly Cys Asn
145                 150                 155                 160

Met Phe Ser Tyr Asp Phe Asn Val Glu Glu Thr Tyr Pro Gly Lys Leu
                165                 170                 175

Leu Leu Ser Ile Met Asp Lys Ile Thr Ser Thr Leu Pro Asp Val Asn
            180                 185                 190

Lys Asn Ser Ile Thr Ile Gly Ala Asn Gln Tyr Glu Val Arg Ile Asn
        195                 200                 205

Ser Glu Gly Arg Lys Glu Leu Leu Ala His Ser Gly Lys Trp Ile Asn
    210                 215                 220

Lys Glu Glu Ala
225


<210> SEQ ID NO 6
<211> LENGTH: 1039
<212> TYPE: PRT
<213> ORGANISM: Clostridium difficile

<400> SEQUENCE: 6

Ile Met Ser Asp Leu Ser Ser Lys Glu Tyr Ile Phe Phe Asp Ser Ile
1               5                   10                  15

Asp Asn Lys Leu Lys Ala Lys Ser Lys Asn Ile Pro Gly Leu Ala Ser
            20                  25                  30

Ile Ser Glu Asp Ile Lys Thr Leu Leu Leu Asp Ala Ser Val Ser Pro
```

```
        35                  40                  45

Asp Thr Lys Phe Ile Leu Asn Asn Leu Lys Leu Asn Ile Glu Ser Ser
    50                  55                  60

Ile Gly Asp Tyr Ile Tyr Tyr Glu Lys Leu Glu Pro Val Lys Asn Ile
65                  70                  75                  80

Ile His Asn Ser Ile Asp Asp Leu Ile Asp Glu Phe Asn Leu Leu Glu
                85                  90                  95

Asn Val Ser Asp Glu Leu Tyr Glu Leu Lys Lys Leu Asn Asn Leu Asp
            100                 105                 110

Glu Lys Tyr Leu Ile Ser Phe Glu Asp Ile Ser Lys Asn Asn Ser Thr
        115                 120                 125

Tyr Ser Val Arg Phe Ile Asn Lys Ser Asn Gly Glu Ser Val Tyr Val
    130                 135                 140

Glu Thr Glu Lys Glu Ile Phe Ser Lys Tyr Ser Glu His Ile Thr Lys
145                 150                 155                 160

Glu Ile Ser Thr Ile Lys Asn Ser Ile Ile Thr Asp Val Asn Gly Asn
                165                 170                 175

Leu Leu Asp Asn Ile Gln Leu Asp His Thr Ser Gln Val Asn Thr Leu
            180                 185                 190

Asn Ala Ala Phe Phe Ile Gln Ser Leu Ile Asp Tyr Ser Ser Asn Lys
        195                 200                 205

Asp Val Leu Asn Asp Leu Ser Thr Ser Val Lys Val Gln Leu Tyr Ala
    210                 215                 220

Gln Leu Phe Ser Thr Gly Leu Asn Thr Ile Tyr Asp Ser Ile Gln Leu
225                 230                 235                 240

Val Asn Leu Ile Ser Asn Ala Val Asn Asp Thr Ile Asn Val Leu Pro
                245                 250                 255

Thr Ile Thr Glu Gly Ile Pro Ile Val Ser Thr Ile Leu Asp Gly Ile
            260                 265                 270

Asn Leu Gly Ala Ala Ile Lys Glu Leu Leu Asp Glu His Asp Pro Leu
        275                 280                 285

Leu Lys Lys Glu Leu Glu Ala Lys Val Gly Val Leu Ala Ile Asn Met
    290                 295                 300

Ser Leu Ser Ile Ala Ala Thr Val Ala Ser Ile Val Gly Ile Gly Ala
305                 310                 315                 320

Glu Val Thr Ile Phe Leu Leu Pro Ile Ala Gly Ile Ser Ala Gly Ile
                325                 330                 335

Pro Ser Leu Val Asn Asn Glu Leu Ile Leu His Asp Lys Ala Thr Ser
            340                 345                 350

Val Val Asn Tyr Phe Asn His Leu Ser Glu Ser Lys Lys Tyr Gly Pro
        355                 360                 365

Leu Lys Thr Glu Asp Asp Lys Ile Leu Val Pro Ile Asp Asp Leu Val
    370                 375                 380

Ile Ser Glu Ile Asp Phe Asn Asn Asn Ser Ile Lys Leu Gly Thr Cys
385                 390                 395                 400

Asn Ile Leu Ala Met Glu Gly Gly Ser Gly His Thr Val Thr Gly Asn
                405                 410                 415

Ile Asp His Phe Phe Ser Ser Pro Ser Ile Ser Ser His Ile Pro Ser
            420                 425                 430

Leu Ser Ile Tyr Ser Ala Ile Gly Ile Glu Thr Glu Asn Leu Asp Phe
        435                 440                 445

Ser Lys Lys Ile Met Met Leu Pro Asn Ala Pro Ser Arg Val Phe Trp
    450                 455                 460
```

```
Trp Glu Thr Gly Ala Val Pro Gly Leu Arg Ser Leu Glu Asn Asp Gly
465                 470                 475                 480

Thr Arg Leu Leu Asp Ser Ile Arg Asp Leu Tyr Pro Gly Lys Phe Tyr
                485                 490                 495

Trp Arg Phe Tyr Ala Phe Phe Asp Tyr Ala Ile Thr Thr Leu Lys Pro
            500                 505                 510

Val Tyr Glu Asp Thr Asn Ile Lys Ile Lys Leu Asp Lys Asp Thr Arg
        515                 520                 525

Asn Phe Ile Met Pro Thr Ile Thr Thr Asn Glu Ile Arg Asn Lys Leu
    530                 535                 540

Ser Tyr Ser Phe Asp Gly Ala Gly Gly Thr Tyr Ser Leu Leu Leu Ser
545                 550                 555                 560

Ser Tyr Pro Ile Ser Thr Asn Ile Asn Leu Ser Lys Asp Asp Leu Trp
                565                 570                 575

Ile Phe Asn Ile Asp Asn Glu Val Arg Glu Ile Ser Ile Glu Asn Gly
            580                 585                 590

Thr Ile Lys Lys Gly Lys Leu Ile Lys Asp Val Leu Ser Lys Ile Asp
        595                 600                 605

Ile Asn Lys Asn Lys Leu Ile Ile Gly Asn Gln Thr Ile Asp Phe Ser
    610                 615                 620

Gly Asp Ile Asp Asn Lys Asp Arg Tyr Ile Phe Leu Thr Cys Glu Leu
625                 630                 635                 640

Asp Asp Lys Ile Ser Leu Ile Ile Glu Ile Asn Leu Val Ala Lys Ser
                645                 650                 655

Tyr Ser Leu Leu Leu Ser Gly Asp Lys Asn Tyr Leu Ile Ser Asn Leu
            660                 665                 670

Ser Asn Ile Ile Glu Lys Ile Asn Thr Leu Gly Leu Asp Ser Lys Asn
        675                 680                 685

Ile Ala Tyr Asn Tyr Thr Asp Glu Ser Asn Asn Lys Tyr Phe Gly Ala
    690                 695                 700

Ile Ser Lys Thr Ser Gln Lys Ser Ile Ile His Tyr Lys Lys Asp Ser
705                 710                 715                 720

Lys Asn Ile Leu Glu Phe Tyr Asn Asp Ser Thr Leu Glu Phe Asn Ser
                725                 730                 735

Lys Asp Phe Ile Ala Glu Asp Ile Asn Val Phe Met Lys Asp Asp Ile
            740                 745                 750

Asn Thr Ile Thr Gly Lys Tyr Tyr Val Asp Asn Asn Thr Asp Lys Ser
        755                 760                 765

Ile Asp Phe Ser Ile Ser Leu Val Ser Lys Asn Gln Val Lys Val Asn
    770                 775                 780

Gly Leu Tyr Leu Asn Glu Ser Val Tyr Ser Ser Tyr Leu Asp Phe Val
785                 790                 795                 800

Lys Asn Ser Asp Gly His His Asn Thr Ser Asn Phe Met Asn Leu Phe
                805                 810                 815

Leu Asp Asn Ile Ser Phe Trp Lys Leu Phe Gly Phe Glu Asn Ile Asn
            820                 825                 830

Phe Val Ile Asp Lys Tyr Phe Thr Leu Val Gly Lys Thr Asn Leu Gly
        835                 840                 845

Tyr Val Glu Phe Ile Cys Asp Asn Asn Lys Asn Ile Asp Ile Tyr Phe
    850                 855                 860

Gly Glu Trp Lys Thr Ser Ser Ser Lys Ser Thr Ile Phe Ser Gly Asn
865                 870                 875                 880
```

-continued

```
Gly Arg Asn Val Val Val Glu Pro Ile Tyr Asn Pro Asp Thr Gly Glu
                885                 890                 895

Asp Ile Ser Thr Ser Leu Asp Phe Ser Tyr Glu Pro Leu Tyr Gly Ile
            900                 905                 910

Asp Arg Tyr Ile Asn Lys Val Leu Ile Ala Pro Asp Leu Tyr Thr Ser
        915                 920                 925

Leu Ile Asn Ile Asn Thr Asn Tyr Tyr Ser Asn Glu Tyr Tyr Pro Glu
    930                 935                 940

Ile Ile Val Leu Asn Pro Asn Thr Phe His Lys Lys Val Asn Ile Asn
945                 950                 955                 960

Leu Asp Ser Ser Ser Phe Glu Tyr Lys Trp Ser Thr Glu Gly Ser Asp
                965                 970                 975

Phe Ile Leu Val Arg Tyr Leu Glu Glu Ser Asn Lys Lys Ile Leu Gln
            980                 985                 990

Lys Ile Arg Ile Lys Gly Ile Leu  Ser Asn Thr Gln Ser  Phe Asn Lys
        995                 1000                1005

Met Ser  Ile Asp Phe Lys Asp  Ile Lys Lys Leu Ser  Leu Gly Tyr
    1010                1015                1020

Ile Met  Ser Asn Phe Lys Ser  Phe Asn Ser Glu Asn  Glu Leu Asp
    1025                1030                1035

Arg


<210> SEQ ID NO 7
<211> LENGTH: 266
<212> TYPE: PRT
<213> ORGANISM: Clostridium difficile

<400> SEQUENCE: 7

Ala Glu Asp Ile Asn Val Phe Met Lys Asp Asp Ile Asn Thr Ile Thr
1               5                   10                  15

Gly Lys Tyr Tyr Val Asp Asn Asn Thr Asp Lys Ser Ile Asp Phe Ser
            20                  25                  30

Ile Ser Leu Val Ser Lys Asn Gln Val Lys Val Asn Gly Leu Tyr Leu
        35                  40                  45

Asn Glu Ser Val Tyr Ser Ser Tyr Leu Asp Phe Val Lys Asn Ser Asp
    50                  55                  60

Gly His His Asn Thr Ser Asn Phe Met Asn Leu Phe Leu Asp Asn Ile
65                  70                  75                  80

Ser Phe Trp Lys Leu Phe Gly Phe Glu Asn Ile Asn Phe Val Ile Asp
                85                  90                  95

Lys Tyr Phe Thr Leu Val Gly Lys Thr Asn Leu Gly Tyr Val Glu Phe
            100                 105                 110

Ile Cys Asp Asn Asn Lys Asn Ile Asp Ile Tyr Phe Gly Glu Trp Lys
        115                 120                 125

Thr Ser Ser Ser Lys Ser Thr Ile Phe Ser Gly Asn Gly Arg Asn Val
    130                 135                 140

Val Val Glu Pro Ile Tyr Asn Pro Asp Thr Gly Glu Asp Ile Ser Thr
145                 150                 155                 160

Ser Leu Asp Phe Ser Tyr Glu Pro Leu Tyr Gly Ile Asp Arg Tyr Ile
                165                 170                 175

Asn Lys Val Leu Ile Ala Pro Asp Leu Tyr Thr Ser Leu Ile Asn Ile
            180                 185                 190

Asn Thr Asn Tyr Tyr Ser Asn Glu Tyr Tyr Pro Glu Ile Ile Val Leu
        195                 200                 205
```

-continued

```
Asn Pro Asn Thr Phe His Lys Lys Val Asn Ile Asn Leu Asp Ser Ser
    210                 215                 220

Ser Phe Glu Tyr Lys Trp Ser Thr Glu Gly Ser Asp Phe Ile Leu Val
225                 230                 235                 240

Arg Tyr Leu Glu Glu Ser Asn Lys Lys Ile Leu Gln Lys Ile Arg Ile
                245                 250                 255

Lys Gly Ile Leu Ser Asn Thr Gln Ser Phe
            260                 265


<210> SEQ ID NO 8
<211> LENGTH: 902
<212> TYPE: PRT
<213> ORGANISM: Clostridium difficile

<400> SEQUENCE: 8

Asp His Leu Gly Phe Lys Ile Ile Asp Asn Lys Thr Tyr Tyr Tyr Asp
1               5                   10                  15

Glu Asp Ser Lys Leu Val Lys Gly Leu Ile Asn Ile Asn Asn Ser Leu
            20                  25                  30

Phe Tyr Phe Asp Pro Ile Glu Phe Asn Leu Val Thr Gly Trp Gln Thr
        35                  40                  45

Ile Asn Gly Lys Lys Tyr Tyr Phe Asp Ile Asn Thr Gly Ala Ala Leu
    50                  55                  60

Ile Ser Tyr Lys Ile Ile Asn Gly Lys His Phe Tyr Phe Asn Asn Asp
65                  70                  75                  80

Gly Val Met Gln Leu Gly Val Phe Lys Gly Pro Asp Gly Phe Glu Tyr
                85                  90                  95

Phe Ala Pro Ala Asn Thr Gln Asn Asn Asn Ile Glu Gly Gln Ala Ile
            100                 105                 110

Val Tyr Gln Ser Lys Phe Leu Thr Leu Asn Gly Lys Lys Tyr Tyr Phe
        115                 120                 125

Asp Asn Asp Ser Lys Ala Val Thr Gly Trp Arg Ile Ile Asn Asn Glu
    130                 135                 140

Lys Tyr Tyr Phe Asn Pro Asn Asn Ala Ile Ala Ala Val Gly Leu Gln
145                 150                 155                 160

Val Ile Asp Asn Asn Lys Tyr Tyr Phe Asn Pro Asp Thr Ala Ile Ile
                165                 170                 175

Ser Lys Gly Trp Gln Thr Val Asn Gly Ser Arg Tyr Tyr Phe Asp Thr
            180                 185                 190

Asp Thr Ala Ile Ala Phe Asn Gly Tyr Lys Thr Ile Asp Gly Lys His
        195                 200                 205

Phe Tyr Phe Asp Ser Asp Cys Val Val Lys Ile Gly Val Phe Ser Thr
    210                 215                 220

Ser Asn Gly Phe Glu Tyr Phe Ala Pro Ala Asn Thr Tyr Asn Asn Asn
225                 230                 235                 240

Ile Glu Gly Gln Ala Ile Val Tyr Gln Ser Lys Phe Leu Thr Leu Asn
                245                 250                 255

Gly Lys Lys Tyr Tyr Phe Asp Asn Asn Ser Lys Ala Val Thr Gly Trp
            260                 265                 270

Gln Thr Ile Asp Ser Lys Lys Tyr Tyr Phe Asn Thr Asn Thr Ala Glu
        275                 280                 285

Ala Ala Thr Gly Trp Gln Thr Ile Asp Gly Lys Lys Tyr Tyr Phe Asn
    290                 295                 300

Thr Asn Thr Ala Glu Ala Ala Thr Gly Trp Gln Thr Ile Asp Gly Lys
305                 310                 315                 320
```

-continued

```
Lys Tyr Tyr Phe Asn Thr Asn Thr Ala Ile Ala Ser Thr Gly Tyr Thr
                325                 330                 335

Ile Ile Asn Gly Lys His Phe Tyr Phe Asn Thr Asp Gly Ile Met Gln
            340                 345                 350

Ile Gly Val Phe Lys Gly Pro Asn Gly Phe Glu Tyr Phe Ala Pro Ala
        355                 360                 365

Asn Thr Asp Ala Asn Asn Ile Glu Gly Gln Ala Ile Leu Tyr Gln Asn
    370                 375                 380

Glu Phe Leu Thr Leu Asn Gly Lys Lys Tyr Tyr Phe Gly Ser Asp Ser
385                 390                 395                 400

Lys Ala Val Thr Gly Trp Arg Ile Ile Asn Asn Lys Lys Tyr Tyr Phe
                405                 410                 415

Asn Pro Asn Asn Ala Ile Ala Ala Ile His Leu Cys Thr Ile Asn Asn
            420                 425                 430

Asp Lys Tyr Tyr Phe Ser Tyr Asp Gly Ile Leu Gln Asn Gly Tyr Ile
        435                 440                 445

Thr Ile Glu Arg Asn Asn Phe Tyr Phe Asp Ala Asn Asn Glu Ser Lys
    450                 455                 460

Met Val Thr Gly Val Phe Lys Gly Pro Asn Gly Phe Glu Tyr Phe Ala
465                 470                 475                 480

Pro Ala Asn Thr His Asn Asn Asn Ile Glu Gly Gln Ala Ile Val Tyr
                485                 490                 495

Gln Asn Lys Phe Leu Thr Leu Asn Gly Lys Lys Tyr Tyr Phe Asp Asn
            500                 505                 510

Asp Ser Lys Ala Val Thr Gly Trp Gln Thr Ile Asp Gly Lys Lys Tyr
        515                 520                 525

Tyr Phe Asn Leu Asn Thr Ala Glu Ala Ala Thr Gly Trp Gln Thr Ile
    530                 535                 540

Asp Gly Lys Lys Tyr Tyr Phe Asn Leu Asn Thr Ala Glu Ala Ala Thr
545                 550                 555                 560

Gly Trp Gln Thr Ile Asp Gly Lys Lys Tyr Tyr Phe Asn Thr Asn Thr
                565                 570                 575

Phe Ile Ala Ser Thr Gly Tyr Thr Ser Ile Asn Gly Lys His Phe Tyr
            580                 585                 590

Phe Asn Thr Asp Gly Ile Met Gln Ile Gly Val Phe Lys Gly Pro Asn
        595                 600                 605

Gly Phe Glu Tyr Phe Ala Pro Ala Asn Thr His Asn Asn Asn Ile Glu
    610                 615                 620

Gly Gln Ala Ile Leu Tyr Gln Asn Lys Phe Leu Thr Leu Asn Gly Lys
625                 630                 635                 640

Lys Tyr Tyr Phe Gly Ser Asp Ser Lys Ala Val Thr Gly Leu Arg Thr
                645                 650                 655

Ile Asp Gly Lys Lys Tyr Tyr Phe Asn Thr Asn Thr Ala Val Ala Val
            660                 665                 670

Thr Gly Trp Gln Thr Ile Asn Gly Lys Lys Tyr Tyr Phe Asn Thr Asn
        675                 680                 685

Thr Ser Ile Ala Ser Thr Gly Tyr Thr Ile Ile Ser Gly Lys His Phe
    690                 695                 700

Tyr Phe Asn Thr Asp Gly Ile Met Gln Ile Gly Val Phe Lys Gly Pro
705                 710                 715                 720

Asp Gly Phe Glu Tyr Phe Ala Pro Ala Asn Thr Asp Ala Asn Asn Ile
                725                 730                 735
```

-continued

```
Glu Gly Gln Ala Ile Arg Tyr Gln Asn Arg Phe Leu Tyr Leu His Asp
            740                 745                 750

Asn Ile Tyr Tyr Phe Gly Asn Asn Ser Lys Ala Ala Thr Gly Trp Val
        755                 760                 765

Thr Ile Asp Gly Asn Arg Tyr Tyr Phe Glu Pro Asn Thr Ala Met Gly
    770                 775                 780

Ala Asn Gly Tyr Lys Thr Ile Asp Asn Lys Asn Phe Tyr Phe Arg Asn
785                 790                 795                 800

Gly Leu Pro Gln Ile Gly Val Phe Lys Gly Ser Asn Gly Phe Glu Tyr
                805                 810                 815

Phe Ala Pro Ala Asn Thr Asp Ala Asn Asn Ile Glu Gly Gln Ala Ile
            820                 825                 830

Arg Tyr Gln Asn Arg Phe Leu His Leu Leu Gly Lys Ile Tyr Tyr Phe
        835                 840                 845

Gly Asn Asn Ser Lys Ala Val Thr Gly Trp Gln Thr Ile Asn Gly Lys
    850                 855                 860

Val Tyr Tyr Phe Met Pro Asp Thr Ala Met Ala Ala Ala Gly Gly Leu
865                 870                 875                 880

Phe Glu Ile Asp Gly Val Ile Tyr Phe Phe Gly Val Asp Gly Val Lys
                885                 890                 895

Ala Pro Gly Ile Tyr Gly
            900


<210> SEQ ID NO 9
<211> LENGTH: 204
<212> TYPE: PRT
<213> ORGANISM: Clostridium difficile

<400> SEQUENCE: 9

Arg Tyr Tyr Phe Asp Thr Asp Thr Ala Ile Ala Phe Asn Gly Tyr Lys
1               5                   10                  15

Thr Ile Asp Gly Lys His Phe Tyr Phe Asp Ser Asp Cys Val Val Lys
            20                  25                  30

Ile Gly Val Phe Ser Thr Ser Asn Gly Phe Glu Tyr Phe Ala Pro Ala
        35                  40                  45

Asn Thr Tyr Asn Asn Asn Ile Glu Gly Gln Ala Ile Val Tyr Gln Ser
    50                  55                  60

Lys Phe Leu Thr Leu Asn Gly Lys Lys Tyr Tyr Phe Asp Asn Asn Ser
65                  70                  75                  80

Lys Ala Val Thr Gly Trp Gln Thr Ile Asp Ser Lys Lys Tyr Tyr Phe
                85                  90                  95

Asn Thr Asn Thr Ala Glu Ala Ala Thr Gly Trp Gln Thr Ile Asp Gly
            100                 105                 110

Lys Lys Tyr Tyr Phe Asn Thr Asn Thr Ala Glu Ala Ala Thr Gly Trp
        115                 120                 125

Gln Thr Ile Asp Gly Lys Lys Tyr Tyr Phe Asn Thr Asn Thr Ala Ile
    130                 135                 140

Ala Ser Thr Gly Tyr Thr Ile Ile Asn Gly Lys His Phe Tyr Phe Asn
145                 150                 155                 160

Thr Asp Gly Ile Met Gln Ile Gly Val Phe Lys Gly Pro Asn Gly Phe
                165                 170                 175

Glu Tyr Phe Ala Pro Ala Asn Thr Asp Ala Asn Asn Ile Glu Gly Gln
            180                 185                 190

Ala Ile Leu Tyr Gln Asn Glu Phe Leu Thr Leu Asn
        195                 200
```

<210> SEQ ID NO 10
<211> LENGTH: 457
<212> TYPE: PRT
<213> ORGANISM: Clostridium difficile

<400> SEQUENCE: 10

```
Ile Leu Gln Asn Gly Tyr Ile Thr Ile Glu Arg Asn Asn Phe Tyr Phe
1               5                   10                  15

Asp Ala Asn Asn Glu Ser Lys Met Val Thr Gly Val Phe Lys Gly Pro
            20                  25                  30

Asn Gly Phe Glu Tyr Phe Ala Pro Ala Asn Thr His Asn Asn Asn Ile
        35                  40                  45

Glu Gly Gln Ala Ile Val Tyr Gln Asn Lys Phe Leu Thr Leu Asn Gly
    50                  55                  60

Lys Lys Tyr Tyr Phe Asp Asn Asp Ser Lys Ala Val Thr Gly Trp Gln
65                  70                  75                  80

Thr Ile Asp Gly Lys Lys Tyr Tyr Phe Asn Leu Asn Thr Ala Glu Ala
                85                  90                  95

Ala Thr Gly Trp Gln Thr Ile Asp Gly Lys Lys Tyr Tyr Phe Asn Leu
            100                 105                 110

Asn Thr Ala Glu Ala Ala Thr Gly Trp Gln Thr Ile Asp Gly Lys Lys
        115                 120                 125

Tyr Tyr Phe Asn Thr Asn Thr Phe Ile Ala Ser Thr Gly Tyr Thr Ser
    130                 135                 140

Ile Asn Gly Lys His Phe Tyr Phe Asn Thr Asp Gly Ile Met Gln Ile
145                 150                 155                 160

Gly Val Phe Lys Gly Pro Asn Gly Phe Glu Tyr Phe Ala Pro Ala Asn
                165                 170                 175

Thr His Asn Asn Asn Ile Glu Gly Gln Ala Ile Leu Tyr Gln Asn Lys
            180                 185                 190

Phe Leu Thr Leu Asn Gly Lys Lys Tyr Tyr Phe Gly Ser Asp Ser Lys
        195                 200                 205

Ala Val Thr Gly Leu Arg Thr Ile Asp Gly Lys Lys Tyr Tyr Phe Asn
    210                 215                 220

Thr Asn Thr Ala Val Ala Val Thr Gly Trp Gln Thr Ile Asn Gly Lys
225                 230                 235                 240

Lys Tyr Tyr Phe Asn Thr Asn Thr Ser Ile Ala Ser Thr Gly Tyr Thr
                245                 250                 255

Ile Ile Ser Gly Lys His Phe Tyr Phe Asn Thr Asp Gly Ile Met Gln
            260                 265                 270

Ile Gly Val Phe Lys Gly Pro Asp Gly Phe Glu Tyr Phe Ala Pro Ala
        275                 280                 285

Asn Thr Asp Ala Asn Asn Ile Glu Gly Gln Ala Ile Arg Tyr Gln Asn
    290                 295                 300

Arg Phe Leu Tyr Leu His Asp Asn Ile Tyr Tyr Phe Gly Asn Asn Ser
305                 310                 315                 320

Lys Ala Ala Thr Gly Trp Val Thr Ile Asp Gly Asn Arg Tyr Tyr Phe
                325                 330                 335

Glu Pro Asn Thr Ala Met Gly Ala Asn Gly Tyr Lys Thr Ile Asp Asn
            340                 345                 350

Lys Asn Phe Tyr Phe Arg Asn Gly Leu Pro Gln Ile Gly Val Phe Lys
        355                 360                 365

Gly Ser Asn Gly Phe Glu Tyr Phe Ala Pro Ala Asn Thr Asp Ala Asn
```

```
    370                 375                 380

Asn Ile Glu Gly Gln Ala Ile Arg Tyr Gln Asn Arg Phe Leu His Leu
385                 390                 395                 400

Leu Gly Lys Ile Tyr Tyr Phe Gly Asn Asn Ser Lys Ala Val Thr Gly
                405                 410                 415

Trp Gln Thr Ile Asn Gly Lys Val Tyr Tyr Phe Met Pro Asp Thr Ala
            420                 425                 430

Met Ala Ala Ala Gly Gly Leu Phe Glu Ile Asp Gly Val Ile Tyr Phe
        435                 440                 445

Phe Gly Val Asp Gly Val Lys Ala Pro
    450                 455


<210> SEQ ID NO 11
<211> LENGTH: 320
<212> TYPE: PRT
<213> ORGANISM: Clostridium difficile

<400> SEQUENCE: 11

Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr His Asn Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175

Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255

Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285
```

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320

<210> SEQ ID NO 12
<211> LENGTH: 864
<212> TYPE: PRT
<213> ORGANISM: Clostridium difficile

<400> SEQUENCE: 12

Phe Asp Pro Ile Glu Phe Asn Leu Val Thr Gly Trp Gln Thr Ile Asn
1               5                   10                  15

Gly Lys Lys Tyr Tyr Phe Asp Ile Asn Thr Gly Ala Ala Leu Ile Ser
            20                  25                  30

Tyr Lys Ile Ile Asn Gly Lys His Phe Tyr Phe Asn Asn Asp Gly Val
        35                  40                  45

Met Gln Leu Gly Val Phe Lys Gly Pro Asp Gly Phe Glu Tyr Phe Ala
    50                  55                  60

Pro Ala Asn Thr Gln Asn Asn Asn Ile Glu Gly Gln Ala Ile Val Tyr
65                  70                  75                  80

Gln Ser Lys Phe Leu Thr Leu Asn Gly Lys Lys Tyr Tyr Phe Asp Asn
                85                  90                  95

Asp Ser Lys Ala Val Thr Gly Trp Arg Ile Ile Asn Asn Glu Lys Tyr
            100                 105                 110

Tyr Phe Asn Pro Asn Asn Ala Ile Ala Ala Val Gly Leu Gln Val Ile
        115                 120                 125

Asp Asn Asn Lys Tyr Tyr Phe Asn Pro Asp Thr Ala Ile Ile Ser Lys
    130                 135                 140

Gly Trp Gln Thr Val Asn Gly Ser Arg Tyr Tyr Phe Asp Thr Asp Thr
145                 150                 155                 160

Ala Ile Ala Phe Asn Gly Tyr Lys Thr Ile Asp Gly Lys His Phe Tyr
                165                 170                 175

Phe Asp Ser Asp Cys Val Val Lys Ile Gly Val Phe Ser Thr Ser Asn
            180                 185                 190

Gly Phe Glu Tyr Phe Ala Pro Ala Asn Thr Tyr Asn Asn Asn Ile Glu
        195                 200                 205

Gly Gln Ala Ile Val Tyr Gln Ser Lys Phe Leu Thr Leu Asn Gly Lys
    210                 215                 220

Lys Tyr Tyr Phe Asp Asn Asn Ser Lys Ala Val Thr Gly Trp Gln Thr
225                 230                 235                 240

Ile Asp Ser Lys Lys Tyr Tyr Phe Asn Thr Asn Thr Ala Glu Ala Ala
                245                 250                 255

Thr Gly Trp Gln Thr Ile Asp Gly Lys Lys Tyr Tyr Phe Asn Thr Asn
            260                 265                 270

Thr Ala Glu Ala Ala Thr Gly Trp Gln Thr Ile Asp Gly Lys Lys Tyr
        275                 280                 285

Tyr Phe Asn Thr Asn Thr Ala Ile Ala Ser Thr Gly Tyr Thr Ile Ile
    290                 295                 300

Asn Gly Lys His Phe Tyr Phe Asn Thr Asp Gly Ile Met Gln Ile Gly
305                 310                 315                 320

Val Phe Lys Gly Pro Asn Gly Phe Glu Tyr Phe Ala Pro Ala Asn Thr
                325                 330                 335

Asp Ala Asn Asn Ile Glu Gly Gln Ala Ile Leu Tyr Gln Asn Glu Phe
            340                 345                 350

-continued

```
Leu Thr Leu Asn Gly Lys Lys Tyr Tyr Phe Gly Ser Asp Ser Lys Ala
        355                 360                 365

Val Thr Gly Trp Arg Ile Ile Asn Asn Lys Lys Tyr Tyr Phe Asn Pro
    370                 375                 380

Asn Asn Ala Ile Ala Ala Ile His Leu Cys Thr Ile Asn Asn Asp Lys
385                 390                 395                 400

Tyr Tyr Phe Ser Tyr Asp Gly Ile Leu Gln Asn Gly Tyr Ile Thr Ile
                405                 410                 415

Glu Arg Asn Asn Phe Tyr Phe Asp Ala Asn Asn Glu Ser Lys Met Val
            420                 425                 430

Thr Gly Val Phe Lys Gly Pro Asn Gly Phe Glu Tyr Phe Ala Pro Ala
        435                 440                 445

Asn Thr His Asn Asn Asn Ile Glu Gly Gln Ala Ile Val Tyr Gln Asn
    450                 455                 460

Lys Phe Leu Thr Leu Asn Gly Lys Lys Tyr Tyr Phe Asp Asn Asp Ser
465                 470                 475                 480

Lys Ala Val Thr Gly Trp Gln Thr Ile Asp Gly Lys Lys Tyr Tyr Phe
                485                 490                 495

Asn Leu Asn Thr Ala Glu Ala Ala Thr Gly Trp Gln Thr Ile Asp Gly
            500                 505                 510

Lys Lys Tyr Tyr Phe Asn Leu Asn Thr Ala Glu Ala Ala Thr Gly Trp
        515                 520                 525

Gln Thr Ile Asp Gly Lys Lys Tyr Tyr Phe Asn Thr Asn Thr Phe Ile
    530                 535                 540

Ala Ser Thr Gly Tyr Thr Ser Ile Asn Gly Lys His Phe Tyr Phe Asn
545                 550                 555                 560

Thr Asp Gly Ile Met Gln Ile Gly Val Phe Lys Gly Pro Asn Gly Phe
                565                 570                 575

Glu Tyr Phe Ala Pro Ala Asn Thr His Asn Asn Asn Ile Glu Gly Gln
            580                 585                 590

Ala Ile Leu Tyr Gln Asn Lys Phe Leu Thr Leu Asn Gly Lys Lys Tyr
        595                 600                 605

Tyr Phe Gly Ser Asp Ser Lys Ala Val Thr Gly Leu Arg Thr Ile Asp
    610                 615                 620

Gly Lys Lys Tyr Tyr Phe Asn Thr Asn Thr Ala Val Ala Val Thr Gly
625                 630                 635                 640

Trp Gln Thr Ile Asn Gly Lys Lys Tyr Tyr Phe Asn Thr Asn Thr Ser
                645                 650                 655

Ile Ala Ser Thr Gly Tyr Thr Ile Ile Ser Gly Lys His Phe Tyr Phe
            660                 665                 670

Asn Thr Asp Gly Ile Met Gln Ile Gly Val Phe Lys Gly Pro Asp Gly
        675                 680                 685

Phe Glu Tyr Phe Ala Pro Ala Asn Thr Asp Ala Asn Asn Ile Glu Gly
    690                 695                 700

Gln Ala Ile Arg Tyr Gln Asn Arg Phe Leu Tyr Leu His Asp Asn Ile
705                 710                 715                 720

Tyr Tyr Phe Gly Asn Asn Ser Lys Ala Ala Thr Gly Trp Val Thr Ile
                725                 730                 735

Asp Gly Asn Arg Tyr Tyr Phe Glu Pro Asn Thr Ala Met Gly Ala Asn
            740                 745                 750

Gly Tyr Lys Thr Ile Asp Asn Lys Asn Phe Tyr Phe Arg Asn Gly Leu
        755                 760                 765
```

-continued

```
Pro Gln Ile Gly Val Phe Lys Gly Ser Asn Gly Phe Glu Tyr Phe Ala
    770                 775                 780

Pro Ala Asn Thr Asp Ala Asn Asn Ile Glu Gly Gln Ala Ile Arg Tyr
785                 790                 795                 800

Gln Asn Arg Phe Leu His Leu Leu Gly Lys Ile Tyr Tyr Phe Gly Asn
                805                 810                 815

Asn Ser Lys Ala Val Thr Gly Trp Gln Thr Ile Asn Gly Lys Val Tyr
            820                 825                 830

Tyr Phe Met Pro Asp Thr Ala Met Ala Ala Ala Gly Gly Leu Phe Glu
        835                 840                 845

Ile Asp Gly Val Ile Tyr Phe Phe Gly Val Asp Gly Val Lys Ala Pro
    850                 855                 860


<210> SEQ ID NO 13
<211> LENGTH: 403
<212> TYPE: PRT
<213> ORGANISM: Clostridium difficile

<400> SEQUENCE: 13

Tyr Gln Asn Lys Phe Leu Thr Leu Asn Gly Lys Lys Tyr Tyr Phe Asp
1               5                   10                  15

Asn Asp Ser Lys Ala Val Thr Gly Trp Gln Thr Ile Asp Gly Lys Lys
            20                  25                  30

Tyr Tyr Phe Asn Leu Asn Thr Ala Glu Ala Ala Thr Gly Trp Gln Thr
        35                  40                  45

Ile Asp Gly Lys Lys Tyr Tyr Phe Asn Leu Asn Thr Ala Glu Ala Ala
    50                  55                  60

Thr Gly Trp Gln Thr Ile Asp Gly Lys Lys Tyr Tyr Phe Asn Thr Asn
65                  70                  75                  80

Thr Phe Ile Ala Ser Thr Gly Tyr Thr Ser Ile Asn Gly Lys His Phe
                85                  90                  95

Tyr Phe Asn Thr Asp Gly Ile Met Gln Ile Gly Val Phe Lys Gly Pro
            100                 105                 110

Asn Gly Phe Glu Tyr Phe Ala Pro Ala Asn Thr His Asn Asn Asn Ile
        115                 120                 125

Glu Gly Gln Ala Ile Leu Tyr Gln Asn Lys Phe Leu Thr Leu Asn Gly
    130                 135                 140

Lys Lys Tyr Tyr Phe Gly Ser Asp Ser Lys Ala Val Thr Gly Leu Arg
145                 150                 155                 160

Thr Ile Asp Gly Lys Lys Tyr Tyr Phe Asn Thr Asn Thr Ala Val Ala
                165                 170                 175

Val Thr Gly Trp Gln Thr Ile Asn Gly Lys Lys Tyr Tyr Phe Asn Thr
            180                 185                 190

Asn Thr Ser Ile Ala Ser Thr Gly Tyr Thr Ile Ile Ser Gly Lys His
        195                 200                 205

Phe Tyr Phe Asn Thr Asp Gly Ile Met Gln Ile Gly Val Phe Lys Gly
    210                 215                 220

Pro Asp Gly Phe Glu Tyr Phe Ala Pro Ala Asn Thr Asp Ala Asn Asn
225                 230                 235                 240

Ile Glu Gly Gln Ala Ile Arg Tyr Gln Asn Arg Phe Leu Tyr Leu His
                245                 250                 255

Asp Asn Ile Tyr Tyr Phe Gly Asn Asn Ser Lys Ala Ala Thr Gly Trp
            260                 265                 270

Val Thr Ile Asp Gly Asn Arg Tyr Tyr Phe Glu Pro Asn Thr Ala Met
        275                 280                 285
```

```
Gly Ala Asn Gly Tyr Lys Thr Ile Asp Asn Lys Asn Phe Tyr Phe Arg
    290                 295                 300

Asn Gly Leu Pro Gln Ile Gly Val Phe Lys Gly Ser Asn Gly Phe Glu
305                 310                 315                 320

Tyr Phe Ala Pro Ala Asn Thr Asp Ala Asn Asn Ile Glu Gly Gln Ala
                325                 330                 335

Ile Arg Tyr Gln Asn Arg Phe Leu His Leu Leu Gly Lys Ile Tyr Tyr
            340                 345                 350

Phe Gly Asn Asn Ser Lys Ala Val Thr Gly Trp Gln Thr Ile Asn Gly
        355                 360                 365

Lys Val Tyr Tyr Phe Met Pro Asp Thr Ala Met Ala Ala Ala Gly Gly
    370                 375                 380

Leu Phe Glu Ile Asp Gly Val Ile Tyr Phe Phe Gly Val Asp Gly Val
385                 390                 395                 400

Lys Ala Pro
```

<210> SEQ ID NO 14
<211> LENGTH: 872
<212> TYPE: PRT
<213> ORGANISM: Clostridium difficile

<400> SEQUENCE: 14

```
Ser Leu Phe Tyr Phe Asp Pro Ile Glu Phe Asn Leu Val Thr Gly Trp
1               5                   10                  15

Gln Thr Ile Asn Gly Lys Lys Tyr Tyr Phe Asp Ile Asn Thr Gly Ala
            20                  25                  30

Ala Leu Ile Ser Tyr Lys Ile Ile Asn Gly Lys His Phe Tyr Phe Asn
        35                  40                  45

Asn Asp Gly Val Met Gln Leu Gly Val Phe Lys Gly Pro Asp Gly Phe
    50                  55                  60

Glu Tyr Phe Ala Pro Ala Asn Thr Gln Asn Asn Asn Ile Glu Gly Gln
65                  70                  75                  80

Ala Ile Val Tyr Gln Ser Lys Phe Leu Thr Leu Asn Gly Lys Lys Tyr
                85                  90                  95

Tyr Phe Asp Asn Asp Ser Lys Ala Val Thr Gly Trp Arg Ile Ile Asn
            100                 105                 110

Asn Glu Lys Tyr Tyr Phe Asn Pro Asn Asn Ala Ile Ala Ala Val Gly
        115                 120                 125

Leu Gln Val Ile Asp Asn Asn Lys Tyr Tyr Phe Asn Pro Asp Thr Ala
    130                 135                 140

Ile Ile Ser Lys Gly Trp Gln Thr Val Asn Gly Ser Arg Tyr Tyr Phe
145                 150                 155                 160

Asp Thr Asp Thr Ala Ile Ala Phe Asn Gly Tyr Lys Thr Ile Asp Gly
                165                 170                 175

Lys His Phe Tyr Phe Asp Ser Asp Cys Val Val Lys Ile Gly Val Phe
            180                 185                 190

Ser Thr Ser Asn Gly Phe Glu Tyr Phe Ala Pro Ala Asn Thr Tyr Asn
        195                 200                 205

Asn Asn Ile Glu Gly Gln Ala Ile Val Tyr Gln Ser Lys Phe Leu Thr
    210                 215                 220

Leu Asn Gly Lys Lys Tyr Tyr Phe Asp Asn Asn Ser Lys Ala Val Thr
225                 230                 235                 240

Gly Trp Gln Thr Ile Asp Ser Lys Lys Tyr Tyr Phe Asn Thr Asn Thr
                245                 250                 255
```

-continued

```
Ala Glu Ala Ala Thr Gly Trp Gln Thr Ile Asp Gly Lys Lys Tyr Tyr
            260                 265                 270

Phe Asn Thr Asn Thr Ala Glu Ala Ala Thr Gly Trp Gln Thr Ile Asp
        275                 280                 285

Gly Lys Lys Tyr Tyr Phe Asn Thr Asn Thr Ala Ile Ala Ser Thr Gly
    290                 295                 300

Tyr Thr Ile Ile Asn Gly Lys His Phe Tyr Phe Asn Thr Asp Gly Ile
305                 310                 315                 320

Met Gln Ile Gly Val Phe Lys Gly Pro Asn Gly Phe Glu Tyr Phe Ala
                325                 330                 335

Pro Ala Asn Thr Asp Ala Asn Asn Ile Glu Gly Gln Ala Ile Leu Tyr
            340                 345                 350

Gln Asn Glu Phe Leu Thr Leu Asn Gly Lys Lys Tyr Tyr Phe Gly Ser
        355                 360                 365

Asp Ser Lys Ala Val Thr Gly Trp Arg Ile Ile Asn Asn Lys Lys Tyr
    370                 375                 380

Tyr Phe Asn Pro Asn Asn Ala Ile Ala Ala Ile His Leu Cys Thr Ile
385                 390                 395                 400

Asn Asn Asp Lys Tyr Tyr Phe Ser Tyr Asp Gly Ile Leu Gln Asn Gly
                405                 410                 415

Tyr Ile Thr Ile Glu Arg Asn Asn Phe Tyr Phe Asp Ala Asn Asn Glu
            420                 425                 430

Ser Lys Met Val Thr Gly Val Phe Lys Gly Pro Asn Gly Phe Glu Tyr
        435                 440                 445

Phe Ala Pro Ala Asn Thr His Asn Asn Asn Ile Glu Gly Gln Ala Ile
    450                 455                 460

Val Tyr Gln Asn Lys Phe Leu Thr Leu Asn Gly Lys Lys Tyr Tyr Phe
465                 470                 475                 480

Asp Asn Asp Ser Lys Ala Val Thr Gly Trp Gln Thr Ile Asp Gly Lys
                485                 490                 495

Lys Tyr Tyr Phe Asn Leu Asn Thr Ala Glu Ala Ala Thr Gly Trp Gln
            500                 505                 510

Thr Ile Asp Gly Lys Lys Tyr Tyr Phe Asn Leu Asn Thr Ala Glu Ala
        515                 520                 525

Ala Thr Gly Trp Gln Thr Ile Asp Gly Lys Lys Tyr Tyr Phe Asn Thr
    530                 535                 540

Asn Thr Phe Ile Ala Ser Thr Gly Tyr Thr Ser Ile Asn Gly Lys His
545                 550                 555                 560

Phe Tyr Phe Asn Thr Asp Gly Ile Met Gln Ile Gly Val Phe Lys Gly
                565                 570                 575

Pro Asn Gly Phe Glu Tyr Phe Ala Pro Ala Asn Thr His Asn Asn Asn
            580                 585                 590

Ile Glu Gly Gln Ala Ile Leu Tyr Gln Asn Lys Phe Leu Thr Leu Asn
        595                 600                 605

Gly Lys Lys Tyr Tyr Phe Gly Ser Asp Ser Lys Ala Val Thr Gly Leu
    610                 615                 620

Arg Thr Ile Asp Gly Lys Lys Tyr Tyr Phe Asn Thr Asn Thr Ala Val
625                 630                 635                 640

Ala Val Thr Gly Trp Gln Thr Ile Asn Gly Lys Lys Tyr Tyr Phe Asn
                645                 650                 655

Thr Asn Thr Ser Ile Ala Ser Thr Gly Tyr Thr Ile Ile Ser Gly Lys
            660                 665                 670
```

-continued

```
His Phe Tyr Phe Asn Thr Asp Gly Ile Met Gln Ile Gly Val Phe Lys
        675                 680                 685

Gly Pro Asp Gly Phe Glu Tyr Phe Ala Pro Ala Asn Thr Asp Ala Asn
    690                 695                 700

Asn Ile Glu Gly Gln Ala Ile Arg Tyr Gln Asn Arg Phe Leu Tyr Leu
705                 710                 715                 720

His Asp Asn Ile Tyr Tyr Phe Gly Asn Asn Ser Lys Ala Ala Thr Gly
                725                 730                 735

Trp Val Thr Ile Asp Gly Asn Arg Tyr Tyr Phe Glu Pro Asn Thr Ala
            740                 745                 750

Met Gly Ala Asn Gly Tyr Lys Thr Ile Asp Asn Lys Asn Phe Tyr Phe
        755                 760                 765

Arg Asn Gly Leu Pro Gln Ile Gly Val Phe Lys Gly Ser Asn Gly Phe
    770                 775                 780

Glu Tyr Phe Ala Pro Ala Asn Thr Asp Ala Asn Asn Ile Glu Gly Gln
785                 790                 795                 800

Ala Ile Arg Tyr Gln Asn Arg Phe Leu His Leu Leu Gly Lys Ile Tyr
                805                 810                 815

Tyr Phe Gly Asn Asn Ser Lys Ala Val Thr Gly Trp Gln Thr Ile Asn
            820                 825                 830

Gly Lys Val Tyr Tyr Phe Met Pro Asp Thr Ala Met Ala Ala Ala Gly
        835                 840                 845

Gly Leu Phe Glu Ile Asp Gly Val Ile Tyr Phe Phe Gly Val Asp Gly
    850                 855                 860

Val Lys Ala Pro Gly Ile Tyr Gly
865                 870
```

<210> SEQ ID NO 15
<211> LENGTH: 743
<212> TYPE: PRT
<213> ORGANISM: Clostridium difficile

<400> SEQUENCE: 15

```
Ala Val Gly Leu Gln Val Ile Asp Asn Asn Lys Tyr Tyr Phe Asn Pro
1               5                   10                  15

Asp Thr Ala Ile Ile Ser Lys Gly Trp Gln Thr Val Asn Gly Ser Arg
            20                  25                  30

Tyr Tyr Phe Asp Thr Asp Thr Ala Ile Ala Phe Asn Gly Tyr Lys Thr
        35                  40                  45

Ile Asp Gly Lys His Phe Tyr Phe Asp Ser Asp Cys Val Val Lys Ile
    50                  55                  60

Gly Val Phe Ser Thr Ser Asn Gly Phe Glu Tyr Phe Ala Pro Ala Asn
65                  70                  75                  80

Thr Tyr Asn Asn Asn Ile Glu Gly Gln Ala Ile Val Tyr Gln Ser Lys
                85                  90                  95

Phe Leu Thr Leu Asn Gly Lys Lys Tyr Tyr Phe Asp Asn Asn Ser Lys
            100                 105                 110

Ala Val Thr Gly Trp Gln Thr Ile Asp Ser Lys Lys Tyr Tyr Phe Asn
        115                 120                 125

Thr Asn Thr Ala Glu Ala Ala Thr Gly Trp Gln Thr Ile Asp Gly Lys
    130                 135                 140

Lys Tyr Tyr Phe Asn Thr Asn Thr Ala Glu Ala Ala Thr Gly Trp Gln
145                 150                 155                 160

Thr Ile Asp Gly Lys Lys Tyr Tyr Phe Asn Thr Asn Thr Ala Ile Ala
                165                 170                 175
```

-continued

```
Ser Thr Gly Tyr Thr Ile Ile Asn Gly Lys His Phe Tyr Phe Asn Thr
            180                 185                 190

Asp Gly Ile Met Gln Ile Gly Val Phe Lys Gly Pro Asn Gly Phe Glu
        195                 200                 205

Tyr Phe Ala Pro Ala Asn Thr Asp Ala Asn Asn Ile Glu Gly Gln Ala
    210                 215                 220

Ile Leu Tyr Gln Asn Glu Phe Leu Thr Leu Asn Gly Lys Lys Tyr Tyr
225                 230                 235                 240

Phe Gly Ser Asp Ser Lys Ala Val Thr Gly Trp Arg Ile Ile Asn Asn
                245                 250                 255

Lys Lys Tyr Tyr Phe Asn Pro Asn Asn Ala Ile Ala Ala Ile His Leu
            260                 265                 270

Cys Thr Ile Asn Asn Asp Lys Tyr Tyr Phe Ser Tyr Asp Gly Ile Leu
        275                 280                 285

Gln Asn Gly Tyr Ile Thr Ile Glu Arg Asn Asn Phe Tyr Phe Asp Ala
    290                 295                 300

Asn Asn Glu Ser Lys Met Val Thr Gly Val Phe Lys Gly Pro Asn Gly
305                 310                 315                 320

Phe Glu Tyr Phe Ala Pro Ala Asn Thr His Asn Asn Asn Ile Glu Gly
                325                 330                 335

Gln Ala Ile Val Tyr Gln Asn Lys Phe Leu Thr Leu Asn Gly Lys Lys
            340                 345                 350

Tyr Tyr Phe Asp Asn Asp Ser Lys Ala Val Thr Gly Trp Gln Thr Ile
        355                 360                 365

Asp Gly Lys Lys Tyr Tyr Phe Asn Leu Asn Thr Ala Glu Ala Ala Thr
    370                 375                 380

Gly Trp Gln Thr Ile Asp Gly Lys Lys Tyr Tyr Phe Asn Leu Asn Thr
385                 390                 395                 400

Ala Glu Ala Ala Thr Gly Trp Gln Thr Ile Asp Gly Lys Lys Tyr Tyr
                405                 410                 415

Phe Asn Thr Asn Thr Phe Ile Ala Ser Thr Gly Tyr Thr Ser Ile Asn
            420                 425                 430

Gly Lys His Phe Tyr Phe Asn Thr Asp Gly Ile Met Gln Ile Gly Val
        435                 440                 445

Phe Lys Gly Pro Asn Gly Phe Glu Tyr Phe Ala Pro Ala Asn Thr His
    450                 455                 460

Asn Asn Asn Ile Glu Gly Gln Ala Ile Leu Tyr Gln Asn Lys Phe Leu
465                 470                 475                 480

Thr Leu Asn Gly Lys Lys Tyr Tyr Phe Gly Ser Asp Ser Lys Ala Val
                485                 490                 495

Thr Gly Leu Arg Thr Ile Asp Gly Lys Lys Tyr Tyr Phe Asn Thr Asn
            500                 505                 510

Thr Ala Val Ala Val Thr Gly Trp Gln Thr Ile Asn Gly Lys Lys Tyr
        515                 520                 525

Tyr Phe Asn Thr Asn Thr Ser Ile Ala Ser Thr Gly Tyr Thr Ile Ile
    530                 535                 540

Ser Gly Lys His Phe Tyr Phe Asn Thr Asp Gly Ile Met Gln Ile Gly
545                 550                 555                 560

Val Phe Lys Gly Pro Asp Gly Phe Glu Tyr Phe Ala Pro Ala Asn Thr
                565                 570                 575

Asp Ala Asn Asn Ile Glu Gly Gln Ala Ile Arg Tyr Gln Asn Arg Phe
            580                 585                 590
```

```
Leu Tyr Leu His Asp Asn Ile Tyr Tyr Phe Gly Asn Asn Ser Lys Ala
        595                 600                 605

Ala Thr Gly Trp Val Thr Ile Asp Gly Asn Arg Tyr Tyr Phe Glu Pro
    610                 615                 620

Asn Thr Ala Met Gly Ala Asn Gly Tyr Lys Thr Ile Asp Asn Lys Asn
625                 630                 635                 640

Phe Tyr Phe Arg Asn Gly Leu Pro Gln Ile Gly Val Phe Lys Gly Ser
                645                 650                 655

Asn Gly Phe Glu Tyr Phe Ala Pro Ala Asn Thr Asp Ala Asn Asn Ile
            660                 665                 670

Glu Gly Gln Ala Ile Arg Tyr Gln Asn Arg Phe Leu His Leu Leu Gly
        675                 680                 685

Lys Ile Tyr Tyr Phe Gly Asn Asn Ser Lys Ala Val Thr Gly Trp Gln
    690                 695                 700

Thr Ile Asn Gly Lys Val Tyr Tyr Phe Met Pro Asp Thr Ala Met Ala
705                 710                 715                 720

Ala Ala Gly Gly Leu Phe Glu Ile Asp Gly Val Ile Tyr Phe Phe Gly
                725                 730                 735

Val Asp Gly Val Lys Ala Pro
            740


<210> SEQ ID NO 16
<211> LENGTH: 816
<212> TYPE: PRT
<213> ORGANISM: Clostridium difficile

<400> SEQUENCE: 16

Met Gln Leu Gly Val Phe Lys Gly Pro Asp Gly Phe Glu Tyr Phe Ala
1               5                   10                  15

Pro Ala Asn Thr Gln Asn Asn Asn Ile Glu Gly Gln Ala Ile Val Tyr
            20                  25                  30

Gln Ser Lys Phe Leu Thr Leu Asn Gly Lys Lys Tyr Tyr Phe Asp Asn
        35                  40                  45

Asp Ser Lys Ala Val Thr Gly Trp Arg Ile Ile Asn Asn Glu Lys Tyr
    50                  55                  60

Tyr Phe Asn Pro Asn Asn Ala Ile Ala Ala Val Gly Leu Gln Val Ile
65                  70                  75                  80

Asp Asn Asn Lys Tyr Tyr Phe Asn Pro Asp Thr Ala Ile Ile Ser Lys
                85                  90                  95

Gly Trp Gln Thr Val Asn Gly Ser Arg Tyr Tyr Phe Asp Thr Asp Thr
            100                 105                 110

Ala Ile Ala Phe Asn Gly Tyr Lys Thr Ile Asp Gly Lys His Phe Tyr
        115                 120                 125

Phe Asp Ser Asp Cys Val Val Lys Ile Gly Val Phe Ser Thr Ser Asn
    130                 135                 140

Gly Phe Glu Tyr Phe Ala Pro Ala Asn Thr Tyr Asn Asn Asn Ile Glu
145                 150                 155                 160

Gly Gln Ala Ile Val Tyr Gln Ser Lys Phe Leu Thr Leu Asn Gly Lys
                165                 170                 175

Lys Tyr Tyr Phe Asp Asn Asn Ser Lys Ala Val Thr Gly Trp Gln Thr
            180                 185                 190

Ile Asp Ser Lys Lys Tyr Tyr Phe Asn Thr Asn Thr Ala Glu Ala Ala
        195                 200                 205

Thr Gly Trp Gln Thr Ile Asp Gly Lys Lys Tyr Tyr Phe Asn Thr Asn
    210                 215                 220
```

Thr Ala Glu Ala Ala Thr Gly Trp Gln Thr Ile Asp Gly Lys Lys Tyr
225 230 235 240

Tyr Phe Asn Thr Asn Thr Ala Ile Ala Ser Thr Gly Tyr Thr Ile Ile
245 250 255

Asn Gly Lys His Phe Tyr Phe Asn Thr Asp Gly Ile Met Gln Ile Gly
260 265 270

Val Phe Lys Gly Pro Asn Gly Phe Glu Tyr Phe Ala Pro Ala Asn Thr
275 280 285

Asp Ala Asn Asn Ile Glu Gly Gln Ala Ile Leu Tyr Gln Asn Glu Phe
290 295 300

Leu Thr Leu Asn Gly Lys Lys Tyr Tyr Phe Gly Ser Asp Ser Lys Ala
305 310 315 320

Val Thr Gly Trp Arg Ile Ile Asn Asn Lys Lys Tyr Tyr Phe Asn Pro
325 330 335

Asn Asn Ala Ile Ala Ala Ile His Leu Cys Thr Ile Asn Asn Asp Lys
340 345 350

Tyr Tyr Phe Ser Tyr Asp Gly Ile Leu Gln Asn Gly Tyr Ile Thr Ile
355 360 365

Glu Arg Asn Asn Phe Tyr Phe Asp Ala Asn Asn Glu Ser Lys Met Val
370 375 380

Thr Gly Val Phe Lys Gly Pro Asn Gly Phe Glu Tyr Phe Ala Pro Ala
385 390 395 400

Asn Thr His Asn Asn Asn Ile Glu Gly Gln Ala Ile Val Tyr Gln Asn
405 410 415

Lys Phe Leu Thr Leu Asn Gly Lys Lys Tyr Tyr Phe Asp Asn Asp Ser
420 425 430

Lys Ala Val Thr Gly Trp Gln Thr Ile Asp Gly Lys Lys Tyr Tyr Phe
435 440 445

Asn Leu Asn Thr Ala Glu Ala Ala Thr Gly Trp Gln Thr Ile Asp Gly
450 455 460

Lys Lys Tyr Tyr Phe Asn Leu Asn Thr Ala Glu Ala Ala Thr Gly Trp
465 470 475 480

Gln Thr Ile Asp Gly Lys Lys Tyr Tyr Phe Asn Thr Asn Thr Phe Ile
485 490 495

Ala Ser Thr Gly Tyr Thr Ser Ile Asn Gly Lys His Phe Tyr Phe Asn
500 505 510

Thr Asp Gly Ile Met Gln Ile Gly Val Phe Lys Gly Pro Asn Gly Phe
515 520 525

Glu Tyr Phe Ala Pro Ala Asn Thr His Asn Asn Asn Ile Glu Gly Gln
530 535 540

Ala Ile Leu Tyr Gln Asn Lys Phe Leu Thr Leu Asn Gly Lys Lys Tyr
545 550 555 560

Tyr Phe Gly Ser Asp Ser Lys Ala Val Thr Gly Leu Arg Thr Ile Asp
565 570 575

Gly Lys Lys Tyr Tyr Phe Asn Thr Asn Thr Ala Val Ala Val Thr Gly
580 585 590

Trp Gln Thr Ile Asn Gly Lys Lys Tyr Tyr Phe Asn Thr Asn Thr Ser
595 600 605

Ile Ala Ser Thr Gly Tyr Thr Ile Ile Ser Gly Lys His Phe Tyr Phe
610 615 620

Asn Thr Asp Gly Ile Met Gln Ile Gly Val Phe Lys Gly Pro Asp Gly
625 630 635 640

-continued

```
Phe Glu Tyr Phe Ala Pro Ala Asn Thr Asp Ala Asn Asn Ile Glu Gly
                645                 650                 655

Gln Ala Ile Arg Tyr Gln Asn Arg Phe Leu Tyr Leu His Asp Asn Ile
            660                 665                 670

Tyr Tyr Phe Gly Asn Asn Ser Lys Ala Ala Thr Gly Trp Val Thr Ile
        675                 680                 685

Asp Gly Asn Arg Tyr Tyr Phe Glu Pro Asn Thr Ala Met Gly Ala Asn
    690                 695                 700

Gly Tyr Lys Thr Ile Asp Asn Lys Asn Phe Tyr Phe Arg Asn Gly Leu
705                 710                 715                 720

Pro Gln Ile Gly Val Phe Lys Gly Ser Asn Gly Phe Glu Tyr Phe Ala
                725                 730                 735

Pro Ala Asn Thr Asp Ala Asn Asn Ile Glu Gly Gln Ala Ile Arg Tyr
            740                 745                 750

Gln Asn Arg Phe Leu His Leu Leu Gly Lys Ile Tyr Tyr Phe Gly Asn
        755                 760                 765

Asn Ser Lys Ala Val Thr Gly Trp Gln Thr Ile Asn Gly Lys Val Tyr
    770                 775                 780

Tyr Phe Met Pro Asp Thr Ala Met Ala Ala Ala Gly Gly Leu Phe Glu
785                 790                 795                 800

Ile Asp Gly Val Ile Tyr Phe Phe Gly Val Asp Gly Val Lys Ala Pro
                805                 810                 815


<210> SEQ ID NO 17
<211> LENGTH: 767
<212> TYPE: PRT
<213> ORGANISM: Clostridium difficile

<400> SEQUENCE: 17

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205
```

-continued

```
Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu Gly
    530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
        595                 600                 605

Gln Lys Asn Ile Glu Asp Ser Glu Ile Ala Tyr Tyr Tyr Asn Pro Gly
    610                 615                 620
```

```
Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
            660                 665                 670

Thr Glu Ile Glu Ala Ala Ile Asp Leu Ala Lys Glu Asp Ile Ser Pro
        675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
            740                 745                 750

Glu Leu Leu Asp His Ser Gly Glu Trp Ile Asn Lys Glu Glu Ser
        755                 760                 765


<210> SEQ ID NO 18
<211> LENGTH: 543
<212> TYPE: PRT
<213> ORGANISM: Clostridium difficile

<400> SEQUENCE: 18

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240
```

-continued

```
Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
            500                 505                 510

Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu
    530                 535                 540


<210> SEQ ID NO 19
<211> LENGTH: 224
<212> TYPE: PRT
<213> ORGANISM: Clostridium difficile

<400> SEQUENCE: 19

Gly Glu Asp Asp Asn Leu Asp Phe Ser Gln Asn Ile Val Val Asp Lys
1               5                   10                  15

Glu Tyr Leu Leu Glu Lys Ile Ser Ser Leu Ala Arg Ser Ser Glu Arg
            20                  25                  30

Gly Tyr Ile His Tyr Ile Val Gln Leu Gln Gly Asp Lys Ile Ser Tyr
        35                  40                  45

Glu Ala Ala Cys Asn Leu Phe Ala Lys Thr Pro Tyr Asp Ser Val Leu
    50                  55                  60

Phe Gln Lys Asn Ile Glu Asp Ser Glu Ile Ala Tyr Tyr Tyr Asn Pro
```

```
65                  70                  75                  80

Gly Asp Gly Glu Ile Gln Glu Ile Asp Lys Tyr Lys Ile Pro Ser Ile
                85                  90                  95

Ile Ser Asp Arg Pro Lys Ile Lys Leu Thr Phe Ile Gly His Gly Lys
            100                 105                 110

Asp Glu Phe Asn Thr Asp Ile Phe Ala Gly Phe Asp Val Asp Ser Leu
        115                 120                 125

Ser Thr Glu Ile Glu Ala Ala Ile Asp Leu Ala Lys Glu Asp Ile Ser
    130                 135                 140

Pro Lys Ser Ile Glu Ile Asn Leu Leu Gly Cys Asn Met Phe Ser Tyr
145                 150                 155                 160

Ser Ile Asn Val Glu Glu Thr Tyr Pro Gly Lys Leu Leu Leu Lys Val
                165                 170                 175

Lys Asp Lys Ile Ser Glu Leu Met Pro Ser Ile Ser Gln Asp Ser Ile
            180                 185                 190

Ile Val Ser Ala Asn Gln Tyr Glu Val Arg Ile Asn Ser Glu Gly Arg
        195                 200                 205

Arg Glu Leu Leu Asp His Ser Gly Glu Trp Ile Asn Lys Glu Glu Ser
    210                 215                 220


<210> SEQ ID NO 20
<211> LENGTH: 1066
<212> TYPE: PRT
<213> ORGANISM: Clostridium difficile

<400> SEQUENCE: 20

Ile Ile Lys Asp Ile Ser Ser Lys Glu Tyr Ile Ser Phe Asn Pro Lys
1               5                   10                  15

Glu Asn Lys Ile Thr Val Lys Ser Lys Asn Leu Pro Glu Leu Ser Thr
            20                  25                  30

Leu Leu Gln Glu Ile Arg Asn Asn Ser Asn Ser Ser Asp Ile Glu Leu
        35                  40                  45

Glu Glu Lys Val Met Leu Thr Glu Cys Glu Ile Asn Val Ile Ser Asn
    50                  55                  60

Ile Asp Thr Gln Ile Val Glu Glu Arg Ile Glu Glu Ala Lys Asn Leu
65                  70                  75                  80

Thr Ser Asp Ser Ile Asn Tyr Ile Lys Asp Glu Phe Lys Leu Ile Glu
                85                  90                  95

Ser Ile Ser Asp Ala Leu Cys Asp Leu Lys Gln Gln Asn Glu Leu Glu
            100                 105                 110

Asp Ser His Phe Ile Ser Phe Glu Asp Ile Ser Glu Thr Asp Glu Gly
        115                 120                 125

Phe Ser Ile Arg Phe Ile Asn Lys Glu Thr Gly Glu Ser Ile Phe Val
    130                 135                 140

Glu Thr Glu Lys Thr Ile Phe Ser Glu Tyr Ala Asn His Ile Thr Glu
145                 150                 155                 160

Glu Ile Ser Lys Ile Lys Gly Thr Ile Phe Asp Thr Val Asn Gly Lys
                165                 170                 175

Leu Val Lys Lys Val Asn Leu Asp Thr Thr His Glu Val Asn Thr Leu
            180                 185                 190

Asn Ala Ala Phe Phe Ile Gln Ser Leu Ile Glu Tyr Asn Ser Ser Lys
        195                 200                 205

Glu Ser Leu Ser Asn Leu Ser Val Ala Met Lys Val Gln Val Tyr Ala
    210                 215                 220
```

Gln Leu Phe Ser Thr Gly Leu Asn Thr Ile Thr Asp Ala Ala Lys Val
225 230 235 240

Val Glu Leu Val Ser Thr Ala Leu Asp Glu Thr Ile Asp Leu Leu Pro
245 250 255

Thr Leu Ser Glu Gly Leu Pro Ile Ile Ala Thr Ile Ile Asp Gly Val
260 265 270

Ser Leu Gly Ala Ala Ile Lys Glu Leu Ser Glu Thr Ser Asp Pro Leu
275 280 285

Leu Arg Gln Glu Ile Glu Ala Lys Ile Gly Ile Met Ala Val Asn Leu
290 295 300

Thr Thr Ala Thr Thr Ala Ile Ile Thr Ser Ser Leu Gly Ile Ala Ser
305 310 315 320

Gly Phe Ser Ile Leu Leu Val Pro Leu Ala Gly Ile Ser Ala Gly Ile
325 330 335

Pro Ser Leu Val Asn Asn Glu Leu Val Leu Arg Asp Lys Ala Thr Lys
340 345 350

Val Val Asp Tyr Phe Lys His Val Ser Leu Val Glu Thr Glu Gly Val
355 360 365

Phe Thr Leu Leu Asp Asp Lys Ile Met Met Pro Gln Asp Asp Leu Val
370 375 380

Ile Ser Glu Ile Asp Phe Asn Asn Asn Ser Ile Val Leu Gly Lys Cys
385 390 395 400

Glu Ile Trp Arg Met Glu Gly Gly Ser Gly His Thr Val Thr Asp Asp
405 410 415

Ile Asp His Phe Phe Ser Ala Pro Ser Ile Thr Tyr Arg Glu Pro His
420 425 430

Leu Ser Ile Tyr Asp Val Leu Glu Val Gln Lys Glu Glu Leu Asp Leu
435 440 445

Ser Lys Asp Leu Met Val Leu Pro Asn Ala Pro Asn Arg Val Phe Ala
450 455 460

Trp Glu Thr Gly Trp Thr Pro Gly Leu Arg Ser Leu Glu Asn Asp Gly
465 470 475 480

Thr Lys Leu Leu Asp Arg Ile Arg Asp Asn Tyr Glu Gly Glu Phe Tyr
485 490 495

Trp Arg Tyr Phe Ala Phe Ile Ala Asp Ala Leu Ile Thr Thr Leu Lys
500 505 510

Pro Arg Tyr Glu Asp Thr Asn Ile Arg Ile Asn Leu Asp Ser Asn Thr
515 520 525

Arg Ser Phe Ile Val Pro Ile Ile Thr Thr Glu Tyr Ile Arg Glu Lys
530 535 540

Leu Ser Tyr Ser Phe Tyr Gly Ser Gly Gly Thr Tyr Ala Leu Ser Leu
545 550 555 560

Ser Gln Tyr Asn Met Gly Ile Asn Ile Glu Leu Ser Glu Ser Asp Val
565 570 575

Trp Ile Ile Asp Val Asp Asn Val Val Arg Asp Val Thr Ile Glu Ser
580 585 590

Asp Lys Ile Lys Lys Gly Asp Leu Ile Glu Gly Ile Leu Ser Thr Leu
595 600 605

Ser Ile Glu Glu Asn Lys Ile Ile Leu Asn Ser His Glu Ile Asn Phe
610 615 620

Ser Gly Glu Val Asn Gly Ser Asn Gly Phe Val Ser Leu Thr Phe Ser
625 630 635 640

Ile Leu Glu Gly Ile Asn Ala Ile Ile Glu Val Asp Leu Leu Ser Lys

-continued

```
                645                 650                 655

Ser Tyr Lys Leu Leu Ile Ser Gly Glu Leu Lys Ile Leu Met Leu Asn
            660                 665                 670

Ser Asn His Ile Gln Gln Lys Ile Asp Tyr Ile Gly Phe Asn Ser Glu
        675                 680                 685

Leu Gln Lys Asn Ile Pro Tyr Ser Phe Val Asp Ser Glu Gly Lys Glu
    690                 695                 700

Asn Gly Phe Ile Asn Gly Ser Thr Lys Glu Gly Leu Phe Val Ser Glu
705                 710                 715                 720

Leu Pro Asp Val Val Leu Ile Ser Lys Val Tyr Met Asp Asp Ser Lys
                725                 730                 735

Pro Ser Phe Gly Tyr Tyr Ser Asn Asn Leu Lys Asp Val Lys Val Ile
            740                 745                 750

Thr Lys Asp Asn Val Asn Ile Leu Thr Gly Tyr Tyr Leu Lys Asp Asp
        755                 760                 765

Ile Lys Ile Ser Leu Ser Leu Thr Leu Gln Asp Glu Lys Thr Ile Lys
    770                 775                 780

Leu Asn Ser Val His Leu Asp Glu Ser Gly Val Ala Glu Ile Leu Lys
785                 790                 795                 800

Phe Met Asn Arg Lys Gly Asn Thr Asn Thr Ser Asp Ser Leu Met Ser
                805                 810                 815

Phe Leu Glu Ser Met Asn Ile Lys Ser Ile Phe Val Asn Phe Leu Gln
            820                 825                 830

Ser Asn Ile Lys Phe Ile Leu Asp Ala Asn Phe Ile Ile Ser Gly Thr
        835                 840                 845

Thr Ser Ile Gly Gln Phe Glu Phe Ile Cys Asp Glu Asn Asp Asn Ile
    850                 855                 860

Gln Pro Tyr Phe Ile Lys Phe Asn Thr Leu Glu Thr Asn Tyr Thr Leu
865                 870                 875                 880

Tyr Val Gly Asn Arg Gln Asn Met Ile Val Glu Pro Asn Tyr Asp Leu
                885                 890                 895

Asp Asp Ser Gly Asp Ile Ser Ser Thr Val Ile Asn Phe Ser Gln Lys
            900                 905                 910

Tyr Leu Tyr Gly Ile Asp Ser Cys Val Asn Lys Val Val Ile Ser Pro
        915                 920                 925

Asn Ile Tyr Thr Asp Glu Ile Asn Ile Thr Pro Val Tyr Glu Thr Asn
    930                 935                 940

Asn Thr Tyr Pro Glu Val Ile Val Leu Asp Ala Asn Tyr Ile Asn Glu
945                 950                 955                 960

Lys Ile Asn Val Asn Ile Asn Asp Leu Ser Ile Arg Tyr Val Trp Ser
                965                 970                 975

Asn Asp Gly Asn Asp Phe Ile Leu Met Ser Thr Ser Glu Glu Asn Lys
            980                 985                 990

Val Ser Gln Val Lys Ile Arg Phe  Val Asn Val Phe Lys  Asp Lys Thr
        995                 1000                1005

Leu Ala  Asn Lys Leu Ser Phe  Asn Phe Ser Asp Lys  Gln Asp Val
    1010                1015                1020

Pro Val  Ser Glu Ile Ile Leu  Ser Phe Thr Pro Ser  Tyr Tyr Glu
    1025                1030                1035

Asp Gly  Leu Ile Gly Tyr Asp  Leu Gly Leu Val Ser  Leu Tyr Asn
    1040                1045                1050

Glu Lys  Phe Tyr Ile Asn Asn  Phe Gly Met Met Val  Ser
    1055                1060                1065
```

<210> SEQ ID NO 21
<211> LENGTH: 514
<212> TYPE: PRT
<213> ORGANISM: Clostridium difficile

<400> SEQUENCE: 21

```
Ile Thr Gly Phe Val Thr Val Gly Asp Asp Lys Tyr Tyr Phe Asn Pro
1               5                   10                  15

Ile Asn Gly Gly Ala Ala Ser Ile Gly Glu Thr Ile Ile Asp Asp Lys
            20                  25                  30

Asn Tyr Tyr Phe Asn Gln Ser Gly Val Leu Gln Thr Gly Val Phe Ser
        35                  40                  45

Thr Glu Asp Gly Phe Lys Tyr Phe Ala Pro Ala Asn Thr Leu Asp Glu
    50                  55                  60

Asn Leu Glu Gly Glu Ala Ile Asp Phe Thr Gly Lys Leu Ile Ile Asp
65                  70                  75                  80

Glu Asn Ile Tyr Tyr Phe Asp Asp Asn Tyr Arg Gly Ala Val Glu Trp
                85                  90                  95

Lys Glu Leu Asp Gly Glu Met His Tyr Phe Ser Pro Glu Thr Gly Lys
            100                 105                 110

Ala Phe Lys Gly Leu Asn Gln Ile Gly Asp Tyr Lys Tyr Tyr Phe Asn
        115                 120                 125

Ser Asp Gly Val Met Gln Lys Gly Phe Val Ser Ile Asn Asp Asn Lys
    130                 135                 140

His Tyr Phe Asp Asp Ser Gly Val Met Lys Val Gly Tyr Thr Glu Ile
145                 150                 155                 160

Asp Gly Lys His Phe Tyr Phe Ala Glu Asn Gly Glu Met Gln Ile Gly
                165                 170                 175

Val Phe Asn Thr Glu Asp Gly Phe Lys Tyr Phe Ala His His Asn Glu
            180                 185                 190

Asp Leu Gly Asn Glu Glu Gly Glu Glu Ile Ser Tyr Ser Gly Ile Leu
        195                 200                 205

Asn Phe Asn Asn Lys Ile Tyr Tyr Phe Asp Asp Ser Phe Thr Ala Val
    210                 215                 220

Val Gly Trp Lys Asp Leu Glu Asp Gly Ser Lys Tyr Tyr Phe Asp Glu
225                 230                 235                 240

Asp Thr Ala Glu Ala Tyr Ile Gly Leu Ser Leu Ile Asn Asp Gly Gln
                245                 250                 255

Tyr Tyr Phe Asn Asp Asp Gly Ile Met Gln Val Gly Phe Val Thr Ile
            260                 265                 270

Asn Asp Lys Val Phe Tyr Phe Ser Asp Ser Gly Ile Ile Glu Ser Gly
        275                 280                 285

Val Gln Asn Ile Asp Asp Asn Tyr Phe Tyr Ile Asp Asp Asn Gly Ile
    290                 295                 300

Val Gln Ile Gly Val Phe Asp Thr Ser Asp Gly Tyr Lys Tyr Phe Ala
305                 310                 315                 320

Pro Ala Asn Thr Val Asn Asp Asn Ile Tyr Gly Gln Ala Val Glu Tyr
                325                 330                 335

Ser Gly Leu Val Arg Val Gly Glu Asp Val Tyr Tyr Phe Gly Glu Thr
            340                 345                 350

Tyr Thr Ile Glu Thr Gly Trp Ile Tyr Asp Met Glu Asn Glu Ser Asp
        355                 360                 365

Lys Tyr Tyr Phe Asn Pro Glu Thr Lys Lys Ala Cys Lys Gly Ile Asn
```

-continued

```
    370                 375                 380

Leu Ile Asp Asp Ile Lys Tyr Tyr Phe Asp Glu Lys Gly Ile Met Arg
385                 390                 395                 400

Thr Gly Leu Ile Ser Phe Glu Asn Asn Asn Tyr Tyr Phe Asn Glu Asn
                405                 410                 415

Gly Glu Met Gln Phe Gly Tyr Ile Asn Ile Glu Asp Lys Met Phe Tyr
            420                 425                 430

Phe Gly Glu Asp Gly Val Met Gln Ile Gly Val Phe Asn Thr Pro Asp
        435                 440                 445

Gly Phe Lys Tyr Phe Ala His Gln Asn Thr Leu Asp Glu Asn Phe Glu
    450                 455                 460

Gly Glu Ser Ile Asn Tyr Thr Gly Trp Leu Asp Leu Asp Glu Lys Arg
465                 470                 475                 480

Tyr Tyr Phe Thr Asp Glu Tyr Ile Ala Ala Thr Gly Ser Val Ile Ile
                485                 490                 495

Asp Gly Glu Glu Tyr Tyr Phe Asp Pro Asp Thr Ala Gln Leu Val Ile
            500                 505                 510

Ser Glu


<210> SEQ ID NO 22
<211> LENGTH: 210
<212> TYPE: PRT
<213> ORGANISM: Clostridium difficile

<400> SEQUENCE: 22

Val Gln Ile Gly Val Phe Asp Thr Ser Asp Gly Tyr Lys Tyr Phe Ala
1               5                   10                  15

Pro Ala Asn Thr Val Asn Asp Asn Ile Tyr Gly Gln Ala Val Glu Tyr
            20                  25                  30

Ser Gly Leu Val Arg Val Gly Glu Asp Val Tyr Tyr Phe Gly Glu Thr
        35                  40                  45

Tyr Thr Ile Glu Thr Gly Trp Ile Tyr Asp Met Glu Asn Glu Ser Asp
    50                  55                  60

Lys Tyr Tyr Phe Asn Pro Glu Thr Lys Lys Ala Cys Lys Gly Ile Asn
65                  70                  75                  80

Leu Ile Asp Asp Ile Lys Tyr Tyr Phe Asp Glu Lys Gly Ile Met Arg
                85                  90                  95

Thr Gly Leu Ile Ser Phe Glu Asn Asn Asn Tyr Tyr Phe Asn Glu Asn
            100                 105                 110

Gly Glu Met Gln Phe Gly Tyr Ile Asn Ile Glu Asp Lys Met Phe Tyr
        115                 120                 125

Phe Gly Glu Asp Gly Val Met Gln Ile Gly Val Phe Asn Thr Pro Asp
    130                 135                 140

Gly Phe Lys Tyr Phe Ala His Gln Asn Thr Leu Asp Glu Asn Phe Glu
145                 150                 155                 160

Gly Glu Ser Ile Asn Tyr Thr Gly Trp Leu Asp Leu Asp Glu Lys Arg
                165                 170                 175

Tyr Tyr Phe Thr Asp Glu Tyr Ile Ala Ala Thr Gly Ser Val Ile Ile
            180                 185                 190

Asp Gly Glu Glu Tyr Tyr Phe Asp Pro Asp Thr Ala Gln Leu Val Ile
        195                 200                 205

Ser Glu
    210
```

-continued

<210> SEQ ID NO 23
<211> LENGTH: 311
<212> TYPE: PRT
<213> ORGANISM: Clostridium difficile

<400> SEQUENCE: 23

```
Tyr Ser Gly Ile Leu Asn Phe Asn Asn Lys Ile Tyr Tyr Phe Asp Asp
1               5                   10                  15

Ser Phe Thr Ala Val Val Gly Trp Lys Asp Leu Glu Asp Gly Ser Lys
            20                  25                  30

Tyr Tyr Phe Asp Glu Asp Thr Ala Glu Ala Tyr Ile Gly Leu Ser Leu
        35                  40                  45

Ile Asn Asp Gly Gln Tyr Tyr Phe Asn Asp Asp Gly Ile Met Gln Val
    50                  55                  60

Gly Phe Val Thr Ile Asn Asp Lys Val Phe Tyr Phe Ser Asp Ser Gly
65                  70                  75                  80

Ile Ile Glu Ser Gly Val Gln Asn Ile Asp Asp Asn Tyr Phe Tyr Ile
                85                  90                  95

Asp Asp Asn Gly Ile Val Gln Ile Gly Val Phe Asp Thr Ser Asp Gly
            100                 105                 110

Tyr Lys Tyr Phe Ala Pro Ala Asn Thr Val Asn Asp Asn Ile Tyr Gly
        115                 120                 125

Gln Ala Val Glu Tyr Ser Gly Leu Val Arg Val Gly Glu Asp Val Tyr
    130                 135                 140

Tyr Phe Gly Glu Thr Tyr Thr Ile Glu Thr Gly Trp Ile Tyr Asp Met
145                 150                 155                 160

Glu Asn Glu Ser Asp Lys Tyr Tyr Phe Asn Pro Glu Thr Lys Lys Ala
                165                 170                 175

Cys Lys Gly Ile Asn Leu Ile Asp Asp Ile Lys Tyr Tyr Phe Asp Glu
            180                 185                 190

Lys Gly Ile Met Arg Thr Gly Leu Ile Ser Phe Glu Asn Asn Asn Tyr
        195                 200                 205

Tyr Phe Asn Glu Asn Gly Glu Met Gln Phe Gly Tyr Ile Asn Ile Glu
    210                 215                 220

Asp Lys Met Phe Tyr Phe Gly Glu Asp Gly Val Met Gln Ile Gly Val
225                 230                 235                 240

Phe Asn Thr Pro Asp Gly Phe Lys Tyr Phe Ala His Gln Asn Thr Leu
                245                 250                 255

Asp Glu Asn Phe Glu Gly Glu Ser Ile Asn Tyr Thr Gly Trp Leu Asp
            260                 265                 270

Leu Asp Glu Lys Arg Tyr Tyr Phe Thr Asp Glu Tyr Ile Ala Ala Thr
        275                 280                 285

Gly Ser Val Ile Ile Asp Gly Glu Glu Tyr Tyr Phe Asp Pro Asp Thr
    290                 295                 300

Ala Gln Leu Val Ile Ser Glu
305                 310
```

<210> SEQ ID NO 24
<211> LENGTH: 872
<212> TYPE: PRT
<213> ORGANISM: Clostridium difficile

<400> SEQUENCE: 24

```
His Met Ser Leu Val Asn Arg Lys Gln Leu Glu Lys Met Ala Asn Val
1               5                   10                  15

Arg Phe Arg Thr Gln Glu Asp Glu Tyr Val Ala Ile Leu Asp Ala Leu
```

-continued

```
            20                  25                  30

Glu Glu Tyr His Asn Met Ser Glu Asn Thr Val Val Glu Lys Tyr Leu
        35                  40                  45

Lys Leu Lys Asp Ile Asn Ser Leu Thr Asp Ile Tyr Ile Asp Thr Tyr
    50                  55                  60

Lys Lys Ser Gly Arg Asn Lys Ala Leu Lys Lys Phe Lys Glu Tyr Leu
65                  70                  75                  80

Val Thr Glu Val Leu Glu Leu Lys Asn Asn Asn Leu Thr Pro Val Glu
                85                  90                  95

Lys Asn Leu His Phe Val Trp Ile Gly Gly Gln Ile Asn Asp Thr Ala
            100                 105                 110

Ile Asn Tyr Ile Asn Gln Trp Lys Asp Val Asn Ser Asp Tyr Asn Val
        115                 120                 125

Asn Val Phe Tyr Asp Ser Asn Ala Phe Leu Ile Asn Thr Leu Lys Lys
    130                 135                 140

Thr Val Val Glu Ser Ala Ile Asn Asp Thr Leu Glu Ser Phe Arg Glu
145                 150                 155                 160

Asn Leu Asn Asp Pro Arg Phe Asp Tyr Asn Lys Phe Phe Arg Lys Arg
                165                 170                 175

Met Glu Ile Ile Tyr Asp Lys Gln Lys Asn Phe Ile Asn Tyr Tyr Lys
            180                 185                 190

Ala Gln Arg Glu Glu Asn Pro Glu Leu Ile Ile Asp Asp Ile Val Lys
        195                 200                 205

Thr Tyr Leu Ser Asn Glu Tyr Ser Lys Glu Ile Asp Glu Leu Asn Thr
    210                 215                 220

Tyr Ile Glu Glu Ser Leu Asn Lys Ile Thr Gln Asn Ser Gly Asn Asp
225                 230                 235                 240

Val Arg Asn Phe Glu Glu Phe Lys Asn Gly Glu Ser Phe Asn Leu Tyr
                245                 250                 255

Glu Gln Glu Leu Val Glu Arg Trp Asn Leu Ala Ala Ala Ser Ala Ile
            260                 265                 270

Leu Ala Ile Ser Ala Leu Lys Glu Ile Gly Gly Met Ala Leu Ala Val
        275                 280                 285

Ala Met Leu Pro Gly Ile Gln Pro Asp Leu Phe Glu Ser Ile Glu Lys
    290                 295                 300

Pro Ser Ser Val Thr Val Asp Phe Trp Glu Met Thr Lys Leu Glu Ala
305                 310                 315                 320

Ile Met Lys Tyr Lys Glu Tyr Ile Pro Glu Tyr Thr Ser Glu His Phe
                325                 330                 335

Asp Met Leu Asp Glu Glu Val Gln Ser Ser Phe Glu Ser Val Leu Ala
            340                 345                 350

Ser Lys Ser Asp Lys Ser Glu Ile Phe Ser Ser Leu Gly Asp Met Glu
        355                 360                 365

Ala Ser Pro Leu Glu Val Lys Ile Ala Phe Asn Ser Lys Gly Ile Ile
    370                 375                 380

Asn Gln Gly Leu Ile Ser Val Lys Asp Ser Tyr Cys Ser Asn Leu Ile
385                 390                 395                 400

Val Lys Gln Ile Glu Asn Arg Tyr Lys Ile Leu Asn Asn Ser Leu Asn
                405                 410                 415

Pro Ala Ile Ser Glu Asp Asn Asp Phe Asn Thr Thr Thr Asn Thr Phe
            420                 425                 430

Ile Asp Ser Ile Met Ala Glu Ala Asn Ala Asp Asn Gly Arg Phe Met
        435                 440                 445
```

```
Met Glu Leu Gly Lys Tyr Leu Arg Val Gly Phe Phe Pro Asp Val Lys
    450                 455                 460

Thr Thr Ile Asn Leu Ser Gly Pro Glu Ala Tyr Ala Ala Ala Tyr Gln
465                 470                 475                 480

Asp Leu Leu Met Phe Lys Glu Gly Ser Met Asn Ile His Leu Ile Glu
                485                 490                 495

Ala Asp Leu Arg Asn Phe Glu Ile Ser Lys Thr Asn Ile Ser Gln Ser
            500                 505                 510

Thr Glu Gln Glu Met Ala Ser Leu Trp Ser Phe Asp Asp Ala Arg Ala
        515                 520                 525

Lys Ala Gln Phe Glu Glu Tyr Lys Arg Asn Tyr Phe Glu Gly Ser Leu
    530                 535                 540

Gly Ser Gly Gly Gly Gly Ala Ser Thr Gly Tyr Thr Ser Ile Asn Gly
545                 550                 555                 560

Lys His Phe Tyr Phe Asn Thr Asp Gly Ile Met Gln Ile Gly Val Phe
                565                 570                 575

Lys Gly Pro Asn Gly Phe Glu Tyr Phe Ala Pro Ala Asn Thr His Asn
            580                 585                 590

Asn Asn Ile Glu Gly Gln Ala Ile Leu Tyr Gln Asn Lys Phe Leu Thr
        595                 600                 605

Leu Asn Gly Lys Lys Tyr Tyr Phe Gly Ser Asp Ser Lys Ala Val Thr
    610                 615                 620

Gly Leu Arg Thr Ile Asp Gly Lys Lys Tyr Tyr Phe Asn Thr Asn Thr
625                 630                 635                 640

Ala Val Ala Val Thr Gly Trp Gln Thr Ile Asn Gly Lys Lys Tyr Tyr
                645                 650                 655

Phe Asn Thr Asn Thr Ser Ile Ala Ser Thr Gly Tyr Thr Ile Ile Ser
            660                 665                 670

Gly Lys His Phe Tyr Phe Asn Thr Asp Gly Ile Met Gln Ile Gly Val
        675                 680                 685

Phe Lys Gly Pro Asp Gly Phe Glu Tyr Phe Ala Pro Ala Asn Thr Asp
    690                 695                 700

Ala Asn Asn Ile Glu Gly Gln Ala Ile Arg Tyr Gln Asn Arg Phe Leu
705                 710                 715                 720

Tyr Leu His Asp Asn Ile Tyr Tyr Phe Gly Asn Asn Ser Lys Ala Ala
                725                 730                 735

Thr Gly Trp Val Thr Ile Asp Gly Asn Arg Tyr Tyr Phe Glu Pro Asn
            740                 745                 750

Thr Ala Met Gly Ala Asn Gly Tyr Lys Thr Ile Asp Asn Lys Asn Phe
        755                 760                 765

Tyr Phe Arg Asn Gly Leu Pro Gln Ile Gly Val Phe Lys Gly Ser Asn
    770                 775                 780

Gly Phe Glu Tyr Phe Ala Pro Ala Asn Thr Asp Ala Asn Asn Ile Glu
785                 790                 795                 800

Gly Gln Ala Ile Arg Tyr Gln Asn Arg Phe Leu His Leu Leu Gly Lys
                805                 810                 815

Ile Tyr Tyr Phe Gly Asn Asn Ser Lys Ala Val Thr Gly Trp Gln Thr
            820                 825                 830

Ile Asn Gly Lys Val Tyr Tyr Phe Met Pro Asp Thr Ala Met Ala Ala
        835                 840                 845

Ala Gly Gly Leu Phe Glu Ile Asp Gly Val Ile Tyr Phe Phe Gly Val
    850                 855                 860
```

Asp Gly Val Lys Ala Pro Leu Glu
865 870

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
Linker peptide

<400> SEQUENCE: 25

Gly Ser Gly Gly Gly Gly
1 5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
Linker peptide

<400> SEQUENCE: 26

Gly Ser Gly Ser Gly Gly Gly Gly
1 5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
Linker peptide

<400> SEQUENCE: 27

Ala Ala Ala Leu Glu
1 5

<210> SEQ ID NO 28
<211> LENGTH: 26
<212> TYPE: PRT
<213> ORGANISM: Artificial Sequence
<220> FEATURE:
<223> OTHER INFORMATION: Description of Artificial Sequence: Synthetic
IC-31 peptide

<400> SEQUENCE: 28

Ile Cys Ile Cys Ile Cys Ile Cys Ile Cys Ile Cys Ile Cys Ile Cys
1 5 10 15

Ile Cys Ile Cys Ile Cys Ile Cys Ile Cys
20 25

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
Polycationic polymer peptide

<400> SEQUENCE: 29

Lys Leu Lys Leu Leu Leu Leu Leu Lys Leu Lys
1 5 10

<210> SEQ ID NO 30
<211> LENGTH: 8133

<212> TYPE: DNA
<213> ORGANISM: Clostridium difficile

<400> SEQUENCE: 30
atgtctttaa tatctaaaga agagttaata aaactcgcat atagcattag accaagagaa 60
aatgagtata aaactatact aactaattta gacgaatata ataagttaac tacaaacaat 120
aatgaaaata aatatttaca attaaaaaaa ctaaatgaat caattgatgt ttttatgaat 180
aaatataaaa cttcaagcag aaatagagca ctctctaatc taaaaaaaga tatattaaaa 240
gaagtaattc ttattaaaaa ttccaataca agccctgtag aaaaaaattt acattttgta 300
tggataggtg gagaagtcag tgatattgct cttgaataca taaaacaatg ggctgatatt 360
aatgcagaat ataatattaa actgtggtat gatagtgaag cattcttagt aaatacacta 420
aaaaaggcta tagttgaatc ttctaccact gaagcattac agctactaga ggaagagatt 480
caaaatcctc aatttgataa tatgaaattt tacaaaaaaa ggatggaatt tatatatgat 540
agacaaaaaa ggtttataaa ttattataaa tctcaaatca ataaacctac agtacctaca 600
atagatgata ttataaagtc tcatctagta tctgaatata atagagatga aactgtatta 660
gaatcatata gaacaaattc tttgagaaaa ataaatagta atcatgggat agatatcagg 720
gctaatagtt tgtttacaga acaagagtta ttaaatattt atagtcagga gttgttaaat 780
cgtggaaatt tagctgcagc atctgacata gtaagattat tagccctaaa aaattttggc 840
ggagtatatt tagatgttga tatgcttcca ggtattcact ctgatttatt taaaacaata 900
tctagaccta gctctattgg actagaccgt tgggaaatga taaaattaga ggctattatg 960
aagtataaaa aatatataaa taattataca tcagaaaact ttgataaact tgatcaacaa 1020
ttaaaagata attttaaact cattatagaa agtaaaagtg aaaaatctga gatattttct 1080
aaattagaaa atttaaatgt atctgatctt gaaattaaaa tagctttcgc tttaggcagt 1140
gttataaatc aagccttgat atcaaaacaa ggttcatatc ttactaacct agtaatagaa 1200
caagtaaaaa atagatatca atttttaaac caacacctta acccagccat agagtctgat 1260
aataacttca cagatactac taaaattttt catgattcat tatttaattc agctaccgca 1320
gaaaactcta tgtttttaac aaaaatagca ccatacttac aagtaggttt tatgccagaa 1380
gctcgctcca caataagttt aagtggtcca ggagcttatg cgtcagctta ctatgatttc 1440
ataaatttac aagaaaatac tatagaaaaa actttaaaag catcagattt aatagaattt 1500
aaattcccag aaaataatct atctcaattg acagaacaag aaataaatag tctatggagc 1560
tttgatcaag caagtgcaaa atatcaattt gagaaatatg taagagatta tactggtgga 1620
tctctttctg aagacaatgg ggtagacttt aataaaaata ctgccctcga caaaaactat 1680
ttattaaata ataaaattcc atcaaacaat gtagaagaag ctggaagtaa aaattatgtt 1740
cattatatca tacagttaca aggagatgat ataagttatg aagcaacatg caatttattt 1800
tctaaaaatc ctaaaaatag tattattata caacgaaata tgaatgaaag tgcaaaaagc 1860
tactttttaa gtgatgatgg agaatctatt ttagaattaa ataaatatag gatacctgaa 1920
agattaaaaa ataaggaaaa agtaaaagta acctttattg gacatggtaa agatgaattc 1980
aacacaagcg aatttgctag attaagtgta gattcacttt ccaatgagat aagttcattt 2040
ttagatacca taaaattaga tatatcacct aaaaatgtag aagtaaactt acttggatgt 2100
aatatgttta gttatgattt taatgttgaa gaaacttatc ctgggaagtt gctattaagt 2160
attatggaca aaattacttc cactttacct gatgtaaata aaaattctat tactatagga 2220

-continued

```
gcaaatcaat atgaagtaag aattaatagt gagggaagaa aagaacttct ggctcactca   2280
ggtaaatgga taaataaaga agaagctatt atgagcgatt tatctagtaa agaatacatt   2340
tttttgatt ctatagataa taagctaaaa gcaaagtcca agaatattcc aggattagca   2400
tcaatatcag aagatataaa aacattatta cttgatgcaa gtgttagtcc tgatacaaaa   2460
tttattttaa ataatcttaa gcttaatatt gaatcttcta ttggtgatta catttattat   2520
gaaaaattag agcctgttaa aaatataatt cacaattcta tagatgattt aatagatgag   2580
ttcaatctac ttgaaaatgt atctgatgaa ttatatgaat taaaaaaatt aaataatcta   2640
gatgagaagt atttaatatc ttttgaagat atctcaaaaa ataattcaac ttactctgta   2700
agatttatta acaaaagtaa tggtgagtca gtttatgtag aaacagaaaa agaaattttt   2760
tcaaaatata gcgaacatat tacaaaagaa ataagtacta taaagaatag tataattaca   2820
gatgttaatg gtaatttatt ggataatata cagttagatc atacttctca agttaataca   2880
ttaaacgcag cattctttat tcaatcatta atagattata gtagcaataa agatgtactg   2940
aatgatttaa gtacctcagt taaggttcaa ctttatgctc aactatttag tacaggttta   3000
aatactatat atgactctat ccaattagta aatttaatat caaatgcagt aaatgatact   3060
ataaatgtac tacctacaat aacagagggg atacctattg tatctactat attagacgga   3120
ataaacttag gtgcagcaat taaggaatta ctagacgaac atgacccatt actaaaaaaa   3180
gaattagaag ctaaggtggg tgttttagca ataaatatgt cattatctat agctgcaact   3240
gtagcttcaa ttgttggaat aggtgctgaa gttactattt tcttattacc tatagctggt   3300
atatctgcag gaataccttc attagttaat aatgaattaa tattgcatga taaggcaact   3360
tcagtggtaa actattttaa tcatttgtct gaatctaaaa aatatggccc tcttaaaaca   3420
gaagatgata aaattttagt tcctattgat gatttagtaa tatcagaaat agattttaat   3480
aataattcga taaaactagg aacatgtaat atattagcaa tggagggggg atcaggacac   3540
acagtgactg gtaatataga tcactttttc tcatctccat ctataagttc tcatattcct   3600
tcattatcaa tttattctgc aataggtata gaaacagaaa atctagattt ttcaaaaaaa   3660
ataatgatgt tacctaatgc tccttcaaga gtgttttggt gggaaactgg agcagttcca   3720
ggtttaagat cattggaaaa tgacggaact agattacttg attcaataag agatttatac   3780
ccaggtaaat tttactggag attctatgct tttttcgatt atgcaataac tacattaaaa   3840
ccagtttatg aagacactaa tattaaaatt aaactagata aagatactag aaacttcata   3900
atgccaacta taactactaa cgaaattaga aacaaattat cttattcatt tgatggagca   3960
ggaggaactt actctttatt attatcttca tatccaatat caacgaatat aaatttatct   4020
aaagatgatt tatggatatt taatattgat aatgaagtaa gagaaatatc tatagaaaat   4080
ggtactatta aaaaaggaaa gttaataaaa gatgttttaa gtaaaattga tataaataaa   4140
aataaactta ttataggcaa tcaaacaata gatttttcag gcgatataga taataaagat   4200
agatatatat tcttgacttg tgagttagat gataaaatta gtttaataat agaaataaat   4260
cttgttgcaa aatcttatag tttgttattg tctggggata aaaattattt gatatccaat   4320
ttatctaata ttattgagaa aatcaatact ttaggcctag atagtaaaaa tatagcgtac   4380
aattacactg atgaatctaa taataaatat tttggagcta tatctaaaac aagtcaaaaa   4440
agcataatac attataaaaa agacagtaaa aatatattag aattttataa tgacagtaca   4500
ttagaattta acagtaaaga ttttattgct gaagatataa atgtatttat gaaagatgat   4560
attaatacta taacaggaaa atactatgtt gataataata ctgataaaag tatagatttc   4620
```

-continued tctatttctt tagttagtaa aaatcaagta aaagtaaatg gattatattt aaatgaatcc 4680
gtatactcat cttaccttga ttttgtgaaa aattcagatg gacaccataa tacttctaat 4740
tttatgaatt tatttttgga caatataagt ttctggaaat tgtttgggtt tgaaaatata 4800
aattttgtaa tcgataaata ctttaccctt gttggtaaaa ctaatcttgg atatgtagaa 4860
tttatttgtg acaataataa aaatatagat atatattttg gtgaatggaa aacatcgtca 4920
tctaaaagca ctatatttag cggaaatggt agaaatgttg tagtagagcc tatatataat 4980
cctgatacgg gtgaagatat atctacttca ctagattttt cctatgaacc tctctatgga 5040
atagatagat atatcaataa agtattgata gcacctgatt tatatacaag tttaataaat 5100
attaatacca attattattc aaatgagtac taccctgaga ttatagttct taacccaaat 5160
acattccaca aaaaagtaaa tataaattta gatagttctt cttttgagta taaatggtct 5220
acagaaggaa gtgactttat tttagttaga tacttagaag aaagtaataa aaaaatatta 5280
caaaaaataa gaatcaaagg tatcttatct aatactcaat catttaataa aatgagtata 5340
gattttaaag atattaaaaa actatcatta ggatatataa tgagtaattt taaatcattt 5400
aattctgaaa atgaattaga tagagatcat ttaggattta aaataataga taataaaact 5460
tattactatg atgaagatag taaattagtt aaaggattaa tcaatataaa taattcatta 5520
ttctattttg atcctataga atttaactta gtaactggat ggcaaactat caatggtaaa 5580
aaatattatt ttgatataaa tactggagca gctttaatta gttataaaat tattaatggt 5640
aaacactttt attttaataa tgatggtgtg atgcagttgg gagtatttaa aggacctgat 5700
ggatttgaat attttgcacc tgccaatact caaaataata acatagaagg tcaggctata 5760
gtttatcaaa gtaaattctt aactttgaat ggcaaaaaat attattttga taatgactca 5820
aaagcagtca ctggatggag aattattaac aatgagaaat attactttaa tcctaataat 5880
gctattgctg cagtcggatt gcaagtaatt gacaataata agtattattt caatcctgac 5940
actgctatca tctcaaaagg ttggcagact gttaatggta gtagatacta ctttgatact 6000
gataccgcta ttgcctttaa tggttataaa actattgatg gtaaacactt ttattttgat 6060
agtgattgtg tagtgaaaat aggtgtgttt agtacctcta atggatttga atattttgca 6120
cctgctaata cttataataa taacatagaa ggtcaggcta tagtttatca aagtaaattc 6180
ttaactttga atggtaaaaa atattacttt gataataact caaaagcagt taccggatgg 6240
caaactattg atagtaaaaa atattacttt aatactaaca ctgctgaagc agctactgga 6300
tggcaaacta ttgatggtaa aaaatattac tttaatacta acactgctga agcagctact 6360
ggatggcaaa ctattgatgg taaaaaatat tactttaata ctaacactgc tatagcttca 6420
actggttata caattattaa tggtaaacat ttttatttta atactgatgg tattatgcag 6480
ataggagtgt ttaaaggacc taatggattt gaatattttg cacctgctaa tacggatgct 6540
aacaacatag aaggtcaagc tatactttac caaaatgaat tcttaacttt gaatggtaaa 6600
aaatattact ttggtagtga ctcaaaagca gttactggat ggagaattat taacaataag 6660
aaatattact ttaatcctaa taatgctatt gctgcaattc atctatgcac tataaataat 6720
gacaagtatt actttagtta tgatggaatt cttcaaaatg gatatattac tattgaaaga 6780
aataatttct attttgatgc taataatgaa tctaaaatgg taacaggagt atttaaagga 6840
cctaatggat ttgagtattt tgcacctgct aatactcaca ataataacat agaaggtcag 6900
gctatagttt accagaacaa attcttaact ttgaatggca aaaaatatta ttttgataat 6960

-continued gactcaaaag cagttactgg atggcaaacc attgatggta aaaaatatta ctttaatctt 7020
aacactgctg aagcagctac tggatggcaa actattgatg gtaaaaaata ttactttaat 7080
cttaacactg ctgaagcagc tactggatgg caaactattg atggtaaaaa atattacttt 7140
aatactaaca ctttcatagc ctcaactggt tatacaagta ttaatggtaa acatttttat 7200
tttaatactg atggtattat gcagatagga gtgtttaaag gacctaatgg atttgaatac 7260
tttgcacctg ctaatactca taataataac atagaaggtc aagctatact ttaccaaaat 7320
aaattcttaa ctttgaatgg taaaaaatat tactttggta gtgactcaaa agcagttacc 7380
ggattgcgaa ctattgatgg taaaaaatat tactttaata ctaacactgc tgttgcagtt 7440
actggatggc aaactattaa tggtaaaaaa tactacttta atactaacac ttctatagct 7500
tcaactggtt atacaattat tagtggtaaa catttttatt ttaatactga tggtattatg 7560
cagataggag tgtttaaagg acctgatgga tttgaatact ttgcacctgc taatacagat 7620
gctaacaata tagaaggtca agctatacgt tatcaaaata gattcctata tttacatgac 7680
aatatatatt attttggtaa taattcaaaa gcagctactg gttgggtaac tattgatggt 7740
aatagatatt acttcgagcc taatacagct atgggtgcga atggttataa aactattgat 7800
aataaaaatt tttactttag aaatggttta cctcagatag gagtgtttaa agggtctaat 7860
ggatttgaat actttgcacc tgctaatacg gatgctaaca atatagaagg tcaagctata 7920
cgttatcaaa atagattcct acatttactt ggaaaaaatat attactttgg taataattca 7980
aaagcagtta ctggatggca aactattaat ggtaaagtat attactttat gcctgatact 8040
gctatggctg cagctggtgg acttttcgag attgatggtg ttatatattt ctttggtgtt 8100
gatggagtaa aagcccctgg gatatatggc taa 8133

<210> SEQ ID NO 31
<211> LENGTH: 7101
<212> TYPE: DNA
<213> ORGANISM: Clostridium difficile

<400> SEQUENCE: 31
atgagtttag ttaatagaaa acagttagaa aaaatggcaa atgtaagatt tcgtactcaa 60
gaagatgaat atgttgcaat attggatgct ttagaagaat atcataatat gtcagagaat 120
actgtagtcg aaaaatattt aaaattaaaa gatataaata gtttaacaga tatttatata 180
gatacatata aaaaatctgg tagaaataaa gccttaaaaa aatttaagga atatctagtt 240
acagaagtat tagagctaaa gaataataat ttaactccag ttgagaaaaa tttacatttt 300
gtttggattg gaggtcaaat aaatgacact gctattaatt atataaatca atggaaagat 360
gtaaatagtg attataatgt taatgttttt tatgatagta atgcattttt gataaacaca 420
ttgaaaaaaa ctgtagtaga atcagcaata aatgatacac ttgaatcatt tagagaaaac 480
ttaaatgacc ctagatttga ctataataaa ttcttcagaa aacgtatgga aataatttat 540
gataaacaga aaaatttcat aaactactat aaagctcaaa gagaagaaaa tcctgaactt 600
ataattgatg atattgtaaa gacatatctt tcaaatgagt attcaaagga gatagatgaa 660
cttaatacct atattgaaga atccttaaat aaaattacac agaatagtgg aaatgatgtt 720
agaaactttg aagaatttaa aaatggagag tcattcaact tatatgaaca agagttggta 780
gaaaggtgga atttagctgc tgcttctgac atattaagaa tatctgcatt aaaagaaatt 840
ggtggtatgt atttagatgt tgatatgtta ccaggaatac aaccagactt atttgagtct 900
atagagaaac ctagttcagt aacagtggat ttttgggaaa tgacaaagtt agaagctata 960

-continued

```
atgaaataca aagaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaaatattg aataatagtt taaatccagc tattagcgag   1260
gataatgatt ttaatactac aacgaatacc tttattgata gtataatggc tgaagctaat   1320
gcagataatg gtagatttat gatggaacta ggaaagtatt taagagttgg tttcttccca   1380
gatgttaaaa ctactattaa cttaagtggc cctgaagcat atgcggcagc ttatcaagat   1440
ttattaatgt ttaaagaagg cagtatgaat atccatttga tagaagctga tttaagaaac   1500
tttgaaatct ctaaaactaa tatttctcaa tcaactgaac aagaaatggc tagcttatgg   1560
tcatttgacg atgcaagagc taaagctcaa tttgaagaat ataaaaggaa ttattttgaa   1620
ggttctcttg gtgaagatga taatcttgat ttttctcaaa atatagtagt tgacaaggag   1680
tatcttttag aaaaaatatc ttcattagca agaagttcag agagaggata tatacactat   1740
attgttcagt tacaaggaga taaaattagt tatgaagcag catgtaactt atttgcaaag   1800
actccttatg atagtgtact gtttcagaaa aatatagaag attcagaaat tgcatattat   1860
tataatcctg gagatggtga aatacaagaa atagacaagt ataaaattcc aagtataatt   1920
tctgatagac ctaagattaa attaacattt attggtcatg gtaaagatga atttaatact   1980
gatatatttg caggttttga tgtagattca ttatccacag aaatagaagc agcaatagat   2040
ttagctaaag aggatatttc tcctaagtca atagaaataa atttattagg atgtaatatg   2100
tttagctact ctatcaacgt agaggagact tatcctggaa aattattact taaagttaaa   2160
gataaaatat cagaattaat gccatctata agtcaagact ctattatagt aagtgcaaat   2220
caatatgaag ttagaataaa tagtgaagga agaagagaat tattggatca ttctggtgaa   2280
tggataaata aagaagaaag tattataaag gatatttcat caaaagaata tatatcattt   2340
aatcctaaag aaaataaaat tacagtaaaa tctaaaaatt tacctgagct atctacatta   2400
ttacaagaaa ttagaaataa ttctaattca agtgatattg aactagaaga aaaagtaatg   2460
ttaacagaat gtgagataaa tgttatttca aatatagata cgcaaattgt tgaggaaagg   2520
attgaagaag ctaagaattt aacttctgac tctattaatt atataaaaga tgaatttaaa   2580
ctaatagaat ctatttctga tgcactatgt gacttaaaac aacagaatga attagaagat   2640
tctcatttta tatcttttga ggacatatca gagactgatg agggatttag tataagattt   2700
attaataaag aaactggaga atctatattt gtagaaactg aaaaaacaat attctctgaa   2760
tatgctaatc atataactga agagatttct aagataaaag gtactatatt tgatactgta   2820
aatggtaagt tagtaaaaaa agtaaattta gatactacac acgaagtaaa tactttaaat   2880
gctgcatttt ttatacaatc attaatagaa tataatagtt ctaaagaatc tcttagtaat   2940
ttaagtgtag caatgaaagt ccaagtttac gctcaattat ttagtactgg tttaaatact   3000
attacagatg cagccaaagt tgttgaatta gtatcaactg cattagatga aactatagac   3060
ttacttccta cattatctga aggattacct ataattgcaa ctattataga tggtgtaagt   3120
ttaggtgcag caatcaaaga gctaagtgaa acgagtgacc cattattaag acaagaaata   3180
gaagctaaga taggtataat ggcagtaaat ttaacaacag ctacaactgc aatcattact   3240
tcatctttgg ggatagctag tggatttagt atacttttag ttcctttagc aggaatttca   3300
```

-continued gcaggtatac caagcttagt aaacaatgaa cttgtacttc gagataaggc aacaaaggtt 3360
gtagattatt ttaaacatgt ttcattagtt gaaactgaag gagtatttac tttattagat 3420
gataaaataa tgatgccaca agatgattta gtgatatcag aaatagattt taataataat 3480
tcaatagttt taggtaaatg tgaaatctgg agaatggaag gtggttcagg tcatactgta 3540
actgatgata tagatcactt cttttcagca ccatcaataa catatagaga gccacactta 3600
tctatatatg acgtattgga agtacaaaaa gaagaacttg atttgtcaaa agatttaatg 3660
gtattaccta atgctccaaa tagagtattt gcttgggaaa caggatggac accaggttta 3720
agaagcttag aaaatgatgg cacaaaactg ttagaccgta taagagataa ctatgaaggt 3780
gagttttatt ggagatattt tgcttttata gctgatgctt taataacaac attaaaacca 3840
agatatgaag atactaatat aagaataaat ttagatagta atactagaag ttttatagtt 3900
ccaataataa ctacagaata tataagagaa aaattatcat attctttcta tggttcagga 3960
ggaacttatg cattgtctct ttctcaatat aatatgggta taaatataga attaagtgaa 4020
agtgatgttt ggattataga tgttgataat gttgtgagag atgtaactat agaatctgat 4080
aaaattaaaa aaggtgattt aatagaaggt attttatcta cactaagtat tgaagagaat 4140
aaaattatct taaatagcca tgagattaat ttttctggtg aggtaaatgg aagtaatgga 4200
tttgtttctt taacattttc aattttagaa ggaataaatg caattataga agttgattta 4260
ttatctaaat catataaatt acttatttct ggcgaattaa aaatattgat gttaaattca 4320
aatcatattc aacagaaaat agattatata ggattcaata gcgaattaca gaaaaatata 4380
ccatatagct ttgtagatag tgaaggaaaa gagaatggtt ttattaatgg ttcaacaaaa 4440
gaaggtttat ttgtatctga attacctgat gtagttctta taagtaaggt ttatatggat 4500
gatagtaagc cttcatttgg atattatagt aataatttga aagatgtcaa agttataact 4560
aaagataatg ttaatatatt aacaggttat tatcttaagg atgatataaa aatctctctt 4620
tctttgactc tacaagatga aaaaactata aagttaaata gtgtgcattt agatgaaagt 4680
ggagtagctg agattttgaa gttcatgaat agaaaaggta atacaaatac ttcagattct 4740
ttaatgagct ttttagaaag tatgaatata aaaagtattt tcgttaattt cttacaatct 4800
aatattaagt ttatattaga tgctaatttt ataataagtg gtactacttc tattggccaa 4860
tttgagttta tttgtgatga aaatgataat atacaaccat atttcattaa gtttaataca 4920
ctagaaacta attatacttt atatgtagga aatagacaaa atatgatagt ggaaccaaat 4980
tatgatttag atgattctgg agatatatct tcaactgtta tcaatttctc tcaaaagtat 5040
ctttatggaa tagacagttg tgttaataaa gttgtaattt caccaaatat ttatacagat 5100
gaaataaata taacgcctgt atatgaaaca aataatactt atccagaagt tattgtatta 5160
gatgcaaatt atataaatga aaaaataaat gttaatatca atgatctatc tatacgatat 5220
gtatggagta atgatggtaa tgattttatt cttatgtcaa ctagtgaaga aaataaggtg 5280
tcacaagtta aaataagatt cgttaatgtt tttaaagata agactttggc aaataagcta 5340
tcttttaact ttagtgataa acaagatgta cctgtaagtg aaataatctt atcatttaca 5400
ccttcatatt atgaggatgg attgattggc tatgatttgg gtctagtttc tttatataat 5460
gagaaatttt atattaataa ctttggaatg atggtatctg gattaatata tattaatgat 5520
tcattatatt attttaaacc accagtaaat aatttgataa ctggatttgt gactgtaggc 5580
gatgataaat actactttaa tccaattaat ggtggagctg cttcaattgg agagacaata 5640
attgatgaca aaaattatta tttcaaccaa agtggagtgt tacaaacagg tgtatttagt 5700

```
acagaagatg gatttaaata ttttgcccca gctaatacac ttgatgaaaa cctagaagga   5760
gaagcaattg attttactgg aaaattaatt attgacgaaa atatttatta ttttgatgat   5820
aattatagag gagctgtaga atggaaagaa ttagatggtg aaatgcacta ttttagccca   5880
gaaacaggta aagcttttaa aggtctaaat caaataggtg attataaata ctatttcaat   5940
tctgatggag ttatgcaaaa aggatttgtt agtataaatg ataataaaca ctattttgat   6000
gattctggtg ttatgaaagt aggttacact gaaatagatg gcaagcattt ctactttgct   6060
gaaaacggag aaatgcaaat aggagtattt aatacagaag atggatttaa atattttgct   6120
catcataatg aagatttagg aaatgaagaa ggtgaagaaa tctcatattc tggtatatta   6180
aatttcaata ataaaattta ctattttgat gattcattta cagctgtagt tggatggaaa   6240
gatttagagg atggttcaaa gtattatttt gatgaagata cagcagaagc atatataggt   6300
ttgtcattaa taaatgatgg tcaatattat tttaatgatg atggaattat gcaagttgga   6360
tttgtcacta taaatgataa agtcttctac ttctctgact ctggaattat agaatctgga   6420
gtacaaaaca tagatgacaa ttatttctat atagatgata atggtatagt tcaaattggt   6480
gtatttgata cttcagatgg atataaatat tttgcacctg ctaatactgt aaatgataat   6540
atttacggac aagcagttga atatagtggt ttagttagag ttggtgaaga tgtatattat   6600
tttggagaaa catatacaat tgagactgga tggatatatg atatggaaaa tgaaagtgat   6660
aaatattatt tcaatccaga aactaaaaaa gcatgcaaag gtattaattt aattgatgat   6720
ataaaatatt attttgatga gaagggcata atgagaacgg gtcttatatc atttgaaaat   6780
aataattatt actttaatga gaatggtgaa atgcaatttg gttatataaa tatagaagat   6840
aagatgttct attttggtga agatggtgtc atgcagattg gagtatttaa tacaccagat   6900
ggatttaaat actttgcaca tcaaaatact ttggatgaga attttgaggg agaatcaata   6960
aactatactg gttggttaga tttagatgaa aagagatatt attttacaga tgaatatatt   7020
gcagcaactg gttcagttat tattgatggt gaggagtatt attttgatcc tgatacagct   7080
caattagtga ttagtgaata g                                             7101
```

<210> SEQ ID NO 32
<211> LENGTH: 2307
<212> TYPE: DNA
<213> ORGANISM: Clostridium difficile

<400> SEQUENCE: 32

```
atgtctttaa tatctaaaga agagttaata aaactcgcat atagcattag accaagagaa     60
aatgagtata aaactatact aactaattta gacgaatata ataagttaac tacaaacaat    120
aatgaaaata aatatttaca attaaaaaaa ctaaatgaat caattgatgt ttttatgaat    180
aaatataaaa cttcaagcag aaatagagca ctctctaatc taaaaaaaga tatattaaaa    240
gaagtaattc ttattaaaaa ttccaataca agccctgtag aaaaaaattt acattttgta    300
tggataggtg gagaagtcag tgatattgct cttgaataca taaaacaatg ggctgatatt    360
aatgcagaat ataatattaa actgtggtat gatagtgaag cattcttagt aaatacacta    420
aaaaaggcta tagttgaatc ttctaccact gaagcattac agctactaga ggaagagatt    480
caaaatcctc aatttgataa tatgaaattt tacaaaaaaa ggatggaatt tatatatgat    540
agacaaaaaa ggtttataaa ttattataaa tctcaaatca ataaacctac agtacctaca    600
atagatgata ttataaagtc tcatctagta tctgaatata atagagatga aactgtatta    660
```

-continued gaatcatata gaacaaattc tttgagaaaa ataaatagta atcatgggat agatatcagg 720
gctaatagtt tgtttacaga acaagagtta ttaaatattt atagtcagga gttgttaaat 780
cgtggaaatt tagctgcagc atctgacata gtaagattat tagccctaaa aaattttggc 840
ggagtatatt tagatgttga tatgcttcca ggtattcact ctgatttatt taaaacaata 900
tctagaccta gctctattgg actagaccgt tgggaaatga taaaattaga ggctattatg 960
aagtataaaa aatatataaa taattataca tcagaaaact ttgataaact tgatcaacaa 1020
ttaaaagata attttaaact cattatagaa agtaaaagtg aaaaatctga gatattttct 1080
aaattagaaa atttaaatgt atctgatctt gaaattaaaa tagctttcgc tttaggcagt 1140
gttataaatc aagccttgat atcaaaacaa ggttcatatc ttactaacct agtaatagaa 1200
caagtaaaaa atagatatca atttttaaac caacacctta acccagccat agagtctgat 1260
aataacttca cagatactac taaaattttt catgattcat tatttaattc agctaccgca 1320
gaaaactcta tgtttttaac aaaaatagca ccatacttac aagtaggttt tatgccagaa 1380
gctcgctcca caataagttt aagtggtcca ggagcttatg cgtcagctta ctatgatttc 1440
ataaatttac aagaaaatac tatagaaaaa actttaaaag catcagattt aatagaattt 1500
aaattcccag aaaataatct atctcaattg acagaacaag aaataaatag tctatggagc 1560
tttgatcaag caagtgcaaa atatcaattt gagaaatatg taagagatta tactggtgga 1620
tctctttctg aagacaatgg ggtagacttt aataaaaata ctgccctcga caaaaactat 1680
ttattaaata ataaaattcc atcaaacaat gtagaagaag ctggaagtaa aaattatgtt 1740
cattatatca tacagttaca aggagatgat ataagttatg aagcaacatg caatttattt 1800
tctaaaaatc ctaaaaatag tattattata caacgaaata tgaatgaaag tgcaaaaagc 1860
tactttttaa gtgatgatgg agaatctatt ttagaattaa ataaatatag gatacctgaa 1920
agattaaaaa ataaggaaaa agtaaaagta acctttattg gacatggtaa agatgaattc 1980
aacacaagcg aatttgctag attaagtgta gattcacttt ccaatgagat aagttcattt 2040
ttagatacca taaaattaga tatatcacct aaaaatgtag aagtaaactt acttggatgt 2100
aatatgttta gttatgattt taatgttgaa gaaacttatc ctgggaagtt gctattaagt 2160
attatggaca aaattacttc cactttacct gatgtaaata aaaattctat tactatagga 2220
gcaaatcaat atgaagtaag aattaatagt gagggaagaa aagaacttct ggctcactca 2280
ggtaaatgga taaataaaga agaagct 2307

<210> SEQ ID NO 33
<211> LENGTH: 1623
<212> TYPE: DNA
<213> ORGANISM: Clostridium difficile

<400> SEQUENCE: 33
atgtctttaa tatctaaaga agagttaata aaactcgcat atagcattag accaagagaa 60
aatgagtata aaactatact aactaattta gacgaatata ataagttaac tacaaacaat 120
aatgaaaata aatatttaca attaaaaaaa ctaaatgaat caattgatgt ttttatgaat 180
aaatataaaa cttcaagcag aaatagagca ctctctaatc taaaaaaaga tatattaaaa 240
gaagtaattc ttattaaaaa ttccaataca agccctgtag aaaaaaattt acattttgta 300
tggataggtg gagaagtcag tgatattgct cttgaataca taaaacaatg ggctgatatt 360
aatgcagaat ataatattaa actgtggtat gatagtgaag cattcttagt aaatacacta 420
aaaaaggcta tagttgaatc ttctaccact gaagcattac agctactaga ggaagagatt 480

```
caaaatcctc aatttgataa tatgaaattt tacaaaaaaa ggatggaatt tatatatgat    540
agacaaaaaa ggtttataaa ttattataaa tctcaaatca ataaacctac agtacctaca    600
atagatgata ttataaagtc tcatctagta tctgaatata atagagatga aactgtatta    660
gaatcatata gaacaaattc tttgagaaaa ataaatagta atcatgggat agatatcagg    720
gctaatagtt tgtttacaga acaagagtta ttaaatattt atagtcagga gttgttaaat    780
cgtggaaatt tagctgcagc atctgacata gtaagattat tagccctaaa aaattttggc    840
ggagtatatt tagatgttga tatgcttcca ggtattcact ctgatttatt taaaacaata    900
tctagaccta gctctattgg actagaccgt tgggaaatga taaaattaga ggctattatg    960
aagtataaaa aatatataaa taattataca tcagaaaact ttgataaact tgatcaacaa   1020
ttaaaagata attttaaact cattatagaa agtaaaagtg aaaaatctga gatattttct   1080
aaattagaaa atttaaatgt atctgatctt gaaattaaaa tagctttcgc tttaggcagt   1140
gttataaatc aagccttgat atcaaaacaa ggttcatatc ttactaacct agtaatagaa   1200
caagtaaaaa atagatatca atttttaaac caacacctta acccagccat agagtctgat   1260
aataacttca cagatactac taaaattttt catgattcat tatttaattc agctaccgca   1320
gaaaactcta tgtttttaac aaaaatagca ccatacttac aagtaggttt tatgccagaa   1380
gctcgctcca caataagttt aagtggtcca ggagcttatg cgtcagctta ctatgatttc   1440
ataaatttac aagaaaatac tatagaaaaa actttaaaag catcagattt aatagaattt   1500
aaattcccag aaaataatct atctcaattg acagaacaag aaataaatag tctatggagc   1560
tttgatcaag caagtgcaaa atatcaattt gagaaatatg taagagatta tactggtgga   1620
tct                                                                 1623
```

<210> SEQ ID NO 34
<211> LENGTH: 684
<212> TYPE: DNA
<213> ORGANISM: Clostridium difficile

<400> SEQUENCE: 34

```
tctgaagaca atggggtaga ctttaataaa aatactgccc tcgacaaaaa ctatttatta     60
aataataaaa ttccatcaaa caatgtagaa gaagctggaa gtaaaaaatta tgttcattat    120
atcatacagt tacaaggaga tgatataagt tatgaagcaa catgcaattt attttctaaa    180
aatcctaaaa atagtattat tatacaacga aatatgaatg aaagtgcaaa aagctacttt    240
ttaagtgatg atggagaatc tattttagaa ttaaataaat ataggatacc tgaaagatta    300
aaaaataagg aaaaagtaaa agtaaccttt attggacatg gtaaagatga attcaacaca    360
agcgaatttg ctagattaag tgtagattca ctttccaatg agataagttc atttttagat    420
accataaaat tagatatatc acctaaaaat gtagaagtaa acttacttgg atgtaatatg    480
tttagttatg attttaatgt tgaagaaact tatcctggga agttgctatt aagtattatg    540
gacaaaatta cttccacttt acctgatgta aataaaaatt ctattactat aggagcaaat    600
caatatgaag taagaattaa tagtgaggga agaaaagaac ttctggctca ctcaggtaaa    660
tggataaata aagaagaagc tctt                                          684
```

<210> SEQ ID NO 35
<211> LENGTH: 3114
<212> TYPE: DNA
<213> ORGANISM: Clostridium difficile -continued

<400> SEQUENCE: 35

```
atgagcgatt tatctagtaa agaatacatt ttttttgatt ctatagataa taagctaaaa     60
gcaaagtcca agaatattcc aggattagca tcaatatcag aagatataaa aacattatta    120
cttgatgcaa gtgttagtcc tgatacaaaa tttattttaa ataatcttaa gcttaatatt    180
gaatcttcta ttggtgatta catttattat gaaaaattag agcctgttaa aaatataatt    240
cacaattcta tagatgattt aatagatgag ttcaatctac ttgaaaatgt atctgatgaa    300
ttatatgaat taaaaaaatt aaataatcta gatgagaagt atttaatatc ttttgaagat    360
atctcaaaaa ataattcaac ttactctgta agatttatta acaaaagtaa tggtgagtca    420
gtttatgtag aaacagaaaa agaaattttt tcaaaatata gcgaacatat tacaaaagaa    480
ataagtacta taaagaatag tataattaca gatgttaatg gtaatttatt ggataatata    540
cagttagatc atacttctca agttaataca ttaaacgcag cattctttat tcaatcatta    600
atagattata gtagcaataa agatgtactg aatgatttaa gtacctcagt taaggttcaa    660
ctttatgctc aactatttag tacaggttta aatactatat atgactctat ccaattagta    720
aatttaatat caaatgcagt aaatgatact ataaatgtac tacctacaat aacagagggg    780
atacctattg tatctactat attagacgga ataaacttag gtgcagcaat taaggaatta    840
ctagacgaac atgacccatt actaaaaaaa gaattagaag ctaaggtggg tgttttagca    900
ataaatatgt cattatctat agctgcaact gtagcttcaa ttgttggaat aggtgctgaa    960
gttactattt tcttattacc tatagctggt atatctgcag gaataccttc attagttaat   1020
aatgaattaa tattgcatga taaggcaact tcagtggtaa actattttaa tcatttgtct   1080
gaatctaaaa aatatggccc tcttaaaaca gaagatgata aaattttagt tcctattgat   1140
gatttagtaa tatcagaaat agattttaat aataattcga taaaactagg aacatgtaat   1200
atattagcaa tggagggggg atcaggacac acagtgactg gtaatataga tcactttttc   1260
tcatctccat ctataagttc tcatattcct tcattatcaa tttattctgc aataggtata   1320
gaaacagaaa atctagattt ttcaaaaaaa ataatgatgt tacctaatgc tccttcaaga   1380
gtgttttggt gggaaactgg agcagttcca ggtttaagat cattggaaaa tgacggaact   1440
agattacttg attcaataag agatttatac ccaggtaaat tttactggag attctatgct   1500
tttttcgatt atgcaataac tacattaaaa ccagtttatg aagacactaa tattaaaatt   1560
aaactagata aagatactag aaacttcata atgccaacta taactactaa cgaaattaga   1620
aacaaattat cttattcatt tgatggagca ggaggaactt actctttatt attatcttca   1680
tatccaatat caacgaatat aaatttatct aaagatgatt tatggatatt taatattgat   1740
aatgaagtaa gagaaatatc tatagaaaat ggtactatta aaaaaggaaa gttaataaaa   1800
gatgttttaa gtaaaattga tataaataaa aataaactta ttataggcaa tcaaacaata   1860
gatttttcag gcgatataga taataaagat agatatatat tcttgacttg tgagttagat   1920
gataaaatta gtttaataat agaaataaat cttgttgcaa aatcttatag tttgttattg   1980
tctggggata aaaattattt gatatccaat ttatctaata ttattgagaa aatcaatact   2040
ttaggcctag atagtaaaaa tatagcgtac aattacactg atgaatctaa taataaatat   2100
tttggagcta tatctaaaac aagtcaaaaa agcataatac attataaaaa agacagtaaa   2160
aatatattag aattttataa tgacagtaca ttagaattta acagtaaaga ttttattgct   2220
gaagatataa atgtatttat gaaagatgat attaatacta taacaggaaa atactatgtt   2280
gataataata ctgataaaag tatagatttc tctatttctt tagttagtaa aaatcaagta   2340
```

-continued

```
aaagtaaatg gattatattt aaatgaatcc gtatactcat cttaccttga ttttgtgaaa   2400

aattcagatg gacaccataa tacttctaat tttatgaatt tatttttgga caatataagt   2460

ttctggaaat tgtttgggtt tgaaaatata aattttgtaa tcgataaata ctttaccctt   2520

gttggtaaaa ctaatcttgg atatgtagaa tttatttgtg acaataataa aaatatagat   2580

atatattttg gtgaatggaa aacatcgtca tctaaaagca ctatatttag cggaaatggt   2640

agaaatgttg tagtagagcc tatatataat cctgatacgg gtgaagatat atctacttca   2700

ctagattttt cctatgaacc tctctatgga atagatagat atatcaataa agtattgata   2760

gcacctgatt tatatacaag tttaataaat attaatacca attattattc aaatgagtac   2820

taccctgaga ttatagttct taacccaaat acattccaca aaaaagtaaa tataaattta   2880

gatagttctt cttttgagta taaatggtct acagaaggaa gtgactttat tttagttaga   2940

tacttagaag aaagtaataa aaaaatatta caaaaaataa gaatcaaagg tatcttatct   3000

aatactcaat catttaataa aatgagtata gattttaaag atattaaaaa actatcatta   3060

ggatatataa tgagtaattt taaatcattt aattctgaaa atgaattaga taga         3114
```

<210> SEQ ID NO 36
<211> LENGTH: 798
<212> TYPE: DNA
<213> ORGANISM: Clostridium difficile

<400> SEQUENCE: 36

```
gaagatataa atgtatttat gaaagatgat attaatacta taacaggaaa atactatgtt     60

gataataata ctgataaaag tatagatttc tctatttctt tagttagtaa aaatcaagta    120

aaagtaaatg gattatattt aaatgaatcc gtatactcat cttaccttga ttttgtgaaa    180

aattcagatg gacaccataa tacttctaat tttatgaatt tatttttgga caatataagt    240

ttctggaaat tgtttgggtt tgaaaatata aattttgtaa tcgataaata ctttaccctt    300

gttggtaaaa ctaatcttgg atatgtagaa tttatttgtg acaataataa aaatatagat    360

atatattttg gtgaatggaa aacatcgtca tctaaaagca ctatatttag cggaaatggt    420

agaaatgttg tagtagagcc tatatataat cctgatacgg gtgaagatat atctacttca    480

ctagattttt cctatgaacc tctctatgga atagatagat atatcaataa agtattgata    540

gcacctgatt tatatacaag tttaataaat attaatacca attattattc aaatgagtac    600

taccctgaga ttatagttct taacccaaat acattccaca aaaaagtaaa tataaattta    660

gatagttctt cttttgagta taaatggtct acagaaggaa gtgactttat tttagttaga    720

tacttagaag aaagtaataa aaaaatatta caaaaaataa gaatcaaagg tatcttatct    780

aatactcaat catttaat                                                  798
```

<210> SEQ ID NO 37
<211> LENGTH: 2649
<212> TYPE: DNA
<213> ORGANISM: Clostridium difficile

<400> SEQUENCE: 37

```
gatcatttag gatttaaaat aatagataat aaaacttatt actatgatga agatagtaaa     60

ttagttaaag gattaatcaa tataaataat tcattattct attttgatcc tatagaattt    120

aacttagtaa ctggatggca aactatcaat ggtaaaaaat attattttga tataaatact    180

ggagcagctt taattagtta taaaattatt aatggtaaac acttttattt taataatgat    240
```

-continued

```
ggtgtgatgc agttgggagt atttaaagga cctgatggat ttgaatattt tgcacctgcc    300
aatactcaaa ataataacat agaaggtcag gctatagttt atcaaagtaa attcttaact    360
ttgaatggca aaaaatatta ttttgataat gactcaaaag cagtcactgg atggagaatt    420
attaacaatg agaaatatta ctttaatcct aataatgcta ttgctgcagt cggattgcaa    480
gtaattgaca ataataagta ttatttcaat cctgacactg ctatcatctc aaaaggttgg    540
cagactgtta atggtagtag atactacttt gatactgata ccgctattgc ctttaatggt    600
tataaaacta ttgatggtaa acacttttat tttgatagtg attgtgtagt gaaaataggt    660
gtgtttagta cctctaatgg atttgaatat tttgcacctg ctaatactta taataataac    720
atagaaggtc aggctatagt ttatcaaagt aaattcttaa ctttgaatgg taaaaaatat    780
tactttgata ataactcaaa agcagttacc ggatggcaaa ctattgatag taaaaaatat    840
tactttaata ctaacactgc tgaagcagct actggatggc aaactattga tggtaaaaaa    900
tattacttta atactaacac tgctgaagca gctactggat ggcaaactat tgatggtaaa    960
aaatattact ttaatactaa cactgctata gcttcaactg gttatacaat tattaatggt   1020
aaacattttt attttaatac tgatggtatt atgcagatag gagtgtttaa aggacctaat   1080
ggatttgaat attttgcacc tgctaatacg gatgctaaca acatagaagg tcaagctata   1140
ctttaccaaa atgaattctt aactttgaat ggtaaaaaat attactttgg tagtgactca   1200
aaagcagtta ctggatggag aattattaac aataagaaat attactttaa tcctaataat   1260
gctattgctg caattcatct atgcactata aataatgaca agtattactt tagttatgat   1320
ggaattcttc aaaatggata tattactatt gaaagaaata atttctattt tgatgctaat   1380
aatgaatcta aaatggtaac aggagtattt aaaggaccta atggatttga gtattttgca   1440
cctgctaata ctcacaataa taacatagaa ggtcaggcta tagtttacca gaacaaattc   1500
ttaactttga atggcaaaaa atattatttt gataatgact caaaagcagt tactggatgg   1560
caaaccattg atggtaaaaa atattacttt aatcttaaca ctgctgaagc agctactgga   1620
tggcaaacta ttgatggtaa aaaatattac tttaatctta acactgctga agcagctact   1680
ggatggcaaa ctattgatgg taaaaaatat tactttaata ctaacacttt catagcctca   1740
actggttata caagtattaa tggtaaacat ttttatttta atactgatgg tattatgcag   1800
ataggagtgt ttaaaggacc taatggattt gaatactttg cacctgctaa tactcataat   1860
aataacatag aaggtcaagc tatactttac caaaataaat tcttaacttt gaatggtaaa   1920
aaatattact ttggtagtga ctcaaaagca gttaccggat tgcgaactat tgatggtaaa   1980
aaatattact ttaatactaa cactgctgtt gcagttactg gatggcaaac tattaatggt   2040
aaaaaatact actttaatac taacacttct atagcttcaa ctggttatac aattattagt   2100
ggtaaacatt tttattttaa tactgatggt attatgcaga taggagtgtt taaaggacct   2160
gatggatttg aatactttgc acctgctaat acagatgcta acaatataga aggtcaagct   2220
atacgttatc aaaatagatt cctatattta catgacaata tatattattt tggtaataat   2280
tcaaaagcag ctactggttg ggtaactatt gatggtaata gatattactt cgagcctaat   2340
acagctatgg gtgcgaatgg ttataaaact attgataata aaaattttta ctttagaaat   2400
ggtttacctc agataggagt gtttaaaggg tctaatcgtt atcaaaatag attcctacat   2460
ttacttggaa aaatatatta ctttggtaat aattcaaaag cagttactgg atggcaaact   2520
attaatggta aagtatatta ctttatgcct gatactgcta tggctgcagc tggtggactt   2580
ttcgagattg atggtgttat atatttcttt ggtgttgatg gagtaaaagc ccctgggata   2640
```

```
tatggctaa                                                            2649

<210> SEQ ID NO 38
<211> LENGTH: 612
<212> TYPE: DNA
<213> ORGANISM: Clostridium difficile

<400> SEQUENCE: 38

agatactact ttgatactga taccgctatt gcctttaatg gttataaaac tattgatggt      60

aaacactttt attttgatag tgattgtgta gtgaaaatag gtgtgtttag tacctctaat     120

ggatttgaat attttgcacc tgctaatact tataataata acatagaagg tcaggctata     180

gtttatcaaa gtaaattctt aactttgaat ggtaaaaaat attactttga taataactca     240

aaagcagtta ccggatggca aactattgat agtaaaaaat attactttaa tactaacact     300

gctgaagcag ctactggatg gcaaactatt gatggtaaaa aatattactt taatactaac     360

actgctgaag cagctactgg atggcaaact attgatggta aaaaatatta ctttaatact     420

aacactgcta tagcttcaac tggttataca attattaatg gtaaacattt ttattttaat     480

actgatggta ttatgcagat aggagtgttt aaaggaccta atggatttga atattttgca     540

cctgctaata cggatgctaa caacatagaa ggtcaagcta tactttacca aaatgaattc     600

ttaactttga at                                                         612

<210> SEQ ID NO 39
<211> LENGTH: 1371
<212> TYPE: DNA
<213> ORGANISM: Clostridium difficile

<400> SEQUENCE: 39

atcctgcaga acggctatat caccatcgaa cgtaataact tctacttcga tgccaataac      60

gaatccaaaa tggtgacggg cgtgtttaaa ggcccaaatg gttttgagta tttcgcgccg     120

gcaaacaccc acaataacaa cattgaaggt caagccattg tttaccaaaa caaattcctg     180

accctaaatg gaaaaaaata ttactttgat aacgacagca aagcggtcac cggctggcag     240

acaatcgacg gtaaaaaata ttactttaat cttaacaccg cagaagcggc caccggctgg     300

caaaccatcg atggtaaaaa atattacttc aacttgaaca ccgcagaagc ggccaccggc     360

tggcagacca tcgatggtaa aaaatactac tttaatacca acaccttcat tgctagcacc     420

ggttatactt cgatcaacgg taaacatttt tactttaata ccgacggtat catgcaaatt     480

ggcgtattca aaggtcctaa cggctttgaa tactttgcgc cagcaaatac ccacaacaat     540

aacattgaag gtcaggccat tctgtaccaa aacaaattcc tgaccctaaa tggtaaaaaa     600

tattacttcg gtagtgacag caaagcggtt acaggcctaa ggaccatcga tggtaaaaaa     660

tattacttta acaccaacac cgcagtcgcg gttaccggct ggcagaccat caatggtaaa     720

aaatactact ttaacaccaa cacctctatt gccagcaccg gttacacgat catctcgggt     780

aaacatttct attttaatac cgatggtatc atgcaaattg gcgtatttaa aggtccggac     840

ggcttcgaat actttgcgcc tgcaaacacg gatgccaaca atattgaggg tcaggcaatt     900

agatatcaaa accgcttcct ctacctgcat gacaatattt attactttgg taacaatagc     960

aaagcggcca ccggttgggt gaccatcgat ggtaaccgtt attacttcga gccaaatacg    1020

gcaatgggtg ctaacggtta taaaaccatc gacaataaaa acttctactt tcgcaatggt    1080

ctgccgcaaa ttggcgtatt taaaggatct aacggcttcg aatactttgc gcctgccaat    1140
```

acagatgcaa acaacattga aggtcaggcc attagatacc aaaatcgttt cctccattta 1200
cttggcaaaa tttattactt tggtaacaat agcaaagcgg tcaccggttg gcaaaccatc 1260
aacggtaaag tgtattactt tatgccagat accgcaatgg ccgcggcagg tggcttgttc 1320
gagatcgacg gtgttattta cttcttcggt gtcgatggcg tgaaagctcc g 1371

<210> SEQ ID NO 40
<211> LENGTH: 955
<212> TYPE: DNA
<213> ORGANISM: Clostridium difficile

<400> SEQUENCE: 40
gcctcaactg gttatacaag tattaatggt aaacattttt attttaatac tgatggtatt 60
atgcagatag gagtgtttaa aggacctaat ggatttgaat actttgcacc tgctaatact 120
cataataata acatagaagg tcaagctata ctttaccaaa ataaattctt aactttgaat 180
ggtaaaaaat attactttgg tagtgactca aaagcagtta ccggattgcg aactattgat 240
ggtaaaaaat attactttaa tactaacact gctgttgcag ttactggatg gcaaactatt 300
aatggtaaaa aatactactt taatactaac acttctatag cttcaactgg ttatacaatt 360
attagtggta aacattttta ttttaatact gatggtatta tgcagatagg agtgtttaaa 420
ggacctgatg gatttgaata ctttgcacct gctaatacag atgctaacaa tatagaaggt 480
caagctatac gttatcaaaa tagattccta tatttacatg acaatatata ttattttggt 540
aataattcaa aagcagctac tggttgggta actattgatg gtaatagata ttacttcgag 600
cctaatacag ctatgggtgc gaatggttat aaaactattg ataataaaaa tttttacttt 660
agaaatggtt tacctcagat aggagtgttt aaagggtcta atggatttga atactttgca 720
cctgctaata cggatgctaa caatatagaa ggtcaagcta tacgttatca aaatagattc 780
ctacatttac ttggaaaaat atattacttt ggtaataatt caaaagcagt tactggatgg 840
caaactatta atggtaaagt atattacttt atgcctgata ctgctatggc tgcagctggt 900
ggacttttcg agattgatgg tgttatatat ttctttggtg ttgatggagt aaaag 955

<210> SEQ ID NO 41
<211> LENGTH: 2592
<212> TYPE: DNA
<213> ORGANISM: Clostridium difficile

<400> SEQUENCE: 41
tttgatccta tagaatttaa cttagtaact ggatggcaaa ctatcaatgg taaaaaatat 60
tattttgata taaatactgg agcagcttta attagttata aaattattaa tggtaaacac 120
ttttatttta ataatgatgg tgtgatgcag ttgggagtat ttaaaggacc tgatggattt 180
gaatattttg cacctgccaa tactcaaaat aataacatag aaggtcaggc tatagtttat 240
caaagtaaat tcttaacttt gaatggcaaa aaatattatt ttgataatga ctcaaaagca 300
gtcactggat ggagaattat taacaatgag aaatattact ttaatcctaa taatgctatt 360
gctgcagtcg gattgcaagt aattgacaat aataagtatt atttcaatcc tgacactgct 420
atcatctcaa aaggttggca gactgttaat ggtagtagat actactttga tactgatacc 480
gctattgcct ttaatggtta taaaactatt gatggtaaac acttttattt tgatagtgat 540
tgtgtagtga aaataggtgt gtttagtacc tctaatggat ttgaatattt tgcacctgct 600
aatacttata ataataacat agaaggtcag gctatagttt atcaaagtaa attcttaact 660
ttgaatggta aaaaatatta ctttgataat aactcaaaag cagttaccgg atggcaaact 720

-continued attgatagta aaaaatatta ctttaatact aacactgctg aagcagctac tggatggcaa 780
actattgatg gtaaaaaata ttactttaat actaacactg ctgaagcagc tactggatgg 840
caaactattg atggtaaaaa atattacttt aatactaaca ctgctatagc ttcaactggt 900
tatacaatta ttaatggtaa acatttttat tttaatactg atggtattat gcagatagga 960
gtgtttaaag gacctaatgg atttgaatat tttgcacctg ctaatacgga tgctaacaac 1020
atagaaggtc aagctatact ttaccaaaat gaattcttaa ctttgaatgg taaaaaatat 1080
tactttggta gtgactcaaa agcagttact ggatggagaa ttattaacaa taagaaatat 1140
tactttaatc ctaataatgc tattgctgca attcatctat gcactataaa taatgacaag 1200
tattacttta gttatgatgg aattcttcaa aatggatata ttactattga aagaaataat 1260
ttctattttg atgctaataa tgaatctaaa atggtaacag gagtatttaa aggacctaat 1320
ggatttgagt attttgcacc tgctaatact cacaataata acatagaagg tcaggctata 1380
gtttaccaga acaaattctt aactttgaat ggcaaaaaat attattttga taatgactca 1440
aaagcagtta ctggatggca aaccattgat ggtaaaaaat attactttaa tcttaacact 1500
gctgaagcag ctactggatg gcaaactatt gatggtaaaa aatattactt taatcttaac 1560
actgctgaag cagctactgg atggcaaact attgatggta aaaaatatta ctttaatact 1620
aacactttca tagcctcaac tggttataca agtattaatg gtaaacattt ttattttaat 1680
actgatggta ttatgcagat aggagtgttt aaaggaccta atggatttga atactttgca 1740
cctgctaata ctcataataa taacatagaa ggtcaagcta tactttacca aaataaattc 1800
ttaactttga atggtaaaaa atattacttt ggtagtgact caaaagcagt taccggattg 1860
cgaactattg atggtaaaaa atattacttt aatactaaca ctgctgttgc agttactgga 1920
tggcaaacta ttaatggtaa aaaatactac tttaatacta acacttctat agcttcaact 1980
ggttatacaa ttattagtgg taaacatttt tattttaata ctgatggtat tatgcagata 2040
ggagtgttta aaggacctga tggatttgaa tactttgcac ctgctaatac agatgctaac 2100
aatatagaag gtcaagctat acgttatcaa aatagattcc tatatttaca tgacaatata 2160
tattattttg gtaataattc aaaagcagct actggttggg taactattga tggtaataga 2220
tattacttcg agcctaatac agctatgggt gcgaatggtt ataaaactat tgataataaa 2280
aatttttact ttagaaatgg tttacctcag ataggagtgt ttaaagggtc taatggattt 2340
gaatactttg cacctgctaa tacggatgct aacaatatag aaggtcaagc tatacgttat 2400
caaaatagat tcctacattt acttggaaaa atatattact ttggtaataa ttcaaaagca 2460
gttactggat ggcaaactat taatggtaaa gtatattact ttatgcctga tactgctatg 2520
gctgcagctg gtggactttt cgagattgat ggtgttatat atttctttgg tgttgatgga 2580
gtaaaagccc ct 2592

<210> SEQ ID NO 42
<211> LENGTH: 807
<212> TYPE: DNA
<213> ORGANISM: Clostridium difficile

<400> SEQUENCE: 42
taccaaaata aattcttaac tttgaatggt aaaaaatatt actttggtag tgactcaaaa 60
gcagttaccg gattgcgaac tattgatggt aaaaaatatt actttaatac taacactgct 120
gttgcagtta ctggatggca aactattaat ggtaaaaaat actactttaa tactaacact 180

-continued

```
tctatagctt caactggtta tacaattatt agtggtaaac atttttattt taatactgat    240
ggtattatgc agataggagt gtttaaagga cctgatggat ttgaatactt tgcacctgct    300
aatacagatg ctaacaatat agaaggtcaa gctatacgtt atcaaaatag attcctatat    360
ttacatgaca atatatatta ttttggtaat aattcaaaag cagctactgg ttgggtaact    420
attgatggta atagatatta cttcgagcct aatacagcta tgggtgcgaa tggttataaa    480
actattgata ataaaaattt ttactttaga aatggtttac ctcagatagg agtgtttaaa    540
gggtctaatg gatttgaata ctttgcacct gctaatacgg atgctaacaa tatagaaggt    600
caagctatac gttatcaaaa tagattccta catttacttg gaaaaatata ttactttggt    660
aataattcaa aagcagttac tggatggcaa actattaatg gtaaagtata ttactttatg    720
cctgatactg ctatggctgc agctggtgga cttttcgaga ttgatggtgt tatatatttc    780
tttggtgttg atggagtaaa agcccct                                        807
```

<210> SEQ ID NO 43
<211> LENGTH: 2616
<212> TYPE: DNA
<213> ORGANISM: Clostridium difficile

<400> SEQUENCE: 43

```
tcattattct attttgatcc tatagaattt aacttagtaa ctggatggca aactatcaat     60
ggtaaaaaat attattttga tataaatact ggagcagctt taattagtta taaaattatt    120
aatggtaaac acttttattt taataatgat ggtgtgatgc agttgggagt atttaaagga    180
cctgatggat ttgaatattt tgcacctgcc aatactcaaa ataataacat agaaggtcag    240
gctatagttt atcaaagtaa attcttaact ttgaatggca aaaaatatta ttttgataat    300
gactcaaaag cagtcactgg atggagaatt attaacaatg agaaatatta ctttaatcct    360
aataatgcta ttgctgcagt cggattgcaa gtaattgaca ataataagta ttatttcaat    420
cctgacactg ctatcatctc aaaaggttgg cagactgtta atggtagtag atactacttt    480
gatactgata ccgctattgc ctttaatggt tataaaacta ttgatggtaa acacttttat    540
tttgatagtg attgtgtagt gaaaataggt gtgtttagta cctctaatgg atttgaatat    600
tttgcacctg ctaatactta taataataac atagaaggtc aggctatagt ttatcaaagt    660
aaattcttaa ctttgaatgg taaaaaatat tactttgata ataactcaaa agcagttacc    720
ggatggcaaa ctattgatag taaaaaatat tactttaata ctaacactgc tgaagcagct    780
actggatggc aaactattga tggtaaaaaa tattacttta atactaacac tgctgaagca    840
gctactggat ggcaaactat tgatggtaaa aaatattact ttaatactaa cactgctata    900
gcttcaactg gttatacaat tattaatggt aaacattttt attttaatac tgatggtatt    960
atgcagatag gagtgtttaa aggacctaat ggatttgaat attttgcacc tgctaatacg   1020
gatgctaaca acatagaagg tcaagctata ctttaccaaa atgaattctt aactttgaat   1080
ggtaaaaaat attactttgg tagtgactca aaagcagtta ctggatggag aattattaac   1140
aataagaaat attactttaa tcctaataat gctattgctg caattcatct atgcactata   1200
aataatgaca agtattactt tagttatgat ggaattcttc aaaatggata tattactatt   1260
gaaagaaata atttctattt tgatgctaat aatgaatcta aaatggtaac aggagtattt   1320
aaaggaccta atggatttga gtattttgca cctgctaata ctcacaataa taacatagaa   1380
ggtcaggcta tagtttacca gaacaaattc ttaactttga atggcaaaaa atattatttt   1440
gataatgact caaaagcagt tactggatgg caaaccattg atggtaaaaa atattacttt   1500
```

```
aatcttaaca ctgctgaagc agctactgga tggcaaacta ttgatggtaa aaaatattac   1560

tttaatctta acactgctga agcagctact ggatggcaaa ctattgatgg taaaaaatat   1620

tactttaata ctaacacttt catagcctca actggttata caagtattaa tggtaaacat   1680

ttttatttta atactgatgg tattatgcag ataggagtgt ttaaaggacc taatggattt   1740

gaatactttg cacctgctaa tactcataat aataacatag aaggtcaagc tatactttac   1800

caaaataaat tcttaacttt gaatggtaaa aaatattact ttggtagtga ctcaaaagca   1860

gttaccggat tgcgaactat tgatggtaaa aaatattact ttaatactaa cactgctgtt   1920

gcagttactg gatggcaaac tattaatggt aaaaaatact actttaatac taacacttct   1980

atagcttcaa ctggttatac aattattagt ggtaaacatt tttattttaa tactgatggt   2040

attatgcaga taggagtgtt taaaggacct gatggatttg aatactttgc acctgctaat   2100

acagatgcta acaatataga aggtcaagct atacgttatc aaaatagatt cctatattta   2160

catgacaata tatattattt tggtaataat tcaaaagcag ctactggttg ggtaactatt   2220

gatggtaata gatattactt cgagcctaat acagctatgg gtgcgaatgg ttataaaact   2280

attgataata aaaattttta ctttagaaat ggtttacctc agataggagt gtttaaaggg   2340

tctaatggat ttgaatactt tgcacctgct aatacggatg ctaacaatat agaaggtcaa   2400

gctatacgtt atcaaaatag attcctacat ttacttggaa aaatatatta ctttggtaat   2460

aattcaaaag cagttactgg atggcaaact attaatggta aagtatatta ctttatgcct   2520

gatactgcta tggctgcagc tggtggactt ttcgagattg atggtgttat atatttcttt   2580

ggtgttgatg gagtaaaagc ccctgggata tatggc                             2616
```

<210> SEQ ID NO 44
<211> LENGTH: 2229
<212> TYPE: DNA
<213> ORGANISM: Clostridium difficile

<400> SEQUENCE: 44

```
gcagtcggat tgcaagtaat tgacaataat aagtattatt tcaatcctga cactgctatc     60

atctcaaaag gttggcagac tgttaatggt agtagatact actttgatac tgataccgct    120

attgccttta atggttataa aactattgat ggtaaacact tttattttga tagtgattgt    180

gtagtgaaaa taggtgtgtt tagtacctct aatggatttg aatattttgc acctgctaat    240

acttataata ataacataga aggtcaggct atagtttatc aaagtaaatt cttaactttg    300

aatggtaaaa aatattactt tgataataac tcaaaagcag ttaccggatg gcaaactatt    360

gatagtaaaa aatattactt taatactaac actgctgaag cagctactgg atggcaaact    420

attgatggta aaaaatatta ctttaatact aacactgctg aagcagctac tggatggcaa    480

actattgatg gtaaaaaata ttactttaat actaacactg ctatagcttc aactggttat    540

acaattatta atggtaaaca tttttatttt aatactgatg gtattatgca gataggagtg    600

tttaaaggac ctaatggatt tgaatatttt gcacctgcta atacggatgc taacaacata    660

gaaggtcaag ctatacttta ccaaaatgaa ttcttaactt tgaatggtaa aaaatattac    720

tttggtagtg actcaaaagc agttactgga tggagaatta ttaacaataa gaaatattac    780

tttaatccta ataatgctat tgctgcaatt catctatgca ctataaataa tgacaagtat    840

tactttagtt atgatggaat tcttcaaaat ggatatatta ctattgaaag aaataatttc    900

tattttgatg ctaataatga atctaaaatg gtaacaggag tatttaaagg acctaatgga    960
```

```
tttgagtatt ttgcacctgc taatactcac aataataaca tagaaggtca ggctatagtt   1020

taccagaaca aattcttaac tttgaatggc aaaaaatatt attttgataa tgactcaaaa   1080

gcagttactg gatggcaaac cattgatggt aaaaaatatt actttaatct taacactgct   1140

gaagcagcta ctggatggca aactattgat ggtaaaaaat attactttaa tcttaacact   1200

gctgaagcag ctactggatg gcaaactatt gatggtaaaa aatattactt taatactaac   1260

actttcatag cctcaactgg ttatacaagt attaatggta aacattttta ttttaatact   1320

gatggtatta tgcagatagg agtgtttaaa ggacctaatg gatttgaata ctttgcacct   1380

gctaatactc ataataataa catagaaggt caagctatac tttaccaaaa taaattctta   1440

actttgaatg gtaaaaaata ttactttggt agtgactcaa aagcagttac cggattgcga   1500

actattgatg gtaaaaaata ttactttaat actaacactg ctgttgcagt tactggatgg   1560

caaactatta atggtaaaaa atactacttt aatactaaca cttctatagc ttcaactggt   1620

tatacaatta ttagtggtaa acatttttat tttaatactg atggtattat gcagatagga   1680

gtgtttaaag gacctgatgg atttgaatac tttgcacctg ctaatacaga tgctaacaat   1740

atagaaggtc aagctatacg ttatcaaaat agattcctat atttacatga caatatatat   1800

tattttggta ataattcaaa agcagctact ggttgggtaa ctattgatgg taatagatat   1860

tacttcgagc ctaatacagc tatgggtgcg aatggttata aaactattga taataaaaat   1920

ttttacttta gaaatggttt acctcagata ggagtgttta aagggtctaa tggatttgaa   1980

tactttgcac ctgctaatac ggatgctaac aatatagaag gtcaagctat acgttatcaa   2040

aatagattcc tacatttact tggaaaaata tattactttg gtaataattc aaaagcagtt   2100

actggatggc aaactattaa tggtaaagta tattacttta tgcctgatac tgctatggct   2160

gcagctggtg gacttttcga gattgatggt gttatatatt tctttggtgt tgatggagta   2220

aaagcccct                                                           2229
```

<210> SEQ ID NO 45
<211> LENGTH: 2448
<212> TYPE: DNA
<213> ORGANISM: Clostridium difficile

<400> SEQUENCE: 45

```
atgcagttgg gagtatttaa aggacctgat ggatttgaat attttgcacc tgccaatact     60

caaaataata acatagaagg tcaggctata gtttatcaaa gtaaattctt aactttgaat    120

ggcaaaaaat attattttga taatgactca aaagcagtca ctggatggag aattattaac    180

aatgagaaat attactttaa tcctaataat gctattgctg cagtcggatt gcaagtaatt    240

gacaataata agtattattt caatcctgac actgctatca tctcaaaagg ttggcagact    300

gttaatggta gtagatacta ctttgatact gataccgcta ttgcctttaa tggttataaa    360

actattgatg gtaaacactt ttattttgat agtgattgtg tagtgaaaat aggtgtgttt    420

agtacctcta atggatttga atattttgca cctgctaata cttataataa taacatagaa    480

ggtcaggcta tagtttatca aagtaaattc ttaactttga atggtaaaaa atattacttt    540

gataataact caaaagcagt taccggatgg caaactattg atagtaaaaa atattacttt    600

aatactaaca ctgctgaagc agctactgga tggcaaacta ttgatggtaa aaaatattac    660

tttaatacta acactgctga agcagctact ggatggcaaa ctattgatgg taaaaaaatat    720

tactttaata ctaacactgc tatagcttca actggttata caattattaa tggtaaacat    780

ttttatttta atactgatgg tattatgcag ataggagtgt ttaaaggacc taatggattt    840
```

```
gaatattttg cacctgctaa tacggatgct aacaacatag aaggtcaagc tatactttac    900
caaaatgaat tcttaacttt gaatggtaaa aaatattact ttggtagtga ctcaaaagca    960
gttactggat ggagaattat taacaataag aaatattact ttaatcctaa taatgctatt   1020
gctgcaattc atctatgcac tataaataat gacaagtatt actttagtta tgatggaatt   1080
cttcaaaatg gatatattac tattgaaaga aataatttct attttgatgc taataatgaa   1140
tctaaaatgg taacaggagt atttaaagga cctaatggat ttgagtattt tgcacctgct   1200
aatactcaca ataataacat agaaggtcag gctatagttt accagaacaa attcttaact   1260
ttgaatggca aaaaatatta ttttgataat gactcaaaag cagttactgg atggcaaacc   1320
attgatggta aaaaatatta ctttaatctt aacactgctg aagcagctac tggatggcaa   1380
actattgatg gtaaaaaata ttactttaat cttaacactg ctgaagcagc tactggatgg   1440
caaactattg atggtaaaaa atattacttt aatactaaca ctttcatagc ctcaactggt   1500
tatacaagta ttaatggtaa acatttttat tttaatactg atggtattat gcagatagga   1560
gtgtttaaag gacctaatgg atttgaatac tttgcacctg ctaatactca taataataac   1620
atagaaggtc aagctatact ttaccaaaat aaattcttaa ctttgaatgg taaaaaatat   1680
tactttggta gtgactcaaa agcagttacc ggattgcgaa ctattgatgg taaaaaatat   1740
tactttaata ctaacactgc tgttgcagtt actggatggc aaactattaa tggtaaaaaa   1800
tactacttta atactaacac ttctatagct tcaactggtt atacaattat tagtggtaaa   1860
catttttatt ttaatactga tggtattatg cagataggag tgtttaaagg acctgatgga   1920
tttgaatact ttgcacctgc taatacagat gctaacaata tagaaggtca agctatacgt   1980
tatcaaaata gattcctata tttacatgac aatatatatt attttggtaa taattcaaaa   2040
gcagctactg gttgggtaac tattgatggt aatagatatt acttcgagcc taatacagct   2100
atgggtgcga atggttataa aactattgat aataaaaatt tttactttag aaatggttta   2160
cctcagatag gagtgtttaa agggtctaat ggatttgaat actttgcacc tgctaatacg   2220
gatgctaaca atatagaagg tcaagctata cgttatcaaa atagattcct acatttactt   2280
ggaaaaatat attactttgg taataattca aaagcagtta ctggatggca aactattaat   2340
ggtaaagtat attactttat gcctgatact gctatggctg cagctggtgg acttttcgag   2400
attgatggtg ttatatattt ctttggtgtt gatggagtaa aagcccct                2448
```

<210> SEQ ID NO 46
<211> LENGTH: 2301
<212> TYPE: DNA
<213> ORGANISM: Clostridium difficile

<400> SEQUENCE: 46

```
atgagtttag ttaatagaaa acagttagaa aaaatggcaa atgtaagatt tcgtactcaa     60
gaagatgaat atgttgcaat attggatgct ttagaagaat atcataatat gtcagagaat    120
actgtagtcg aaaaatattt aaaattaaaa gatataaata gtttaacaga tatttatata    180
gatacatata aaaaatctgg tagaaataaa gccttaaaaa aatttaagga atatctagtt    240
acagaagtat tagagctaaa gaataataat ttaactccag ttgagaaaaa tttacatttt    300
gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
```

-continued ttaaatgacc ctagatttga ctataataaa ttcttcagaa aacgtatgga aataatttat 540
gataaacaga aaaatttcat aaactactat aaagctcaaa gagaagaaaa tcctgaactt 600
ataattgatg atattgtaaa gacatatctt tcaaatgagt attcaaagga gatagatgaa 660
cttaatacct atattgaaga atccttaaat aaaattacac agaatagtgg aaatgatgtt 720
agaaactttg aagaatttaa aaatggagag tcattcaact tatatgaaca agagttggta 780
gaaaggtgga atttagctgc tgcttctgac atattaagaa tatctgcatt aaaagaaatt 840
ggtggtatgt atttagatgt tgatatgtta ccaggaatac aaccagactt atttgagtct 900
atagagaaac ctagttcagt aacagtggat ttttgggaaa tgacaaagtt agaagctata 960
atgaaataca aagaatatat accagaatat acctcagaac attttgacat gttagacgaa 1020
gaagttcaaa gtagttttga atctgttcta gcttctaagt cagataaatc agaaatattc 1080
tcatcacttg gtgatatgga ggcatcacca ctagaagtta aaattgcatt taatagtaag 1140
ggtattataa atcaagggct aatttctgtg aaagactcat attgtagcaa tttaatagta 1200
aaacaaatcg agaatagata taaaatattg aataatagtt taaatccagc tattagcgag 1260
gataatgatt ttaatactac aacgaatacc tttattgata gtataatggc tgaagctaat 1320
gcagataatg gtagatttat gatggaacta ggaaagtatt taagagttgg tttcttccca 1380
gatgttaaaa ctactattaa cttaagtggc cctgaagcat atgcggcagc ttatcaagat 1440
ttattaatgt ttaaagaagg cagtatgaat atccatttga tagaagctga tttaagaaac 1500
tttgaaatct ctaaaactaa tatttctcaa tcaactgaac aagaaatggc tagcttatgg 1560
tcatttgacg atgcaagagc taaagctcaa tttgaagaat ataaaaggaa ttattttgaa 1620
ggttctcttg gtgaagatga taatcttgat ttttctcaaa atatagtagt tgacaaggag 1680
tatcttttag aaaaaatatc ttcattagca agaagttcag agagaggata tatacactat 1740
attgttcagt tacaaggaga taaaattagt tatgaagcag catgtaactt atttgcaaag 1800
actccttatg atagtgtact gtttcagaaa aatatagaag attcagaaat tgcatattat 1860
tataatcctg gagatggtga aatacaagaa atagacaagt ataaaattcc aagtataatt 1920
tctgatagac ctaagattaa attaacattt attggtcatg gtaaagatga atttaatact 1980
gatatatttg caggttttga tgtagattca ttatccacag aaatagaagc agcaatagat 2040
ttagctaaag aggatatttc tcctaagtca atagaaataa atttattagg atgtaatatg 2100
tttagctact ctatcaacgt agaggagact tatcctggaa aattattact taaagttaaa 2160
gataaaatat cagaattaat gccatctata agtcaagact ctattatagt aagtgcaaat 2220
caatatgaag ttagaataaa tagtgaagga agaagagaat tattggatca ttctggtgaa 2280
tggataaata aagaagaaag t 2301

<210> SEQ ID NO 47
<211> LENGTH: 1629
<212> TYPE: DNA
<213> ORGANISM: Clostridium difficile

<400> SEQUENCE: 47
atgagtttag ttaatagaaa acagttagaa aaaatggcaa atgtaagatt tcgtactcaa 60
gaagatgaat atgttgcaat attggatgct ttagaagaat atcataatat gtcagagaat 120
actgtagtcg aaaaatattt aaaattaaaa gatataaata gtttaacaga tatttatata 180
gatacatata aaaaatctgg tagaaataaa gccttaaaaa aatttaagga atatctagtt 240
acagaagtat tagagctaaa gaataataat ttaactccag ttgagaaaaa tttacatttt 300

```
gtttggattg gaggtcaaat aaatgacact gctattaatt atataaatca atggaaagat    360
gtaaatagtg attataatgt taatgttttt tatgatagta atgcattttt gataaacaca    420
ttgaaaaaaa ctgtagtaga atcagcaata aatgatacac ttgaatcatt tagagaaaac    480
ttaaatgacc ctagatttga ctataataaa ttcttcagaa aacgtatgga aataatttat    540
gataaacaga aaaatttcat aaactactat aaagctcaaa gagaagaaaa tcctgaactt    600
ataattgatg atattgtaaa gacatatctt tcaaatgagt attcaaagga gatagatgaa    660
cttaatacct atattgaaga atccttaaat aaaattacac agaatagtgg aaatgatgtt    720
agaaactttg aagaatttaa aaatggagag tcattcaact tatatgaaca agagttggta    780
gaaaggtgga atttagctgc tgcttctgac atattaagaa tatctgcatt aaaagaaatt    840
ggtggtatgt atttagatgt tgatatgtta ccaggaatac aaccagactt atttgagtct    900
atagagaaac ctagttcagt aacagtggat ttttgggaaa tgacaaagtt agaagctata    960
atgaaataca aagaatatat accagaatat acctcagaac attttgacat gttagacgaa   1020
gaagttcaaa gtagttttga atctgttcta gcttctaagt cagataaatc agaaatattc   1080
tcatcacttg gtgatatgga ggcatcacca ctagaagtta aaattgcatt taatagtaag   1140
ggtattataa atcaagggct aatttctgtg aaagactcat attgtagcaa tttaatagta   1200
aaacaaatcg agaatagata taaaatattg aataatagtt taaatccagc tattagcgag   1260
gataatgatt ttaatactac aacgaatacc tttattgata gtataatggc tgaagctaat   1320
gcagataatg gtagatttat gatggaacta ggaaagtatt taagagttgg tttcttccca   1380
gatgttaaaa ctactattaa cttaagtggc cctgaagcat atgcggcagc ttatcaagat   1440
ttattaatgt ttaaagaagg cagtatgaat atccatttga tagaagctga tttaagaaac   1500
tttgaaatct ctaaaactaa tatttctcaa tcaactgaac aagaaatggc tagcttatgg   1560
tcatttgacg atgcaagagc taaagctcaa tttgaagaat ataaaaggaa ttattttgaa   1620
ggttctctt                                                           1629
```

<210> SEQ ID NO 48
<211> LENGTH: 672
<212> TYPE: DNA
<213> ORGANISM: Clostridium difficile

<400> SEQUENCE: 48

```
ggtgaagatg ataatcttga tttttctcaa aatatagtag ttgacaagga gtatctttta     60
gaaaaaatat cttcattagc aagaagttca gagagaggat atatacacta tattgttcag    120
ttacaaggag ataaaattag ttatgaagca gcatgtaact tatttgcaaa gactccttat    180
gatagtgtac tgtttcagaa aaatatagaa gattcagaaa ttgcatatta ttataatcct    240
ggagatggtg aaatacaaga aatagacaag tataaaattc caagtataat ttctgataga    300
cctaagatta aattaacatt tattggtcat ggtaaagatg aatttaatac tgatatattt    360
gcaggttttg atgtagattc attatccaca gaaatagaag cagcaataga tttagctaaa    420
gaggatattt ctcctaagtc aatagaaata aatttattag gatgtaatat gtttagctac    480
tctatcaacg tagaggagac ttatcctgga aaattattac ttaaagttaa agataaaata    540
tcagaattaa tgccatctat aagtcaagac tctattatag taagtgcaaa tcaatatgaa    600
gttagaataa atagtgaagg aagaagagaa ttattggatc attctggtga atggataaat    660
aaagaagaaa gt                                                        672
```

<210> SEQ ID NO 49
<211> LENGTH: 3198
<212> TYPE: DNA
<213> ORGANISM: Clostridium difficile

<400> SEQUENCE: 49
attataaagg atatttcatc aaaagaatat atatcattta atcctaaaga aaataaaatt 60
acagtaaaat ctaaaaattt acctgagcta tctacattat tacaagaaat tagaaataat 120
tctaattcaa gtgatattga actagaagaa aaagtaatgt taacagaatg tgagataaat 180
gttatttcaa atatagatac gcaaattgtt gaggaaagga ttgaagaagc taagaattta 240
acttctgact ctattaatta tataaaagat gaatttaaac taatagaatc tatttctgat 300
gcactatgtg acttaaaaca acagaatgaa ttagaagatt ctcattttat atcttttgag 360
gacatatcag agactgatga gggatttagt ataagattta ttaataaaga aactggagaa 420
tctatatttg tagaaactga aaaaacaata ttctctgaat atgctaatca tataactgaa 480
gagatttcta agataaaagg tactatattt gatactgtaa atggtaagtt agtaaaaaaa 540
gtaaatttag atactacaca cgaagtaaat actttaaatg ctgcattttt tatacaatca 600
ttaatagaat ataatagttc taaagaatct cttagtaatt taagtgtagc aatgaaagtc 660
caagtttacg ctcaattatt tagtactggt ttaaatacta ttacagatgc agccaaagtt 720
gttgaattag tatcaactgc attagatgaa actatagact tacttcctac attatctgaa 780
ggattaccta taattgcaac tattatagat ggtgtaagtt taggtgcagc aatcaaagag 840
ctaagtgaaa cgagtgaccc attattaaga caagaaatag aagctaagat aggtataatg 900
gcagtaaatt taacaacagc tacaactgca atcattactt catctttggg gatagctagt 960
ggatttagta tacttttagt tcctttagca ggaatttcag caggtatacc aagcttagta 1020
aacaatgaac ttgtacttcg agataaggca acaaaggttg tagattattt taaacatgtt 1080
tcattagttg aaactgaagg agtatttact ttattagatg ataaaataat gatgccacaa 1140
gatgatttag tgatatcaga aatagatttt aataatatt caatagtttt aggtaaatgt 1200
gaaatctgga gaatggaagg tggttcaggt catactgtaa ctgatgatat agatcacttc 1260
ttttcagcac catcaataac atatagagag ccacacttat ctatatatga cgtattggaa 1320
gtacaaaaag aagaacttga tttgtcaaaa gatttaatgg tattacctaa tgctccaaat 1380
agagtatttg cttgggaaac aggatggaca ccaggtttaa gaagcttaga aaatgatggc 1440
acaaaactgt tagaccgtat aagagataac tatgaaggtg agttttattg gagatatttt 1500
gcttttatag ctgatgcttt aataacaaca ttaaaaccaa gatatgaaga tactaatata 1560
agaataaatt tagatagtaa tactagaagt tttatagttc caataataac tacagaatat 1620
ataagagaaa aattatcata ttctttctat ggttcaggag gaacttatgc attgtctctt 1680
tctcaatata atatgggtat aaatatagaa ttaagtgaaa gtgatgtttg gattatagat 1740
gttgataatg ttgtgagaga tgtaactata gaatctgata aaattaaaaa aggtgattta 1800
atagaaggta ttttatctac actaagtatt gaagagaata aaattatctt aaatagccat 1860
gagattaatt tttctggtga ggtaaatgga agtaatggat ttgtttcttt aacattttca 1920
attttagaag gaataaatgc aattatagaa gttgatttat tatctaaatc atataaatta 1980
cttatttctg gcgaattaaa aatattgatg ttaaattcaa atcatattca acagaaaata 2040
gattatatag gattcaatag cgaattacag aaaaatatac catatagctt tgtagatagt 2100
gaaggaaaag agaatggttt tattaatggt tcaacaaaag aaggtttatt tgtatctgaa 2160

-continued ttacctgatg tagttcttat aagtaaggtt tatatggatg atagtaagcc ttcatttgga 2220
tattatagta ataatttgaa agatgtcaaa gttataacta aagataatgt taatatatta 2280
acaggttatt atcttaagga tgatataaaa atctctcttt ctttgactct acaagatgaa 2340
aaaactataa agttaaatag tgtgcattta gatgaaagtg gagtagctga gattttgaag 2400
ttcatgaata gaaaaggtaa tacaaatact tcagattctt taatgagctt tttagaaagt 2460
atgaatataa aaagtatttt cgttaatttc ttacaatcta atattaagtt tatattagat 2520
gctaatttta taataagtgg tactacttct attggccaat ttgagtttat ttgtgatgaa 2580
aatgataata tacaaccata tttcattaag tttaatacac tagaaactaa ttatacttta 2640
tatgtaggaa atagacaaaa tatgatagtg gaaccaaatt atgatttaga tgattctgga 2700
gatatatctt caactgttat caatttctct caaaagtatc tttatggaat agacagttgt 2760
gttaataaag ttgtaatttc accaaatatt tatacagatg aaataaatat aacgcctgta 2820
tatgaaacaa ataatactta tccagaagtt attgtattag atgcaaatta tataaatgaa 2880
aaaataaatg ttaatatcaa tgatctatct atacgatatg tatggagtaa tgatggtaat 3000
gattttattc ttatgtcaac tagtgaagaa aataaggtgt cacaagttaa aataagattc 3000
gttaatgttt ttaaagataa gactttggca aataagctat cttttaactt tagtgataaa 3060
caagatgtac ctgtaagtga aataatctta tcatttacac cttcatatta tgaggatgga 3120
ttgattggct atgatttggg tctagtttct ttatataatg agaaatttta tattaataac 3180
tttggaatga tggtatct 3198

<210> SEQ ID NO 50
<211> LENGTH: 1545
<212> TYPE: DNA
<213> ORGANISM: Clostridium difficile

<400> SEQUENCE: 50
ataactggat ttgtgactgt aggcgatgat aaatactact ttaatccaat taatggtgga 60
gctgcttcaa ttggagagac aataattgat gacaaaaatt attatttcaa ccaaagtgga 120
gtgttacaaa caggtgtatt tagtacagaa gatggattta aatattttgc cccagctaat 180
acacttgatg aaaacctaga aggagaagca attgatttta ctggaaaatt aattattgac 240
gaaaatattt attattttga tgataattat agaggagctg tagaatggaa agaattagat 300
ggtgaaatgc actattttag cccagaaaca ggtaaagctt ttaaaggtct aaatcaaata 360
ggtgattata aatactattt caattctgat ggagttatgc aaaaaggatt tgttagtata 420
aatgataata aacactattt tgatgattct ggtgttatga aagtaggtta cactgaaata 480
gatggcaagc atttctactt tgctgaaaac ggagaaatgc aaataggagt atttaataca 540
gaagatggat ttaaatattt tgctcatcat aatgaagatt taggaaatga agaaggtgaa 600
gaaatctcat attctggtat attaaatttc aataataaaa tttactattt tgatgattca 660
tttacagctg tagttggatg gaaagattta gaggatggtt caaagtatta ttttgatgaa 720
gatacagcag aagcatatat aggtttgtca ttaataaatg atggtcaata ttattttaat 780
gatgatggaa ttatgcaagt tggatttgtc actataaatg ataaagtctt ctacttctct 840
gactctggaa ttatagaatc tggagtacaa aacatagatg acaattattt ctatatagat 900
gataatggta tagttcaaat tggtgtattt gatacttcag atggatataa atattttgca 960
cctgctaata ctgtaaatga taatatttac ggacaagcag ttgaatatag tggtttagtt 1020

-continued

```
agagttggtg aagatgtata ttattttgga gaaacatata caattgagac tggatggata   1080

tatgatatgg aaaatgaaag tgataaatat tatttcaatc cagaaactaa aaaagcatgc   1140

aaaggtatta atttaattga tgatataaaa tattattttg atgagaaggg cataatgaga   1200

acgggtctta tatcatttga aaataataat tattacttta atgagaatgg tgaaatgcaa   1260

tttggttata taaatataga agataagatg ttctattttg gtgaagatgg tgtcatgcag   1320

attggagtat ttaatacacc agatggattt aaatactttg cacatcaaaa tactttggat   1380

gagaattttg agggagaatc aataaactat actggttggt tagatttaga tgaaaagaga   1440

tattatttta cagatgaata tattgcagca actggttcag ttattattga tggtgaggag   1500

tattattttg atcctgatac agctcaatta gtgattagtg aatag                   1545
```

<210> SEQ ID NO 51
<211> LENGTH: 633
<212> TYPE: DNA
<213> ORGANISM: Clostridium difficile

<400> SEQUENCE: 51

```
gttcaaattg gtgtatttga tacttcagat ggatataaat attttgcacc tgctaatact     60

gtaaatgata atatttacgg acaagcagtt gaatatagtg gtttagttag agttggtgaa    120

gatgtatatt attttggaga aacatataca attgagactg gatggatata tgatatggaa    180

aatgaaagtg ataaatatta tttcaatcca gaaactaaaa aagcatgcaa aggtattaat    240

ttaattgatg atataaaata ttattttgat gagaagggca taatgagaac gggtcttata    300

tcatttgaaa ataataatta ttactttaat gagaatggtg aaatgcaatt tggttatata    360

aatatagaag ataagatgtt ctattttggt gaagatggtg tcatgcagat tggagtattt    420

aatacaccag atggatttaa atactttgca catcaaaata ctttggatga gaattttgag    480

ggagaatcaa taaactatac tggttggtta gatttagatg aaaagagata ttattttaca    540

gatgaatata ttgcagcaac tggttcagtt attattgatg gtgaggagta ttattttgat    600

cctgatacag ctcaattagt gattagtgaa tag                                 633
```

<210> SEQ ID NO 52
<211> LENGTH: 933
<212> TYPE: DNA
<213> ORGANISM: Clostridium difficile

<400> SEQUENCE: 52

```
tattctggta tattaaattt caataataaa atttactatt ttgatgattc atttacagct     60

gtagttggat ggaaagattt agaggatggt tcaaagtatt attttgatga agatacagca    120

gaagcatata taggtttgtc attaataaat gatggtcaat attattttaa tgatgatgga    180

attatgcaag ttggatttgt cactataaat gataaagtct tctacttctc tgactctgga    240

attatagaat ctggagtaca aaacatagat gacaattatt tctatataga tgataatggt    300

atagttcaaa ttggtgtatt tgatacttca gatggatata aatattttgc acctgctaat    360

actgtaaatg ataatattta cggacaagca gttgaatata gtggtttagt tagagttggt    420

gaagatgtat attattttgg agaaacatat acaattgaga ctggatggat atatgatatg    480

gaaaatgaaa gtgataaata ttatttcaat ccagaaacta aaaaagcatg caaaggtatt    540

aatttaattg atgatataaa atattatttt gatgagaagg gcataatgag aacgggtctt    600

atatcatttg aaaataataa ttattacttt aatgagaatg gtgaaatgca atttggttat    660

ataaatatag aagataagat gttctatttt ggtgaagatg gtgtcatgca gattggagta    720
```

tttaatacac cagatggatt taaatacttt gcacatcaaa atactttgga tgagaatttt 780
gagggagaat caataaacta tactggttgg ttagatttag atgaaaagag atattatttt 840
acagatgaat atattgcagc aactggttca gttattattg atggtgagga gtattatttt 900
gatcctgata cagctcaatt agtgattagt gaa 933

<210> SEQ ID NO 53
<211> LENGTH: 2616
<212> TYPE: DNA
<213> ORGANISM: Artificial Sequence
<220> FEATURE:
<223> OTHER INFORMATION: Description of Artificial Sequence: Synthetic
B4 hybrid polynucleotide

<400> SEQUENCE: 53
catatgagtc tggttaaccg taaacaactg gaaaaaatgg cgaatgtgcg ctttagaacc 60
caggaagatg aatatgttgc gattctagat gcactggaag aataccataa catgtcagag 120
aataccgtgg tagaaaaata tctgaaactg aaagatatta actctctgac ggatatctat 180
attgacacgt acaaaaaaag cggtcgtaat aaagctctga aaaaatttaa ggaatatctc 240
gttacggaag tgctggagct caagaacaat aacctgaccc cggttgagaa aaatctgcat 300
ttcgtttgga tcggcggtca gattaacgac accgccatca attacattaa ccagtggaaa 360
gatgtgaata gcgattataa cgttaatgtc ttttatgact cgaacgcgtt tctaattaac 420
acgctaaaaa aaaccgtggt ggaaagcgcg attaatgata ctcttgagag ctttcgcgaa 480
aacctgaacg acccacgttt cgactacaat aaattcttcc gcaaaagaat ggaaattatc 540
tatgataaac aaaaaaactt cattaactac tataaagcac aacgtgaaga aaatccggaa 600
ctgattatcg acgatatcgt gaagacgtac ttgagcaacg agtatagcaa ggagattgat 660
gaacttaata catacatcga agaatcactg aacaaaatca cgcaaaatag tggcaacgac 720
gttcgcaact ttgaggaatt taaaaatggc gagagcttca acttatatga acaggagcta 780
gtggaacgat ggaacctggc cgcagcctcc gcgattctgg cgatttctgc gctgaaagaa 840
atcggtggta tggcgctggc ggtcgcgatg ctgccgggca ttcagccgga cctgtttgag 900
tccattgaga aacctagtag cgtgacggta gacttctggg aaatgacgaa gttagaagca 960
attatgaaat acaaagaata tattccggaa tacacaagcg aacactttga catgctggac 1020
gaggaagttc agtcgagctt tgaatctgtc ctcgccagca agagcgataa aagcgaaatt 1080
ttcagcagcc tgggtgatat ggaggcgagc ccgctcgaag ttaaaatcgc gtttaattcg 1140
aagggtatca ttaaccaagg actcatctcc gtaaaagaca gctattgttc aaatctgatt 1200
gtgaaacaga tagagaaccg ctataaaatt ctaaataaca gtctgaatcc ggcaatctca 1260
gaggacaacg atttcaatac cactacaaac acatttatcg atagtattat ggccgaagca 1320
aatgcggaca acggtcgttt tatgatggaa ctcggtaagt acctgcgcgt cggtttcttc 1380
ccggatgtta aaaccaccat caacttatcg ggaccagaag cgtatgctgc ggcctaccag 1440
gatctgctga tgtttaaaga aggaagcatg aatatacatc taattgaagc agacctgcgt 1500
aacttcgaga tatctaaaac caacatctcc caaagcaccg aacaggaaat ggcctcactg 1560
tggagctttg acgatgcgcg cgcaaaagcc cagtttgaag aatataaacg aaattacttt 1620
gaaggtagct tgggatccgg agggggtggt gctagcaccg gttatacttc gatcaacggt 1680
aaacattttt actttaatac cgacggtatc atgcaaattg gcgtattcaa aggtcctaac 1740
ggctttgaat actttgcgcc agcaaatacc cacaacaata acattgaagg tcaggccatt 1800

```
ctgtaccaaa acaaattcct gaccctaaat ggtaaaaaat attacttcgg tagtgacagc   1860

aaagcggtta caggcctaag gaccatcgat ggtaaaaaat attactttaa caccaacacc   1920

gcagtcgcgg ttaccggctg gcagaccatc aatggtaaaa aatactactt taacaccaac   1980

acctctattg ccagcaccgg ttacacgatc atctcgggta aacatttcta ttttaatacc   2040

gatggtatca tgcaaattgg cgtatttaaa ggtccggacg gcttcgaata ctttgcgcct   2100

gcaaacacgg atgccaacaa tattgagggt caggcaatta gatatcaaaa ccgcttcctc   2160

tacctgcatg acaatattta ttactttggt aacaatagca aagcggccac cggttgggtg   2220

accatcgatg gtaaccgtta ttacttcgag ccaaatacgg caatgggtgc taacggttat   2280

aaaaccatcg acaataaaaa cttctacttt cgcaatggtc tgccgcaaat tggcgtattt   2340

aaaggatcta acggcttcga atactttgcg cctgccaata cagatgcaaa caacattgaa   2400

ggtcaggcca ttagatacca aaatcgtttc ctccatttac ttggcaaaat ttattacttt   2460

ggtaacaata gcaaagcggt caccggttgg caaaccatca acggtaaagt gtattacttt   2520

atgccagata ccgcaatggc cgcggcaggt ggcttgttcg agatcgacgg tgttatttac   2580

ttcttcggtg tcgatggcgt gaaagctccg ctcgag                             2616
```

```
<210> SEQ ID NO 54
<211> LENGTH: 769
<212> TYPE: PRT
<213> ORGANISM: Artificial Sequence
<220> FEATURE:
<223> OTHER INFORMATION: Description of Artificial Sequence: Synthetic
      Mutated sequence polynucleotide

<400> SEQUENCE: 54

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160

Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205
```

-continued

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Ala Leu Ala Val Ala Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser Leu Ser Glu
    530                 535                 540

Asp Asn Gly Val Asp Phe Asn Lys Asn Thr Ala Leu Asp Lys Asn Tyr
545                 550                 555                 560

Leu Leu Asn Asn Lys Ile Pro Ser Asn Asn Val Glu Glu Ala Gly Ser
                565                 570                 575

Lys Asn Tyr Val His Tyr Ile Ile Gln Leu Gln Gly Asp Asp Ile Ser
            580                 585                 590

Tyr Glu Ala Thr Cys Asn Leu Phe Ser Lys Asn Pro Lys Asn Ser Ile
        595                 600                 605

Ile Ile Gln Arg Asn Met Asn Glu Ser Ala Lys Ser Tyr Phe Leu Ser
    610                 615                 620

Asp Asp Gly Glu Ser Ile Leu Glu Leu Asn Lys Tyr Arg Ile Pro Glu

-continued

```
625                 630                 635                 640

Arg Leu Lys Asn Lys Glu Lys Val Lys Val Thr Phe Ile Gly His Gly
                645                 650                 655

Lys Asp Glu Phe Asn Thr Ser Glu Phe Ala Arg Leu Ser Val Asp Ser
            660                 665                 670

Leu Ser Asn Glu Ile Ser Ser Phe Leu Asp Thr Ile Lys Leu Asp Ile
        675                 680                 685

Ser Pro Lys Asn Val Glu Val Asn Leu Leu Gly Cys Asn Met Phe Ser
    690                 695                 700

Tyr Asp Phe Asn Val Glu Glu Thr Tyr Pro Gly Lys Leu Leu Leu Ser
705                 710                 715                 720

Ile Met Asp Lys Ile Thr Ser Thr Leu Pro Asp Val Asn Lys Asn Ser
                725                 730                 735

Ile Thr Ile Gly Ala Asn Gln Tyr Glu Val Arg Ile Asn Ser Glu Gly
            740                 745                 750

Arg Lys Glu Leu Leu Ala His Ser Gly Lys Trp Ile Asn Lys Glu Glu
        755                 760                 765

Ala


<210> SEQ ID NO 55
<211> LENGTH: 2307
<212> TYPE: DNA
<213> ORGANISM: Artificial Sequence
<220> FEATURE:
<223> OTHER INFORMATION: Description of Artificial Sequence: Synthetic
      Mutated sequence polynucleotide

<400> SEQUENCE: 55

atgtctttaa tatctaaaga agagttaata aaactcgcat atagcattag accaagagaa     60

aatgagtata aaactatact aactaattta gacgaatata ataagttaac tacaaacaat    120

aatgaaaata aatatttaca attaaaaaaa ctaaatgaat caattgatgt ttttatgaat    180

aaatataaaa cttcaagcag aaatagagca ctctctaatc taaaaaaaga tatattaaaa    240

gaagtaattc ttattaaaaa ttccaataca agccctgtag aaaaaaattt acattttgta    300

tggataggtg gagaagtcag tgatattgct cttgaataca taaaacaatg ggctgatatt    360

aatgcagaat ataatattaa actgtggtat gatagtgaag cattcttagt aaatacacta    420

aaaaaggcta tagttgaatc ttctaccact gaagcattac agctactaga ggaagagatt    480

caaaatcctc aatttgataa tatgaaattt tacaaaaaaa ggatggaatt tatatatgat    540

agacaaaaaa ggtttataaa ttattataaa tctcaaatca ataaacctac agtacctaca    600

atagatgata ttataaagtc tcatctagta tctgaatata atagagatga aactgtatta    660

gaatcatata gaacaaattc tttgagaaaa ataaatagta atcatgggat agatatcagg    720

gctaatagtt tgtttacaga acaagagtta ttaaatattt atagtcagga gttgttaaat    780

cgtggaaatt tagctgcagc atctgacata gtaagattat tagccctaaa aaattttggc    840

ggagtagcct tagccgttgc catgcttcca ggtattcact ctgatttatt taaaacaata    900

tctagaccta gctctattgg actagaccgt tgggaaatga taaaattaga ggctattatg    960

aagtataaaa aatatataaa taattataca tcagaaaact ttgataaact tgatcaacaa   1020

ttaaaagata attttaaact cattatagaa agtaaaagtg aaaaatctga gatattttct   1080

aaattagaaa atttaaatgt atctgatctt gaaattaaaa tagctttcgc tttaggcagt   1140

gttataaatc aagccttgat atcaaaacaa ggttcatatc ttactaacct agtaatagaa   1200
```

-continued

```
caagtaaaaa atagatatca atttttaaac caacacctta acccagccat agagtctgat   1260

aataacttca cagatactac taaaattttt catgattcat tatttaattc agctaccgca   1320

gaaaactcta tgtttttaac aaaaatagca ccatacttac aagtaggttt tatgccagaa   1380

gctcgctcca caataagttt aagtggtcca ggagcttatg cgtcagctta ctatgatttc   1440

ataaatttac aagaaaatac tatagaaaaa actttaaaag catcagattt aatagaattt   1500

aaattcccag aaaataatct atctcaattg acagaacaag aaataaatag tctatggagc   1560

tttgatcaag caagtgcaaa atatcaattt gagaaatatg taagagatta tactggtgga   1620

tctctttctg aagacaatgg ggtagacttt aataaaaata ctgccctcga caaaaactat   1680

ttattaaata ataaaattcc atcaaacaat gtagaagaag ctggaagtaa aaattatgtt   1740

cattatatca tacagttaca aggagatgat ataagttatg aagcaacatg caatttattt   1800

tctaaaaatc ctaaaaatag tattattata caacgaaata tgaatgaaag tgcaaaaagc   1860

tactttttaa gtgatgatgg agaatctatt ttagaattaa ataaatatag gatacctgaa   1920

agattaaaaa ataaggaaaa agtaaaagta acctttattg gacatggtaa agatgaattc   1980

aacacaagcg aatttgctag attaagtgta gattcacttt ccaatgagat aagttcattt   2040

ttagatacca taaaattaga tatatcacct aaaaatgtag aagtaaactt acttggatgt   2100

aatatgttta gttatgattt taatgttgaa gaaacttatc ctgggaagtt gctattaagt   2160

attatggaca aaattacttc cactttacct gatgtaaata aaaattctat tactatagga   2220

gcaaatcaat atgaagtaag aattaatagt gagggaagaa aagaacttct ggctcactca   2280

ggtaaatgga taaataaaga agaagct                                       2307
```

```
<210> SEQ ID NO 56
<211> LENGTH: 541
<212> TYPE: PRT
<213> ORGANISM: Artificial Sequence
<220> FEATURE:
<223> OTHER INFORMATION: Description of Artificial Sequence: Synthetic
      Mutated sequence polypeptide

<400> SEQUENCE: 56

Met Ser Leu Ile Ser Lys Glu Glu Leu Ile Lys Leu Ala Tyr Ser Ile
1               5                   10                  15

Arg Pro Arg Glu Asn Glu Tyr Lys Thr Ile Leu Thr Asn Leu Asp Glu
            20                  25                  30

Tyr Asn Lys Leu Thr Thr Asn Asn Asn Glu Asn Lys Tyr Leu Gln Leu
        35                  40                  45

Lys Lys Leu Asn Glu Ser Ile Asp Val Phe Met Asn Lys Tyr Lys Thr
    50                  55                  60

Ser Ser Arg Asn Arg Ala Leu Ser Asn Leu Lys Lys Asp Ile Leu Lys
65                  70                  75                  80

Glu Val Ile Leu Ile Lys Asn Ser Asn Thr Ser Pro Val Glu Lys Asn
                85                  90                  95

Leu His Phe Val Trp Ile Gly Gly Glu Val Ser Asp Ile Ala Leu Glu
            100                 105                 110

Tyr Ile Lys Gln Trp Ala Asp Ile Asn Ala Glu Tyr Asn Ile Lys Leu
        115                 120                 125

Trp Tyr Asp Ser Glu Ala Phe Leu Val Asn Thr Leu Lys Lys Ala Ile
    130                 135                 140

Val Glu Ser Ser Thr Thr Glu Ala Leu Gln Leu Leu Glu Glu Glu Ile
145                 150                 155                 160
```

```
Gln Asn Pro Gln Phe Asp Asn Met Lys Phe Tyr Lys Lys Arg Met Glu
                165                 170                 175

Phe Ile Tyr Asp Arg Gln Lys Arg Phe Ile Asn Tyr Tyr Lys Ser Gln
            180                 185                 190

Ile Asn Lys Pro Thr Val Pro Thr Ile Asp Asp Ile Ile Lys Ser His
        195                 200                 205

Leu Val Ser Glu Tyr Asn Arg Asp Glu Thr Val Leu Glu Ser Tyr Arg
    210                 215                 220

Thr Asn Ser Leu Arg Lys Ile Asn Ser Asn His Gly Ile Asp Ile Arg
225                 230                 235                 240

Ala Asn Ser Leu Phe Thr Glu Gln Glu Leu Leu Asn Ile Tyr Ser Gln
                245                 250                 255

Glu Leu Leu Asn Arg Gly Asn Leu Ala Ala Ala Ser Asp Ile Val Arg
            260                 265                 270

Leu Leu Ala Leu Lys Asn Phe Gly Gly Val Ala Leu Ala Val Ala Met
        275                 280                 285

Leu Pro Gly Ile His Ser Asp Leu Phe Lys Thr Ile Ser Arg Pro Ser
    290                 295                 300

Ser Ile Gly Leu Asp Arg Trp Glu Met Ile Lys Leu Glu Ala Ile Met
305                 310                 315                 320

Lys Tyr Lys Lys Tyr Ile Asn Asn Tyr Thr Ser Glu Asn Phe Asp Lys
                325                 330                 335

Leu Asp Gln Gln Leu Lys Asp Asn Phe Lys Leu Ile Ile Glu Ser Lys
            340                 345                 350

Ser Glu Lys Ser Glu Ile Phe Ser Lys Leu Glu Asn Leu Asn Val Ser
        355                 360                 365

Asp Leu Glu Ile Lys Ile Ala Phe Ala Leu Gly Ser Val Ile Asn Gln
    370                 375                 380

Ala Leu Ile Ser Lys Gln Gly Ser Tyr Leu Thr Asn Leu Val Ile Glu
385                 390                 395                 400

Gln Val Lys Asn Arg Tyr Gln Phe Leu Asn Gln His Leu Asn Pro Ala
                405                 410                 415

Ile Glu Ser Asp Asn Asn Phe Thr Asp Thr Thr Lys Ile Phe His Asp
            420                 425                 430

Ser Leu Phe Asn Ser Ala Thr Ala Glu Asn Ser Met Phe Leu Thr Lys
        435                 440                 445

Ile Ala Pro Tyr Leu Gln Val Gly Phe Met Pro Glu Ala Arg Ser Thr
    450                 455                 460

Ile Ser Leu Ser Gly Pro Gly Ala Tyr Ala Ser Ala Tyr Tyr Asp Phe
465                 470                 475                 480

Ile Asn Leu Gln Glu Asn Thr Ile Glu Lys Thr Leu Lys Ala Ser Asp
                485                 490                 495

Leu Ile Glu Phe Lys Phe Pro Glu Asn Asn Leu Ser Gln Leu Thr Glu
            500                 505                 510

Gln Glu Ile Asn Ser Leu Trp Ser Phe Asp Gln Ala Ser Ala Lys Tyr
        515                 520                 525

Gln Phe Glu Lys Tyr Val Arg Asp Tyr Thr Gly Gly Ser
    530                 535                 540
```

<210> SEQ ID NO 57
<211> LENGTH: 1623
<212> TYPE: DNA
<213> ORGANISM: Artificial Sequence
<220> FEATURE:
<223> OTHER INFORMATION: Description of Artificial Sequence: Synthetic Mutated sequence polynucleotide

<400> SEQUENCE: 57

```
atgtctttaa tatctaaaga agagttaata aaactcgcat atagcattag accaagagaa     60
aatgagtata aaactatact aactaattta gacgaatata ataagttaac tacaaacaat    120
aatgaaaata aatatttaca attaaaaaaa ctaaatgaat caattgatgt tttatgaat     180
aaatataaaa cttcaagcag aaatagagca ctctctaatc taaaaaaaga tatattaaaa    240
gaagtaattc ttattaaaaa ttccaataca agccctgtag aaaaaaattt acattttgta    300
tggataggtg gagaagtcag tgatattgct cttgaataca taaaacaatg ggctgatatt    360
aatgcagaat ataatattaa actgtggtat gatagtgaag cattcttagt aaatacacta    420
aaaaaggcta tagttgaatc ttctaccact gaagcattac agctactaga ggaagagatt    480
caaaatcctc aatttgataa tatgaaattt tacaaaaaaa ggatggaatt tatatatgat    540
agacaaaaaa ggtttataaa ttattataaa tctcaaatca ataaacctac agtacctaca    600
atagatgata ttataaagtc tcatctagta tctgaatata atagagatga aactgtatta    660
gaatcatata gaacaaattc tttgagaaaa ataaatagta atcatgggat agatatcagg    720
gctaatagtt tgtttacaga acaagagtta ttaaatattt atagtcagga gttgttaaat    780
cgtggaaatt tagctgcagc atctgacata gtaagattat tagccctaaa aaattttggc    840
ggagtagcct tagccgttgc catgcttcca ggtattcact ctgatttatt taaaacaata    900
tctagaccta gctctattgg actagaccgt tgggaaatga taaaattaga ggctattatg    960
aagtataaaa aatatataaa taattataca tcagaaaact ttgataaact tgatcaacaa   1020
ttaaaagata attttaaact cattatagaa agtaaaagtg aaaaatctga gatattttct   1080
aaattagaaa atttaaatgt atctgatctt gaaattaaaa tagctttcgc tttaggcagt   1140
gttataaatc aagccttgat atcaaaacaa ggttcatatc ttactaacct agtaatagaa   1200
caagtaaaaa atagatatca atttttaaac caacacctta acccagccat agagtctgat   1260
aataacttca cagatactac taaaattttt catgattcat tatttaattc agctaccgca   1320
gaaaactcta tgtttttaac aaaaatagca ccatacttac aagtaggttt tatgccagaa   1380
gctcgctcca caataagttt aagtggtcca ggagcttatg cgtcagctta ctatgatttc   1440
ataaatttac aagaaaatac tatagaaaaa actttaaaag catcagattt aatagaattt   1500
aaattcccag aaaataatct atctcaattg acagaacaag aaataaatag tctatggagc   1560
tttgatcaag caagtgcaaa atatcaattt gagaaatatg taagagatta tactggtgga   1620
tct                                                                 1623
```

<210> SEQ ID NO 58
<211> LENGTH: 766
<212> TYPE: PRT
<213> ORGANISM: Artificial Sequence
<220> FEATURE:
<223> OTHER INFORMATION: Description of Artificial Sequence: Synthetic
Mutated sequence polypeptide

<400> SEQUENCE: 58

```
Ser Leu Val Asn Arg Lys Gln Leu Glu Lys Met Ala Asn Val Arg Phe
1               5                   10                  15

Arg Thr Gln Glu Asp Glu Tyr Val Ala Ile Leu Asp Ala Leu Glu Glu
            20                  25                  30

Tyr His Asn Met Ser Glu Asn Thr Val Val Glu Lys Tyr Leu Lys Leu
        35                  40                  45
```

```
Lys Asp Ile Asn Ser Leu Thr Asp Ile Tyr Ile Asp Thr Tyr Lys Lys
    50                  55                  60

Ser Gly Arg Asn Lys Ala Leu Lys Lys Phe Lys Glu Tyr Leu Val Thr
65                  70                  75                  80

Glu Val Leu Glu Leu Lys Asn Asn Asn Leu Thr Pro Val Glu Lys Asn
                85                  90                  95

Leu His Phe Val Trp Ile Gly Gly Gln Ile Asn Asp Thr Ala Ile Asn
            100                 105                 110

Tyr Ile Asn Gln Trp Lys Asp Val Asn Ser Asp Tyr Asn Val Asn Val
        115                 120                 125

Phe Tyr Asp Ser Asn Ala Phe Leu Ile Asn Thr Leu Lys Lys Thr Val
    130                 135                 140

Val Glu Ser Ala Ile Asn Asp Thr Leu Glu Ser Phe Arg Glu Asn Leu
145                 150                 155                 160

Asn Asp Pro Arg Phe Asp Tyr Asn Lys Phe Phe Arg Lys Arg Met Glu
                165                 170                 175

Ile Ile Tyr Asp Lys Gln Lys Asn Phe Ile Asn Tyr Tyr Lys Ala Gln
            180                 185                 190

Arg Glu Glu Asn Pro Glu Leu Ile Ile Asp Asp Ile Val Lys Thr Tyr
        195                 200                 205

Leu Ser Asn Glu Tyr Ser Lys Glu Ile Asp Glu Leu Asn Thr Tyr Ile
    210                 215                 220

Glu Glu Ser Leu Asn Lys Ile Thr Gln Asn Ser Gly Asn Asp Val Arg
225                 230                 235                 240

Asn Phe Glu Glu Phe Lys Asn Gly Glu Ser Phe Asn Leu Tyr Glu Gln
                245                 250                 255

Glu Leu Val Glu Arg Trp Asn Leu Ala Ala Ala Ser Ala Ile Leu Ala
            260                 265                 270

Ile Ser Ala Leu Lys Glu Ile Gly Gly Met Ala Leu Ala Val Ala Met
        275                 280                 285

Leu Pro Gly Ile Gln Pro Asp Leu Phe Glu Ser Ile Glu Lys Pro Ser
    290                 295                 300

Ser Val Thr Val Asp Phe Trp Glu Met Thr Lys Leu Glu Ala Ile Met
305                 310                 315                 320

Lys Tyr Lys Glu Tyr Ile Pro Glu Tyr Thr Ser Glu His Phe Asp Met
                325                 330                 335

Leu Asp Glu Glu Val Gln Ser Ser Phe Glu Ser Val Leu Ala Ser Lys
            340                 345                 350

Ser Asp Lys Ser Glu Ile Phe Ser Ser Leu Gly Asp Met Glu Ala Ser
        355                 360                 365

Pro Leu Glu Val Lys Ile Ala Phe Asn Ser Lys Gly Ile Ile Asn Gln
    370                 375                 380

Gly Leu Ile Ser Val Lys Asp Ser Tyr Cys Ser Asn Leu Ile Val Lys
385                 390                 395                 400

Gln Ile Glu Asn Arg Tyr Lys Ile Leu Asn Asn Ser Leu Asn Pro Ala
                405                 410                 415

Ile Ser Glu Asp Asn Asp Phe Asn Thr Thr Thr Asn Thr Phe Ile Asp
            420                 425                 430

Ser Ile Met Ala Glu Ala Asn Ala Asp Asn Gly Arg Phe Met Met Glu
        435                 440                 445

Leu Gly Lys Tyr Leu Arg Val Gly Phe Phe Pro Asp Val Lys Thr Thr
    450                 455                 460
```

```
Ile Asn Leu Ser Gly Pro Glu Ala Tyr Ala Ala Ala Tyr Gln Asp Leu
465                 470                 475                 480

Leu Met Phe Lys Glu Gly Ser Met Asn Ile His Leu Ile Glu Ala Asp
                485                 490                 495

Leu Arg Asn Phe Glu Ile Ser Lys Thr Asn Ile Ser Gln Ser Thr Glu
            500                 505                 510

Gln Glu Met Ala Ser Leu Trp Ser Phe Asp Asp Ala Arg Ala Lys Ala
        515                 520                 525

Gln Phe Glu Glu Tyr Lys Arg Asn Tyr Phe Glu Gly Ser Leu Gly Glu
    530                 535                 540

Asp Asp Asn Leu Asp Phe Ser Gln Asn Ile Val Val Asp Lys Glu Tyr
545                 550                 555                 560

Leu Leu Glu Lys Ile Ser Ser Leu Ala Arg Ser Ser Glu Arg Gly Tyr
                565                 570                 575

Ile His Tyr Ile Val Gln Leu Gln Gly Asn Lys Ile Ser Tyr Glu Ala
            580                 585                 590

Ala Cys Asn Leu Phe Ala Lys Thr Pro Tyr Asp Ser Val Leu Phe Gln
        595                 600                 605

Lys Asn Ile Glu Asp Ser Glu Ile Ala Tyr Tyr Tyr Asn Pro Gly Asp
    610                 615                 620

Gly Glu Ile Gln Glu Ile Asp Lys Tyr Lys Ile Pro Ser Ile Ile Ser
625                 630                 635                 640

Asp Arg Pro Lys Ile Lys Leu Thr Phe Ile Gly Ala Gly Lys Asp Glu
                645                 650                 655

Phe Asn Thr Asp Ile Phe Ala Gly Phe Asp Val Asp Ser Leu Ser Thr
            660                 665                 670

Glu Ile Glu Ala Ala Ile Asp Leu Ala Lys Glu Asp Ile Ser Pro Lys
        675                 680                 685

Ser Ile Glu Ile Asn Leu Leu Gly Ala Asn Met Phe Ser Tyr Ser Ile
    690                 695                 700

Asn Val Glu Glu Thr Tyr Pro Gly Lys Leu Leu Leu Lys Val Lys Asp
705                 710                 715                 720

Lys Ile Ser Glu Leu Met Pro Ser Ile Ser Gln Asp Ser Ile Ile Val
                725                 730                 735

Ser Ala Asn Gln Tyr Glu Val Arg Ile Asn Ser Glu Gly Arg Arg Glu
            740                 745                 750

Leu Leu Asp His Ser Gly Glu Trp Ile Asn Lys Glu Glu Ser
        755                 760                 765
```

```
<210> SEQ ID NO 59
<211> LENGTH: 2303
<212> TYPE: DNA
<213> ORGANISM: Artificial Sequence
<220> FEATURE:
<223> OTHER INFORMATION: Description of Artificial Sequence: Synthetic
      Mutated sequence polynucleotide

<400> SEQUENCE: 59

ggcagtctgg ttaaccgtaa acaactggaa aaaatggcga atgtgcgctt tagaacccag     60

gaagatgaat atgttgcgat tctagatgca ctggaagaat accataacat gtcagagaat    120

accgtggtag aaaaatatct gaaactgaaa gatattaact ctctgacgga tatctatatt    180

gacacgtaca aaaaaagcgg tcgtaataaa gctctgaaaa aatttaagga atatctcgtt    240

acggaagtgc tggagctcaa gaacaataac ctgaccccgg ttgagaaaaa tctgcatttc    300

gtttggatcg gcggtcagat taacgacacc gccatcaatt acattaacca gtggaaagat    360
```

gtgaatagcg attataacgt taatgtcttt tatgactcga acgcgtttct aattaacacg 420
ctaaaaaaaa ccgtggtgga aagcgcgatt aatgatactc ttgagagctt tcgcgaaaac 480
ctgaacgacc cacgtttcga ctacaataaa ttcttccgca aaagaatgga aattatctat 540
gataaacaaa aaaacttcat taactactat aaagcacaac gtgaagaaaa tccggaactg 600
attatcgacg atatcgtgaa gacgtacttg agcaacgagt atagcaagga gattgatgaa 660
cttaatacat acatcgaaga atcactgaac aaaatcacgc aaaatagtgg caacgacgtt 720
cgcaactttg aggaatttaa aaatggcgag agcttcaact tatatgaaca ggagctagtg 780
gaacgatgga acctggccgc agcctccgcg attctggcga tttctgcgct gaaagaaatc 840
ggtggtatgg cgctggcggt cgcgatgctg ccgggcattc agccggacct gtttgagtcc 900
attgagaaac ctagtagcgt gacggtagac ttctgggaaa tgacgaagtt agaagcaatt 960
atgaaataca aagaatatat tccggaatac acaagcgaac actttgacat gctggacgag 1020
gaagttcagt cgagctttga atctgtcctc gccagcaaga gcgataaaag cgaaattttc 1080
agcagcctgg gtgatatgga ggcgagcccg ctcgaagtta aaatcgcgtt taattcgaag 1140
ggtatcatta accaaggact catctccgta aaagacagct attgttcaaa tctgattgtg 1200
aaacagatag agaaccgcta taaaattcta aataacagtc tgaatccggc aatctcagag 1260
gacaacgatt tcaataccac tacaaacaca tttatcgata gtattatggc cgaagcaaat 1320
gcggacaacg gtcgttttat gatggaactc ggtaagtacc tgcgcgtcgg tttcttcccg 1380
gatgttaaaa ccaccatcaa cttatcggga ccagaagcgt atgctgcggc ctaccaggat 1440
ctgctgatgt ttaaagaagg aagcatgaat atacatctaa ttgaagcaga cctgcgtaac 1500
ttcgagatat ctaaaaccaa catctcccaa agcaccgaac aggaaatggc ctcactgtgg 1560
agctttgacg atgcgcgcgc aaaagcccag tttgaagaat ataaacgaaa ttactttgaa 1620
ggtagcttgg gtgaagatga caaccttgat ttctctcaaa atattgtggt cgacaaggag 1680
tatctgctgg aaaaaatttc cagcttagcg cgttcgagcg agcgcggcta tattcactac 1740
atcgttcaac tgcagggcaa caaaatcagt tatgaagcgg cgtgcaacct gtttgcgaag 1800
accccgtatg acagtgtgct atttcaaaaa aacattgaag atagcgagat cgcgtactat 1860
tacaatcctg gcgatggtga aattcaggaa attgacaagt ataaaatccc gtcgattatc 1920
tctgaccgtc caaagatcaa actgacgttt atcggtgcgg gtaaagatga attcaacacc 1980
gatatttttg cgggttttga cgtggatagc ctgtcaacgg aaattgaagc ggcgattgat 2040
ttagcaaaag aggacatctc cccgaagagc attgaaatta atctgctggg cgcgaacatg 2100
ttttcataca gcataaacgt ggaggagacc tatcctggta aactgctgtt gaaagtcaaa 2160
gataaaatta gcgaattaat gccgtctatt agccaagact ccatcattgt gtcggcgaat 2220
cagtacgaag ttcgcattaa cagtgaaggc cgtcgcgagc tgctagatca ttctggtgaa 2280
tggattaata aagaagaaag tgg 2303

<210> SEQ ID NO 60
<211> LENGTH: 542
<212> TYPE: PRT
<213> ORGANISM: Artificial Sequence
<220> FEATURE:
<223> OTHER INFORMATION: Description of Artificial Sequence: Synthetic
Mutated sequence polypeptide

<400> SEQUENCE: 60

Ser Leu Val Asn Arg Lys Gln Leu Glu Lys Met Ala Asn Val Arg Phe

-continued

```
1               5                   10                  15

Arg Thr Gln Glu Asp Glu Tyr Val Ala Ile Leu Asp Ala Leu Glu Glu
            20                  25                  30

Tyr His Asn Met Ser Glu Asn Thr Val Val Glu Lys Tyr Leu Lys Leu
        35                  40                  45

Lys Asp Ile Asn Ser Leu Thr Asp Ile Tyr Ile Asp Thr Tyr Lys Lys
    50                  55                  60

Ser Gly Arg Asn Lys Ala Leu Lys Lys Phe Lys Glu Tyr Leu Val Thr
65                  70                  75                  80

Glu Val Leu Glu Leu Lys Asn Asn Asn Leu Thr Pro Val Glu Lys Asn
                85                  90                  95

Leu His Phe Val Trp Ile Gly Gly Gln Ile Asn Asp Thr Ala Ile Asn
            100                 105                 110

Tyr Ile Asn Gln Trp Lys Asp Val Asn Ser Asp Tyr Asn Val Asn Val
        115                 120                 125

Phe Tyr Asp Ser Asn Ala Phe Leu Ile Asn Thr Leu Lys Lys Thr Val
    130                 135                 140

Val Glu Ser Ala Ile Asn Asp Thr Leu Glu Ser Phe Arg Glu Asn Leu
145                 150                 155                 160

Asn Asp Pro Arg Phe Asp Tyr Asn Lys Phe Phe Arg Lys Arg Met Glu
                165                 170                 175

Ile Ile Tyr Asp Lys Gln Lys Asn Phe Ile Asn Tyr Tyr Lys Ala Gln
            180                 185                 190

Arg Glu Glu Asn Pro Glu Leu Ile Ile Asp Asp Ile Val Lys Thr Tyr
        195                 200                 205

Leu Ser Asn Glu Tyr Ser Lys Glu Ile Asp Glu Leu Asn Thr Tyr Ile
    210                 215                 220

Glu Glu Ser Leu Asn Lys Ile Thr Gln Asn Ser Gly Asn Asp Val Arg
225                 230                 235                 240

Asn Phe Glu Glu Phe Lys Asn Gly Glu Ser Phe Asn Leu Tyr Glu Gln
                245                 250                 255

Glu Leu Val Glu Arg Trp Asn Leu Ala Ala Ala Ser Ala Ile Leu Ala
            260                 265                 270

Ile Ser Ala Leu Lys Glu Ile Gly Gly Met Ala Leu Ala Val Ala Met
        275                 280                 285

Leu Pro Gly Ile Gln Pro Asp Leu Phe Glu Ser Ile Glu Lys Pro Ser
    290                 295                 300

Ser Val Thr Val Asp Phe Trp Glu Met Thr Lys Leu Glu Ala Ile Met
305                 310                 315                 320

Lys Tyr Lys Glu Tyr Ile Pro Glu Tyr Thr Ser Glu His Phe Asp Met
                325                 330                 335

Leu Asp Glu Glu Val Gln Ser Ser Phe Glu Ser Val Leu Ala Ser Lys
            340                 345                 350

Ser Asp Lys Ser Glu Ile Phe Ser Ser Leu Gly Asp Met Glu Ala Ser
        355                 360                 365

Pro Leu Glu Val Lys Ile Ala Phe Asn Ser Lys Gly Ile Ile Asn Gln
    370                 375                 380

Gly Leu Ile Ser Val Lys Asp Ser Tyr Cys Ser Asn Leu Ile Val Lys
385                 390                 395                 400

Gln Ile Glu Asn Arg Tyr Lys Ile Leu Asn Asn Ser Leu Asn Pro Ala
                405                 410                 415

Ile Ser Glu Asp Asn Asp Phe Asn Thr Thr Thr Asn Thr Phe Ile Asp
            420                 425                 430
```

```
Ser Ile Met Ala Glu Ala Asn Ala Asp Asn Gly Arg Phe Met Met Glu
        435                 440                 445

Leu Gly Lys Tyr Leu Arg Val Gly Phe Phe Pro Asp Val Lys Thr Thr
    450                 455                 460

Ile Asn Leu Ser Gly Pro Glu Ala Tyr Ala Ala Ala Tyr Gln Asp Leu
465                 470                 475                 480

Leu Met Phe Lys Glu Gly Ser Met Asn Ile His Leu Ile Glu Ala Asp
                485                 490                 495

Leu Arg Asn Phe Glu Ile Ser Lys Thr Asn Ile Ser Gln Ser Thr Glu
            500                 505                 510

Gln Glu Met Ala Ser Leu Trp Ser Phe Asp Asp Ala Arg Ala Lys Ala
        515                 520                 525

Gln Phe Glu Glu Tyr Lys Arg Asn Tyr Phe Glu Gly Ser Leu
    530                 535                 540


<210> SEQ ID NO 61
<211> LENGTH: 1626
<212> TYPE: DNA
<213> ORGANISM: Artificial Sequence
<220> FEATURE:
<223> OTHER INFORMATION: Description of Artificial Sequence: Synthetic
      Mutated sequence polynucleotide

<400> SEQUENCE: 61

agtctggtta accgtaaaca actggaaaaa atggcgaatg tgcgctttag aacccaggaa     60

gatgaatatg ttgcgattct agatgcactg gaagaatacc ataacatgtc agagaatacc    120

gtggtagaaa aatatctgaa actgaaagat attaactctc tgacggatat ctatattgac    180

acgtacaaaa aaagcggtcg taataaagct ctgaaaaaat ttaaggaata tctcgttacg    240

gaagtgctgg agctcaagaa caataacctg accccggttg agaaaaatct gcatttcgtt    300

tggatcggcg gtcagattaa cgacaccgcc atcaattaca ttaaccagtg gaaagatgtg    360

aatagcgatt ataacgttaa tgtcttttat gactcgaacg cgtttctaat taacacgcta    420

aaaaaaaccg tggtggaaag cgcgattaat gatactcttg agagctttcg cgaaaacctg    480

aacgacccac gtttcgacta caataaattc ttccgcaaaa gaatggaaat tatctatgat    540

aaacaaaaaa acttcattaa ctactataaa gcacaacgtg aagaaaatcc ggaactgatt    600

atcgacgata tcgtgaagac gtacttgagc aacgagtata gcaaggagat tgatgaactt    660

aatacataca tcgaagaatc actgaacaaa atcacgcaaa atagtggcaa cgacgttcgc    720

aactttgagg aatttaaaaa tggcgagagc ttcaacttat atgaacagga gctagtggaa    780

cgatggaacc tggccgcagc ctccgcgatt ctggcgattt ctgcgctgaa agaaatcggt    840

ggtatggcgc tggcggtcgc gatgctgccg ggcattcagc cggacctgtt tgagtccatt    900

gagaaaccta gtagcgtgac ggtagacttc tgggaaatga cgaagttaga agcaattatg    960

aaatacaaag aatatattcc ggaatacaca agcgaacact ttgacatgct ggacgaggaa   1020

gttcagtcga gctttgaatc tgtcctcgcc agcaagagcg ataaaagcga aattttcagc   1080

agcctgggtg atatggaggc gagcccgctc gaagttaaaa tcgcgtttaa ttcgaagggt   1140

atcattaacc aaggactcat ctccgtaaaa gacagctatt gttcaaatct gattgtgaaa   1200

cagatagaga accgctataa aattctaaat aacagtctga atccggcaat ctcagaggac   1260

aacgatttca ataccactac aaacacattt atcgatagta ttatggccga agcaaatgcg   1320

gacaacggtc gttttatgat ggaactcggt aagtacctgc gcgtcggttt cttcccggat   1380
```

```
gttaaaacca ccatcaactt atcgggacca gaagcgtatg ctgcggccta ccaggatctg   1440

ctgatgttta aagaaggaag catgaatata catctaattg aagcagacct gcgtaacttc   1500

gagatatcta aaaccaacat ctcccaaagc accgaacagg aaatggcctc actgtggagc   1560

tttgacgatg cgcgcgcaaa agcccagttt gaagaatata aacgaaatta ctttgaaggt   1620

agcttg                                                              1626
```

<210> SEQ ID NO 62
<211> LENGTH: 228
<212> TYPE: PRT
<213> ORGANISM: Artificial Sequence
<220> FEATURE:
<223> OTHER INFORMATION: Description of Artificial Sequence: Synthetic Mutated sequence polypeptide

<400> SEQUENCE: 62

```
Leu Ser Glu Asp Asn Gly Val Asp Phe Asn Lys Asn Thr Ala Leu Asp
1               5                   10                  15

Lys Asn Tyr Leu Leu Asn Asn Lys Ile Pro Ser Asn Asn Val Glu Glu
            20                  25                  30

Ala Gly Ser Lys Asn Tyr Val His Tyr Ile Ile Gln Leu Gln Gly Asn
        35                  40                  45

Asp Ile Ser Tyr Glu Ala Thr Cys Asn Leu Phe Ser Lys Asn Pro Lys
    50                  55                  60

Asn Ser Ile Ile Ile Gln Arg Asn Met Asn Glu Ser Ala Lys Ser Tyr
65                  70                  75                  80

Phe Leu Ser Asp Asp Gly Glu Ser Ile Leu Glu Leu Asn Lys Tyr Arg
                85                  90                  95

Ile Pro Glu Arg Leu Lys Asn Lys Glu Lys Val Lys Val Thr Phe Ile
            100                 105                 110

Gly Ala Gly Lys Asp Glu Phe Asn Thr Ser Glu Phe Ala Arg Leu Ser
        115                 120                 125

Val Asp Ser Leu Ser Asn Glu Ile Ser Ser Phe Leu Asp Thr Ile Lys
    130                 135                 140

Leu Asp Ile Ser Pro Lys Asn Val Glu Val Asn Leu Leu Gly Ala Asn
145                 150                 155                 160

Met Phe Ser Tyr Asp Phe Asn Val Glu Glu Thr Tyr Pro Gly Lys Leu
                165                 170                 175

Leu Leu Ser Ile Met Asp Lys Ile Thr Ser Thr Leu Pro Asp Val Asn
            180                 185                 190

Lys Asn Ser Ile Thr Ile Gly Ala Asn Gln Tyr Glu Val Arg Ile Asn
        195                 200                 205

Ser Glu Gly Arg Lys Glu Leu Leu Ala His Ser Gly Lys Trp Ile Asn
    210                 215                 220

Lys Glu Glu Ala
225
```

<210> SEQ ID NO 63
<211> LENGTH: 735
<212> TYPE: DNA
<213> ORGANISM: Artificial Sequence
<220> FEATURE:
<223> OTHER INFORMATION: Description of Artificial Sequence: Synthetic Mutated sequence polynucleotide

<400> SEQUENCE: 63

```
atgggcagca gccatcatca tcatcatcac gaaaacctgt acttccaggg cctgtccgaa     60
```

```
gacaatggag tggacttcaa caaaaatacc gctctagaca aaaactatct gctgaacaat    120

aaaatcccga gcaacaacgt ggaagaagca ggctcgaaaa attacgttca ttatataatt    180

caattacagg gcaacgatat tagctacgaa gcgacgtgca acctgttttc taaaaatcca    240

aaaaacagta tcatcattca aaggaatatg aacgagtcgg cgaaatcata ctttctgagt    300

gatgacggcg aaagcatcct ggaactgaat aaatatcgaa ttcctgaacg tctgaaaaac    360

aaggaaaaag tgaaagtgac attcatcggt gcgggtaaag atgaattcaa cacttcagaa    420

tttgcccgcc tgtcggtgga tagcctttca aatgagatta gcagcttttt agacacaatt    480

aaactggata ttagcccgaa aaacgtggaa gtgaacctgt tgggcgcgaa tatgttcagt    540

tatgatttta acgtcgaaga aacctaccca ggaaagctac tcctgtcgat catggacaaa    600

atcacctcaa ccctgcctga cgtgaataaa aactccatca ccattggcgc gaatcagtat    660

gaggtgcgta tcaacagtga gggccgcaaa gaactgctag cacacagcgg taaatggatt    720

aataaagaag aagcc                                                     735


<210> SEQ ID NO 64
<211> LENGTH: 224
<212> TYPE: PRT
<213> ORGANISM: Artificial Sequence
<220> FEATURE:
<223> OTHER INFORMATION: Description of Artificial Sequence: Synthetic
      Mutated sequence polypeptide

<400> SEQUENCE: 64

Gly Glu Asp Asp Asn Leu Asp Phe Ser Gln Asn Ile Val Val Asp Lys
1               5                   10                  15

Glu Tyr Leu Leu Glu Lys Ile Ser Ser Leu Ala Arg Ser Ser Glu Arg
            20                  25                  30

Gly Tyr Ile His Tyr Ile Val Gln Leu Gln Gly Asn Lys Ile Ser Tyr
        35                  40                  45

Glu Ala Ala Cys Asn Leu Phe Ala Lys Thr Pro Tyr Asp Ser Val Leu
    50                  55                  60

Phe Gln Lys Asn Ile Glu Asp Ser Glu Ile Ala Tyr Tyr Tyr Asn Pro
65                  70                  75                  80

Gly Asp Gly Glu Ile Gln Glu Ile Asp Lys Tyr Lys Ile Pro Ser Ile
                85                  90                  95

Ile Ser Asp Arg Pro Lys Ile Lys Leu Thr Phe Ile Gly Ala Gly Lys
            100                 105                 110

Asp Glu Phe Asn Thr Asp Ile Phe Ala Gly Phe Asp Val Asp Ser Leu
        115                 120                 125

Ser Thr Glu Ile Glu Ala Ala Ile Asp Leu Ala Lys Glu Asp Ile Ser
    130                 135                 140

Pro Lys Ser Ile Glu Ile Asn Leu Leu Gly Ala Asn Met Phe Ser Tyr
145                 150                 155                 160

Ser Ile Asn Val Glu Glu Thr Tyr Pro Gly Lys Leu Leu Leu Lys Val
                165                 170                 175

Lys Asp Lys Ile Ser Glu Leu Met Pro Ser Ile Ser Gln Asp Ser Ile
            180                 185                 190

Ile Val Ser Ala Asn Gln Tyr Glu Val Arg Ile Asn Ser Glu Gly Arg
        195                 200                 205

Arg Glu Leu Leu Asp His Ser Gly Glu Trp Ile Asn Lys Glu Glu Ser
    210                 215                 220


<210> SEQ ID NO 65
```

<211> LENGTH: 672
<212> TYPE: DNA
<213> ORGANISM: Artificial Sequence
<220> FEATURE:
<223> OTHER INFORMATION: Description of Artificial Sequence: Synthetic
Mutated sequence polynucleotide

<400> SEQUENCE: 65
ggtgaagatg acaaccttga tttctctcaa aatattgtgg tcgacaagga gtatctgctg 60
gaaaaaattt ccagcttagc gcgttcgagc gagcgcggct atattcacta catcgttcaa 120
ctgcagggca acaaaatcag ttatgaagcg gcgtgcaacc tgtttgcgaa gaccccgtat 180
gacagtgtgc tatttcaaaa aaacattgaa gatagcgaga tcgcgtacta ttacaatcct 240
ggcgatggtg aaattcagga aattgacaag tataaaatcc cgtcgattat ctctgaccgt 300
ccaaagatca aactgacgtt tatcggtgcg ggtaaagatg aattcaacac cgatattttt 360
gcgggttttg acgtggatag cctgtcaacg gaaattgaag cggcgattga tttagcaaaa 420
gaggacatct ccccgaagag cattgaaatt aatctgctgg gcgcgaacat gttttcatac 480
agcataaacg tggaggagac ctatcctggt aaactgctgt tgaaagtcaa agataaaatt 540
agcgaattaa tgccgtctat tagccaagac tccatcattg tgtcggcgaa tcagtacgaa 600
gttcgcatta acagtgaagg ccgtcgcgag ctgctagatc attctggtga atggattaat 660
aaagaagaaa gt 672

<210> SEQ ID NO 66
<211> LENGTH: 624
<212> TYPE: DNA
<213> ORGANISM: Artificial Sequence
<220> FEATURE:
<223> OTHER INFORMATION: Description of Artificial Sequence: Synthetic
Mutated sequence polynucleotide

<400> SEQUENCE: 66
catatgcgtt actacttcga taccgataca gccatcgctt ttaacggtta taaaaccatc 60
gacggtaaac acttttactt tgatagcgat tgtgtggtaa aaattggtgt attctcgaca 120
agcaatggct ttgaatattt tgcgccggca aacacctata ataacaacat tgaaggtcaa 180
gccattgtct accagagtaa attcctgacc ctaaatggta aaaaatatta cttcgacaac 240
aacagcaaag cggttacagg ctggcagacc atcgattcga aaaaatatta ctttaatacc 300
aacaccgcag aagcggccac cggttggcaa accatcgatg gtaaaaaata ctactttaac 360
accaacaccg cagaagcggc caccggctgg cagaccatcg acggtaaaaa atattacttc 420
aataccaaca ccgcaattgc cagcaccggt tacacgatca tcaacggtaa acatttttat 480
tttaataccg atggtatcat gcaaattggc gtattcaaag gcccaaacgg ctttgaatat 540
tttgcgcctg caaatacaga tgccaacaac attgagggtc aggcaatttt gtaccaaaac 600
gaattcctga ccctaaatct cgag 624

<210> SEQ ID NO 67
<211> LENGTH: 2601
<212> TYPE: DNA
<213> ORGANISM: Artificial Sequence
<220> FEATURE:
<223> OTHER INFORMATION: Description of Artificial Sequence: Synthetic
Mutated sequence polynucleotide

<400> SEQUENCE: 67
catatggacc caattgaatt taacctggtg accggttggc aaaccataaa cggtaaaaaa 60

-continued

```
tattattttg acattaatac cggcgcggca ctgatcagtt acaaaatcat caacggtaaa    120
cacttttatt tcaataacga tggtgtaatg caactaggcg tgtttaaagg ccctgatggt    180
tttgaatact tcgcgccggc taatacccag aacaataaca ttgaaggtca agccattgtc    240
tatcagtcga aattcttaac cctaaacgga aaaaaatatt actttgacaa tgacagcaaa    300
gcggtaaccg gctggcgcat catcaacaac gagaaatatt actttaatcc aaacaatgca    360
atcgccgcgg taggcctaca agtgatcgac aacaataagt attacttcaa ccctgacacc    420
gcaataataa gcaaaggttg gcaaaccgtt aatggtagtc gttactactt cgataccgat    480
acagccatcg cttttaacgg ttataaaacc atcgacggta aacactttta ctttgatagc    540
gattgtgtgg taaaaattgg tgtattctcg acaagcaatg gctttgaata ttttgcgccg    600
gcaaacacct ataataacaa cattgaaggt caagccattg tctaccagag taaattcctg    660
accctaaatg gtaaaaaata ttacttcgac aacaacagca aagcggttac aggctggcag    720
accatcgatt cgaaaaaata ttactttaat accaacaccg cagaagcggc caccggttgg    780
caaaccatcg atggtaaaaa atactacttt aacaccaaca ccgcagaagc ggccaccggc    840
tggcagacca tcgacggtaa aaaatattac ttcaatacca acaccgcaat tgccagcacc    900
ggttacacga tcatcaacgg taaacatttt tattttaata ccgatggtat catgcaaatt    960
ggcgtattca aaggcccaaa cggctttgaa tattttgcgc ctgcaaatac agatgccaac   1020
aacattgagg gtcaggcaat tttgtaccaa aacgaattcc tgaccctaaa tggtaaaaaa   1080
tactacttcg gtagtgacag caaagcggtc accggttggc gcatcatcaa caacaagaaa   1140
tattacttta atccgaacaa tgccatcgca gcgatccatc tctgcaccat taacaatgac   1200
aagtattact ttagctacga cggcatcctg cagaacggct atatcaccat cgaacgtaat   1260
aacttctact tcgatgccaa taacgaatcc aaaatggtga cgggcgtgtt taaaggccca   1320
aatggttttg agtatttcgc gccggcaaac acccacaata acaacattga aggtcaagcc   1380
attgtttacc aaaacaaatt cctgacccta aatggaaaaa aatattactt tgataacgac   1440
agcaaagcgg tcaccggctg gcagacaatc gacggtaaaa aatattactt taatcttaac   1500
accgcagaag cggccaccgg ctggcaaacc atcgatggta aaaaatatta cttcaacttg   1560
aacaccgcag aagcggccac cggctggcag accatcgatg gtaaaaaata ctactttaat   1620
accaacacct tcattgctag caccggttat acttcgatca acggtaaaca tttttacttt   1680
aataccgacg gtatcatgca aattggcgta ttcaaaggtc ctaacggctt tgaatacttt   1740
gcgccagcaa atacccacaa caataacatt gaaggtcagg ccattctgta ccaaaacaaa   1800
ttcctgaccc taaatggtaa aaaatattac ttcggtagtg acagcaaagc ggttacaggc   1860
ctaaggacca tcgatggtaa aaaatattac tttaacacca acaccgcagt cgcggttacc   1920
ggctggcaga ccatcaatgg taaaaaatac tactttaaca ccaacacctc tattgccagc   1980
accggttaca cgatcatctc gggtaaacat ttctatttta ataccgatgg tatcatgcaa   2040
attggcgtat ttaaaggtcc ggacggcttc gaatactttg cgcctgcaaa cacggatgcc   2100
aacaatattg agggtcaggc aattagatat caaaaccgct tcctctacct gcatgacaat   2160
atttattact ttggtaacaa tagcaaagcg gccaccggtt gggtgaccat cgatggtaac   2220
cgttattact tcgagccaaa tacggcaatg ggtgctaacg gttataaaac catcgacaat   2280
aaaaacttct actttcgcaa tggtctgccg caaattggcg tatttaaagg atctaacggc   2340
ttcgaatact ttgcgcctgc caatacagat gcaaacaaca ttgaaggtca ggccattaga   2400
taccaaaatc gtttcctcca tttacttggc aaaatttatt actttggtaa caatagcaaa   2460
```

```
gcggtcaccg gttggcaaac catcaacggt aaagtgtatt actttatgcc agataccgca   2520

atggccgcgg caggtggctt gttcgagatc gacggtgtta tttacttctt cggtgtcgat   2580

ggcgtgaaag ctccgctcga g                                               2601
```

<210> SEQ ID NO 68
<211> LENGTH: 1548
<212> TYPE: DNA
<213> ORGANISM: Artificial Sequence
<220> FEATURE:
<223> OTHER INFORMATION: Description of Artificial Sequence: Synthetic Mutated sequence polynucleotide

<400> SEQUENCE: 68

```
attaccggct tcgtaaccgt gggagacgat aaatactact ttaacccgat caatggtggt     60

gccgcaagca tcggcgagac gattatcgat gacaaaaact attatttcaa ccagagcggc    120

gtactgcaaa cgggtgtgtt ttcgacggag gacggcttca aatactttgc tccggccaat    180

actctggatg aaaacctcga aggcgaagcg atcgatttta ccggtaaact gatcatcgac    240

gaaaacatct attattttga cgataattac cgtggcgcag tggaatggaa agaactggat    300

ggtgagatgc actatttctc accggaaacg ggtaaagcct ttaaaggtct caaccagatt    360

ggtgactaca aatactattt caattccgat ggcgtcatgc agaaaggctt tgttagtatt    420

aacgataata aacactattt tgacgattct ggtgtcatga aagtgggtta caccgaaatt    480

gatggaaagc atttctactt cgcagaaaac ggcgaaatgc agattggtgt gtttaacacg    540

gaagacggct ttaaatactt cgcccaccat aatgaagatt taggcaacga agagggtgaa    600

gaaataagct attccggtat tctgaatttc aacaataaaa tctactactt tgatgacagc    660

tttactgcag tggttggctg gaaagatctg gaggacggta gcaagtatta tttcgatgaa    720

gatacggcgg aagcgtacat tggtctaagc ctgattaacg acggtcaata ttactttaat    780

gatgatggca tcatgcaggt cggttttgta accattaacg acaaagtatt ctacttcagc    840

gactctggca tcattgaatc cggcgtgcag aacattgatg acaattattt ctatattgat    900

gacaacggta ttgttcagat cggtgtgttt gataccagcg atggctacaa atatttcgcg    960

ccggccaata ccgtgaacga caatatctac ggccaagcgg tcgaatatag tggtctggtt   1020

cgcgtcggtg aagatgtgta ctattttggt gagacgtata ctatcgagac cggctggatt   1080

tacgatatgg aaaacgaatc ggacaaatat tacttcaatc cggaaaccaa aaaagcgtgc   1140

aaaggtatca acctgatcga tgatattaaa tattattttg acgagaaggg aattatgcgt   1200

acaggtttga ttagcttcga aaataacaat tactacttta acgagaatgg tgaaatgcag   1260

tttggttata ttaacattga agataagatg ttctactttg gtgaagatgg tgtaatgcaa   1320

atcggcgtgt tcaatacgcc ggacggcttt aaatactttg cgcatcagaa caccctagat   1380

gagaattttg agggcgagag cattaactat accggttggc tggatttaga cgaaaagcgc   1440

tactatttca cggatgaata tatcgcggcg accggtagcg ttatcatcga tggtgaggag   1500

tactattttg accctgatac ggcacaactg gtaatcagcg aactcgag                 1548
```

<210> SEQ ID NO 69
<211> LENGTH: 636
<212> TYPE: DNA
<213> ORGANISM: Artificial Sequence
<220> FEATURE:
<223> OTHER INFORMATION: Description of Artificial Sequence: Synthetic Mutated polynucleotide

<400> SEQUENCE: 69
gttcagatcg gtgtgtttga taccagcgat ggctacaaat atttcgcgcc ggccaatacc 60
gtgaacgaca atatctacgg ccaagcggtc gaatatagtg gtctggttcg cgtcggtgaa 120
gatgtgtact attttggtga gacgtatact atcgagaccg gctggattta cgatatggaa 180
aacgaatcgg acaaatatta cttcaatccg gaaaccaaaa aagcgtgcaa aggtatcaac 240
ctgatcgatg atattaaata ttattttgac gagaagggaa ttatgcgtac aggtttgatt 300
agcttcgaaa ataacaatta ctactttaac gagaatggtg aaatgcagtt tggttatatt 360
aacattgaag ataagatgtt ctactttggt gaagatggtg taatgcaaat cggcgtgttc 420
aatacgccgg acggctttaa atactttgcg catcagaaca ccctagatga gaattttgag 480
ggcgagagca ttaactatac cggttggctg gatttagacg aaaagcgcta ctatttcacg 540
gatgaatata tcgcggcgac cggtagcgtt atcatcgatg gtgaggagta ctattttgac 600
cctgatacgg cacaactggt aatcagcgaa ctcgag 636

<210> SEQ ID NO 70
<211> LENGTH: 624
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 70
catatgcgtt actacttcga taccgataca gccatcgctt ttaacggtta taaaaccatc 60
gacggtaaac acttttactt tgatagcgat tgtgtggtaa aaattggtgt attctcgaca 120
agcaatggct ttgaatattt tgcgccggca aacacctata ataacaacat tgaaggtcaa 180
gccattgtct accagagtaa attcctgacc ctaaatggta aaaaatatta cttcgacaac 240
aacagcaaag cggttacagg ctggcagacc atcgattcga aaaaatatta ctttaatacc 300
aacaccgcag aagcggccac cggttggcaa accatcgatg gtaaaaaata ctactttaac 360
accaacaccg cagaagcggc caccggctgg cagaccatcg acggtaaaaa atattacttc 420
aataccaaca ccgcaattgc cagcaccggt tacacgatca tcaacggtaa acatttttat 480
tttaataccg atggtatcat gcaaattggc gtattcaaag gcccaaacgg ctttgaatat 540
tttgcgcctg caaatacaga tgccaacaac attgagggtc aggcaatttt gtaccaaaac 600
gaattcctga ccctaaatct cgag 624

<210> SEQ ID NO 71
<211> LENGTH: 207
<212> TYPE: PRT
<213> ORGANISM: Artificial Sequence
<220> FEATURE:
<223> OTHER INFORMATION: Description of Artificial Sequence: Synthetic
polynucleotide

<400> SEQUENCE: 71

Met Arg Tyr Tyr Phe Asp Thr Asp Thr Ala Ile Ala Phe Asn Gly Tyr
1 5 10 15

Lys Thr Ile Asp Gly Lys His Phe Tyr Phe Asp Ser Asp Cys Val Val
20 25 30

Lys Ile Gly Val Phe Ser Thr Ser Asn Gly Phe Glu Tyr Phe Ala Pro
35 40 45

Ala Asn Thr Tyr Asn Asn Asn Ile Glu Gly Gln Ala Ile Val Tyr Gln
50 55 60

```
Ser Lys Phe Leu Thr Leu Asn Gly Lys Lys Tyr Tyr Phe Asp Asn Asn
65                  70                  75                  80

Ser Lys Ala Val Thr Gly Trp Gln Thr Ile Asp Ser Lys Lys Tyr Tyr
                85                  90                  95

Phe Asn Thr Asn Thr Ala Glu Ala Ala Thr Gly Trp Gln Thr Ile Asp
            100                 105                 110

Gly Lys Lys Tyr Tyr Phe Asn Thr Asn Thr Ala Glu Ala Ala Thr Gly
        115                 120                 125

Trp Gln Thr Ile Asp Gly Lys Lys Tyr Tyr Phe Asn Thr Asn Thr Ala
    130                 135                 140

Ile Ala Ser Thr Gly Tyr Thr Ile Ile Asn Gly Lys His Phe Tyr Phe
145                 150                 155                 160

Asn Thr Asp Gly Ile Met Gln Ile Gly Val Phe Lys Gly Pro Asn Gly
                165                 170                 175

Phe Glu Tyr Phe Ala Pro Ala Asn Thr Asp Ala Asn Asn Ile Glu Gly
            180                 185                 190

Gln Ala Ile Leu Tyr Gln Asn Glu Phe Leu Thr Leu Asn Leu Glu
        195                 200                 205
```

<210> SEQ ID NO 72
<211> LENGTH: 2601
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 72

```
catatggacc caattgaatt taacctggtg accggttggc aaaccataaa cggtaaaaaa     60

tattattttg acattaatac cggcgcggca ctgatcagtt acaaaatcat caacggtaaa    120

cacttttatt tcaataacga tggtgtaatg caactaggcg tgtttaaagg ccctgatggt    180

tttgaatact tcgcgccggc taatacccag aacaataaca ttgaaggtca agccattgtc    240

tatcagtcga aattcttaac cctaaacgga aaaaaatatt actttgacaa tgacagcaaa    300

gcggtaaccg gctggcgcat catcaacaac gagaaatatt actttaatcc aaacaatgca    360

atcgccgcgg taggcctaca agtgatcgac aacaataagt attacttcaa ccctgacacc    420

gcaataataa gcaaaggttg gcaaaccgtt aatggtagtc gttactactt cgataccgat    480

acagccatcg cttttaacgg ttataaaacc atcgacggta aacactttta ctttgatagc    540

gattgtgtgg taaaaattgg tgtattctcg acaagcaatg gctttgaata ttttgcgccg    600

gcaaacacct ataataacaa cattgaaggt caagccattg tctaccagag taaattcctg    660

accctaaatg gtaaaaaata ttacttcgac aacaacagca aagcggttac aggctggcag    720

accatcgatt cgaaaaaata ttactttaat accaacaccg cagaagcggc caccggttgg    780

caaaccatcg atggtaaaaa atactacttt aacaccaaca ccgcagaagc ggccaccggc    840

tggcagacca tcgacggtaa aaaatattac ttcaatacca acaccgcaat tgccagcacc    900

ggttacacga tcatcaacgg taaacatttt tattttaata ccgatggtat catgcaaatt    960

ggcgtattca aaggcccaaa cggctttgaa tattttgcgc ctgcaaatac agatgccaac   1020

aacattgagg gtcaggcaat tttgtaccaa aacgaattcc tgaccctaaa tggtaaaaaa   1080

tactacttcg gtagtgacag caaagcggtc accggttggc gcatcatcaa caacaagaaa   1140

tattacttta atccgaacaa tgccatcgca gcgatccatc tctgcaccat taacaatgac   1200
```

-continued aagtattact ttagctacga cggcatcctg cagaacggct atatcaccat cgaacgtaat 1260
aacttctact tcgatgccaa taacgaatcc aaaatggtga cgggcgtgtt taaaggccca 1320
aatggttttg agtatttcgc gccggcaaac acccacaata acaacattga aggtcaagcc 1380
attgtttacc aaaacaaatt cctgacccta aatggaaaaa aatattactt tgataacgac 1440
agcaaagcgg tcaccggctg gcagacaatc gacggtaaaa aatattactt taatcttaac 1500
accgcagaag cggccaccgg ctggcaaacc atcgatggta aaaaatatta cttcaacttg 1560
aacaccgcag aagcggccac cggctggcag accatcgatg gtaaaaaata ctactttaat 1620
accaacacct tcattgctag caccggttat acttcgatca acggtaaaca tttttacttt 1680
aataccgacg gtatcatgca aattggcgta ttcaaaggtc ctaacggctt tgaatacttt 1740
gcgccagcaa atacccacaa caataacatt gaaggtcagg ccattctgta ccaaaacaaa 1800
ttcctgaccc taaatggtaa aaaatattac ttcggtagtg acagcaaagc ggttacaggc 1860
ctaaggacca tcgatggtaa aaaatattac tttaacacca acaccgcagt cgcggttacc 1920
ggctggcaga ccatcaatgg taaaaaatac tactttaaca ccaacacctc tattgccagc 1980
accggttaca cgatcatctc gggtaaacat ttctatttta ataccgatgg tatcatgcaa 2040
attggcgtat ttaaaggtcc ggacggcttc gaatactttg cgcctgcaaa cacggatgcc 2100
aacaatattg agggtcaggc aattagatat caaaaccgct tcctctacct gcatgacaat 2160
atttattact ttggtaacaa tagcaaagcg gccaccggtt gggtgaccat cgatggtaac 2220
cgttattact tcgagccaaa tacggcaatg ggtgctaacg gttataaaac catcgacaat 2280
aaaaacttct actttcgcaa tggtctgccg caaattggcg tatttaaagg atctaacggc 2340
ttcgaatact ttgcgcctgc caatacagat gcaaacaaca ttgaaggtca ggccattaga 2400
taccaaaatc gtttcctcca tttacttggc aaaatttatt actttggtaa caatagcaaa 2460
gcggtcaccg gttggcaaac catcaacggt aaagtgtatt actttatgcc agataccgca 2520
atggccgcgg caggtggctt gttcgagatc gacggtgtta tttacttctt cggtgtcgat 2580
ggcgtgaaag ctccgctcga g 2601

<210> SEQ ID NO 73
<211> LENGTH: 866
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Met Asp Pro Ile Glu Phe Asn Leu Val Thr Gly Trp Gln Thr Ile Asn
1               5                   10                  15

Gly Lys Lys Tyr Tyr Phe Asp Ile Asn Thr Gly Ala Ala Leu Ile Ser
            20                  25                  30

Tyr Lys Ile Ile Asn Gly Lys His Phe Tyr Phe Asn Asn Asp Gly Val
        35                  40                  45

Met Gln Leu Gly Val Phe Lys Gly Pro Asp Gly Phe Glu Tyr Phe Ala
    50                  55                  60

Pro Ala Asn Thr Gln Asn Asn Asn Ile Glu Gly Gln Ala Ile Val Tyr
65                  70                  75                  80

Gln Ser Lys Phe Leu Thr Leu Asn Gly Lys Lys Tyr Tyr Phe Asp Asn
                85                  90                  95

Asp Ser Lys Ala Val Thr Gly Trp Arg Ile Ile Asn Asn Glu Lys Tyr
            100                 105                 110

-continued

```
Tyr Phe Asn Pro Asn Asn Ala Ile Ala Ala Val Gly Leu Gln Val Ile
        115                 120                 125

Asp Asn Asn Lys Tyr Tyr Phe Asn Pro Asp Thr Ala Ile Ile Ser Lys
    130                 135                 140

Gly Trp Gln Thr Val Asn Gly Ser Arg Tyr Tyr Phe Asp Thr Asp Thr
145                 150                 155                 160

Ala Ile Ala Phe Asn Gly Tyr Lys Thr Ile Asp Gly Lys His Phe Tyr
                165                 170                 175

Phe Asp Ser Asp Cys Val Val Lys Ile Gly Val Phe Ser Thr Ser Asn
            180                 185                 190

Gly Phe Glu Tyr Phe Ala Pro Ala Asn Thr Tyr Asn Asn Asn Ile Glu
        195                 200                 205

Gly Gln Ala Ile Val Tyr Gln Ser Lys Phe Leu Thr Leu Asn Gly Lys
    210                 215                 220

Lys Tyr Tyr Phe Asp Asn Asn Ser Lys Ala Val Thr Gly Trp Gln Thr
225                 230                 235                 240

Ile Asp Ser Lys Lys Tyr Tyr Phe Asn Thr Asn Thr Ala Glu Ala Ala
                245                 250                 255

Thr Gly Trp Gln Thr Ile Asp Gly Lys Lys Tyr Tyr Phe Asn Thr Asn
            260                 265                 270

Thr Ala Glu Ala Ala Thr Gly Trp Gln Thr Ile Asp Gly Lys Lys Tyr
        275                 280                 285

Tyr Phe Asn Thr Asn Thr Ala Ile Ala Ser Thr Gly Tyr Thr Ile Ile
    290                 295                 300

Asn Gly Lys His Phe Tyr Phe Asn Thr Asp Gly Ile Met Gln Ile Gly
305                 310                 315                 320

Val Phe Lys Gly Pro Asn Gly Phe Glu Tyr Phe Ala Pro Ala Asn Thr
                325                 330                 335

Asp Ala Asn Asn Ile Glu Gly Gln Ala Ile Leu Tyr Gln Asn Glu Phe
            340                 345                 350

Leu Thr Leu Asn Gly Lys Lys Tyr Tyr Phe Gly Ser Asp Ser Lys Ala
        355                 360                 365

Val Thr Gly Trp Arg Ile Ile Asn Asn Lys Lys Tyr Tyr Phe Asn Pro
    370                 375                 380

Asn Asn Ala Ile Ala Ala Ile His Leu Cys Thr Ile Asn Asn Asp Lys
385                 390                 395                 400

Tyr Tyr Phe Ser Tyr Asp Gly Ile Leu Gln Asn Gly Tyr Ile Thr Ile
                405                 410                 415

Glu Arg Asn Asn Phe Tyr Phe Asp Ala Asn Asn Glu Ser Lys Met Val
            420                 425                 430

Thr Gly Val Phe Lys Gly Pro Asn Gly Phe Glu Tyr Phe Ala Pro Ala
        435                 440                 445

Asn Thr His Asn Asn Asn Ile Glu Gly Gln Ala Ile Val Tyr Gln Asn
    450                 455                 460

Lys Phe Leu Thr Leu Asn Gly Lys Lys Tyr Tyr Phe Asp Asn Asp Ser
465                 470                 475                 480

Lys Ala Val Thr Gly Trp Gln Thr Ile Asp Gly Lys Lys Tyr Tyr Phe
                485                 490                 495

Asn Leu Asn Thr Ala Glu Ala Ala Thr Gly Trp Gln Thr Ile Asp Gly
            500                 505                 510

Lys Lys Tyr Tyr Phe Asn Leu Asn Thr Ala Glu Ala Ala Thr Gly Trp
        515                 520                 525
```

```
Gln Thr Ile Asp Gly Lys Lys Tyr Tyr Phe Asn Thr Asn Thr Phe Ile
    530                 535                 540

Ala Ser Thr Gly Tyr Thr Ser Ile Asn Gly Lys His Phe Tyr Phe Asn
545                 550                 555                 560

Thr Asp Gly Ile Met Gln Ile Gly Val Phe Lys Gly Pro Asn Gly Phe
                565                 570                 575

Glu Tyr Phe Ala Pro Ala Asn Thr His Asn Asn Asn Ile Glu Gly Gln
            580                 585                 590

Ala Ile Leu Tyr Gln Asn Lys Phe Leu Thr Leu Asn Gly Lys Lys Tyr
        595                 600                 605

Tyr Phe Gly Ser Asp Ser Lys Ala Val Thr Gly Leu Arg Thr Ile Asp
    610                 615                 620

Gly Lys Lys Tyr Tyr Phe Asn Thr Asn Thr Ala Val Ala Val Thr Gly
625                 630                 635                 640

Trp Gln Thr Ile Asn Gly Lys Lys Tyr Tyr Phe Asn Thr Asn Thr Ser
                645                 650                 655

Ile Ala Ser Thr Gly Tyr Thr Ile Ile Ser Gly Lys His Phe Tyr Phe
            660                 665                 670

Asn Thr Asp Gly Ile Met Gln Ile Gly Val Phe Lys Gly Pro Asp Gly
        675                 680                 685

Phe Glu Tyr Phe Ala Pro Ala Asn Thr Asp Ala Asn Asn Ile Glu Gly
    690                 695                 700

Gln Ala Ile Arg Tyr Gln Asn Arg Phe Leu Tyr Leu His Asp Asn Ile
705                 710                 715                 720

Tyr Tyr Phe Gly Asn Asn Ser Lys Ala Ala Thr Gly Trp Val Thr Ile
                725                 730                 735

Asp Gly Asn Arg Tyr Tyr Phe Glu Pro Asn Thr Ala Met Gly Ala Asn
            740                 745                 750

Gly Tyr Lys Thr Ile Asp Asn Lys Asn Phe Tyr Phe Arg Asn Gly Leu
        755                 760                 765

Pro Gln Ile Gly Val Phe Lys Gly Ser Asn Gly Phe Glu Tyr Phe Ala
    770                 775                 780

Pro Ala Asn Thr Asp Ala Asn Asn Ile Glu Gly Gln Ala Ile Arg Tyr
785                 790                 795                 800

Gln Asn Arg Phe Leu His Leu Leu Gly Lys Ile Tyr Tyr Phe Gly Asn
                805                 810                 815

Asn Ser Lys Ala Val Thr Gly Trp Gln Thr Ile Asn Gly Lys Val Tyr
            820                 825                 830

Tyr Phe Met Pro Asp Thr Ala Met Ala Ala Ala Gly Gly Leu Phe Glu
        835                 840                 845

Ile Asp Gly Val Ile Tyr Phe Phe Gly Val Asp Gly Val Lys Ala Pro
    850                 855                 860

Leu Glu
865
```

<210> SEQ ID NO 74
<211> LENGTH: 1383
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 74
catatgatcc tgcagaacgg ctatatcacc atcgaacgta ataacttcta cttcgatgcc 60

-continued

```
aataacgaat ccaaaatggt gacgggcgtg tttaaaggcc caaatggttt tgagtatttc    120

gcgccggcaa acacccacaa taacaacatt gaaggtcaag ccattgttta ccaaaacaaa    180

ttcctgaccc taaatggaaa aaaatattac tttgataacg acagcaaagc ggtcaccggc    240

tggcagacaa tcgacggtaa aaaatattac tttaatctta acaccgcaga agcggccacc    300

ggctggcaaa ccatcgatgg taaaaaatat tacttcaact tgaacaccgc agaagcggcc    360

accggctggc agaccatcga tggtaaaaaa tactacttta ataccaacac cttcattgct    420

agcaccggtt atacttcgat caacggtaaa catttttact ttaataccga cggtatcatg    480

caaattggcg tattcaaagg tcctaacggc tttgaatact ttgcgccagc aaatacccac    540

aacaataaca ttgaaggtca ggccattctg taccaaaaca aattcctgac cctaaatggt    600

aaaaaatatt acttcggtag tgacagcaaa gcggttacag gcctaaggac catcgatggt    660

aaaaaatatt actttaacac caacaccgca gtcgcggtta ccggctggca gaccatcaat    720

ggtaaaaaat actactttaa caccaacacc tctattgcca gcaccggtta cacgatcatc    780

tcgggtaaac atttctattt taataccgat ggtatcatgc aaattggcgt atttaaaggt    840

ccggacggct tcgaatactt tgcgcctgca aacacggatg ccaacaatat tgagggtcag    900

gcaattagat atcaaaaccg cttcctctac ctgcatgaca atatttatta ctttggtaac    960

aatagcaaag cggccaccgg ttgggtgacc atcgatggta accgttatta cttcgagcca   1020

aatacggcaa tgggtgctaa cggttataaa accatcgaca ataaaaactt ctactttcgc   1080

aatggtctgc cgcaaattgg cgtatttaaa ggatctaacg gcttcgaata ctttgcgcct   1140

gccaatacag atgcaaacaa cattgaaggt caggccatta gataccaaaa tcgtttcctc   1200

catttacttg gcaaaattta ttactttggt aacaatagca aagcggtcac cggttggcaa   1260

accatcaacg gtaaagtgta ttactttatg ccagataccg caatggccgc ggcaggtggc   1320

ttgttcgaga tcgacggtgt tatttacttc ttcggtgtcg atggcgtgaa agctccgctc   1380

gag                                                                 1383
```

```
<210> SEQ ID NO 75
<211> LENGTH: 460
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Met Ile Leu Gln Asn Gly Tyr Ile Thr Ile Glu Arg Asn Asn Phe Tyr
1               5                   10                  15

Phe Asp Ala Asn Asn Glu Ser Lys Met Val Thr Gly Val Phe Lys Gly
            20                  25                  30

Pro Asn Gly Phe Glu Tyr Phe Ala Pro Ala Asn Thr His Asn Asn Asn
        35                  40                  45

Ile Glu Gly Gln Ala Ile Val Tyr Gln Asn Lys Phe Leu Thr Leu Asn
    50                  55                  60

Gly Lys Lys Tyr Tyr Phe Asp Asn Asp Ser Lys Ala Val Thr Gly Trp
65                  70                  75                  80

Gln Thr Ile Asp Gly Lys Lys Tyr Tyr Phe Asn Leu Asn Thr Ala Glu
                85                  90                  95

Ala Ala Thr Gly Trp Gln Thr Ile Asp Gly Lys Lys Tyr Tyr Phe Asn
            100                 105                 110

Leu Asn Thr Ala Glu Ala Ala Thr Gly Trp Gln Thr Ile Asp Gly Lys
```

```
        115                 120                 125

Lys Tyr Tyr Phe Asn Thr Asn Thr Phe Ile Ala Ser Thr Gly Tyr Thr
    130                 135                 140

Ser Ile Asn Gly Lys His Phe Tyr Phe Asn Thr Asp Gly Ile Met Gln
145                 150                 155                 160

Ile Gly Val Phe Lys Gly Pro Asn Gly Phe Glu Tyr Phe Ala Pro Ala
                165                 170                 175

Asn Thr His Asn Asn Asn Ile Glu Gly Gln Ala Ile Leu Tyr Gln Asn
            180                 185                 190

Lys Phe Leu Thr Leu Asn Gly Lys Lys Tyr Tyr Phe Gly Ser Asp Ser
        195                 200                 205

Lys Ala Val Thr Gly Leu Arg Thr Ile Asp Gly Lys Lys Tyr Tyr Phe
    210                 215                 220

Asn Thr Asn Thr Ala Val Ala Val Thr Gly Trp Gln Thr Ile Asn Gly
225                 230                 235                 240

Lys Lys Tyr Tyr Phe Asn Thr Asn Thr Ser Ile Ala Ser Thr Gly Tyr
                245                 250                 255

Thr Ile Ile Ser Gly Lys His Phe Tyr Phe Asn Thr Asp Gly Ile Met
            260                 265                 270

Gln Ile Gly Val Phe Lys Gly Pro Asp Gly Phe Glu Tyr Phe Ala Pro
        275                 280                 285

Ala Asn Thr Asp Ala Asn Asn Ile Glu Gly Gln Ala Ile Arg Tyr Gln
    290                 295                 300

Asn Arg Phe Leu Tyr Leu His Asp Asn Ile Tyr Tyr Phe Gly Asn Asn
305                 310                 315                 320

Ser Lys Ala Ala Thr Gly Trp Val Thr Ile Asp Gly Asn Arg Tyr Tyr
                325                 330                 335

Phe Glu Pro Asn Thr Ala Met Gly Ala Asn Gly Tyr Lys Thr Ile Asp
            340                 345                 350

Asn Lys Asn Phe Tyr Phe Arg Asn Gly Leu Pro Gln Ile Gly Val Phe
        355                 360                 365

Lys Gly Ser Asn Gly Phe Glu Tyr Phe Ala Pro Ala Asn Thr Asp Ala
    370                 375                 380

Asn Asn Ile Glu Gly Gln Ala Ile Arg Tyr Gln Asn Arg Phe Leu His
385                 390                 395                 400

Leu Leu Gly Lys Ile Tyr Tyr Phe Gly Asn Asn Ser Lys Ala Val Thr
                405                 410                 415

Gly Trp Gln Thr Ile Asn Gly Lys Val Tyr Tyr Phe Met Pro Asp Thr
            420                 425                 430

Ala Met Ala Ala Ala Gly Gly Leu Phe Glu Ile Asp Gly Val Ile Tyr
        435                 440                 445

Phe Phe Gly Val Asp Gly Val Lys Ala Pro Leu Glu
    450                 455                 460


<210> SEQ ID NO 76
<211> LENGTH: 889
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Met Gly Ser Ser His His His His His His Glu Asn Leu Tyr Phe Gln
1               5                   10                  15
```

-continued

```
Gly Ser Leu Phe Tyr Phe Asp Pro Ile Glu Phe Asn Leu Val Thr Gly
            20                  25                  30

Trp Gln Thr Ile Asn Gly Lys Lys Tyr Tyr Phe Asp Ile Asn Thr Gly
        35                  40                  45

Ala Ala Leu Ile Ser Tyr Lys Ile Ile Asn Gly Lys His Phe Tyr Phe
    50                  55                  60

Asn Asn Asp Gly Val Met Gln Leu Gly Val Phe Lys Gly Pro Asp Gly
65                  70                  75                  80

Phe Glu Tyr Phe Ala Pro Ala Asn Thr Gln Asn Asn Asn Ile Glu Gly
                85                  90                  95

Gln Ala Ile Val Tyr Gln Ser Lys Phe Leu Thr Leu Asn Gly Lys Lys
            100                 105                 110

Tyr Tyr Phe Asp Asn Asp Ser Lys Ala Val Thr Gly Trp Arg Ile Ile
        115                 120                 125

Asn Asn Glu Lys Tyr Tyr Phe Asn Pro Asn Asn Ala Ile Ala Ala Val
    130                 135                 140

Gly Leu Gln Val Ile Asp Asn Asn Lys Tyr Tyr Phe Asn Pro Asp Thr
145                 150                 155                 160

Ala Ile Ile Ser Lys Gly Trp Gln Thr Val Asn Gly Ser Arg Tyr Tyr
                165                 170                 175

Phe Asp Thr Asp Thr Ala Ile Ala Phe Asn Gly Tyr Lys Thr Ile Asp
            180                 185                 190

Gly Lys His Phe Tyr Phe Asp Ser Asp Cys Val Val Lys Ile Gly Val
        195                 200                 205

Phe Ser Thr Ser Asn Gly Phe Glu Tyr Phe Ala Pro Ala Asn Thr Tyr
    210                 215                 220

Asn Asn Asn Ile Glu Gly Gln Ala Ile Val Tyr Gln Ser Lys Phe Leu
225                 230                 235                 240

Thr Leu Asn Gly Lys Lys Tyr Tyr Phe Asp Asn Asn Ser Lys Ala Val
                245                 250                 255

Thr Gly Trp Gln Thr Ile Asp Ser Lys Lys Tyr Tyr Phe Asn Thr Asn
            260                 265                 270

Thr Ala Glu Ala Ala Thr Gly Trp Gln Thr Ile Asp Gly Lys Lys Tyr
        275                 280                 285

Tyr Phe Asn Thr Asn Thr Ala Glu Ala Ala Thr Gly Trp Gln Thr Ile
    290                 295                 300

Asp Gly Lys Lys Tyr Tyr Phe Asn Thr Asn Thr Ala Ile Ala Ser Thr
305                 310                 315                 320

Gly Tyr Thr Ile Ile Asn Gly Lys His Phe Tyr Phe Asn Thr Asp Gly
                325                 330                 335

Ile Met Gln Ile Gly Val Phe Lys Gly Pro Asn Gly Phe Glu Tyr Phe
            340                 345                 350

Ala Pro Ala Asn Thr Asp Ala Asn Asn Ile Glu Gly Gln Ala Ile Leu
        355                 360                 365

Tyr Gln Asn Glu Phe Leu Thr Leu Asn Gly Lys Lys Tyr Tyr Phe Gly
    370                 375                 380

Ser Asp Ser Lys Ala Val Thr Gly Trp Arg Ile Ile Asn Asn Lys Lys
385                 390                 395                 400

Tyr Tyr Phe Asn Pro Asn Asn Ala Ile Ala Ala Ile His Leu Cys Thr
                405                 410                 415

Ile Asn Asn Asp Lys Tyr Tyr Phe Ser Tyr Asp Gly Ile Leu Gln Asn
            420                 425                 430

Gly Tyr Ile Thr Ile Glu Arg Asn Asn Phe Tyr Phe Asp Ala Asn Asn
```

```
        435                 440                 445

Glu Ser Lys Met Val Thr Gly Val Phe Lys Gly Pro Asn Gly Phe Glu
    450                 455                 460

Tyr Phe Ala Pro Ala Asn Thr His Asn Asn Asn Ile Glu Gly Gln Ala
465                 470                 475                 480

Ile Val Tyr Gln Asn Lys Phe Leu Thr Leu Asn Gly Lys Lys Tyr Tyr
                485                 490                 495

Phe Asp Asn Asp Ser Lys Ala Val Thr Gly Trp Gln Thr Ile Asp Gly
            500                 505                 510

Lys Lys Tyr Tyr Phe Asn Leu Asn Thr Ala Glu Ala Ala Thr Gly Trp
        515                 520                 525

Gln Thr Ile Asp Gly Lys Lys Tyr Tyr Phe Asn Leu Asn Thr Ala Glu
    530                 535                 540

Ala Ala Thr Gly Trp Gln Thr Ile Asp Gly Lys Lys Tyr Tyr Phe Asn
545                 550                 555                 560

Thr Asn Thr Phe Ile Ala Ser Thr Gly Tyr Thr Ser Ile Asn Gly Lys
                565                 570                 575

His Phe Tyr Phe Asn Thr Asp Gly Ile Met Gln Ile Gly Val Phe Lys
            580                 585                 590

Gly Pro Asn Gly Phe Glu Tyr Phe Ala Pro Ala Asn Thr His Asn Asn
        595                 600                 605

Asn Ile Glu Gly Gln Ala Ile Leu Tyr Gln Asn Lys Phe Leu Thr Leu
    610                 615                 620

Asn Gly Lys Lys Tyr Tyr Phe Gly Ser Asp Ser Lys Ala Val Thr Gly
625                 630                 635                 640

Leu Arg Thr Ile Asp Gly Lys Lys Tyr Tyr Phe Asn Thr Asn Thr Ala
                645                 650                 655

Val Ala Val Thr Gly Trp Gln Thr Ile Asn Gly Lys Lys Tyr Tyr Phe
            660                 665                 670

Asn Thr Asn Thr Ser Ile Ala Ser Thr Gly Tyr Thr Ile Ile Ser Gly
        675                 680                 685

Lys His Phe Tyr Phe Asn Thr Asp Gly Ile Met Gln Ile Gly Val Phe
    690                 695                 700

Lys Gly Pro Asp Gly Phe Glu Tyr Phe Ala Pro Ala Asn Thr Asp Ala
705                 710                 715                 720

Asn Asn Ile Glu Gly Gln Ala Ile Arg Tyr Gln Asn Arg Phe Leu Tyr
                725                 730                 735

Leu His Asp Asn Ile Tyr Tyr Phe Gly Asn Asn Ser Lys Ala Ala Thr
            740                 745                 750

Gly Trp Val Thr Ile Asp Gly Asn Arg Tyr Tyr Phe Glu Pro Asn Thr
        755                 760                 765

Ala Met Gly Ala Asn Gly Tyr Lys Thr Ile Asp Asn Lys Asn Phe Tyr
    770                 775                 780

Phe Arg Asn Gly Leu Pro Gln Ile Gly Val Phe Lys Gly Ser Asn Gly
785                 790                 795                 800

Phe Glu Tyr Phe Ala Pro Ala Asn Thr Asp Ala Asn Asn Ile Glu Gly
                805                 810                 815

Gln Ala Ile Arg Tyr Gln Asn Arg Phe Leu His Leu Leu Gly Lys Ile
            820                 825                 830

Tyr Tyr Phe Gly Asn Asn Ser Lys Ala Val Thr Gly Trp Gln Thr Ile
        835                 840                 845

Asn Gly Lys Val Tyr Tyr Phe Met Pro Asp Thr Ala Met Ala Ala Ala
    850                 855                 860
```

Gly Gly Leu Phe Glu Ile Asp Gly Val Ile Tyr Phe Phe Gly Val Asp
865 870 875 880

Gly Val Lys Ala Pro Gly Ile Tyr Gly
885

<210> SEQ ID NO 77
<211> LENGTH: 2667
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 77
atgggcagca gccatcatca tcatcatcac gaaaacctgt acttccaggg ctcattattc 60
tattttgatc ctatagaatt taacttagta actggatggc aaactatcaa tggtaaaaaa 120
tattattttg atataaatac tggagcagct ttaattagtt ataaaattat taatggtaaa 180
cacttttatt ttaataatga tggtgtgatg cagttgggag tatttaaagg acctgatgga 240
tttgaatatt ttgcacctgc caatactcaa aataataaca tagaaggtca ggctatagtt 300
tatcaaagta aattcttaac tttgaatggc aaaaaatatt attttgataa tgactcaaaa 360
gcagtcactg gatggagaat tattaacaat gagaaatatt actttaatcc taataatgct 420
attgctgcag tcggattgca agtaattgac aataataagt attatttcaa tcctgacact 480
gctatcatct caaaaggttg gcagactgtt aatggtagta gatactactt tgatactgat 540
accgctattg cctttaatgg ttataaaact attgatggta aacactttta ttttgatagt 600
gattgtgtag tgaaaatagg tgtgtttagt acctctaatg gatttgaata ttttgcacct 660
gctaatactt ataataataa catagaaggt caggctatag tttatcaaag taaattctta 720
actttgaatg gtaaaaaata ttactttgat aataactcaa aagcagttac cggatggcaa 780
actattgata gtaaaaaata ttactttaat actaacactg ctgaagcagc tactggatgg 840
caaactattg atggtaaaaa atattacttt aatactaaca ctgctgaagc agctactgga 900
tggcaaacta ttgatggtaa aaaatattac tttaatacta acactgctat agcttcaact 960
ggttatacaa ttattaatgg taaacatttt tattttaata ctgatggtat tatgcagata 1020
ggagtgttta aaggacctaa tggatttgaa tattttgcac ctgctaatac ggatgctaac 1080
aacatagaag gtcaagctat actttaccaa aatgaattct taactttgaa tggtaaaaaa 1140
tattactttg gtagtgactc aaaagcagtt actggatgga gaattattaa caataagaaa 1200
tattacttta atcctaataa tgctattgct gcaattcatc tatgcactat aaataatgac 1260
aagtattact ttagttatga tggaattctt caaaatggat atattactat tgaaagaaat 1320
aatttctatt ttgatgctaa taatgaatct aaaatggtaa caggagtatt taaaggacct 1380
aatggatttg agtattttgc acctgctaat actcacaata ataacataga aggtcaggct 1440
atagtttacc agaacaaatt cttaactttg aatggcaaaa aatattattt tgataatgac 1500
tcaaaagcag ttactggatg gcaaaccatt gatggtaaaa aatattactt taatcttaac 1560
actgctgaag cagctactgg atggcaaact attgatggta aaaaatatta ctttaatctt 1620
aacactgctg aagcagctac tggatggcaa actattgatg gtaaaaaata ttactttaat 1680
actaacactt tcatagcctc aactggttat acaagtatta atggtaaaca tttttatttt 1740
aatactgatg gtattatgca gataggagtg tttaaaggac ctaatggatt tgaatacttt 1800
gcacctgcta atactcataa taataacata gaaggtcaag ctatacttta ccaaaataaa 1860

-continued

```
ttcttaactt tgaatggtaa aaaatattac tttggtagtg actcaaaagc agttaccgga   1920

ttgcgaacta ttgatggtaa aaaatattac tttaatacta acactgctgt tgcagttact   1980

ggatggcaaa ctattaatgg taaaaaatac tactttaata ctaacacttc tatagcttca   2040

actggttata caattattag tggtaaacat ttttatttta atactgatgg tattatgcag   2100

ataggagtgt ttaaaggacc tgatggattt gaatactttg cacctgctaa tacagatgct   2160

aacaatatag aaggtcaagc tatacgttat caaaatagat tcctatattt acatgacaat   2220

atatattatt ttggtaataa ttcaaaagca gctactggtt gggtaactat tgatggtaat   2280

agatattact tcgagcctaa tacagctatg ggtgcgaatg gttataaaac tattgataat   2340

aaaaattttt actttagaaa tggtttacct cagataggag tgtttaaagg gtctaatgga   2400

tttgaatact ttgcacctgc taatacggat gctaacaata tagaaggtca agctatacgt   2460

tatcaaaata gattcctaca tttacttgga aaaatatatt actttggtaa taattcaaaa   2520

gcagttactg gatggcaaac tattaatggt aaagtatatt actttatgcc tgatactgct   2580

atggctgcag ctggtggact tttcgagatt gatggtgtta tatatttctt tggtgttgat   2640

ggagtaaaag cccctgggat atatggc                                       2667
```

```
<210> SEQ ID NO 78
<211> LENGTH: 833
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Met Gly Ser Ser His His His His His His Glu Asn Leu Tyr Phe Gln
1               5                   10                  15

Gly Met Gln Leu Gly Val Phe Lys Gly Pro Asp Gly Phe Glu Tyr Phe
            20                  25                  30

Ala Pro Ala Asn Thr Gln Asn Asn Asn Ile Glu Gly Gln Ala Ile Val
        35                  40                  45

Tyr Gln Ser Lys Phe Leu Thr Leu Asn Gly Lys Lys Tyr Tyr Phe Asp
    50                  55                  60

Asn Asp Ser Lys Ala Val Thr Gly Trp Arg Ile Ile Asn Asn Glu Lys
65                  70                  75                  80

Tyr Tyr Phe Asn Pro Asn Asn Ala Ile Ala Ala Val Gly Leu Gln Val
                85                  90                  95

Ile Asp Asn Asn Lys Tyr Tyr Phe Asn Pro Asp Thr Ala Ile Ile Ser
            100                 105                 110

Lys Gly Trp Gln Thr Val Asn Gly Ser Arg Tyr Tyr Phe Asp Thr Asp
        115                 120                 125

Thr Ala Ile Ala Phe Asn Gly Tyr Lys Thr Ile Asp Gly Lys His Phe
    130                 135                 140

Tyr Phe Asp Ser Asp Cys Val Val Lys Ile Gly Val Phe Ser Thr Ser
145                 150                 155                 160

Asn Gly Phe Glu Tyr Phe Ala Pro Ala Asn Thr Tyr Asn Asn Asn Ile
                165                 170                 175

Glu Gly Gln Ala Ile Val Tyr Gln Ser Lys Phe Leu Thr Leu Asn Gly
            180                 185                 190

Lys Lys Tyr Tyr Phe Asp Asn Asn Ser Lys Ala Val Thr Gly Trp Gln
        195                 200                 205
```

-continued

```
Thr Ile Asp Ser Lys Lys Tyr Tyr Phe Asn Thr Asn Thr Ala Glu Ala
    210                 215                 220

Ala Thr Gly Trp Gln Thr Ile Asp Gly Lys Lys Tyr Tyr Phe Asn Thr
225                 230                 235                 240

Asn Thr Ala Glu Ala Ala Thr Gly Trp Gln Thr Ile Asp Gly Lys Lys
                245                 250                 255

Tyr Tyr Phe Asn Thr Asn Thr Ala Ile Ala Ser Thr Gly Tyr Thr Ile
            260                 265                 270

Ile Asn Gly Lys His Phe Tyr Phe Asn Thr Asp Gly Ile Met Gln Ile
        275                 280                 285

Gly Val Phe Lys Gly Pro Asn Gly Phe Glu Tyr Phe Ala Pro Ala Asn
    290                 295                 300

Thr Asp Ala Asn Asn Ile Glu Gly Gln Ala Ile Leu Tyr Gln Asn Glu
305                 310                 315                 320

Phe Leu Thr Leu Asn Gly Lys Lys Tyr Tyr Phe Gly Ser Asp Ser Lys
                325                 330                 335

Ala Val Thr Gly Trp Arg Ile Ile Asn Asn Lys Lys Tyr Tyr Phe Asn
            340                 345                 350

Pro Asn Asn Ala Ile Ala Ala Ile His Leu Cys Thr Ile Asn Asn Asp
        355                 360                 365

Lys Tyr Tyr Phe Ser Tyr Asp Gly Ile Leu Gln Asn Gly Tyr Ile Thr
    370                 375                 380

Ile Glu Arg Asn Asn Phe Tyr Phe Asp Ala Asn Asn Glu Ser Lys Met
385                 390                 395                 400

Val Thr Gly Val Phe Lys Gly Pro Asn Gly Phe Glu Tyr Phe Ala Pro
                405                 410                 415

Ala Asn Thr His Asn Asn Asn Ile Glu Gly Gln Ala Ile Val Tyr Gln
            420                 425                 430

Asn Lys Phe Leu Thr Leu Asn Gly Lys Lys Tyr Tyr Phe Asp Asn Asp
        435                 440                 445

Ser Lys Ala Val Thr Gly Trp Gln Thr Ile Asp Gly Lys Lys Tyr Tyr
    450                 455                 460

Phe Asn Leu Asn Thr Ala Glu Ala Ala Thr Gly Trp Gln Thr Ile Asp
465                 470                 475                 480

Gly Lys Lys Tyr Tyr Phe Asn Leu Asn Thr Ala Glu Ala Ala Thr Gly
                485                 490                 495

Trp Gln Thr Ile Asp Gly Lys Lys Tyr Tyr Phe Asn Thr Asn Thr Phe
            500                 505                 510

Ile Ala Ser Thr Gly Tyr Thr Ser Ile Asn Gly Lys His Phe Tyr Phe
        515                 520                 525

Asn Thr Asp Gly Ile Met Gln Ile Gly Val Phe Lys Gly Pro Asn Gly
    530                 535                 540

Phe Glu Tyr Phe Ala Pro Ala Asn Thr His Asn Asn Asn Ile Glu Gly
545                 550                 555                 560

Gln Ala Ile Leu Tyr Gln Asn Lys Phe Leu Thr Leu Asn Gly Lys Lys
                565                 570                 575

Tyr Tyr Phe Gly Ser Asp Ser Lys Ala Val Thr Gly Leu Arg Thr Ile
            580                 585                 590

Asp Gly Lys Lys Tyr Tyr Phe Asn Thr Asn Thr Ala Val Ala Val Thr
        595                 600                 605

Gly Trp Gln Thr Ile Asn Gly Lys Lys Tyr Tyr Phe Asn Thr Asn Thr
    610                 615                 620

Ser Ile Ala Ser Thr Gly Tyr Thr Ile Ile Ser Gly Lys His Phe Tyr
```

```
625                 630                 635                 640

Phe Asn Thr Asp Gly Ile Met Gln Ile Gly Val Phe Lys Gly Pro Asp
                645                 650                 655

Gly Phe Glu Tyr Phe Ala Pro Ala Asn Thr Asp Ala Asn Asn Ile Glu
            660                 665                 670

Gly Gln Ala Ile Arg Tyr Gln Asn Arg Phe Leu Tyr Leu His Asp Asn
        675                 680                 685

Ile Tyr Tyr Phe Gly Asn Asn Ser Lys Ala Ala Thr Gly Trp Val Thr
    690                 695                 700

Ile Asp Gly Asn Arg Tyr Tyr Phe Glu Pro Asn Thr Ala Met Gly Ala
705                 710                 715                 720

Asn Gly Tyr Lys Thr Ile Asp Asn Lys Asn Phe Tyr Phe Arg Asn Gly
                725                 730                 735

Leu Pro Gln Ile Gly Val Phe Lys Gly Ser Asn Gly Phe Glu Tyr Phe
            740                 745                 750

Ala Pro Ala Asn Thr Asp Ala Asn Asn Ile Glu Gly Gln Ala Ile Arg
        755                 760                 765

Tyr Gln Asn Arg Phe Leu His Leu Leu Gly Lys Ile Tyr Tyr Phe Gly
    770                 775                 780

Asn Asn Ser Lys Ala Val Thr Gly Trp Gln Thr Ile Asn Gly Lys Val
785                 790                 795                 800

Tyr Tyr Phe Met Pro Asp Thr Ala Met Ala Ala Ala Gly Gly Leu Phe
                805                 810                 815

Glu Ile Asp Gly Val Ile Tyr Phe Phe Gly Val Asp Gly Val Lys Ala
            820                 825                 830

Pro
```

<210> SEQ ID NO 79
<211> LENGTH: 2499
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 79

```
atgggcagca gccatcatca tcatcatcac gaaaacctgt acttccaggg catgcagttg     60

ggagtattta aaggacctga tggatttgaa tattttgcac ctgccaatac tcaaaataat    120

aacatagaag gtcaggctat agtttatcaa agtaaattct taactttgaa tggcaaaaaa    180

tattattttg ataatgactc aaaagcagtc actggatgga gaattattaa caatgagaaa    240

tattacttta atcctaataa tgctattgct gcagtcggat tgcaagtaat tgacaataat    300

aagtattatt tcaatcctga cactgctatc atctcaaaag gttggcagac tgttaatggt    360

agtagatact actttgatac tgataccgct attgccttta atggttataa aactattgat    420

ggtaaacact tttattttga tagtgattgt gtagtgaaaa taggtgtgtt tagtacctct    480

aatggatttg aatattttgc acctgctaat acttataata ataacataga aggtcaggct    540

atagtttatc aaagtaaatt cttaactttg aatggtaaaa aatattactt tgataataac    600

tcaaaagcag ttaccggatg gcaaactatt gatagtaaaa aatattactt taatactaac    660

actgctgaag cagctactgg atggcaaact attgatggta aaaaatatta ctttaatact    720

aacactgctg aagcagctac tggatggcaa actattgatg gtaaaaaata ttactttaat    780

actaacactg ctatagcttc aactggttat acaattatta atggtaaaca ttttttattt    840
```

-continued

```
aatactgatg gtattatgca gataggagtg tttaaaggac ctaatggatt tgaatatttt    900
gcacctgcta atacggatgc taacaacata gaaggtcaag ctatacttta ccaaaatgaa    960
ttcttaactt tgaatggtaa aaaatattac tttggtagtg actcaaaagc agttactgga   1020
tggagaatta ttaacaataa gaaatattac tttaatccta ataatgctat tgctgcaatt   1080
catctatgca ctataaataa tgacaagtat tactttagtt atgatggaat tcttcaaaat   1140
ggatatatta ctattgaaag aaataatttc tattttgatg ctaataatga atctaaaatg   1200
gtaacaggag tatttaaagg acctaatgga tttgagtatt ttgcacctgc taatactcac   1260
aataataaca tagaaggtca ggctatagtt taccagaaca aattcttaac tttgaatggc   1320
aaaaaatatt attttgataa tgactcaaaa gcagttactg gatggcaaac cattgatggt   1380
aaaaaatatt actttaatct taacactgct gaagcagcta ctggatggca aactattgat   1440
ggtaaaaaat attactttaa tcttaacact gctgaagcag ctactggatg gcaaactatt   1500
gatggtaaaa aatattactt taatactaac actttcatag cctcaactgg ttatacaagt   1560
attaatggta aacattttta ttttaatact gatggtatta tgcagatagg agtgtttaaa   1620
ggacctaatg gatttgaata ctttgcacct gctaatactc ataataataa catagaaggt   1680
caagctatac tttaccaaaa taaattctta actttgaatg gtaaaaaata ttactttggt   1740
agtgactcaa aagcagttac cggattgcga actattgatg gtaaaaaata ttactttaat   1800
actaacactg ctgttgcagt tactggatgg caaactatta atggtaaaaa atactacttt   1860
aatactaaca cttctatagc ttcaactggt tatacaatta ttagtggtaa acatttttat   1920
tttaatactg atggtattat gcagatagga gtgtttaaag gacctgatgg atttgaatac   1980
tttgcacctg ctaatacaga tgctaacaat atagaaggtc aagctatacg ttatcaaaat   2040
agattcctat atttacatga caatatatat tattttggta ataattcaaa agcagctact   2100
ggttgggtaa ctattgatgg taatagatat tacttcgagc ctaatacagc tatgggtgcg   2160
aatggttata aaactattga taataaaaat ttttacttta gaaatggttt acctcagata   2220
ggagtgttta aagggtctaa tggatttgaa tactttgcac ctgctaatac ggatgctaac   2280
aatatagaag gtcaagctat acgttatcaa aatagattcc tacatttact tggaaaaata   2340
tattactttg gtaataattc aaaagcagtt actggatggc aaactattaa tggtaaagta   2400
tattacttta tgcctgatac tgctatggct gcagctggtg gacttttcga gattgatggt   2460
gttatatatt tctttggtgt tgatggagta aaagcccct                          2499
```

<210> SEQ ID NO 80
<211> LENGTH: 760
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 80

```
Met Gly Ser Ser His His His His His His Glu Asn Leu Tyr Phe Gln
1               5                   10                  15

Gly Ala Val Gly Leu Gln Val Ile Asp Asn Asn Lys Tyr Tyr Phe Asn
            20                  25                  30

Pro Asp Thr Ala Ile Ile Ser Lys Gly Trp Gln Thr Val Asn Gly Ser
        35                  40                  45

Arg Tyr Tyr Phe Asp Thr Asp Thr Ala Ile Ala Phe Asn Gly Tyr Lys
    50                  55                  60
```

```
Thr Ile Asp Gly Lys His Phe Tyr Phe Asp Ser Asp Cys Val Val Lys
65                  70                  75                  80

Ile Gly Val Phe Ser Thr Ser Asn Gly Phe Glu Tyr Phe Ala Pro Ala
                85                  90                  95

Asn Thr Tyr Asn Asn Asn Ile Glu Gly Gln Ala Ile Val Tyr Gln Ser
            100                 105                 110

Lys Phe Leu Thr Leu Asn Gly Lys Lys Tyr Tyr Phe Asp Asn Asn Ser
        115                 120                 125

Lys Ala Val Thr Gly Trp Gln Thr Ile Asp Ser Lys Lys Tyr Tyr Phe
    130                 135                 140

Asn Thr Asn Thr Ala Glu Ala Ala Thr Gly Trp Gln Thr Ile Asp Gly
145                 150                 155                 160

Lys Lys Tyr Tyr Phe Asn Thr Asn Thr Ala Glu Ala Ala Thr Gly Trp
                165                 170                 175

Gln Thr Ile Asp Gly Lys Lys Tyr Tyr Phe Asn Thr Asn Thr Ala Ile
            180                 185                 190

Ala Ser Thr Gly Tyr Thr Ile Ile Asn Gly Lys His Phe Tyr Phe Asn
        195                 200                 205

Thr Asp Gly Ile Met Gln Ile Gly Val Phe Lys Gly Pro Asn Gly Phe
    210                 215                 220

Glu Tyr Phe Ala Pro Ala Asn Thr Asp Ala Asn Asn Ile Glu Gly Gln
225                 230                 235                 240

Ala Ile Leu Tyr Gln Asn Glu Phe Leu Thr Leu Asn Gly Lys Lys Tyr
                245                 250                 255

Tyr Phe Gly Ser Asp Ser Lys Ala Val Thr Gly Trp Arg Ile Ile Asn
            260                 265                 270

Asn Lys Lys Tyr Tyr Phe Asn Pro Asn Asn Ala Ile Ala Ala Ile His
        275                 280                 285

Leu Cys Thr Ile Asn Asn Asp Lys Tyr Tyr Phe Ser Tyr Asp Gly Ile
    290                 295                 300

Leu Gln Asn Gly Tyr Ile Thr Ile Glu Arg Asn Asn Phe Tyr Phe Asp
305                 310                 315                 320

Ala Asn Asn Glu Ser Lys Met Val Thr Gly Val Phe Lys Gly Pro Asn
                325                 330                 335

Gly Phe Glu Tyr Phe Ala Pro Ala Asn Thr His Asn Asn Asn Ile Glu
            340                 345                 350

Gly Gln Ala Ile Val Tyr Gln Asn Lys Phe Leu Thr Leu Asn Gly Lys
        355                 360                 365

Lys Tyr Tyr Phe Asp Asn Asp Ser Lys Ala Val Thr Gly Trp Gln Thr
    370                 375                 380

Ile Asp Gly Lys Lys Tyr Tyr Phe Asn Leu Asn Thr Ala Glu Ala Ala
385                 390                 395                 400

Thr Gly Trp Gln Thr Ile Asp Gly Lys Lys Tyr Tyr Phe Asn Leu Asn
                405                 410                 415

Thr Ala Glu Ala Ala Thr Gly Trp Gln Thr Ile Asp Gly Lys Lys Tyr
            420                 425                 430

Tyr Phe Asn Thr Asn Thr Phe Ile Ala Ser Thr Gly Tyr Thr Ser Ile
        435                 440                 445

Asn Gly Lys His Phe Tyr Phe Asn Thr Asp Gly Ile Met Gln Ile Gly
    450                 455                 460

Val Phe Lys Gly Pro Asn Gly Phe Glu Tyr Phe Ala Pro Ala Asn Thr
465                 470                 475                 480

His Asn Asn Asn Ile Glu Gly Gln Ala Ile Leu Tyr Gln Asn Lys Phe
```

```
                485                 490                 495

Leu Thr Leu Asn Gly Lys Lys Tyr Tyr Phe Gly Ser Asp Ser Lys Ala
            500                 505                 510

Val Thr Gly Leu Arg Thr Ile Asp Gly Lys Lys Tyr Tyr Phe Asn Thr
        515                 520                 525

Asn Thr Ala Val Ala Val Thr Gly Trp Gln Thr Ile Asn Gly Lys Lys
    530                 535                 540

Tyr Tyr Phe Asn Thr Asn Thr Ser Ile Ala Ser Thr Gly Tyr Thr Ile
545                 550                 555                 560

Ile Ser Gly Lys His Phe Tyr Phe Asn Thr Asp Gly Ile Met Gln Ile
                565                 570                 575

Gly Val Phe Lys Gly Pro Asp Gly Phe Glu Tyr Phe Ala Pro Ala Asn
            580                 585                 590

Thr Asp Ala Asn Asn Ile Glu Gly Gln Ala Ile Arg Tyr Gln Asn Arg
        595                 600                 605

Phe Leu Tyr Leu His Asp Asn Ile Tyr Tyr Phe Gly Asn Asn Ser Lys
    610                 615                 620

Ala Ala Thr Gly Trp Val Thr Ile Asp Gly Asn Arg Tyr Tyr Phe Glu
625                 630                 635                 640

Pro Asn Thr Ala Met Gly Ala Asn Gly Tyr Lys Thr Ile Asp Asn Lys
                645                 650                 655

Asn Phe Tyr Phe Arg Asn Gly Leu Pro Gln Ile Gly Val Phe Lys Gly
            660                 665                 670

Ser Asn Gly Phe Glu Tyr Phe Ala Pro Ala Asn Thr Asp Ala Asn Asn
        675                 680                 685

Ile Glu Gly Gln Ala Ile Arg Tyr Gln Asn Arg Phe Leu His Leu Leu
    690                 695                 700

Gly Lys Ile Tyr Tyr Phe Gly Asn Asn Ser Lys Ala Val Thr Gly Trp
705                 710                 715                 720

Gln Thr Ile Asn Gly Lys Val Tyr Tyr Phe Met Pro Asp Thr Ala Met
                725                 730                 735

Ala Ala Ala Gly Gly Leu Phe Glu Ile Asp Gly Val Ile Tyr Phe Phe
            740                 745                 750

Gly Val Asp Gly Val Lys Ala Pro
        755                 760


<210> SEQ ID NO 81
<211> LENGTH: 2280
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

atgggcagca gccatcatca tcatcatcac gaaaacctgt acttccaggg cgcagtcgga      60

ttgcaagtaa ttgacaataa taagtattat ttcaatcctg acactgctat catctcaaaa     120

ggttggcaga ctgttaatgg tagtagatac tactttgata ctgataccgc tattgccttt     180

aatggttata aaactattga tggtaaacac ttttattttg atagtgattg tgtagtgaaa     240

ataggtgtgt ttagtacctc taatggattt gaatattttg cacctgctaa tacttataat     300

aataacatag aaggtcaggc tatagtttat caaagtaaat tcttaacttt gaatggtaaa     360

aaatattact ttgataataa ctcaaaagca gttaccggat ggcaaactat tgatagtaaa     420

aaatattact ttaatactaa cactgctgaa gcagctactg gatggcaaac tattgatggt     480
```

aaaaaatatt actttaatac taacactgct gaagcagcta ctggatggca aactattgat 540
ggtaaaaaat attactttaa tactaacact gctatagctt caactggtta tacaattatt 600
aatggtaaac atttttattt taatactgat ggtattatgc agataggagt gtttaaagga 660
cctaatggat ttgaatattt tgcacctgct aatacggatg ctaacaacat agaaggtcaa 720
gctatacttt accaaaatga attcttaact ttgaatggta aaaaatatta ctttggtagt 780
gactcaaaag cagttactgg atggagaatt attaacaata agaaatatta ctttaatcct 840
aataatgcta ttgctgcaat tcatctatgc actataaata atgacaagta ttactttagt 900
tatgatggaa ttcttcaaaa tggatatatt actattgaaa gaaataattt ctattttgat 960
gctaataatg aatctaaaat ggtaacagga gtatttaaag gacctaatgg atttgagtat 1020
tttgcacctg ctaatactca caataataac atagaaggtc aggctatagt ttaccagaac 1080
aaattcttaa ctttgaatgg caaaaaatat tattttgata atgactcaaa agcagttact 1140
ggatggcaaa ccattgatgg taaaaaatat tactttaatc ttaacactgc tgaagcagct 1200
actggatggc aaactattga tggtaaaaaa tattacttta atcttaacac tgctgaagca 1260
gctactggat ggcaaactat tgatggtaaa aaatattact ttaatactaa cactttcata 1320
gcctcaactg gttatacaag tattaatggt aaacattttt attttaatac tgatggtatt 1380
atgcagatag gagtgtttaa aggacctaat ggatttgaat actttgcacc tgctaatact 1440
cataataata acatagaagg tcaagctata ctttaccaaa ataaattctt aactttgaat 1500
ggtaaaaaat attactttgg tagtgactca aaagcagtta ccggattgcg aactattgat 1560
ggtaaaaaat attactttaa tactaacact gctgttgcag ttactggatg gcaaactatt 1620
aatggtaaaa aatactactt taatactaac acttctatag cttcaactgg ttatacaatt 1680
attagtggta aacattttta ttttaatact gatggtatta tgcagatagg agtgtttaaa 1740
ggacctgatg gatttgaata ctttgcacct gctaatacag atgctaacaa tatagaaggt 1800
caagctatac gttatcaaaa tagattccta tatttacatg acaatatata ttattttggt 1860
aataattcaa aagcagctac tggttgggta actattgatg gtaatagata ttacttcgag 1920
cctaatacag ctatgggtgc gaatggttat aaaactattg ataataaaaa tttttacttt 1980
agaaatggtt tacctcagat aggagtgttt aaagggtcta atggatttga atactttgca 2040
cctgctaata cggatgctaa caatatagaa ggtcaagcta tacgttatca aaatagattc 2100
ctacatttac ttggaaaaat atattacttt ggtaataatt caaaagcagt tactggatgg 2160
caaactatta atggtaaagt atattacttt atgcctgata ctgctatggc tgcagctggt 2220
ggacttttcg agattgatgg tgttatatat ttctttggtg ttgatggagt aaaagcccct 2280

<210> SEQ ID NO 82
<211> LENGTH: 858
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 82
atgggcagca gccatcatca tcatcatcac gaaaacctgt acttccaggg ctaccaaaat 60
aaattcttaa ctttgaatgg taaaaaatat tactttggta gtgactcaaa agcagttacc 120
ggattgcgaa ctattgatgg taaaaaatat tactttaata ctaacactgc tgttgcagtt 180
actggatggc aaactattaa tggtaaaaaa tactacttta atactaacac ttctatagct 240

```
tcaactggtt atacaattat tagtggtaaa catttttatt ttaatactga tggtattatg    300

cagataggag tgtttaaagg acctgatgga tttgaatact ttgcacctgc taatacagat    360

gctaacaata tagaaggtca agctatacgt tatcaaaata gattcctata tttacatgac    420

aatatatatt attttggtaa taattcaaaa gcagctactg gttgggtaac tattgatggt    480

aatagatatt acttcgagcc taatacagct atgggtgcga atggttataa aactattgat    540

aataaaaatt tttactttag aaatggttta cctcagatag gagtgtttaa agggtctaat    600

ggatttgaat actttgcacc tgctaatacg gatgctaaca atatagaagg tcaagctata    660

cgttatcaaa atagattcct acatttactt ggaaaaatat attactttgg taataattca    720

aaagcagtta ctggatggca aactattaat ggtaaagtat attactttat gcctgatact    780

gctatggctg cagctggtgg acttttcgag attgatggtg ttatatattt ctttggtgtt    840

gatggagtaa aagcccct                                                  858
```

<210> SEQ ID NO 83
<211> LENGTH: 420
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

```
Met Gly Ser Ser His His His His His His Glu Asn Leu Tyr Phe Gln
1               5                   10                  15

Gly Tyr Gln Asn Lys Phe Leu Thr Leu Asn Gly Lys Lys Tyr Tyr Phe
            20                  25                  30

Asp Asn Asp Ser Lys Ala Val Thr Gly Trp Gln Thr Ile Asp Gly Lys
        35                  40                  45

Lys Tyr Tyr Phe Asn Leu Asn Thr Ala Glu Ala Ala Thr Gly Trp Gln
    50                  55                  60

Thr Ile Asp Gly Lys Lys Tyr Tyr Phe Asn Leu Asn Thr Ala Glu Ala
65                  70                  75                  80

Ala Thr Gly Trp Gln Thr Ile Asp Gly Lys Lys Tyr Tyr Phe Asn Thr
                85                  90                  95

Asn Thr Phe Ile Ala Ser Thr Gly Tyr Thr Ser Ile Asn Gly Lys His
            100                 105                 110

Phe Tyr Phe Asn Thr Asp Gly Ile Met Gln Ile Gly Val Phe Lys Gly
        115                 120                 125

Pro Asn Gly Phe Glu Tyr Phe Ala Pro Ala Asn Thr His Asn Asn Asn
    130                 135                 140

Ile Glu Gly Gln Ala Ile Leu Tyr Gln Asn Lys Phe Leu Thr Leu Asn
145                 150                 155                 160

Gly Lys Lys Tyr Tyr Phe Gly Ser Asp Ser Lys Ala Val Thr Gly Leu
                165                 170                 175

Arg Thr Ile Asp Gly Lys Lys Tyr Tyr Phe Asn Thr Asn Thr Ala Val
            180                 185                 190

Ala Val Thr Gly Trp Gln Thr Ile Asn Gly Lys Lys Tyr Tyr Phe Asn
        195                 200                 205

Thr Asn Thr Ser Ile Ala Ser Thr Gly Tyr Thr Ile Ile Ser Gly Lys
    210                 215                 220

His Phe Tyr Phe Asn Thr Asp Gly Ile Met Gln Ile Gly Val Phe Lys
225                 230                 235                 240
```

```
Gly Pro Asp Gly Phe Glu Tyr Phe Ala Pro Ala Asn Thr Asp Ala Asn
                245                 250                 255

Asn Ile Glu Gly Gln Ala Ile Arg Tyr Gln Asn Arg Phe Leu Tyr Leu
            260                 265                 270

His Asp Asn Ile Tyr Tyr Phe Gly Asn Asn Ser Lys Ala Ala Thr Gly
        275                 280                 285

Trp Val Thr Ile Asp Gly Asn Arg Tyr Tyr Phe Glu Pro Asn Thr Ala
    290                 295                 300

Met Gly Ala Asn Gly Tyr Lys Thr Ile Asp Asn Lys Asn Phe Tyr Phe
305                 310                 315                 320

Arg Asn Gly Leu Pro Gln Ile Gly Val Phe Lys Gly Ser Asn Gly Phe
                325                 330                 335

Glu Tyr Phe Ala Pro Ala Asn Thr Asp Ala Asn Asn Ile Glu Gly Gln
            340                 345                 350

Ala Ile Arg Tyr Gln Asn Arg Phe Leu His Leu Leu Gly Lys Ile Tyr
        355                 360                 365

Tyr Phe Gly Asn Asn Ser Lys Ala Val Thr Gly Trp Gln Thr Ile Asn
    370                 375                 380

Gly Lys Val Tyr Tyr Phe Met Pro Asp Thr Ala Met Ala Ala Ala Gly
385                 390                 395                 400

Gly Leu Phe Glu Ile Asp Gly Val Ile Tyr Phe Phe Gly Val Asp Gly
                405                 410                 415

Val Lys Ala Pro
            420


<210> SEQ ID NO 84
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr His Asn Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175
```

```
Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255

Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320

Leu Glu
```

<210> SEQ ID NO 85
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85

```
atgggcagca gccatcatca tcatcatcac gaaaacctgt acttccaggg cctgtccgaa     60

gacaatggag tggacttcaa caaaaatacc gctctagaca aaaactatct gctgaacaat    120

aaaatcccga gcaacaacgt ggaagaagca ggctcgaaaa attacgttca ttatataatt    180

caattacagg gcaacgatat tagctacgaa gcgacgtgca acctgttttc taaaaatcca    240

aaaaacagta tcatcattca aaggaatatg aacgagtcgg cgaaatcata ctttctgagt    300

gatgacggcg aaagcatcct ggaactgaat aaatatcgaa ttcctgaacg tctgaaaaac    360

aaggaaaaag tgaaagtgac attcatcggt gcgggtaaag atgaattcaa cacttcagaa    420

tttgcccgcc tgtcggtgga tagcctttca aatgagatta gcagcttttt agacacaatt    480

aaactggata ttagcccgaa aaacgtggaa gtgaacctgt tgggcgcgaa tatgttcagt    540

tatgatttta acgtcgaaga aacctaccca ggaaagctac tcctgtcgat catggacaaa    600

atcacctcaa ccctgcctga cgtgaataaa aactccatca ccattggcgc gaatcagtat    660

gaggtgcgta tcaacagtga gggccgcaaa gaactgctag cacacagcgg taaatggatt    720

aataaagaag aagcc                                                     735
```

<210> SEQ ID NO 86
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Met Gly Ser Ser His His His His His His Glu Asn Leu Tyr Phe Gln
```

```
1               5                   10                  15

Gly Leu Ser Glu Asp Asn Gly Val Asp Phe Asn Lys Asn Thr Ala Leu
            20                  25                  30

Asp Lys Asn Tyr Leu Leu Asn Asn Lys Ile Pro Ser Asn Asn Val Glu
        35                  40                  45

Glu Ala Gly Ser Lys Asn Tyr Val His Tyr Ile Ile Gln Leu Gln Gly
    50                  55                  60

Asn Asp Ile Ser Tyr Glu Ala Thr Cys Asn Leu Phe Ser Lys Asn Pro
65                  70                  75                  80

Lys Asn Ser Ile Ile Ile Gln Arg Asn Met Asn Glu Ser Ala Lys Ser
                85                  90                  95

Tyr Phe Leu Ser Asp Asp Gly Glu Ser Ile Leu Glu Leu Asn Lys Tyr
            100                 105                 110

Arg Ile Pro Glu Arg Leu Lys Asn Lys Glu Lys Val Lys Val Thr Phe
        115                 120                 125

Ile Gly Ala Gly Lys Asp Glu Phe Asn Thr Ser Glu Phe Ala Arg Leu
    130                 135                 140

Ser Val Asp Ser Leu Ser Asn Glu Ile Ser Ser Phe Leu Asp Thr Ile
145                 150                 155                 160

Lys Leu Asp Ile Ser Pro Lys Asn Val Glu Val Asn Leu Leu Gly Ala
                165                 170                 175

Asn Met Phe Ser Tyr Asp Phe Asn Val Glu Glu Thr Tyr Pro Gly Lys
            180                 185                 190

Leu Leu Leu Ser Ile Met Asp Lys Ile Thr Ser Thr Leu Pro Asp Val
        195                 200                 205

Asn Lys Asn Ser Ile Thr Ile Gly Ala Asn Gln Tyr Glu Val Arg Ile
    210                 215                 220

Asn Ser Glu Gly Arg Lys Glu Leu Leu Ala His Ser Gly Lys Trp Ile
225                 230                 235                 240

Asn Lys Glu Glu Ala
                245


<210> SEQ ID NO 87
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87

atgggcagca gccatcatca tcatcatcac gaaaacctgt acttccaggg cgaagatata     60

aatgtattta tgaaagatga tattaatact ataacaggaa aatactatgt tgataataat    120

actgataaaa gtatagattt ctctatttct ttagttagta aaaatcaagt aaaagtaaat    180

ggattatatt taaatgaatc cgtatactca tcttaccttg attttgtgaa aaattcagat    240

ggacaccata atacttctaa ttttatgaat ttatttttgg acaatataag tttctggaaa    300

ttgtttgggt ttgaaaatat aaattttgta atcgataaat actttaccct tgttggtaaa    360

actaatcttg gatatgtaga atttatttgt gacaataata aaaatataga tatatatttt    420

ggtgaatgga aaacatcgtc atctaaaagc actatattta gcggaaatgg tagaaatgtt    480

gtagtagagc ctatatataa tcctgatacg ggtgaagata tatctacttc actagatttt    540

tcctatgaac ctctctatgg aatagatata tatatcaata aagtattgat agcacctgat    600

ttatatacaa gtttaataaa tattaatacc aattattatt caaatgagta ctaccctgag    660
```

```
attatagttc ttaacccaaa tacattccac aaaaaagtaa atataaattt agatagttct    720

tcttttgagt ataaatggtc tacagaagga agtgacttta ttttagttag atacttagaa    780

gaaagtaata aaaaaatatt acaaaaaata agaatcaaag gtatcttatc taatactcaa    840

tcattt                                                                846
```

```
<210> SEQ ID NO 88
<211> LENGTH: 282
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Met Gly Ser Ser His His His His His His Glu Asn Leu Tyr Phe Gln
1               5                   10                  15

Gly Glu Asp Ile Asn Val Phe Met Lys Asp Asp Ile Asn Thr Ile Thr
            20                  25                  30

Gly Lys Tyr Tyr Val Asp Asn Asn Thr Asp Lys Ser Ile Asp Phe Ser
        35                  40                  45

Ile Ser Leu Val Ser Lys Asn Gln Val Lys Val Asn Gly Leu Tyr Leu
    50                  55                  60

Asn Glu Ser Val Tyr Ser Ser Tyr Leu Asp Phe Val Lys Asn Ser Asp
65                  70                  75                  80

Gly His His Asn Thr Ser Asn Phe Met Asn Leu Phe Leu Asp Asn Ile
                85                  90                  95

Ser Phe Trp Lys Leu Phe Gly Phe Glu Asn Ile Asn Phe Val Ile Asp
            100                 105                 110

Lys Tyr Phe Thr Leu Val Gly Lys Thr Asn Leu Gly Tyr Val Glu Phe
        115                 120                 125

Ile Cys Asp Asn Asn Lys Asn Ile Asp Ile Tyr Phe Gly Glu Trp Lys
    130                 135                 140

Thr Ser Ser Ser Lys Ser Thr Ile Phe Ser Gly Asn Gly Arg Asn Val
145                 150                 155                 160

Val Val Glu Pro Ile Tyr Asn Pro Asp Thr Gly Glu Asp Ile Ser Thr
                165                 170                 175

Ser Leu Asp Phe Ser Tyr Glu Pro Leu Tyr Gly Ile Asp Arg Tyr Ile
            180                 185                 190

Asn Lys Val Leu Ile Ala Pro Asp Leu Tyr Thr Ser Leu Ile Asn Ile
        195                 200                 205

Asn Thr Asn Tyr Tyr Ser Asn Glu Tyr Tyr Pro Glu Ile Ile Val Leu
    210                 215                 220

Asn Pro Asn Thr Phe His Lys Lys Val Asn Ile Asn Leu Asp Ser Ser
225                 230                 235                 240

Ser Phe Glu Tyr Lys Trp Ser Thr Glu Gly Ser Asp Phe Ile Leu Val
                245                 250                 255

Arg Tyr Leu Glu Glu Ser Asn Lys Lys Ile Leu Gln Lys Ile Arg Ile
            260                 265                 270

Lys Gly Ile Leu Ser Asn Thr Gln Ser Phe
        275                 280


<210> SEQ ID NO 89
<211> LENGTH: 723
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 89

```
atgggcagca gccatcatca tcatcatcac gaaaacctgt acttccaggg cggtgaagat     60

gacaaccttg atttctctca aaatattgtg gtcgacaagg agtatctgct ggaaaaaatt    120

tccagcttag cgcgttcgag cgagcgcggc tatattcact acatcgttca actgcagggc    180

aacaaaatca gttatgaagc ggcgtgcaac ctgtttgcga agaccccgta tgacagtgtg    240

ctatttcaaa aaaacattga agatagcgag atcgcgtact attacaatcc tggcgatggt    300

gaaattcagg aaattgacaa gtataaaatc ccgtcgatta tctctgaccg tccaaagatc    360

aaactgacgt ttatcggtgc gggtaaagat gaattcaaca ccgatatttt tgcgggtttt    420

gacgtggata gcctgtcaac ggaaattgaa gcggcgattg atttagcaaa agaggacatc    480

tccccgaaga gcattgaaat taatctgctg ggcgcgaaca tgttttcata cagcataaac    540

gtggaggaga cctatcctgg taaactgctg ttgaaagtca aagataaaat tagcgaatta    600

atgccgtcta ttagccaaga ctccatcatt gtgtcggcga atcagtacga agttcgcatt    660

aacagtgaag gccgtcgcga gctgctagat cattctggtg aatggattaa taaagaagaa    720

agt                                                                  723
```

<210> SEQ ID NO 90
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

```
Met Gly Ser Ser His His His His His His Glu Asn Leu Tyr Phe Gln
1               5                   10                  15

Gly Gly Glu Asp Asp Asn Leu Asp Phe Ser Gln Asn Ile Val Val Asp
            20                  25                  30

Lys Glu Tyr Leu Leu Glu Lys Ile Ser Ser Leu Ala Arg Ser Ser Glu
        35                  40                  45

Arg Gly Tyr Ile His Tyr Ile Val Gln Leu Gln Gly Asn Lys Ile Ser
    50                  55                  60

Tyr Glu Ala Ala Cys Asn Leu Phe Ala Lys Thr Pro Tyr Asp Ser Val
65                  70                  75                  80

Leu Phe Gln Lys Asn Ile Glu Asp Ser Glu Ile Ala Tyr Tyr Tyr Asn
                85                  90                  95

Pro Gly Asp Gly Glu Ile Gln Glu Ile Asp Lys Tyr Lys Ile Pro Ser
            100                 105                 110

Ile Ile Ser Asp Arg Pro Lys Ile Lys Leu Thr Phe Ile Gly Ala Gly
        115                 120                 125

Lys Asp Glu Phe Asn Thr Asp Ile Phe Ala Gly Phe Asp Val Asp Ser
    130                 135                 140

Leu Ser Thr Glu Ile Glu Ala Ala Ile Asp Leu Ala Lys Glu Asp Ile
145                 150                 155                 160

Ser Pro Lys Ser Ile Glu Ile Asn Leu Leu Gly Ala Asn Met Phe Ser
                165                 170                 175

Tyr Ser Ile Asn Val Glu Glu Thr Tyr Pro Gly Lys Leu Leu Leu Lys
            180                 185                 190
```

```
Val Lys Asp Lys Ile Ser Glu Leu Met Pro Ser Ile Ser Gln Asp Ser
        195                 200                 205

Ile Ile Val Ser Ala Asn Gln Tyr Glu Val Arg Ile Asn Ser Glu Gly
    210                 215                 220

Arg Arg Glu Leu Leu Asp His Ser Gly Glu Trp Ile Asn Lys Glu Glu
225                 230                 235                 240

Ser


<210> SEQ ID NO 91
<211> LENGTH: 2351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

atgggcagca gccatcatca tcatcatcac gaaaacctgt acttccaggg cagtctggtt     60

aaccgtaaac aactggaaaa aatggcgaat gtgcgcttta gaacccagga agatgaatat    120

gttgcgattc tagatgcact ggaagaatac cataacatgt cagagaatac cgtggtagaa    180

aaatatctga aactgaaaga tattaactct ctgacggata tctatattga cacgtacaaa    240

aaaagcggtc gtaataaagc tctgaaaaaa tttaaggaat atctcgttac ggaagtgctg    300

gagctcaaga acaataacct gaccccggtt gagaaaaatc tgcatttcgt ttggatcggc    360

ggtcagatta acgacaccgc catcaattac attaaccagt ggaaagatgt gaatagcgat    420

tataacgtta atgtctttta tgactcgaac gcgtttctaa ttaacacgct aaaaaaaacc    480

gtggtggaaa gcgcgattaa tgatactctt gagagctttc gcgaaaacct gaacgaccca    540

cgtttcgact acaataaatt cttccgcaaa agaatggaaa ttatctatga taaacaaaaa    600

aacttcatta actactataa agcacaacgt gaagaaaatc cggaactgat tatcgacgat    660

atcgtgaaga cgtacttgag caacgagtat agcaaggaga ttgatgaact taatacatac    720

atcgaagaat cactgaacaa aatcacgcaa aatagtggca acgacgttcg caactttgag    780

gaatttaaaa atggcgagag cttcaactta tatgaacagg agctagtgga acgatggaac    840

ctggccgcag cctccgcgat tctggcgatt tctgcgctga aagaaatcgg tggtatggcg    900

ctggcggtcg cgatgctgcc gggcattcag ccggacctgt ttgagtccat tgagaaacct    960

agtagcgtga cggtagactt ctgggaaatg acgaagttag aagcaattat gaaatacaaa   1020

gaatatattc cggaatacac aagcgaacac tttgacatgc tggacgagga agttcagtcg   1080

agctttgaat ctgtcctcgc cagcaagagc gataaaagcg aaattttcag cagcctgggt   1140

gatatggagg cgagcccgct cgaagttaaa atcgcgttta attcgaaggg tatcattaac   1200

caaggactca tctccgtaaa agacagctat tgttcaaatc tgattgtgaa acagatagag   1260

aaccgctata aaattctaaa taacagtctg aatccggcaa tctcagagga caacgatttc   1320

aataccacta caaacacatt tatcgatagt attatggccg aagcaaatgc ggacaacggt   1380

cgttttatga tggaactcgg taagtacctg cgcgtcggtt tcttcccgga tgttaaaacc   1440

accatcaact tatcgggacc agaagcgtat gctgcggcct accaggatct gctgatgttt   1500

aaagaaggaa gcatgaatat acatctaatt gaagcagacc tgcgtaactt cgagatatct   1560

aaaaccaaca tctcccaaag caccgaacag gaaatggcct cactgtggag ctttgacgat   1620

gcgcgcgcaa aagcccagtt tgaagaatat aaacgaaatt actttgaagg tagcttgggt   1680

gaagatgaca accttgattt ctctcaaaat attgtggtcg acaaggagta tctgctggaa   1740
```

aaaatttcca gcttagcgcg ttcgagcgag cgcggctata ttcactacat cgttcaactg 1800
cagggcaaca aaatcagtta tgaagcggcg tgcaacctgt ttgcgaagac cccgtatgac 1860
agtgtgctat ttcaaaaaaa cattgaagat agcgagatcg cgtactatta caatcctggc 1920
gatggtgaaa ttcaggaaat tgacaagtat aaaatcccgt cgattatctc tgaccgtcca 1980
aagatcaaac tgacgtttat cggtgcgggt aaagatgaat tcaacaccga tatttttgcg 2040
ggttttgacg tggatagcct gtcaacggaa attgaagcgg cgattgattt agcaaaagag 2100
gacatctccc cgaagagcat tgaaattaat ctgctgggcg cgaacatgtt ttcatacagc 2160
ataaacgtgg aggagaccta tcctggtaaa ctgctgttga aagtcaaaga taaaattagc 2220
gaattaatgc cgtctattag ccaagactcc atcattgtgt cggcgaatca gtacgaagtt 2280
cgcattaaca gtgaaggccg tcgcgagctg ctagatcatt ctggtgaatg gattaataaa 2340
gaagaaagtg g 2351

<210> SEQ ID NO 92
<211> LENGTH: 783
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 92

Met Gly Ser Ser His His His His His His Glu Asn Leu Tyr Phe Gln
1 5 10 15

Gly Ser Leu Val Asn Arg Lys Gln Leu Glu Lys Met Ala Asn Val Arg
20 25 30

Phe Arg Thr Gln Glu Asp Glu Tyr Val Ala Ile Leu Asp Ala Leu Glu
35 40 45

Glu Tyr His Asn Met Ser Glu Asn Thr Val Val Glu Lys Tyr Leu Lys
50 55 60

Leu Lys Asp Ile Asn Ser Leu Thr Asp Ile Tyr Ile Asp Thr Tyr Lys
65 70 75 80

Lys Ser Gly Arg Asn Lys Ala Leu Lys Lys Phe Lys Glu Tyr Leu Val
85 90 95

Thr Glu Val Leu Glu Leu Lys Asn Asn Asn Leu Thr Pro Val Glu Lys
100 105 110

Asn Leu His Phe Val Trp Ile Gly Gly Gln Ile Asn Asp Thr Ala Ile
115 120 125

Asn Tyr Ile Asn Gln Trp Lys Asp Val Asn Ser Asp Tyr Asn Val Asn
130 135 140

Val Phe Tyr Asp Ser Asn Ala Phe Leu Ile Asn Thr Leu Lys Lys Thr
145 150 155 160

Val Val Glu Ser Ala Ile Asn Asp Thr Leu Glu Ser Phe Arg Glu Asn
165 170 175

Leu Asn Asp Pro Arg Phe Asp Tyr Asn Lys Phe Phe Arg Lys Arg Met
180 185 190

Glu Ile Ile Tyr Asp Lys Gln Lys Asn Phe Ile Asn Tyr Tyr Lys Ala
195 200 205

Gln Arg Glu Glu Asn Pro Glu Leu Ile Ile Asp Asp Ile Val Lys Thr
210 215 220

Tyr Leu Ser Asn Glu Tyr Ser Lys Glu Ile Asp Glu Leu Asn Thr Tyr
225 230 235 240

```
Ile Glu Glu Ser Leu Asn Lys Ile Thr Gln Asn Ser Gly Asn Asp Val
                245                 250                 255

Arg Asn Phe Glu Glu Phe Lys Asn Gly Glu Ser Phe Asn Leu Tyr Glu
            260                 265                 270

Gln Glu Leu Val Glu Arg Trp Asn Leu Ala Ala Ala Ser Ala Ile Leu
        275                 280                 285

Ala Ile Ser Ala Leu Lys Glu Ile Gly Gly Met Ala Leu Ala Val Ala
    290                 295                 300

Met Leu Pro Gly Ile Gln Pro Asp Leu Phe Glu Ser Ile Glu Lys Pro
305                 310                 315                 320

Ser Ser Val Thr Val Asp Phe Trp Glu Met Thr Lys Leu Glu Ala Ile
                325                 330                 335

Met Lys Tyr Lys Glu Tyr Ile Pro Glu Tyr Thr Ser Glu His Phe Asp
            340                 345                 350

Met Leu Asp Glu Glu Val Gln Ser Ser Phe Glu Ser Val Leu Ala Ser
        355                 360                 365

Lys Ser Asp Lys Ser Glu Ile Phe Ser Ser Leu Gly Asp Met Glu Ala
    370                 375                 380

Ser Pro Leu Glu Val Lys Ile Ala Phe Asn Ser Lys Gly Ile Ile Asn
385                 390                 395                 400

Gln Gly Leu Ile Ser Val Lys Asp Ser Tyr Cys Ser Asn Leu Ile Val
                405                 410                 415

Lys Gln Ile Glu Asn Arg Tyr Lys Ile Leu Asn Asn Ser Leu Asn Pro
            420                 425                 430

Ala Ile Ser Glu Asp Asn Asp Phe Asn Thr Thr Thr Asn Thr Phe Ile
        435                 440                 445

Asp Ser Ile Met Ala Glu Ala Asn Ala Asp Asn Gly Arg Phe Met Met
    450                 455                 460

Glu Leu Gly Lys Tyr Leu Arg Val Gly Phe Phe Pro Asp Val Lys Thr
465                 470                 475                 480

Thr Ile Asn Leu Ser Gly Pro Glu Ala Tyr Ala Ala Ala Tyr Gln Asp
                485                 490                 495

Leu Leu Met Phe Lys Glu Gly Ser Met Asn Ile His Leu Ile Glu Ala
            500                 505                 510

Asp Leu Arg Asn Phe Glu Ile Ser Lys Thr Asn Ile Ser Gln Ser Thr
        515                 520                 525

Glu Gln Glu Met Ala Ser Leu Trp Ser Phe Asp Asp Ala Arg Ala Lys
    530                 535                 540

Ala Gln Phe Glu Glu Tyr Lys Arg Asn Tyr Phe Glu Gly Ser Leu Gly
545                 550                 555                 560

Glu Asp Asp Asn Leu Asp Phe Ser Gln Asn Ile Val Val Asp Lys Glu
                565                 570                 575

Tyr Leu Leu Glu Lys Ile Ser Ser Leu Ala Arg Ser Ser Glu Arg Gly
            580                 585                 590

Tyr Ile His Tyr Ile Val Gln Leu Gln Gly Asn Lys Ile Ser Tyr Glu
        595                 600                 605

Ala Ala Cys Asn Leu Phe Ala Lys Thr Pro Tyr Asp Ser Val Leu Phe
    610                 615                 620

Gln Lys Asn Ile Glu Asp Ser Glu Ile Ala Tyr Tyr Tyr Asn Pro Gly
625                 630                 635                 640

Asp Gly Glu Ile Gln Glu Ile Asp Lys Tyr Lys Ile Pro Ser Ile Ile
                645                 650                 655

Ser Asp Arg Pro Lys Ile Lys Leu Thr Phe Ile Gly Ala Gly Lys Asp
```

```
            660                 665                 670

Glu Phe Asn Thr Asp Ile Phe Ala Gly Phe Asp Val Asp Ser Leu Ser
        675                 680                 685

Thr Glu Ile Glu Ala Ala Ile Asp Leu Ala Lys Glu Asp Ile Ser Pro
    690                 695                 700

Lys Ser Ile Glu Ile Asn Leu Leu Gly Ala Asn Met Phe Ser Tyr Ser
705                 710                 715                 720

Ile Asn Val Glu Glu Thr Tyr Pro Gly Lys Leu Leu Leu Lys Val Lys
                725                 730                 735

Asp Lys Ile Ser Glu Leu Met Pro Ser Ile Ser Gln Asp Ser Ile Ile
            740                 745                 750

Val Ser Ala Asn Gln Tyr Glu Val Arg Ile Asn Ser Glu Gly Arg Arg
        755                 760                 765

Glu Leu Leu Asp His Ser Gly Glu Trp Ile Asn Lys Glu Glu Ser
    770                 775                 780


<210> SEQ ID NO 93
<211> LENGTH: 1677
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

atgggcagca gccatcatca tcatcatcac gaaaacctgt acttccaggg cagtctggtt     60

aaccgtaaac aactggaaaa aatggcgaat gtgcgcttta gaacccagga agatgaatat    120

gttgcgattc tagatgcact ggaagaatac cataacatgt cagagaatac cgtggtagaa    180

aaatatctga aactgaaaga tattaactct ctgacggata tctatattga cacgtacaaa    240

aaaagcggtc gtaataaagc tctgaaaaaa tttaaggaat atctcgttac ggaagtgctg    300

gagctcaaga acaataacct gaccccggtt gagaaaaatc tgcatttcgt ttggatcggc    360

ggtcagatta acgacaccgc catcaattac attaaccagt ggaaagatgt gaatagcgat    420

tataacgtta atgtctttta tgactcgaac gcgtttctaa ttaacacgct aaaaaaaacc    480

gtggtggaaa gcgcgattaa tgatactctt gagagctttc gcgaaaacct gaacgaccca    540

cgtttcgact acaataaatt cttccgcaaa agaatggaaa ttatctatga taaacaaaaa    600

aacttcatta actactataa agcacaacgt gaagaaaatc cggaactgat tatcgacgat    660

atcgtgaaga cgtacttgag caacgagtat agcaaggaga ttgatgaact taatacatac    720

atcgaagaat cactgaacaa aatcacgcaa aatagtggca acgacgttcg caactttgag    780

gaatttaaaa atggcgagag cttcaactta tatgaacagg agctagtgga acgatggaac    840

ctggccgcag cctccgcgat tctggcgatt tctgcgctga aagaaatcgg tggtatggcg    900

ctggcggtcg cgatgctgcc gggcattcag ccggacctgt ttgagtccat tgagaaacct    960

agtagcgtga cggtagactt ctgggaaatg acgaagttag aagcaattat gaaatacaaa   1020

gaatatattc cggaatacac aagcgaacac tttgacatgc tggacgagga agttcagtcg   1080

agctttgaat ctgtcctcgc cagcaagagc gataaaagcg aaattttcag cagcctgggt   1140

gatatggagg cgagcccgct cgaagttaaa atcgcgttta attcgaaggg tatcattaac   1200

caaggactca tctccgtaaa agacagctat tgttcaaatc tgattgtgaa acagatagag   1260

aaccgctata aaattctaaa taacagtctg aatccggcaa tctcagagga caacgatttc   1320

aataccacta caaacacatt tatcgatagt attatggccg aagcaaatgc ggacaacggt   1380
```

```
cgttttatga tggaactcgg taagtacctg cgcgtcggtt tcttcccgga tgttaaaacc   1440

accatcaact tatcgggacc agaagcgtat gctgcggcct accaggatct gctgatgttt   1500

aaagaaggaa gcatgaatat acatctaatt gaagcagacc tgcgtaactt cgagatatct   1560

aaaaccaaca tctcccaaag caccgaacag gaaatggcct cactgtggag ctttgacgat   1620

gcgcgcgcaa aagcccagtt tgaagaatat aaacgaaatt actttgaagg tagcttg      1677


<210> SEQ ID NO 94
<211> LENGTH: 559
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Met Gly Ser Ser His His His His His His Glu Asn Leu Tyr Phe Gln
1               5                   10                  15

Gly Ser Leu Val Asn Arg Lys Gln Leu Glu Lys Met Ala Asn Val Arg
            20                  25                  30

Phe Arg Thr Gln Glu Asp Glu Tyr Val Ala Ile Leu Asp Ala Leu Glu
        35                  40                  45

Glu Tyr His Asn Met Ser Glu Asn Thr Val Val Glu Lys Tyr Leu Lys
    50                  55                  60

Leu Lys Asp Ile Asn Ser Leu Thr Asp Ile Tyr Ile Asp Thr Tyr Lys
65                  70                  75                  80

Lys Ser Gly Arg Asn Lys Ala Leu Lys Lys Phe Lys Glu Tyr Leu Val
                85                  90                  95

Thr Glu Val Leu Glu Leu Lys Asn Asn Asn Leu Thr Pro Val Glu Lys
            100                 105                 110

Asn Leu His Phe Val Trp Ile Gly Gly Gln Ile Asn Asp Thr Ala Ile
        115                 120                 125

Asn Tyr Ile Asn Gln Trp Lys Asp Val Asn Ser Asp Tyr Asn Val Asn
    130                 135                 140

Val Phe Tyr Asp Ser Asn Ala Phe Leu Ile Asn Thr Leu Lys Lys Thr
145                 150                 155                 160

Val Val Glu Ser Ala Ile Asn Asp Thr Leu Glu Ser Phe Arg Glu Asn
                165                 170                 175

Leu Asn Asp Pro Arg Phe Asp Tyr Asn Lys Phe Phe Arg Lys Arg Met
            180                 185                 190

Glu Ile Ile Tyr Asp Lys Gln Lys Asn Phe Ile Asn Tyr Tyr Lys Ala
        195                 200                 205

Gln Arg Glu Glu Asn Pro Glu Leu Ile Ile Asp Asp Ile Val Lys Thr
    210                 215                 220

Tyr Leu Ser Asn Glu Tyr Ser Lys Glu Ile Asp Glu Leu Asn Thr Tyr
225                 230                 235                 240

Ile Glu Glu Ser Leu Asn Lys Ile Thr Gln Asn Ser Gly Asn Asp Val
                245                 250                 255

Arg Asn Phe Glu Glu Phe Lys Asn Gly Glu Ser Phe Asn Leu Tyr Glu
            260                 265                 270

Gln Glu Leu Val Glu Arg Trp Asn Leu Ala Ala Ala Ser Ala Ile Leu
        275                 280                 285

Ala Ile Ser Ala Leu Lys Glu Ile Gly Gly Met Ala Leu Ala Val Ala
    290                 295                 300
```

```
Met Leu Pro Gly Ile Gln Pro Asp Leu Phe Glu Ser Ile Glu Lys Pro
305                 310                 315                 320

Ser Ser Val Thr Val Asp Phe Trp Glu Met Thr Lys Leu Glu Ala Ile
                325                 330                 335

Met Lys Tyr Lys Glu Tyr Ile Pro Glu Tyr Thr Ser Glu His Phe Asp
            340                 345                 350

Met Leu Asp Glu Glu Val Gln Ser Ser Phe Glu Ser Val Leu Ala Ser
        355                 360                 365

Lys Ser Asp Lys Ser Glu Ile Phe Ser Ser Leu Gly Asp Met Glu Ala
    370                 375                 380

Ser Pro Leu Glu Val Lys Ile Ala Phe Asn Ser Lys Gly Ile Ile Asn
385                 390                 395                 400

Gln Gly Leu Ile Ser Val Lys Asp Ser Tyr Cys Ser Asn Leu Ile Val
                405                 410                 415

Lys Gln Ile Glu Asn Arg Tyr Lys Ile Leu Asn Asn Ser Leu Asn Pro
            420                 425                 430

Ala Ile Ser Glu Asp Asn Asp Phe Asn Thr Thr Thr Asn Thr Phe Ile
        435                 440                 445

Asp Ser Ile Met Ala Glu Ala Asn Ala Asp Asn Gly Arg Phe Met Met
    450                 455                 460

Glu Leu Gly Lys Tyr Leu Arg Val Gly Phe Phe Pro Asp Val Lys Thr
465                 470                 475                 480

Thr Ile Asn Leu Ser Gly Pro Glu Ala Tyr Ala Ala Ala Tyr Gln Asp
                485                 490                 495

Leu Leu Met Phe Lys Glu Gly Ser Met Asn Ile His Leu Ile Glu Ala
            500                 505                 510

Asp Leu Arg Asn Phe Glu Ile Ser Lys Thr Asn Ile Ser Gln Ser Thr
        515                 520                 525

Glu Gln Glu Met Ala Ser Leu Trp Ser Phe Asp Asp Ala Arg Ala Lys
    530                 535                 540

Ala Gln Phe Glu Glu Tyr Lys Arg Asn Tyr Phe Glu Gly Ser Leu
545                 550                 555
```

<210> SEQ ID NO 95
<211> LENGTH: 1599
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
atgggcagca gccatcatca tcatcatcac gaaaacctgt acttccaggg cattaccggc      60

ttcgtaaccg tgggagacga taaatactac tttaacccga tcaatggtgg tgccgcaagc     120

atcggcgaga cgattatcga tgacaaaaac tattatttca accagagcgg cgtactgcaa     180

acgggtgtgt tttcgacgga ggacggcttc aaatactttg ctccggccaa tactctggat     240

gaaaacctcg aaggcgaagc gatcgatttt accggtaaac tgatcatcga cgaaaacatc     300

tattattttg acgataatta ccgtggcgca gtggaatgga aagaactgga tggtgagatg     360

cactatttct caccggaaac gggtaaagcc tttaaaggtc tcaaccagat tggtgactac     420

aaatactatt tcaattccga tggcgtcatg cagaaaggct ttgttagtat taacgataat     480

aaacactatt ttgacgattc tggtgtcatg aaagtgggtt acaccgaaat tgatggaaag     540

catttctact tcgcagaaaa cggcgaaatg cagattggtg tgtttaacac ggaagacggc     600
```

```
tttaaatact tcgcccacca taatgaagat ttaggcaacg aagagggtga agaaataagc    660

tattccggta ttctgaattt caacaataaa atctactact ttgatgacag ctttactgca    720

gtggttggct ggaaagatct ggaggacggt agcaagtatt atttcgatga agatacggcg    780

gaagcgtaca ttggtctaag cctgattaac gacggtcaat attactttaa tgatgatggc    840

atcatgcagg tcggttttgt aaccattaac gacaaagtat tctacttcag cgactctggc    900

atcattgaat ccggcgtgca gaacattgat gacaattatt tctatattga tgacaacggt    960

attgttcaga tcggtgtgtt tgataccagc gatggctaca aatatttcgc gccggccaat   1020

accgtgaacg acaatatcta cggccaagcg gtcgaatata gtggtctggt tcgcgtcggt   1080

gaagatgtgt actattttgg tgagacgtat actatcgaga ccggctggat ttacgatatg   1140

gaaaacgaat cggacaaata ttacttcaat ccggaaacca aaaaagcgtg caaaggtatc   1200

aacctgatcg atgatattaa atattatttt gacgagaagg gaattatgcg tacaggtttg   1260

attagcttcg aaaataacaa ttactacttt aacgagaatg gtgaaatgca gtttggttat   1320

attaacattg aagataagat gttctacttt ggtgaagatg gtgtaatgca aatcggcgtg   1380

ttcaatacgc cggacggctt taaatacttt gcgcatcaga acaccctaga tgagaatttt   1440

gagggcgaga gcattaacta taccggttgg ctggatttag acgaaaagcg ctactatttc   1500

acggatgaat atatcgcggc gaccggtagc gttatcatcg atggtgagga gtactatttt   1560

gaccctgata cggcacaact ggtaatcagc gaactcgag                           1599
```

```
<210> SEQ ID NO 96
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Met Gly Ser Ser His His His His His His Glu Asn Leu Tyr Phe Gln
1               5                   10                  15

Gly Ile Thr Gly Phe Val Thr Val Gly Asp Asp Lys Tyr Tyr Phe Asn
            20                  25                  30

Pro Ile Asn Gly Gly Ala Ala Ser Ile Gly Glu Thr Ile Ile Asp Asp
        35                  40                  45

Lys Asn Tyr Tyr Phe Asn Gln Ser Gly Val Leu Gln Thr Gly Val Phe
    50                  55                  60

Ser Thr Glu Asp Gly Phe Lys Tyr Phe Ala Pro Ala Asn Thr Leu Asp
65                  70                  75                  80

Glu Asn Leu Glu Gly Glu Ala Ile Asp Phe Thr Gly Lys Leu Ile Ile
                85                  90                  95

Asp Glu Asn Ile Tyr Tyr Phe Asp Asp Asn Tyr Arg Gly Ala Val Glu
            100                 105                 110

Trp Lys Glu Leu Asp Gly Glu Met His Tyr Phe Ser Pro Glu Thr Gly
        115                 120                 125

Lys Ala Phe Lys Gly Leu Asn Gln Ile Gly Asp Tyr Lys Tyr Tyr Phe
    130                 135                 140

Asn Ser Asp Gly Val Met Gln Lys Gly Phe Val Ser Ile Asn Asp Asn
145                 150                 155                 160

Lys His Tyr Phe Asp Asp Ser Gly Val Met Lys Val Gly Tyr Thr Glu
                165                 170                 175

Ile Asp Gly Lys His Phe Tyr Phe Ala Glu Asn Gly Glu Met Gln Ile
```

```
            180                 185                 190

Gly Val Phe Asn Thr Glu Asp Gly Phe Lys Tyr Phe Ala His His Asn
        195                 200                 205

Glu Asp Leu Gly Asn Glu Glu Gly Glu Glu Ile Ser Tyr Ser Gly Ile
    210                 215                 220

Leu Asn Phe Asn Asn Lys Ile Tyr Tyr Phe Asp Asp Ser Phe Thr Ala
225                 230                 235                 240

Val Val Gly Trp Lys Asp Leu Glu Asp Gly Ser Lys Tyr Tyr Phe Asp
                245                 250                 255

Glu Asp Thr Ala Glu Ala Tyr Ile Gly Leu Ser Leu Ile Asn Asp Gly
            260                 265                 270

Gln Tyr Tyr Phe Asn Asp Asp Gly Ile Met Gln Val Gly Phe Val Thr
        275                 280                 285

Ile Asn Asp Lys Val Phe Tyr Phe Ser Asp Ser Gly Ile Ile Glu Ser
    290                 295                 300

Gly Val Gln Asn Ile Asp Asp Asn Tyr Phe Tyr Ile Asp Asp Asn Gly
305                 310                 315                 320

Ile Val Gln Ile Gly Val Phe Asp Thr Ser Asp Gly Tyr Lys Tyr Phe
                325                 330                 335

Ala Pro Ala Asn Thr Val Asn Asp Asn Ile Tyr Gly Gln Ala Val Glu
            340                 345                 350

Tyr Ser Gly Leu Val Arg Val Gly Glu Asp Val Tyr Tyr Phe Gly Glu
        355                 360                 365

Thr Tyr Thr Ile Glu Thr Gly Trp Ile Tyr Asp Met Glu Asn Glu Ser
    370                 375                 380

Asp Lys Tyr Tyr Phe Asn Pro Glu Thr Lys Lys Ala Cys Lys Gly Ile
385                 390                 395                 400

Asn Leu Ile Asp Asp Ile Lys Tyr Tyr Phe Asp Glu Lys Gly Ile Met
                405                 410                 415

Arg Thr Gly Leu Ile Ser Phe Glu Asn Asn Asn Tyr Tyr Phe Asn Glu
            420                 425                 430

Asn Gly Glu Met Gln Phe Gly Tyr Ile Asn Ile Glu Asp Lys Met Phe
        435                 440                 445

Tyr Phe Gly Glu Asp Gly Val Met Gln Ile Gly Val Phe Asn Thr Pro
    450                 455                 460

Asp Gly Phe Lys Tyr Phe Ala His Gln Asn Thr Leu Asp Glu Asn Phe
465                 470                 475                 480

Glu Gly Glu Ser Ile Asn Tyr Thr Gly Trp Leu Asp Leu Asp Glu Lys
                485                 490                 495

Arg Tyr Tyr Phe Thr Asp Glu Tyr Ile Ala Ala Thr Gly Ser Val Ile
            500                 505                 510

Ile Asp Gly Glu Glu Tyr Tyr Phe Asp Pro Asp Thr Ala Gln Leu Val
        515                 520                 525

Ile Ser Glu Leu Glu
    530
```

<210> SEQ ID NO 97
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97

```
atgggcagca gccatcatca tcatcatcac gaaaacctgt acttccaggg cgttcagatc     60

ggtgtgtttg ataccagcga tggctacaaa tatttcgcgc cggccaatac cgtgaacgac    120

aatatctacg gccaagcggt cgaatatagt ggtctggttc gcgtcggtga agatgtgtac    180

tattttggtg agacgtatac tatcgagacc ggctggattt acgatatgga aaacgaatcg    240

gacaaatatt acttcaatcc ggaaaccaaa aaagcgtgca aaggtatcaa cctgatcgat    300

gatattaaat attattttga cgagaaggga attatgcgta caggtttgat tagcttcgaa    360

aataacaatt actactttaa cgagaatggt gaaatgcagt ttggttatat taacattgaa    420

gataagatgt tctactttgg tgaagatggt gtaatgcaaa tcggcgtgtt caatacgccg    480

gacggcttta aatactttgc gcatcagaac accctagatg agaattttga gggcgagagc    540

attaactata ccggttggct ggatttagac gaaaagcgct actatttcac ggatgaatat    600

atcgcggcga ccggtagcgt tatcatcgat ggtgaggagt actattttga ccctgatacg    660

gcacaactgg taatcagcga actcgag                                        687
```

```
<210> SEQ ID NO 98
<211> LENGTH: 229
<212> TYPE: PRT
<213> ORGANISM: Artificial Sequence
<220> FEATURE:
<223> OTHER INFORMATION: Description of Artificial Sequence: Synthetic
      polynucleotide

<400> SEQUENCE: 98

Met Gly Ser Ser His His His His His His Glu Asn Leu Tyr Phe Gln
1               5                   10                  15

Gly Val Gln Ile Gly Val Phe Asp Thr Ser Asp Gly Tyr Lys Tyr Phe
            20                  25                  30

Ala Pro Ala Asn Thr Val Asn Asp Asn Ile Tyr Gly Gln Ala Val Glu
        35                  40                  45

Tyr Ser Gly Leu Val Arg Val Gly Glu Asp Val Tyr Tyr Phe Gly Glu
    50                  55                  60

Thr Tyr Thr Ile Glu Thr Gly Trp Ile Tyr Asp Met Glu Asn Glu Ser
65                  70                  75                  80

Asp Lys Tyr Tyr Phe Asn Pro Glu Thr Lys Lys Ala Cys Lys Gly Ile
                85                  90                  95

Asn Leu Ile Asp Asp Ile Lys Tyr Tyr Phe Asp Glu Lys Gly Ile Met
            100                 105                 110

Arg Thr Gly Leu Ile Ser Phe Glu Asn Asn Asn Tyr Tyr Phe Asn Glu
        115                 120                 125

Asn Gly Glu Met Gln Phe Gly Tyr Ile Asn Ile Glu Asp Lys Met Phe
    130                 135                 140

Tyr Phe Gly Glu Asp Gly Val Met Gln Ile Gly Val Phe Asn Thr Pro
145                 150                 155                 160

Asp Gly Phe Lys Tyr Phe Ala His Gln Asn Thr Leu Asp Glu Asn Phe
                165                 170                 175

Glu Gly Glu Ser Ile Asn Tyr Thr Gly Trp Leu Asp Leu Asp Glu Lys
            180                 185                 190

Arg Tyr Tyr Phe Thr Asp Glu Tyr Ile Ala Ala Thr Gly Ser Val Ile
        195                 200                 205

Ile Asp Gly Glu Glu Tyr Tyr Phe Asp Pro Asp Thr Ala Gln Leu Val
    210                 215                 220

Ile Ser Glu Leu Glu
225
```

<210> SEQ ID NO 99
<211> LENGTH: 915
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99
atgggcagca gccatcatca tcatcatcac gaaaacctgt acttccaggg ctattctggt 60
atattaaatt tcaataataa aatttactat tttgatgatt catttacagc tgtagttgga 120
tggaaagatt tagaggatgg ttcaaagtat tattttgatg aagatacagc agaagcatat 180
ataggtttgt cattaataaa tgatggtcaa tattatttta atgatgatgg aattatgcaa 240
gttggatttg tcactataaa tgataaagtc ttctacttct ctgactctgg aattatagaa 300
tctggagtac aaaacataga tgacaattat ttctatatag atgataatgg tatagttcaa 360
attggtgtat ttgatacttc agatggatat aaatattttg cacctgctaa tactgtaaat 420
gataatattt acggacaagc agttgaatat agtggtttag ttagagttgg tgaagatgta 480
tattattttg gagaaacata tacaattgag actggatgga tatatgatat ggaaaatgaa 540
agtgataaat attatttcaa tccagaaact aaaaaagcat gcaaaggtat taatttaatt 600
gatgatataa aatattattt tgatgagaag ggcataatga gaacgggtct tatatcattt 660
gaaaataata attattactt taatgagaat ggtgaaatgc aatttggtta tataaatata 720
gaagataaga tgttctattt tggtgaagat ggtgtcatgc agattggagt atttaataca 780
ccagatggat ttaaatactt tgcacatcaa aatactttgg atgagaattt tgagggagaa 840
tcaataaact atactggttg gttagattta gatgaaaaga gatattattt tacagatgaa 900
tatattgcag caact 915

<210> SEQ ID NO 100
<211> LENGTH: 305
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Met Gly Ser Ser His His His His His His Glu Asn Leu Tyr Phe Gln
1 5 10 15

Gly Tyr Ser Gly Ile Leu Asn Phe Asn Asn Lys Ile Tyr Tyr Phe Asp
20 25 30

Asp Ser Phe Thr Ala Val Val Gly Trp Lys Asp Leu Glu Asp Gly Ser
35 40 45

Lys Tyr Tyr Phe Asp Glu Asp Thr Ala Glu Ala Tyr Ile Gly Leu Ser
50 55 60

Leu Ile Asn Asp Gly Gln Tyr Tyr Phe Asn Asp Asp Gly Ile Met Gln
65 70 75 80

Val Gly Phe Val Thr Ile Asn Asp Lys Val Phe Tyr Phe Ser Asp Ser
85 90 95

Gly Ile Ile Glu Ser Gly Val Gln Asn Ile Asp Asp Asn Tyr Phe Tyr
100 105 110

Ile Asp Asp Asn Gly Ile Val Gln Ile Gly Val Phe Asp Thr Ser Asp
115 120 125

-continued

```
Gly Tyr Lys Tyr Phe Ala Pro Ala Asn Thr Val Asn Asp Asn Ile Tyr
    130                 135                 140

Gly Gln Ala Val Glu Tyr Ser Gly Leu Val Arg Val Gly Glu Asp Val
145                 150                 155                 160

Tyr Tyr Phe Gly Glu Thr Tyr Thr Ile Glu Thr Gly Trp Ile Tyr Asp
                165                 170                 175

Met Glu Asn Glu Ser Asp Lys Tyr Tyr Phe Asn Pro Glu Thr Lys Lys
            180                 185                 190

Ala Cys Lys Gly Ile Asn Leu Ile Asp Asp Ile Lys Tyr Tyr Phe Asp
        195                 200                 205

Glu Lys Gly Ile Met Arg Thr Gly Leu Ile Ser Phe Glu Asn Asn Asn
    210                 215                 220

Tyr Tyr Phe Asn Glu Asn Gly Glu Met Gln Phe Gly Tyr Ile Asn Ile
225                 230                 235                 240

Glu Asp Lys Met Phe Tyr Phe Gly Glu Asp Gly Val Met Gln Ile Gly
                245                 250                 255

Val Phe Asn Thr Pro Asp Gly Phe Lys Tyr Phe Ala His Gln Asn Thr
            260                 265                 270

Leu Asp Glu Asn Phe Glu Gly Glu Ser Ile Asn Tyr Thr Gly Trp Leu
        275                 280                 285

Asp Leu Asp Glu Lys Arg Tyr Tyr Phe Thr Asp Glu Tyr Ile Ala Ala
    290                 295                 300

Thr
305


<210> SEQ ID NO 101
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr Asp Asn Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175
```

```
Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255

Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320
```

<210> SEQ ID NO 102
<211> LENGTH: 320
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 102

```
Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr His Ala Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175

Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
```

```
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255

Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320


<210> SEQ ID NO 103
<211> LENGTH: 320
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr Asp Ala Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175

Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255
```

-continued

```
Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320


<210> SEQ ID NO 104
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Ser Arg Ile Thr Arg
        35                  40


<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Any amino acid

<400> SEQUENCE: 105

Thr Glu Ser Thr Cys Arg Xaa Gln Ala
1               5


<210> SEQ ID NO 106
<211> LENGTH: 361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Ser Arg Ile Thr Arg Ala Ser Thr Gly Tyr Thr Ser
        35                  40                  45

Ile Asn Gly Lys His Phe Tyr Phe Asn Thr Asp Gly Ile Met Gln Ile
    50                  55                  60

Gly Val Phe Lys Gly Pro Asn Gly Phe Glu Tyr Phe Ala Pro Ala Asn
65                  70                  75                  80

Thr His Asn Asn Asn Ile Glu Gly Gln Ala Ile Leu Tyr Gln Asn Lys
                85                  90                  95
```

```
Phe Leu Thr Leu Asn Gly Lys Lys Tyr Tyr Phe Gly Ser Asp Ser Lys
            100                 105                 110

Ala Val Thr Gly Leu Arg Thr Ile Asp Gly Lys Lys Tyr Tyr Phe Asn
        115                 120                 125

Thr Asn Thr Ala Val Ala Val Thr Gly Trp Gln Thr Ile Asn Gly Lys
    130                 135                 140

Lys Tyr Tyr Phe Asn Thr Asn Thr Ser Ile Ala Ser Thr Gly Tyr Thr
145                 150                 155                 160

Ile Ile Ser Gly Lys His Phe Tyr Phe Asn Thr Asp Gly Ile Met Gln
                165                 170                 175

Ile Gly Val Phe Lys Gly Pro Asp Gly Phe Glu Tyr Phe Ala Pro Ala
            180                 185                 190

Asn Thr Asp Ala Asn Asn Ile Glu Gly Gln Ala Ile Arg Tyr Gln Asn
        195                 200                 205

Arg Phe Leu Tyr Leu His Asp Asn Ile Tyr Tyr Phe Gly Asn Asn Ser
    210                 215                 220

Lys Ala Ala Thr Gly Trp Val Thr Ile Asp Gly Asn Arg Tyr Tyr Phe
225                 230                 235                 240

Glu Pro Asn Thr Ala Met Gly Ala Asn Gly Tyr Lys Thr Ile Asp Asn
                245                 250                 255

Lys Asn Phe Tyr Phe Arg Asn Gly Leu Pro Gln Ile Gly Val Phe Lys
            260                 265                 270

Gly Ser Asn Gly Phe Glu Tyr Phe Ala Pro Ala Asn Thr Asp Ala Asn
        275                 280                 285

Asn Ile Glu Gly Gln Ala Ile Arg Tyr Gln Asn Arg Phe Leu His Leu
    290                 295                 300

Leu Gly Lys Ile Tyr Tyr Phe Gly Asn Asn Ser Lys Ala Val Thr Gly
305                 310                 315                 320

Trp Gln Thr Ile Asn Gly Lys Val Tyr Tyr Phe Met Pro Asp Thr Ala
                325                 330                 335

Met Ala Ala Ala Gly Gly Leu Phe Glu Ile Asp Gly Val Ile Tyr Phe
            340                 345                 350

Phe Gly Val Asp Gly Val Lys Ala Pro
        355                 360


<210> SEQ ID NO 107
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (327)..(327)
<223> OTHER INFORMATION: Any amino acid

<400> SEQUENCE: 107

Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30

Glu Tyr Phe Ala Pro Ala Asn Thr His Asn Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
```

65 70 75 80

Gly Lys Lys Tyr Tyr Phe Asn Thr Asn Thr Ala Val Ala Val Thr Gly
85 90 95

Trp Gln Thr Ile Asn Gly Lys Lys Tyr Tyr Phe Asn Thr Asn Thr Ser
100 105 110

Ile Ala Ser Thr Gly Tyr Thr Ile Ile Ser Gly Lys His Phe Tyr Phe
115 120 125

Asn Thr Asp Gly Ile Met Gln Ile Gly Val Phe Lys Gly Pro Asp Gly
130 135 140

Phe Glu Tyr Phe Ala Pro Ala Asn Thr Asp Ala Asn Asn Ile Glu Gly
145 150 155 160

Gln Ala Ile Arg Tyr Gln Asn Arg Phe Leu Tyr Leu His Asp Asn Ile
165 170 175

Tyr Tyr Phe Gly Asn Asn Ser Lys Ala Ala Thr Gly Trp Val Thr Ile
180 185 190

Asp Gly Asn Arg Tyr Tyr Phe Glu Pro Asn Thr Ala Met Gly Ala Asn
195 200 205

Gly Tyr Lys Thr Ile Asp Asn Lys Asn Phe Tyr Phe Arg Asn Gly Leu
210 215 220

Pro Gln Ile Gly Val Phe Lys Gly Ser Asn Gly Phe Glu Tyr Phe Ala
225 230 235 240

Pro Ala Asn Thr Asp Ala Asn Asn Ile Glu Gly Gln Ala Ile Arg Tyr
245 250 255

Gln Asn Arg Phe Leu His Leu Leu Gly Lys Ile Tyr Tyr Phe Gly Asn
260 265 270

Asn Ser Lys Ala Val Thr Gly Trp Gln Thr Ile Asn Gly Lys Val Tyr
275 280 285

Tyr Phe Met Pro Asp Thr Ala Met Ala Ala Ala Gly Gly Leu Phe Glu
290 295 300

Ile Asp Gly Val Ile Tyr Phe Phe Gly Val Asp Gly Val Lys Ala Pro
305 310 315 320

Thr Glu Ser Thr Cys Arg Xaa Gln Ala
325

<210> SEQ ID NO 108
<211> LENGTH: 370
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (368)..(368)
<223> OTHER INFORMATION: Any amino acid

<400> SEQUENCE: 108

Met Arg Gly Ser His His His His His His Gly Met Ala Ser Met Thr
1 5 10 15

Gly Gly Gln Gln Met Gly Arg Asp Leu Tyr Asp Asp Asp Asp Lys Asp
20 25 30

Arg Trp Gly Ser Ser Arg Ile Thr Arg Ala Ser Thr Gly Tyr Thr Ser
35 40 45

Ile Asn Gly Lys His Phe Tyr Phe Asn Thr Asp Gly Ile Met Gln Ile
50 55 60

Gly Val Phe Lys Gly Pro Asn Gly Phe Glu Tyr Phe Ala Pro Ala Asn
65 70 75 80

```
Thr His Asn Asn Asn Ile Glu Gly Gln Ala Ile Leu Tyr Gln Asn Lys
                85                  90                  95

Phe Leu Thr Leu Asn Gly Lys Lys Tyr Tyr Phe Gly Ser Asp Ser Lys
            100                 105                 110

Ala Val Thr Gly Leu Arg Thr Ile Asp Gly Lys Lys Tyr Tyr Phe Asn
        115                 120                 125

Thr Asn Thr Ala Val Ala Val Thr Gly Trp Gln Thr Ile Asn Gly Lys
    130                 135                 140

Lys Tyr Tyr Phe Asn Thr Asn Thr Ser Ile Ala Ser Thr Gly Tyr Thr
145                 150                 155                 160

Ile Ile Ser Gly Lys His Phe Tyr Phe Asn Thr Asp Gly Ile Met Gln
                165                 170                 175

Ile Gly Val Phe Lys Gly Pro Asp Gly Phe Glu Tyr Phe Ala Pro Ala
            180                 185                 190

Asn Thr Asp Ala Asn Asn Ile Glu Gly Gln Ala Ile Arg Tyr Gln Asn
        195                 200                 205

Arg Phe Leu Tyr Leu His Asp Asn Ile Tyr Tyr Phe Gly Asn Asn Ser
    210                 215                 220

Lys Ala Ala Thr Gly Trp Val Thr Ile Asp Gly Asn Arg Tyr Tyr Phe
225                 230                 235                 240

Glu Pro Asn Thr Ala Met Gly Ala Asn Gly Tyr Lys Thr Ile Asp Asn
                245                 250                 255

Lys Asn Phe Tyr Phe Arg Asn Gly Leu Pro Gln Ile Gly Val Phe Lys
            260                 265                 270

Gly Ser Asn Gly Phe Glu Tyr Phe Ala Pro Ala Asn Thr Asp Ala Asn
        275                 280                 285

Asn Ile Glu Gly Gln Ala Ile Arg Tyr Gln Asn Arg Phe Leu His Leu
    290                 295                 300

Leu Gly Lys Ile Tyr Tyr Phe Gly Asn Asn Ser Lys Ala Val Thr Gly
305                 310                 315                 320

Trp Gln Thr Ile Asn Gly Lys Val Tyr Tyr Phe Met Pro Asp Thr Ala
                325                 330                 335

Met Ala Ala Ala Gly Gly Leu Phe Glu Ile Asp Gly Val Ile Tyr Phe
            340                 345                 350

Phe Gly Val Asp Gly Val Lys Ala Pro Thr Glu Ser Thr Cys Arg Xaa
        355                 360                 365

Gln Ala
    370
```

<210> SEQ ID NO 109
<211> LENGTH: 361
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Arg Trp Gly Ser Ser Arg Ile Thr Arg Ala Ser Thr Gly Tyr Thr Ser
        35                  40                  45

Ile Asn Gly Lys His Phe Tyr Phe Asn Thr Asp Gly Ile Met Gln Ile
```

```
    50                  55                  60

Gly Val Phe Lys Gly Pro Asn Gly Phe Glu Tyr Phe Ala Pro Ala Asn
65                  70                  75                  80

Thr Asp Ala Asn Asn Ile Glu Gly Gln Ala Ile Leu Tyr Gln Asn Lys
                85                  90                  95

Phe Leu Thr Leu Asn Gly Lys Lys Tyr Tyr Phe Gly Ser Asp Ser Lys
            100                 105                 110

Ala Val Thr Gly Leu Arg Thr Ile Asp Gly Lys Lys Tyr Tyr Phe Asn
        115                 120                 125

Thr Asn Thr Ala Val Ala Val Thr Gly Trp Gln Thr Ile Asn Gly Lys
    130                 135                 140

Lys Tyr Tyr Phe Asn Thr Asn Thr Ser Ile Ala Ser Thr Gly Tyr Thr
145                 150                 155                 160

Ile Ile Ser Gly Lys His Phe Tyr Phe Asn Thr Asp Gly Ile Met Gln
                165                 170                 175

Ile Gly Val Phe Lys Gly Pro Asp Gly Phe Glu Tyr Phe Ala Pro Ala
            180                 185                 190

Asn Thr Asp Ala Asn Asn Ile Glu Gly Gln Ala Ile Arg Tyr Gln Asn
        195                 200                 205

Arg Phe Leu Tyr Leu His Asp Asn Ile Tyr Tyr Phe Gly Asn Asn Ser
    210                 215                 220

Lys Ala Ala Thr Gly Trp Val Thr Ile Asp Gly Asn Arg Tyr Tyr Phe
225                 230                 235                 240

Glu Pro Asn Thr Ala Met Gly Ala Asn Gly Tyr Lys Thr Ile Asp Asn
                245                 250                 255

Lys Asn Phe Tyr Phe Arg Asn Gly Leu Pro Gln Ile Gly Val Phe Lys
            260                 265                 270

Gly Ser Asn Gly Phe Glu Tyr Phe Ala Pro Ala Asn Thr Asp Ala Asn
        275                 280                 285

Asn Ile Glu Gly Gln Ala Ile Arg Tyr Gln Asn Arg Phe Leu His Leu
    290                 295                 300

Leu Gly Lys Ile Tyr Tyr Phe Gly Asn Asn Ser Lys Ala Val Thr Gly
305                 310                 315                 320

Trp Gln Thr Ile Asn Gly Lys Val Tyr Tyr Phe Met Pro Asp Thr Ala
                325                 330                 335

Met Ala Ala Ala Gly Gly Leu Phe Glu Ile Asp Gly Val Ile Tyr Phe
            340                 345                 350

Phe Gly Val Asp Gly Val Lys Ala Pro
        355                 360
```

<210> SEQ ID NO 110
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (327)..(327)
<223> OTHER INFORMATION: Any amino acid

<400> SEQUENCE: 110

```
Ala Ser Thr Gly Tyr Thr Ser Ile Asn Gly Lys His Phe Tyr Phe Asn
1               5                   10                  15

Thr Asp Gly Ile Met Gln Ile Gly Val Phe Lys Gly Pro Asn Gly Phe
            20                  25                  30
```

```
Glu Tyr Phe Ala Pro Ala Asn Thr Asp Ala Asn Asn Ile Glu Gly Gln
        35                  40                  45

Ala Ile Leu Tyr Gln Asn Lys Phe Leu Thr Leu Asn Gly Lys Lys Tyr
    50                  55                  60

Tyr Phe Gly Ser Asp Ser Lys Ala Val Thr Gly Leu Arg Thr Ile Asp
65                  70                  75                  80

Gly Lys Lys Tyr Tyr Phe Asn Thr Asn Thr Ala Val Ala Val Thr Gly
                85                  90                  95

Trp Gln Thr Ile Asn Gly Lys Lys Tyr Tyr Phe Asn Thr Asn Thr Ser
            100                 105                 110

Ile Ala Ser Thr Gly Tyr Thr Ile Ile Ser Gly Lys His Phe Tyr Phe
        115                 120                 125

Asn Thr Asp Gly Ile Met Gln Ile Gly Val Phe Lys Gly Pro Asp Gly
    130                 135                 140

Phe Glu Tyr Phe Ala Pro Ala Asn Thr Asp Ala Asn Asn Ile Glu Gly
145                 150                 155                 160

Gln Ala Ile Arg Tyr Gln Asn Arg Phe Leu Tyr Leu His Asp Asn Ile
                165                 170                 175

Tyr Tyr Phe Gly Asn Asn Ser Lys Ala Ala Thr Gly Trp Val Thr Ile
            180                 185                 190

Asp Gly Asn Arg Tyr Tyr Phe Glu Pro Asn Thr Ala Met Gly Ala Asn
        195                 200                 205

Gly Tyr Lys Thr Ile Asp Asn Lys Asn Phe Tyr Phe Arg Asn Gly Leu
    210                 215                 220

Pro Gln Ile Gly Val Phe Lys Gly Ser Asn Gly Phe Glu Tyr Phe Ala
225                 230                 235                 240

Pro Ala Asn Thr Asp Ala Asn Asn Ile Glu Gly Gln Ala Ile Arg Tyr
                245                 250                 255

Gln Asn Arg Phe Leu His Leu Leu Gly Lys Ile Tyr Tyr Phe Gly Asn
            260                 265                 270

Asn Ser Lys Ala Val Thr Gly Trp Gln Thr Ile Asn Gly Lys Val Tyr
        275                 280                 285

Tyr Phe Met Pro Asp Thr Ala Met Ala Ala Ala Gly Gly Leu Phe Glu
    290                 295                 300

Ile Asp Gly Val Ile Tyr Phe Phe Gly Val Asp Gly Val Lys Ala Pro
305                 310                 315                 320

Thr Glu Ser Thr Cys Arg Xaa Gln Ala
                325
```

<210> SEQ ID NO 111
<211> LENGTH: 370
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (368)..(368)
<223> OTHER INFORMATION: Any amino acid

<400> SEQUENCE: 111

```
Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30
```

```
Arg Trp Gly Ser Ser Arg Ile Thr Arg Ala Ser Thr Gly Tyr Thr Ser
        35                  40                  45

Ile Asn Gly Lys His Phe Tyr Phe Asn Thr Asp Gly Ile Met Gln Ile
    50                  55                  60

Gly Val Phe Lys Gly Pro Asn Gly Phe Glu Tyr Phe Ala Pro Ala Asn
65                  70                  75                  80

Thr Asp Ala Asn Asn Ile Glu Gly Gln Ala Ile Leu Tyr Gln Asn Lys
                85                  90                  95

Phe Leu Thr Leu Asn Gly Lys Lys Tyr Tyr Phe Gly Ser Asp Ser Lys
            100                 105                 110

Ala Val Thr Gly Leu Arg Thr Ile Asp Gly Lys Lys Tyr Tyr Phe Asn
        115                 120                 125

Thr Asn Thr Ala Val Ala Val Thr Gly Trp Gln Thr Ile Asn Gly Lys
    130                 135                 140

Lys Tyr Tyr Phe Asn Thr Asn Thr Ser Ile Ala Ser Thr Gly Tyr Thr
145                 150                 155                 160

Ile Ile Ser Gly Lys His Phe Tyr Phe Asn Thr Asp Gly Ile Met Gln
                165                 170                 175

Ile Gly Val Phe Lys Gly Pro Asp Gly Phe Glu Tyr Phe Ala Pro Ala
            180                 185                 190

Asn Thr Asp Ala Asn Asn Ile Glu Gly Gln Ala Ile Arg Tyr Gln Asn
        195                 200                 205

Arg Phe Leu Tyr Leu His Asp Asn Ile Tyr Tyr Phe Gly Asn Asn Ser
    210                 215                 220

Lys Ala Ala Thr Gly Trp Val Thr Ile Asp Gly Asn Arg Tyr Tyr Phe
225                 230                 235                 240

Glu Pro Asn Thr Ala Met Gly Ala Asn Gly Tyr Lys Thr Ile Asp Asn
                245                 250                 255

Lys Asn Phe Tyr Phe Arg Asn Gly Leu Pro Gln Ile Gly Val Phe Lys
            260                 265                 270

Gly Ser Asn Gly Phe Glu Tyr Phe Ala Pro Ala Asn Thr Asp Ala Asn
        275                 280                 285

Asn Ile Glu Gly Gln Ala Ile Arg Tyr Gln Asn Arg Phe Leu His Leu
    290                 295                 300

Leu Gly Lys Ile Tyr Tyr Phe Gly Asn Asn Ser Lys Ala Val Thr Gly
305                 310                 315                 320

Trp Gln Thr Ile Asn Gly Lys Val Tyr Tyr Phe Met Pro Asp Thr Ala
                325                 330                 335

Met Ala Ala Ala Gly Gly Leu Phe Glu Ile Asp Gly Val Ile Tyr Phe
            340                 345                 350

Phe Gly Val Asp Gly Val Lys Ala Pro Thr Glu Ser Thr Cys Arg Xaa
        355                 360                 365

Gln Ala
    370
```

<210> SEQ ID NO 112
<211> LENGTH: 1113
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: modified_base
<222> LOCATION: (1102)..(1103)
<223> OTHER INFORMATION: a, c, t, g, unknown or other
<220> FEATURE:

-continued

```
<221> NAME/KEY: modified_base
<222> LOCATION: (1102)..(1103)
<223> OTHER INFORMATION: a, c, t, g, unknown or other

<400> SEQUENCE: 112

atgcggggtt ctcatcatca tcatcatcat ggtatggcta gcatgactgg tggacagcaa      60

atgggtcggg atctgtacga cgatgacgat aaggatcgat ggggatcctc tagaatcact     120

agagcctcaa ctggttatac aagtattaat ggtaaacatt tttattttaa tactgatggt     180

attatgcaga taggagtgtt taaaggacct aatggatttg aatactttgc acctgctaat     240

acggatgcta acaacataga aggtcaagct atactttacc aaaataaatt cttaactttg     300

aatggtaaaa aatattactt tggtagtgac tcaaaagcag ttaccggact gcgaactatt     360

gatggtaaaa aatattactt taatactaac actgctgttg cagttactgg atggcaaact     420

attaatggta aaaaatacta ctttaatact aacacttcta tagcttcaac tggttataca     480

attattagtg gtaaacattt ttattttaat actgatggta ttatgcagat aggagtgttt     540

aaaggacctg atggatttga atactttgca cctgctaata cagatgctaa caatatagaa     600

ggtcaagcta tacgttatca aaatagattc ctatatttac atgacaatat atattatttt     660

ggtaataatt caaaagcggc tactggttgg gtaactattg atggtaatag atattacttc     720

gagcctaata cagctatggg tgcgaatggt tataaaacta ttgataataa aaatttttac     780

tttagaaatg gtttacctca gataggagtg tttaaagggt ctaatggatt tgaatacttt     840

gcacctgcta atacggatgc taacaatata gaaggtcaag ctatacgtta tcaaaataga     900

ttcctacatt tacttggaaa aatatattac tttggtaata attcaaaagc agttactgga     960

tggcaaacta ttaatggtaa agtatattac tttatgcctg atactgctat ggctgcagct    1020

ggtggacttt tcgagattga tggtgttata tatttctttg gtgttgatgg agtaaaagcc    1080

cctacagagt cgacctgcag gnngcaagct tga                                 1113
```

CLOSTRIDIUM DIFFICILE TOXIN-BASED VACCINE

CROSS REFERENCE TO RELATED APPLICATIONS

This application is the U.S. National Phase of International Application No. PCT/IB2012/002955, filed Dec. 7, 2012 and published in English, which claims the benefit of GB1217321.7, filed Sep. 27, 2012 and GB1121149.7, filed Dec. 8, 2011. The applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 10, 2014, is named PAT054763-US-PCT_SL.txt and is 411,753 bytes in size.

TECHNICAL FIELD

This invention is in the field of toxin-based vaccines against *Clostridium difficile.*

BACKGROUND ART

*C. difficile* is a Gram-negative, spore forming anaerobic bacterium that can reside asymptomatically in the intestinal tract of humans. Depletion of other intestinal flora, for example by antibiotic and chemotherapeutic treatment, creates an ecological niche which allows *C. difficile* spores to germinate in the colon, resulting in serious intestinal disease [1]. Antibiotic treatment can therefore transform this normally harmless micro-organism into the causative agent of a spectrum of intestinal diseases, an outcome that is particularly prevalent in hospitalised patients.

*C. difficile* is the predominant pathogen of nosocomial intestinal infections [2, 3] and causes approximately 20% of the cases of antibiotic-associated diarrhoea, up to 75% of the cases of antibiotic-associated colitis, and nearly all cases of pseudomembranous colitis [4]. Host factors such as advancing age, pre-existing severe illness and weakened immune defences predispose individuals to symptomatic infection [1]. Such *C. difficile*-associated disease (CDAD) usually occurs in intensive care units, particularly affecting patients over 60 years of age.

Treatment of CDAD typically involves the cessation of the offending antibiotic, initiation of oral metronidazole or vancomycin therapy and fluid replacement. However, the emergence of antibiotic-resistant enteropathogens has led to concerns over the use of antibiotics to treat CDAD. Moreover, up to 20% of patients relapse within 1-2 weeks of completing a course of antibiotics and the risk of relapse increases markedly with each additional relapse [5,6]. It is also reported that over 50% of the relapse incidents are due to a re-infection with a different *C. difficile* strain, rather than recurrence of the primary infection [7]. Preventive measures are based on patient isolation, implementation of hand hygiene and contact precaution, which have had variable and often limited success.

There is at present, no effective vaccine against CDAD. It is an object of the invention to provide compositions which are effective in raising immune responses against *C. difficile* for use in the development of vaccines for preventing and/or treating *C. difficile* associated diseases.

DISCLOSURE OF THE INVENTION

The invention thus provides an immunogenic composition comprising a combination of *Clostridium difficile* antigens, said combination comprising:

a) a ToxB-GT antigen and a TcdA antigen; or b) a ToxA-GT antigen and a TcdB antigen.

Thus, the invention provides an immunogenic composition comprising a combination of *Clostridium difficile* antigens, said combination comprising a) a ToxB-GT antigen and a TcdA antigen; or b) a ToxA-GT antigen and a TcdB antigen. Preferably, the ToxB-GT antigen and/or the ToxA-GT antigen are detoxified.

In one embodiment, the ToxB-GT antigen is a polypeptide that comprises or consists of an amino acid sequence: (a) having 80% or more identity to SEQ ID NO:18 or SEQ ID NO: 60; and/or b) that is a fragment of at least 7 consecutive amino acids of SEQ ID NO:18 or SEQ ID NO: 60, or of a polypeptide having 80% or more identity to SEQ ID NO:18 or SEQ ID NO: 60 and that comprises an epitope of SEQ ID NO:18 or SEQ ID NO: 60; the ToxA-GT antigen is a polypeptide that comprises or consists of an amino acid sequence: (a) having 80% or more identity to SEQ ID NO:4 or SEQ ID NO: 56; and/or b) that is a fragment of at least 7 consecutive amino acids of SEQ ID NO:4 or SEQ ID NO: 56, or of a polypeptide having 80% or more identity to SEQ ID NO:18 or SEQ ID NO:56 and that comprises an epitope of SEQ ID NO:4 or SEQ ID NO:56; the TcdA antigen is a polypeptide that comprises or consists of an amino acid sequence: (a) having 80% or more identity to SEQ ID NO:1; and/or b) that is a fragment of at least 7 consecutive amino acids of SEQ ID NO:1, or of a polypeptide having 80% or more identity to SEQ ID NO:1 and that comprises an epitope of SEQ ID NO:1; and the TcdB antigen is a polypeptide that comprises or consists of an amino acid sequence: (a) having 80% or more identity to SEQ ID NO:2; and/or b) that is a fragment of at least 7 consecutive amino acids of SEQ ID NO:2, or of a polypeptide having 80% or more identity to SEQ ID NO:2 and that comprises an epitope of SEQ ID NO:2.

In one embodiment, the immunogenic composition comprises a ToxB-GT antigen and 1, 2, 3, 4, 5, 6, 7, 8, 9, 10, 11, 12, 13, 14, 15 or more TcdA antigens, optionally selected from (1) a ToxA-ED antigen (SEQ ID NO: 3), (2) a ToxA-GT antigen (SEQ ID NO: 4), (3) a ToxA-CP antigen (SEQ ID NO:5), (4) a ToxA-T antigen (SEQ ID NO: 6), (5) a ToxA-T4 antigen (SEQ ID NO: 7), (6) a ToxA-B antigen (SEQ ID NO: 8), (7) a ToxA-PTA2 antigen (SEQ ID NO: 9), (8) a ToxA-P5-7 antigen (SEQ ID NO: 10), (9) a ToxA-P5-6 antigen (SEQ ID NO: 11), (10) a ToxA-P9-10 antigen (SEQ ID NO: 12), (11) a ToxA-B2 antigen (SEQ ID NO: 13), (12) a ToxA-B3 antigen (SEQ ID NO: 14), (13) a ToxA-B5 antigen (SEQ ID NO: 15), (14) a ToxA-B6 antigen (SEQ ID NO: 16) or a full-length TcdA antigen (SEQ ID NO:1). The immunogenic composition optionally further comprises 1, 2, 3, 4, 5, 6, 7, 8 or more additional TcdB antigens, optionally selected from (1) a ToxB-ED antigen (SEQ ID NO: 17), (2) a ToxB-GT antigen (SEQ ID NO: 18), (3) a ToxB-CP antigen (SEQ ID NO:19) (4) a ToxB-T antigen (SEQ ID NO: 20), (5) a ToxB-B antigen (SEQ ID NO: 21), (6) a ToxB-B2 antigen (SEQ ID NO: 22) (7) ToxB-B7 (SEQ ID NO: 23) or (8) a full-length TcdB antigen (SEQ ID NO:2).

In one embodiment, the immunogenic composition comprises a ToxA-GT antigen and 1, 2, 3, 4, 5, 6, 7, 8, 9 or more TcdB antigens, optionally selected from (1) a ToxB-ED antigen (SEQ ID NO: 17), (2) a ToxB-GT antigen (SEQ ID NO: 18), (3) a ToxB-CP antigen (SEQ ID NO:19) (4) a ToxB-T antigen (SEQ ID NO: 20), (5) a ToxB-B antigen (SEQ ID NO: 21), (6) a ToxB-B2 antigen (SEQ ID NO: 22) (7) ToxB-B7 (SEQ ID NO: 23) or (8) a full-length TcdB antigen (SEQ ID NO:2). The immunogenic composition optionally further comprises 1, 2, 3, 4, 5, 6, 7, 8, 9, 10, 11, 12, 13, 14, 15 or more additional TcdA antigens, optionally selected from (1) a ToxA-ED antigen (SEQ ID NO: 3), (2) a ToxA-GT antigen (SEQ ID NO: 4), (3) a ToxA-CP antigen (SEQ ID NO:5), (4) a ToxA-T antigen (SEQ ID NO: 6), (5) a ToxA-T4 antigen (SEQ ID NO: 7), (6) a ToxA-B antigen (SEQ ID NO: 8), (7) a ToxA-PTA2 antigen (SEQ ID NO: 9), (8) a ToxA-P5-7 antigen (SEQ ID NO: 10), (9) a ToxA-P5-6 antigen (SEQ ID NO: 11), (10) a ToxA-P9-10 antigen (SEQ ID NO: 12), (11) a ToxA-B2 antigen (SEQ ID NO: 13), (12) a ToxA-B3 antigen (SEQ ID NO: 14), (13) a ToxA-B5 antigen (SEQ ID NO: 15), (14) a ToxA-B6 antigen (SEQ ID NO: 16) or a full-length TcdA antigen (SEQ ID NO:1).

In one embodiment, the immunogenic composition comprises i) a ToxA-GT antigen or a ToxB-GT antigen; and ii) at least one TcdA antigen selected from ToxA-B, ToxA-PTA2, ToxA-P5-7, ToxA-P5-6, ToxA-P9-10, ToxA-B2, ToxA-B3, ToxA-B5 and/or ToxA-B6; and at least one TcdB antigen selected from ToxB-B, ToxB-B2 antigen, and/or ToxA-B7.

In one embodiment, the immunogenic composition comprises i) a ToxA-GT antigen and a ToxB-GT antigen; and ii) at least one TcdA antigen selected from ToxA-B, ToxA-PTA2, ToxA-P5-7, ToxA-P5-6, ToxA-P9-10, ToxA-B2, ToxA-B3, ToxA-B5 and/or ToxA-B6; and at least one TcdB antigen selected from ToxB-B, ToxB-B2 antigen, and/or ToxA-B7.

In one embodiment, the immunogenic composition comprises a ToxB-GT antigen, a TcdA antigen and a further TcdB antigen, optionally wherein said composition comprises (a) ToxB-GT+ToxA-B2+ToxB-B, or (b) ToxB-GT+ToxB-B+ToxA-P5-6. In one embodiment, the composition comprises a ToxB-GT antigen, a ToxA-GT antigen, a further TcdA antigen and a further TcdB antigen, optionally wherein said combination comprises ToxB-GT+ToxA-GT+ToxA-B2+ToxB-B.

In one embodiment, at least two of the antigens in the composition are in the form of a hybrid polypeptide. In another embodiment, none of the antigens are in the form of a hybrid polypeptide.

In some embodiments, the immunogenic composition induces neutralisation titers against *C. difficile* toxin A and toxin B.

In some embodiments, the immunogenic composition comprises at least one further *C. difficile* antigen, optionally wherein said further *C. difficile* antigen is a saccharide antigen.

In some embodiments, the immunogenic composition is a vaccine composition. In some embodiments, the vaccine composition further comprises an adjuvant. In some embodiments, the vaccine composition is use as a pharmaceutical. In some embodiments, the vaccine composition is for use in raising an immune response in a mammal, preferably a human. In some embodiments, the vaccine composition is for use in treating or preventing *C. difficile* associated disease.

In one embodiment, the invention provides a method for raising an immune response in a mammal comprising the step of administering to the mammal an effective amount of the immunogenic composition or vaccine described herein.

All pathogenic strains of *C. difficile* express one or two large exo-toxins (TcdA and TcdB, also referred to herein as ToxA and ToxB, and Toxin A and Toxin B). TcdA and TcdB belong to the large clostridial cytotoxin (LCD) family and exhibit 49% amino acid identity. They are single-polypeptide chain, high molecular weight exo-toxins (308 and 270 kDa, respectively) which are organised into multi-domain structures [8,9]. The genes encoding TcdA and TcdB, tcdA and tcdB, are located in the 19.6 kb *C. difficile* pathogenicity locus [10]. Like other members of the LCD family, TcdA and TcdB are organised as modular domains with each domain performing a distinct function [11]. The domain structures of TcdA and TcdB are illustrated in FIG. 1.

An overview of the mechanism of action of TcdA/B is provided in reference 11. Briefly, the C-terminus of TcdA/B (denoted "B" in FIG. 1) is responsible for toxin binding to the surface of epithelial cells. The C-terminal region of both toxins is composed of residue repeats known as the clostridial repetitive oligopeptides or cell wall binding domains due to their homology to the repeats of *Streptococcus pneumoniae* LytA, and is responsible for cell surface recognition and endocytosis [12]. Recently, the crystal structure of a C-terminal fragment of TcdA has been solved, revealing a solenoid-like structure, which consists of 32 short repeats with 15-21 residues and seven long repeats with 30 residues (reference 13). The C-terminal repeat regions of TcdA and TcdB are similar and may be identified routinely.

Binding of TcdA/B to epithelial cells induces receptor-mediated endocytosis, facilitating entry into the cytoplasm. Once internalised, the toxins require an acidic endosome for transport to the cytosol. A decrease in endosomal pH is thought to induce a conformational change which results in exposure of the hydrophobic translocation domain (denoted "T" in FIG. 1) and insertion of the enzymatic N-terminus (comprising an glycosyl-transferase domain and a cysteine protease domain, denoted "GT" and "CP" in FIG. 1, respectively), allowing entry into the endosome via pore formation [13]. Recently, references 14 and 15 demonstrated that inositol hexakisphosphate from the host cell induces the autocatalytic cleavage of the N-terminal region at the cysteine protease ("CP") site, thus releasing the N-terminal glucosyltransferase ("GT") domain into the cytosol (the remainder of the toxin is thought to remain in the endosome). Upon cleavage, the GT domain is thought to be capable of transferring glucose residues from UDP-glucose to Rho-GTPases, thus inactivating cell signalling [16] Inhibition of Rho-GTPases causes a series of cascading effects, including dysregulation of actin cytoskeleton and tight junction integrity which collectively lead to increased membrane permeability and loss of barrier function [17], diarrhoea, inflammation, and an influx of neutrophils and other members of the innate immune response [18].

The TcdA and TcdB exo-toxins are thus the proteins primarily responsible for clinical symptoms caused by *C. difficile [*19, 20, 21] and have been the focus of attempts to develop vaccines to treat and prevent CDAD. Reference 19 found that antibodies against recombinant TcdA are sufficient to prevent diarrhoea if administered prior to challenge. Immune responses to TcdB may also play a role in disease expression and/or immunity, as highlighted by numerous reports of diarrhoea and pseudomembranous colitis associated with TcdA negative, TcdB positive strains of *C. difficile [*22, 23, 24, 25].

Pre-clinical studies using a mixture of formaldehyde-inactivated TcdA and TcdB have suggested that both TcdA and TcdB may be involved in the pathogenesis of *C.*

*difficile*-associated diarrhoea and in generating protective immunity [26]. TcdA and TcdB may be purified from cell cultures, but the inactivation processes represents a major limitation in the preparation of toxoid-based vaccines. Toxin inactivation is typically achieved by formaldehyde treatment, which cross-links amino acids in the toxin polypeptide. The problem with formaldehyde inactivation is that the toxins are potentially subjected to unknown chemical modification and/or partial inactivation. Indeed, formalin-inactivated molecules have been shown to have impaired binding capabilities and reduced immunogenicity [27]. There are also a number of safety issues regarding use of toxoids derived from *C. difficile* toxins purified from cell culture in vaccines.

As discussed in reference 28, TcdA is considered to be primarily responsible for the clinical symptoms of CDAD. Experiments with purified toxoids have indicated that TcdA alone is able to evoke the symptoms of CDAD, but TcdB is unable to do so unless it is mixed with TcdA, or there is prior damage to the gut mucosa [29]. Clinical evidence obtained from animal models indicates that binding domain of TcdA can elicit serum antibodies that neutralize the cytotoxic and lethal effects of TcdA (30, 31, 32, 33). Also, a recombinant non-toxic peptide containing these repeating units has been shown to elicit neutralizing antibodies that can protect laboratory animals against challenge with both TcdA and *C. difficile* (34, 35, 36, 33). Interestingly, however, a recent study showed that toxin B is essential for *C. difficile* virulence and that a strain producing TcdA alone was avirulent (29, 37), and so the current model of *C. difficile* virulence remains unsettled. Thus, it is currently unclear what components of TcdA and TcdB may be used to induce an immune response to treat or prevent CDAD. The current consensus, however, is that effective immunisation against CDAD is likely to require peptides comprising the binding domains of TcdA and TcdB (38, 39) and that antibodies directed against the binding domains confer protection against toxin pathology.

Reference 40 discloses chimeric proteins retaining all of the functional domains present in the wild-type toxins (i.e. GT, CP, T and B domains), but in which the binding domain of ToxA has been replaced by the binding domain of ToxB and vice versa. In line with the current consensus, it was suggested that the binding domain is the key domain for immunogenicity. In addition, the authors indicated that the chimeric nature of their holotoxin constructs which retained all of the functional domains of the native toxins, was essential.

Surprisingly, however, the inventors have found that native toxin structure is not necessary for immunogenicity and that fragments comprising the GT domain of TcdA or TcdB are particularly suitable for generating an immune response provided that they are combined with TcdB fragments when the GT domain of TcdA is used or TcdA fragments when the GT domain of TcdA is used. The GT domains employed in such combinations are typically detoxified. Such combinations generate the production of neutralisation titers against both TcdA and TcdB, and are more effective at providing a protective response against CDAD in animal models than combinations comprising binding domain fragments. These combinations thus provide an improved vaccine against CDAD. Furthermore, the use of recombinant polypeptide fragments also avoids safety issues related to the use of toxoids derived from *C. difficile* toxins purified from cell culture in vaccines.

ToxB-GT Antigens

The full-length TcdB antigen (also referred to herein as ToxB and ToxinB) comprises the amino acid sequence of SEQ ID NO: 2 (encoded by the nucleic acid sequence of SEQ ID NO: 31). Detoxified TcdB antigen is referred to herein as Toxoid B.

The abbreviation "ToxB-GT" refers to the glucosyl transferase domain of TcdB, which is located within the N-terminal region of the enzymatic domain (ED). The ToxB-GT domain (SEQ ID NO: 18, encoded by the nucleic acid sequence of SEQ ID NO: 47) is a fragment of TcdB that corresponds to amino acids 1-543 of SEQ ID NO: 2.

The ToxB-GT antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 18; and/or (b) that is a fragment of at least "n" consecutive amino acids of SEQ ID NO: 18, or of a polypeptide having 50% or more identity to SEQ ID NO:18, wherein "n" is 7 or more (e.g. 8, 10, 12, 14, 16, 18, 20, 25, 30, 35, 40, 45, 50, 60, 70, 80, 90, 100, 150, 250, 300, 400, 500, 540, or more). Preferred fragments comprise an epitope of SEQ ID NO: 18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 18 while retaining at least one epitope of SEQ ID NO:18. Amino acid fragments of ToxB-GT may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, or up to 540, consecutive amino acid residues of SEQ ID NO: 18.

The ToxB-GT antigen included in the compositions of the invention may be detoxified. Detoxification may be achieved by mutating the amino acid sequence or the encoding nucleic acid sequence of the wild-type ToxB-GT antigen using any appropriate method known in the art e.g. site-directed mutagenesis. Preferably, the ToxB-GT antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxB-GT antigen sequence of SEQ ID NO:18. For example, the ToxB-GT antigen comprises one or more amino acid substitutions (i.e. 1, 2, 3, 4, 5, 6, 7, 8, 9, 10, 11, 12, 13, 14, 15, 16, 17, 18, 19, 20, 21, 22, 23, 24, 25, or more mutations), e.g. at amino acid positions 17, 102, 139, 269, 270, 273, 284, 286, 288, 384, 449, 444, 445, 448, 449, 450, 451, 452, 455, 461, 463, 472, 515, 518, and/or 520, relative to the wild-type ToxB-GT antigen sequence of SEQ ID NO:18. For example, the ToxB-GT antigen may comprise substitutions at 1, 2, 3, 4 or 5 positions corresponding to amino acids 270, 273, 284, 286 and/or 288 of the Tox-GT antigen sequence of SEQ ID NO: 18. In particular, 1, 2, 3, 4 or 5 amino acids at positions corresponding to amino acids 270, 273, 284, 286 and/or 288 of the ToxB-GT antigen sequence of SEQ ID NO:18 may be substituted, preferably by alanine residues. Where amino acids 270, 273, 284, 286 and/or 288 of SEQ ID NO: 18 are substituted, the substitutions are preferably D270A, R273A, Y284A, D286A and/or D288A, most preferably D270A, R273A, Y284A, D286A and D288A. These substitutions correspond to substitutions D270A, R273A, Y284A, D286A and D288A of SEQ ID NO: 2. The amino acid sequence of a detoxified ToxB-GT antigen having alanine substitutions at these positions is provided in SEQ ID NO: 60.

Where the ToxB-GT comprises two amino acid substitutions, the substitutions are preferably not at amino acid positions 102 and 278, or amino acid positions 102 and 288, of the ToxB-GT antigen sequence of SEQ ID NO:18. The detoxified ToxB-GT antigen included in the compositions of the invention may thus be a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 60; and/or (b) that is a fragment of at least "n" consecutive amino acids of SEQ ID NO: 60, or of a polypeptide having 50% or more identity to SEQ ID NO: 60, wherein "n" is 7 or more (e.g. 8, 10, 12, 14, 16, 18, 20, 25, 30, 35, 40, 45, 50, 60, 70, 80, 90, 100, 150, 250, 300, 400, 500, 540, or more) Amino acid fragments of detoxified ToxB-GT may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, or up to 540, consecutive amino acid residues of SEQ ID NO: 60. Preferred fragments comprise an epitope of SEQ ID NO: 60. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 60 while retaining at least one epitope of SEQ ID NO: 60.

The abbreviation "ToxB-ED" refers to the enzymatic domain of TcdB. The ToxB-ED domain (SEQ ID NO: 17, encoded by the nucleic acid sequence of SEQ ID NO: 46) is a fragment of TcdB that corresponds to amino acids 1-767 of SEQ ID NO: 2. The ToxB-ED domain of TcdB thus comprises the ToxB-GT domain. The ToxB-GT antigen included in the composition of the invention may thus be a ToxB-ED antigen.

The ToxB-ED antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 17; and/or (b) that is a fragment of at least "n" consecutive amino acids of SEQ ID NO: 17, or of a polypeptide having 50% or more identity to SEQ ID NO:17, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 650, 700, 750, or more). Preferred fragments comprise an epitope of SEQ ID NO: 17. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 17 while retaining at least one epitope of SEQ ID NO:17.

Amino acid fragments of ToxB-ED may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to 700, or up to 750 consecutive amino acid residues of SEQ ID NO: 17.

The ToxB-ED antigen included in the compositions of the invention may be detoxified. Detoxification may be achieved by mutating the amino acid sequence or the encoding nucleic acid sequence of the wild-type ToxB-ED antigen using any appropriate method known in the art e.g. site-directed mutagenesis. Preferably, the ToxB-ED antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxB-ED antigen sequence of SEQ ID NO:17. For example, the ToxB-ED antigen comprises one or more amino acid substitutions (i.e. 1, 2, 3, 4, 5, 6, 7, 8, 9, 10, 11, 12, 13, 14, 15, 16, 17, 18, 19, 20, 21, 22, 23, 24, 25, or more mutations), e.g. at amino acid positions 17, 102, 139, 269, 270, 273, 284, 286, 288, 384, 449, 444, 445, 448, 449, 450, 451, 452, 455, 461, 463, 472, 515, 518, and/or 520, relative to the wild-type ToxB-ED antigen sequence of SEQ ID NO:17. For example, the ToxB-ED antigen may comprise substitutions at 1, 2, 3, 4 or 5 positions corresponding to amino acids 270, 273, 284, 286 and/or 288 of the ToxB-ED antigen sequence of SEQ ID NO:17. In particular, 1, 2, 3, 4 or 5 amino acids at positions corresponding to amino acids 270, 273, 284, 286 and/or 288 of the ToxB-ED antigen sequence of SEQ ID NO:17 may be substituted, preferably by alanine residues. The ToxB-ED antigen may also comprise substitutions at 1, 2, or 3 positions corresponding to amino acids 587, 653, and/or 698 of the ToxB-ED antigen sequence of SEQ ID NO:17. In particular, 1, 2, or 3 amino acids at positions corresponding to amino acids 587, 653, and/or 698 of the ToxB-ED antigen sequence of SEQ ID NO:17 may be substituted, preferably by alanine or asparagine residues. Where amino acids 587, 653, and/or 698 of SEQ ID NO: 17 are substituted, the substitutions are preferably D587N, H653A, and/or C698A, most preferably D587N, H653A, and C698A. These substitutions correspond to substitutions D587N, H653A, and C698A of SEQ ID NO: 2. The amino acid sequences of a detoxified ToxB-ED antigen having substitutions at positions 270, 273, 284, 286, 288, 587, 657 and 698 (relative to SEQ ID NO: 2) is provided in SEQ ID NO: 58.

Where the ToxB-ED comprises two amino acid substitutions, the substitutions are preferably not at amino acid positions 102 and 278, or amino acid positions 102 and 288, of the ToxB-ED antigen sequence of SEQ ID NO:17.

The detoxified ToxB-ED antigen included in the compositions of the invention may thus be a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 58; and/or (b) that is a fragment of at least "n" consecutive amino acids of SEQ ID NO 58: or of a polypeptide having 50% or more identified to SEQ ID NO: 58, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 650, 700, 750, or more). Amino acid fragments of detoxified ToxB-ED may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to 700, or up to 750 consecutive amino acid residues of SEQ ID NO: 58.

Preferred fragments comprise an epitope of SEQ ID NO: 58. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 58 while retaining at least one epitope of SEQ ID NO: 58.

ToxB-GT antigens and ToxB-ED antigens included in the compositions of the invention may also include the ToxB-CP and or ToxB-T domains defined below which are present in the full-length TcdB antigen. ToxB-GT antigens and ToxB-ED antigens may, for example, comprise n amino acids from the N-terminal region of the ToxB-T domain described below, wherein n=1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 400, 500, 600, 700, 800, 900, 1000, 1025, 1050, 1051, 1052, 1053, 1054, 1055, 1056, 1057, 1058, 1059, 1060, 1061, 1062, 1063, 1064, or 1065.

ToxB-GT and ToxB-ED antigens included in the compositions of the invention preferably do not comprise the binding domain of TcdB. In particular, the ToxB-GT and ToxB-ED preferably do not comprise the ToxB-B domain described in more detail below or fragments of this domain, e.g. the ToxB-B2 and/or ToxB-B7 domains described in more detail below.

ToxA-GT Antigens

The full-length TcdA antigen (also referred to herein as ToxA and Toxin A) comprises the amino acid sequence of SEQ ID NO: 1 (encoded by the nucleic acid sequence of SEQ ID NO: 30). Detoxified TcdA antigen is referred to herein as Toxoid A.

The abbreviation "ToxA-GT" refers to the glucosyl transferase domain of TcdA, which is located within the N-terminal region of the enzymatic domain (ED). The ToxA-GT domain (SEQ ID NO: 4, encoded by the nucleic acid sequence of SEQ ID NO: 33) is a fragment of TcdA that corresponds to amino acids 1-541 of SEQ ID NO: 1.

The ToxA-GT antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 4; and/or (b) that is a fragment of at least "n" consecutive amino acids of SEQ ID NO: 4, or of a polypeptide having 50% or more identity to SEQ ID NO:4, wherein "n" is 7 or more (e.g. 8, 10, 12, 14, 16, 18, 20, 25, 30, 35, 40, 45, 50, 60, 70, 80, 90, 100, 150, 250, 300, 400, 500, 540, or more). Preferred fragments comprise an epitope of SEQ ID NO: 4. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 4 while retaining at least one epitope of SEQ ID NO:4.

Amino acid fragments of ToxA-GT may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, or up to 540, consecutive amino acid residues of SEQ ID NO: 4.

The ToxA-GT antigen included in the compositions of the invention may be detoxified. Detoxification may be achieved by mutating the amino acid sequence or the encoding nucleic acid sequence of the wild-type ToxA-GT antigen using any appropriate method known in the art e.g. site-directed mutagenesis. Preferably, the ToxA-GT antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxA-GT antigen sequence of SEQ ID NO:4. For example, the ToxA-GT antigen may comprise substitutions at 1, 2 or 3 positions corresponding to amino acids 283, 285 and 287 of the ToxA-GT antigen sequence of SEQ ID NO:4. In particular, 1, 2, or 3 amino acids at positions corresponding to amino acids 283, 285 and 287 of the ToxA-GT antigen sequence of SEQ ID NO:4 may be substituted, preferably by alanine residues (i.e. Y283A, D285A, D287A). These mutations correspond to positions 283, 285 and 287 of SEQ ID NO: 1. The amino acid sequence of a detoxified ToxA-GT antigen having alanine substitutions at these positions is provided in SEQ ID NO: 56.

Where the ToxA-GT antigen comprises one amino acid substitution, the substitution is preferably not at amino acid position 278 of the ToxA-GT antigen sequence of SEQ ID NO: 4. Where the ToxA-GT antigen comprises two amino acid substitutions, the substitutions are preferably not at amino acid positions 101 and 278, of the ToxA-GT antigen sequence of SEQ ID NO:4. Where the ToxA-GT antigen comprises three amino acid substitutions, the substitutions are preferably not at amino acid positions 101, 278 and 519, or amino acid positions 101, 287 and 519, of the ToxA-GT antigen sequence of SEQ ID NO:4.

The detoxified ToxA-GT antigen included in the compositions of the invention may thus be a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 56; and/or (b) that is a fragment of at least "n" consecutive amino acids of SEQ ID NO: 56, or of a polypeptide having 50% or more identity to SEQ ID NO: 56, wherein "n" is 7 or more (e.g. 8, 10, 12, 14, 16, 18, 20, 25, 30, 35, 40, 45, 50, 60, 70, 80, 90, 100, 150, 250, 300, 400, 500, 540, or more). Preferred fragments comprise an epitope of SEQ ID NO: 56. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 56 while retaining at least one epitope of SEQ ID NO: 56 Amino acid fragments of detoxified ToxB-GT may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, or up to 540, consecutive amino acid residues of SEQ ID NO: 56.

The abbreviation "ToxA-ED" refers to the enzymatic domain of TcdA. The ToxA-ED domain (SEQ ID NO: 3, encoded by the nucleic acid sequence of SEQ ID NO: 32) is a fragment of TcdA that corresponds to amino acids 1-769 of SEQ ID NO: 1. The ToxA-ED domain of TcdA thus comprises the ToxA-GT domain. The ToxA-GT antigen included in the composition of the invention may thus be a ToxA-ED antigen.

The ToxA-ED antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 3; and/or (b) that is a fragment of at least "n" consecutive amino acids of SEQ ID NO: 3, or of a polypeptide having 50% or more identity to SEQ ID NO:3, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, or more). Preferred fragments comprise an epitope of SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO:3.

Amino acid fragments of ToxA-ED may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to, 700, or up to 750, consecutive amino acid residues of SEQ ID NO: 3.

The ToxA-ED antigen included in the compositions of the invention may be detoxified. Detoxification may be achieved by mutating the amino acid sequence or the encoding nucleic acid sequence of the wild-type ToxA-ED antigen using any appropriate method known in the art e.g. site-directed mutagenesis. Preferably, the ToxA-ED antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxA-ED antigen sequence of SEQ ID NO:3. For example, the ToxA-ED antigen may comprise substitutions at 1, 2 or 3 positions corresponding to amino acids 283, 285 and 287 of the ToxA-ED antigen sequence of SEQ ID NO: 3. In particular, 1, 2, or 3 amino acids at positions corresponding to amino acids 283, 285 and 287 of the ToxA-ED antigen sequence of SEQ ID NO: 3 may be substituted, preferably by alanine residues. The amino acid sequence of a detoxified ToxA-ED antigen having alanine substitutions at these positions is provided in SEQ ID NO: 54.

The ToxA-ED antigen may also comprise substitutions at 1, 2, or 3 positions corresponding to amino acids 589, 655, and/or 700 of the ToxA-ED antigen sequence of SEQ ID NO:3. In particular, 1, 2, or 3 amino acids at positions corresponding to amino acids 589, 655, and/or 700 of the ToxA-ED antigen sequence of SEQ ID NO:3 may be substituted, preferably by alanine or asparagine residues. Where amino acids 589, 655 and/or 700 are substituted, the substitutions are preferably D589N, H655A and/or C700A, most preferably D589N, H655A and C700A.

Where the ToxA-ED antigen comprises one amino acid substitution, the substitution is preferably not at amino acid position 278 of the ToxA-ED antigen sequence of SEQ ID NO: 3. Where the ToxA-ED antigen comprises two amino acid substitutions, the substitutions are preferably not at amino acid positions 101 and 278, of the ToxA-ED antigen sequence of SEQ ID NO:3. Where the ToxA-ED antigen comprises three amino acid substitutions, the substitutions are preferably not at amino acid positions 101, 278 and 519, or amino acid positions 101, 287 and 519, of the ToxA-ED antigen sequence of SEQ ID NO:3.

The detoxified ToxA-ED antigen included in the compositions of the invention may thus be a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 54; and/or (b) that is a fragment of at least "n" consecutive amino acids of SEQ ID NO: 54 or of a polypeptide having 50% or more identified to SEQ ID NO: 54, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, or more). Preferred fragments comprise an epitope of SEQ ID NO: 54. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 54 while retaining at least one epitope of SEQ ID NO: 54. Amino acid fragments of detoxified ToxA-ED may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to, 700, or up to 750, consecutive amino acid residues of SEQ ID NO: 54.

ToxA-GT antigens and ToxA-ED antigens included in the compositions of the invention may also include the ToxA-CP and or ToxA-T domains defined below which are present in the full-length TcdA antigen. ToxA-GT antigens and ToxA-ED antigens may, for example, comprise n amino acids from the N-terminal region of the ToxA-T domain described below, wherein n=1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 125, 150, 175, 200, 250, 300, 400, 500, 600, 700, 800, 900, 1000, 1025, 1050, 1051, 1052, 1053, 1054, 1055, 1056, 1057, 1058, 1059, 1060, 1061, 1062, 1063, 1064, or 1065.

ToxA-GT and ToxA-ED antigens included in the compositions of the invention preferably do not comprise the binding domain of TcdA. In particular, the ToxA-GT and ToxA-ED preferably do not comprise the ToxA-B domain described in more detail below or fragments of this domain, e.g. the ToxA-PTA2, ToxA-P5-7, ToxA-P5-6, ToxA-P9-10, ToxA-B2, ToxA-B3, ToxA-B5 and/or ToxA-B6 domains described in more detail below.

TcdA Antigens

Compositions of the invention may comprise a TcdA antigen. The TcdA antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 1; and/or (b) that is a fragment of at least "n" consecutive amino acids of SEQ ID NO: 1 or of a polypeptide having 50% or more identified to SEQ ID NO:1, wherein "n" is 7 or more (e.g. 8, 10, 12, 14, 16, 18, 20, 25, 30, 35, 40, 45, 50, 60, 70, 80, 90, 100, 150, 250, 500, 750, 1000, 1250, 1500, 1750, 2000, 2250, 2500, or more). Amino acid fragments of TcdA may comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to, 700, up to 750, up to 1000, up to 1250, up to 1500, up to 1750, up to 2000, up to 2250, or up to 2500, consecutive amino acid residues of SEQ ID NO: 1. Preferred fragments of TcdA comprise an epitope of SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one epitope of SEQ ID NO: 1. Other fragments of TcdA omit one or more protein domains. Protein domains that may be omitted can include functional protein domains, such as the "B", "T", "GT", "CP", "ToxA-ED", "ToxA-GT", "ToxA-CP", "ToxA-T", "ToxA-T4", "ToxA-PTA2", "ToxA-P5-7", "ToxA-P5-6", "ToxA-P9-10", "ToxA-B2", "ToxA-B3", "ToxA-B5", and "ToxA-B6" domains discussed herein.

Fragments of the TcdA antigen that may be included in the compositions of the invention are preferably selected from the group consisting of: "ToxA-ED", "ToxA-GT", "ToxA-CP", "ToxA-T", "ToxA-T4", "ToxA-PTA2", "ToxA-P5-7", "ToxA-P5-6", "ToxA-P9-10", "ToxA-B2", "ToxA-B3", "ToxA-B5" and "ToxA-B6". This set of fragments is referred to herein as the "TcdA antigen group". Thus, compositions of the invention may comprise one or more (i.e. 1, 2, 3, 4, 5, 6, 7, 8, 9, 10, 11, 12, 13, 14 or 15) TcdA antigens selected from the group consisting of: (1) a ToxA- ED antigen, (2) a ToxA-GT antigen, (3) a ToxA-CP antigen, (4) a ToxA-T antigen, (5) a ToxA-T4 antigen, (6) a ToxA-B antigen, (7) a ToxA-PTA2 antigen, (8) a ToxA-P5-7 antigen, (9) a ToxA-P5-6 antigen, (10) a ToxA-P9-10 antigen, (11) a ToxA-B2 antigen, (12) a ToxA-B3 antigen, (13) a ToxA-B5 antigen, (14) a ToxA-B6 antigen, and (15) a full-length TcdA antigen. Wherein compositions of the invention comprise one TcdA fragment, the one TcdA fragment is preferably not a ToxA-CP antigen alone.

The (1) ToxA-GT antigen, (2) ToxA-ED antigen, and (15) full-length TcdA antigen are defined above. The remaining antigens are defined in more detail below.

(3) ToxA-CP Antigen

The ToxA-CP domain (SEQ ID NO: 5, encoded by the nucleic acid sequence of SEQ ID NO: 34) corresponds to amino acids 542-769 of SEQ ID NO: 1. The abbreviation "ToxA-CP" refers to the cysteine protease domain of TcdA, which is located within the C-terminal region of the enzymatic domain.

The ToxA-CP antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 5; and/or (b) that is a fragment of at least "n" consecutive amino acids of SEQ ID NO: 5, or of a polypeptide having 50% or more identity to SEQ ID NO:5, wherein "n" is 7 or more (e.g. 8, 10, 12, 14, 16, 18, 20, 25, 30, 35, 40, 45, 50, 60, 70, 80, 90, 100, 150, 200, 225 or more). Preferred fragments comprise an epitope of SEQ ID NO: 5. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 5 while retaining at least one epitope of SEQ ID NO:5. Amino acid fragments of ToxA-CP may thus comprise an amino acid sequence of e.g. up to 30, up to 40, up to 50, up to 60, up to 70, up to 80, up to 90, up to 100, up to 125, up to 150, up to 175, up to 200, or up to 225, consecutive amino acid residues of SEQ ID NO: 5.

The ToxA-CP antigen included in the compositions of the invention may be detoxified. Detoxification may be achieved by mutating the amino acid sequence or the encoding nucleic acid sequence of the wild-type ToxA-CP antigen using any appropriate method known in the art e.g. site-directed mutagenesis. Preferably, the ToxA-CP antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxA-CP antigen sequence of SEQ ID NO:5. For example, the ToxA-CP antigen may comprise substitutions at 1, 2 or 3 positions corresponding to amino acids 48, 114 and 159 of the ToxA-CP antigen sequence of SEQ ID NO:5. In particular, 1, 2, or 3 amino acids at positions corresponding to amino acids 48, 114 and 159 of the ToxA-CP antigen sequence of SEQ ID NO:5 may be substituted, preferably by alanine or asparagine residues. Where amino acids 48, 114 and/or 159 of SEQ ID NO: 5 are substituted, the substitutions are preferably D48N, H114A and/or A159A, most preferably D48N, H114A and A159A. These substitutions correspond to substitutions D589N, H655A and C700A of SEQ ID NO: 1. The amino acid sequence of a detoxified ToxA-CP antigen having alanine or asparagine substitutions at these positions is provided in SEQ ID NO: 62.

Amino acid fragments of detoxified ToxA-CP may thus comprise an amino acid sequence of e.g. up to 30, up to 40, up to 50, up to 60, up to 70, up to 80, up to 90, up to 100, up to 125, up to 150, up to 175, up to 200, or up to 225, consecutive amino acid residues of SEQ ID NO: 62.

Where compositions of the invention contain only one TcdA antigen, the one TcdA antigen is preferably not ToxA-CP alone. Where compositions of the invention comprise a ToxA-CP antigen, the antigen may be a ToxA-ED antigen.

(4) ToxA-T Antigen

The ToxA-T domain (SEQ ID NO: 6, encoded by the nucleic acid sequence of SEQ ID NO: 35) corresponds to amino acids 770-1808 of SEQ ID NO: 1. The abbreviation "ToxA-T" refers to the translocation domain of TcdA.

The ToxA-T antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 6; and/or (b) that is a fragment of at least "n" consecutive amino acids of SEQ ID NO: 6, or of a polypeptide having 50% or more identity to SEQ ID NO:6, wherein "n" is 7 or more (e.g. 8, 10, 12, 14, 16, 18, 20, 25, 30, 35, 40, 45, 50, 60, 70, 80, 90, 100, 150, 200, 250, 300, 400, 500, 550, 600, 700, 800, 900, 1000, or more). Preferred fragments comprise an epitope of SEQ ID NO: 6. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 6 while retaining at least one epitope of SEQ ID NO:6. Amino acid fragments of ToxA-T may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, up to 900, or up to 1000, consecutive amino acid residues of SEQ ID NO: 6.

(5) ToxA-T4

The ToxA-T4 domain (SEQ ID NO: 7, encoded by the nucleic acid sequence of SEQ ID NO: 36) corresponds to amino acids 1510-1775 of SEQ ID NO: 1. The abbreviation "ToxA-T4" refers to a region within TcdA. The ToxA-T4 region was found to be insoluble.

The ToxA-T4 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 7; and/or (b) that is a fragment of at least "n" consecutive amino acids of SEQ ID NO: 7, or of a polypeptide having 50% or more identity to SEQ ID NO:7, wherein "n" is 7 or more (e.g. 8, 10, 12, 14, 16, 18, 20, 25, 30, 35, 40, 45, 50, 60, 70, 80, 90, 100, 150, 250, or more). Preferred fragments comprise an epitope of SEQ ID NO: 7. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 7 while retaining at least one epitope of SEQ ID NO:7 Amino acid fragments of ToxA-T4 may thus comprise an amino acid sequence of e.g. up to 30, up to 40, up to 50, up to 60, up to 70, up to 80, up to 90, up to 100, up to 125, up to 150, up to 175, up to 200, up to 250, or up to 260, consecutive amino acid residues of SEQ ID NO: 7.

(6) ToxA-B Antigen

The ToxA-B domain (SEQ ID NO: 8, encoded by the nucleic acid sequence of SEQ ID NO: 37) corresponds to amino acids 1809-2710 of SEQ ID NO: 1. The abbreviation "ToxA-B" refers to a fragment of the binding domain of TcdA. The binding domain of TcdA (denoted "B" in FIG. 1) is responsible for toxin binding to the surface of epithelial cells. The inventors have found that fragments of the binding domain are effective in combination with GT antigens at eliciting an immune response. Compositions of the invention thus employ fragments of the binding domain (e.g. ToxA-B, ToxA-PTA2, ToxA-P5-7, ToxA-P5-6, ToxA-P9-10, ToxA-B2, ToxA-B3, ToxA-B5 and/or ToxA-B6).

The ToxA-B antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 8; and/or (b) that is a fragment of at least "n" consecutive amino acids of SEQ ID NO: 8, or of a polypeptide having 50% or more identity to SEQ ID NO:8, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 800, 900, or more). Preferred fragments comprise an epitope of SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 8 while retaining at least one epitope of SEQ ID NO:8. Amino acid fragments of ToxA-B may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, or up to 900, consecutive amino acid residues of SEQ ID NO: 8.

(7) ToxA-PTA2

The ToxA-PTA2 domain (SEQ ID NO: 9, encoded by the nucleic acid sequence of SEQ ID NO: 38) corresponds to amino acids 1995-2198 of SEQ ID NO: 1. The abbreviation "ToxA-PTA2" refers to a region within the binding domain of TcdA and was found to be insoluble. As described in WO98/59053, the ToxA-PTA2 fragment comprises 8 tandem repeat sequences from within the C-terminal repeat region of Toxin A.

The ToxA-PTA2 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 9; and/or (b) that is a fragment of at least "n" consecutive amino acids of SEQ ID NO: 9, or of a polypeptide having 50% or more identity to SEQ ID NO:9, wherein "n" is 7 or more (e.g. 8, 10, 12, 14, 16, 18, 20, 25, 30, 35, 40, 45, 50, 60, 70, 80, 90, 100, 150, 200, or more). Preferred fragments comprise an epitope of SEQ ID NO: 9. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 9 while retaining at least one epitope of SEQ ID NO:9. Amino acid fragments of ToxA-PTA2 may thus comprise an amino acid sequence of e.g. up to 30, up to 40, up to 50, up to 60, up to 70, up to 80, up to 90, up to 100, up to 125, up to 150, up to 175, or up to 200, consecutive amino acid residues of SEQ ID NO: 9.

(8) ToxA-P5-7 Antigen

The ToxA-P5-7 antigen (SEQ ID NO: 10, encoded by the nucleic acid sequence of SEQ ID NO: 39) corresponds to amino acids 2249-2706 of SEQ ID NO: 1. The abbreviation "ToxA-P5-7" refers to a region within the binding domain of TcdA. As described in WO98/59053, the ToxA-P5-7 fragment comprises 20 tandem repeat sequences from within the C-terminal repeat region of Toxin A.

The ToxA-P5-7 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 10; and/or (b) that is a fragment of at least "n" consecutive amino acids of SEQ ID NO: 10, or of a polypeptide having 50% or more identity to SEQ ID NO:10, wherein "n" is 7 or more (e.g. 8, 10, 12, 14, 16, 18, 20, 25, 30, 35, 40, 45, 50, 60, 70, 80, 90, 100, 150, 250, 300, 400, 450, or more). Preferred fragments comprise an epitope of SEQ ID NO: 10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 10 while retaining at least one epitope of SEQ ID NO:10 Amino acid fragments of ToxA-P5-7 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, or up to 450, consecutive amino acid residues of SEQ ID NO: 10.

(9) ToxA-P5-6 Antigen

The ToxA-P5-6 domain (also referred to as "P5-6") (SEQ ID NO: 11, encoded by the nucleic acid sequence of SEQ ID NO: 40) corresponds to amino acids 2387-2706 of SEQ ID NO: 1. The abbreviation "ToxA-P5-6" refers to a region within the binding domain of TcdA. As described in WO98/59053, the ToxA-P5-6 fragment comprises 14 tandem repeat sequences from within the C-terminal repeat region of Toxin A.

The ToxA-P5-6 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 11; and/or (b) that is a fragment of at least "n" consecutive amino acids of SEQ ID NO: 11, or of a polypeptide having 50% or more identity to SEQ ID NO:11, wherein "n" is 7 or more (e.g. 8, 10, 12, 14, 16, 18, 20, 25, 30, 35, 40, 45, 50, 60, 70, 80, 90, 100, 150, 250, 300, or more). Preferred fragments comprise an epitope of SEQ ID NO: 11. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 11 while retaining at least one epitope of SEQ ID NO:11 Amino acid fragments of ToxA-P5-6 may thus comprise an amino acid sequence of e.g. up to 30, up to 40, up to 50, up to 60, up to 70, up to 80, up to 90, up to 100, up to 125, up to 150, up to 175, up to 200, up to 250, or up to 300, consecutive amino acid residues of SEQ ID NO: 11.

The ToxA-p5-6 antigen may comprise a mutation in at least one amino acid (for example 1, 2, 3, 5, 6, 7, 8, 9, 10 or more) relative to SEQ ID NO:11. A mutation preferably involves a single amino acid and is preferably a point mutation. The mutations may each independently be a deletion, an insertion or a substitution. For example, a mutated ToxA-p5-6 antigen may include one or more (e.g. 1, 2, 3, 4, 5, 6, 7, 8, 9, etc.) single amino acid deletions relative to the ToxA-p5-6 sequence SEQ ID NO: 11. By way of further example, a mutated ToxA-p5-6 antigen may include one or more (e.g. 1, 2, 3, 4, 5, 6, 7, 8, 9, etc.) insertions (e.g. each of 1, 2, 3, 4 or 5 amino acids) relative to the ToxA-p5-6 sequence SEQ ID NO: 11. Deletions, substitutions or insertions may be at the N-terminus and/or C-terminus, or may be between the two termini. Thus a truncation is an example of a deletion. Truncations may involve deletion of up to 40 (or more) amino acids at the N-terminus and/or C-terminus Particular insertions include the addition of two amino acids at the C-terminal, for example Leucine (L) and Glutamic acid (E) as shown in SEQ ID NO: 84.

Preferred mutations are amino acid substitutions. Amino acid substitutions may be from one amino acid to any one of the other nineteen naturally occurring amino acids. A conservative substitution is commonly defined as a substitution introducing an amino acid having sufficiently similar chemical properties, e.g. having a related side chain (e.g. a basic, positively charged amino acid should be replaced by another basic, positively charged amino acid), in order to preserve the structure and the biological function of the molecule. Genetically-encoded amino acids may be divided into five families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; (4) charged i.e. aspartic acid, glutamic acid, arginine, lysine, histidine and (5) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Particularly, substitutions may be made at positions 41 and/or 42 of the ToxA-p5-6 antigen numbered according to SEQ ID 11. Particularly the histidine (H) at position 41 may be substituted with aspartic acid (D) as shown in SEQ ID NO: 101 (a substitution named H41D). Particularly asparagine (N) at position 42 may be substituted by alanine (A) as shown in SEQ ID NO: 102 (a substitution named N42A). Yet more particularly, the ToxA-P5-6 antigen may comprise both of these two mutations H41D and N42A as exemplified in SEQ ID NO: 103.

The ToxA-p5-6 antigen may be part of a hybrid polypeptide of formula: A-Bp5-6-C wherein:

A is an optional N-terminal additional amino acid sequence. The additional amino acid sequence may be either derived from vector sequences, from MCS or the sequences could be from extraneous polypeptides that aid in hyper expression of proteins. The additional amino acids could be used for affinity purification or for antibody detection. The additional amino acid sequence may be any known in the art such as GST tag, His tag, T7 tag Trx tag, MBP tag, His-GM tag etc. Particularly, the additional amino acid sequence comprises the sequence MRGSHHHHHHGMASMTG-GQQMGRDLYDDDDKDRWGSSRITR (SEQ ID NO: 104)

B is ToxA-p5-6 antigen having an amino acid sequence selected from the group consisting of SEQ ID NO 11, SEQ ID NO 84, SEQ ID NO 101, SEQ ID NO 102 and SEQ ID NO: 103.

C is an optional C-terminal amino sequence having the following sequence TESTCRXQA (SEQ ID NO: 105) wherein X is one of the twenty naturally occurring amino acids.

Examples of hybrid polypeptides comprising ToxA-p5-6 antigen are shown in SEQ ID NOs: 106, 107, 108, 109, 110, and 111. Seq ID NO: 111 is encoded by the nucleic acid sequence of SEQ ID NO: 112. Preferred ToxA-p5-6 antigens for use in combinations of the invention include SEQ ID NO:11 and SEQ ID NO: 111.

(10) ToxA-P9-10 Antigen

The ToxA-P9-10 domain (SEQ ID NO: 12, encoded by the nucleic acid sequence of SEQ ID NO: 41) corresponds to amino acids 1843-2706 of SEQ ID NO: 1. The abbreviation "ToxA-P9-10" refers to a region within the binding domain of TcdA. As described in WO98/59053, the ToxA-P9-10 fragment comprises all 36 tandem repeat sequences from within the C-terminal repeat region of Toxin A.

The ToxA-P9-10 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 12; and/or (b) that is a fragment of at least "n" consecutive amino acids of SEQ ID NO: 12, or of a polypeptide having 50% or more identity to SEQ ID NO:12, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 800, 850, or more). Preferred fragments comprise an epitope of SEQ ID NO: 12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 12 while retaining at least one epitope of SEQ ID NO:12. Amino acid fragments of ToxA-P9-10 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, or up to 850, consecutive amino acid residues of SEQ ID NO: 12.

(11) ToxA-B2 Antigen

The ToxA-B2 domain (SEQ ID NO: 13, encoded by the nucleic acid sequence of SEQ ID NO: 42) corresponds to amino acids 2303-2706 of SEQ ID NO: 1. The abbreviation "ToxA-B2" refers to a region within the binding domain of TcdA. The three-dimensional structure of the TcdA binding domain was predicted by computer modelling using the crystal structure of the C-terminal fragment as template (see reference 41, PDB code 2F6E). ToxA-B2 was designed to include 6 of the 13 putative structural units forming the binding domain (see FIG. 2).

The ToxA-B2 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 13; and/or (b) that is a fragment of at least "n" consecutive amino acids of SEQ ID NO: 13, or of a polypeptide having 50% or more identity to SEQ ID NO:13, wherein "n" is 7 or more (e.g. 8, 10, 12, 14, 16, 18, 20, 25, 30, 35, 40, 45, 50, 60, 70, 80, 90, 100, 150, 250, 300, 400 or more). Preferred fragments comprise an epitope of SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO:13. Amino acid fragments of ToxA-B2 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, consecutive amino acid residues of SEQ ID NO: 13.

(12) ToxA-B3 Antigen

The ToxA-B3 domain (SEQ ID NO: 14, encoded by the nucleic acid sequence of SEQ ID NO: 43) corresponds to amino acids 1839-2710 of SEQ ID NO: 1. The abbreviation "ToxA-B3" refers to a region within the binding domain of TcdA. The three-dimensional structure of the TcdA binding domain was predicted by computer modelling using the crystal structure of the C-terminal fragment as template (see reference 41, PDB code 2F6E). ToxA-B3 was designed to include 12 of the 13 putative structural units forming the binding domain (see FIG. 3).

The ToxA-B3 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 14; and/or (b) that is a fragment of at least "n" consecutive amino acids of SEQ ID NO: 14, or of a polypeptide having 50% or more identity to SEQ ID NO:14, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 800, 850, or more). Preferred fragments comprise an epitope of SEQ ID NO: 14. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 14 while retaining at least one epitope of SEQ ID NO:14 Amino acid fragments of ToxA-B3 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, or up to 850, consecutive amino acid residues of SEQ ID NO: 14.

(13) ToxA-B5 Antigen

The ToxA-B5 domain (SEQ ID NO: 15, encoded by the nucleic acid sequence of SEQ ID NO: 44) corresponds to amino acids 1964-2706 of SEQ ID NO: 1. The abbreviation "ToxA-B5" refers to a region within the binding domain of TcdA. The three-dimensional structure of the TcdA binding domain was predicted by computer modelling using the crystal structure of the C-terminal fragment as template (see reference 41, PDB code 2F6E). ToxA-B5 was designed to include 10.5 of the 13 putative structural units forming the binding domain (see FIG. 4).

The ToxA-B5 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 15; and/or (b) that is a fragment of at least "n" consecutive amino acids of SEQ ID NO: 15, or of a polypeptide having 50% or more identity to SEQ ID NO:15, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 740 or more). Preferred fragments comprise an epitope of SEQ ID NO: 15. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 15 while retaining at least one epitope of SEQ ID NO:15. Amino acid fragments of ToxA-B5 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, or up to 740, consecutive amino acid residues of SEQ ID NO: 15.

(14) ToxA-B6 Antigen

The ToxA-B6 domain (SEQ ID NO: 16, encoded by the nucleic acid sequence of SEQ ID NO: 45) corresponds to amino acids 1890-2706 of SEQ ID NO: 1. The abbreviation "ToxA-B6" refers to a region within the binding domain of TcdA. The three-dimensional structure of the TcdA binding domain was predicted by computer modelling using the crystal structure of the C-terminal fragment as template (see reference 41, PDB code 2F6E). ToxA-B6 was designed to include 11.5 of the 13 putative structural units forming the binding domain (see FIG. 5).

The ToxA-B6 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 16; and/or (b) that is a fragment of at least "n" consecutive amino acids of SEQ ID NO: 16, or of a polypeptide having 50% or more identity to SEQ ID NO:16, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 800 or more). Preferred fragments comprise an epitope of SEQ ID NO: 16. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 16 while retaining at least one epitope of SEQ ID NO:16. Amino acid fragments of ToxA-B6 may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, or up to 850, consecutive amino acid residues of SEQ ID NO: 16.

The TcdB Antigens

Compositions of the invention may comprise a TcdB antigen. The TcdB antigen included in the polypeptides of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 2; and/or (b) that is a fragment of at least "n" consecutive amino acids of SEQ ID NO: 2 or of a polypeptide having 50% or more identified to SEQ ID NO:2, wherein "n" is 7 or more (e.g. 8, 10, 12, 14, 16, 18, 20, 25, 30, 35, 40, 45, 50, 60, 70, 80, 90, 100, 150, 250, 500, 750, 1000, 1250, 1500, 1750, 2000, 2250, 2400, or more).). Amino acid fragments of TcdB may comprise an amino acid sequence of e.g. up to 30, up to 40, up to 50, up to 60, up to 70, up to 80, up to 90, up to 100, up to 125, up to 150, up to 175, up to 200, up to 250, up to 300, up to 350, up to 400, up to 450, up to 500, up to 550, up to 600, up to 650, up to, 700, up to 750, up to 1000, up to 1250, up to 1500, up to 1750, up to 2000, up to 2250, or up to 2400, consecutive amino acid residues of SEQ ID NO: 2. Preferred fragments of TcdB comprise an epitope of SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 2 while retaining at least one epitope of SEQ ID NO: 2. Other fragments of TcdB omit one or more protein domains. Protein domains that may be omitted can include functional protein domains, such as the "B", "T", "GT", "CP", ""ToxB-ED", "ToxB-GT", "ToxB-CP", "ToxB-T", "ToxB-B", "ToxB-B2" and "ToxB-B7" domains discussed herein.

The TcdB fragments that may be included in the composition of the invention are preferably selected from the group consisting of: "ToxB-ED", "ToxB-GT", "ToxB-CP", "ToxB-T", "ToxB-B", "ToxB-B2", and ToxB-B7. This set of antigens is referred to herein as the "TcdB antigen group".

Thus, compositions of the invention may comprise one or more (i.e. 1, 2, 3, 4, 5, 6, 7, or all 8) TcdB antigens selected from the group consisting of: (1) a ToxB-ED antigen, (2) a ToxB-GT antigen, (3) a ToxB-CP antigen, (4) a ToxB-T antigen, (5) a ToxB-B antigen, (6) a ToxB-B2 antigen, (7) a ToxA-B7 antigen and (8) a full-length TcdB antigen. Wherein compositions of the invention comprise only one TcdB fragment, the one TcdB fragment is preferably not ToxB-CP alone.

The (1) ToxB-GT antigen, (2) ToxB-ED antigen and (8) full-length TcdB antigen are defined above. The remaining antigens are defined in more detail below.

(3) ToxB-CP Antigen

The ToxB-CP domain (SEQ ID NO: 19, encoded by the nucleic acid sequence of SEQ ID NO: 48) corresponds to amino acids 544-767 of SEQ ID NO: 2. The abbreviation "ToxB-CP" refers to the cysteine protease domain of TcdB, which is located within the C-terminal region of the enzymatic domain.

The ToxB-CP antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 19; and/or (b) that is a fragment of at least "n" consecutive amino acids of SEQ ID NO: 19, or of a polypeptide having 50% or more identity to SEQ ID NO:19, wherein "n" is 7 or more (e.g. 8, 10, 12, 14, 16, 18, 20, 25, 30, 35, 40, 45, 50, 60, 70, 80, 90, 100, 150, 200, 230, or more). Preferred fragments comprise an epitope of SEQ ID NO: 19. Amino acid fragments of ToxB-CP may thus comprise an amino acid sequence of e.g. up to 30, up to 40, up to 50, up to 60, up to 70, up to 80, up to 90, up to 100, up to 125, up to 150, up to 175, up to 200, or up to 230, consecutive amino acid residues of SEQ ID NO: 19. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 19 while retaining at least one epitope of SEQ ID NO:19.

The ToxB-CP antigen included in the compositions of the invention may be detoxified. Detoxification may be achieved by mutating the amino acid sequence or the encoding nucleic acid sequence of the wild-type ToxB-CP antigen using any appropriate method known in the art e.g. site-directed mutagenesis. Preferably, the ToxB-CP antigen comprises one or more amino acid substitutions (i.e. 1, 2, 3, 4, 5, 6, 7, 8, 9, 10, 11, 12, 13, 14, 15, 16, 17, 18, 19, 20, 25, 30, or more mutations), relative to the wild-type ToxB-CP antigen sequence of SEQ ID NO: 19. For example, the ToxB-CP antigen may comprise substitutions at 1, 2 or 3 positions corresponding to amino acids 44, 110 and 155 of the ToxB-CP antigen sequence of SEQ ID NO:19. In particular, 1, 2, or 3 amino acids at positions corresponding to amino acids 44, 110 and 155 of the ToxB-CP antigen sequence of SEQ ID NO:19 may be substituted, preferably by alanine or asparagine residues. Where amino acids 44, 110, and/or 155 of SEQ ID NO: 19 are substituted, the substitutions are preferably D44N, H110A, and/or C155A, most preferably D44N, H110A, and/or C155A. The amino acid sequence of a detoxified ToxB-CP antigen having alanine or asparagine substitutions at these positions is provided in SEQ ID NO: 64. These substitutions correspond to substitutions D587N, H653A, and C698A of SEQ ID NO 2 Amino acid fragments of detoxified ToxB-CP may thus comprise an amino acid sequence of e.g. up to 30, up to 40, up to 50, up to 60, up to 70, up to 80, up to 90, up to 100, up to 125, up to 150, up to 175, up to 200, or up to 225, consecutive amino acid residues of SEQ ID NO: 64.

Where compositions of the invention contain only one TcdB antigen, the one TcdB antigen is preferably not ToxB-CP alone. Where compositions of the invention comprise a ToxB-CP antigen, the antigen may be a ToxB-ED antigen.

(4) ToxB-T Antigen

The ToxB-T domain (SEQ ID NO: 20, encoded by the nucleic acid sequence of SEQ ID NO: 49) corresponds to amino acids 768-1833 of SEQ ID NO: 2. The abbreviation "ToxB-T" refers to the translocation domain of TcdB.

The ToxB-T antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 20; and/or (b) that is a fragment of at least "n" consecutive amino acids of SEQ ID NO: 20, or of a polypeptide having 50% or more identity to SEQ ID NO:20, wherein "n" is 7 or more (e.g. 8, 10, 12, 14, 16, 18, 20, 25, 30, 35, 40, 45, 50, 60, 70, 80, 90, 100, 150, 250, 300, 400, 500, 550, 600, 700, 800, 900, 1000, 1050, or more). Preferred fragments comprise an epitope of SEQ ID NO: 20. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 20 while retaining at least one epitope of SEQ ID NO:20. Amino acid fragments of ToxB-T may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 500, up to 550, up to 600, up to 700, up to 800, 900, 1000, or up to 1050, consecutive amino acid residues of SEQ ID NO: 20.

(5) ToxB-B Antigen

The ToxB-B domain (SEQ ID NO: 21, encoded by the nucleic acid sequence of SEQ ID NO: 50) corresponds to amino acids 1853-2366 of SEQ ID NO: 2. The abbreviation "ToxB-B" refers to a fragment of the binding domain of TcdB. The inventors have found that fragments of the binding domain are effective in combination with GT antigens at eliciting an immune response. Compositions of the invention thus employ fragments of the binding domain (e.g. ToxB-B, ToxB-B2 antigen, and/or ToxA-B7).

The ToxB-B antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 21; and/or (b) that is a fragment of at least "n" consecutive amino acids of SEQ ID NO: 21, or of a polypeptide having 50% or more identity to SEQ ID NO:21, wherein "n" is 7 or more (e.g. 8, 10, 12, 14, 16, 18, 20, 25, 30, 35, 40, 45, 50, 60, 70, 80, 90, 100, 150, 250, 300, 400, 500, or more). Preferred fragments comprise an epitope of SEQ ID NO: 21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 21 while retaining at least one epitope of SEQ ID NO:21 Amino acid fragments of ToxB-B may thus comprise an amino acid sequence of e.g. up to 30, up to 40, up to 50, up to 60, up to 70, up to 80, up to 90, up to 100, up to 125, up to 150, up to 175, up to 200, up to 250, up to 300, up to 400, up to 450, or up to 500 consecutive amino acid residues of SEQ ID NO:

(6) ToxB-B2 Antigen

The ToxB-B2 domain (SEQ ID NO: 22, encoded by the nucleic acid sequence of SEQ ID NO: 51) corresponds to amino acids 2157-2366 of SEQ ID NO: 2. The abbreviation "ToxA-B2" refers to the C-terminal region of the binding domain of TcdB. The three-dimensional structure of the TcdB binding domain was predicted by computer modelling using the crystal structure of the C-terminal fragment as template (see reference 41, PDB code 2F6E). ToxB-B2 was designed to include 4 of the 9 putative structural units forming the binding domain (see FIG. 6).

The ToxB-B2 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 22; and/or (b) that is a fragment of at least "n" consecutive amino acids of SEQ ID NO: 22, or of a polypeptide having 50% or more identity to SEQ ID NO:22, wherein "n" is 7 or more (e.g. 8, 10, 12, 14, 16, 18, 20, 25, 30, 35, 40, 45, 50, 60, 70, 80, 90, 100, 150, 175, 200, or more). Preferred fragments comprise an epitope of SEQ ID NO: 22. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 22 while retaining at least one epitope of SEQ ID NO:22.

Amino acid fragments of ToxB-B2 may thus comprise an amino acid sequence of e.g. up to 30, up to 40, up to 50, up to 60, up to 70, up to 80, up to 90, up to 100, up to 125, up to 150, up to 175, or up to 200 consecutive amino acid residues of SEQ ID NO: 22.

(7) ToxB-B7 Antigen

The ToxB-B7 domain (SEQ ID NO: 23, encoded by the nucleic acid sequence of SEQ ID NO: 52) corresponds to amino acids 2056-2366 of SEQ ID NO: 2.

The ToxB-B7 antigen included in the compositions of the invention is a polypeptide that comprises or consists of an amino acid sequence: (a) having 50% or more identity (e.g. 60%, 65%, 70%, 75%, 80%, 85%, 90%, 91%, 92%, 93%, 94%, 95%, 96%, 97%, 98%, 98.5%, 99%, 99.5%, 99.8%, 99.9%, or more) to SEQ ID NO: 23; and/or (b) that is a fragment of at least "n" consecutive amino acids of SEQ ID NO: 23, or of a polypeptide having 50% or more identity to SEQ ID NO:23, wherein "n" is 7 or more (e.g. 8, 10, 12, 14, 16, 18, 20, 25, 30, 35, 40, 45, 50, 60, 70, 80, 90, 100, 150, 200, 250, 300 or more). Preferred fragments comprise an epitope of SEQ ID NO: 23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 23 while retaining at least one epitope of SEQ ID NO:23.

Amino acid fragments of ToxB-B7 may thus comprise an amino acid sequence of e.g. up to 30, up to 40, up to 50, up to 60, up to 70, up to 80, up to 90, up to 100, up to 125, up to 150, up to 175, up to 200, up to 250, or up to 300 consecutive amino acid residues of SEQ ID NO: 23.

Antigen Combinations

Compositions of the invention may comprise a ToxB-GT antigen and one or more TcdA antigens (e.g. 1, 2, 3, 4, 5, 6, 7, 8, 9, 10, 11, 12, 13, 14 or 15 TcdA antigens selected from (1) a ToxA-ED antigen, (2) a ToxA-GT antigen, (3) a ToxA-CP antigen, (4) a ToxA-T antigen, (5) a ToxA-T4 antigen, (6) a ToxA-B antigen, (7) a ToxA-PTA2 antigen, (8) a ToxA-P5-7 antigen, (9) a ToxA-P5-6 antigen, (10) a ToxA-P9-10 antigen, (11) a ToxA-B2 antigen, (12) a ToxA-B3 antigen, (13) a ToxA-B5 antigen, (14) a ToxA-B6 antigen, and (15) a full-length TcdA antigen, as described above). Such compositions may further comprise one or more additional TcdB antigens (e.g. 1, 2, 3, 4, 5, 6, 7, or 8 TcdB antigens selected from the group consisting of: (1) a ToxB-ED antigen, (2) a ToxB-GT antigen, (3) a ToxB-CP antigen, (4) a ToxB-T antigen, (5) a ToxB-B antigen, (6) a ToxB-B2 antigen, (7) a ToxA-B7 antigen and (8) a full-length TcdB antigen, as TcdB described above).

Alternatively, compositions of the invention may comprise a ToxA-GT antigen and one or more TcdB antigens (e.g. 1, 2, 3, 4, 5, 6, 7, or 8 TcdB antigens selected from the group consisting of: (1) a ToxB-ED antigen, (2) a ToxB-GT antigen, (3) a ToxB-CP antigen, (4) a ToxB-T antigen, (5) a ToxB-B antigen, (6) a ToxB-B2 antigen, (7) a ToxA-B7 antigen and (8) a full-length TcdB antigen, as TcdB described above). Such compositions may further comprise one or more additional TcdA antigens (e.g. 1, 2, 3, 4, 5, 6, 7, 8, 9, 10, 11, 12, 13, 14 or 15 TcdA antigens selected from (1) a ToxA-ED antigen, (2) a ToxA-GT antigen, (3) a ToxA-CP antigen, (4) a ToxA-T antigen, (5) a ToxA-T4 antigen, (6) a ToxA-B antigen, (7) a ToxA-PTA2 antigen, (8) a ToxA-P5-7 antigen, (9) a ToxA-P5-6 antigen, (10) a ToxA-P9-10 antigen, (11) a ToxA-B2 antigen, (12) a ToxA-B3 antigen, (13) a ToxA-B5 antigen, (14) a ToxA-B6 antigen, and (15) a full-length TcdA antigen, as described above).

Specific examples of combinations of antigens that may be included in the compositions of the invention are set out below.

In some embodiments, the immunogenic composition comprises a combination of i) one ToxB-GT antigen and one TcdA antigen or ii) one ToxA-GT antigen and one TcdB antigen.

In some embodiments, the composition comprises ToxA-GT and one antigen from the TcdB antigen group e.g. ToxA-GT+ToxB-ED, ToxA-GT+ToxB-GT, ToxA-GT+ToxB-CP, ToxA-GT+ToxB-T, ToxA-GT+ToxB-B, ToxA-GT+ToxB-B2, ToxA-ED+ToxB-B7, ToxA-ED+ToxB-ED, ToxA-ED+ToxB-GT, ToxA-ED+ToxB-CP, ToxA-ED+ToxB-T, ToxA-ED+ToxB-B, ToxA-ED+ToxB-B2, and ToxA-ED+ToxB-B7.

In some embodiments, the composition comprises ToxB-GT and one antigen from the TcdA antigen group e.g. ToxB-GT+ToxA-ED, ToxB-GT+ToxA-GT, ToxB-GT+ToxA-CP, ToxB-GT+ToxA-T, ToxB-GT+ToxA-T4, ToxB-GT+ToxA-PTA2, ToxB-GT+ToxA-P5-7, ToxB-GT+ToxA-P5-6, ToxB-GT+ToxA-P9-10, ToxB-GT+ToxA-B2, ToxB-GT+ToxA-B3, ToxB-GT+ToxA-B5, ToxB-GT+ToxA-B6, ToxB-ED+ToxA-ED, ToxB-ED+ToxA-GT, ToxB-ED+ToxA-CP, ToxB-ED+ToxA-T, ToxB-ED+ToxA-T4, ToxB-ED+ToxA-PTA2, ToxB-ED+ToxA-P5-7, ToxB-ED+ToxA-P5-6, ToxB-ED+ToxA-P9-10, ToxB-ED+ToxA-B2, ToxB-ED+ToxA-B3, ToxB-ED+ToxA-B5, and ToxB-ED+ToxA-B6. Preferably, the composition comprises (a) ToxB-GT+ToxA-P5-6, (b) ToxB-GT+ToxA-B2, (c) ToxB-GT+ToxB-B+ToxA-B2, or (d) ToxB-GT+ToxB-B+ToxA-P5-6.

In another embodiment, the immunogenic composition comprises 3 antigens. Such an immunogenic composition may comprise a combination of i) one ToxB-GT antigen and two TcdA antigens; ii) one ToxA-GT antigen and two TcdB antigens; or iii) one ToxB-GT antigen, one ToxA-GT antigen and one further TcdA or TcdB antigen, e.g. ToxB-GT+ToxA-B2+ToxB-B, ToxB-GT+ToxB-B+ToxA-P5-6.

The immunogenic composition may comprise four antigens. For example, the composition may comprise a ToxB-GT antigen, a ToxA-GT antigen and two additional antigens from the TcdA and/or TcdB antigen groups, e.g. ToxB-GT+ToxB-B+ToxA-GT+ToxA-B2.

It has been found that combinations comprising the ToxA-GT and/or ToxB-GT antigens are surprisingly effective when combined with fragments derived form the binding domains of both TcdA and TcdB. In particular, the composition may therefore comprise a combination of i) a ToxA-GT antigen or a ToxB-GT antigen and (ii) at least one TcdA antigen selected from ToxA-B, ToxA-PTA2, ToxA-P5-7, ToxA-P5-6, ToxA-P9-10, ToxA-B2, ToxA-B3, ToxA-B5 and/or ToxA-B6; and at least one TcdB antigen selected from ToxB-B, ToxB-B2 antigen, and/or ToxA-B7. The composition may also comprise a combination of i) a ToxA-GT antigen and a ToxB-GT antigen and (ii) at least one TcdA antigen selected from ToxA-B, ToxA-PTA2, ToxA-P5-7, ToxA-P5-6, ToxA-P9-10, ToxA-B2, ToxA-B3, ToxA-B5 and/or ToxA-B6; and at least one TcdB antigen selected from ToxB-B, ToxB-B2 antigen, and/or ToxA-B7.

The composition may further comprise e.g. 1, 2, 3, 4, 5, 6, 7, 8, 9, 10 or more additional fragments. Such further fragments are preferably selected from TcdA antigen group and/or from the TcdB antigen group.

Hybrid Polypeptides

The antigens in the composition may be present as individual separate polypeptides and/or “hybrid” polypeptides. In some embodiments, none of the antigens are in the form of hybrid polypeptides. In some embodiments, none of the antigens are in the form of hybrid polypeptides. Hybrid polypeptides (also referred to herein as chimeras, or chimeric proteins) are described in more detail below.

The antigens may be present in the compositions of the invention as individual separate polypeptides (i.e. mixed together). As an alternative, compositions of the invention comprise a “hybrid” polypeptide, where at least two (e.g. 2, 3, 4, 5, or more) antigens are expressed as a single polypeptide chain. Compositions of the invention may also comprise at least one individual separate polypeptide antigens and at least one hybrid polypeptide. Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

Hybrid polypeptides may comprise a ToxB-GT antigen and one or more TcdA antigens. The hybrid polypeptide thus comprises two or more antigens that are not the same. Thus, the hybrid polypeptide may comprise amino acid sequences from i.e. 2, 3, 4, 5, 6, 7, 8, 9, 10 or more different antigens, and may comprise multiple copies of each antigen i.e. 2, 3, 4, 5, 6, 7, 8, 9, 10, or more copies.

Hybrid polypeptides may comprise a ToxA-GT antigen and one or more TcdB antigens. The hybrid polypeptide thus comprises two or more antigens that are not the same. Thus, the hybrid polypeptide may comprise amino acid sequences from i.e. 2, 3, 4, 5, 6, 7, 8, 9, 10 or more different antigens, and may comprise multiple copies of each type of fragment i.e. 2, 3, 4, 5, 6, 7, 8, 9, 10, or more copies.

The TcdA antigens are preferably selected from the TcdA antigen group, e.g. the hybrid polypeptide may comprise 1, 2, 3, 4, 5, 6, 7, 8, 9, 10, 11, 12, 13, 14, 15 or 16 of the antigens in the TcdA antigen group. The TcdB antigens are preferably selected from the TcdB antigen group, e.g. the hybrid polypeptide may comprise 1, 2, 3, 4, 5, 6, 7 or 8 of the antigens in the TcdB antigen group.

Different hybrid polypeptides may be mixed together in a single formulation. Hybrids may be combined with non-hybrid antigens. Within such combinations, a TcdA/TcdB antigen may be present in more than one hybrid polypeptide and/or as a non-hybrid polypeptide. Preferably, a TcdA/TcdB antigen is present either as a hybrid or as a non-hybrid, but not as both.

The hybrid polypeptides can also be combined with conjugates or non-*C. difficile* antigens.

Hybrid polypeptides can be represented by the formula $NH_2$-A-{-X-L-}$_n$-B-COOH, wherein: X is an amino acid sequence of a toxin fragment, preferably a toxoid fragment, as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a -X- moiety has a leader polypeptide sequence in its wild-type form, this may be included or omitted in the hybrid protein. In some embodiments, the leader polypeptides will be deleted except for that of the -X- moiety located at the N-terminus of the hybrid protein i.e. the leader polypeptide of $X_1$ will be retained, but the leader polypeptides of $X_2$ . . . $X_n$ will be omitted. This is equivalent to deleting all leader polypeptides and using the leader polypeptide of $X_1$ as moiety -A-.

For each n instances of {-X-L-}, linker amino acid sequence -L- may be present or absent. For instance, when n=2 the hybrid may be $NH_2$-$X_1$-$L_1$-$X_2$-$L_2$-COOH, $NH_2$-$X_1$-$X_2$-COOH, $NH_2$-$X_1$-$L_1$-$X_2$-COOH, $NH_2$-$X_1$-$X_2$-$L_2$-COOH, etc. Linker amino acid sequence(s)-L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short polypeptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO:25) or GSGSGGGG (SEQ ID NO:26), with the Gly-Ser dipeptide being formed from a BamHI restriction site, thus aiding cloning and manipulation, and the $(Gly)_4$ tetrapeptide being a typical poly-glycine linker. Other suitable linkers, particularly for use as the final $L_n$ are a Leu-Glu dipeptide or SEQ ID NO: 27.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short polypeptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

-B- is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short polypeptide sequences which facilitate cloning or purification (e.g. comprising histidine tags i.e. $His_n$ where n=3, 4, 5, 6, 7, 8, 9, 10 or more), or sequences which enhance protein stability. Other suitable C-terminal amino acid sequences will be apparent to those skilled in the art.

For example, the invention provides a hybrid polypeptide ("B4 hybrid") consisting of ToxB-GT (SEQ ID NO: 18) fused to ToxA-P5-6 (SEQ ID NO: 11) via a peptide linker (SEQ ID NO: 25). A schematic representation of the B4 hybrid is provided in FIG. 7 (SEQ ID NO: 24, encoded by the nucleic acid sequence of SEQ ID NO: 53).

The hybrid polypeptides of the invention are typically not holotoxins, i.e. they do not comprise all of the functional domains (GT, CP, T and B) present in a native toxin or holotoxin. For example, where a hybrid polypeptide comprising a ToxB-GT antigen also comprises a binding domain fragment of TcdB (e.g. ToxB-B, ToxB-B2 and/or ToxB-B7), the hybrid does not comprise the CP and T domains of Tcd B in the order in which they are found in a native toxin B. Similarly, where a hybrid polypeptide comprising a ToxA-GT antigen also comprises a binding domain fragment of TcdA (e.g. ToxA-B, ToxA-PTA2, ToxA-P5-7, ToxA-P5-6, ToxA-P9-10, ToxA-B2, ToxA-B3, ToxA-B5 and/or ToxA-B6), the hybrid does not comprise the CP and T domains of TcdA in the order in which they are found in a native toxin A.

In some embodiments, the functional domains in a hybrid polypeptide are in a different order from N-terminus to C-terminus to the order of the functional domains found in the native toxin e.g. the T domain may be N-terminal of the GT domain.

Similarly, the TcdA and TcdB fragments may be in any order. For example, where a hybrid polypeptide comprises two TcdA antigens and one TcdB antigen, they may be in the order A-A-B, A-B-A, B-A-A from N-terminus to C-terminus, or where a hybrid polypeptide comprises two TcdB antigens and one TcdA antigen, they may be in the order B-B-A, B-A-B, A-B-B from N-terminus to C-terminus. In general, TcdA and TcdB antigens may alternate e.g. A-B-A or B-A-B.

In particular, the hybrid polypeptide preferably does not comprise the ToxB-ED and ToxB-T domains of TcdB fused to the ToxA-B domain of TcdA, wherein the B-domain of TcdA is fused to the C-terminus of the T-domain of TcdB, either directly or via a linker (e.g. a modified full length TcdB, wherein the B-domain of TcdB is substituted for the B-domain of TcdA). The hybrid polypeptide preferably does not comprise the GT domain of TcdB fused to the CP, T and B domains (in N-C direction) of TcdA, wherein the GT-domain of TcdB is fused to the C-terminus of the CP-domain of TcdA, either directly or via a linker (e.g. a modified full length TcdA, wherein the GT-domain of TcdA is substituted for the GT-domain of TcdB). The hybrid polypeptide preferably does not comprise the B-domain of TcdA fused to the GT, CP and T domains (in N-C direction) of TcdB, wherein the B-domain of TcdA is fused to the C-terminus of the GT-domain of TcdB, either directly or via a linker.

Preparing Compositions of the Invention

The invention also provides a process for preparing a composition of the invention comprising a step of mixing antigens of any of the combinations of antigens as defined above. For example, the invention provides a process comprising a step of mixing (i) a ToxA-GT antigen and (ii) one or more (i.e. 1, 2, 3, or 4) TcdB antigens, and optionally (iii) one or more (i.e. 1, 2, 3, or 4) further TcdA antigens. For example, the process may comprise a step of mixing a ToxA-GT antigen and one or more antigens selected from the TcdB antigen group and optionally one or more antigens selected from the TcdA antigen group.

The invention also provides a process comprising a step of mixing (i) a ToxB-GT antigen and (ii) one or more (i.e. 1, 2, 3, or 4) TcdA antigens, and optionally (iii) one or more (i.e. 1, 2, 3, or 4) TcdB antigens. For example, the process may comprise a step of mixing a polypeptide comprising a ToxB-GT antigen and one or more antigens selected from the TcdA antigen group and optionally one or more antigens selected from the TcdB antigen group.

A process according to the invention for preparing a mixture of TcdA and TcdB antigens may comprise a further step of formulating the mixture of a combination of TcdA and TcdB antigens of the invention as a medicament, e.g. as a vaccine. Such processes may further comprise a step of packaging the formulation for storage or distribution as a medicament, e.g. as a vaccine.

Polypeptides Used with the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides used with the invention can be prepared by various means (e.g. recombinant expression, purification from cell culture, chemical synthesis, etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other *C. difficile* or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

Polypeptides used with the invention are preferably *C. difficile* polypeptides.

Polypeptides used with the invention are preferably isolated or purified.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence -P-Q- or -Q-P-, wherein: -P- is an amino acid sequence as defined above and -Q- is not a sequence as defined above i.e. the invention provides fusion proteins. Where the N-terminus codon of -P- is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more), maltose-binding protein, or glutathione-S-transferase (GST).

The invention also provides a process for producing a polypeptide of the invention, comprising the step of culturing a host cell transformed with nucleic acid of the invention under conditions which induce polypeptide expression.

Although expression of the polypeptides of the invention may take place in a *C. difficile*, the invention will usually use a heterologous host for expression (recombinant expression). The heterologous host may be prokaryotic (e.g. a bacterium) or eukaryotic. It may be *E. coli*, but other suitable hosts include *Brevibacillus chosinensis, Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc. Compared to the wild-type *C. difficile* genes encoding polypeptides of the invention, it is helpful to change codons to optimise expression efficiency in such hosts without affecting the encoded amino acids.

The invention provides a process for producing a polypeptide of the invention, comprising the step of synthesising at least part of the polypeptide by chemical means.

Nucleic Acids

The invention also provides compositions comprising nucleic acids (e.g. combinations of nucleic acids, vectors, or vector combinations) encoding the combinations of polypeptides or hybrid polypeptides of the invention described above.

Nucleotide sequences encoding combinations of antigens of the invention are known or may be designed according to the genetic code. Thus, in the context of the present invention, such a nucleotide sequence may encode one or more of the polypeptide sequences disclosed herein, or may encode an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more, e.g. 90% identity or more, or 95% identity or more, or 99% identity or more, to any of said polypeptides; and/or (b) comprising a fragment of at least 'n' consecutive amino acids of any of said polypeptides: 1, wherein 'n' is 7 or more (e.g. 8, 10, 12, 14, 16, 18, 20, 25, 30, 35, 40, 50, 60, 70, 80, 90, 100, 150, 200, 250 or more; e.g. 20 or more; or e.g. 50 or more; or e.g. 80 or more).

The native nucleotide sequences of the nucleic acids encoding all of the TcdA and TcdB antigens described above are given in the sequence listing and summarised in the sequence listing table. The nucleotide sequences encoding some of these antigens has been optimised using a codon optimisation process and optimised nucleotide sequences are also provided in some cases. Examples of codon optimised sequences include nucleic acid sequences comprising the nucleotide sequences of SEQ ID NOs: 55, 57, 59, 61, 63 and 65-69). The invention includes compositions comprising nucleic acids identified in the sequence listing table encoding the combinations of antigens described above. The invention also provides nucleic acid which can hybridize to these nucleic acids. Hybridization reactions can be performed under conditions of different "stringency". Conditions that increase stringency of a hybridization reaction of widely known and published in the art (e.g. page 7.52 of [42]). Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art [43, 44, 42, 45, etc.].

A nucleic acid may hybridize to a target under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

The invention includes nucleic acid comprising sequences complementary to these sequences (e.g. for antisense or probing, or for use as primers).

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids encoding antigens described herein are preferably provided in purified or substantially purified form i.e. substantially free from other nucleic acids (e.g. free from naturally-occurring nucleic acids), particularly from other *C. difficile* or host cell nucleic acids, generally being at least about 50% pure (by weight), and usually at least about 90% pure. Nucleic acids of the invention are preferably *C. difficile* nucleic acids.

Nucleic acids encoding antigens described herein may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acids may be attached to a solid support (e.g. a bead, plate, filter, film, slide, microarray support, resin, etc.). Nucleic acids may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. polypeptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids encoding antigens described herein may be part of a vector i.e. part of a nucleic acid construct designed for transduction/transfection of one or more cell types. Vectors may be, for example, “cloning vectors” which are designed for isolation, propagation and replication of inserted nucleotides, “expression vectors” which are designed for expression of a nucleotide sequence in a host cell, “viral vectors” which is designed to result in the production of a recombinant virus or virus-like particle, or “shuttle vectors”, which comprise the attributes of more than one type of vector. Preferred vectors are plasmids. A “host cell” includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

The term “complement” or “complementary” when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids encoding antigens described herein can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid encoding antigens described herein, wherein the nucleic acid is synthesised in part or in whole using chemical means.

The invention provides vectors comprising nucleotide sequences encoding antigens described herein (e.g. cloning or expression vectors) and host cells transformed with such vectors.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Strains and Variants

Antigens are defined above by reference to *C. difficile* ToxA and ToxB from *C. difficile* strain 630. The basic reference sequence for ToxA and ToxB can easily be found in public gene databases. For instance, GenBank accession number AM180355 is the complete *C. difficile* genome sequence, and the individual ToxA and ToxB sequences are given as “locus_tag” entries in the genome sequence’s “features” section. Functional annotations are also given in the databases.

Immunogenic compositions of the invention are useful for immunisation against CDAD caused by multiple different strains of *C. difficile*. The invention is not limited to compositions comprising fragments only from the 630 strain. Sequences of several strains of *C. difficile* are available, including those of *C. difficile* strains R20291(SM), *C. difficile* strain 196, *C. difficile* strain BII, *C. difficile* strain BI/NAP1/027 (ribotype 027), *C. difficile* strain M120 and *C. difficile* strain M68, strain 855, strain QCD-63q42, strain ATCC43255. Standard search and alignment techniques can be used to identify in any further genome sequences the homolog of any particular toxin sequence from the *C. difficile* strain 630. For example in strain ATCC43255, strain CIP107932, strain QCD-23 m63, strain QCD-32g58, strain QCD-37x79, strain QCD-63q42, strain QCD-66c26, strain QCD-76w55, strain QCD-97b34, strain CD196, strain CDBI1, strain CDCF5, strain CDSM, strain CDM68, strain CDM120 or strain R20291. Moreover, the available sequences from the *C. difficile* strain 630 can be used to design primers for amplification of homologous sequences from other strains. Thus the invention is not limited to polypeptides from this strain, but rather encompasses such variants and homologs from other strains of *C. difficile*, as well as non-natural variants. In general, suitable variants of a particular SEQ ID NO include its allelic variants, its polymorphic forms, its homologs, its orthologs, its paralogs, its mutants, etc.

Thus, for instance, polypeptides used with the invention may, compared to the strain 630 reference sequence, include one or more (e.g. 1, 2, 3, 4, 5, 6, 7, 8, 9, etc) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the strain 630 sequences. The polypeptides may also include one or more (e.g. 1, 2, 3, 4, 5, 6, 7, 8, 9, etc.) insertions (e.g. each of 1, 2, 3, 4 or 5 amino acids) relative to the TcdA and/or TcdB sequences.

Similarly, a polypeptide used with the invention may comprise an amino acid sequence that:

(a) is identical (i.e. 100% identical) to a sequence disclosed in the sequence listing;

(b) shares sequence identity (e.g. 60%, 65%, 70%, 75%, 80%, 85%, 90%, 91%, 92%, 93%, 94%, 95%, 96%, 97%, 98%, 99%, 99.5% or more) with a sequence disclosed in the sequence listing;

(c) has 1, 2, 3, 4, 5, 6, 7, 8, 9 or 10 (or more) single amino acid alterations (deletions, insertions, substitutions), which may be at separate locations or may be contiguous, as compared to the sequences of (a) or (b); and (d) when aligned with a particular sequence from the sequence listing using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [46], using default parameters (e.g. with Gap opening penalty=10.0, and with Gap extension penalty=0.5, using the EBLOSUM62 scoring matrix). This algorithm is conveniently implemented in the needle tool in the EMBOSS package [47].

In general, when a polypeptide of the invention comprises a sequence that is not identical to a complete *C difficile* sequence from the sequence listing (e.g. when it comprises a sequence listing with <100% sequence identity thereto, or when it comprises a fragment thereof) it is preferred in each individual instance that the polypeptide can elicit an antibody that recognises its respective toxin (either TcdA or TcdB), preferably the complete *C. difficile* sequence provided in the sequence listing.

Where hybrid polypeptides are used, the individual antigens within the hybrid (i.e. individual -X-moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus.

Immunogenic Compositions and Medicaments

The term "immunogenic" in the context of an antigen described herein is used to mean that the antigen is capable of eliciting an immune response, such as a cell-mediated and/or an antibody response, against the wild-type *C. difficile* protein from which it is derived, for example, when used to immunise a subject (preferably a mammal, more preferably a human or a mouse).

An immunogenic composition of the invention comprises an antigen according to the invention. Immunogenic compositions of the invention may be useful as vaccines. Vaccines according to the invention may either be prophylactic (i.e. to prevent infection) or therapeutic (i.e. to treat infection), but will typically be prophylactic. The term "protected against infection" means that the immune system of a subject has been primed (e.g. by vaccination) to to trigger an immune response and repel the infection. A vaccinated subject may thus get infected, but is better able to repel the infection than a control subject.

Compositions may thus be pharmaceutically acceptable. They will usually include components in addition to the antigens e.g. they typically include one or more pharmaceutical carrier(s) and/or excipient(s). A thorough discussion of such components is available in [48].

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 μg/ml) mercurial material e.g. thiomersal-free. Vaccines containing no mercury are more preferred. Preservative-free vaccines are particularly preferred.

To improve thermal stability, a composition may include a temperature protective agent. Further details of such agents are provided below.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminium hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, further discussed below.

Adjuvants which may be used in compositions of the invention include, but are not limited to:

- mineral salts, such as aluminium salts and calcium salts, including hydroxides (e.g. oxyhydroxides), phosphates (e.g. hydroxyphosphates, orthophosphates) and sulphates, etc. [e.g. see chapters 8 & 9 of ref. 49];
- oil-in-water emulsions, such as squalene-water emulsions, including MF59 (5% Squalene, 0.5% Tween 80, and 0.5% Span 85, formulated into submicron particles using a microfluidizer) [Chapter 10 of ref. 49, see also ref. 50-53, chapter 10 of ref. 54 and chapter 12 of ref. 55], complete Freund's adjuvant (CFA) and incomplete Freund's adjuvant (IFA);
- saponin formulations [chapter 22 of ref. 49], such as QS21 [56] and ISCOMs [chapter 23 of ref. 49];
- virosomes and virus-like particles (VLPs) [57-63];
- bacterial or microbial derivatives, such as non-toxic derivatives of enterobacterial lipopolysaccharide (LPS), Lipid A derivatives [64, 65], immunostimulatory oligonucleotides [66-71], such as IC-31™ [72] (deoxynucleotide comprising 26-mer sequence 5'-(IC)$_{13}$-3' (SEQ ID NO:28) and polycationic polymer polypeptide comprising 11-mer amino acid sequence KLKLLLLLKLK (SEQ ID NO:29)) and ADP-ribosylating toxins and detoxified derivatives thereof [73-82];
- human immunomodulators, including cytokines, such as interleukins (e.g. IL-1, IL-2, IL-4, IL-5, IL-6, IL-7, IL-12 [83, 84], interferons (e.g. interferon-γ), macrophage colony stimulating factor, and tumor necrosis factor;
- bioadhesives and mucoadhesives, such as chitosan and derivatives thereof, esterified hyaluronic acid microspheres [85] or mucoadhesives, such as cross-linked derivatives of poly(acrylic acid), polyvinyl alcohol, polyvinyl pyrollidone, polysaccharides and carboxymethylcellulos [86];
- microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.);
- liposomes [Chapters 13 & 14 of [49, 87-89];
- polyoxyethylene ethers and polyoxyethylene esters [90];
- PCPP formulations [91 and 92];
- muramyl polypeptides, including N-acetyl-muramyl-L-threonyl-D-isoglutamine (thr-MDP), N-acetyl-normuramyl-1-alanyl-d-isoglutamine (nor-MDP), and N-acetylmuramyl-1-alanyl-d-isoglutaminyl-1-alanine-2-(1'-2'-dipalmitoyl-sn-glycero-3-hydroxyphosphoryloxy)-ethylamine MTP-PE); and
- imidazoquinolone compounds, including Imiquamod and its homologues (e.g. "Resiquimod 3M") [93 and 94].

Immunogenic compositions and vaccines of the invention may also comprise combinations of aspects of one or more of the adjuvants identified above. For example, the following adjuvant compositions may be used in the invention: (1) a saponin and an oil-in-water emulsion [95]; (2) a saponin (e.g. QS21)+a non-toxic LPS derivative (e.g. 3dMPL) [96]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [97]; (5) combinations of 3dMPL with, for example, QS21 and/or oil-in-water emulsions [98]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of [49].

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used (this has been reported as effective in pneumococcal immunisation [99]).

The compositions of the invention may elicit both a cell mediated immune response as well as a humoral immune response. This immune response will preferably induce long lasting (e.g. neutralising) antibodies and a cell mediated immunity that can quickly respond upon exposure to *C. difficile*.

Two types of T cells, CD4 and CD8 cells, are generally thought necessary to initiate and/or enhance cell mediated immunity and humoral immunity. CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic polypeptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

The compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 100, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20,000 Da. In a preferred embodiment, the polyethylene glycol can have an average molecular weight of about 300 Da ('PEG-300').

Compositions of the invention may be formed by mixing (i) an aqueous composition comprising two or more (e.g. 2, 3, or 4) antigen(s) of the antigen combinations of the invention with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising two or more (e.g. 2, 3, or 4) antigen(s) of the antigen combinations of the invention, with (ii) a liquid composition comprising the temperature protective agent. Thus component (ii) can be used to reconstitute component (i).

Methods of Treatment, and Administration of the Vaccine

The invention also provides a method for raising an immune response in a mammal comprising the step of administering an effective amount of a composition of the invention.

The invention also provides an immunogenic composition comprising a combination of *Clostridium difficile* antigens, said combination comprising a) a ToxB-GT antigen and a TcdA antigen (e.g. 1, 2, 3, 4, 5, 6, 7, 8, 9, 10, 11, 12, 13, 14 or more polypeptide fragments of TcdA); and/or b) ToxA-GT antigen and a TcdB antigen (e.g. 1, 2, 3, 4, 5, 6, 7, or more polypeptide fragments of TcdB) for use as a medicament e.g. for use in raising an immune response in a mammal. Particular immunogenic compositions comprise a combination of *Clostridium difficile* antigens, said combination comprising (i) ToxB-GT antigen and ToxA-P5-6 antigen or (ii) ToxB-GT antigen and ToxA-B2 antigen for use as a medicament e.g. for use in raising an immune response in a mammal.

The invention also provides an immunogenic composition comprising a combination of *Clostridium difficile* antigens, said combination comprising a) a ToxB-GT antigen and a TcdA antigen (e.g. 1, 2, 3, 4, 5, 6, 7, 8, 9, 10, 11, 12, 13, 14 or more polypeptide fragments of TcdA); and/or b) a ToxA-GT antigen and a TcdB antigen (e.g. 1, 2, 3, 4, 5, 6, 7, or more polypeptide fragments of TcdB) in the manufacture of a medicament for raising an immune response in a mammal. Particular immunogenic compositions comprise a combination of *Clostridium difficile* antigens, said combination comprising (i) ToxB-GT antigen and ToxA-P5-6 antigen or (ii)

ToxB-GT antigen and ToxA-B2 antigen in the manufacture of a medicament for raising an immune response in a mammal.

The immune response is preferably protective and preferably involves antibodies and/or cell-mediated immunity. The method may raise a booster response.

By raising an immune response in the mammal by these uses and methods, the mammal can be protected against *C. difficile* infection. More particularly, the mammal may be protected against CDAD, including one or more of diarrhoea, antibiotic associated diarrhoea (AAD), abdominal pain, fever, leukocytosis, pseudomembranous colitis or toxic megacolon. Compositions of the invention are effective against *C. difficile* of various different serotypes. Compositions of the invention may be useful in protecting against CDAD resulting from *C. difficile* strains 630, B1, B1/NAP1/027 (ribotype 027), R20291(SM), 196, BI1, M120 M68, 855, QCD-63q42, ATCC43255, CIP107932, QCD-23 m63, QCD-32g58, QCD-37x79, QCD-63q42, QCD-66c26, QCD-76w55, QCD-97b34, CD196, CDBI1, CDCF5, CDSM, CDM68, CDM120 or R20291 etc.

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human, a large veterinary mammal (e.g. horses, cattle, deer, goats, pigs) and/or a domestic pet (e.g. dogs, cats, gerbils, hamsters, guinea pigs, chinchillas). Most preferably, the mammal is preferably a human. Immunogenic compositions according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

One way of checking efficacy of therapeutic treatment involves monitoring *C. difficile* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by challenging animal models of *C. difficile* infection, e.g., hamsters, guinea pigs or mice, with the vaccine compositions. One such model is described herein.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a pneumonia vaccine, measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc.

Mucosal Immunisation

The invention provides an immunogenic composition comprising (i) a polypeptide comprising ToxB-GT and one or more polypeptide fragments of TcdA (e.g. 1, 2, 3, 4, 5, 6, 7, 8, 9, 10, 11, 12, 13, 14 or more polypeptide fragments of TcdA) and/or a polypeptide comprising ToxA-GT and one or more polypeptide fragments of TcdB (e.g. 1, 2, 3, 4, 5, 6, 7, or more polypeptide fragments of TcdB), and (ii) a bacterial ADP-ribosylating toxins and or detoxified derivative thereof. The invention also provides a method for raising an immune response in a mammal comprising the step of administering an effective amount of such an immunogenic composition to the mammal.

Further Antigenic Components of Compositions of the Invention

The invention also provides compositions further comprising at least one further *C. difficile* antigen. Further *C. difficile* antigens include, for example, saccharide antigens. Saccharide antigens may be conjugated to peptides of the invention using standard conjugation techniques known in the art. A preferred saccharide antigen for use in compositions of the invention is the cell wall polysaccharide II (referred to herein as "PS-II"), thought to be a conserved surface antigen in *C. difficile*. The structure of the PS-II repeating unit is described in [101]:

[→6)-β-D-Glcp-(1→3)-β-D-GalpNAc-(1→4)-α-D-Glcp-(1→4)-[β-D-Glcp-(1→3]-β-D-GalpNAc-(1→3)-α-D-Manp-(1→P]

For example, a polypeptide described above (such as ToxB-GT) may be chemically conjugated to e.g. PS-II.

The invention also provides compositions further comprising at least one antigen that is not a *C. difficile* antigen.

In particular, the invention also provides a composition comprising a polypeptide or the invention and one or more of the following further antigens:

- a saccharide antigen from *N. meningitidis* serogroup A, C, W135 and/or Y (preferably all four).
- a saccharide or polypeptide antigen from *Streptococcus pneumoniae* [e.g. 102, 103, 104].
- an antigen from hepatitis A virus, such as inactivated virus [e.g. 105, 106].
- an antigen from hepatitis B virus, such as the surface and/or core antigens [e.g. 106, 107].
- a diphtheria antigen, such as a diphtheria toxoid [e.g. chapter 3 of ref. 108] or the $CRM_{197}$ mutant [e.g. 109].
- a tetanus antigen, such as a tetanus toxoid [e.g. chapter 4 of ref. 108].
- an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 110 & 111].
- a saccharide antigen from *Haemophilus influenzae* B [e.g. 112].
- polio antigen(s) [e.g. 113, 114] such as IPV.
- measles, mumps and/or rubella antigens [e.g. chapters 9, 10 & 11 of ref. 108].
- influenza antigen(s) [e.g. chapter 19 of ref. 108], such as the haemagglutinin and/or neuraminidase surface proteins.
- an antigen from *Moraxella catarrhalis* [e.g. 115].
- an protein antigen from *Streptococcus agalactiae* (group B *streptococcus*) [e.g. 116, 117].
- a saccharide antigen from *Streptococcus agalactiae* (group B *streptococcus*).
- an antigen from *Streptococcus pyogenes* (group A *streptococcus*) [e.g. 117, 118, 119].
- an antigen from *Staphylococcus aureus* [e.g. 120].

The composition may comprise one or more of these further antigens.

Toxic protein antigens may be detoxified where necessary (e.g. detoxification of pertussis toxin by chemical and/or genetic means [111]).

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Saccharide antigens are preferably in the form of conjugates. Carrier proteins for the conjugates include diphtheria toxin, tetanus toxin, the *N. meningitidis* outer membrane protein [121], synthetic polypeptides [122,123], heat shock proteins [124,125], pertussis proteins [126,127], protein D from *H. influenzae [*128], cytokines [129], lymphokines [129], streptococcal proteins, hormones [129], growth factors [129], toxin A or B from *C. difficile [*130], iron-uptake proteins [131], etc. A preferred carrier protein is the CRM197 mutant of diphtheria toxin [132].

Antigens in the composition will typically be present at a concentration of at least 1 μg/ml each. In general, the concentration of any given antigen will be sufficient to elicit an immune response against that antigen.

As an alternative to using proteins antigens in the immunogenic compositions of the invention, nucleic acid (preferably DNA e.g. in the form of a plasmid) encoding the antigen may be used.

Antigens are preferably adsorbed to an aluminium salt.

Antibodies

Antibodies against *C. difficile* TcdA and TcdB can be used for passive immunisation [e.g. 133, 134, 135, 136, 137, 138 and 139]. Thus the invention provides combinations of antibodies corresponding to, and specific to, the antigen combinations of the invention as disclosed herein. Preferably, the composition comprises an antibody that is specific to a ToxB-GT antigen, and/or an epitope thereof and an antibody that is specific to a TcdA antigen, and/or an epitope thereof; and/or an antibody that is specific to a ToxA-GT antigen, and/or an epitope thereof and an antibody that is specific to a TcdB antigen, and/or an epitope thereof. Combinations of antibodies according to the invention are provided for simultaneous, separate or sequential administration. The invention also provides and immunogenic and pharmaceutical compositions comprising such antibodies. Herein, in the context of the invention, the term "antibody" or "antibodies" comprises the combinations of antibodies of the invention. The invention also provides compositions comprising combinations of antibodies of the invention.

The invention also provides the use of antibodies of the invention in medicine and in therapy, e.g. for passive immunisation against CDAD. The invention also provides a method for treating a mammal comprising the step of administering an effective amount such a composition. As described above for immunogenic compositions, these methods and uses allow a mammal to be protected against CDAD. In particular, antibodies of the invention may be used in methods of treating or preventing infections by *C. difficile*, comprising the step of administering to the mammal an effective amount of a combination of antibodies as described herein, or a composition comprising such a combination. In these methods, the at least two (e.g. 2, 3, or 4) antibodies of the invention may be administered simultaneously, separately or sequentially.

The term "antibody" includes intact immunoglobulin molecules, as well as fragments thereof which are capable of binding an antigen. These include hybrid (chimeric) antibody molecules [140, 141]; F(ab')2 and F(ab) fragments and Fv molecules; non-covalent heterodimers [142, 143]; single-chain Fv molecules (sFv) [144]; dimeric and trimeric antibody fragment constructs; minibodies [145, 146]; humanized antibody molecules [147-149]; and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred. Antibodies and antibody combinations of the invention may be purified or isolated.

The invention also provides a process for preparing a mixture of a combination of antibodies of the invention, said process comprising a step of mixing antibodies of any of the combinations of antibodies as defined above. For example, the invention provides a process comprising a step of mixing at least two (i.e. 2, 3, or 4) antibodies selected from: (a) an antibody which recognises a ToxA-GT antigen, and/or an epitope thereof, and an antibody which a TcdB antigen and/or an epitope thereof. For example, the process may comprise a step of mixing an antibody which recognises a ToxA-GT antigen, and/or an epitope thereof, and an antibody which recognises a TcdB antigen and/or an epitope thereof. The invention also provides a process comprising a step of mixing at least two (i.e. 2, 3, or 4) antibodies selected from: (a) an antibody which recognises a ToxB-GT antigen, and/or an epitope thereof, and an antibody which recognises a TcdA antigen, and/or an epitope thereof. For example, the process may comprise a step of mixing an antibody which recognises a ToxB-GT antigen, and/or an epitope thereof, and an antibody which recognises a TcdA antigen and/or an epitope thereof. A process according to the invention for preparing a mixture of antibodies may comprise a further step of formulating the mixture as a medicament. Such processes may further comprise a step of packaging the formulation for storage or distribution as a medicament.

General

The practice of the present invention will employ, unless otherwise indicated, conventional methods of chemistry, biochemistry, molecular biology, immunology and pharmacology, within the skill of the art. Such techniques are explained fully in the literature. See, e.g., [150-157, etc].

Where the invention concerns an "epitope", this epitope may be a B-cell epitope and/or a T-cell epitope. Such epitopes can be identified empirically (e.g. using PEPSCAN [158,159] or similar methods), or they can be predicted (e.g. using the Jameson-Wolf antigenic index [160], matrix-based approaches [161], MAPITOPE [162], TEPITOPE [163, 164], neural networks [165], OptiMer & EpiMer [166, 167], ADEPT [168], Tsites [169], hydrophilicity [170], antigenic index [171] or the methods disclosed in [172-176, etc.]. Epitopes are the parts of an antigen that are recognised by and bind to the antigen binding sites of antibodies or T-cell receptors, and they may also be referred to as "antigenic determinants".

The terms "antigen" and "amino acid sequence", as they are used in this document, should be taken to include reference to each of the above sequences, as well as to their fragments, homologues, derivatives and variants. The term "toxin" refers to a poisonous substance, especially a protein, that is produced by living cells or organisms and is capable of causing disease when introduced into the tissues of a subject and is often capable of inducing production of neutralizing antibodies or antitoxins in a subject.

The term "toxoid" refers to a toxin or fragment thereof which has undergone "detoxification" or "toxoiding" (e.g. by recombinant means, by chemical modification etc.) but has maintained its ability to combine with, or induce production of anti-toxin antibodies e.g. when administered to a subject.

The term "neutralising titer" refers to a composition comprising "neutralising peptides" or "neutralising antibodies" that inhibit or neutralise the biological effect of an infectious body (e.g. a toxin).

Where an antigen "domain" is omitted, this may involve omission of a signal polypeptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y. The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The term "about" in relation to a numerical value x means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 177. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 178.

MODES FOR CARRYING OUT THE INVENTION

The inventors identified recombinant fragments of TcdA and TcdB which may be used as immunogens for use in a vaccine to prevent CDAD.

Fragments

Figure 1:
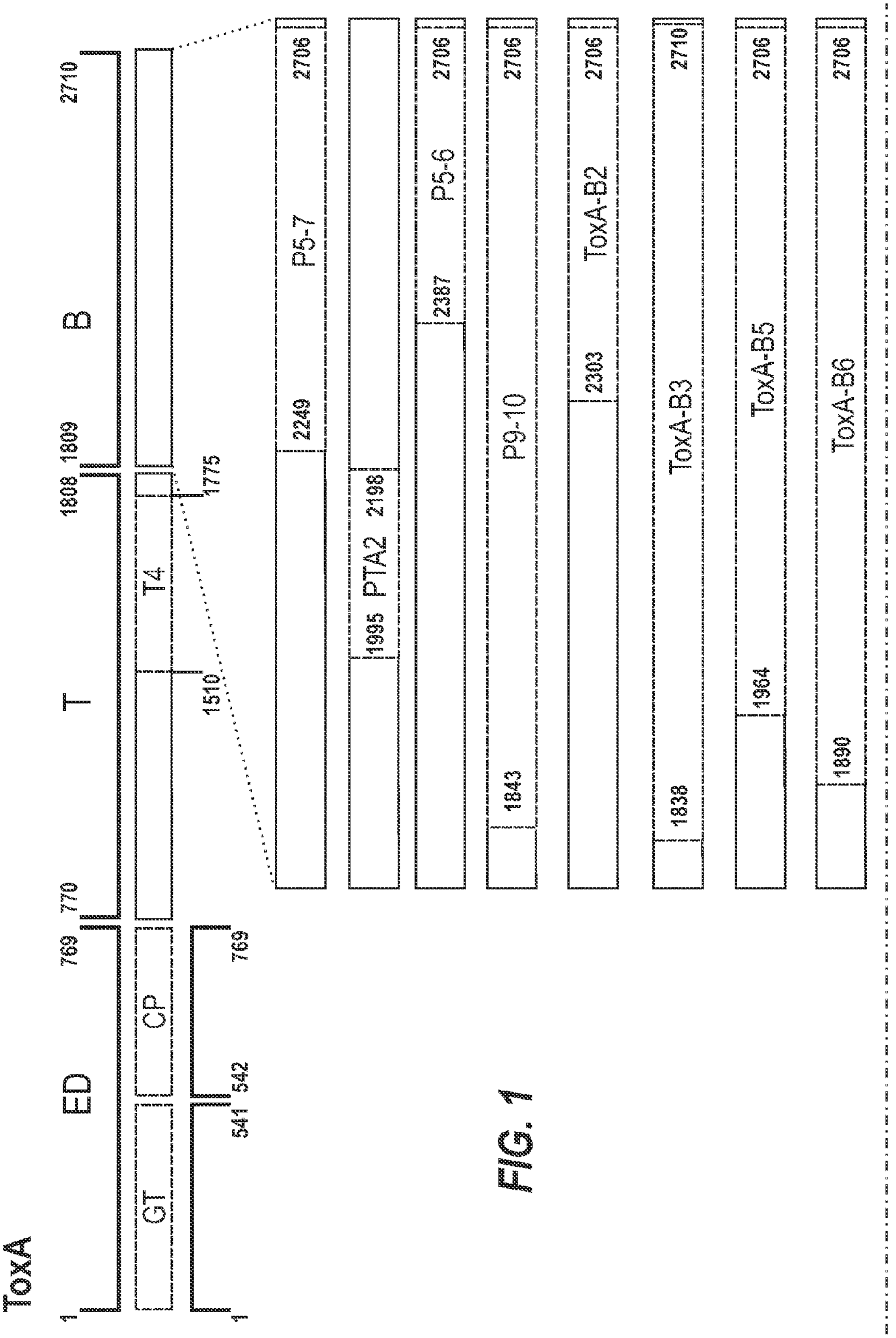
FIG. 1. Schematic representation of the recombinant toxin fragments used in this study. All polypeptides were expressed in *Escherichia coli*, except ToxA_GT, which was expressed in *Brevibacillus choshinensis*. ED=enzymatic domain; GT=glucosyl-transferase domain; CP=cysteine protease domain; T=translocation domain; B=binding domain. All domains are soluble, with the exception of the T4 and PTA2 domains of TcdA, which are insoluble.
Figure 2:
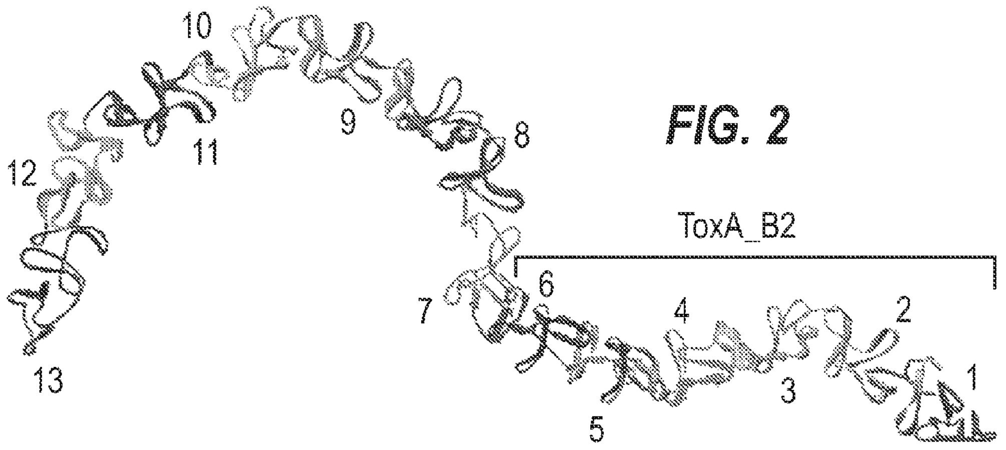
FIG. 2. ToxA-B2 was designed to include 6 of the 13 putative structural units forming the binding domain. The three-dimensional structure of the TcdA binding domain was predicted by computer modelling using the crystal structure of the C-terminal fragment as template (see reference 41, PDB code 2F6E).
Figure 3:
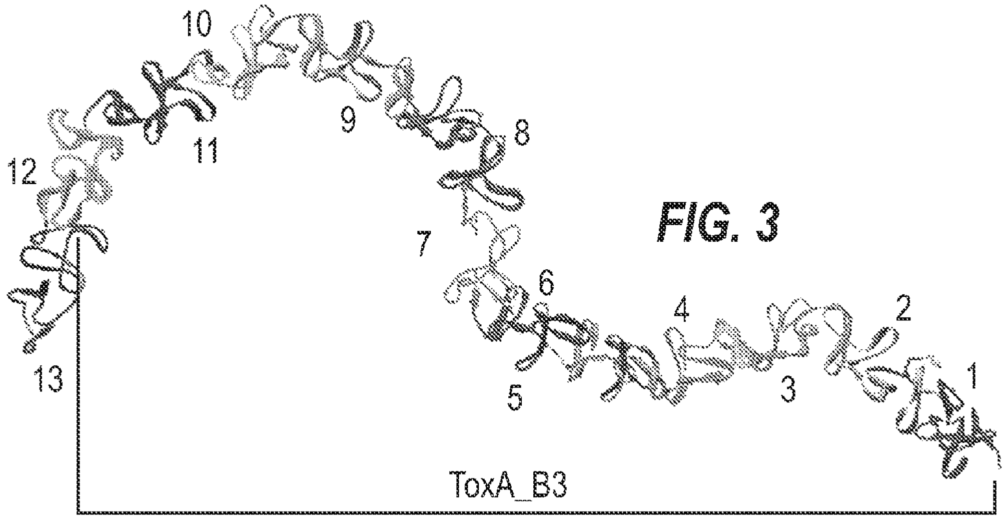
FIG. 3. ToxA-B3 was designed to include 12 of the 13 putative structural units forming the binding domain. The three-dimensional structure of the TcdA binding domain was predicted by computer modelling using the crystal structure of the C-terminal fragment as template (see reference 41, PDB code 2F6E).
Figure 4:
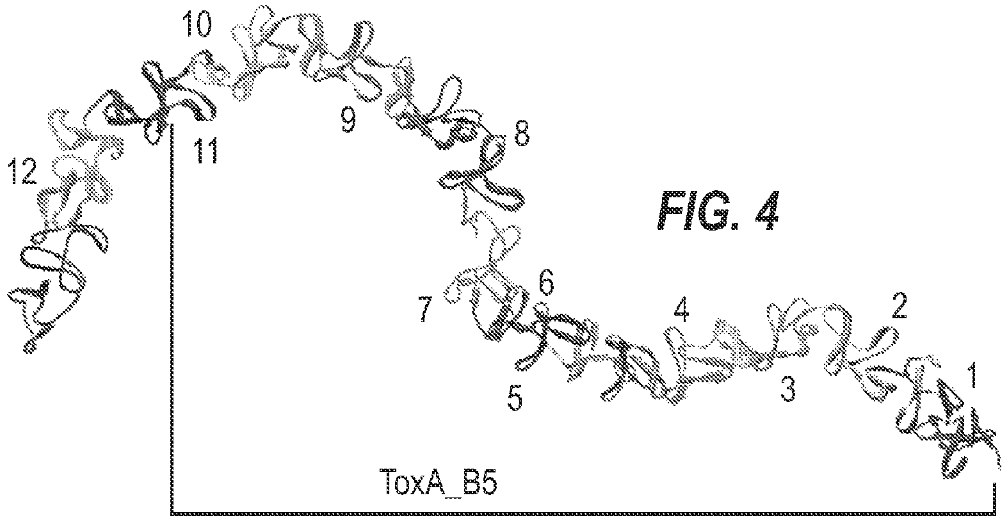
FIG. 4. ToxA-B5 was designed to include 10.5 of the 13 putative structural units forming the binding domain. The three-dimensional structure of the TcdA binding domain was predicted by computer modelling using the crystal structure of the C-terminal fragment as template (see reference 41, PDB code 2F6E).
Figure 5:
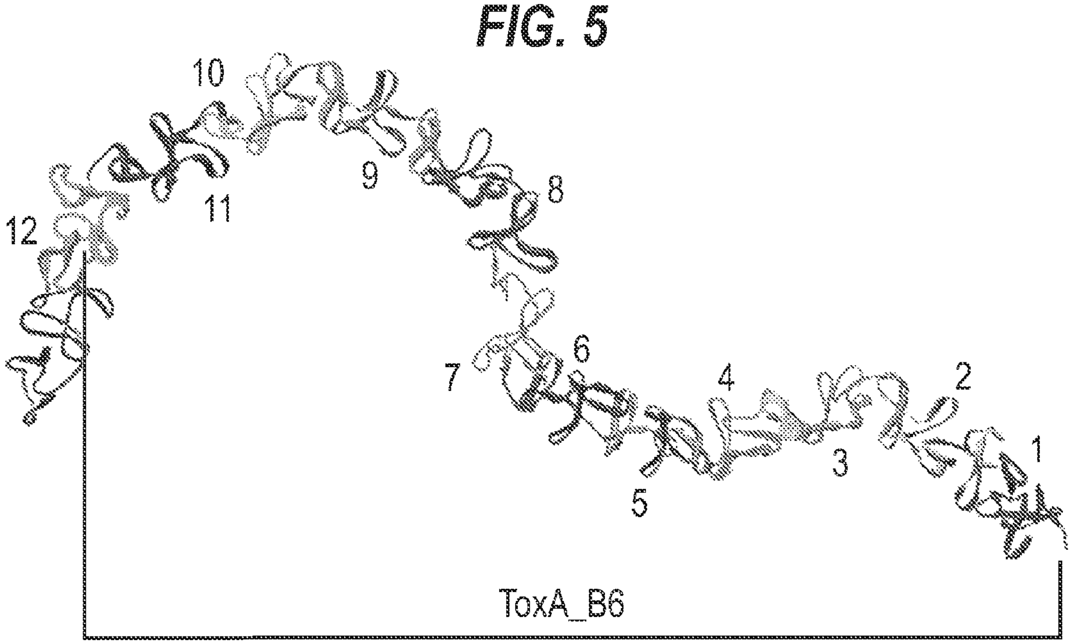
FIG. 5. ToxA-B6 was designed to include 11.5 of the 13 putative structural units forming the binding domain. The three-dimensional structure of the TcdA binding domain was predicted by computer modelling using the crystal structure of the C-terminal fragment as template (see reference 41, PDB code 2F6E).
Figure 6:
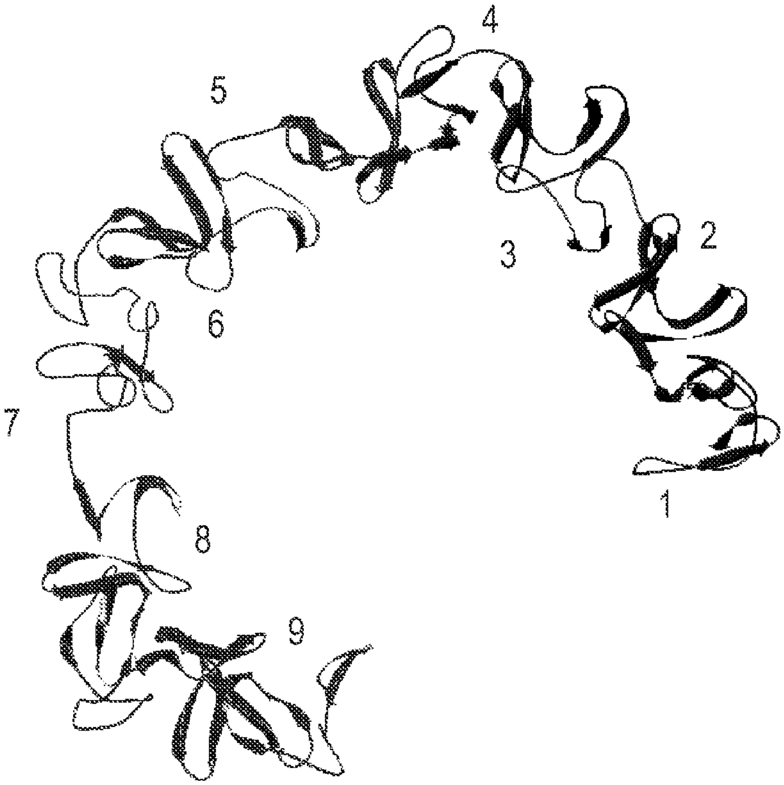
FIG. 6. ToxB-B2 was designed to include 4 of the 9 putative structural units forming the binding domain The three-dimensional structure of the TcdB binding domain was predicted by computer modelling using the crystal structure of the C-terminal fragment as template (see reference 41, PDB code 2F6E).
Figure 7:
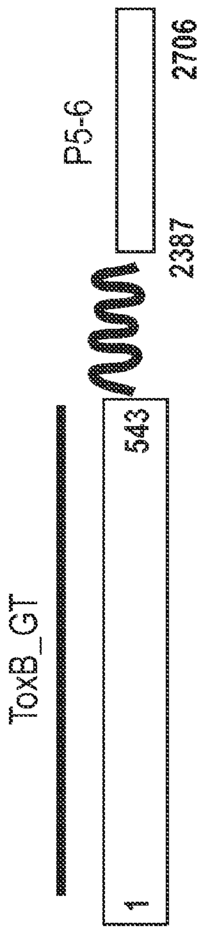
FIG. 7. Schematic representation of the B4 hybrid. ToxB_GT (SEQ ID NO: 18) is fused to ToxA-P5-6 (SEQ ID NO: 11) via a linker peptide (SEQ ID NO: 25).
Figure 8:
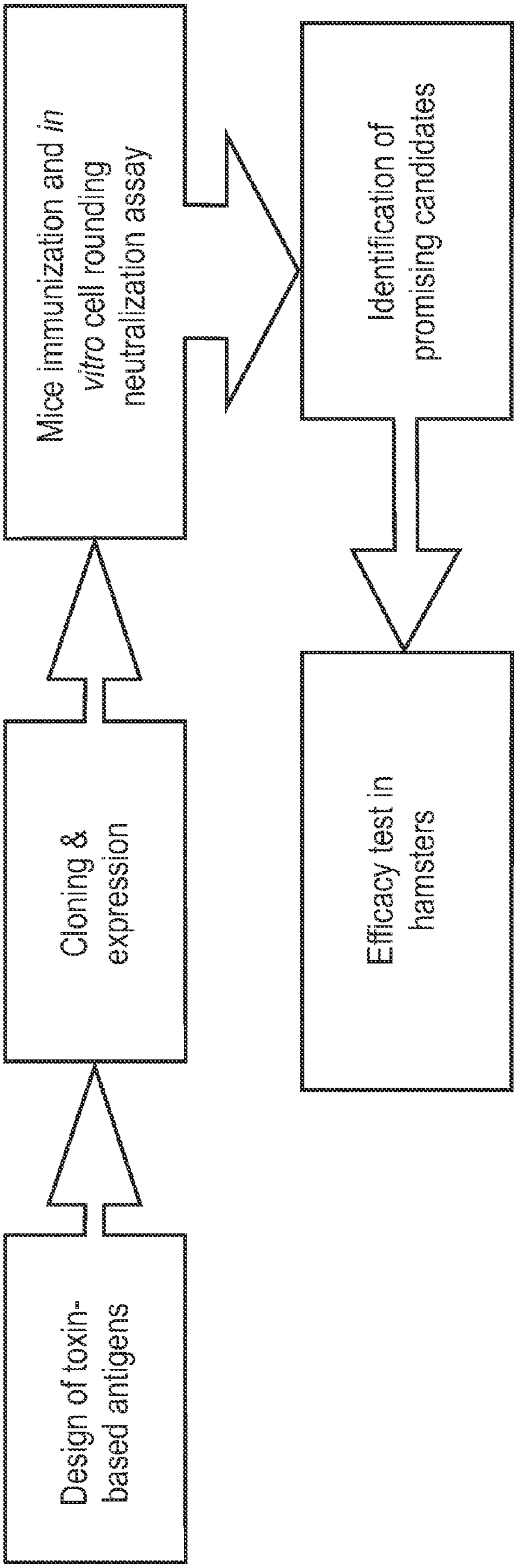
FIG. 8. Flow chart summarizing the experimental strategy used for the identification of candidate fragments.
Figure 37:
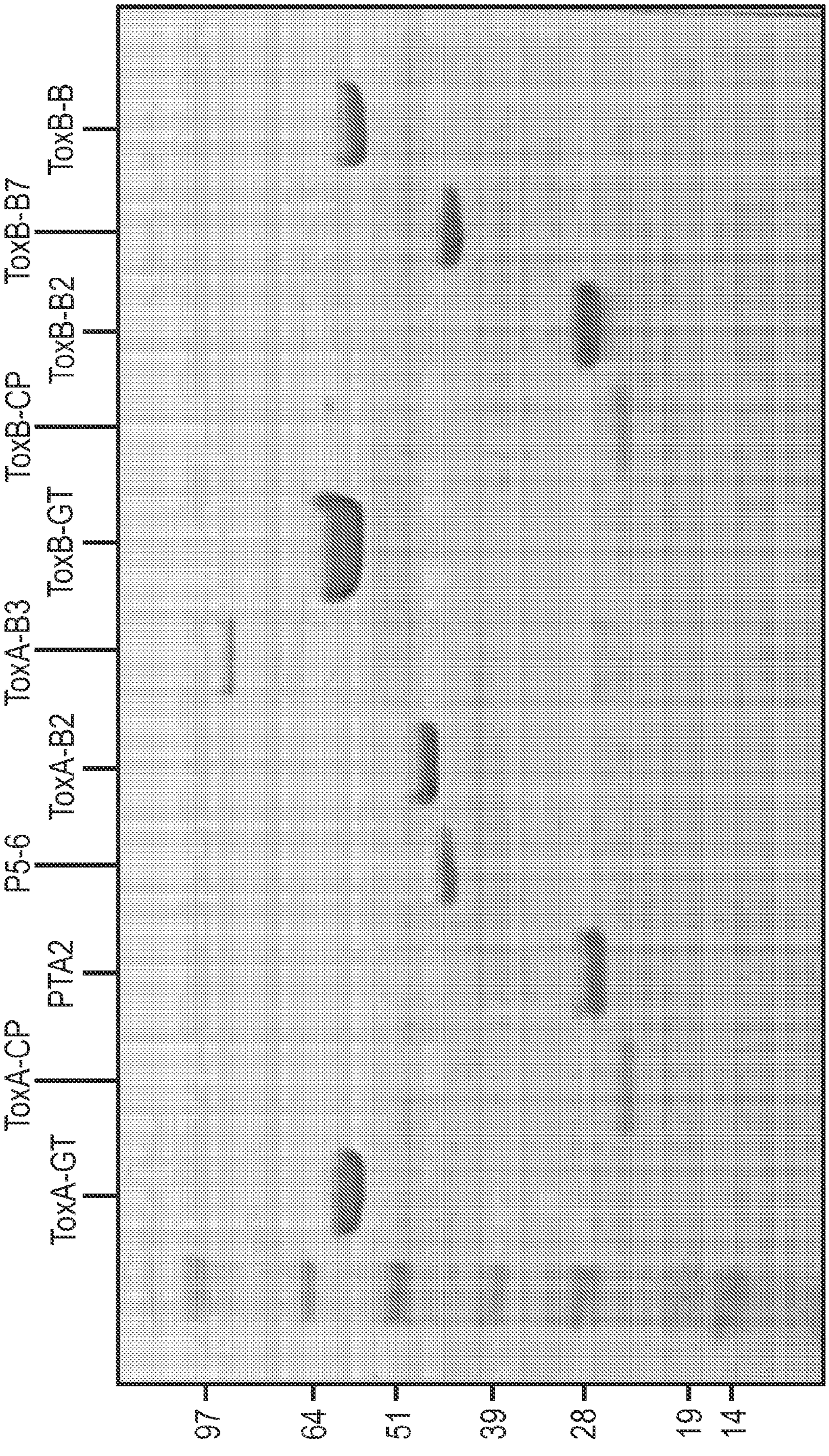
FIG. 37. SDS-PAGE gel of recombinant purified fragments.

A schematic representation of the experimental approach is provided in FIG. 8. The inventors designed a panel of toxin-based fragments of TcdA and TcdB (11 fragments of TcdA and 6 fragments of TcdB). The toxin-based fragments used in this study are described in FIG. 1. These fragments were chosen to cover as far as possible the whole lengths of TcdA and TcdB, and the boundaries of these fragments were determined on the basis of their crystal structures. In the case of the cell binding domains of ToxA and ToxB (see FIG. 1 for summary), computer models were used. By using recombinant techniques, it is possible to use an expression system e.g. *E. coli, Brevibacillus choshinensis*, etc., to easily generate polypeptide fragments and which are more stable and resistant to degradation than inactivated toxoids, as well also avoid many of the safety concerns regarding the use of inactivated toxoids. Fragments used in the examples comprising ToxA-GT or ToxB-GT were detoxified. A Coomassie-stained SDS-PAGE gel of peptides used for immunization is shown in FIG. 37.

Cloning, Expression and Purification of Recombinant Toxin Fragments

Sequences were cloned into the pet15b+ vector (Nterm-HIS tag) using the Polymerase Incomplete Primer Extension (PIPE) method. Normal PCR generates mixtures of incomplete extension products. Using simple primer design, short overlapping sequences were introduced at the ends of these incomplete extension mixtures which allow complementary strands to anneal and produce hybrid vector/insert combinations. All hybrids were transformed directly into *E. coli* HK100 recipient cells. Single ampicillin resistant colonies were selected and checked for the presence of recombinant plasmid by colony PCR. Competent *E. coli* BL21(DE3) cells were transformed with the plasmids purified from positive clones (ToxA_GT, was expressed in *Brevibacillus choshinensis*). The ToxA-p5-6 antigen was expressed as a hybrid polypeptide comprising the N-terminal amino acid sequence of SEQ ID NO 104 and the C-terminal amino acid sequence of SEQ ID NO 105. The amino acid sequence of this hybrid polypeptide is shown in SEQ ID NO 111. SEQ ID NO: 111 is encoded by the nucleic acid sequence of SEQ ID NO: 112.

The PIPE method was employed to generate ToxA-GT (Y283A, D285A, D287A), TcdA-CP (D589A, H655A and C700A, numbered relative to SEQ ID NO: 1), ToxB-GT (D270A, R273A, Y284A, D286A and D288A) and ToxB-CP (D587A, H653A and C698A) mutants with abrogated enzymatic activity.

Protein expression was induced by addition of 1 mM IPTG (isopropyl β-D-1-thiogalactopyranoside) to the culture during exponential growth phase, followed by incubation for 4 hours at 25° C. Cell extracts were loaded onto SDS—PAGE gels to check for protein expression (data not shown).

For ToxA_GT, the catalytic domain (residues 1-541) of the WT *C. difficile* Toxin A was cloned into pNI-His vector (Takara Bio). Site-directed mutagenesis was performed to obtain the (Y283A, D285A, D287A) ToxA-GT mutant. The plasmid was electroporated into the *B. choshinensis* HPD31-SP3 strain (Takara Bio). *B. choshinensis* expression cells were grown in TMNm at 25° C., 1600 rpm for 48 hours. The protein was purified by IMAC chromatography and than buffer-exchanged into PBS using PD-10 desalting column (GE). Protein quantification was performed by BCA assay.

For some experiments, PSII was conjugated to two different carrier proteins (*C. difficile* recombinant proteins: ToxA_B2 and ToxB_GT) after chemical modification of the mannose sugar of the repeating unit at the reducing end. First step was the mannose sugar reduction with 50 mM $NaBH_4$ (Sigma) in 10 mM NaPi buffer pH 9.0 at room temperature for 2 hours; the reduced PSII was purified by Sephadex G25 chromatography (G&E Healthcare) in water and then oxidized with 15 equivalent of $NaIO_4$ (Sigma) in 10 mM NaPi buffer pH 7.2 at room temperature for 2 hours at the dark. The oxidized PSII was then purified by Sephadex G25 chromatography (G&E Healthcare) in water. The oxidized PSII (10 mg/ml) was then conjugated to carrier proteins using a stoichiometry of 4:1 (weight PSII per weight Protein) in 200 mM NaPi/1M NaCl buffer pH 8.0, and in presence of $NaBH_3CN$ (2:1, weight PSII per weight $NaBH_3CN$). The mixture was incubated for 48-72 hours at 37° C., mixing very gently with a magnetic stirrer. Conjugates were purified from excess of unconjugated PSII using size exclusion Superdex 75 chromatography (G&E Healthcare) in 10 mM NaPi/10 mM NaCl buffer pH7.2. Conjugates were characterized by SDS-PAGE using 7% Tris-Acetate gels (NuPAGE, from Invitrogen) in NuPAGE Tris-Acetate SDS running buffer (20×, Invitrogen). Protein concentration was determined by MicroBCA protein assay kit (Thermo Scientific). Total saccharide concentration was determined by HPAEC-PAD analysis. Unconjugated saccharide was separated by SPE C4 hydrophobic interaction column (0.5 mL resin, Bioselect, Grace Vydac) and subsequently estimated by HPAEC-PAD analysis.

Purification and Inactivation of Toxoid A and Toxoid B

*C. difficile* strain VPI 10463 spore stocks were inoculated on BHIS plates (brain heart infusion supplemented with yeast extract [5 mg/ml] and L-cysteine [0.1%]) and incubated at 36° C. for 2 days. Colonies were added from prepared plate to the Tryptone-Yeast Extract-Mannitol (TYM) media and incubated for 16 hours at 35 C.° in anaerobic chamber. 200 μl of 90% glycerol was added together with 800 μl of the *C. difficile* culture (1 OD at 590 nm) to the 1-ml cryogenic vial. The vial was immediately placed in a −80° C. freezer for storage. 100 μl of glycerol stock was added to 10 ml TYM media and incubated for 16 Hours at 35° C. in anaerobic chamber. Each 1 liter of Tryptone-Yeast Extract (TY) media was inoculated with seed culture (1/100 dilution). Culture was incubated at 35° C. for 5 days in anaerobic chamber. Samples were then centrifuged at 3000 g for 15 minutes at 4° C., and filtered through a 0.22 μm pore size filter. The supernatant was then concentrated by tangential flow filtration.

Fraction I: AS50

80.03 g of ammonium sulphate were added to 6× concentrated culture supernatant from strain VPI 10463 in Tryptone Yeast extract medium (265 ml) over the course of 2 h at 0° C. (50% saturation). Stirring was continued for 3 h at 0° C., then the precipitate was sedimented by centrifugation at 10000 rpm, for 30 minutes at 4° C. The pellet was resuspended in buffer A and dialyzed at 4° C. against two changes of buffer (A: 50 mM Tris-HCl, pH 7.5, 50 mM NaCl; B: 50 mM Tris-HCl, pH7.5, 1 M NaCl) (2×1 l) yielding a final volume of 27 ml (Fraction I) conc. 6.118 mg/ml, mini BCA.

Fraction II: HiTrap Q HP, pH 7.5

ToxA and ToxB were separated by chromatography on 2×5 ml HiTrap Q HP columns, connected in series. A linear gradient from 0-100% B was applied with 30 CV, 2 ml/min. ToxA elutes around 20% B, ToxB around 50% B (data not shown). 20 μl of fractions I, 4, 14-44 were analyzed on 7% PAA gels in Tris-Acetate buffer (data not shown).

Fraction IIIb: HiTrap Q HP, pH 5.0

ToxB (Fraction IIb) was further purified by chromatography on HiTrap Q HP at pH 5.0. Buffer included C: 20 mM piperazine-HCl, pH 5.0, 50 mM NaCl; D, 20 mM piperazine-HCl, pH 5.0, 1 M NaCl. A segmented gradient was applied, 30-60% D, 15 CV. ToxB elutes at 40% D (data not shown). 10 μl of each fraction was analyzed on a 7% PAA gel in Tris-Acetate buffer (data not shown).

Fraction IIIa: HiTrap Q HP, pH 7.5

B was applied with 30 CV, 2 ml/min to a segmented gradient from 2-20%. ToxA elutes around 15% B. 20 μl of each fraction was analyzed on a 7% PAA gel in Tris-Acetate buffer (data not shown). Pool was dialyzed against 2 l 50 mM Tris-HCl, 50 mM NaCl, 4° C. over night. Final volume: 52 ml (Fraction IIIa).

A final quality control was performed.

For Western blots, preparations were loaded on a 7% Tris Acetate SDS-PAA gel, and transferred to nitrocellulose using the I-Blot machine (12 min transfer). Membranes were washed 3× in TBST, and blocked over night with 1% BSA (Promega) in TBST. Primary antibodies were added at 1:5000 for 1 h in TBST. Membranes were washed 3 times for 5 min in TBST. Secondary antibody (Promega anti-rabbit AP conjugate) was added at 1:8000 in TBST for 45 min. The blot was washed three times in TBST and two times for 5 min in MilliQ water. Blots were developed for 20 sec in stabilized AP substrate (Promega) (data not shown).

ToxA and Tox B preparations were found to be completely free of cross contamination.

For permanent storage, dialysis was performed. Dialysis buffer comprised 50 mM Tris-HCl, 500 mM NaCl and 10% Glycerol. Samples were dialyzed against 2 changes of 500 ml buffer. Samples were quantified after dialysis (data not shown).

Detoxification of Toxoids

Preparations were dialyzed against PBS. Tris could react with formaldehyde. Starting with 1.5 mg of each protein (ToxA: 1.5 mg corresponded. to 9.375 ml (9.7 ml) and ToxB: 1.5 mg corresponded to 4.411 ml (4.5 ml)). Samples were dialyzed against 1 l each of PBS, 40 h, 4° C. Tox A was dialyzed for 4 h against 20% PEG 20.000 in PBS. Volume was reduced to 3.7 ml Formylation of ToxA and ToxB MW of ToxA and B: is approximately 300 kDa. Preparations included 0.25 mg/ml of ToxA and 0.35 mg/ml of ToxB. Lysin stock comprised 1 M lysine.HCl in PBS. Summaries are included in Table 1 (a and b) below:

TABLE 1(a)

Summary of Toxoid A formulation

| | ToxA | Final Conc. |
|---|---|---|
| Protein | 3500 ul | 0.58. μM |
| Lysin (1M) | 279.6 | 56 mM |
| Formaldehyde (36.5%) | 8.2 | 10 mM |
| PBS | 1212.2 | |
| Total | 5000 | |

TABLE 1(b)

Summary of Toxoid B formulation

| | ToxB | Final Conc. |
|---|---|---|
| Protein | 4000 ul | 0.93 μM |
| Lysin (1M) | 50 | 10 mM |
| Formaldehyde (0.4%) | 150 | 3.9 mM |
| PBS | 800 | |
| Total | 5000 | |

After 120 h at 37° C. on a rotary shaker 1 ml each was withdrawn and dialyzed against 2×500 ml PBS for 2×24 h. Samples were confirmed as being activated using a cell-based toxicity assay (data not shown).

Immunisation of Mice

Fragments were then used to immunize mice, to determine whether the fragments are immunogenic.

For each antigen, two groups of 8 female CD1 mice were used. Each group was immunised with 10 ugrs of antigen, formulated in Alum adjuvant (group 1) or Freund's adjuvant. Immunisations were performed intraperitoneally at days 0, 21, and 35. Final bleeding and culling was performed at day 49. Total antibody response of mice immunised with toxin fragments was then determined by ELISA. Microtiter plates were coated with TcdA and TcdB and incubated with antibodies against fragments, followed by alkaline phosphatase-conjugated secondary antibodies. After addition of the substrate, (p-nitrophenyl phosphate or pNPP), plates were analyzed by a plate reader at a dual wavelength of 405/620-650 nm. Antibody titres were quantified via interpolation against a reference standard curve.

Figure 9:
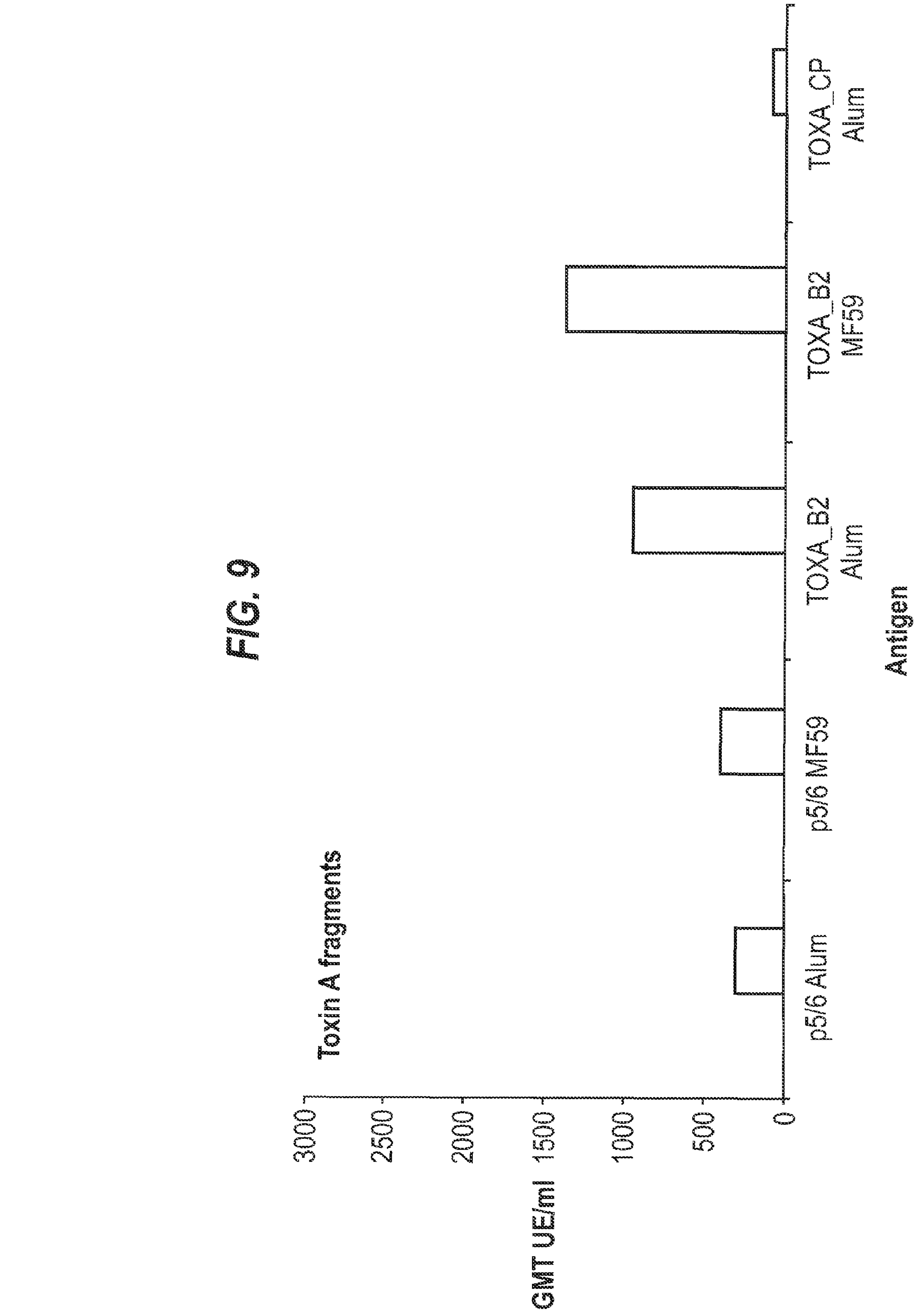
FIG. 9. Geometric mean titres (GMTs) of antibodies directed against sub-domains of TcdA (A) and TcdB (B), as determined by ELISA.
Figure 9:
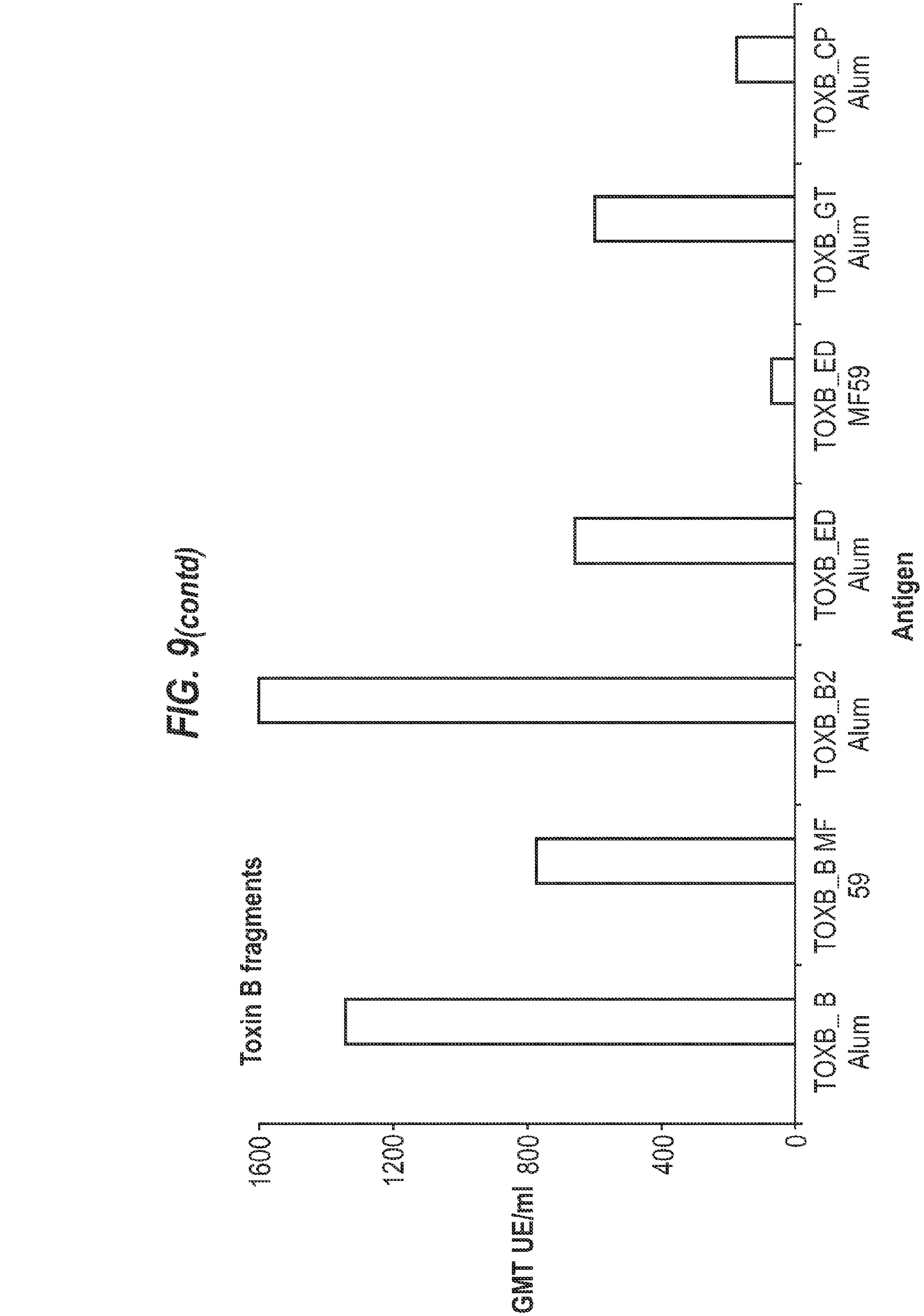
Figure 38A:
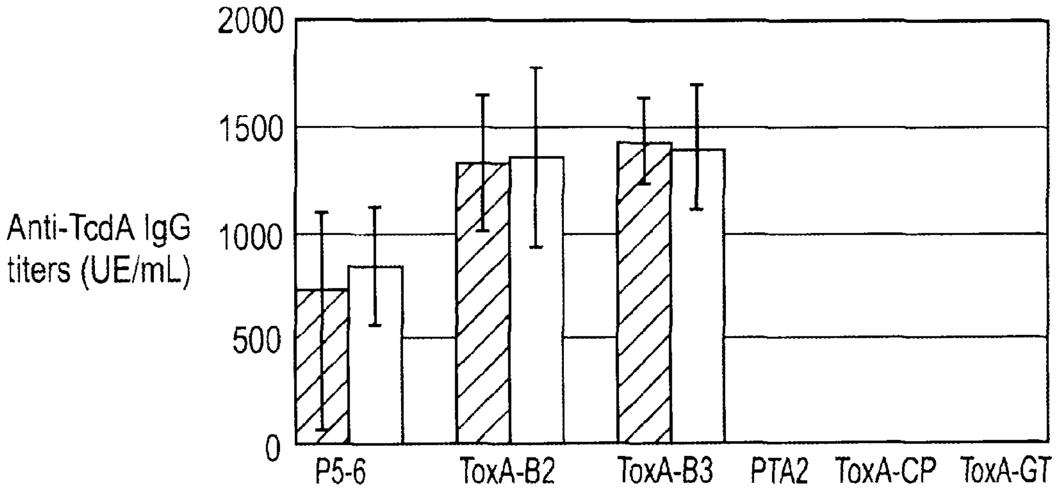
FIG. 38. Anti-ToxA (A) and ToxB (B) IgG titers (UE/mL), adjuvanted with Alum or MF59. IgG response after mice immunised with recombinant ToxA (A) and ToxB fragments (B). Anti toxin A and toxin B IgG titers were measured by ELISA in sera from mice immunized i.p. with each fragment with Al(OH)3 (left colmn in pair) or MF59 (right column in pair) adjuvant. Results are shown as geometric mean±SD on at least three experiments.
Figure 38B:
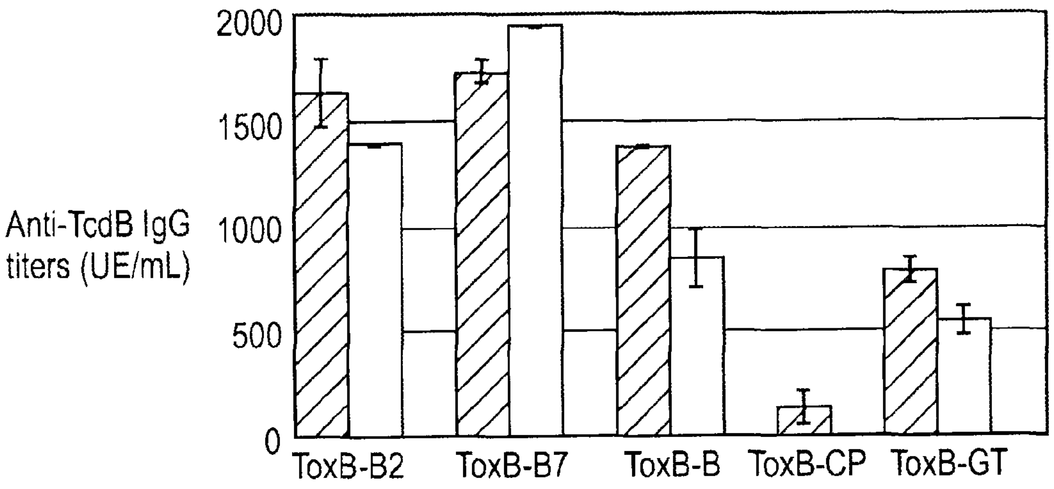

ELISA studies showing total antibody responses of mice immunized with toxin fragments are shown in FIG. 9. Interestingly, the ToxB-GT fragment was as immunogenic as the full length TcdB-ED domain. With the exception of ToxA-CP, all toxin fragments are immunogenic. The IgG responses (adjuvanted with Alum or MF59) are shown in FIG. 38.

In vitro Cell Rounding Neutralization Assay

The in vitro neutralization assay is based on evidence that *C. difficile* toxins destabilize the actin cytoskeleton causing a cytopathic effect with a typical cell rounding. Anti-toxin antibodies can neutralize the cytotoxicity, thus preventing the cell rounding. Immune sera were therefore used to evaluate the ability of the fragments to neutralize in vitro the toxic effects of TcdA and TcdB.

Human fibroblasts (IMR-90) were grown to 80-90% confluence. Each cell line has a different sensitivity to toxins, and so the minimal doses of TcdA and TcdB required to cause 100% cell rounding in 24 hours ($CTU_{100}$) were determined. $CTU_{100}$ was established as 20 ng/mL for TcdA and 10 pg/mL for TcdB. Two-fold dilutions of sera from 1:8 to 1:32,000 were pre-incubated with 1 $CTU_{100}$ of each toxin for 90 min at 37° C. Mixtures of sera plus toxins were then added to the cells, followed by observation after 16-18 hours. The endpoint titers represent the reciprocal of the highest dilution able to inhibit cell rounding. Positive controls were sera α-toxoid A and B and negative controls were the pre-immune sera and the sera from mice treated with adjuvant alone.

Results

Figure 10:
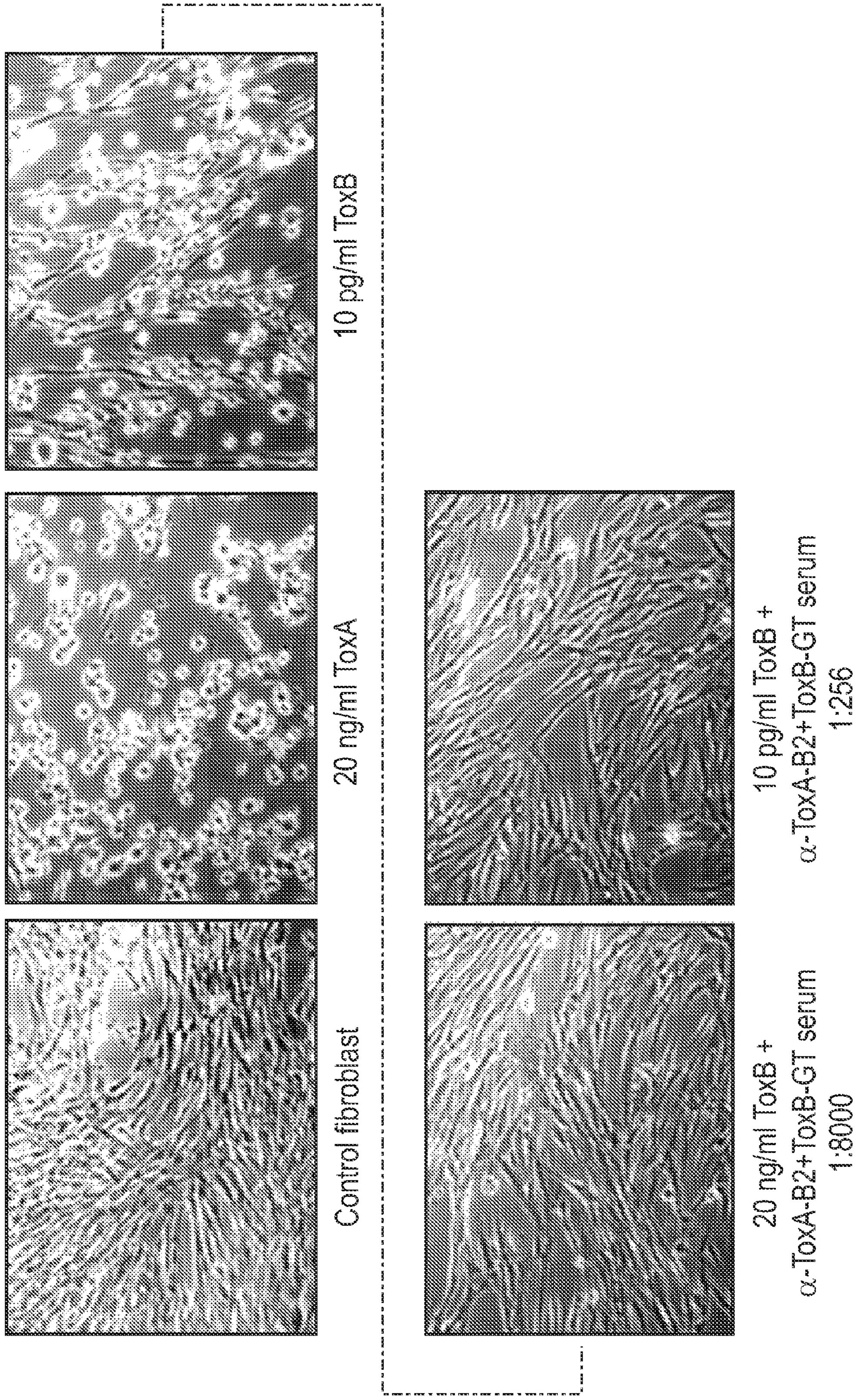
FIG. 10. Example of an in vitro neutralization experiment showing the TcdA/B-induced cell rounding and the neutralization by serum against ToxA_B2+ToxB-GT.

Neutralization titers are summarized in Tables 2 and 3, and the results of a typical neutralization experiment are shown in FIG. 10. Soluble fragments of ToxA binding domain were found to induce strong neutralizing antibodies, irrespective of whether they were adjuvanted with MF59 or Alum. Insoluble fragments, ToxA-PTA2, ToxA-CP and ToxA-T4 did not induce neutralizing antibodies. ToxA-CP (which was not identified as being immunogenic) also did not induce neutralizing antibodies. Sera raised against ToxA did not cross-neutralise ToxB (Table 2).

TABLE 2

Neutralisation titers of sera raised against sub-domains of TcdA

| Antigen | ToxA 20 ng/ml Alum | ToxA 20 ng/ml MF59 | ToxB 10 pg/ml Alum | ToxB 10 pg/ml MF59 |
|---|---|---|---|---|
| P5_6 | 2000 | 2000 | 0/16 | 0/16 |
| ToxA_B2 | 8000 | 8000 | 0 | 0 |
| ToxA-B5 | 4000 | 4000 | 0 | 0 |
| ToxA-B6 | 2000 | 2000 | 0 | 0 |
| ToxA-B3 | 4000 | 2000 | 0 | 0 |
| ToxA-PTA2 | 0 | — | 0 | — |
| ToxA-T4 | 0 | — | 0 | — |
| ToxA-GT | 1000 | 256 | 0 | 0 |
| P5_6 + ToxA-GT | 4000 | 4000 | 0 | 0 |
| ToxA-CP | 0 | 0 | 0 | 0 |
| ToxoidA | 16000 | 16000 | 0 | |

(differences in experimental repeats are denoted by "/").

TABLE 3

Neutralisation titers of sera raised against sub-domains of TcdB.

| Antigen | ToxA 20 ng/ml Alum | ToxA 20 ng/ml MF59 | ToxB 10 pg/ml Alum | ToxB 10 pg/ml MF59 |
|---|---|---|---|---|
| ToxB-B | 0 | 0 | 128/256 | 128/256 |
| ToxB-B2 | 0 | 0 | 0 | 0 |
| ToxB-B7 | 0 | 0 | 0 | 0 |
| ToxB-ED | 0 | 0 | 128* | 128* |
| ToxB-GT | 0 | 0 | 128*/256 | 256 |
| ToxB-CP | 0 | 0 | 0 | 0 |
| ToxB-GT + ToxB-B | 0 | 0 | 512 | 256 |
| Toxoid B | | | 2000 | 2000 |

*indicates 50% neutralization (differences in experimental repeats are denoted by "/").

ToxB-B, ToxB-ED and ToxB-GT induced a weak neutralizing antibody response, which were similar when adjuvanted with MF59 or Alum. By contrast, Tox-B2, ToxB-B7, ToxB-CP did not induce neutralizing antibodies. Sera raised against ToxB did not cross-neutralise ToxA (Table 3).

Thus, antibodies directed to TcdA are not able to cross-neutralize TcdB and vice versa.

The mouse immunization studies (above) and the results obtained from the in vitro cell rounding assay collectively suggest that the N-terminal region of the ED of TcdA and/or TcdB (i.e. the GT domain) is immunogenic and important for raising neutralizing antibodies against its respective toxin. Moreover, the neutralizing antibody response induced by the ToxB-GT fragment (and also the ToxB-ED fragment, comprising the ToxB-GT sequence) was the same, or better, than the neutralizing antibody response obtained using the majority of the binding domain of TcdB (i.e. the ToxB-B fragment).

The toxicity test was also performed to confirm whether the D270A, Y284A, D286A and D288A mutations in ToxB-GT led to a decrease in toxicity, as compared to the native, full length toxin B. A range of 10 concentrations ranging from 20 ng/ml to 40 ugr/ml were tested using the assay protocol outlined above. Fibroblasts incubated with mutated ToxB-GT did not show any morphological alterations at the concentrations tested, while native full-length toxin B caused cell rounding at 10 pg/ml under the same experimental conditions (data not shown). Therefore, the D270A, Y284A, D286A and D288A mutations led to loss of toxicity under the experimental conditions tested.

Combinations of Fragments

To determine whether it is possible to obtain sera capable of inducing concomitant neutralization of both toxin A and toxin B, the inventors then combined the most promising toxin fragments. Neutralization titres of the sera against the toxin combinations are summarized in Table 4.

TABLE 4

Neutralization titres of sera raised against combinations of single sub-domains of TcdA and TcdB.

| Antigen | 20 ToxA ng/ml Alum | 20 ToxA ng/ml MF59 | 10 ToxB pg/ml Alum | 10 ToxB pg/ml MF59 |
|---|---|---|---|---|
| p5_6 + ToxB-B | 8000 | 4000 | 256 | 128 |
| p5_6 + ToxB-B2 | 8000 | 4000 | 0 | 0 |
| p5_6 + ToxB-GT | 8000 | 4000 | 128 | 64/128 |
| p5_6 + PTA2 + ToxB-GT + ToxB-B | 8000 | 4000 | 1000 | 64 |
| p5_6 + ToxB-GT + ToxB-B | 2000 | 2000 | 256 | 128 |
| ToxA_B2 _ ToxB-B | 4000 | 2000/4000 | 256 | 256 |
| ToxA_B2 + ToxB-GT | 8000 | 8000 | 256 | 256 |
| ToxA_B2 + ToxB-B7 | 2000 | 2000 | 0 | 0 |
| ToxA_B3 + ToxB-B | 4000 | 4000 | 128 | 128 |
| ToxA_B3 + ToxB-GT | 4000 | 2000 | 128 | 128 |
| ToxA_B3 + ToxB-B + ToxB-GT | 4000 | 2000 | 256 | 256 |
| ToxA_B3 + ToxB-B2 | 4000 | 2000 | 0 | 0 |
| ToxA_B5 + ToxB-GT | 4000 | 4000 | 512 | 32 |
| ToxA_B6 + ToxB-B7 | 2000 | 1000 | 0 | 0 |
| Chimera | 4000 | 4000 | | |
| Toxoid A + Toxoid B | 16000 | 16000 | 2000 | 2000 |

(differences in experimental repeats are denoted by "/").

The inventors found that antibodies directed to several of the tested combinations are able to cross-neutralize TcdB and vice versa. By contrast, combinations of P5_6+ToxB-B2, ToxA_B2+ToxB-B7, ToxA_B3+ToxB_B2 and ToxA_B6+ToxB-B7 did not cross-neutralise. ToxA-P5_6+ToxB-B, and ToxA-B2+ToxB-GT emerged as most promising fragment combinations, further highlighting the ability of ToxB-GT to functionally substitute the ToxB-B region.

Interestingly, all combinations comprising ToxB-GT were able to induce neutralization titers against Toxin A and Toxin B, and combinations as well as equivalent combinations comprising the majority of the binding domain of TcdB (i.e. ToxB-B).

Chimeric Proteins

The inventors designed chimeric proteins combining different TcdA and TcdB domains into a single polypeptide (summarised in Table 5). In "B1", ToxB-ED is N-terminal of ToxA-P5-6; in "B1 small", ToxB-CP is N-terminal of ToxA-P5-6; and in "B4", ToxB-GT is N-terminal of ToxA-P5-6. In vitro neutralization studies were performed using these chimeras under the same experimental conditions as for the fragments. Results are summarised in Table 5. Three chimeric proteins containing the p5_6 fragment fused to the enzymatic domains of TcdB induce sera able to neutralize TcdA but not TcdB. Interestingly, the ToxA neutralizing activity induced by p5_6 is variable across the three p5_6 chimerae. This is likely due to changes in folding and/or immunogenicity. Similarly, the B4 chimera which contains fragments of binding domains of TcdA and TcdB induced antibodies with efficient neutralizing activity against TcdA but not against TcdB (Table 5).

TABLE 5

| Neutralization titres of sera raised against chimeric proteins. | | | | |
|---|---|---|---|---|
| | Tox A 20 ng/ml | | Tox B 10 pg/ml | |
| Antigen | Alum | MF59 | Alum | MF59 |
| B1 (ToxB-ED/p5_6) | 256* | | 0 | |
| B1small (ToxB-CP/p5_6) | 8000 | 8000 | 0 | 0 |
| B4 (ToxB-GT/p5_6) | 4000 | | 0 | |
| ToxoidA + ToxoidB | 16000 | 16000 | 2000 | 2000 |

These data suggest that compositions comprising a combination of a) a polypeptide comprising ToxB-GT and one or more polypeptide fragments of TcdA or b) a polypeptide comprising ToxA-GT and one or more polypeptide fragments of TcdB perform better than chimeric polypeptides comprising sequences from ToxA and ToxB.

Efficacy Testing in Hamsters

Hamster immunisation studies typically involved 10 Golden Syrian Hamsters. Within each group, 6 hamsters were immunized via intra peritoneal (i.p.) route with four doses of antigen (50 ugr of each antigen formulated in MF59 adjuvant) at days 1, 14, 28 and 36. Two untreated animals and two vaccinated with MF59 adjuvant alone were always included as negative controls. On day 60, all hamsters were treated with clindamycin (30 mg/kg hamster body weight) to remove intestinal commensal flora. After 12 hours, animals were challenged by oral gavage of approximately 250 *C. difficile* spores. Body temperature and presence of clinical symptoms such as diarrhoea were monitored for 14 days after the challenge. Body temperature drop to 35° C. was taken as the humane endpoint of the experiment, at which point, the animal was culled. Body temperature was measured telemetrically using a chip inserted into the body cavity of the animals 3 weeks prior to infection. Table 6 shows the time after infection with the B1 or 630 strain before the body temperature drops by 2° C. (5 hamsters were assessed per *C. difficile* strain).

TABLE 6

| Time from infection with the B1 strain or 630 strain to 2° C. loss of hamster body temp. | | |
|---|---|---|
| Hamster | B1 infected | 630 infected |
| 1 | 31 h | 46 h |
| 2 | 33 h 30 min | 49 h |
| 3 | 33 h 45 min | 48 h 45 min |
| 4 | 32 h 30 min | 46 h 30 min |
| 5 | 32 h | 45 h 50 min |

Post-infection analyses involved confirmation that the hamsters had been infected specifically with the infection strain (using multiple locus variable tandem repeat analysis (MVLA), based on banding patterns from 7 repeat regions), as well as bacterial counts in fecies and gut.

Infection was found not to interfere with anti-toxin immune response, since a sample serum from vaccinated animals with ToxA-B2+ToxA-GT+ToxB-B3+ToxB-GT mutants, collected before the challenge, showed comparable neutralization titers to those measured after challenge (data not shown).

Terminal colonization analyses were also performed on vaccinated and control hamsters. Control animals were culled at day 2 (post-challenge) when endpoint of body temperature of 35° C. was reached. Vaccinated animals were culled at day 15 (post challenge, at the end of experiment). Guts were removed and bacterial counts on recovered bacteria determined. To enumerate the total bacterial load (spores and vegetative cells), each section was opened longitudinally, and the contents were removed by gentle washing in two changes of 10 ml PBS. Tissues were homogenized in 5 ml of PBS for 1 min using a Stomacher, and viable counts were determined for the homogenates. Serial 10-fold dilutions were plated on CCFA blood agar plates containing 20 g/ml amphotericin B to suppress yeast growth. To estimate the numbers of spores present in the samples, the samples were heated for 10 min at 56° C., and the numbers of spores present were determined by the viable count method as described above. Organisms not intimately associated with the mucosa are described herein as "lumen associated" (LA). Organisms more intimately associated (i.e. not removed by simple washing) are described herein as "tissue associated" (TA).

Assessments of toxin content in the gut were also performed. Gut washes were filtered through a 0.22 μm filter to remove bacterial cells. Filtered washes were then placed on confluent Vero cells at 10-fold decreasing concentrations (5-fold for the colon) for 24 hours. After incubation, cells were washed, fixed, and then coloured with Giemsa stain. If toxin was present then cell rounding caused detachment and the absence of colour. Toxin-content data represents the dilutions at which the cells remained attached (stained).

Figure 11:
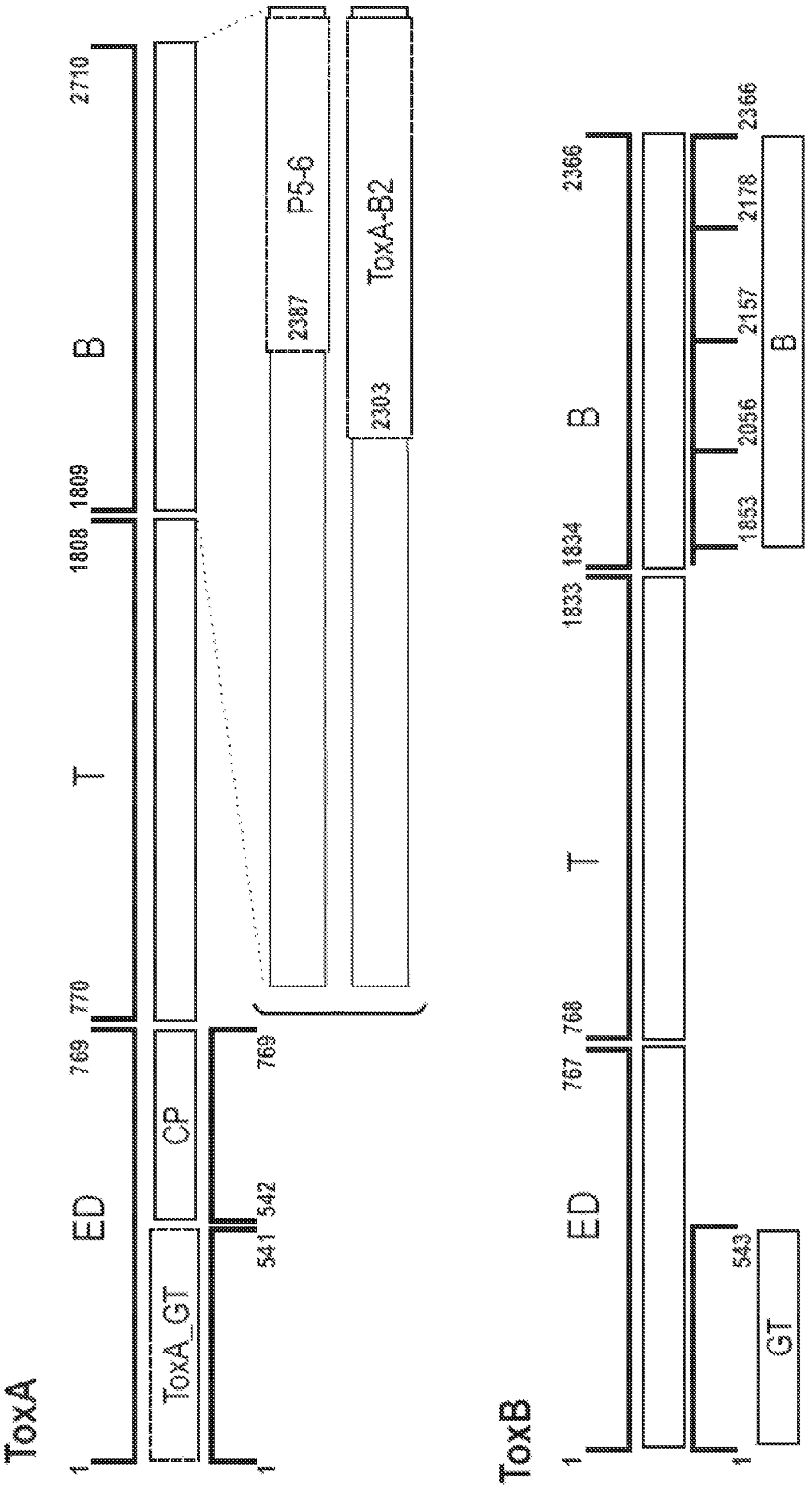
FIG. 11. Schematic representation of the toxin domain fragments used in hamster studies. ED=enzymatic domain; GT=glucosyl transferase domain; CP=cysteine protease domain; T=translocation domain; B=binding domain.

A number of toxin domain fragments were then tested in a hamster model. Details of the tested fragments are provided in FIG. 11. Details of antigen combinations and an overview of the results obtained are provided in Table 7. Results from each trial are described in more detail below.

TABLE 7

| Summary of hamster vaccination experiments. | | |
|---|---|---|
| Antigen | Challenge Strain | Protection |
| ToxA-P5/6 | B1 | 0 out of 6 |
| ToxB_B | B1 | 0 out of 6 |
| ToxB_B + ToxA-P5/6 | 630 | 6 out of 6 |
| ToxB_B + Toxoid A | 5 animals with B1<br>5 animals with 630 | 3 out of 3<br>3 out of 3 |
| Chimera B4 | 630 | 3 out of 5 |
| ToxB-GT + ToxA-P5-6 | 630 | 6 out of 6 |
| ToxB-B + ToxA-P5-6 | B1 | 5 out of 6 |
| ToxB-B + ToxA-P5-6 + ToxB-GT | B1 | 5 out of 6 |
| Toxoid A + Toxoid B | B1 | 5 out of 6 |
| ToxB-GT-PSII + ToxA-P5-6 | 630 | 5 out of 6 and<br>2 out of 2 |
| ToxA-GT + ToxB-GT +<br>ToxB-B + ToxA-B2 | B1 | 5 out of 6 |
| ToxB-GT + ToxA-P5-6 | B1 | 6 out of 6 |
| ToxB-GT + ToxA-B2 | B1 | 6 out of 6 |
| ToxB-GT + ToxA-B2 (20 ugrs) | B1 | 3 out of 8 |
| ToxB-GT + ToxA-P5-6 (20 ugrs) | B1 | 6 out of 6 and<br>8 out of 8 |
| ToxA-GT + ToxB-GT +<br>ToxB-B + ToxA-B2 (20 ugrs) | B1 | 6 out of 7 |

[1] = technical issues led to increased volume and a higher measured number of spores.

Two different *C. difficile* strains were used in these studies, namely the 630 strain (genome sequence is publicly available at NCBI), and the B1 strain. The 630 strain is known to cause prolonged infection with less severe pathology and reduced amounts of toxin in vivo. The B1 strain is known to cause a severe pathology in hamsters (G. Douce, personal communication), with acute infection and high level of damage.

Toxoid A+Toxoid B

A combination of full length inactivated Toxoid A and Toxoid B was used as a positive control. This combination may be considered to represent a "gold standard" against which the combinations of the invention may be compared (see references 179 and 180). Toxoids were produced using fermentation, then purified and finally inactivated.

6 animals received 5 μg of each toxoid (adjuvanted with MF59). 2 received adjuvant only and two were untreated. Amount to be administered was chosen on based on the literature. The main problem with using inactivated toxoids (e.g. using formaldehyde) is that the inactivation could be incomplete, thus posing a potential health risk when applied to a subject, Animals were challenged with the B1 strain. All control animals died, and one vaccinated animal (H1) died shortly after the last control animal, showing body temperature profiles similar to controls (data not shown). All other vaccinated hamsters survived until the end of the experiment (Table 8).

TABLE 8

Results for full length inactivated Toxoid A + Toxoid B. Challenge with B1.

| | | Time at cull | Temp at cull |
|---|---|---|---|
| H1 | Vaccine | 45 h 50 min | 34.17° C. |
| H2 | Vaccine | 14 days | |
| H3 | Vaccine | 14 days | |
| H4 | Vaccine | 14 days | |
| H5 | Vaccine | 14 days | |
| H6 | Vaccine | 14 days | |
| H7 | Vaccine | 29 hr 10 min | 31.98° C. |
| H8 | Vaccine | 31 hr 1 min | 32.58° C. |
| H9 | Vaccine | 30 hr 36 min | 34.25° C. |
| H10 | Vaccine | 28 hr 37 min | 31.3° C. |

Hamsters H2, H3 and H4 showed a short episode of diarrhoea during recovery, and H5 exhibited a longer period of diarrhoea and lethargy. H5 was administered rehydration therapy (sub-cutaneous administration of saline) which led to another episode of diarrhoea, followed by recovery. Therefore, immunisation with full length toxoids was found to protect 83% of hamsters against the B1 strain.

Figure 12:
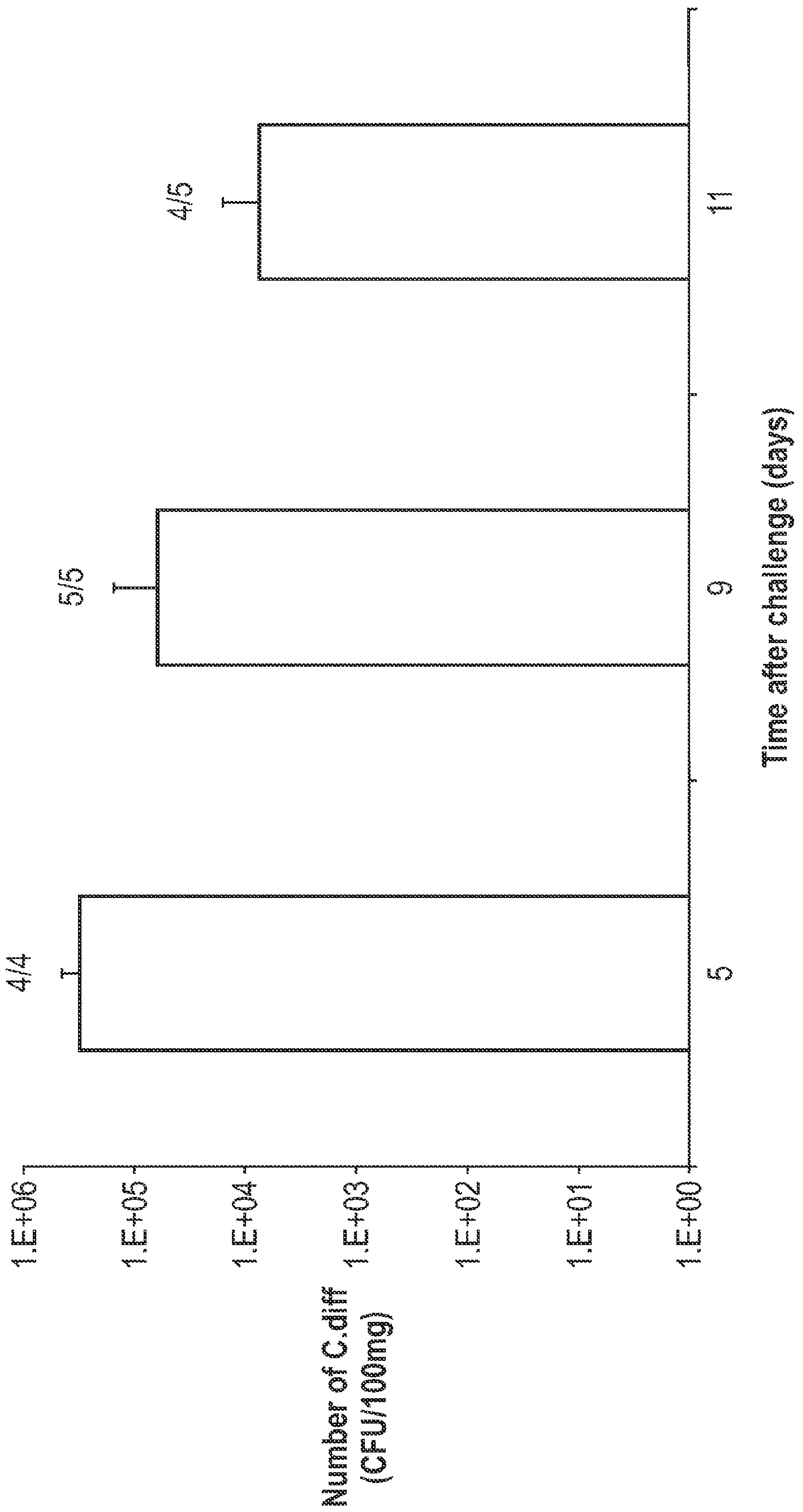
FIG. 12. Toxoid A+Toxoid B. Average bacterial shedding in faeces. Challenged with B1.
Figure 13:
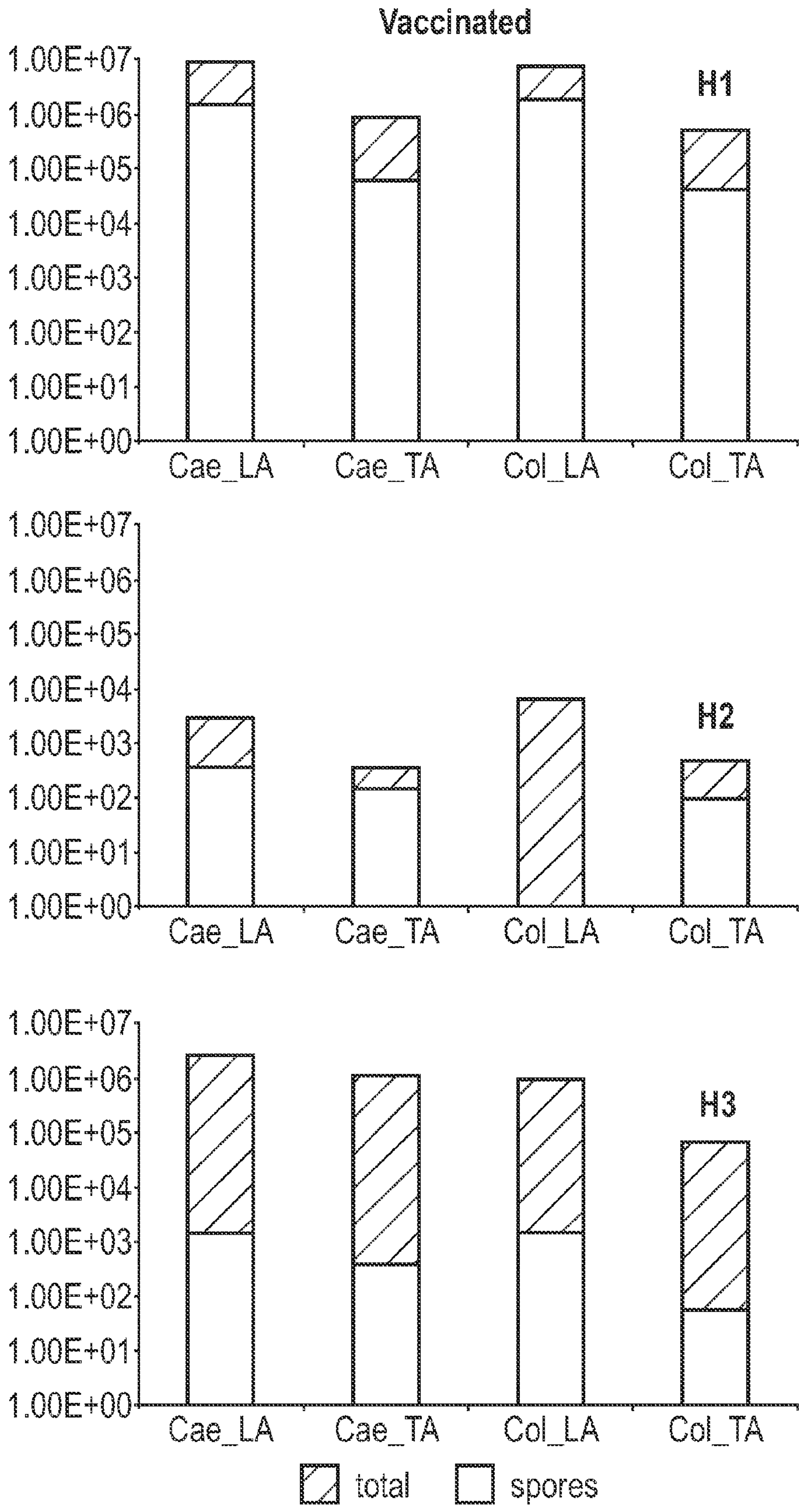
FIG. 13. Toxoid A+Toxoid B—Post-infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)).

An analysis of bacterial shedding revealed that CFU are shed from vaccinated animals for several days (5, 9 and 11) after challenge, even when symptoms (diarrhoea) disappeared. H5 was dehydrated and so it was difficult to detect any faecal pellets at day 5, so, shedding was analysed only after 9 and 11 days. H4 had no detectable *C. difficile* in faeces after 11 days (FIG. 12), although this animal was still colonised in the gut at the end of the experiment. An analysis of colonisation at culling is provided in FIG. 13.

Assessment of toxin B content in the gut revealed that there is less toxin B present in the gut of surviving vaccinated hamsters after 15 days, compared to controls, which died after 2 days (Table 9) This result was also confirmed in the colon (Table 10). H1 is the vaccinated hamster which died during the acute phase of infection and has a high level of toxin B present, which is equivalent to the level of toxin B present in the control animals, which died.

TABLE 9

Toxoid A + Toxoid B - toxin content in the caecal gut. Challenge with B1. Data are represented as dilutions at which cells remain attached.

| Hamster | Vaccinated | Final dilution lysing cells |
|---|---|---|
| H1 | Toxoid A + Toxoid B | $10^8$ |
| H2 | Toxoid A + Toxoid B | $10^1$ |
| H3 | Toxoid A + Toxoid B | $10^1$ |
| H4 | Toxoid A + Toxoid B | 0 |
| H5 | Toxoid A + Toxoid B | $10^1$ |
| H6 | Toxoid A + Toxoid B | $10^1$ |
| H7 | Adjuvant only | $10^5$ |
| H8 | Adjuvant only | $10^7$ |
| H9 | None | $10^4$ |
| H10 | None | $10^6$ |

TABLE 10

Toxoid A + Toxoid B - toxin content in the colon. Challenge with B1. Data are represented as dilutions at which cells remain attached.

| Hamster | Vaccinated | Final dilution lysing cells |
|---|---|---|
| H1 | Toxoid A + Toxoid B | 1:390625 |
| H2 | Toxoid A + Toxoid B | 0 |
| H3 | Toxoid A + Toxoid B | 0 |
| H4 | Toxoid A + Toxoid B | 0 |
| H5 | Toxoid A + Toxoid B | 1:5 |
| H6 | Toxoid A + Toxoid B | 0 |
| H7 | Adjuvant only | 1:125 |
| H8 | Adjuvant only | 1:3125 |
| H9 | None | 1:15625 |
| H10 | None | 1:15625 |

Overall, vaccination with 5 μg of full length toxoid A and full length Toxoid B resulted in protection of 5 out of 6 animals against severe disease. However, vaccination did not protect against diarrhoea which, in the case of H5, lasted for a relatively long time. At the end of the experiment, lower amounts of spores were detectable in vaccinated animals, and three animals also showed lower levels of colonisation. Also, very low amounts of toxin B were detected in vaccinated animals at the end of the experiment, even though they were still colonised. This could be explained by, for example, toxin binding by antibodies and/or a decrease in bacterial toxin expression.

Individual Fragments of ToxA-P5_6 or ToxB_B

Vaccination trials using recombinant fragments were first performed using single fragments of P5_6 or ToxB_B corresponding to portions of the cell binding domain of TcdA and TcdB respectively (50 ugr of antigen adjuvanted with MF59). In both cases, no protection was observed against challenge with approximately 100 spores of B1 strain (data not shown). Sample bleeds were taken from all animals at the experiment endpoint. All animals immunised with ToxA-P5_6 have high antibody titers to the p5-6 protein and Toxin A, as determined by ELISA (data not shown), but these antibodies were not protective against infection. Toxin A neutralising capacity was not assessed. All animals immunised with ToxB_B have high antibody titers to the ToxB_B protein, as determined by ELISA (data not shown). There was insufficient purified toxin B to test for reactogenicity of these sera against whole Toxin B. These antibodies were not protective against infection, and toxin B neutralising capacity was not assessed. Thus, individual antigens do not appear protective, despite the presence of antibodies.

Mixture of Fragments of P5_6 and ToxB_B

Hamsters were then immunized with a mixture of 50 μg of P5_6 and 50 μg of ToxB_B (50 ugr of each antigen adjuvanted with MF59), followed by challenge with strain 630 (results shown in Table 11).

TABLE 11

Immunisation of hamsters with P5_6 plus ToxB_B. Challenge strain 630.

| Hamster | Immunogen | Time to endpoint | Time to endpoint |
|---|---|---|---|
| 1 | ToxB_B + P5_6 | Survived 9 days | |
| 2 | ToxB_B + P5_6 | Survived 9 days | |
| 3 | ToxB_B + P5_6 | Survived 9 days | |
| 4 | ToxB_B + P5_6 | Survived 9 days* | |
| 5 | ToxB_B + P5_6 | Survived 9 days* | |
| 6 | ToxB_B + P5_6 | Survived 9 days | |
| 7 | MF59 alone | | 34 h 36 min |
| 8 | MF59 alone | | 32 h 36 min |
| 9 | None | | 65 h 44 min |
| 10 | None | | 33 h 36 min |
| | Mean | | 41 h 40 min |

*= hamsters showing intermittent diarrhoea with recovery.
Challenge strain was 630.

Vaccinated animals were fully protected from death, but survivors showed mild diarrhoea during recovery. Post infection analyses are shown in Table 12 and FIG. 14. Table 12 shows that the amount of *C. difficile* in faecal material from vaccinated mice remains high for up to a week, indicating that the anti-toxin response does not impact on colonisation.

TABLE 12

ToxB_B + P5_6 - post- infection analysis of *C. difficile* recovered in faecal material.

| Animal | Treatment | *C. difficile* recovered per 100 mg of faecal material: Day 2 post infection | Day 7 post infection | Day 14 post infection |
|---|---|---|---|---|
| 1 | Vaccinated | $6.9 \times 10^5$ | $1.8 \times 10^5$ | *ND |
| 2 | Vaccinated | $4.2 \times 10^5$ | $3 \times 10^4$ | ND |
| 3 | Vaccinated | $1.3 \times 10^6$ | $1.8 \times 10^6$ | ND |
| 4 | Vaccinated | $4.9 \times 10^5$ | $3.7 \times 10^5$ | ND |
| 5 | Vaccinated | $1.8 \times 10^5$ | $4.4 \times 10^5$ | 857 |
| 6 | Vaccinated | $1.6 \times 10^5$ | $7 \times 10^4$ | 40 |

*= ND = bacteria were not detectable.

Figure 14:
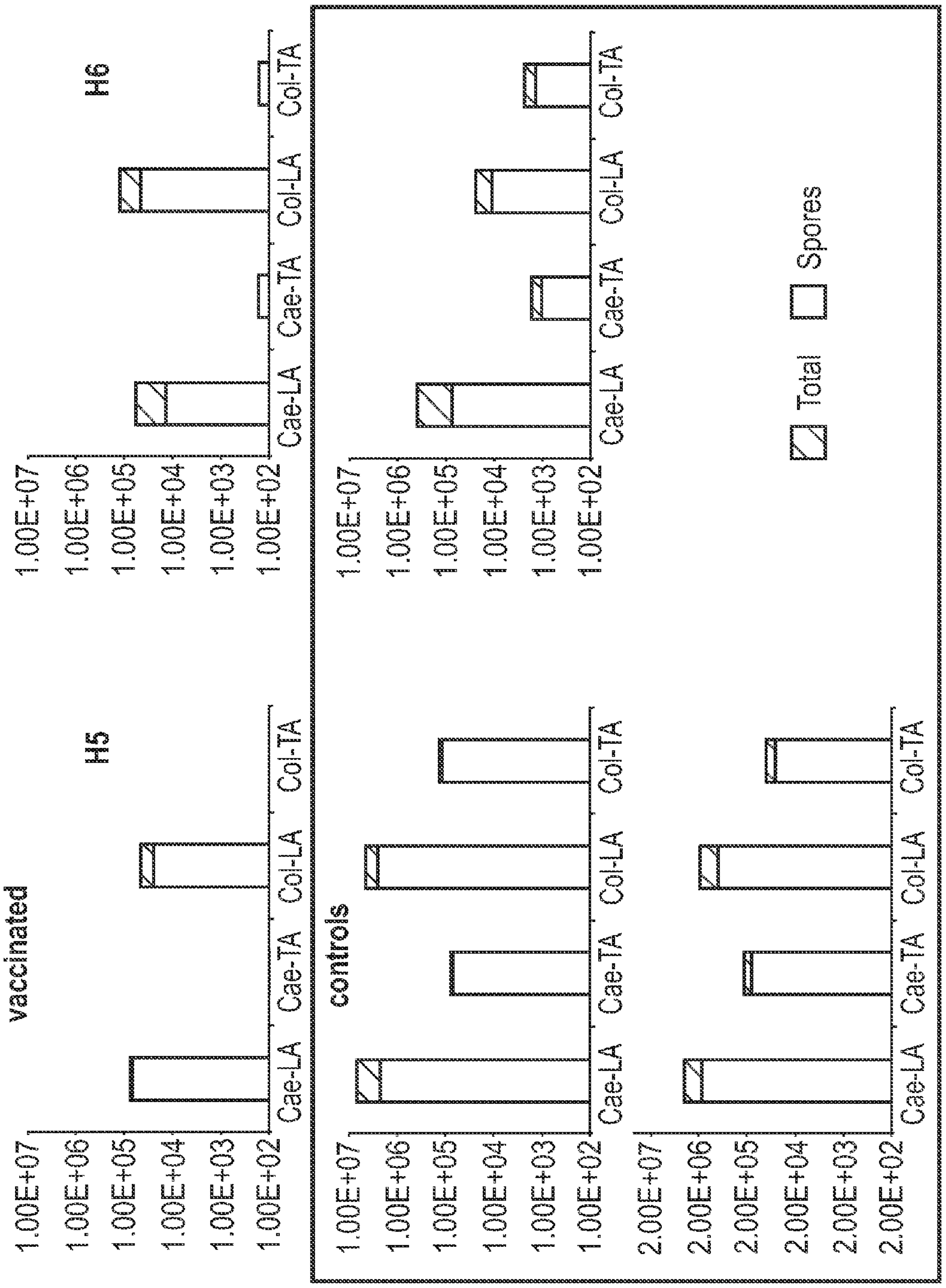
FIG. 14. ToxB_B+P5_6—post-infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)).

However, bacterial counts decrease over time, and can be entirely cleared within 14 days after infection. FIG. 14 shows localisation of bacteria, and reveals that, at the experiment endpoint, controls have higher levels of lumen- and tissue-associated bacteria than vaccinated hamsters. Bacteria recovered post-infection were confirmed to be *C. difficile* strain 630 by MVLA (data not shown).

The combination of P5_6 and ToxB-B thus provides strong protection against *C. difficile* challenge. Interestingly, the anti-toxin response does not appear to impact significantly on colonisation, because all animals remain heavily colonised at e.g. 6 days post challenge. These data also suggest that a combination of (at least fragments of) ToxA and ToxB is necessary for protection.

P5_6 and ToxB_B

Figure 15:
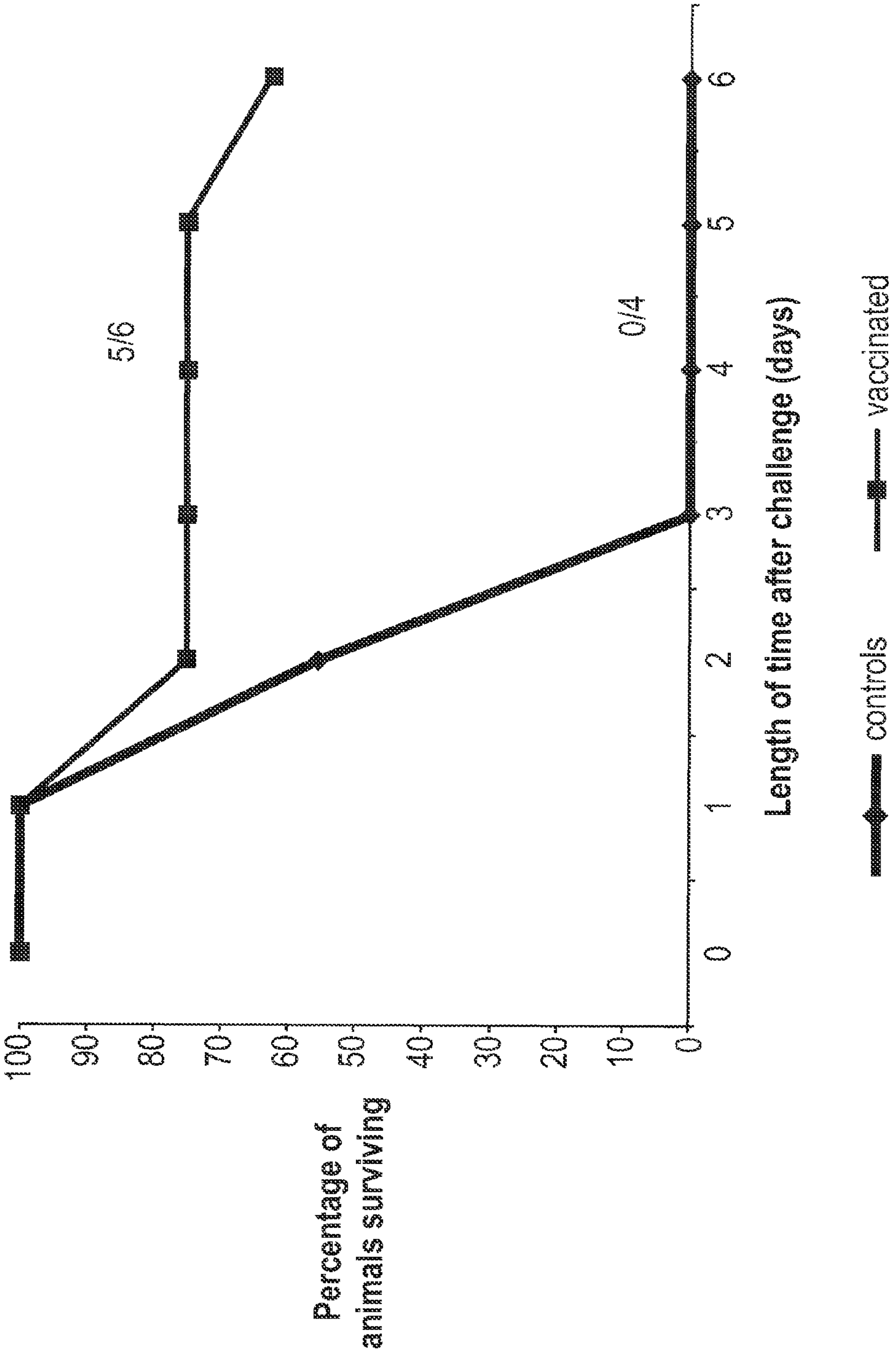
FIG. 15. Graphical representation of the data provided in FIG. 29.

In view of the successful immunisation against strain 630, the inventors tested whether immunisation with P5_6+ToxB_B protected against the more toxigenic B1 strain. 6 animals were immunised with 50 ugrs of each antigen (adjuvanted with MF59), followed by challenge with $10^3$ spores of the B1 strain. As controls, 2 animals received adjuvant alone (H7-H8) and 2 animals received no vaccination (H9-H10). Following challenge, all control animals died. One vaccinated animal (H1) died shortly after the last control animal. All other vaccinated animals (H2-H6) survived until the end of the experiment. (Table 13) This shows that 83% of the animals vaccinated with P5/6+ToxB_B were protected against challenge with the B1 strain (also represented by FIG. 15).

TABLE 13

P5_6 + ToxB_B results. Challenge with B1 strain.

| Animal | Immunogen | Time at cull | Temp at cull |
|---|---|---|---|
| H1 | Vaccine | 33 hr 2 min | 34.16° C. |
| H2 | Vaccine | 15 days | |
| H3 | Vaccine | 15 days | |
| H4 | Vaccine | 15 days | |
| H5 | Vaccine | 15 days | |
| H6 | Vaccine | 15 days | |
| H7 | Adjuvant only | 32 hr 5 min | 34.87° C. |
| H8 | Adjuvant only | 29 hr 50 min | 34.54° C. |
| H9 | Control | 30 hr 36 min | 34.49° C. |
| H10 | Control | 28 hr 37 min | 33.64° C. |

Figure 16:
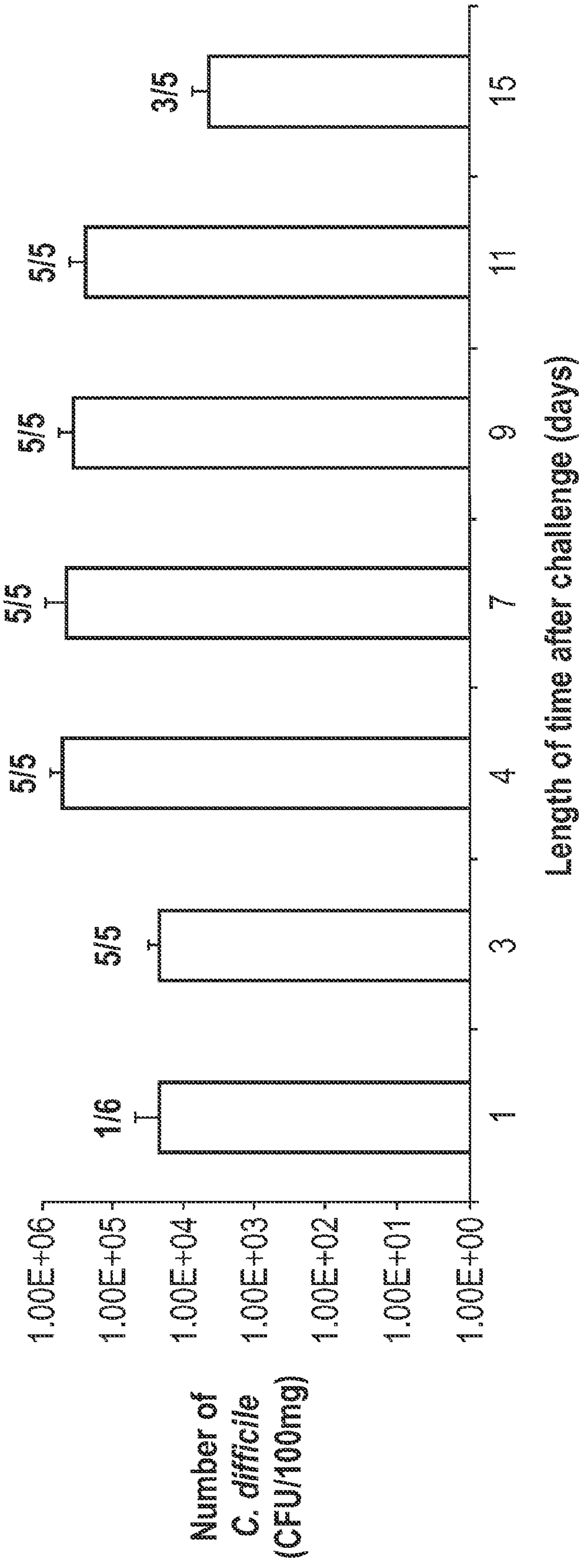
FIG. 16. Bacterial shedding of *C. Difficile* spores in 100 mg faeces from hamsters immunised with P5_6+ToxB_B or controls. Challenged with B1 strain.

The number of colonies per 100 mg faecal material was then determined (FIG. 16). This revealed that the organisms are shed at high numbers for several days after challenge, even when symptoms (diarrhoea) have abated. Interestingly, the numbers shed actually increased for around 5 days post infection, before decreasing. At day 1 post-infection, only 1 out of the 6 vaccinated animals were shedding detectable *C. difficile* in their faeces. By day 3, all surviving vaccinated animals were shedding relatively high numbers of *C. difficile*. These animals shed high levels until day 11. On day 15, only 3 out of the 5 animals were shedding detectable *C. difficile* in their faeces (detection limit approx 200 spores).

Figure 17:
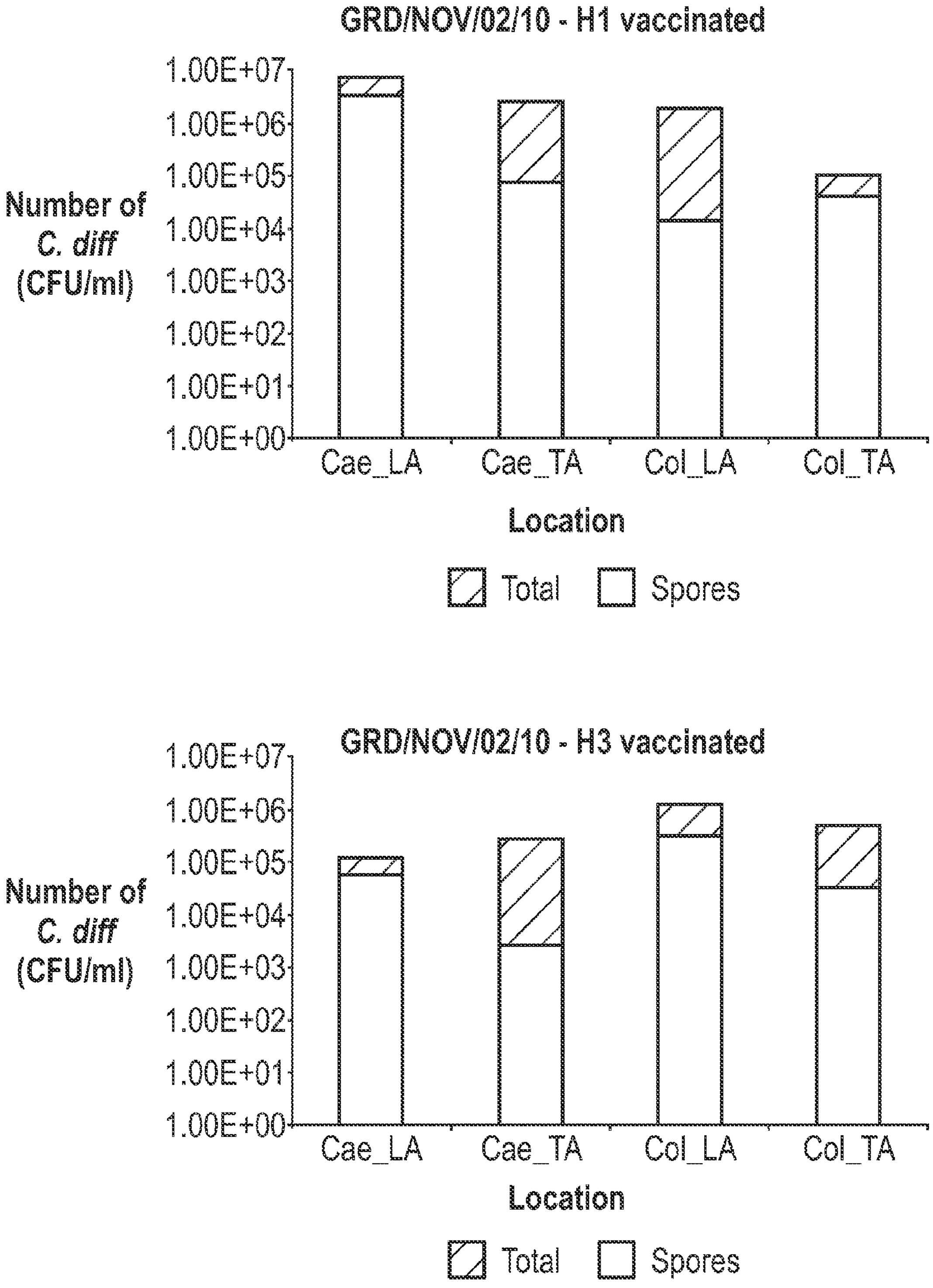
FIG. 17. P5_6+ToxB_B or controls. Challenged with B1 strain. Post-infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)).

An analysis of colonization at culling was also performed (FIG. 17). Hamsters 4 and 5 showed heavy levels of contaminating flora on plated which obscured any low *C. difficile* spores present (these were also the 2 animals from which *C. difficile* could not be recovered from the faeces at day 11).

Assessment of toxin B content in the gut revealed that there is little or no toxin B present in the gut of surviving vaccinated hamsters after 15 days, compared to controls, which died after 2 days (Table 14). H1 is the vaccinated hamster which died during the acute phase of infection and has a high level of toxin present, which is equivalent to the level of toxin present in the control animals, which died. There is less toxin B present in the colon than the caecum in the animals which died during the acute phase of infection.

TABLE 14

P5_6 + ToxB_B or controls. Challenged with B1 strain. Toxin content in the gut (caecum and colon). Data are represented as dilutions at which cells remain attached.

| Hamster | Vaccinated | Final dilution lysing cells (caecum) | Final dilution lysing cells (colon) |
|---|---|---|---|
| H1 | P5_6 + ToxB_B | $10^7$ | 1:5 |
| H2 | P5_6 + ToxB_B | $10^1$ | 1:5 |
| H3 | P5_6 + ToxB_B | $10^1$ | 1:5 |
| H4 | P5_6 + ToxB_B | 0 | 1:5 |
| H5 | P5_6 + ToxB_B | 0 | 0 |
| H6 | P5_6 + ToxB_B | 0 | 0 |
| H7 | Adjuvant only | $10^6$ | 1:15625 |
| H8 | Adjuvant only | $10^3$ | 1:15625 |
| H9 | None | $10^5$ | 1:15625 |
| H10 | None | $10^6$ | 1:15625 |

ToxB_B+P5_6+PSII

Animals are immunized with a mixture of ToxB_B+P5_6+PSII-CRM, in which the polysaccharide is conjugated to the CRM carrier protein. Protection studies are performed, along with an analysis of the faeces, and an assessment of toxin content in the gut.

Toxoid A+ToxB_B

The inventors then tested whether using fragments of the TcdA binding domain affected the protection afforded by using full length Toxoid A. Immunisation with a mixture of full length (inactivated) Toxoid A and ToxB_B (5 ugr of toxoid A and 50 ugr of ToxB_B adjuvanted with MF59) was found to protect against challenge with the 630 strain and also the B1 strain. Unvaccinated animals challenged with the 630 strain had strong diarrhoea and a temperature drop, at which point they were culled (Table 15). By contrast, immunised animals survived challenge with the 630 strain and only one of the vaccinated animals displayed only minor diarrhoea. Animals showed mild diarrhoea with recovery.

TABLE 15

Toxoid A + Toxin B_B results. Challenge with 630.

| Hamster | Immunogen | End of the experiment | Time to endpoint |
|---|---|---|---|
| 1 | Toxoid A + Toxin B_B | Survived | |
| 2 | Toxoid A + Toxin B_B | Survived* | |
| 3 | Toxoid A + Toxin B_B | Survived | |
| 4 | MF59 alone | | 57 h 52 min |
| 5 | No treatment | | 47 h 4 min |
| | Mean | | 52 h 28 min |

One of the animals got very limited diarrhoea*.
Unvaccinated animals had strong diarrhoea and temperature drop.

Unvaccinated animals challenged with the B1 strain also had strong diarrhoea and a temperature drop, at which point they were also culled (Table 16). Immunised animals survived the challenge, with two suffering mild diarrhoea during recovery. Therefore, immunisation with a mixture of Toxoid A and Toxoid B_B protected from death following challenge with the B1 strain, but did not protect against diarrhoea (Table 16).

TABLE 16

Toxoid A + Toxin B_B results. Challenge with B1.

| Hamster | Immunogen | End of the experiment | Time to endpoint |
|---|---|---|---|
| 1 | Toxoid A + Toxin B_B | Survived* | |
| 2 | Toxoid A + Toxin B_B | Survived* | |
| 3 | Toxoid A + Toxin B_B | Survived | |
| 4 | MF59 alone | | 29 h 47 min** |
| 5 | No treatment | | 32 h 24 min** |
| | Mean | | 31 h 15 min |

Mild recovery with diarrhoea*;
strong diarrhoea and temperature drop**.
Vaccinated animals are protected from death, but not temperature drop.

Further Combinations

As discussed above, the inventors determined that fragments comprising the GT domain were immunogenic and capable of inducing neutralisation titers against their respective toxin. To test whether fragments comprising the GT domain are able to confer protection against CDAD, the inventors tested a number of additional combinations using the 630 and B1 challenge strains (summarised in Table 7).

ToxB_GT+P5_6 (630)

First, the inventors tested whether immunisation with a mixture of ToxB_GT and ToxA-P5_6 (adjuvanted with MF59) was found to protect against challenge with the 630 strain. ToxA-P5_6 in combination with the ToxB-B fragment was found to confer 100% protection against challenge with the 630 strain. In this experiment, none of the vaccinated animals showed diarrhoea when challenged with 630, and no clinical symptoms were observed (Table 17). Unvaccinated animals (hamster #9) challenged with the 630 strain had strong diarrhoea and a temperature drop, at which point they were culled.

TABLE 17

ToxB_GT + P5 + 6 results. Challenge with 630.

| Animal | Immunogen | Time to <35° C. | Time at cull | Temp at cull |
|---|---|---|---|---|
| H1 | ToxB_GT + P5_6 | | 15 days | 36.4° C. |
| H2 | ToxB_GT + P5_6 | | 15 days | 36.7° C. |
| H3 | ToxB_GT + P5_6 | | 15 days | 37.2° C. |
| H4 | ToxB_GT + P5_6 | | 15 days | 36.9° C. |
| H5 | ToxB_GT + P5_6 | | 15 days | 36.2° C. |
| H6 | ToxB_GT + P5_6 | | 15 days | 36.2° C. |
| H7 | Adjuvant only | 35 hr 28 min | 41 hr 34 min | 26.2° C. |
| H8 | Adjuvant only | 37 hr 37 min | 41 hr 53 min | 25.9° C. |
| H9 | No treatment | 38 hr 15 min | 42 hr | 33.8° C. |

None of the vaccinated animals suffered from diarrhoea.

Figure 18:
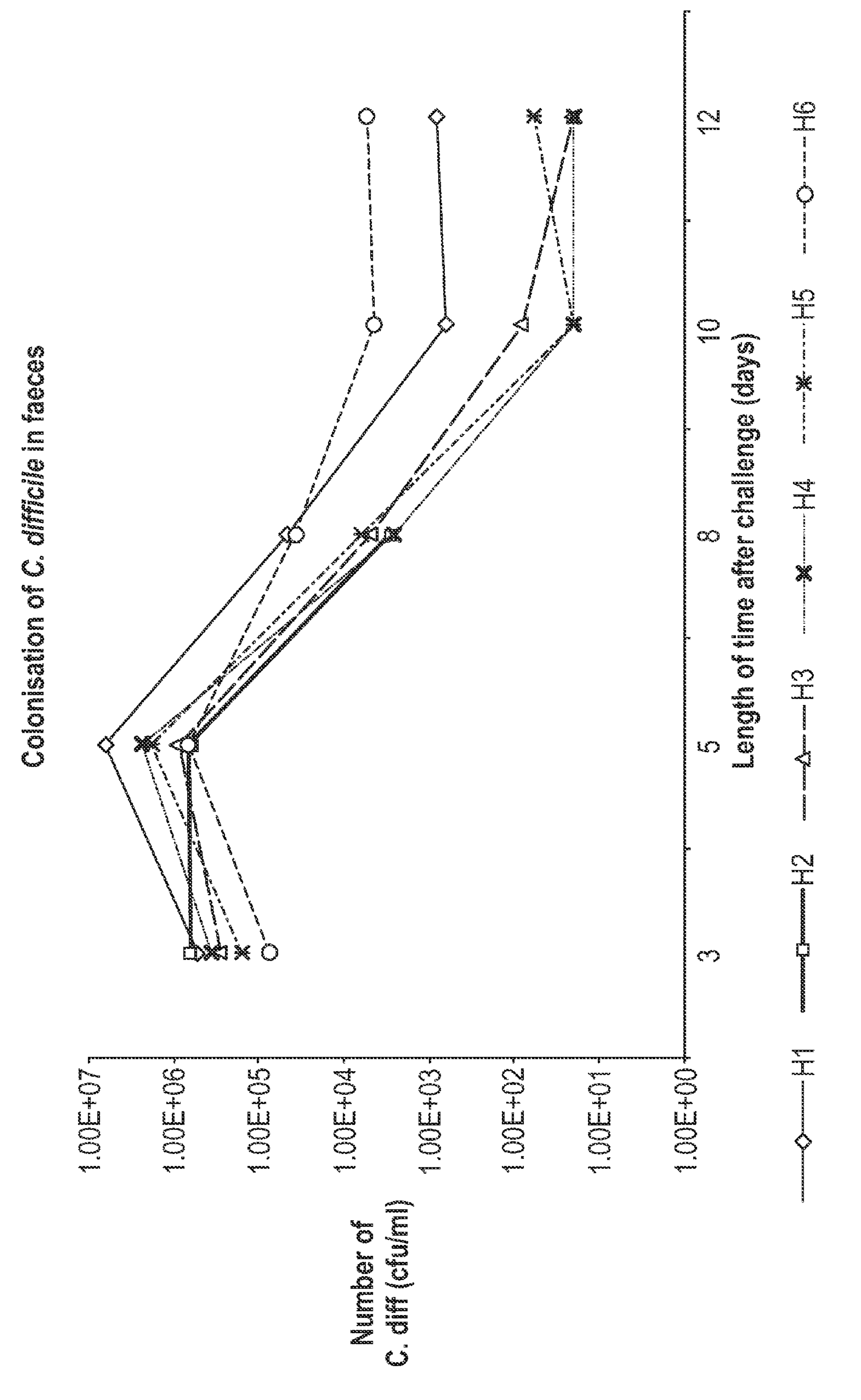
FIG. 18. Immunisation with ToxB_GT+P5+6. Colonisation in faeces of vaccinated animals per (per hamster (upper panel) and average (lower panel)). Challenge with 630 strain.

The number of colonies per 100 mg faecal material was then determined (FIG. 18), demonstrating that that the organisms are shed at high numbers for several days after challenge, even when symptoms (diarrhoea) have abated.

Figure 19:
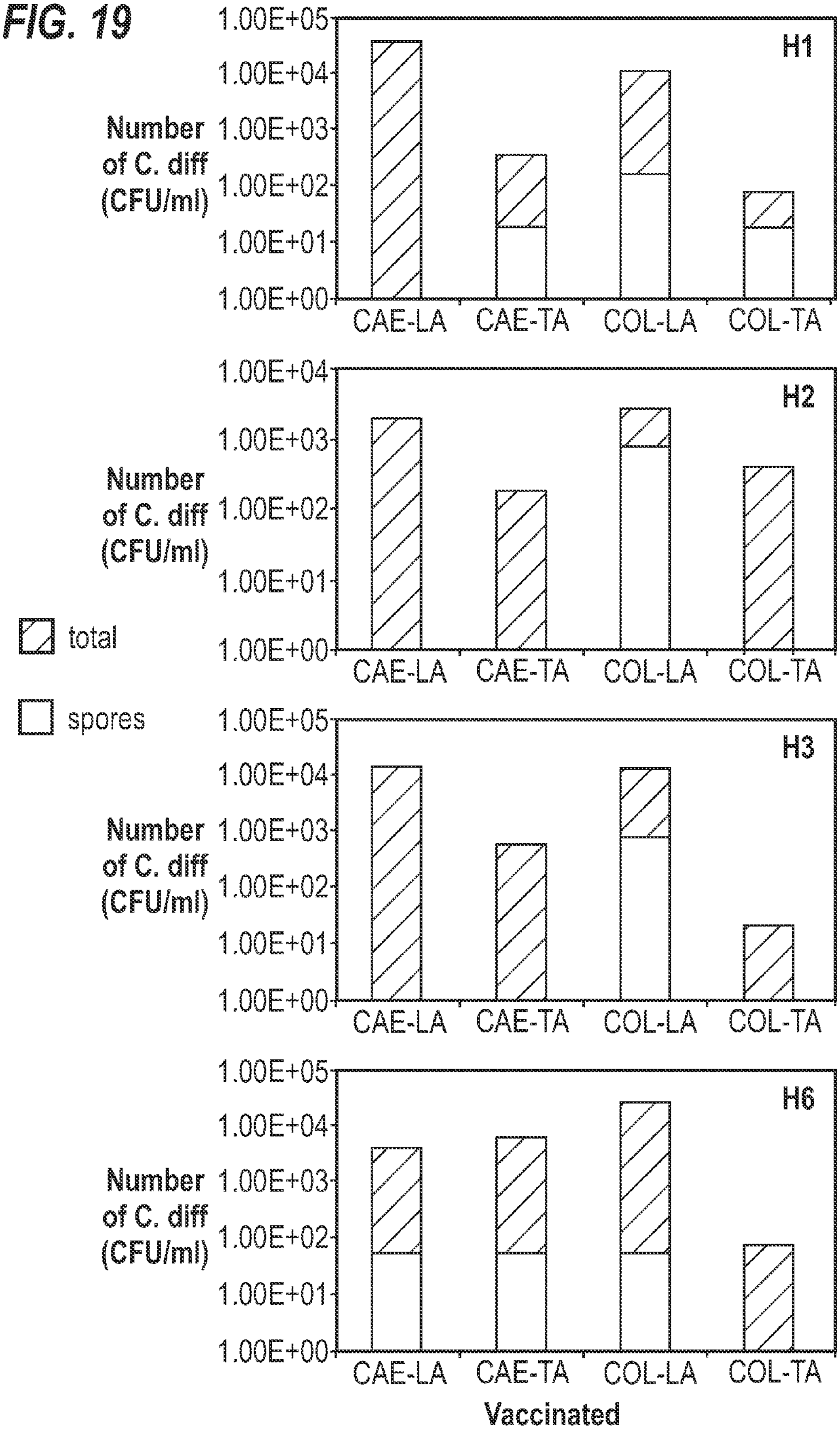
FIG. 19. ToxB_GT+P5_6 Terminal colonisation results. Challenge with 630 strain.

Assessment of terminal colonisation also revealed that all of the vaccinated animals showed a lower number of CFU and lower proportion of spores compared to controls. There were no detectable *C. difficile* spores in hamsters #4 and #5 (data not shown), and hamster #2 showed a ten-fold reduction in terminal colonisation compared to other vaccinated hamsters (FIG. 19).

Assessment of toxin B content in the gut revealed that there is less toxin B present in the vaccinated hamsters after 15 days than in the controls, which died after 2 days (Table 18). This result was also confirmed in the colon (Table 19).

TABLE 18

ToxB_GT + P5_6 - toxin content in the caecal gut. Data are represented as dilutions at which cells remain attached. Challenge with 630 strain.

| Hamster | Vaccinated | Final dilution lysing cells |
|---|---|---|
| H1 | P5_6 + toxB_GT | $10^2$ |
| H2 | P5_6 + toxB_GT | $10^1$ |
| H3 | P5_6 + toxB_GT | $10^1$ |
| H4 | P5_6 + toxB_GT | $10^1$ |
| H5 | P5_6 + toxB_GT | 0 |
| H6 | P5_6 + toxB_GT | $10^1$ |
| H7 | Adjuvant only | $10^5$ |
| H8 | Adjuvant only | $10^4$ |
| H9 | None | $10^4$ |

TABLE 19

ToxB_GT + P5_6 - toxin content in the colon. Data are represented as dilutions at which cells remain attached. Challenge with 630 strain.

| Hamster | Vaccinated | Final dilution lysing cells |
|---|---|---|
| H1 | P5_6 + toxB_GT | 1:5 |
| H2 | P5_6 + toxB_GT | 0 |
| H3 | P5_6 + toxB_GT | 0 |
| H4 | P5_6 + toxB_GT | 0 |
| H5 | P5_6 + toxB_GT | 0 |
| H6 | P5_6 + toxB_GT | 0 |
| H7 | Adjuvant only | 1:3125 |
| H8 | Adjuvant only | 1:25 |
| H9 | None | 1:625 |

Therefore, immunisation with a mixture of ToxB_GT and ToxA-P5_6 provides strong protection against challenge with the 630 strain, which is as good as using the ToxB-B fragment in combination with ToxA-P5_6.

ToxB_GT+P5_6 (B1)

In view of the successful immunisation against strain 630, the inventors tested whether immunisation with P5_6+ToxB_GT protected against the B1 strain. Animals (H1-H6) were immunized with a mixture of ToxB_GT+P5_6 (50 ugrs of each antigen, adjuvanted with MF59). The controls (adjuvant only) had strong diarrhoea and a temperature drop, at which point they were culled. All immunized animals survived against challenge with the B1 strain (6/6) (Table 20), exhibiting a single episode of diarrhoea. This is the first time that this has happened with any combination of recombinant antigens.

TABLE 20

ToxB_GT + P5_6 results. Challenge with B1 strain.

| | Antigens | Time to <35° C. | Time at cull | Temp at cull |
|---|---|---|---|---|
| H1 | ToxB_GT + P5/6 | | 14 days | |
| H2 | ToxB_GT + P5/6 | | 14 days | |
| H3 | ToxB_GT + P5/6 | | 14 days | |
| H4 | ToxB_GT + P5/6 | | 14 days | |
| H5 | ToxB_GT + P5/6 | | 14 days | |
| H6 | ToxB_GT + P5/6 | | 14 days | |
| H7 | Adjuvant only | 37 h 21 m | 37 h 36 m | 34.47° C. |
| H8 | Control | 30 h 1 m | 30 h 56 m | 30.55° C. |

Figure 20:
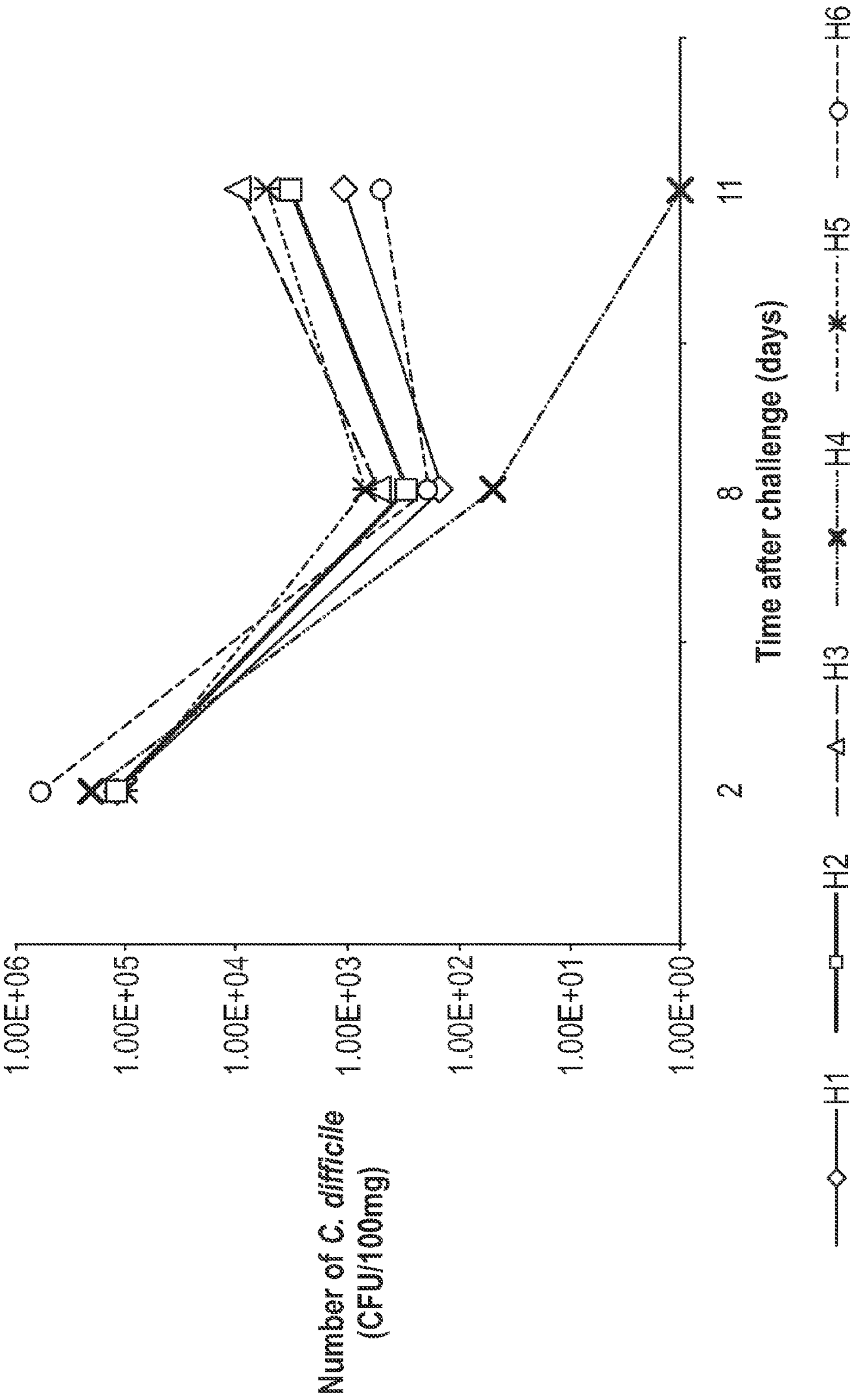
FIG. 20. ToxB_GT+P5_6. Colonisation in faeces of vaccinated animals over time (days). Challenge with B1 strain.

The number of colonies per 100 mg faecal material was then determined (FIG. 20), demonstrating that that the organisms are shed at high numbers for several days after challenge, even when symptoms (diarrhoea) have abated. All surviving animals shed high levels of *C. difficile* in their faeces. Only one animal (H4) had no detectable spores at day 11.

TABLE 21

ToxB_GT + P5_6 - toxin content in the caecal gut. Data are represented as dilutions at which cells remain attached. Challenge with B1.

| Hamster | Vaccinated | Final dilution lysing cells |
|---|---|---|
| H1 | P5/6 + ToxB_GT | $10^1$ |
| H2 | P5/6 + ToxB_GT | $10^1$ |
| H3 | P5/6 + ToxB_GT | $10^3$ |
| H4 | P5/6 + ToxB_GT | 0 |
| H5 | P5/6 + ToxB_GT | $10^2$ |
| H6 | P5/6 + ToxB_GT | $10^3$ |
| H7 | Adjuvant only | $10^5$ |
| H8 | Adjuvant only | $10^6$ |

Figure 21:
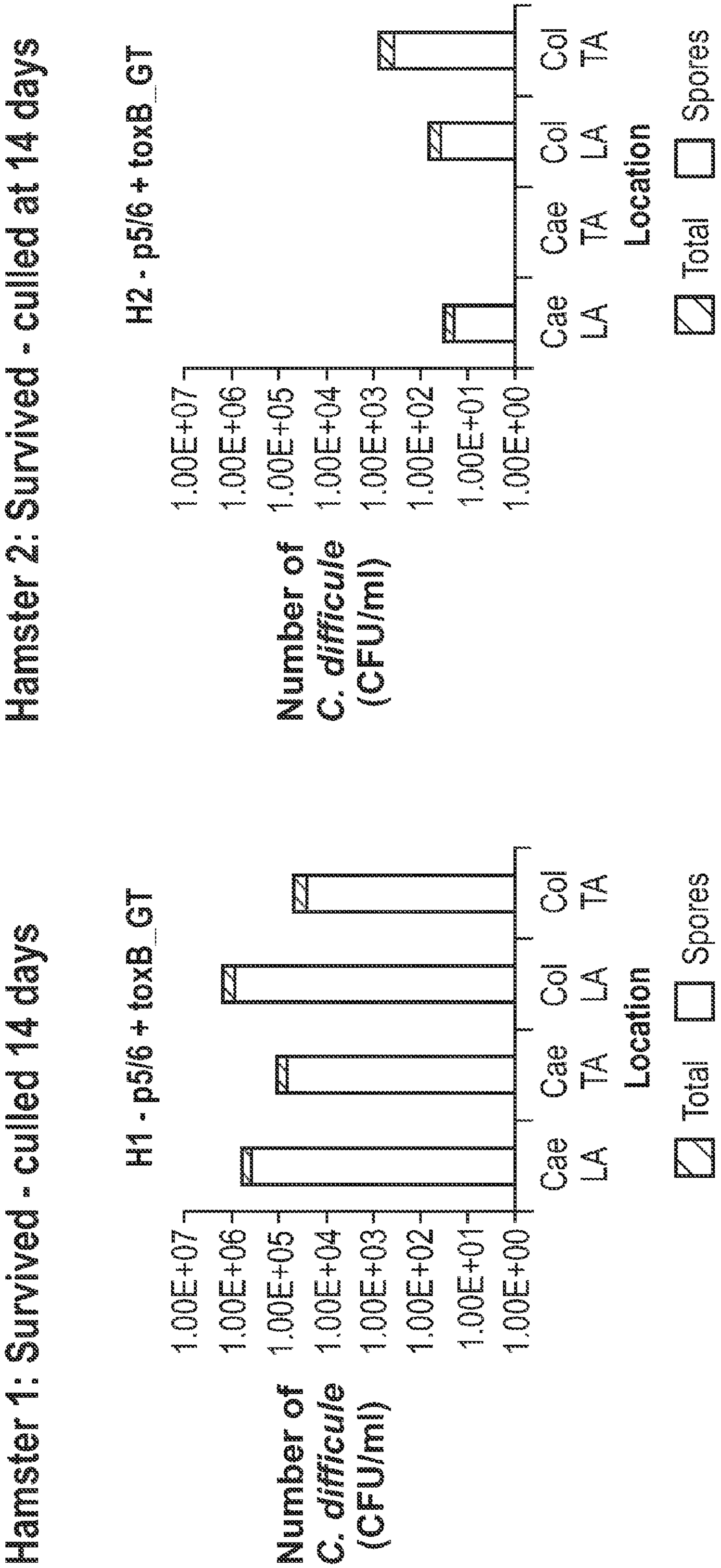
FIG. 21. ToxB_GT+P5_6. Infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)). Challenge with B1 strain.

An analysis of colonization at culling was also performed (FIG. 21). Results showed that all surviving hamsters, except H4, were colonized with *C. difficile* in the caecum and colon at the point of culling. All colonized surviving hamsters appear to have a higher vegetative cell: spore ratio than the animals which died in the acute stage of infection.

TABLE 22

ToxB_GT + P5_6 - toxin content in the colon. Data are represented as dilutions at which cells remain attached. Challenge with B1.

| Hamster | Vaccinated | Final dilution lysing cells |
|---|---|---|
| H1 | P5/6 + ToxB_GT | 1:25 |
| H2 | P5/6 + ToxB_GT | 1:5 |
| H3 | P5/6 + ToxB_GT | 0 |
| H4 | P5/6 + ToxB_GT | 0 |
| H5 | P5/6 + ToxB_GT | 1:5 |
| H6 | P5/6 + ToxB_GT | 0 |
| H7 | Adjuvant only | 1:625 |
| H8 | Non-vaccinated control | 1:625 |

Assessment of toxin B content in the gut revealed that there is less toxin B present in the caecum of the vaccinated animals (H1-H6) than animals which died in the acute phase of infection (H7 and H8) (Table 21). H3 and H6 from the vaccinated group had higher levels of toxin B present than the other vaccinated animals. H4 had no toxin B present, which was expected because there were no detectable *C. difficile* in the gut at the point of culling. This result was also confirmed in the colon (Table 22). As seen in the gut washes from the caecum, there is little or no active toxin B present in the surviving hamsters after 14 days, as compared to the high levels in the control animals, which died. Also, there is apparently less toxin B in the colon than in the caecum, and the only animals showing a significant amount of toxin B in the colon were also the animals which died of acute disease. Again, this could be explained by, for example, toxin binding by antibodies and/or a decrease in bacterial toxin expression.

Figure 40:
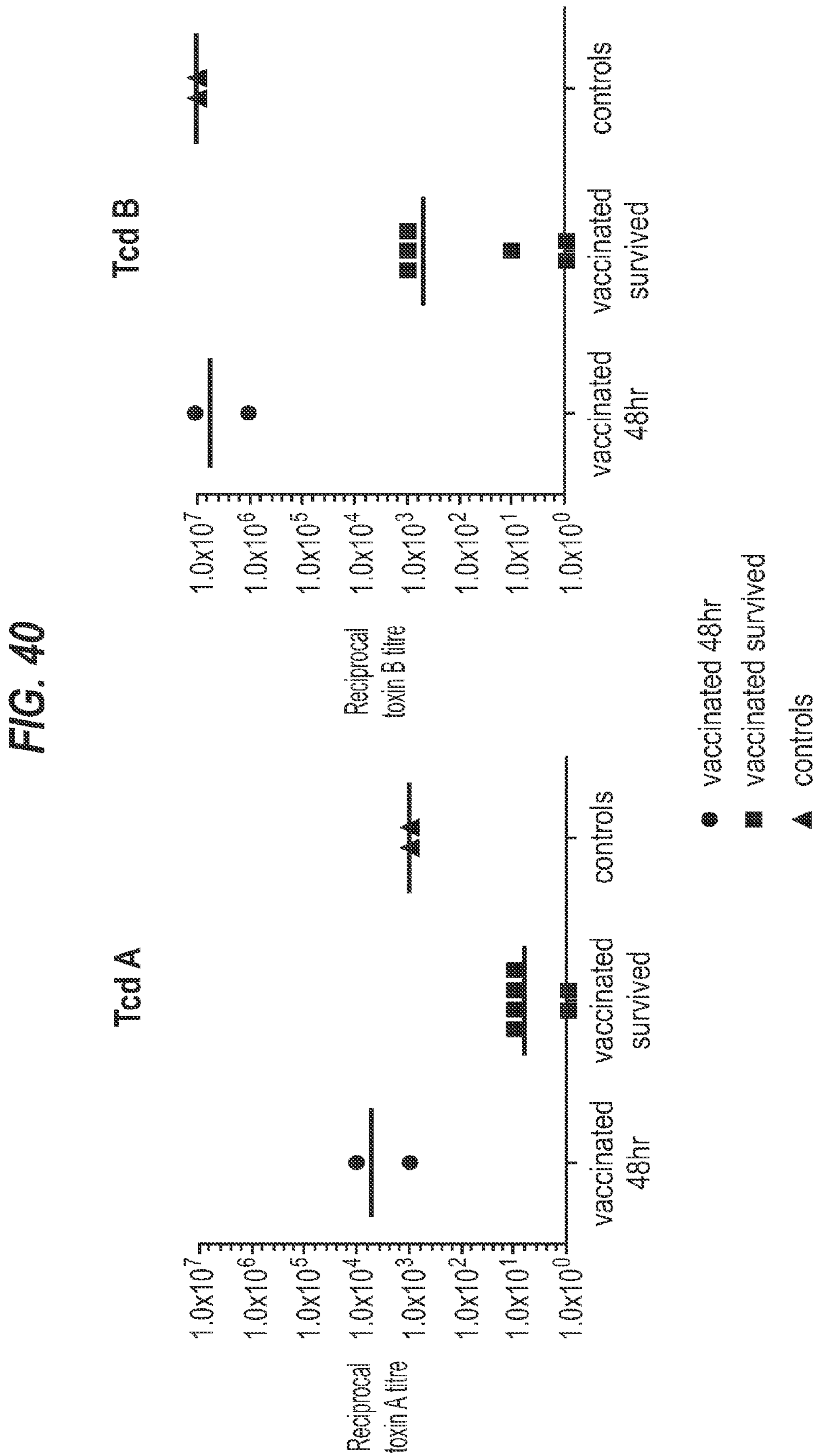
FIG. 40: Toxin A and B levels in hamsters vaccinated with ToxA-P5-6+ToxB-GT combination. Values are the fold dilution required for cell rounding. Filtered caecum samples were taken in vaccinated animals in the acute phase of infection (48 hours post-challenge) and at experimental endpoint (14 days post-challenge). Control animals were treated with adjuvant only and infected in the same experimental conditions.

Overall, vaccination with ToxA-P5-6+ToxB_GT provided 100% survival following challenge with the B1 strain. This combination did not protect the animals from diarrhoea following challenge with the B1 strain, although symptoms were relatively limited. By contrast, ToxA-P5_6 in combination with the ToxB-B fragment was found to confer only 83.3% protection against challenge with the B1 strain, and so using the ToxB-GT fragment in combination with a fragment of TcdA represents an improvement over using the ToxB-B fragment (see also FIG. 40).

ToxB_GT+P5_6 (Lower Doses)

It was now tested whether a lower dose (20 ugrs per antigen) also conferred protection against the B1 strain. All vaccinated animals (H1-H8) survived challenge with the B1 strain, and the control animals (H7-H8) died (Table 23).

TABLE 23

ToxA-P5-6 + ToxB_GT results (reduced dose). Challenge with B1 strain.

| | Antigens | Time to <35° C. | Time at cull | Temp at cull |
|---|---|---|---|---|
| H1 | P5/6 + ToxB_GT (20 μg dose) | | 48 h 28 min | 37.53° C. |
| H2 | P5/6 + ToxB_GT (20 μg dose) | | 14 days | |
| H3 | P5/6 + ToxB_GT (20 μg dose) | | 14 days | |
| H4 | P5/6 + ToxB_GT (20 μg dose) | | 14 days | |
| H5 | P5/6 + ToxB_GT (20 μg dose) | | | 37.13° C. |
| H6 | P5/6 + ToxB_GT (20 μg dose) | | 14 days | |
| H7 | P5/6 + ToxB_GT (20 μg dose) | | 14 days | |
| H8 | P5/6 + ToxB_GT (20 μg dose) | | 14 days | |
| H9 | Control | 29 h 57 m | 30 h 25 m | 34.15° C. |
| H10 | Control | 27 h 46 m | 28 h 15 m | 34.48° C. |

Figure 22:
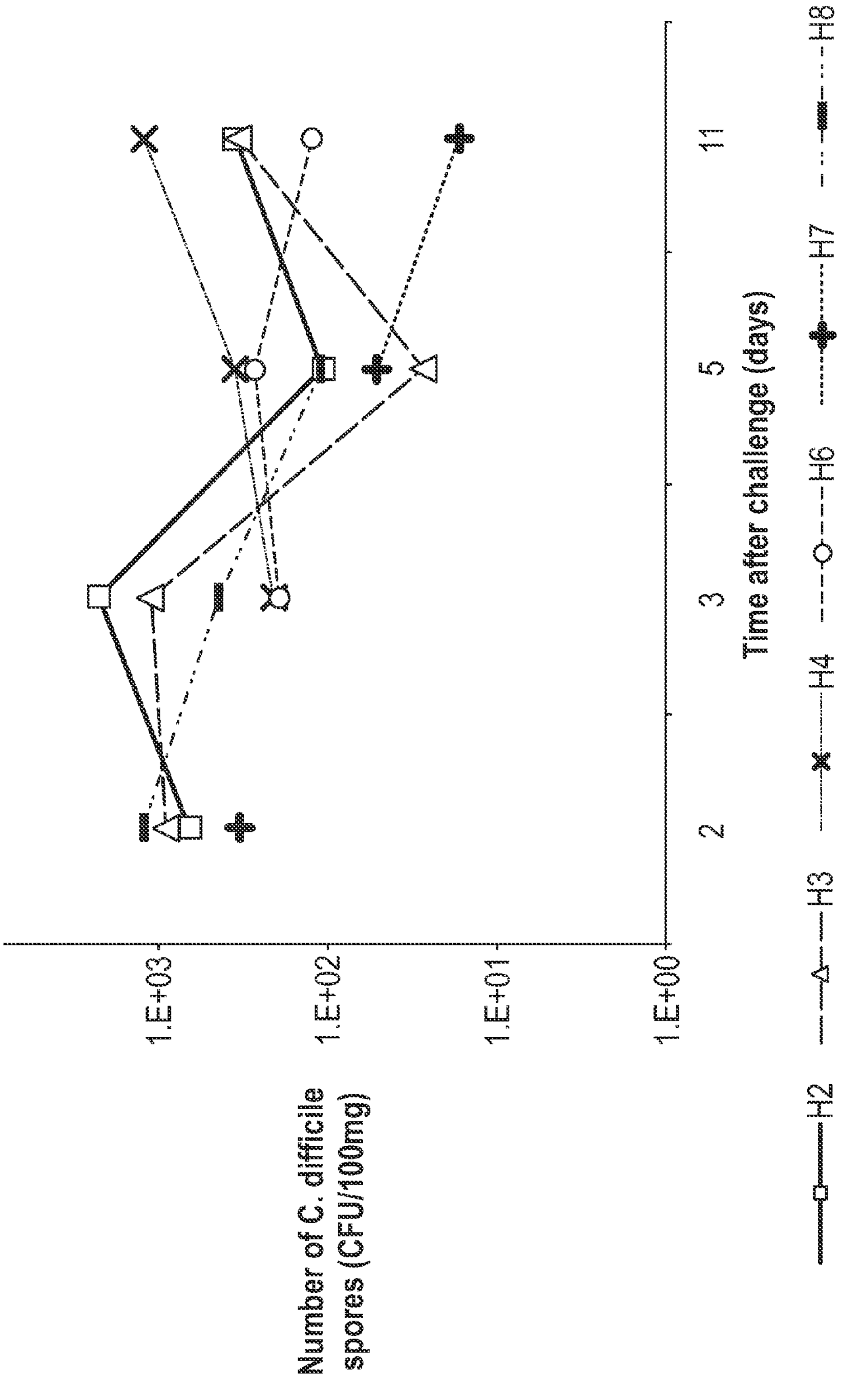
FIG. 22. ToxA-P5-6+ToxB_GT (reduced dose). Colonisation in faeces of vaccinated animals over time (days). Challenge with B1 strain.

All vaccinated animals exhibited a single episode of diarrhoea, except H2 which showed no clinical symptoms. The non-vaccinated controls died shortly after the onset of diarrhoea and were culled when their body temperature dropped below 35° C. H1 and H5 were culled at 48 post-challenge, despite the fact that they had recovered from the diarrhoeal stage of infection (and based on experience would have survived). H1 and H5 were culled at this stage to provide some information on the toxin B present and the damage to the gut, at this stage of infection. The number of colonies per 100 mg faecal material was then determined (FIG. 22), demonstrating that that the organisms are shed at high numbers for several days after challenge, even when symptoms (diarrhoea) have abated. The average shedding of *C. difficile* per vaccination group was calculated, and it appears that the shedding within these animals is reduced compared to any of the aforementioned experiments in which B1 was the challenge strain.

Figure 23:
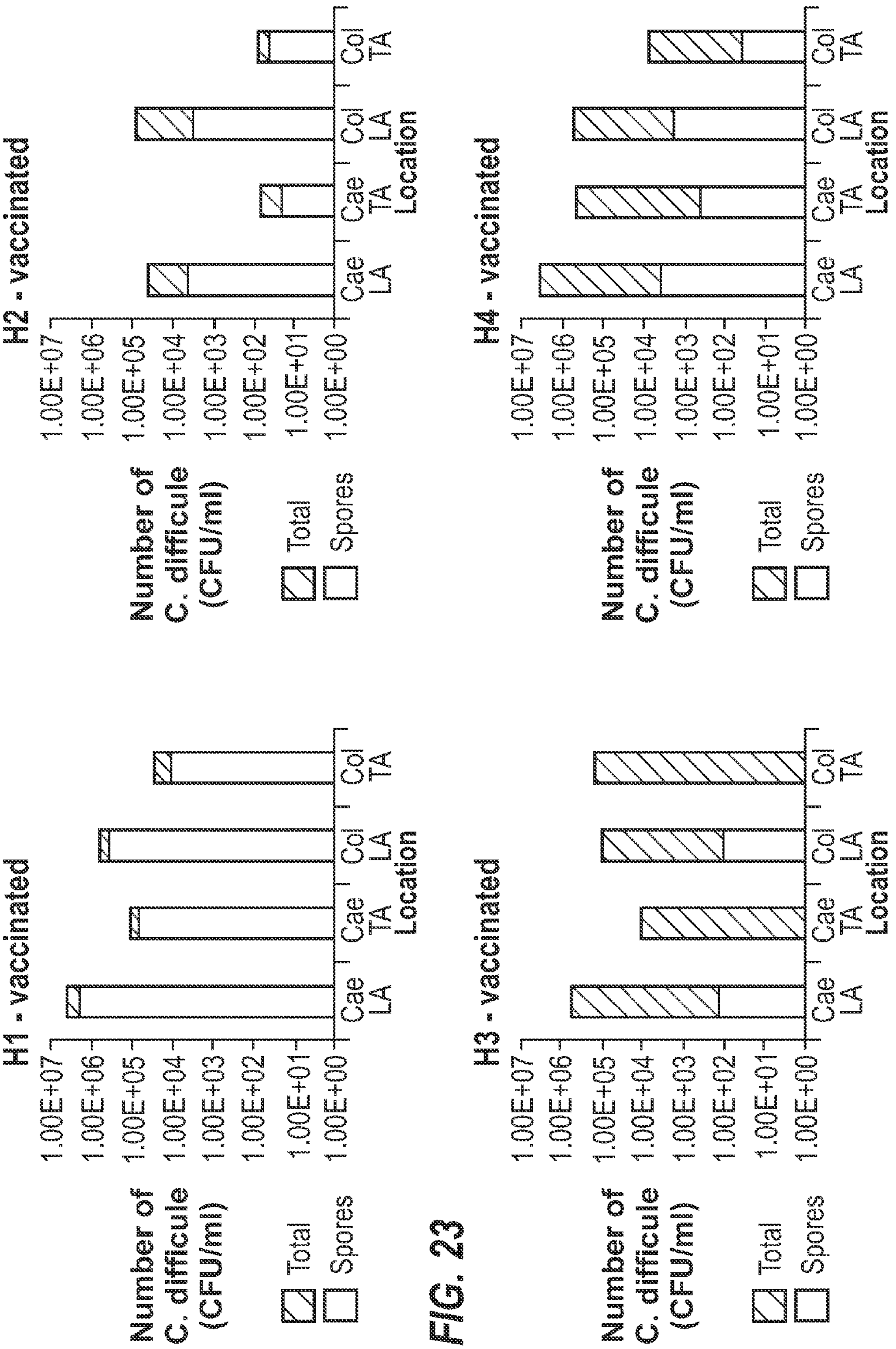
FIG. 23. ToxA-P5-6+ToxB_GT (reduced dose). Infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)). Challenge with B1 strain.

An analysis of colonization at culling was also performed (FIG. 23). Results showed that all surviving hamsters were colonized with *C. difficile* in the caecum and colon at the point of culling. H7 and H8 had no detectable spores present in either the caecum or colon and had lower numbers of vegetative bacteria than the other vaccinated animals at cull, 14 days after challenge. H2, H3, H4 and H6 had a higher ratio of vegetative cells to spores at the time of cull. H6 was colonised to a higher extent than H2, H3 and H4. H1 and H5 were vaccinated animals which had recovered from the challenge and culled 48 hr post challenge. H1 had a longer more severe episode of diarrhoea compared with H5 which only suffered a short, mild episode. Both the animals had recovered from diarrhoea and their tails were dry at the time of cull 48 hr after challenge. H1 and H5 had a comparable numbers of vegetative bacteria and spores to the control animals which died in the acute phase of the infection.

Assessment of toxin B content in the gut revealed that there is little or no active toxin B in the caecum of vaccinated animals culled 14 days after challenge (Table 24).

TABLE 24

ToxA-P5-6 + ToxB_GT (reduced dose) - toxin B content in the caecum. Data are represented as dilutions at which cells remain attached. Challenge with B1.

| Hamster | Vaccinated | Final dilution lysing cells |
|---|---|---|
| H1 | P5/6 + ToxB_GT | $10^7$ |
| H2 | P5/6 + ToxB_GT | $10^3$ |
| H3 | P5/6 + ToxB_GT | 0 |
| H4 | P5/6 + ToxB_GT | $10^3$ |
| H5 | P5/6 + ToxB_GT | $10^6$ |
| H6 | P5/6 + ToxB_GT | $10^3$ |
| H7 | P5/6 + ToxB_GT | $10^1$ |
| H8 | P5/6 + ToxB_GT | 0 |
| H9 | Control | $10^7$ |
| H10 | Control | $10^7$ |

Vaccinated animals which were killed 48 h after challenge had high levels of toxin B present in the caecum and the amount was comparable to animals which died in the acute phase of the infection at roughly 29 h after challenge. These observations were also confirmed in the colon (Table 25).

TABLE 25

ToxA-P5-6 + ToxB_GT (reduced dose)- toxin B content in the colon. Data are represented as dilutions at which cells remain attached. Challenge with B1.

| Hamster | Vaccinated | Final dilution lysing cells |
|---|---|---|
| H1 | P5/6 + ToxB_GT | 1:3125 |
| H2 | P5/6 + ToxB_GT | 0 |
| H3 | P5/6 + ToxB_GT | 0 |
| H4 | P5/6 + ToxB_GT | 0 |
| H5 | P5/6 + ToxB_GT | 1:3125 |
| H6 | P5/6 + ToxB_GT | 1:5 |
| H7 | P5/6 + ToxB_GT | 0 |
| H8 | P5/6 + ToxB_GT | 0 |
| H9 | Non-Vaccinated Control | 1:15625 |
| H10 | Non-Vaccinated Control | 1:15625 |

As seen in the gut washes from the caecum, there is little or no active toxin B present in the surviving hamsters after 14 days, as compared to the high levels in the control animals which died, or the two vaccinated animals culled at 48 h after challenge. Also, there is less toxin B in the colon than in the caecum, and the only animals showing a significant amount of toxin B in the gut were the control animals, which died of acute disease. Those animals culled at 48 h showed reduced levels whilst those animals culled at 14 days post challenge showed minimal or undetectable toxin B levels.

Levels of toxin A content in the gut were also assessed. Gut washes were filtered through a 0.22 μm filter to remove bacterial cells. Filtered washes were then placed on confluent HT29 cells at decreasing concentrations for 24 hours. After incubation, cells were washed, fixed, and then coloured with Giemsa stain. If toxin was present then cell rounding caused detachment and the absence of colour. Toxin-content data represents the dilutions at which the cells remained attached (stained). Assessment of toxin A content in the gut revealed that vaccinated animals culled 14 days after challenge had little or no toxin A present. Vaccinated animals H1 and H5 which were culled at 48 hr after challenge had a comparable amount of toxin A in the gut as the control animals (H9 and H10) which died in the acute phase of the infection (Table 26).

TABLE 26

ToxA-P5-6 + ToxB_GT (reduced dose) - toxin A content in the caecum. Data are represented as dilutions at which cells remain attached. Challenge with B1.

| Hamster | Vaccinated | Final dilution lysing cells |
|---|---|---|
| H1 | P5/6 + ToxB_GT | $10^4$ |
| H2 | P5/6 + ToxB_GT | $10^1$ |
| H3 | P5/6 + ToxB_GT | 0 |
| H4 | P5/6 + ToxB_GT | $10^1$ |
| H5 | P5/6 + ToxB_GT | $10^3$ |
| H6 | P5/6 + ToxB_GT | $10^1$ |
| H7 | P5/6 + ToxB_GT | $10^1$ |
| H8 | P5/6 + ToxB_GT | 0 |
| H9 | Non-Vaccinated Control | $10^3$ |
| H10 | Non-Vaccinated Control | $10^3$ |

Overall, vaccination with p5/6+toxB-GT at 20 μg per antigen per dose protected the animals from death but did not prevent diarrhoea when challenged with *C. difficile* strain B1. All surviving animals were colonised throughout the experiment and shed *C. difficile* spores in their faeces. At the time of culling, all animals were still colonised with *C. difficile* with some only showing low levels of vegetative cells and others showing higher levels of spores and vegetative cells. Animals surviving to the end of the experiment, showed low levels of toxin (either A or B) in the gut lumen.

In contrast, the control animals succumbed to infection approximately 29 h post infection. These animals showed high counts of both vegetative and spores in excised gut tissue and high level of toxin in filtered extracts. Interestingly, the 2 vaccinated animals that had recovered from the diarrhoeal phase of the disease, but were culled at 48 h appeared to show counts and toxin levels that more closely mirrored that of the control animals that the vaccinated ones, with relatively high amounts of toxin present in the lumen. However, the fact that these animals were no longer displaying diarrhoea would suggest that antibodies produced and released from the circulation in response to damage protected the animals from the more fatal consequences of the disease.

Therefore, immunisation using a combination of ToxA-P5-6+ToxB_GT provided 100% survival following challenge with the B1 strain, even when using a lower amount of antigen. Even when using 20 ugrs of each antigen, this combination out-performed ToxA-P5_6 in combination with the ToxB-B fragment, using 50 ugrs of each antigen.

ToxA-P5-6+ToxB-GT Challenged with R20291 (SM)

In view of the high level of protection against the 630 and B1 strains by immunisation with a combination of ToxA-P5-6+ToxB-GT, the inventors tested whether this combination is also protective against challenge with the R20291 (SM) strain. Animals were therefore immunized with a mixture of ToxA-5-6+ToxB-B, adjuvanted with MF59. Protection studies were performed, along with an analysis of the faeces, and an assessment of toxin content in the gut.

ToxB_GT-PSII+P5_6

The inventors then tested whether inclusion of PSII could induce an immune response able to reduce colonization. ToxB_GT was chemically conjugated to PSII, and this conjugate was able to induce PSII-specific antibodies (confirmed by ELISA, data not shown). Also, chemical conjugation to PSII was not found to impair neutralization activity.

The experiment consisted of three groups, which were challenged with strain 630: vaccination with ToxB_GT (PSII)+P5_6 (H1-H6), vaccination with ToxB_GT+P5_6 (H7-8) and treatment with adjuvant alone (H9-H10). Results are shown in Table 27. H1-H3 displayed no episodes of diarrhoea, but H4 had two episodes and was culled after the second episode. Of hamsters H1-H6, 5/6 survived. Of hamsters H7 and H8, 2/2 survived.

TABLE 27

ToxB_GT(PSII) + P5_6 results. Challenge strain 630.

| | | Time to <35° C. | Time at cull | Temp at cull |
|---|---|---|---|---|
| H1 | P5/6 + ToxB_GT-PSII | | 14 days | |
| H2 | P5/6 + ToxB_GT-PSII | | 14 days | |
| H3 | P5/6 + ToxB_GT-PSII | | 14 days | |
| H4 | P5/6 + ToxB_GT-PSII | 89 h 40 m | 89 h 50 m | 34.55° C. |
| H5 | P5/6 + ToxB_GT-PSII | | 14 days | |
| H6 | P5/6 + ToxB_GT-PSII | | 14 days | |
| H7 | P5/6 + ToxB_GT | | 14 days | |
| H8 | P5/6 + ToxB_GT | | 14 days | |
| H9 | Control | 33 h 37 m | 37 h 48 m | 20.0° C. |
| H10 | Control | 54 h 43 m | 64 h 0 m | 29.88° C. |

Figure 24:
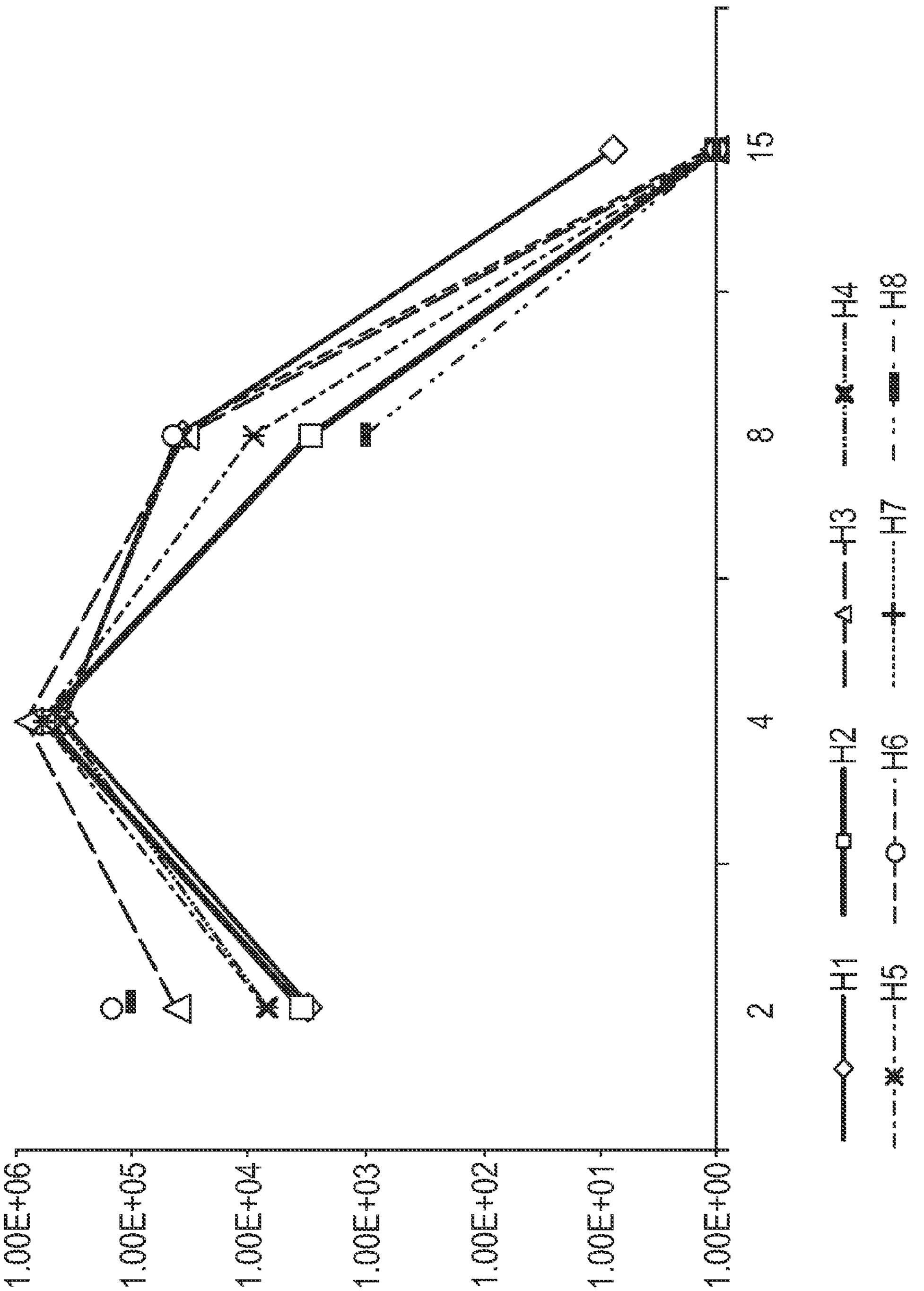
FIG. 24. Immunisation with ToxB_GT(PSII)+P5_6. Colonisation in faeces of vaccinated animals over time (days). Challenge with 630 strain. Some animals are missing specific time points, e.g. where the animal failed to produce faeces on the day of collection (especially after periods of diarrhoea) or had diarrhoea on a specific time point.

The number of colonies per 100 mg faecal material was then determined (FIG. 24), demonstrating that that the organisms are shed at high numbers for several days after challenge, even when symptoms (diarrhoea) have abated. All surviving animals shed high levels of *C. difficile* in their faeces.

Figure 25:
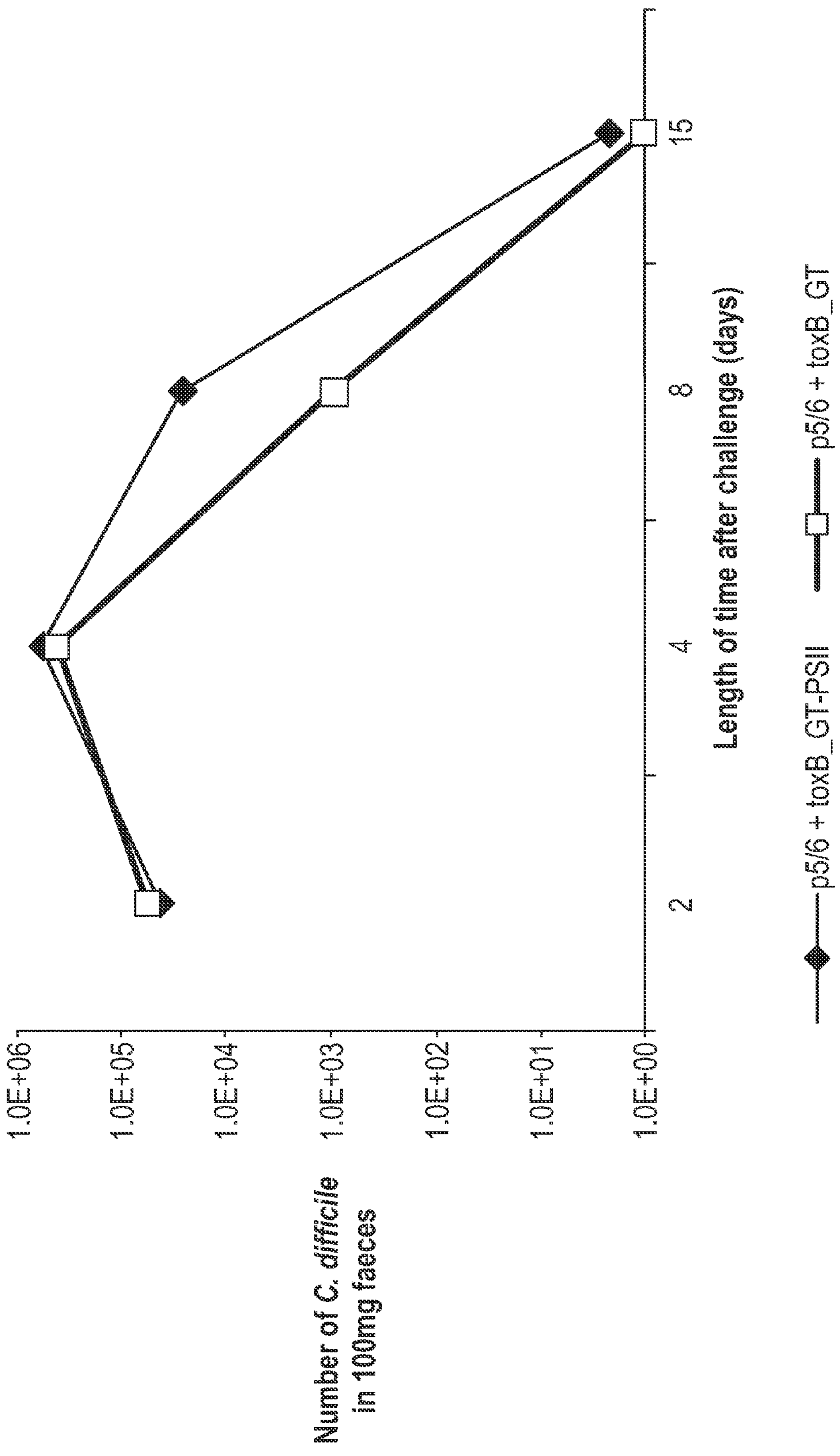
FIG. 25. Average number of *C. difficile* being shed in faeces from surviving vaccinated animals (ToxB_GT(PSII)+P5_6 (H1-H6), or ToxB_GT+P5_6 (H7-8)).
Figure 26A:
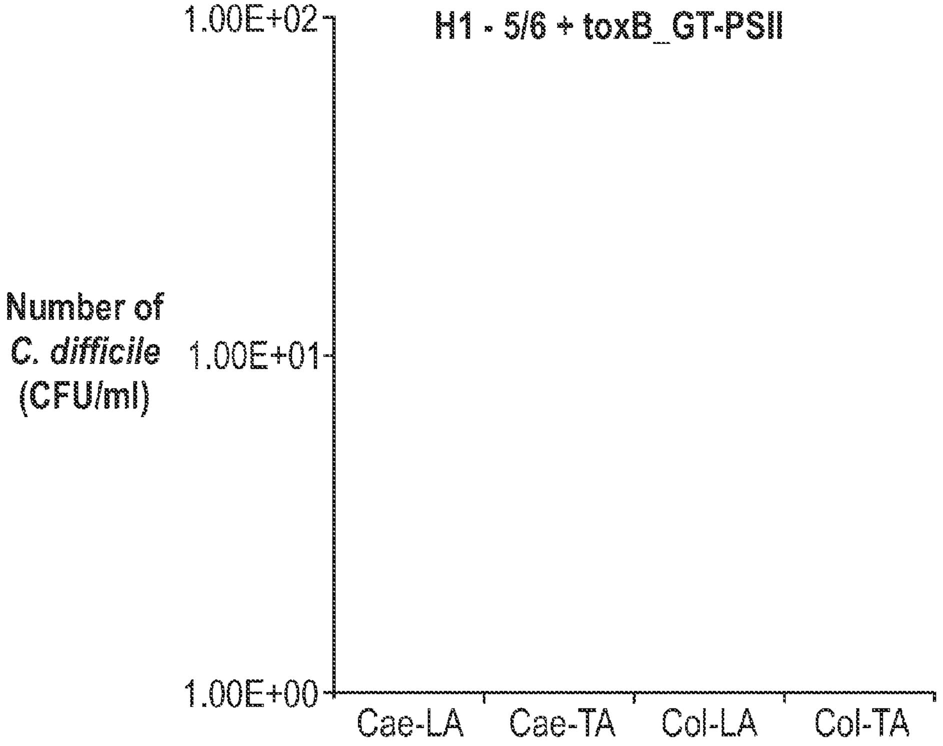
FIG. 26 (a and b). ToxB_GT(PSII)+P5_6 results—infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)).
Figure 26A:
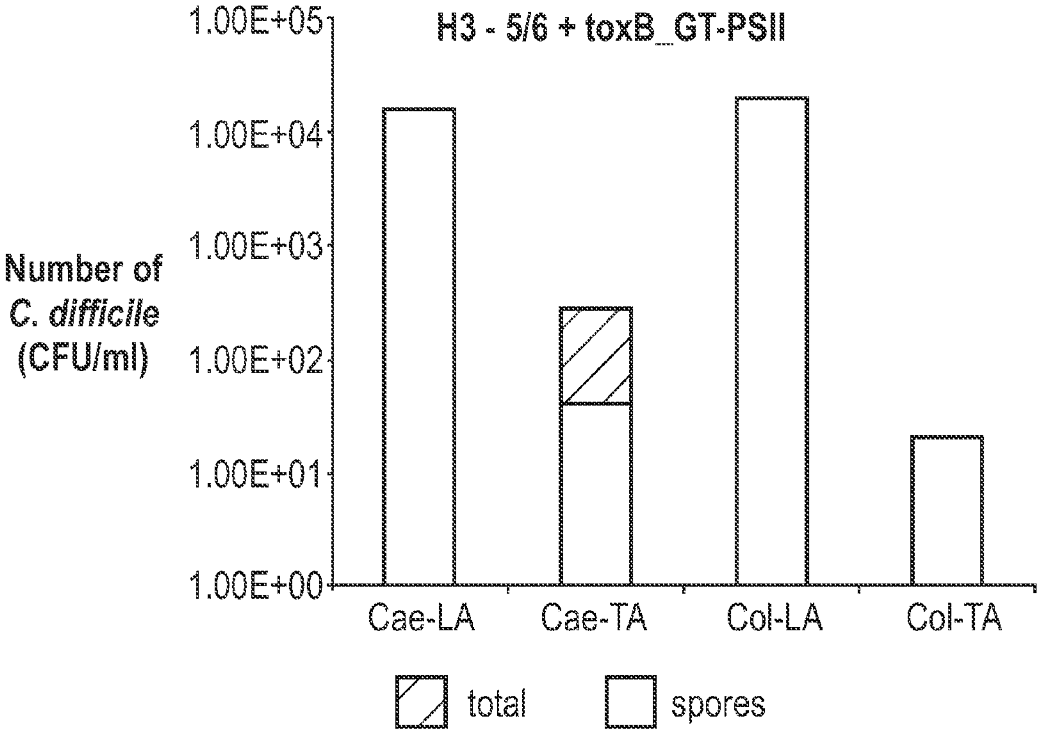
Figure 26B:
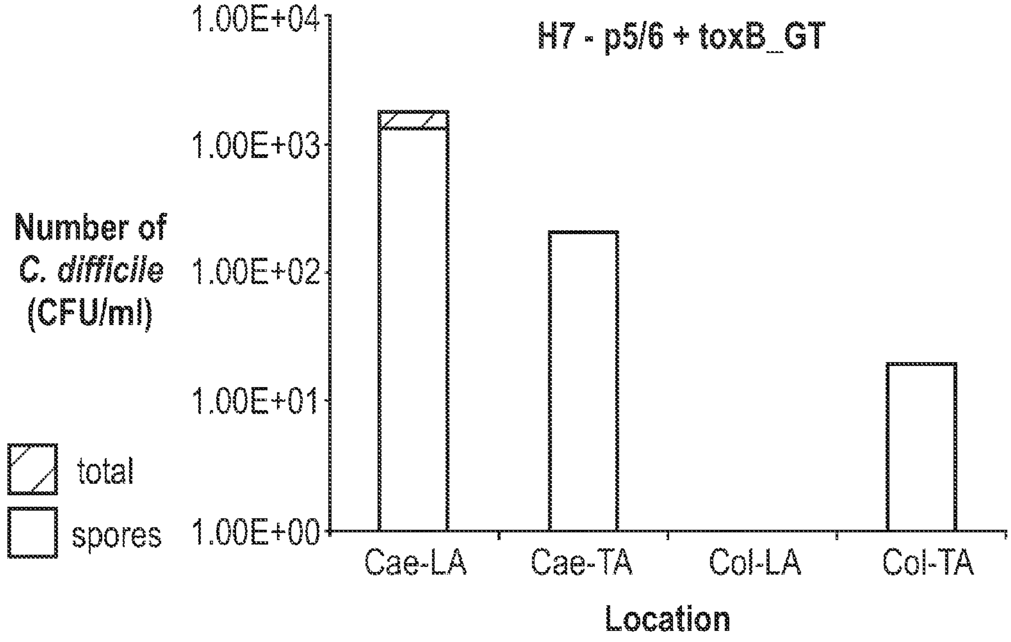
Figure 26B:
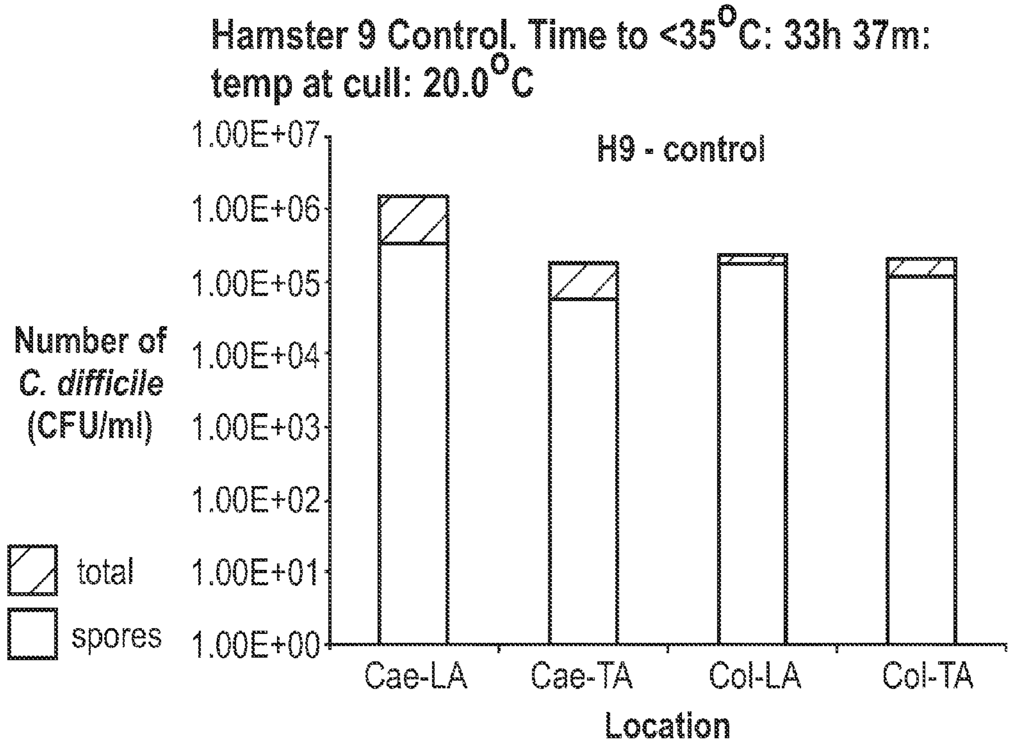

The average number of *C. difficile* being shed in faeces from surviving vaccinated animals (ToxB_GT(PSII)+P5_6 (H1-H6), or ToxB_GT+P5_6 (H7-8)) is shown in (FIG. 25). This shows that there may be a slight advantage in including PS-II on colonization.

An analysis of colonization at culling was also performed (FIG. 26(*a* and *b*)). Results showed low or no colonization of tissue-associated *C. difficile* in surviving (vaccinated) animals. Results obtained for H4 were comparable to negative controls.

Therefore, high colony counts were observed only in animals that did not survive.

Chimera B4

The inventors then tested the protectivity obtained using a hybrid protein comprising ToxB-GT+ToxA-P5-6 (the "B4" chimera). 6 animals (H1-6) were immunized with 50 ugr of the B4 chimera (adjuvanted with MF59). As controls, 2 animals received adjuvant alone (H7-H8) and 2 animals received no vaccination (H9-H10). Antigen was administered intraperitoneally. Animals were challenged with the 630 strain (H1 and H8 were culled prior to challenge). All control animals died, but 3/5 of the vaccinated animals survived until the end of the experiment (Table 28). Therefore, expressing ToxB-GT and ToxA-P5-6 as a chimera appears to reduce the effectiveness of this combination of antigens, compared to using a mixture of single antigens.

TABLE 28

Chimera B4 results. Challenge with 630 strain.

| Hamster | Immunogen | Time to endpoint | Time to |
|---|---|---|---|
| 1 | Culled prior to challenge* | | |
| 2 | B4 chimera | Survived until expt end | |
| 3 | B4 chimera | Survived | |
| 4 | B4 chimera | Survived | |
| 5 | B4 chimera | 165 h | |
| 6 | B4 chimera | 155 h | |

TABLE 28-continued

| Chimera B4 results. Challenge with 630 strain. | | | |
|---|---|---|---|
| Hamster | Immunogen | Time to endpoint | Time to |
| 7 | MF59 alone | | Approx 35 h** |
| 8 | Culled prior to challenge* | | |
| 9 | No treatment | | 62 h 35 min |
| 10 | No treatment | | 37 h 21 min |
| | Mean | | 44 h 58 min |

Vaccinated animals were fully protected against death but not diarrhoea.
*Animals were culled as a result of abscesses associated with chip insertion.

Assessment of colonisation of animals was determined by removal of faecal samples from cages at intervals after challenge. Faeces were weighed, re-suspended in sterile PBS and then plated on selective media. The number of colonies per 100 mg faecal material was then determined (Table 29) demonstrating that that the organisms are shed at high numbers for several days after challenge (bacteria were not detectable in faeces of H6).

TABLE 29

Bacterial shedding of *C. Difficile* spores in 100 mg faeces from hamsters immunised with Chimera B4 or controls. Challenged with 630 strain.

| | | *C. difficile* recovered per 100 mg of faecal material | | | |
|---|---|---|---|---|---|
| Animal | Treatment | Day 3 post infection | Day 5 post infection | Day 11 post infection | Day 15 post infection |
| 2 | Vacci-nated B4 | $1.4 \times 10^4$ | $3.58 \times 10^6$ | $3.12 \times 10^4$ | *ND |
| 3 | Vacci-nated B4 | 83 | $8.82 \times 10^5$ | $3.12 \times 10^4$ | ND |
| 4 | Vacci-nated B4 | 122 | $4.67 \times 10^6$ | $3.12 \times 10^4$ | ND |
| 5 | Vacci-nated B4 | 333 | No faeces | Dead | |
| 6 | Vacci-nated B4 | 0 | $2.76 \times 10^6$ | Dead | |

*ND = Bacteria were not detectable.

ToxB_GT+ToxA_B2

The inventors then tested whether immunisation with ToxB_GT in combination with a different fragment of TcdA was capable of conferring the same high level of protection as for ToxB-GT+ToxA-P5/6. Animals were therefore immunised with a mixture of ToxB-GT+ToxA_B2, and challenged with the B1 strain. Animals (H1-H6) were immunized with a mixture of ToxB_GT+ToxA_B2 (adjuvanted with MF59). The controls (adjuvant only (H7 and H8) and no adjuvant (H9 and H10)) had strong diarrhoea and a temperature drop, at which point they were culled. All immunized animals survived against challenge with the B1 strain (6/6) (Table 30).

TABLE 30

| ToxB_GT + ToxA_B2 results. Challenge with B1 strain. | | | | |
|---|---|---|---|---|
| | Antigens | Time to <35° C. | Time at cull | Temp at cull |
| H1 | toxA_B2 + toxB_GT | | 14 days | |
| H2 | toxA_B2 + toxB_GT | | 14 days | |
| H3 | toxA_B2 + toxB_GT | | 14 days | |
| H4 | toxA_B2 + toxB_GT | | 14 days | |
| H5 | toxA_B2 + toxB_GT | | 14 days | |
| H6 | toxA_B2 + toxB_GT | | 14 days | |
| H7 | Adjuvant only | 31 h 17 m | 31 h 40 m | 33.94° C. |
| H8 | Adjuvant only | 33 h 8 m | 33 h 20 m | 34.59° C. |
| H9 | Control | 30 h 2 m | 30 h 45 m | 32.31° C. |
| H10 | Control | 32 h 7 m | 32 h 35 m | 34.23° C. |

All immunised animals exhibited a single episode of diarrhoea, apart from H3, which exhibited no diarrhoea (H1 exhibited the most severe diarrhoea of this batch and was monitored closely). All animals exhibiting clinical symptoms had shorter bouts of diarrhoea than observed in any of the aforementioned experiments, when challenged with the B1 strain.

Figure 27:
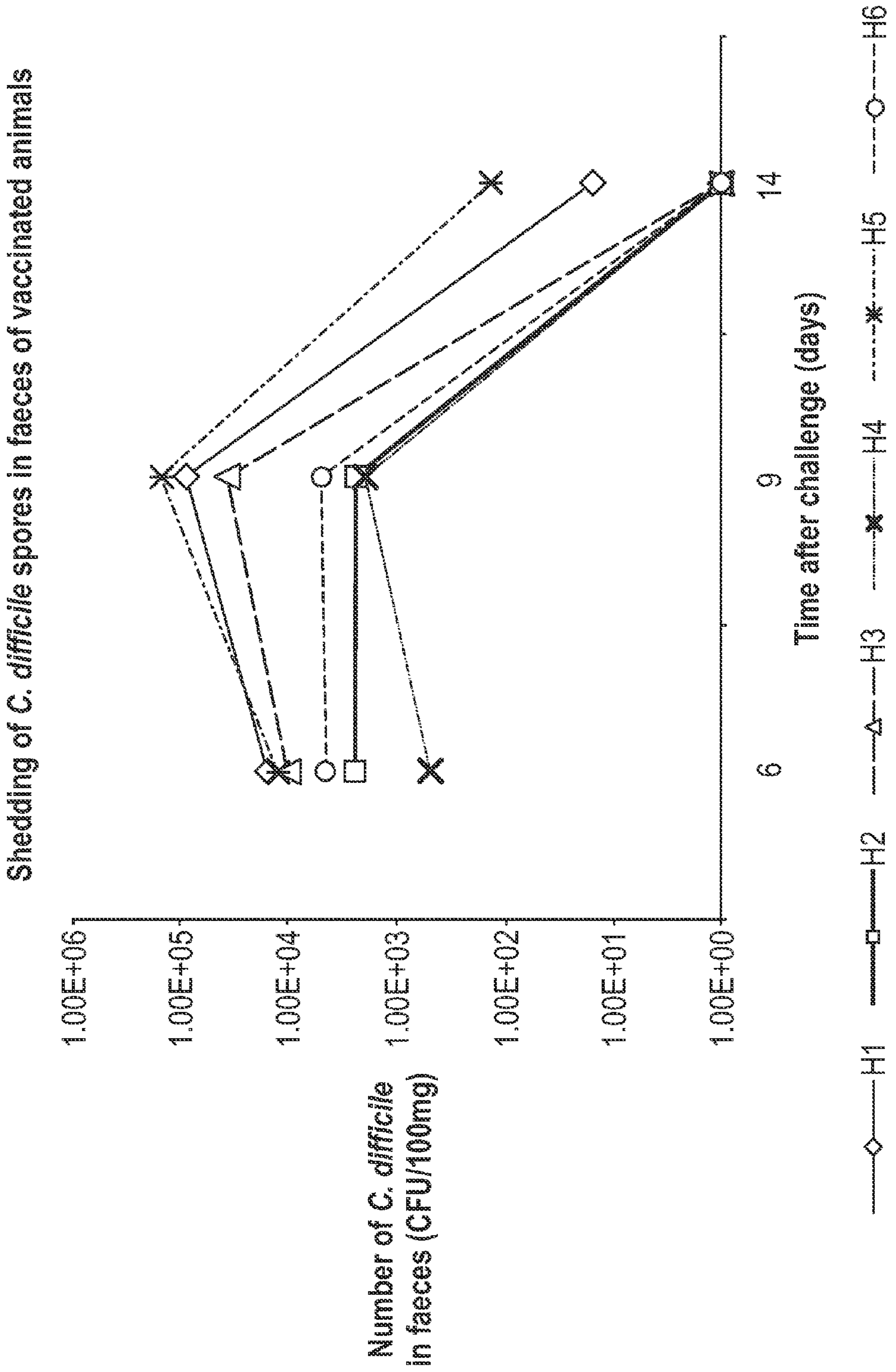
FIG. 27. ToxB_GT+ToxA_B2. Colonisation in faeces of vaccinated animals over time (days). Challenge with B1 strain.

The number of colonies per 100 mg faecal material was then determined (FIG. 27), demonstrating that that the organisms are shed at high numbers for several days after challenge, even when symptoms (diarrhoea) have abated. All surviving animals shed high levels of *C. difficile* in their faeces. By day 14, four immunised hamsters (H2, H3, H4, and H6) had no detectable *C. difficile* spores in their faeces.

Figure 28A:
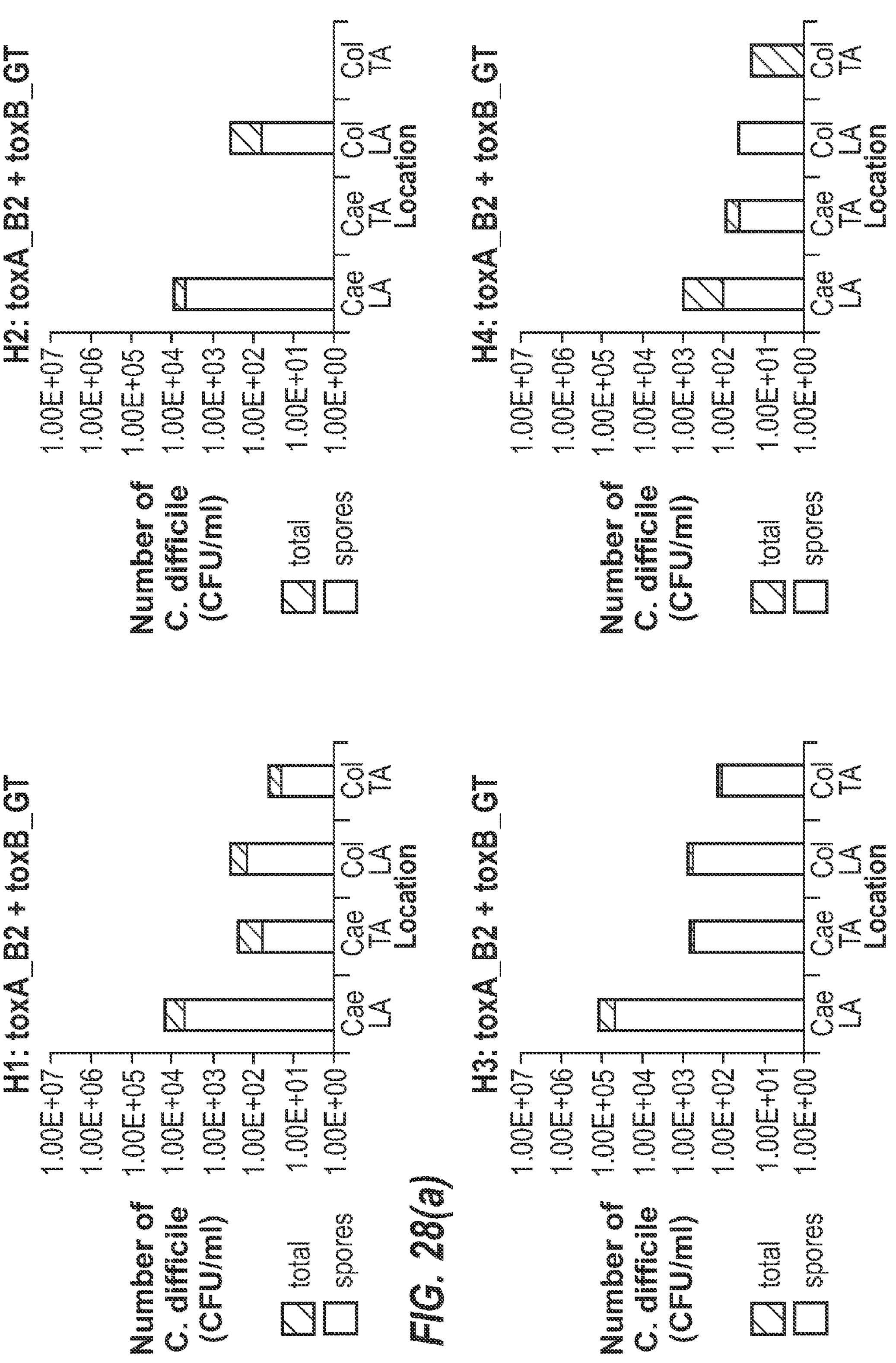
FIG. 28 (a and b). ToxB_GT+ToxA_B2. Infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)). Challenge with B1 strain.
Figure 28B:
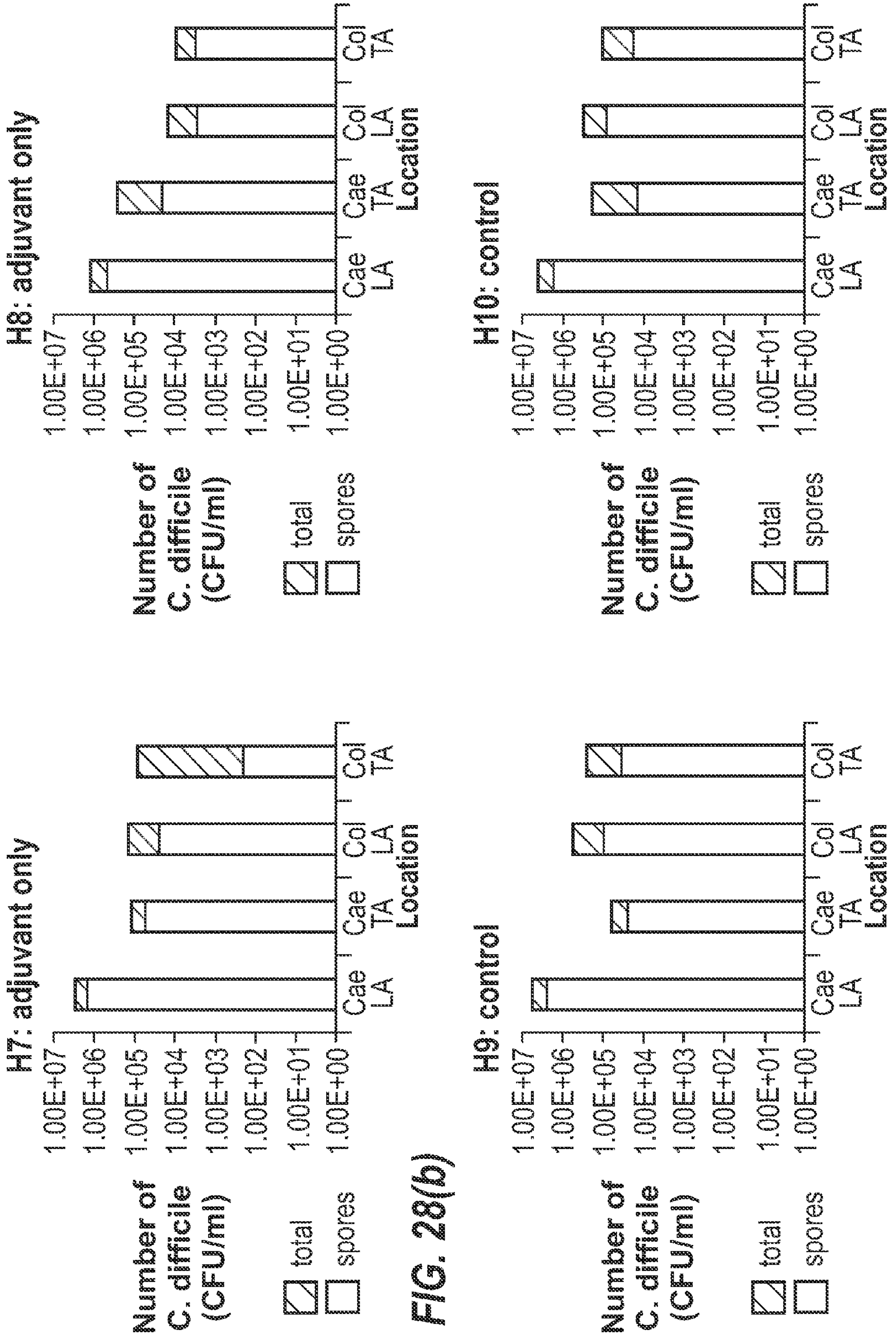

An analysis of colonization at culling was also performed (FIG. 28(*a-b*)). Results showed that all surviving hamsters were colonized with *C. difficile* in the caecum and colon at the point of culling, however the bacterial counts were very low and were approaching the lower end of the detection limit. H2 and H6 appeared to have no detectable bacteria associated with the tissue. All colonized surviving hamsters appear to have a higher vegetative cell:spore ratio than the animals which died in the acute stage of infection.

Assessment of toxin B content in the gut revealed that there is little (H5) or no active toxin B in the caecum of vaccinated animals (H5 had the highest number of bacteria in the gut at the point of culling of all vaccinated animal) (Table 31). This result was also confirmed in the colon (Table 32).

TABLE 31

| B_GT + ToxA_B2 - toxin content in the caecal gut. Data are represented as dilutions at which cells remain attached. Challenge with B1. | | |
|---|---|---|
| Hamster | Vaccinated | Final dilution |
| H1 | toxA_B2 + toxB_GT | 0 |
| H2 | toxA_B2 + toxB_GT | 0 |
| H3 | toxA_B2 + toxB_GT | 0 |
| H4 | toxA_B2 + toxB_GT | 0 |
| H5 | toxA_B2 + toxB_GT | $10^1$ |
| H6 | toxA_B2 + toxB_GT | 0 |
| H7 | Adjuvant only | $10^4$ |
| H8 | Adjuvant only | $10^4$ |
| H9 | Control | $10^4$ |
| H10 | Control | $10^4$ |

TABLE 32

| B_GT + ToxA_B2 - toxin content in the colon. Data are represented as dilutions at which cells remain attached. Challenge with B1. | | |
|---|---|---|
| Hamster | Vaccinated | Final dilution lysing cells |
| H1 | toxA_B2 + toxB_GT | 0 |
| H2 | toxA_B2 + toxB_GT | 1:5 |

TABLE 32-continued

B_GT + ToxA_B2 - toxin content in the colon. Data are represented as dilutions at which cells remain attached. Challenge with B1.

| Hamster | Vaccinated | Final dilution lysing cells |
|---|---|---|
| H3 | toxA_B2 + toxB_GT | 0 |
| H4 | toxA_B2 + toxB_GT | 0 |
| H5 | toxA_B2 + toxB_GT | 1:5 |
| H6 | toxA_B2 + toxB_GT | 0 |
| H7 | Adjuvant only | 1:625 |
| H8 | Adjuvant only | 1:25 |
| H9 | Non-vaccinated control | 1:625 |
| H10 | Non-vaccinated control | 1:25 |

As seen in the gut washes from the caecum, there is little or no active toxin B present in the surviving hamsters after 14 days, as compared to the high levels in the control animals, which died. Also, there is apparently less toxin B in the colon than in the caecum, and the only animals showing a significant amount of toxin B in the colon were also the animals which died of acute disease.

Overall, vaccination with ToxA-B2+ToxB_GT provided 100% survival following challenge with the B1 strain, thereby out-performing the level of protection achieved using full length inactivated toxoids, and matching the high level of protection achieved using ToxB-GT+ToxA-P5-6. This combination did not protect the animals from diarrhoea following challenge with the B1 strain. Nevertheless, symptoms were relatively limited and were even less severe than with any of the aforementioned combinations tested, following challenge with the B1 strain. All surviving animals were colonised throughout the experiment, although 3/6 of the vaccinated animals showed no detectable *C. difficile* spores in the faeces at 14 days post infection (although detectable numbers of *C. difficile* could be cultured directly from the gut at that time). Also, vaccinated animals showed relatively low levels of toxin B in the gut at the end of the experiment. Again, this could be explained by, for example, toxin binding by antibodies and/or a decrease in bacterial toxin expression.

ToxA-B2+ToxB_B+ToxB_GT

The inventors then tested whether vaccination with ToxB-GT+ToxB-B+ToxA-B2, has any effect on protection against CDAD. Animals were immunized with a mixture of ToxA-B2+ToxB_B+ToxB-GT. Protection studies were performed, along with an analysis of the faeces, and an assessment of toxin content in the gut.

ToxB_B+ToxA-P5_6+ToxB_GT

The inventors then tested whether vaccination with ToxB-GT+ToxA-P5-6 in combination with the ToxB-B fragment, has any further effect on protection against CDAD. Animals were therefore immunized with a mixture of ToxB_B+P5_6+ToxB_GT (adjuvanted with MF59). Unvaccinated controls had strong diarrhoea and a temperature drop, at which point they were culled. 5 of the 6 vaccinated hamsters (83%) survived challenge with the B1 strain (Table 33).

TABLE 33

ToxB_GT + ToxB_B + P5_6 in MF59 adjuvant. Challenge with B1. 5 out of 6 vaccinated animals survived. H1 and H4 showed a single episode of diarrhoea lasting roughly one hour.

| | | Time to <35° C. | Time at cull | Temp at cull |
|---|---|---|---|---|
| H1 | Vaccine | | 15 days | |
| H2 | Vaccine | 50 h 50 m | 50 h 54 m | 34.69° C. |
| H3 | Vaccine | | 15 days | |
| H4 | Vaccine | | 15 days | |
| H5 | Vaccine | | 15 days | |
| H6 | Vaccine | | 15 days | |
| H7 | Adjuvant only | 28 h 47 m | 28 hr 47 m | 34.12° C. |
| H8 | Adjuvant only | 28 h 50 m | 28 h 50 m | 33.46° C. |
| H9 | Control | 30 h 48 m | 30 h 48 m | 34.9° C. |
| H10 | Control | 29 h 32 m | 29 h 32 m | 32.2° C. |

Figure 29:
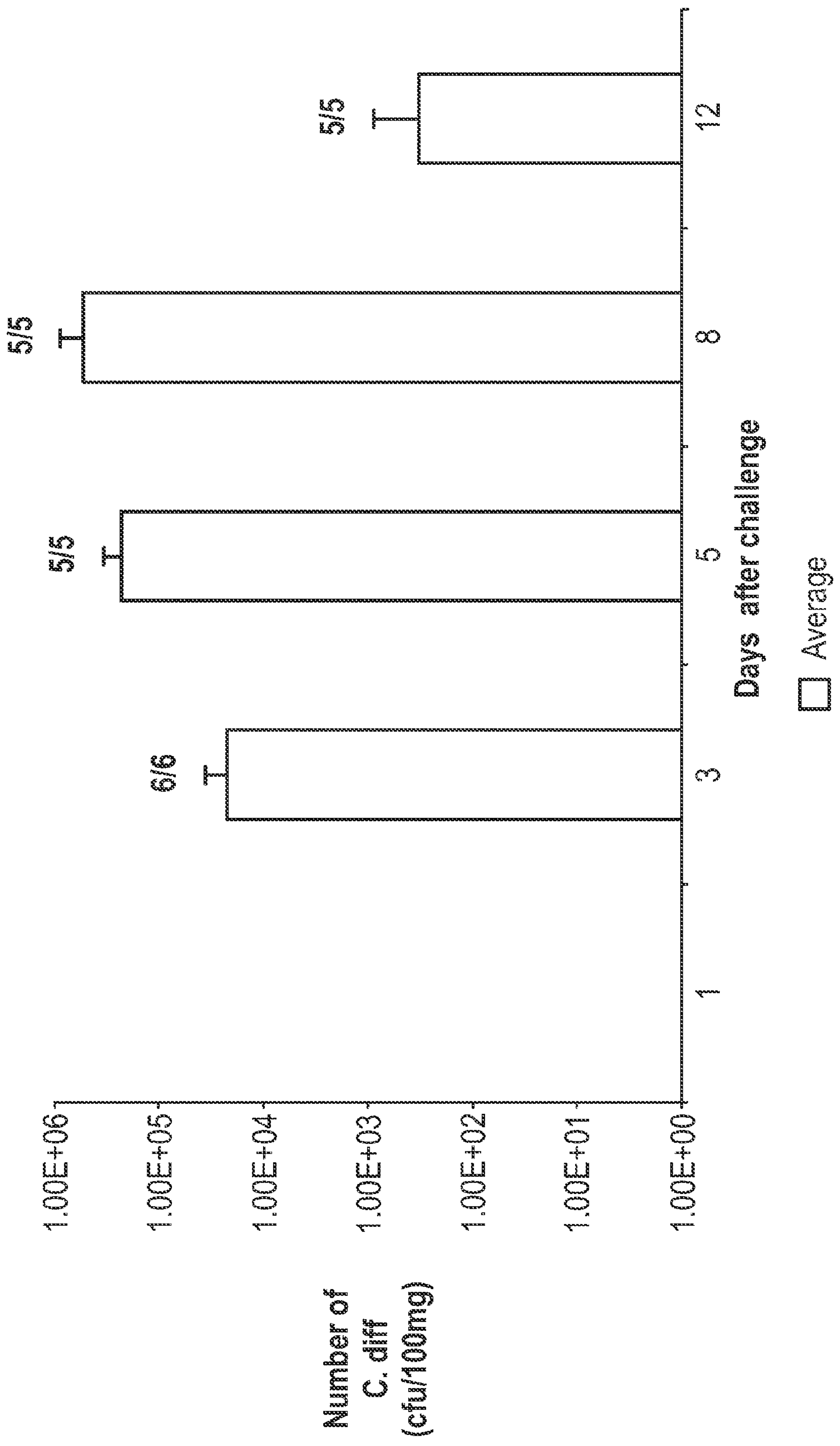
FIG. 29. ToxB_GT+ToxB_B+P5_6. Average colonisation in faeces of vaccinated animals.
Figure 30:
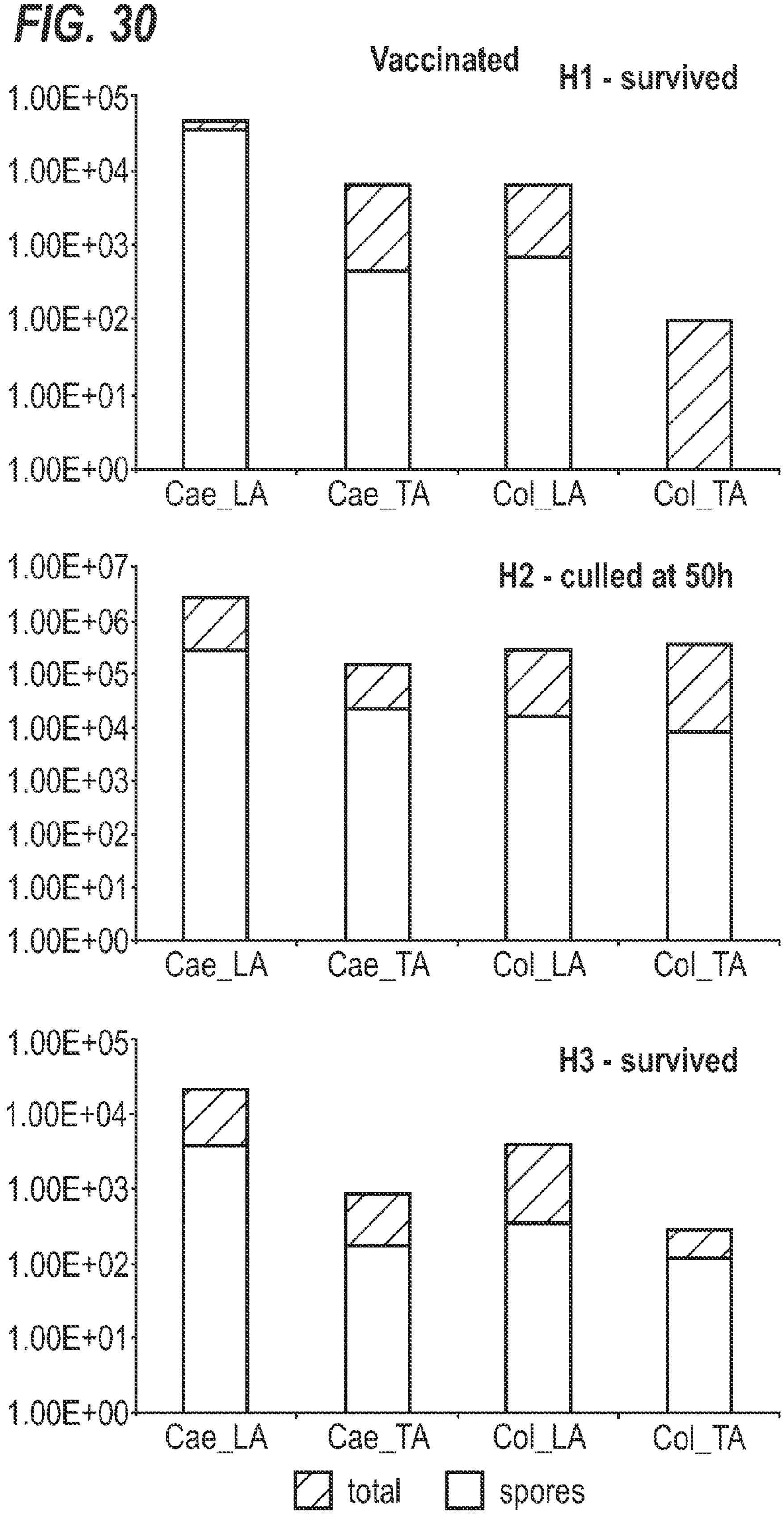
FIG. 30. ToxB_GT+ToxB_B+P5_6. Challenge with B1. Post—infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)).

Hamsters H1 and H4 showed only a single episode of diarrhoea lasting roughly 20 hours, and hamsters H3, H5 and H6 had no episodes of diarrhea. An analysis of faeces (FIG. 29) shows that *C. difficile* organisms are shed at very high numbers for several days following challenge, even when symptoms (diarrhea) have abated. An overview of terminal colonization is provided in FIG. 30.

Assessment of toxin B content in the gut revealed that there is less toxin B present in 5 out of the 6 vaccinated hamsters after 15 days than in the controls, which died after 2 days (Table 34).

TABLE 34

ToxB_B + P5_6 + ToxB_GT. Toxin content in the caecal gut. Data are represented as dilutions at which cells remain attached. Challenge with B1 strain.

| Hamster | Vaccinated | Final dilution lysing cells |
|---|---|---|
| H1 | P5_6 + ToxB_B + toxB-GT | $10^1$ |
| H2 | P5_6 + ToxB_B + toxB-GT | $10^6$ |
| H3 | P5_6 + ToxB_B + toxB-GT | 0 |
| H4 | P5_6 + ToxB_B + toxB-GT | 0 |
| H5 | P5_6 + ToxB_B + toxB-GT | 0 |
| H6 | P5_6 + ToxB_B + toxB-GT | $10^1$ |
| H7 | Adjuvant only | $10^6$ |
| H8 | Adjuvant only | $10^5$ |
| H9 | None | $10^5$ |
| H10 | None | $10^5$ |

This result was also confirmed in the colon (Table 35). H2 died at 50 h 54 mins and had a similar amount of toxin B in the gut as the control animals, which died.

TABLE 35

ToxB_B + P5_6 + ToxB_GT. Toxin content in the colon. Data are represented as dilutions at which cells remain attached. Challenge with B1 strain.

| Hamster | Vaccinated | Final dilution lysing cells |
|---|---|---|
| H1 | P5_6 + ToxB_B + toxB-GT | 0 |
| H2 | P5_6 + ToxB_B + toxB-GT | 1:25 |
| H3 | P5_6 + ToxB_B + toxB-GT | 0 |
| H4 | P5_6 + ToxB_B + toxB-GT | 0 |
| H5 | P5_6 + ToxB_B + toxB-GT | 0 |
| H6 | P5_6 + ToxB_B + toxB-GT | 0 |
| H7 | Adjuvant only | 1:15625 |
| H8 | Adjuvant only | 1:78125 |
| H9 | None | 1:78125 |
| H10 | None | 1:78125 |

Therefore, immunisation with a mixture of ToxB_B+P5_6+ToxB_GT provides strong protection against challenge with the 630 strain, but does not appear to confer any advantage over ToxB-GT+ToxA-P5-6.

ToxA_GT+ToxB_GT+ToxB_B+ToxA_B2

The inventors then tested the level of protectivity conferred by immunisation with a combination of antigens comprising ToxA-GT. Animals were therefore immunized with a mixture of ToxA-GT+ToxB-GT+ToxB-B+ToxA-B2. 6 animals received 50 μg of each antigen (adjuvanted with MF59), (H1-H6). 1 animal received adjuvant only (H7), 2 were untreated (H8-H9) and one was unchallenged (H10). The challenge strain used in this experiment was the B1 strain. All of the control animals died after challenge, exhibiting diarrhoea shortly before a drop in body temperature to the clinical endpoint. One vaccinated animal (H1) exhibited signs of sickness and dehydration, and died shortly after the last control animal, showing a similar body temperature profile to controls (data not shown). All other vaccinated animals survived until the end of the experiment (Table 36). H2-H6 showed a single short episode of diarrhoea during recovery. Therefore 83% of vaccinated subjects were protected from death when challenged with the B1 strain.

TABLE 36

ToxA_GT + ToxB_GT + ToxB_B + ToxA_B2 results. Challenge strain B1.

| | Antigens | Time to <35° C. | Time at cull | Temp at cull |
|---|---|---|---|---|
| H1 | toxA_B2 + toxA_GT + toxB_B + toxB_GT | 33 h 59 m | 34 h 50 m | 34.42° C. |
| H2 | toxA_B2 + toxA_GT + toxB_B + toxB_GT | | 14 days | |
| H3 | toxA_B2 + toxA_GT + toxB_B + toxB_GT | | 14 days | |
| H4 | toxA_B2 + toxA_GT + toxB_B + toxB_GT | | 14 days | |
| H5 | toxA_B2 + toxA_GT + toxB_B + toxB_GT | | 14 days | |
| H6 | toxA_B2 + toxA_GT + toxB_B + toxB_GT | | 14 days | |
| H7 | Adjuvant only | 27 h 30 m | 28 h 3 m | 33.07° C. |
| H8 | Control | 26 h 32 m | 26 h 56 m | 34.08° C. |
| H9 | Control | | 27 h 20 m | |
| H10 | toxA_B2 + toxA_GT + toxB_B + toxB_GT | Not challenged - sera collected | | |

Figure 31:
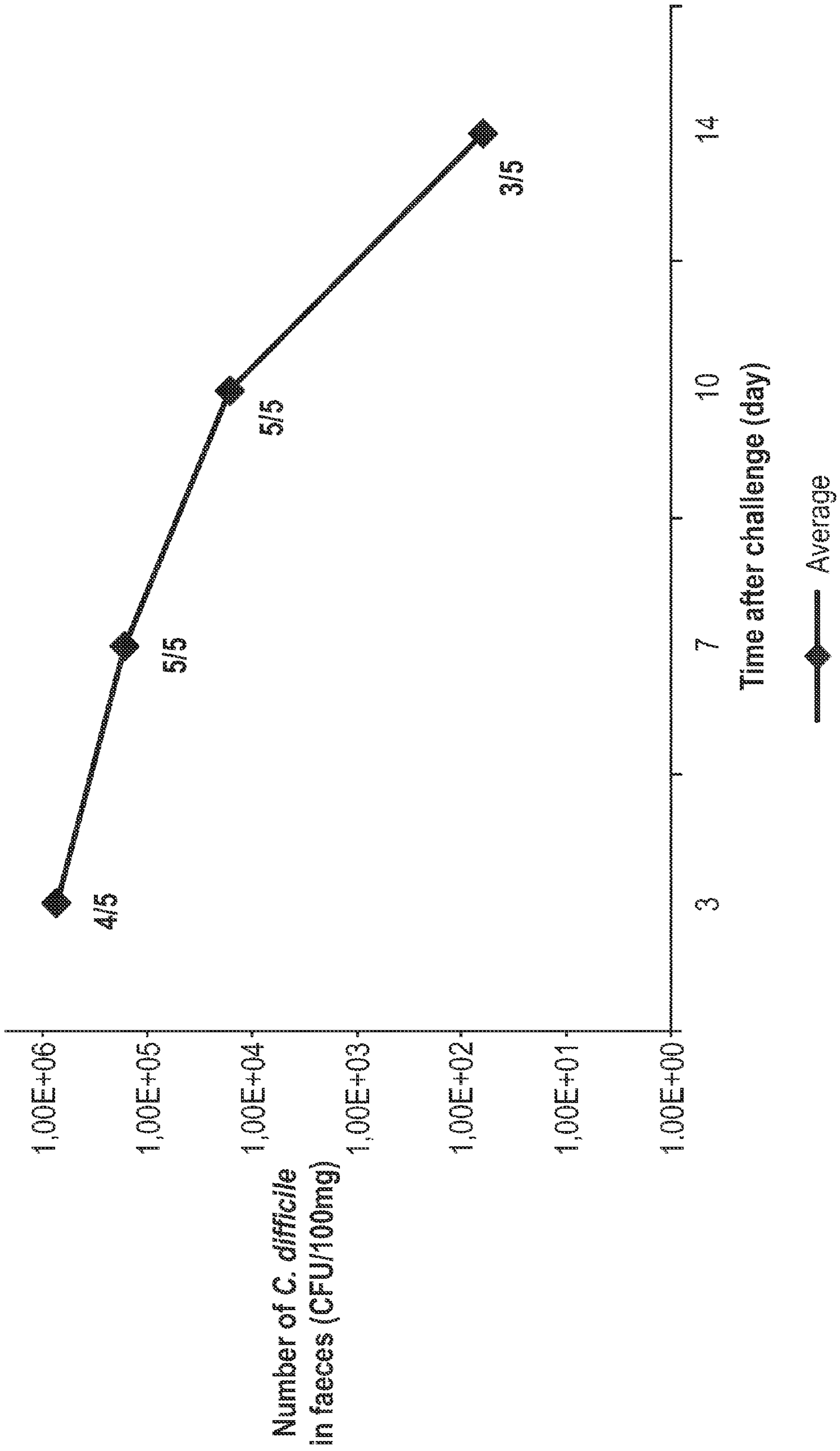
FIG. 31. ToxB_GT+ToxAGT+ToxB_B+ToxA_B2—average bacterial shedding of *C. Difficile* spores in 100 mg faeces. Challenge with B1.
Figure 32:
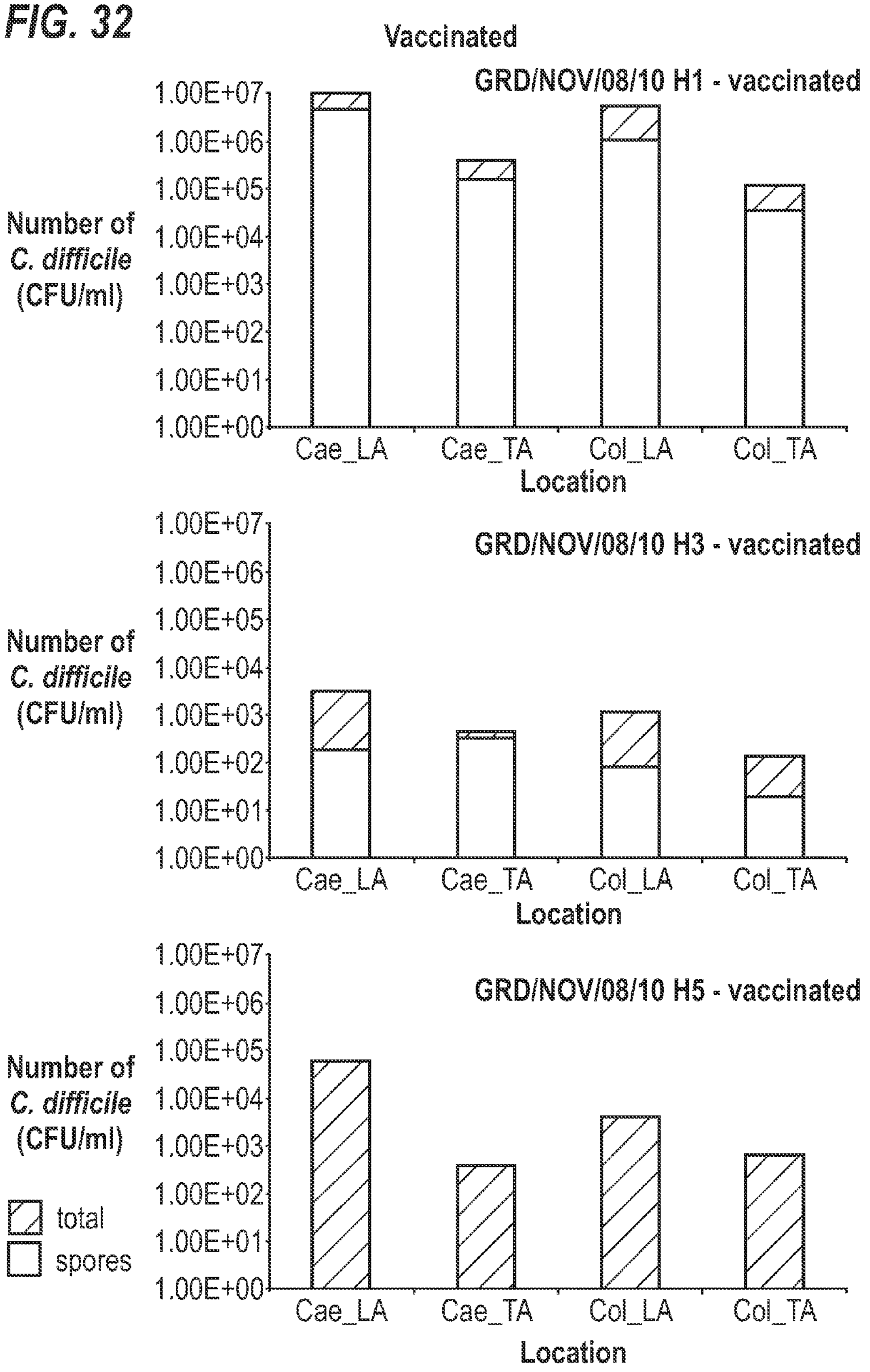
FIG. 32. ToxB_GT+$ToxA_{13}$ GT+ToxB_B+ToxA_B2—colonisation at culling. Challenge with B1.

An analysis of bacterial shedding (FIG. 31) revealed a decrease in *C. difficile* spores in faeces over time (decreasing considerably after day 7), and this trend is comparable to data obtained using full length toxoids. Data are unavailable for H4 on day 3, and H3 and H5 had no detectable spores on day 14. All surviving hamsters had a higher vegetative:spore ratio than the animals which died in the acute phase of infection. An analysis of colonization at culling is provided in FIG. 32.

For hamsters that survived challenge with the B1 strain, toxin B content was analysed at day 14 (Table 37).

TABLE 37

ToxB_GT + ToxA_GT + ToxB_B + ToxA_B2 - toxin content in the caecal gut. Data are represented as dilutions at which cells remain attached. Challenge with B1.

| Hamster | Vaccinated | Final dilution |
|---|---|---|
| H1 | toxA_B2 + toxA_GT + toxB_B + toxB_GT | $10^4$ |
| H2 | toxA_B2 + toxA_GT + toxB_B + toxB_GT | $10^3$ |
| H3 | toxA_B2 + toxA_GT + toxB_B + toxB_GT | 0 |
| H4 | toxA_B2 + toxA_GT + toxB_B + toxB_GT | $10^1$ |
| H5 | toxA_B2 + toxA_GT + toxB_B + toxB_GT | 0 |
| H6 | toxA_B2 + toxA_GT + toxB_B + toxB_GT | 0 |
| H7 | Adjuvant only | $10^4$ |
| H8 | Non-vaccinated control | $10^4$ |
| H9 | Non-vaccinated control | $10^4$ |

Vaccinated animals showed low toxin B levels in the gut despite being colonized by the bacteria (apart from H2, which had more detectable toxin B and which was more heavily colonized at the point of culling). The vaccinated hamster, H1, which died in the acute phase of infection had an equivalent amount of toxin B in the gut to the non-vaccinated and adjuvant-only controls, which dies 28 h after infection. These observations were confirmed in the colon (Table 38). There is apparently less toxin B in the colon than in the caecum, and the only animals showing a significant amount of toxin B in the colon were also the animals which died of acute disease.

TABLE 38

ToxB_GT + ToxA_GT + ToxB_B + ToxA_B2 - toxin content in the colon. Data are represented as dilutions at which cells remain attached. Challenge with B1.

| Hamster | Vaccinated | Final dilution lysing cells |
|---|---|---|
| H1 | toxA_B2 + toxA_GT + toxB_B + toxB_GT | 1:3125 |
| H2 | toxA_B2 + toxA_GT + toxB_B + toxB_GT | 1:25 |
| H3 | toxA_B2 + toxA_GT + toxB_B + toxB_GT | 0 |
| H4 | toxA_B2 + toxA_GT + toxB_B + toxB_GT | 0 |
| H5 | toxA_B2 + toxA_GT + toxB_B + toxB_GT | 0 |
| H6 | toxA_B2 + toxA_GT + toxB_B + toxB_GT | 1:5 |
| H7 | Adjuvant only | 1:625 |
| H8 | Non-vaccinated control | 1:3125 |
| H9 | Non-vaccinated control | 1:15625 |

Overall, vaccination with ToxA_GT+ToxB_GT+ToxB_B+ToxA_B2 protected 5 out of 6 animals from death when challenged with the B1 strain, but did not protect against diarrhoea. The level of protection achieved by including ToxA-GT in the combination was comparable to the level of protection achieved when immunising with full length inactivated toxoids. All surviving animals were colonised throughout the experiment and shed equivalent levels of *C. difficile* spores in the faeces. At the time of cull, all animals were still colonised with *C. difficile*. Surviving vaccinated animals showed a higher ratio of vegetative cells:spores in the gut, compared to controls. With one exception (H2), surviving animals showed low levels of toxin B activity in the guts. Again, this could be explained by, for example, toxin binding by antibodies and/or a decrease in bacterial toxin expression. Overall, this combination showed an efficacy comparable to that obtained using the gold standard immunisation with toxoids.

ToxA_B2+ToxB_GT+ToxB_GT+ToxB_B+ToxA_GT Lower Doses

The inventors then tested whether using a lower antigen dose of ToxA_GT+ToxB_GT+ToxB_B+ToxA_B2 (20 ugrs of each antigen) also conferred high level protection against the B1 strain.

All vaccinated animals (H1-H8) survived challenge with the B1 strain, and the control animals (H7-H8) were culled when their body temperature dropped below 35° C. (Table 39). Note that one vaccinated animal (H2) was culled at 9 days after challenge due to loss of body condition, and not a drop in body temperature (the animal did not gain weight, was dehydrated, and normal gut function had not returned, as evidenced by the absence of formed faecal material).

TABLE 39

ToxB_GT + ToxA_GT + ToxB_B + ToxA_B2 (lower dose) results. Challenge with B1.

| | Antigens | Time to <35° C. | Time at cull | Temp at cull |
|---|---|---|---|---|
| H1 | toxA_B2 + toxA_GT + toxB_GT + toxB_B (20 ug) | | 14 days | |
| H2 | toxA_B2 + toxA_GT + toxB_GT + toxB_B (20 ug) | | 9 days | 36.89° C. |
| H3 | toxA_B2 + toxA_GT + toxB_GT + toxB_B (20 ug) | | 14 days | |
| H4 | toxA_B2 + toxA_GT + toxB_GT + toxB_B (20 ug) | | 14 days | |
| H5 | toxA_B2 + toxA_GT + toxB_GT + toxB_B (20 ug) | | 14 days | |
| H6 | toxA_B2 + toxA_GT + toxB_GT + toxB_B (20 ug) | | 14 days | |
| H7 | toxA_B2 + toxA_GT + toxB_GT + toxB_B (20 ug) | | 14 days | |
| H8 | Adjuvant only | 28 h 43 m | 28 h 45 m | 34.85° C. |
| H9 | Control | 28 h 37 m | 28 h 26 m | 34.82° C. |
| H10 | Control | 26 h 47 m | 26 h 50 m | 34.82° C. |

Figure 33:
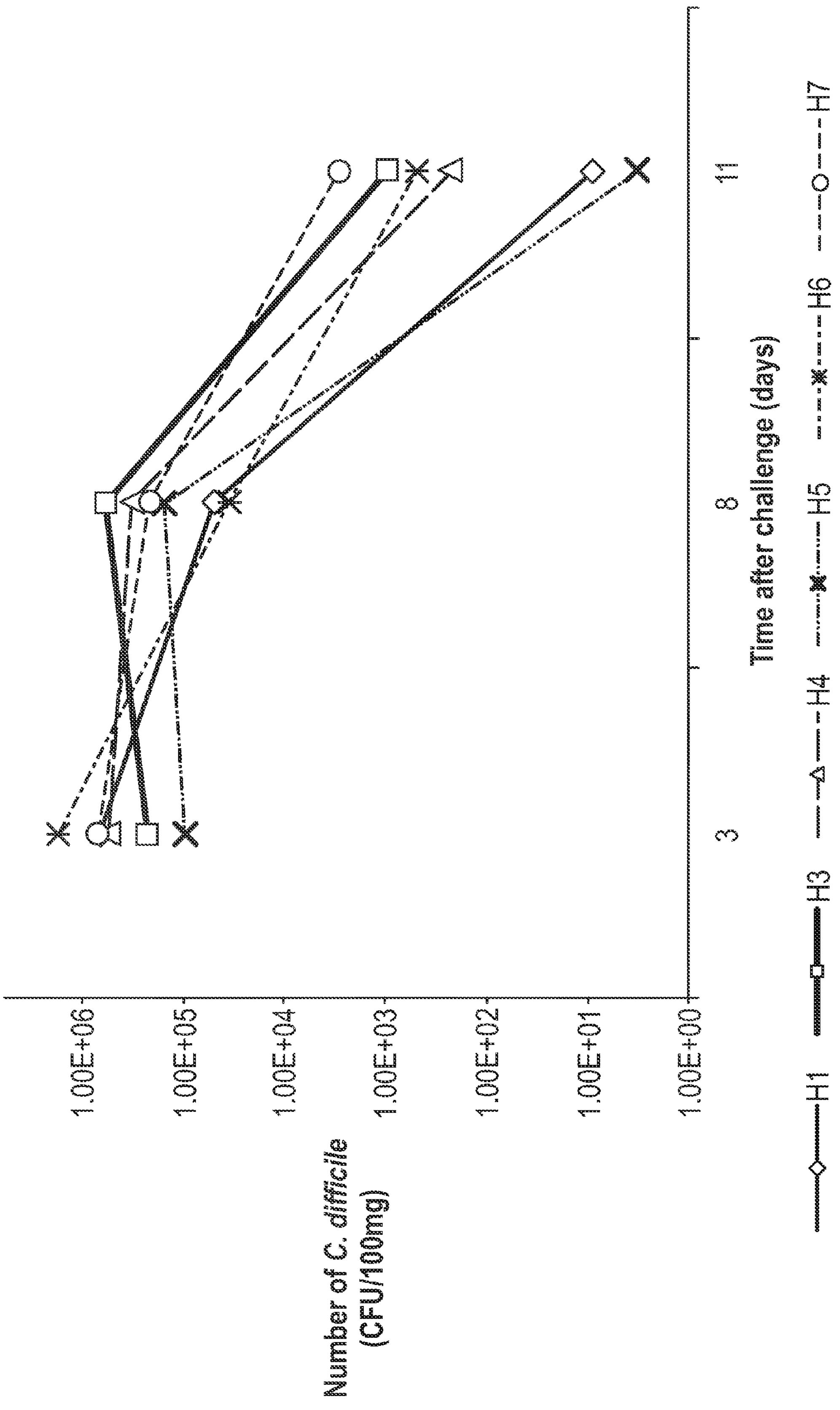
FIG. 33. ToxB_GT+ToxA_GT+ToxB_B+ToxA_B2 (lower dose)—average bacterial shedding of *C. Difficile* spores in 100 mg faeces. Challenge with B1.

The number of colonies per 100 mg faecal material was then determined (FIG. 33), demonstrating that that the organisms are shed at high numbers for several days after challenge, even when symptoms (diarrhoea) have abated. The level of spores in faeces was found to drop considerably after day 8.

Figure 34:
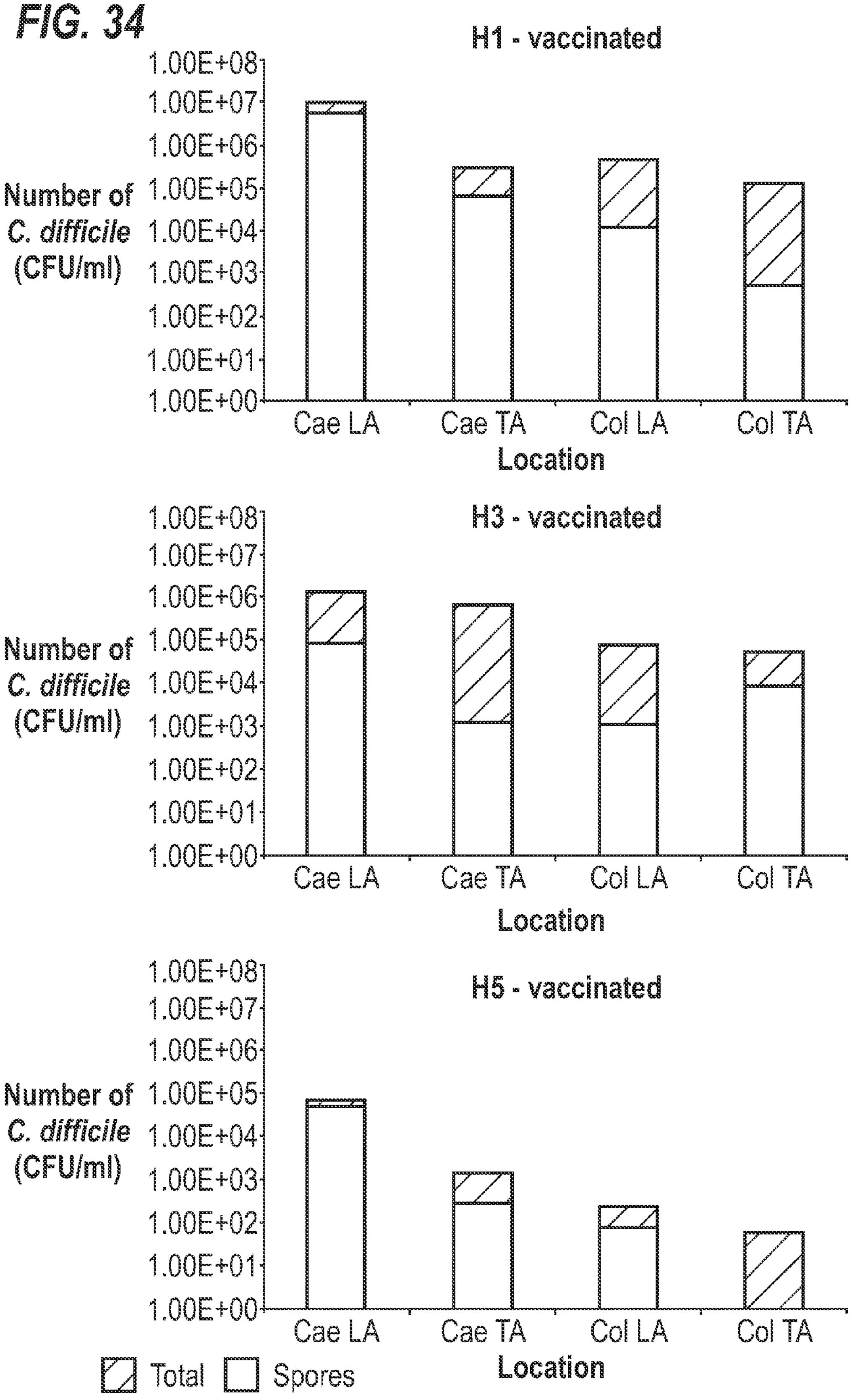
FIG. 34. ToxB_GT+ToxA_GT+ToxB_B+ToxA_B2 (lower dose)—infection analysis of *C. difficile* recovered in faecal material—localisation of bacteria (x=axis is location: "Col"=colon; "Cae"=caecum; "LA"=lumen associated; "TA"=tissue associated. Y=axis is number of *C. difficile* (CFU/ml)) Challenge with B1.

An analysis of colonization at culling was also performed (FIG. 34). Results showed that all surviving hamsters were colonized with *C. difficile* in the gut at the point of culling. H2, which was culled at 9 days after challenge, had comparable amounts of vegetative cells and spores to control animals (H8, H9 and H10) which died in the acute phase of infection. H1, H3 and H4 had high levels of *C. difficile* but there were lower levels of spores present than in animals which died in the acute phase of infection. H5, H6 and H7 had lower numbers of *C. difficile* and lower levels of spores. H6 had no detectable spores associated with the tissue in the caecum or the colon.

Assessment of toxin B content in the caecum revealed that there is little or no active toxin in the caecum of vaccinated animals culled 14 days after challenge (Table 40). Interestingly, the control animal, H8, had little or no active toxin present, which is unexpected because this animal died during the acute phase of infection. H2, which was culled at 9 days after challenge, had a comparable amount of toxin present in the gut as the control animals (H9 and H10), which died in the acute phase of infection. H1 and H3 had active toxin present, whereas H4 and H6 had less toxin present. H5 and H7 had no active toxin present, which correlated with the low number of bacteria present.

TABLE 40

ToxB_GT + ToxA_GT + ToxB_B + ToxA_B2 (lower dose). Toxin B content in the caecum. Data are represented as dilutions at which cells remain attached. Challenge with B1. Challenge with B1.

| Hamster | Antigen | Final dilution lysing cells |
|---|---|---|
| H1 | toxA_B2 + toxA_GT + toxB_GT + toxB_B (low dose) | $10^4$ |
| H2 | toxA_B2 + toxA_GT + toxB_GT + toxB_B (low dose) | $10^8$ |
| H3 | toxA_B2 + toxA_GT + toxB_GT + toxB_B (low dose) | $10^4$ |
| H4 | toxA_B2 + toxA_GT + toxB_GT + toxB_B (low dose) | $10^2$ |
| H5 | toxA_B2 + toxA_GT + toxB_GT + toxB_B (low dose) | 0 |
| H6 | toxA_B2 + toxA_GT + toxB_GT + toxB_B (low dose) | $10^2$ |
| H7 | toxA_B2 + toxA_GT + toxB_GT + toxB_B (low dose) | 0 |
| H8 | Control | $10^1$ |
| H9 | Control | $10^8$ |
| H10 | Control | $10^8$ |

Similar toxin results were observed in the colon (Table 41), where H8 appeared to have no active toxin present in the gut. H9 and H10, which died during the acute phase of infection, had high levels of toxin present in the colon. H2, which was culled at 9 days after challenge, had active toxin present in the colon, whereas animals which were culled at 14 days after challenge had little or no active toxin present.

TABLE 41

ToxB_GT + ToxA_GT + ToxB_B + ToxA_B2 (lower dose). Toxin B content in the colon. Data are represented as dilutions at which cells remain attached. Challenge with B1.

| Hamster | Antigen | Final dilution lysing cells |
|---|---|---|
| H1 | toxA_B2 + toxA_GT + toxB_GT + toxB_B (low dose) | 0 |
| H2 | toxA_B2 + toxA_GT + toxB_GT + toxB_B (low dose) | 1:125 |
| H3 | toxA_B2 + toxA_GT + toxB_GT + toxB_B (low dose) | 1:25 |
| H4 | toxA_B2 + toxA_GT + toxB_GT + toxB_B (low dose) | 0 |
| H5 | toxA_B2 + toxA_GT + toxB_GT + toxB_B (low dose) | 0 |
| H6 | toxA_B2 + toxA_GT + toxB_GT + toxB_B (low dose) | 0 |
| H7 | toxA_B2 + toxA_GT + toxB_GT + toxB_B (low dose) | 0 |
| H8 | Control | 0 |
| H9 | Control | 1:78125 |
| H10 | control | 1:15625 |

Levels of toxin A content in the caecum were also assessed, using the methodology outlined above. Assessment of toxin A content in the gut revealed that H9 and H10 had high levels of toxin A present. H8, which also died in the acute phase of infection, had little active toxin present, although this result is in agreement with the previous measurement of toxin B. H2, which was culled 9 days after challenge, had a higher level of toxin A present in the caecum compared to animals which were culled 14 days after challenge, which had little or no active toxin present (Table 42).

TABLE 42

ToxB_GT + ToxA_GT + ToxB_B + ToxA_B2 (lower dose). Toxin A content in the caecum. Data are represented as dilutions at which cells remain attached. Challenge with B1.

| Hamster | Antigen | Final dilution lysing cells |
|---|---|---|
| H1 | toxA_B2 + toxA_GT + toxB_GT + toxB_B (low dose) | 1:25 |
| H2 | toxA_B2 + toxA_GT + toxB_GT + toxB_B (low dose) | 1:125 |
| H3 | toxA_B2 + toxA_GT + toxB_GT + toxB_B (low dose) | 1:25 |
| H4 | toxA_B2 + toxA_GT + toxB_GT + toxB_B (low dose) | 1:25 |
| H5 | toxA_B2 + toxA_GT + toxB_GT + toxB_B (low dose) | 1:5 |
| H6 | toxA_B2 + toxA_GT + toxB_GT + toxB_B (low dose) | 1:5 |
| H7 | toxA_B2 + toxA_GT + toxB_GT + toxB_B (low dose) | 1:5 |
| H8 | Control | 1:5 |
| H9 | Control | 1:15625 |
| H10 | control | 1:625 |

Overall, immunisation with a lower dose of ToxA-B2+ToxA_GT+ToxB_GT+ToxB_B (20 μg per antigen per dose) also protected the animals from death, but not diarrhoea. All animals which survived initial challenge recovered normal gut function except one (H2). Therefore, immunisation with a lower dose of ToxA-B2+ToxA_GT+ToxB_GT+ToxB_B appears to provide a similar or better level of protection compared to the gold standard, using toxoids.

Neutralisation Titres from Vaccinated Hamsters

Sera from vaccinated hamsters were analyzed by in vitro neutralization assay. Results are shown in Table 43.

TABLE 43

In vitro neutralization titers from vaccinated hamsters.

| Antigen | Challenge strain | Neutralisation titres against ToxA | Neutralisation titres against ToxB |
|---|---|---|---|
| ToxA-P5/6 | B1 | ND | ND |
| ToxB-B | B1 | 0 | 512 |
| ToxA-P5-6 + ToxB-B | 630 | 4000 | 512 |
| ToxoidA + ToxB-B | B1 | 32000 | 512 |
| | 630 | 32000 | 512 |
| Chimera B4 | 630 | 2000 | 512 |
| ToxA-P5-6 + ToxB-GT | 630 | 8000 | 512 |
| ToxA-P5-6 + ToxB-GT | B1 | 16000 | 256 |
| ToxA-P5-6 + ToxB-GT (reduced antigen dose) | B1 | 8000 | 128 |
| ToxA-B2 + ToxB-GT | B1 | 8000 | 256 |
| ToxA-B2 + ToxB-GT (reduced antigen dose) | B1 | 16000 (8000) | 128 (0) |
| ToxA-P5-6 + ToxB-B | B1 | 2000 | 256/512 |
| | | 32 | 32 16 |
| ToxA-P5-6 + ToxB-B + ToxB-GT | B1 | 1000 | 2000 |
| | | 64 | 64 |
| ToxoidA + Toxoid B | B1 | 32000 | 512 |
| | | 16000 | 512 |
| ToxA-P5-6 + ToxB-GT-PSII | 630 | 4000 | 2000 |
| | | 256 | 512 |
| ToxA-P5-6 + ToxB-GT | | 2000 | 2000 |
| ToxA-B2 + ToxA-GT + ToxB-B + ToxB-GT | B1 | 4000 | 512 |
| | | ND/512 | ND 0 |
| ToxA-B2 + ToxA-GT + ToxB-B + ToxB-GT (reduced antigen dose) | B1 | 8000 (512) | 256 (0) |

(differences in experimental repeats are denoted by "/").
Selected neutralisation titers shown for comparison.
Reduced antigen dose is 20 μg per antigen.

Animals immunised with a mixture of fragments comprising at least one fragment from ToxA and at least one fragment from ToxB, as well as full length Toxin A and Toxin B, generated neutralisation titers against both toxins. Of the tested combinations, only ToxA-B2+ToxB-B+ToxB_GT did not generate neutralisation titers against both toxins, and was not found to be protective against the 630 strain. Also, animals immunised with single fragment generated neutralisation titres against only their respective toxin, and were not observed to be protective. These data suggest that protection against *C. difficile* requires the production of neutralisation titers against both toxins.

Analysis of Microbiota

Vaccinated animals challenged with *C. difficile* which recover from a single episode of diarrhoea, continue to shed the organism in the faeces for at least 3 weeks. To analyse the impact of *C. difficile* infection on the microbiome, changes were monitored through 16S amplification of faecal material, pre- and post-infection.

Figure 35:
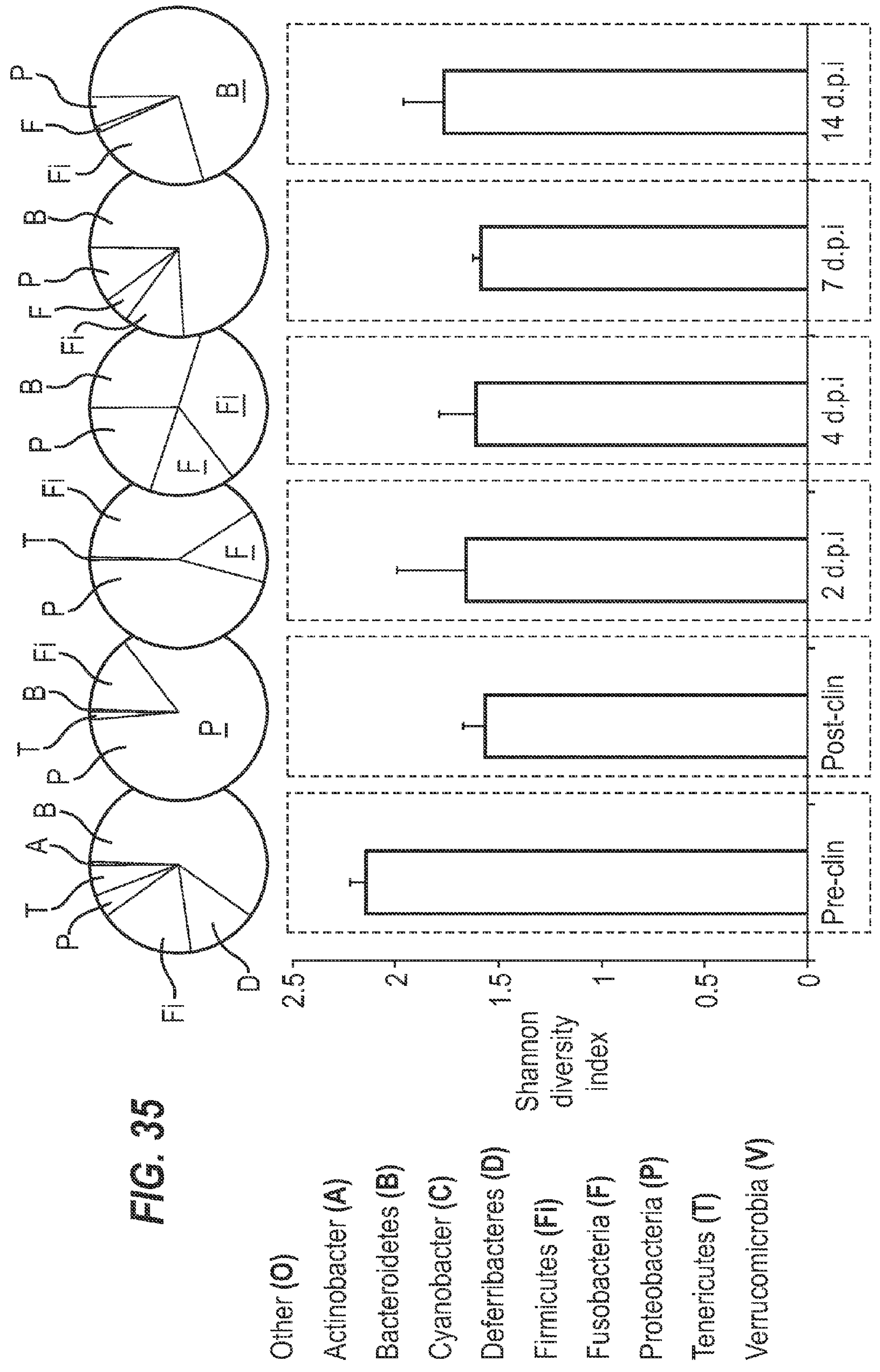
FIG. 35. Microflora changes after clindamycin treatment.

First, the inventors assessed microflora changes after clindamycin treatment (FIG. 35). An average of 3000 sequences returned from 454 sequencing per sample and phylum were assigned. In untreated normal hamsters, Bacteroidetes are the most abundant phyla (59%). Clindamycin treatment results in a dramatic contraction of Bacteroidetes, sequential expansion of Proteobacteria (84%) and loss of overall microbial diversity. Increased recovery of Fusobacteria was observed from day 2. A recovery of diversity was observed by day 5, although by day 15 phylum microbial richness had still not completely returned.

Figure 36:
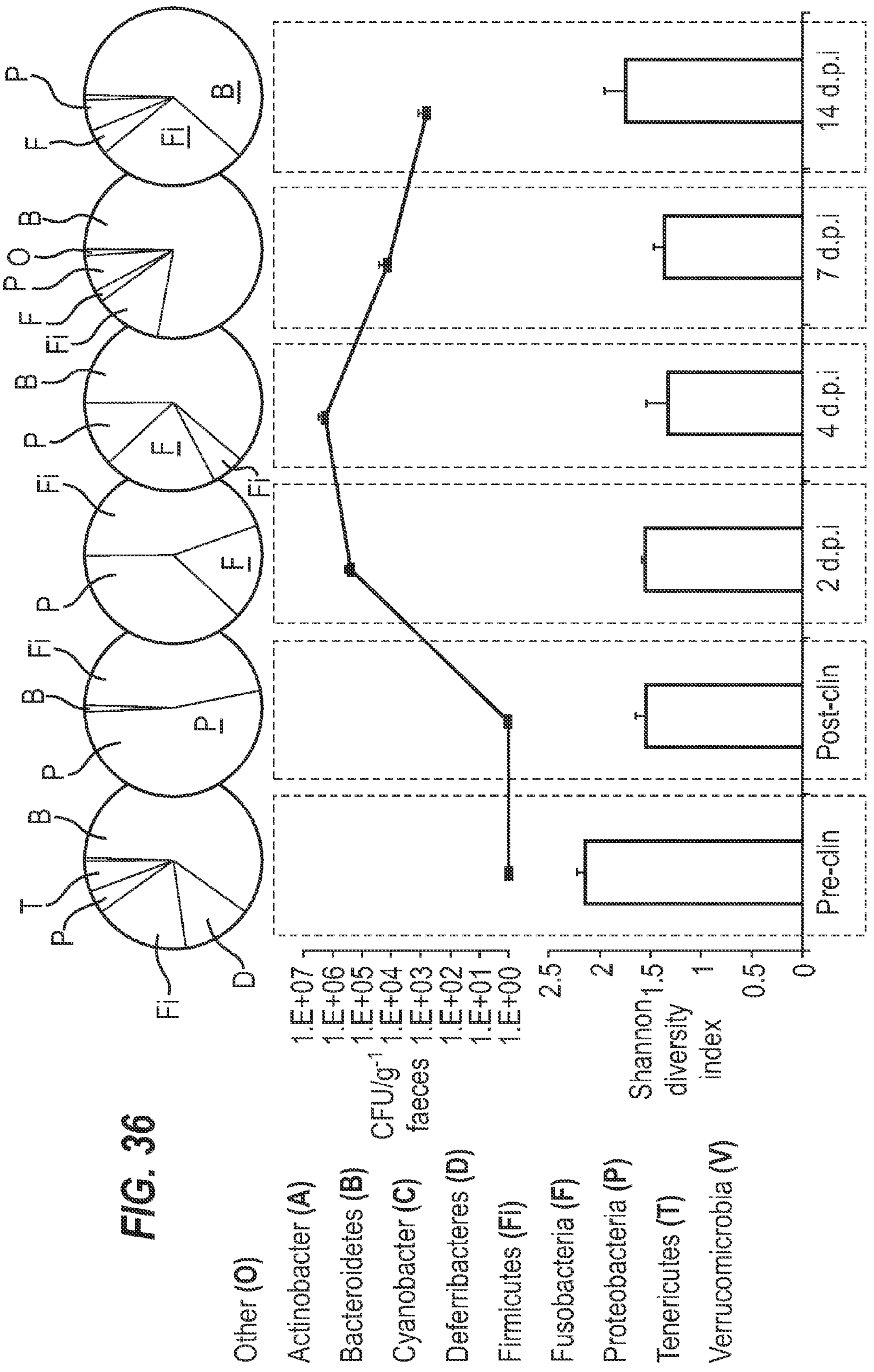
FIG. 36. Modification to microbiota in vaccinated animals.

The inventors then tested microflora changes in vaccinated animals. Vaccination protects hamsters from lethal challenge with toxinogenic *C. difficile* 630, despite bacterial growth and toxin production. As shown in FIG. 36, surviving animals show microbiota changes that are consistent with those observed in clindamycin treated animals. At day 14 these phyla decreased but stayed higher than the other infection regimes. Microbial diversity declined to SDI 1.3 at day 4 but then increased similar to pre-clindamycin levels (SDI 1.7).

Overall, the inventors found that vaccination with toxin fragments that include the enzymatic domain of toxin B provide the highest level of protection against *C. difficile* infection. Administration of the broad-spectrum antibiotic clindamycin resulted in decreased microbial complexity. Whilst the microbiota diversity increased over time it never returned to pre-clindamycin levels. These data, together with clinical data, suggest that *C. difficile* toxin associated damage could enhance microbiota dysbiosis caused by antibiotics, and this may reveal why patients remain susceptible to relapse.

Investigaiton of Toxin-specific IgG in the Intestinal Lumen

Figure 39:
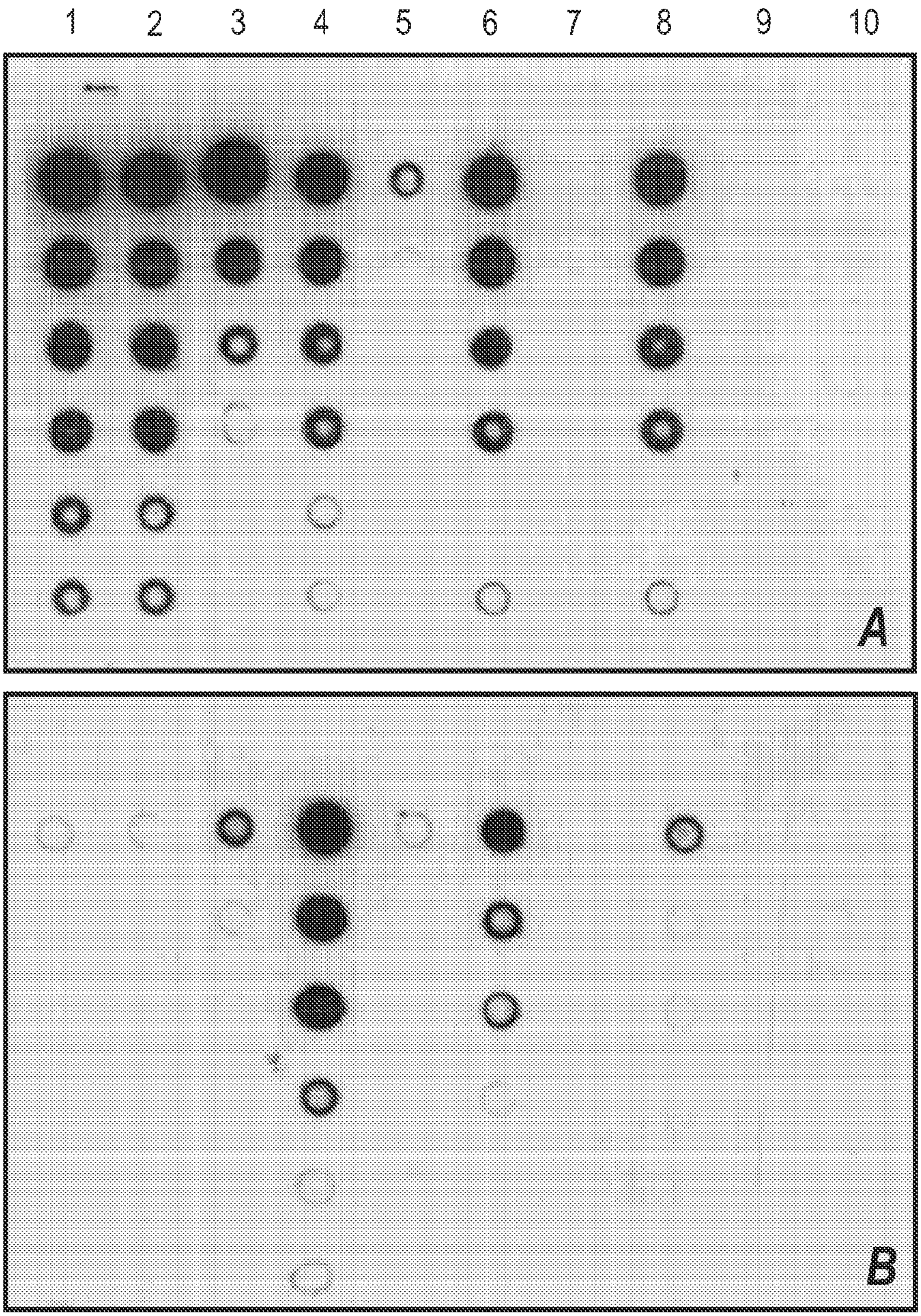
FIG. 39: IgG antibodies against toxin A (A) and toxin B (B) in ceacum samples from hamsters vaccinated with ToxA-P5-6+ToxB-GT. Dot blots were carried out on filtered caecum samples taken from vaccinated animals in the acute phase of infection (48 hours post-challenge) (hamsters 1-2) and at experimental endpoint (14 days post-challenge) (hamsters 3-8). Control animals were treated with adjuvant only and infected in the same experimental conditions (hamsters 9-10).

The presence of toxin-specific IgG in the intestinal lumen of animals vaccinated with ToxA-P5-6+ToxB-GT was investigated. Although response to ToxA was higher in the acute phase of infection, raising amounts of anti-ToxB antibodies were detectable at the endpoint (FIG. 39).

To further evaluate the effects of vaccination with ToxA-P5-6+ToxB-GT, toxins levels produced in vivo were monitored and gut histology was performed.

High toxin levels were detected 48 hours post infection both in control and vaccinated hamsters (FIG. 40), whilst severe gut inflammation accompanied by epithelial necrosis and polymorphonulcear (PMN) influx was only observed in control animals. Tissue from vaccinated animals showed less epithelial damage and limited PMN infiltrate. Hyperplasia associated with appearance of mucin-producing cells and crypt to tip length increase was observed, particularly in the lower colon.

Protected animals showed lower levels of toxin within the intestinal lumen 14 days after infection despite the presence of high numbers of *C. difficile* colonies associated to the intestinal tissue. The gut epithelia appeared to revert to normality with absence of polymorph influx. Interestingly, whilst no alteration of caecum was evident, some hyperplasia persisted in the terminal colon of these animals.

CONCLUSION

The inventors have found that administration of combinations of *Clostridium difficile* antigens comprising ToxB-GT and TcdA fragments are able to provide high levels of protection against CDAD, comparable to, or better than using binding domain-based fragments for immunisation.

Hamster vaccination experiments led to the identification of combinations of fragments which were able to protect animals from the fatal outcome typically observed in absence of vaccination, even following challenge with the B1 strain.

Surprisingly, the inventors also found that immunisation with combinations of the invention as individual separate polypeptides (i.e. mixed together), confers much stronger protection against CDAD, than using hybrid polypeptides. This is exemplified by the "B4 chimera", which showed only a moderate level of protection against the milder 630 strain.

Combinations of the invention strongly reduced the clinical symptoms of CDAD, such as dehydration and diarrhoea. Moreover, the level of protection afforded by the combinations of the invention matched or surpassed the protection provided by using inactivated toxoids. By using recombinant polypeptides, the inventors were also able to overcome the plethora problems associated with vaccination using inactivated toxoids.

The inventors have thus provided multi-strain vaccine candidates against CDAD, which are safer and more easily produced than using inactivated toxoids, and which offer an alternative to binding domain-based immunisation against *C. difficile*.

| Description of sequence | SEQ ID NO: |
|---|---|
| Peptides | |
| Full length TcdA | 1 |
| Full length TcdB | 2 |
| ToxA-ED | 3 |
| ToxA-GT | 4 |
| ToxA-CP | 5 |
| ToxA-T | 6 |
| ToxA-T4 | 7 |
| ToxA-B | 8 |
| ToxA-PTA2 | 9 |
| ToxA-P5-7 | 10 |
| ToxA-P5-6 | 11 |
| ToxA-P9-10 | 12 |
| ToxA-B2 | 13 |
| ToxA-B3 | 14 |
| ToxA-B5 | 15 |
| ToxA-B6 | 16 |
| ToxB-ED | 17 |
| ToxB-GT | 18 |
| ToxB-CP | 19 |
| ToxB-T | 20 |
| ToxB-B | 21 |
| ToxB-B2 | 22 |
| ToxB-B7 | 23 |
| B4 hybrid | 24 |
| Linker | 25 |
| Linker | 26 |
| Linker | 27 |
| IC-31 | 28 |
| Polycationic polymer | 29 |
| Nucleic acids | |
| Full length TcdA | 30 |
| Full length TcdB | 31 |
| ToxA-ED | 32 |
| ToxA-GT | 33 |
| ToxA-CP | 34 |
| ToxA-T | 35 |
| ToxA-T4 | 36 |
| ToxA-B | 37 |
| ToxA-PTA2 | 38 |
| ToxA-P5-7 | 39 |
| ToxA-P5-6 | 40 |
| ToxA-P9-10 | 41 |
| ToxA-B2 | 42 |
| ToxA-B3 | 43 |
| ToxA-B5 | 44 |
| ToxA-B6 | 45 |
| ToxB-ED | 46 |
| ToxB-GT | 47 |
| ToxB-CP | 48 |
| ToxB-T | 49 |
| ToxB-B | 50 |
| ToxB-B2 | 51 |
| ToxB-B7 | 52 |
| B4 hybrid | 53 |
| Mutated sequences | |
| ToxA-ED (peptide) | 54 |
| ToxA-ED (encoding nucleic acid) | 55 |
| ToxA-GT (peptide) | 56 |
| ToxA-GT (encoding nucleic acid) | 57 |
| ToxB-ED (peptide) | 58 |
| ToxB-ED (encoding nucleic acid) | 59 |
| ToxB-GT (peptide) | 60 |
| ToxB-GT (encoding nucleic acid) | 61 |
| ToxA-CP (peptide) | 62 |
| ToxA-CP (encoding nucleic acid) | 63 |
| ToxB-CP (peptide) | 64 |
| ToxB-CP (encoding nucleic acid) | 65 |
| ToxA-PTA2 (encoding nucleic acid) | 66 |
| ToxA-P9-10 (encoding nucleic acid) | 67 |
| ToxB-B (encoding nucleic acid) | 68 |
| ToxB-B2 (encoding nucleic acid) | 69 |
| Additional useful sequences | |
| ToxA-PTA2 (nucleic acid) | 70 |
| ToxA-PTA2 (peptide) | 71 |
| ToxA-P9-10 (nucleic acid) | 72 |
| ToxA-P9-10 (peptide) | 73 |
| ToxA-P5-7 (nucleic acid) | 74 |
| ToxA-P5-7 (peptide) | 75 |
| ToxA-B3 (peptide) | 76 |
| ToxA-B3 (nucleic acid) | 77 |
| ToxA-B6 (peptide) | 78 |
| ToxA-B6 (nucleic acid) | 79 |
| ToxA-B5 (peptide) | 80 |
| ToxA-B5 (nucleic acid) | 81 |
| ToxA-B2 (nucleic acid) | 82 |
| ToxA-B2 (peptide) | 83 |
| ToxA-P5-6 (peptide) | 84 |
| ToxA-CP (nucleic acid) | 85 |
| ToxA-CP (peptide) | 86 |
| ToxA-T4 (nucleic acid) | 87 |
| ToxA-T4 (peptide) | 88 |
| ToxB-CP (nucleic acid) | 89 |
| ToxB-CP (peptide) | 90 |
| ToxB-ED (nucleic acid) | 91 |
| ToxB-ED (peptide) | 92 |
| ToxB-GT (nucleic acid) | 93 |
| ToxB-GT (peptide) | 94 |

-continued

| Description of sequence | SEQ ID NO: |
|---|---|
| ToxB-B (nucleic acid) | 95 |
| ToxB-B (peptide) | 96 |
| ToxB-B2 (nucleic acid) | 97 |
| ToxB-B2 (peptide) | 98 |
| ToxB-B7 (nucleic acid) | 99 |
| ToxB-B7 (peptide) | 100 |
| ToxA-p5-6 H41D (peptide) | 101 |
| ToxA-P5-6 N42A (peptide) | 102 |
| ToxA-P5-6 H41D, N42A (peptide) | 103 |
| Optional N-terminal amino acid sequence | 104 |
| Optional C-terminal amino sequence | 105 |
| Hybrid polypeptide A-ToxA-P5-6wt | 106 |
| Hybrid polypeptide ToxA-P5-6wt-C | 107 |
| Hybrid polypeptide A-ToxA-P5-6wt-C | 108 |
| Hybrid polypeptide A-ToxA-P5-6 H41D, N42A | 109 |
| Hybrid polypeptide ToxA-P5-6 H41D, N42A -C | 110 |
| Hybrid polypeptide A-ToxA-P5-6 H41D, N42A -C) | 111 |
| Nucleic acid sequence encoding the hybrid polypeptide A-ToxA-P5-6 H41D, N42A-C | 112 |

REFERENCES

[1] Giannasca, P. J. and Warny, M. Vaccine. 2004, 22(7), 848-856

[2] Samore, M. H. Compr. Ther. 1993. 19, 151-156

[3] Kelly C. P. et al. N. Engl. J. Med. 1994. 270:13932-13936

[4] Bartlett, J. G. Clin. Infect. Dis. 1994. 18, S285-S272

[5] Teasley, D. G. et al. Lancet. 1983, 2, 1043-1046

[6] McFarland, L. V. et al. JAMA, 1994, 271: 1913-1918

[7] Wilcox, M. H. et al. J. Hosp. Infect. 1998. 38, 93-100

[8] Clatworthy, A. E. et al. Nat. Chem. Biol. 2007. 3: 541-548

[9] Albesa-Jové, et al. J. Mol Biol. 2010. 396: 1260-1270

[10] Voth, D. E. et al. Clin. Microbiol. Rev. 2005. 18: 247-263

[11] Hussack, G. and Tanha, J. Toxins. 2: 998-1018

[12] Demarest, S. J. et al. Mabs. 2010. March-April 2(2) 190-198

[13] Jank, T. et al. Glycobiology. 2007. 917: 15R-22R

[14] Rienke, J. et al. Nature. 2007. 446: 415-419

[15] Egerer, M. et al. J. Biol. Chem. 2007. 282: 25314-25321

[16] Just, I. et al. Nature. 1995. 375: 500-503

[17] Hecht, G. et al. Gastroenterology. 1992. 102: 416-423

[18] Leffler, D. A. et al. Gastroenterology. 2009. 136, 1899-1912

[19] Kink, J. A. and Williams, J. A. Infection and Immunity. 1998, 66(5), 2018-2025

[20] Rupnik et al., Nat. Rev. Microbiol. 2009, 7, 526-536

[21] Just et al., Rev. Physiol. Biochem. Pharmacol. 2004, 152, 23-47

[22] Johnson, S. et al. Ann. Intern. Med. 2001. 135: 434-438

[23] Kuijper, E. J. et al. Eur. J. Clin. Microbiol. Infect. Dis. 2001. 20A: 528-534

[24] Limaye, A. P. et al. J. Clin. Microbiol. 2000. 38:1696-1697

[25] Sambol, S. P. et al. Infect. Immun. 2001. 68:5480-5487

[26] Kotloff, K. L. et al. Infect. Immun. 2001.69: 988-995

[27] Cropley, I. et al. Vaccine. 1995. 13(17):1643-1648

[28] Pavliakova D. et al. Infect. Immun, 2000. 68(4): 2161-2166

[29] Kuehne, S. A. et al. Nature. 2010. 467:711-713

[30] Just, I. et al. J. Biol Chem. 1995. 270: 13932-13939

[31] Lyerly, D. M. et al. Infect. Immun. 1982. 35: 1147-1150

[32] Lyerly, D. M. et al. Claim. Microbiol. Rev. 1988. 1:1-18

[33] Price, S. B. et al. Curr Microbiol. 1987. 16:55-50

[34] Corthier G. et al. 1991. 59:155-159

[35] Giannasaca, R. H. et al. 1999. 67:527-538

[36] Phelps et al. 1991. 67: 150-153

[37] Lyras, D. et al. Nature. (2009) 458:1176-1179

[38] WO00/61762

[39] 3rd International *Clostridium difficile* Symposium, 2010, Bled, Slovenia. Abstract "*The potential use of repeat revions in the binding domain of toxin A and toxin B from C. difficile as a vaccine candidate*".

[940] WO2011/068953

[41] Ho et al. Proc Natl Acad Sci USA. 2005. 102(51): 18373-8

[42] Sambrook et al. (2001) *Molecular Cloning: A Laboratory Manual,* 3rd edition (Cold Spring Harbor Laboratory Press).

[43] U.S. Pat. No. 5,707,829

[44] *Current Protocols in Molecular Biology* (F. M. Ausubel et al. eds., 1987) Supplement 30.

[45] Ausubel et al. (eds) (2002) *Short protocols in molecular biology,* 5th edition (Current Protocols).

[46] Needleman & Wunsch (1970) *J. Mol. Biol.* 48, 443-453.

[47] Rice et al. (2000) *Trends Genet* 16:276-277.

[48] Gennaro (2000) *Remington: The Science and Practice of Pharmacy.* 20th edition, ISBN: 0683306472.

[49] *Vaccine Design* (1995) eds. Powell & Newman. ISBN: 030644867X. Plenum.

[50] WO90/14837.

[51] WO90/14837.

[52] Podda & Del Giudice (2003) *Expert Rev Vaccines* 2:197-203.

[53] Podda (2001) *Vaccine* 19: 2673-2680.

[54] *Vaccine Design: The Subunit and Adjuvant Approach* (eds. Powell & Newman) Plenum Press 1995 (ISBN 0-306-44867-X).

[55] *Vaccine Adjuvants: Preparation Methods and Research Protocols* (Volume 42 of *Methods in Molecular Medicine* series). ISBN: 1-59259-083-7. Ed. O'Hagan.

[56] U.S. Pat. No. 5,057,540.

[57] Niikura et al. (2002) *Virology* 293:273-280.

[58] Lenz et al. (2001) *J Immunol* 166:5346-5355.

[59] Pinto et al. (2003) *J Infect Dis* 188:327-338.

[60] Gerber et al. (2001) *J Virol* 75:4752-4760.

[61] WO03/024480.

[62] WO03/024481.

[63] Gluck et al. (2002) *Vaccine* 20:B10-B16.

[64] Meraldi et al. (2003) *Vaccine* 21:2485-2491.

[65] Pajak et al. (2003) *Vaccine* 21:836-842.

[66] Krieg (2003) *Nature Medicine* 9:831-835.

[67] McCluskie et al. (2002) *FEMS Immunology and Medical Microbiology* 32:179-185.

[68] WO98/40100.

[69] U.S. Pat. No. 6,207,646.

[70] U.S. Pat. No. 6,239,116.

[71] U.S. Pat. No. 6,429,199.

[72] Schellack et al. (2006) *Vaccine* 24:5461-72.

[73] Johnson et al. (1999) *Bioorg Med Chem Lett* 9:2273-2278.

[74] Evans et al. (2003) *Expert Rev Vaccines* 2:219-229.

[75] Beignon et al. (2002) *Infect Immun* 70:3012-3019.

[76] Pizza et al. (2001) *Vaccine* 19:2534-2541.

[77] Pizza et al. (2000) *Int J Med Microbiol* 290:455-461.

[78] Scharton-Kersten et al. (2000) *Infect Immun* 68:5306-5313.

[79] Ryan et al. (1999) *Infect Immun* 67:6270-6280.

[80] Partidos et al. (1999) *Immunol Lett* 67:209-216.

[81] Peppoloni et al. (2003) *Expert Rev Vaccines* 2:285-293.

[82] Pine et al. (2002) *J Control Release* 85:263-270.
[83] WO99/40936.
[84] WO99/44636.
[85] Singh et al] (2001) *J Cont Release* 70:267-276.
[86] WO99/27960.
[87] U.S. Pat. No. 6,090,406.
[88] U.S. Pat. No. 5,916,588.
[89] EP-A-0626169.
[90] WO99/52549.
[91] Andrianov et al. (1998) *Biomaterials* 19:109-115.
[92] Payne et al. (1998) *Adv Drug Delivery Review* 31:185-196.
[93] Stanley (2002) *Clin Exp Dermatol* 27:571-577.
[94] Jones (2003) *Curr Opin Investig Drugs* 4:214-218.
[95] WO99/11241.
[96] WO94/00153.
[97] WO98/57659.
[98] European patent applications 0835318, 0735898 and 0761231.
[99] Ogunniyi et al. (2001) *Infect Immun* 69:5997-6003.
[100] WO2006/110603.
[101] Ganeshapillai et al. (2008) *Carbohydr. Res.,* 343, 703.
[102] Watson (2000) *Pediatr Infect Dis J* 19:331-332.
[103] Rubin (2000) *Pediatr Clin North Am* 47:269-285, v.
[104] Jedrzejas (2001) *Microbiol Mol Biol Rev* 65:187-207.
[105] Bell (2000) *Pediatr Infect Dis J*19:1187-1188.
[106] Iwarson (1995) *APMIS* 103:321-326.
[107] Gerlich et al. (1990) *Vaccine* 8 Suppl:S63-68 & 79-80.
[108] *Vaccines* (1988) eds. Plotkin & Mortimer. ISBN 0-7216-1946-0.
[109] Del Guidice et al. (1998) *Molecular Aspects of Medicine* 19:1-70.
[110] Gustafsson et al. (1996) *N. Engl.* 1 Med. 334:349-355.
[111] Rappuoli et al. (1991) *TIBTECH* 9:232-238.
[112] Costantino et al. (1999) *Vaccine* 17:1251-1263.
[113] Sutter et al. (2000) *Pediatr Clin North Am* 47:287-308.
[114] Zimmerman & Spann (1999) *Am Fam Physician* 59:113-118, 125-126.
[115] McMichael (2000) *Vaccine* 19 Suppl 1:S101-107.
[116] Schuchat (1999) *Lancet* 353(9146):51-6.
[117] WO02/34771.
[118] Dale (1999) *Infect Dis Clin North Am* 13:227-43, viii.
[119] Ferretti et al. (2001) *PNAS USA* 98: 4658-4663.
[120] Kuroda et al. (2001) *Lancet* 357(9264):1225-1240; see also pages 1218-1219.
[121] EP-A-0372501
[122] EP-A-0378881
[123] EP-A-0427347
[124] WO93/17712
[125] WO94/03208
[126] WO98/58668
[127] EP-A-0471177
[128] WO00/56360
[129] WO91/01146
[130] WO00/61761
[131] WO01/72337
[132] *Research Disclosure,* 453077 (January 2002)
[133] Lyerly, D. M. et al. (1986) *Infect. Immun.* 54:70-76
[134] Corthier, et al. (1991) *Infect. Immun.* 59: 1192-1195
[135] Lyerly, D. M. et al. (1991) *Infect. Immun.* 59: 2215-2218
[136] Kelly, C. P. et al. (1996) *Antimicrob. Agents. Chemother.* 40: 373-379
[137] Kink, J. A. et al. (1998) *Infect. Immun.* 66: 2018-2025
[138] Van Dissel, J. T. et al. (2005) *J. Med. Microbiol.* 54: 197-205
[139] Babcock, G. J. et al. (2006). *Infect. Immun.* 74: 6339-6347
[140] Winter et al., (1991) *Nature* 349:293-99
[141] U.S. Pat. No. 4,816,567.
[142] Inbar et al., (1972) *Proc. Natl. Acad. Sci. U.S.A.* 69:2659-62.
[143] Ehrlich et al., (1980) *Biochem* 19:4091-96.
[144] Huston et al., (1988) *Proc. Natl. Acad. Sci. U.S.A.* 85:5897-83.
[145] Pack et al., (1992) *Biochem* 31, 1579-84.
[146] Cumber et al., (1992) *J. Immunology* 149B, 120-26.
[147] Riechmann et al., (1988) *Nature* 332, 323-27.
[148] Verhoeyan et al., (1988) *Science* 239, 1534-36.
[149] GB 2,276,169.
[150] Gennaro (2000) *Remington: The Science and Practice of Pharmacy.* 20th edition, ISBN: 0683306472.
[151] *Methods In Enzymology* (S. Colowick and N. Kaplan, eds., Academic Press, Inc.)
[152] *Handbook of Experimental Immunology*, Vols. I-IV (D. M. Weir and C. C. Blackwell, eds, 1986, Blackwell Scientific Publications)
[153] Sambrook et al. (2001) *Molecular Cloning: A Laboratory Manual,* 3rd edition (Cold Spring Harbor Laboratory Press).
[154] *Handbook of Surface and Colloidal Chemistry* (Birdi, K. S. ed., CRC Press, 1997)
[155] Ausubel et al. (eds) (2002) *Short protocols in molecular biology,* 5th edition (Current Protocols).
[156] *Molecular Biology Techniques: An Intensive Laboratory Course*, (Ream et al., eds., 1998, Academic Press)
[157] *PCR* (*Introduction to Biotechniques Series*), 2nd ed. (Newton & Graham eds., 1997, Springer Verlag)
[158] Geysen et al. (1984) *PNAS USA* 81:3998-4002.
[159] Carter (1994) *Methods Mol Biol* 36:207-23.
[160] Jameson, B A et al. 1988, *CABIOS* 4(1):181-186.
[161] Raddrizzani & Hammer (2000) *Brief Bioinform* 1(2): 179-89.
[162] Bublil et al. (2007) *Proteins* 68(1):294-304.
[163] De Lalla et al. (1999) *J. Immunol.* 163:1725-29.
[164] Kwok et al. (2001) *Trends Immunol* 22:583-88.
[165] Brusic et al. (1998) *Bioinformatics* 14(2):121-30
[166] Meister et al. (1995) *Vaccine* 13(6):581-91.
[167] Roberts et al. (1996) *AIDS Res Hum Retroviruses* 12(7):593-610.
[168] Maksyutov & Zagrebelnaya (1993) *Comput Appl Biosci* 9(3):291-7.
[169] Feller & de la Cruz (1991) *Nature* 349(6311):720-1.
[170] Hopp (1993) polypeptide *Research* 6:183-190.
[171] Welling et al. (1985) *FEBS Lett.* 188:215-218.
[172] Davenport et al. (1995) *Immunogenetics* 42:392-297.
[173] Tsurui & Takahashi (2007) *J Pharmacol Sci.* 105(4): 299-316.
[174] Tong et al. (2007) *Brief Bioinform.* 8(2):96-108.
[175] Schirle et al. (2001) *J Immunol Methods.* 257(1-2):1-16.
[176] Chen et al. (2007) *Amino Acids* 33(3):423-8.
[177] *Current Protocols in Molecular Biology* (F. M. Ausubel et al., eds., 1987) Supplement 30
[178] Smith & Waterman (1981) *Adv. Appl. Math.* 2: 482-489.
[179] Torres et al. (1995) *IAI* 63(12), 4619-4627
[180] Sougioultzis et al. (2005) *Gastroenterology* 128: 764-770

The invention claimed is:

1. An immunogenic composition comprising a combination of *Clostridium difficile* (*C. difficile*) antigens comprising:

a) a *C. difficile* Toxin B (ToxB) glycosyl transferase domain (GT) antigen (ToxB-GT antigen), wherein the ToxB-GT antigen consists of an amino acid sequence selected from the group consisting of:
  (i) an amino acid sequence which is 90% or more identical to SEQ ID NO:18;
  (ii) an amino acid sequence which is 90% or more identical to SEQ ID NO:60;
  (iii) an amino acid sequence which comprises at least 7 consecutive amino acids of SEQ ID NO:18 and which is a fragment of SEQ ID NO:18;
  (iv) an amino acid sequence which comprises at least 7 consecutive amino acids of SEQ ID NO:60 and which is a fragment of SEQ ID NO:60, wherein the Tox-GT antigen is detoxified by two amino acid substitutions relative to the wild-type sequence of SEQ ID NO:18, wherein the two amino acid substitutions are at a positions selected from the group consisting of amino acids corresponding to amino acids 17, 102, 139, 269, 270, 273, 284, 286, 288, 384, 444, 445, 448, 449, 450, 451, 452, 455, 461, 463, 472, 515, 518, and 520 of SEQ ID NO:18, and wherein the two amino acid substitutions are at not at positions corresponding to amino acids 102 and 278 of SEQ ID NO:18 or to positions 102 and 288 of SEQ ID NO:18; and b) a *C. difficile* toxin A(TcdA) antigen which is a fragment of TcdA which contains at least 7 consecutive amino acids from SEQ ID NO:1.

2. The immunogenic composition of claim 1, wherein the ToxB-GT antigen consists of an amino acid sequence which is 90% or more identical to SEQ ID NO:18.

3. The immunogenic composition of claim 1, wherein the ToxB-GT antigen consists of an amino acid sequence which is 90% or more identical to SEQ ID NO:60.

4. The immunogenic composition of claim 1, wherein the one or more amino acid substitutions at one or more amino acid positions are selected from the group consisting of D270A, R273A, Y284A, D286A and D288A.

5. The immunogenic composition of claim 1, wherein the TcdA antigen is a p5-6 domain of *C. difficile* toxin A (ToxA-p5-6) antigen which comprises a mutation in at least one amino acid position relative to SEQ ID NO:11.

6. The immunogenic composition of claim 5, wherein the mutation comprises a mutation selected from the group consisting of:

(a) a deletion of up to 40 amino acids relative to SEQ ID NO: 11 at a position selected from the N-terminus, the C-terminus, and the N- and the C-terminus of SEQ ID NO: 11;

(b) addition of two amino acids at the C-terminus relative to SEQ ID NO: 11; and (c) a substitution at one or more positions selected from positions 41 and 42 of the ToxA-p5-6 antigen numbered according to SEQ ID NO:11.

7. The immunogenic composition of claim 6, wherein the mutation is the addition of two amino acids at the C-terminus relative to SEQ ID NO:11, and wherein the two amino acids are selected from the group consisting of leucine (L), glutamic acid (E), and leucine (L) and glutamic acid (E).

8. The immunogenic composition of claim 6, wherein the mutation is the substitution at one or more positions selected from positions 41 and 42 of the ToxA-p5-6 antigen numbered according to SEQ ID NO:11, and wherein the one or more positions are selected from the group consisting of H41D (SEQ ID NO:101), N42A (SEQ ID NO:102), and H41D+N42A (SEQ ID NO:103).

9. The immunogenic composition of claim 1, further comprising one or more additional antigens selected from the group consisting of (a) a ToxB-ED antigen (SEQ ID NO: 17), (b) a ToxB-CP antigen (SEQ ID NO:19), (c) a ToxB-T antigen (SEQ ID NO: 20), (d) a ToxB-B antigen (SEQ ID NO: 21), (e) a ToxB-B2 antigen (SEQ ID NO: 22), (f) ToxB-B7 (SEQ ID NO: 23), (g) a full-length TcdB antigen (SEQ ID NO:2), (h) a ToxA-ED antigen (SEQ ID NO: 3), (i) a ToxA-GT antigen (SEQ ID NO: 4), (j) a ToxA-CP antigen (SEQ ID NO:5), (k) a ToxA-T antigen (SEQ ID NO: 6), (1) a ToxA-T4 antigen (SEQ ID NO: 7), (m) a ToxA-B antigen (SEQ ID NO: 8), (n) a ToxA-PTA2 antigen (SEQ ID NO: 9), (o) a ToxA-P5-7 antigen (SEQ ID NO: 10), (p) a ToxA-P9-10 antigen (SEQ ID NO: 12), (q) a ToxA-B2 antigen (SEQ ID NO: 13), (r) a ToxA-B3 antigen (SEQ ID NO:14), (s) a ToxA-B5 antigen (SEQ ID NO: 15), (t) a ToxA-B6 antigen (SEQ ID NO:16), and (u) a full-length TcdA antigen (SEQ ID NO:1).

10. The immunogenic composition of claim 1, wherein one of the antigens in the composition is present in a hybrid polypeptide.

11. The immunogenic composition of claim 9, wherein at least two of the antigens in the composition comprise a hybrid polypeptide.

12. The immunogenic composition of claim 10, wherein the hybrid polypeptide comprises (i) ToxB-GT (SEQ ID NO: 18) fused to ToxA-P5-6 (SEQ ID NO: 11).

13. The immunogenic composition of claim 10, wherein the hybrid polypeptide comprises an amino acid sequence selected from the group of sequences consisting of: (a) SEQ ID NO:106, (b)SEQ ID NO: 107, (c) SEQ ID NO: 108, (d)SEQ ID NO: 109, (e) SEQ ID NO: 110, (f) SEQ ID NO: 111, and (g) SEQ ID NO: 24.

14. The immunogenic composition of claim 1, wherein the composition induces neutralisation titers against *C. difficile* toxin A and toxin B.

15. The immunogenic composition of claim 1, further comprising at least one further *C. difficile* antigen.

16. The composition of claim 15, wherein the at least one further *C. difficile* antigen comprises a saccharide antigen.

17. A pharmaceutical composition comprising the immunogenic composition of claim 1 and a pharmaceutically acceptable carrier.

18. The pharmaceutical composition of claim 17, further comprising an adjuvant.

19. The immunogenic composition of claim 1, wherein the TcdA antigen is a polypeptide selected from the group consisting of (a) a polypeptide comprising an amino acid sequence having 90% or more identity to SEQ ID NO:1;

(b) a polypeptide which is a fragment of at least 7 consecutive amino acids of SEQ ID NO:1; and (c) a polypeptide comprising an amino acid sequence 90% or more identical to SEQ ID NO:11, wherein the amino acid sequence lacks 20 amino acids from the C-terminus of SEQ ID NO:11.

20. The immunogenic composition of claim 19, wherein the TcdA antigen is the polypeptide comprising an amino acid sequence 90% or more identical to SEQ ID NO:11, wherein the amino acid sequence lacks 20 amino acids from the C-terminus of SEQ ID NO:11.

21. The immunogenic composition of claim 1, wherein:

(a) the ToxB-GT antigen consists of an amino acid sequence which is 90% or more identical to SEQ ID NO:60; and (b) wherein the TcdA antigen is a polypeptide comprising an amino acid sequence 90% or more identical to SEQ ID NO:11, wherein the amino acid sequence lacks 20 amino acids from the C-terminus of SEQ ID NO:11.

* * * * *